US012479856B2

(12) United States Patent
Wiles et al.

(10) Patent No.: US 12,479,856 B2
(45) Date of Patent: Nov. 25, 2025

(54) PHARMACEUTICAL COMPOUNDS FOR THE TREATMENT OF COMPLEMENT MEDIATED DISORDERS

(71) Applicant: Achillion Pharmaceuticals, Inc., Boston, MA (US)

(72) Inventors: Jason Allan Wiles, Madison, CT (US); Venkat Rao Gadhachanda, Hamden, CT (US); Kyle J. Eastman, Killingworth, CT (US)

(73) Assignee: Achillion Pharmaceuticals, Inc., Boston, MA (US)

( * ) Notice: Subject to any disclaimer, the term of this patent is extended or adjusted under 35 U.S.C. 154(b) by 1009 days.

(21) Appl. No.: 17/440,665

(22) PCT Filed: Mar. 20, 2020

(86) PCT No.: PCT/US2020/024017
§ 371 (c)(1),
(2) Date: Sep. 17, 2021

(87) PCT Pub. No.: WO2020/198062
PCT Pub. Date: Oct. 1, 2020

(65) Prior Publication Data

US 2023/0085372 A1 Mar. 16, 2023

Related U.S. Application Data

(60) Provisional application No. 62/951,669, filed on Dec. 20, 2019, provisional application No. 62/822,553, filed on Mar. 22, 2019.

(51) Int. Cl.

| | |
|---|---|
| ***C07D 491/113*** | (2006.01) |
| ***C07D 207/16*** | (2006.01) |
| ***C07D 333/38*** | (2006.01) |
| ***C07D 409/12*** | (2006.01) |
| ***C07D 417/12*** | (2006.01) |
| ***C07D 471/08*** | (2006.01) |
| ***C07D 519/00*** | (2006.01) |
| ***C07F 7/08*** | (2006.01) |

(52) U.S. Cl.
CPC ........ *C07D 491/113* (2013.01); *C07D 207/16* (2013.01); *C07D 333/38* (2013.01); *C07D 409/12* (2013.01); *C07D 417/12* (2013.01); *C07D 471/08* (2013.01); *C07D 519/00* (2013.01); *C07F 7/0816* (2013.01)

(58) Field of Classification Search
CPC ......................... C07D 491/113; C07D 207/16; C07D 333/38; C07D 409/12; C07D 417/12; C07D 471/08; C07D 519/00; C07F 7/0816
See application file for complete search history.

(56) References Cited

U.S. PATENT DOCUMENTS

| | | | |
|---|---|---|---|
| 5,628,984 | A | 5/1997 | Boucher, Jr. |
| 6,319,897 | B1 | 11/2001 | Lambris et al. |
| 6,489,476 | B1 | 12/2002 | Dang et al. |
| 6,492,402 | B1 | 12/2002 | Lee et al. |
| 6,653,340 | B1 | 11/2003 | Babu et al. |
| 6,683,055 | B1 | 1/2004 | Hillen et al. |
| 7,482,376 | B2 | 1/2009 | Subasinghe et al. |
| 7,629,340 | B2 | 12/2009 | Schmitz et al. |
| 7,888,323 | B2 | 2/2011 | Lambris et al. |
| 7,989,589 | B2 | 8/2011 | Lambris |
| 7,999,081 | B2 | 8/2011 | Tedesco et al. |
| 8,168,584 | B2 | 5/2012 | Deschatelets et al. |
| 8,241,628 | B2 | 8/2012 | Diefenbach-Streiber et al. |
| 8,524,716 | B2 | 9/2013 | Raboisson et al. |
| 8,580,735 | B2 | 11/2013 | Francois et al. |
| 8,883,158 | B2 | 11/2014 | Diefenbach-Streiber et al. |
| 8,946,145 | B2 | 2/2015 | Lambris et al. |
| 9,056,076 | B2 | 6/2015 | Deschatelets et al. |
| 9,085,555 | B2 | 7/2015 | Altmann et al. |
| 9,169,307 | B2 | 10/2015 | Lambris et al. |
| 9,291,622 | B2 | 3/2016 | Zhang et al. |
| 9,371,365 | B2 | 6/2016 | Lambris et al. |
| 9,421,240 | B2 | 8/2016 | Francois et al. |
| 9,468,661 | B2 | 10/2016 | Altmann et al. |
| 9,598,446 | B2 | 3/2017 | Gadhachanda et al. |
| 9,643,986 | B2 | 5/2017 | Wiles et al. |
| 9,663,543 | B2 | 5/2017 | Wiles et al. |
| 9,695,205 | B2 | 7/2017 | Wiles et al. |
| 9,732,103 | B2 | 8/2017 | Wiles et al. |
| 9,732,104 | B2 | 8/2017 | Gadhachanda et al. |
| 9,758,537 | B2 | 9/2017 | Wiles et al. |
| 9,796,741 | B2 | 10/2017 | Gadhachanda et al. |
| 9,828,396 | B2 | 11/2017 | Wiles et al. |
| 9,851,351 | B2 | 12/2017 | Reich et al. |

(Continued)

FOREIGN PATENT DOCUMENTS

| | | | |
|---|---|---|---|
| CN | 103402996 | A | 11/2013 |
| EA | 201890594 | A1 | 8/2018 |

(Continued)

OTHER PUBLICATIONS

International Search Report and Written Opinion for International Application No. PCT/US2021/051559, mailed Feb. 15, 2022 (12 pages).
International Search Report and Written Opinion for International Application No. PCT/US23/29711, mailed Jan. 3, 2024 (11 pages).
PubChem SID 304509504, modified Jan. 29, 2016 (4 pages).
U.S. Appl. No. 16/006,476, Wiles et al.
U.S. Appl. No. 16/006,533, Wiles et al.
"Are There Any Treatments for ALS?" WebMD, <https://www.webmd.com/brain/understanding-als-treatment#1>, retrieved on May 3, 2019 (8 pages).

(Continued)

*Primary Examiner* — Kortney L. Klinkel
*Assistant Examiner* — Richard Grant Peckham
(74) *Attorney, Agent, or Firm* — Clark & Elbing LLP

(57) ABSTRACT

This disclosure provides pharmaceutical compounds to treat medical disorders, such as complement-mediated disorders, including complement Cl-mediated disorders.

12 Claims, No Drawings

(56) References Cited

U.S. PATENT DOCUMENTS 10,000,516 B2 6/2018 Wiles et al.
10,005,802 B2 6/2018 Wiles et al.
10,011,612 B2 7/2018 Wiles et al.
10,081,645 B2 9/2018 Wiles et al.
10,087,203 B2 10/2018 Wiles et al.
10,092,547 B2 10/2018 Wiles et al.
10,092,584 B2 10/2018 Wiles et al.
10,100,072 B2 10/2018 Wiles et al.
10,106,563 B2 10/2018 Wiles et al.
10,138,225 B2 11/2018 Wiles et al.
10,189,869 B2 1/2019 Gadhachanda et al.
10,253,053 B2 4/2019 Wiles et al.
10,287,301 B2 5/2019 Wiles et al.
10,301,336 B2 5/2019 Wiles et al.
10,370,394 B2 8/2019 Wiles et al.
10,385,097 B2 8/2019 Wiles et al.
10,428,094 B2 10/2019 Wiles et al.
10,428,095 B2 10/2019 Wiles et al.
10,464,956 B2 11/2019 Wiles et al.
10,550,140 B2 2/2020 Wiles et al.
10,660,876 B2 5/2020 Wiles et al.
10,662,175 B2 5/2020 Wiles et al.
10,807,952 B2 10/2020 Wiles et al.
10,822,352 B2 11/2020 Wiles et al.
10,906,887 B2 2/2021 Wiles et al.
10,919,884 B2 2/2021 Wiles et al.
11,084,800 B2 8/2021 Wiles et al.
2002/0133004 A1 9/2002 Sekiyama et al.
2004/0127689 A1 7/2004 Sigler et al.
2005/0228000 A1 10/2005 Smallheer et al.
2005/0245497 A1 11/2005 Penfold et al.
2005/0267108 A1 12/2005 Hsieh et al.
2006/0004000 A1 1/2006 D'Orchymont et al.
2007/0155712 A1 7/2007 Zahn et al.
2008/0075720 A1 3/2008 Holers et al.
2008/0075728 A1 3/2008 Newman
2008/0108691 A1 5/2008 Hamann et al.
2008/0255108 A1 10/2008 Subasinghe et al.
2009/0162358 A1 6/2009 Alard et al.
2010/0041628 A1 2/2010 Enomoto et al.
2011/0280808 A1 11/2011 Kroth et al.
2012/0231471 A1 9/2012 Sato et al.
2012/0237515 A1 9/2012 Bell et al.
2012/0295884 A1 11/2012 Altmann et al.
2013/0029912 A1 1/2013 Holers et al.
2013/0035392 A1 2/2013 McGeer et al.
2013/0296377 A1 11/2013 Adams et al.
2013/0324482 A1 12/2013 Francois et al.
2013/0344073 A1 12/2013 Schwaeble et al.
2014/0023667 A1 1/2014 Stamford et al.
2014/0050739 A1 2/2014 Francois et al.
2014/0323407 A1 10/2014 Francois et al.
2014/0371133 A1 12/2014 Francois et al.
2015/0141455 A1 5/2015 Altmann et al.
2015/0148374 A1 5/2015 Hommel et al.
2015/0158915 A1 6/2015 Lambris et al.
2015/0191462 A1 7/2015 Hommel et al.
2015/0239837 A1 8/2015 Wiles et al.
2015/0239838 A1 8/2015 Phadke et al.
2015/0239868 A1 8/2015 Pais et al.
2015/0239893 A1 8/2015 Wang et al.
2015/0239894 A1 8/2015 Gadhachanda et al.
2015/0239895 A1 8/2015 Gadhachanda et al.
2015/0239919 A1 8/2015 Gadhachanda et al.
2015/0239920 A1 8/2015 Gadhachanda et al.
2015/0239921 A1 8/2015 Wiles et al.
2015/0322060 A1 11/2015 Flohr et al.
2015/0368271 A1 12/2015 Su et al.
2016/0015810 A1 1/2016 Deschatelets et al.
2016/0024079 A1 1/2016 Adams et al.
2016/0060297 A1 3/2016 Deschatelets et al.
2016/0194359 A1 7/2016 Francois et al.
2016/0215020 A1 7/2016 Francois et al.
2016/0215022 A1 7/2016 Francois et al.
2016/0361329 A1 12/2016 Wiles et al.
2016/0362398 A1 12/2016 Wiles et al.
2016/0362399 A1 12/2016 Wiles et al.
2016/0362432 A1 12/2016 Wiles et al.
2016/0362433 A1 12/2016 Wiles et al.
2017/0056428 A1 3/2017 Wiles et al.
2017/0057950 A1 3/2017 Wiles et al.
2017/0057983 A1 3/2017 Wiles et al.
2017/0057993 A1 3/2017 Wiles et al.
2017/0066783 A1 3/2017 Wiles et al.
2017/0189410 A1 7/2017 Gadhachanda et al.
2017/0202821 A1 7/2017 Bekker
2017/0202935 A1 7/2017 Lambris et al.
2017/0226142 A1 8/2017 Wiles et al.
2017/0260219 A1 9/2017 Wiles et al.
2017/0298084 A1 10/2017 Wiles et al.
2017/0298085 A1 10/2017 Wiles et al.
2018/0022766 A1 1/2018 Wiles et al.
2018/0022767 A1 1/2018 Wiles et al.
2018/0030075 A1 2/2018 Wiles et al.
2018/0072762 A1 3/2018 Wiles et al.
2018/0177761 A1 6/2018 Wiles et al.
2018/0179185 A1 6/2018 Wiles et al.
2018/0179186 A1 6/2018 Wiles et al.
2018/0179236 A1 6/2018 Wiles et al.
2018/0186782 A1 7/2018 Wiles et al.
2018/0201580 A1 7/2018 Wiles et al.
2018/0305375 A1 10/2018 Wiles et al.
2019/0023729 A1 1/2019 Wiles et al.
2019/0031692 A1 1/2019 Wiles et al.
2019/0038623 A1 2/2019 Huang et al.
2019/0048033 A1 2/2019 Wiles et al.
2019/0085005 A1 3/2019 Wiles et al.
2019/0144473 A1 5/2019 Gadhachanda et al.
2019/0151334 A1 5/2019 Bosworth et al.
2019/0211033 A1 7/2019 Wiles et al.
2019/0359645 A1 11/2019 Birkus et al.
2019/0382376 A1 12/2019 Wiles et al.
2020/0002347 A1 1/2020 Wiles et al.
2020/0062790 A1 2/2020 Wiles et al.
2020/0071301 A1 3/2020 Wiles et al.
2020/0262818 A1 8/2020 Wiles et al.
2021/0179612 A1 6/2021 Cutshall et al.

FOREIGN PATENT DOCUMENTS

JP 2014-506877 A 3/2014
JP 2015-522005 A 8/2015
JP 2015-522006 A 8/2015
JP 2015-522007 A 8/2015
JP 6400738 B2 10/2018
JP 6537532 B2 7/2019
JP 6688352 B2 4/2020
JP 6877406 B2 5/2021
WO WO-93/20099 A2 10/1993
WO WO-95/29697 A1 11/1995
WO WO-99/48492 A1 9/1999
WO WO-2004/007501 A1 1/2004
WO WO-2004/045518 A2 6/2004
WO WO-2004/111041 A1 12/2004
WO WO-2008/047831 A1 4/2008
WO WO-2008/085608 A1 7/2008
WO WO-2009/091826 A2 7/2009
WO WO-2011/057158 A1 5/2011
WO WO-2012/093101 A1 7/2012
WO WO-2012/177782 A1 12/2012
WO WO-2013/166436 A1 11/2013
WO WO-2013/192345 A1 12/2013
WO WO-2014/002051 A2 1/2014
WO WO-2014/002052 A1 1/2014
WO WO-2014/002053 A1 1/2014
WO WO-2014/002054 A1 1/2014
WO WO-2014/002057 A1 1/2014
WO WO-2014/002058 A2 1/2014
WO WO-2014/002059 A1 1/2014
WO WO-2014/005150 A1 1/2014
WO WO-2014/009833 A2 1/2014
WO WO-2014/037480 A1 3/2014
WO WO-2014/116880 A1 7/2014
WO WO-2015/008861 A1 1/2015

(56) References Cited

FOREIGN PATENT DOCUMENTS

| | | | |
|---|---|---|---|
| WO | WO-2015/021166 | A2 | 2/2015 |
| WO | WO-2015/054569 | A1 | 4/2015 |
| WO | WO-2015/130784 | A1 | 9/2015 |
| WO | WO-2015/130795 | A1 | 9/2015 |
| WO | WO-2015/130806 | A1 | 9/2015 |
| WO | WO-2015/130830 | A1 | 9/2015 |
| WO | WO-2015/130838 | A1 | 9/2015 |
| WO | WO-2015/130842 | A2 | 9/2015 |
| WO | WO-2015/130845 | A1 | 9/2015 |
| WO | WO-2015/130854 | A1 | 9/2015 |
| WO | WO-2017/035348 | A1 | 3/2017 |
| WO | WO-2017/035349 | A1 | 3/2017 |
| WO | WO-2017/035351 | A1 | 3/2017 |
| WO | WO-2017/035352 | A1 | 3/2017 |
| WO | WO-2017/035353 | A1 | 3/2017 |
| WO | WO-2017/035355 | A1 | 3/2017 |
| WO | WO-2017/035357 | A1 | 3/2017 |
| WO | WO-2017/035360 | A1 | 3/2017 |
| WO | WO-2017/035361 | A1 | 3/2017 |
| WO | WO-2017/035362 | A1 | 3/2017 |
| WO | WO-2017/035401 | A1 | 3/2017 |
| WO | WO-2017/035405 | A1 | 3/2017 |
| WO | WO-2017/035408 | A1 | 3/2017 |
| WO | WO-2017/035409 | A1 | 3/2017 |
| WO | WO-2017/035411 | A1 | 3/2017 |
| WO | WO-2017/035413 | A2 | 3/2017 |
| WO | WO-2017/035415 | A1 | 3/2017 |
| WO | WO-2017/035417 | A1 | 3/2017 |
| WO | WO-2017/035418 | A1 | 3/2017 |
| WO | WO-2017/098328 | A2 | 6/2017 |
| WO | WO-2017/127761 | A1 | 7/2017 |
| WO | WO-2017/136395 | A1 | 8/2017 |
| WO | WO-2018/005552 | A1 | 1/2018 |
| WO | WO-2018/026722 | A1 | 2/2018 |
| WO | WO-2018/160889 | A1 | 9/2018 |
| WO | WO-2018/160891 | A1 | 9/2018 |
| WO | WO-2018/160892 | A1 | 9/2018 |
| WO | WO-2018/193387 | A1 | 10/2018 |
| WO | WO-2019/070714 | A1 | 4/2019 |
| WO | WO-2020/198062 | A1 | 10/2020 |
| WO | WO-2021/021909 | A1 | 2/2021 |

OTHER PUBLICATIONS

"Arteriosclerosis/atherosclerosis," Mayo Clinic, <https://www.mayoclinic.org/diseases-conditions/arteriosclerosis-atherosclerosis/diagnosis-treatment/drc-20350575>, retrieved on Apr. 24, 2018 (10 pages).

"Cancer," MedLine Plus, <http://www.nlm.nih.gov/medlineplus/cancer.html>, retrieved Jul. 6, 2007 (10 pages).

"Dermatomyositis," Mayo Clinic, <https://www.mayoclinic.org/diseases-conditions/dermatomyositis/diagnosis-treatment/drc-20353192>, retrieved on Aug. 1, 2017 (7 pages).

"History of Changes for Study: NCT03053102—A Treatment Study of ACH-0144471 in Patients With Paroxysmal Nocturnal Hemoglobinuria (PNH)," U.S. National Library of Medicine, available at: <https://clinicaltrials.gov/ct2/history/NCT03053102?V_4=View#StudyPageTop>, submitted Jun. 6, 2017, retrieved Mar. 9, 2021 (3 pages).

"NCT03472885—A Treatment Study of ACH-0144471 in Patients With Paroxysmal Nocturnal Hemoglobinuria (PNH) With Inadequate Response to Eculizumab (PNH)," U.S. National Library of Medicine, available at: <https://clinicaltrials.gov/ct2/show/NCT03472885>, first posted Mar. 21, 2018, last update posted Dec. 3, 2019, retrieved Mar. 27, 2020 (7 pages).

"Reperfusion injury," Wikipedia, <https://en.wikipedia.org/wiki/Reperfusion_injury>, retrieved Apr. 30, 2020 (8 pages).

"Treatment for Multiple Sclerosis," WebMD, <https://www.webmd.com/multiple-sclerosis/ms-treatment#1>, retrieved on May 3, 2019 (24 pages).

"What Are the Treatments for Cirrhosis?," WebMD, <https://www.webmd.com/digestive-disorders/understanding-cirrhosis-treatment#1>, retrieved May 3, 2019 (15 pages).

"What is Cardiovascular Disease?" American Heart Association, <https://www.heart.org/en/health-topics/consumer-healthcare/what-is-cardiovascular-disease>, last reviewed May 31, 2017 (4 pages).

"What is Dementia?" Alzheimer's Association, <https://www.alz.org/alzheimers-dementia/what-is-dementia>, retrieved on Nov. 17, 2020 (6 pages).

Airey et al., "A Convenient Preparation of Thieno[3,2-c]pyrazole," Synthesis. 46: 96-100 (2014).

Armand, "Fatty liver disease: What it is and what to do about it," Harvard Health Publishing, <https://www.health.harvard.edu/blog/fatty-liver-disease-what-it-is-and-what-to-do-about-it-2019011015746>, dated Jan. 10, 2019, retrieved May 2, 2019 (3 pages).

Babiker et al., "Transfer of prostasomal CD59 to CD59-deficient red blood cells results in protection against complement-mediated hemolysis," Am J Reprod Immunol. 47(3): 183-92 (2002) (Abstract Only) (1 page).

Barraclough et al., "Synthesis of (2S,3R)- and (2S,3S)-[3-$^2H_1$]-proline via highly selective hydrolysis of a silyl enol ether," Tetrahedron Letters. 46(1): 4653-4655 (2005).

Barraclough et al., "Two separate and distinct syntheses of stereospecifically deuteriated samples of (2S)-proline," Org Biomol Chem. 4(8):1483-1491 (2006).

Borowitz et al., "Guidelines for the Diagnosis and Monitoring of Paroxysmal Nocturnal Hemoglobinuria and Related Disorders by Flow Cytometry," Cytometry B Clin Cytom. 78B(4): 211-230 (2010).

Brodsky, "Eculizumab: another breakthrough," Blood. 129(8):922-3 (2017).

Carter, "Complement Activation: An Emerging Player in the Pathogenesis of Cardiovascular Disease," Scientifica. 2012:402783 (2012) (14 pages).

CAS RN 1236228-05-9, dated Aug. 16, 2010 (1 page).

CAS RN 1236251-51-6, dated Aug. 17, 2010 (2 pages).

CAS RN 1270608-88-2, dated 2019 (1 page).

CAS RN 1277041-86-7, dated Apr. 8, 2011 (2 pages).

Cofiell et al., "Eculizumab reduces complement activation, inflammation, endothelial damage, thrombosis, and renal injury markers in aHUS," Blood. 125(21):3253-62 (2015).

Cole et al. "Structure of 3,4-Dichloroisocoumarin-Inhibited Factor D," Acta Crystallogr D Biol Crystallogr. 54(Pt 5): 711-717 (1998).

Compound Summary for CID 1129904, PubChem. <https://pubchem.ncbi.nlm.nih.gov/compound/1129904> retrieved Jul. 14, 2020, created Jul. 10, 2005 (10 pages).

Compound Summary for CID 118324207, PubChem, <https://pubchem.ncbi.nlm.nih.gov/compound/118324207>, created Feb. 23, 2016, retrieved on Jul. 14, 2020 (8 pages).

Compound Summary for CID 123543544, PubChem, <https://pubchem.ncbi.nlm.nih.gov/compound/123543544>, created on Jan. 25, 2017, retrieved on Jul. 13, 2020 (8 pages).

Compound Summary for CID 134222466, PubChem, <https://pubchem.ncbi.nlm.nih.gov/compound/134222466>, created on Jun. 23, 2018, retrieved on Jul. 14, 2020 (11 pages).

Compound Summary for CID 59912842, PubChem, <https://pubchem.ncbi.nlm.nih.gov/compound/59912842>, created Aug. 20, 2012, retrieved Jul. 14, 2020 (9 pages).

Damasio, "Alzheimer's disease and related dementias," Cecil Textbook of Medicine, 20th Edition, vol. 2. Bennett and Plum, Jun. 1992 (1996).

Database Registry Chemical Abstracts Service, Columbus, Ohio, Accession No. RN1236248-20-6, Entered STN: Aug. 16, 2010 (1 page).

Database Registry Chemical Abstracts Service, Columbus, Ohio, Accession No. RN1380849-41-1, Entered STN: Jul. 3, 2012 (2 pages).

De Luca et al., "HIV-1 integrase strand-transfer inhibitors: Design, synthesis and molecular modeling investigation," Eur J Med Chem. 46(2): 756-764 (2011).

DeZern et al., "Paroxysmal nocturnal hemoglobinuria: a complement-mediated hemolytic anemia," available in PMC Dec. 30, 2015, published in final edited form as: Hematol Oncol Clin North Am. 29(3):479-94 (2015) (18 pages).

(56) References Cited

OTHER PUBLICATIONS

Donthiri et al., "Copper-Catalyzed C—H Functionalization of Pyridines and Isoquinolines with Vinyl Azides: Synthesis of Imidazo Heterocycles," J Org Chem. 79(22): 11277-11284 (2014).
Dormoy et al., "Synthesis of N-t-Butoxycarbonyl-4,4-dideuterio-L-proline," Synthesis. 1: 81-82 (1986).
Ellis-Pegler et al., "An Orally Administered Small Molecule Factor D Inhibitor (ACH-4471) For Treatment of PNH and Complement Diseases: Preliminary Phase 1 Results In Healthy Volunteers," European Hematology Association. Abstract LB2250, available <https://library.ehaweb.org/eha/2016/21st/135361/roderick.b.ellis-pegler.an.orally.administered.small.molecule.factor.d.html>, dated May 19, 2016 (2 pages).
Ellis-Pegler et al., "An Orally Administered Small Molecule Factor D Inhibitor (ACH-4471) For Treatment of PNH, C3G and Complement—Mediated Diseases: Interim Phase 1 Results In Healthy Volunteers," European Hematology Association, Copenhagen 21st Congress, June 9-12, Abstract ID: EHA-4145 (2016) (1 page).
Gadhachanda et al., CAplus Database Summary Sheet for Document No. 164:507515, Accession No. 2016:627420, CAplus on STN. (2016) (6 pages).
Gavriilaki et al., "275 Small Molecule Factor D Inhibitors Block Complement Activation in Paroxysmal Nocturnal Hemoglobinuria and Atypical Hemolytic Uremic Syndrome," ASH 57th Annual Meeting & Exposition, Session: 101. Dec. 6, 2015 (2 pages).
Golub et al., "Molecular classification of cancer: class discovery and class prediction by gene expression monitoring," Science. 286(5439):531-7 (1999) (8 pages).
Gura, "Systems for identifying new drugs are often faulty," Science. 278(5340): 1041-2 (1997).
Haddrill, "Stargardt's Disease (Fundus Flavimaculatus)," All About Vision, <https://www.allaboutvision.com/conditions/stargardts.htm#article-section-2>, retrieved May 3, 2019 (5 pages).
Harder et al., "Incomplete inhibition by eculizumab: mechanistic evidence for residual C5 activity during strong complement activation," Blood. 129(8):970-80 (2017).
Hartmann et al., "Diagnostic Specificity of Sucrose Hemolysis Test for Paroxysmal Nocturnal Hemoglobinuria," Blood. 35(4):462-475 (1970).
Hecker et al., "Liver-Targeted Prodrugs of 2'-C-Methyladenosine for Therapy of Hepatitis C Virus Infection," J Med Chem. 50(16): 3891-3896 (2007).
Hruby et al., "$^{13}C$ Nuclear Magnetic Resonance Studies of the Peptide Hormones Oxytocin, Arginine Vasopressin, Isotocin, Mesotocin, Glumitocin, Aspartocin, Related Analogues, and Diastereoisomers. Use of Specifically Deuterated Hormone Derivatives for Assignments and Effects of Structural Changes on $^{13}C$ NMR Chemical Shifts in Peptides," J Am Chem Soc. 101(1): 202-212 (1979).
Hu et al., "Evidence of complement dysregulation in outer retina of Stargardt disease donor eyes," Redox Biol. 37:101787 (2020) (10 pages).
International Search Report for International Application No. PCT/US20/24017, mailed Jun. 26, 2020 (3 pages).
Ishibashi et al., "Four-year outcomes of intravitreal aflibercept treatment for neovascular age-related macular degeneration using a treat-and-extend regimen in Japanese patients," Ther Adv Ophthalmol. 13:1-5 (2021).
Jensen et al., "Associations between the Complement System and Choroidal Neovascularization in Wet Age-Related Macular Degeneration," Int J Mol Sci. 21(24):9752 (2020) (28 pages).
Johnson et al., "Relationships between drug activity in NCI preclinical in vitro and in vivo models and early clinical trials," Br J Cancer. 84(10):1424-31 (2001).
Józsi, "Anti-Complement Autoantibodies in Membranoproliferative Glomerulonephritis and Dense Deposit Disease", *An Update on Glomerulopathies—Etiology and Pathogenesis*. Prof. Sharma Prabhakar, 31-46 (2011) (18 pages).
Kathuria, "Membranoproliferative Glomerulonephritis Medication," Medscape, <https://emedicine.medscape.com/article/240056-medication>, updated Jun. 23, 2016, retrieved May 3, 2019 (1 page).
Kinman, "COPD Drugs: A List of Medications to Help Relieve Your Symptoms," Healthline, <https://www.healthline.com/health/copd/drugs>, retrieved on May 3, 2019 (12 pages).
Kocinsky et al., "Abstract SaO018: Factor D inhibition with ACH-4471 to reduce complement alternative pathway hyperactivity and proteinuria in C3 glomerulopathy: preliminary proof of concept data," Nephrology Dialysis Transplantation. 33(Supplement 1):i322-3 (May 2018) (1 page).
Komiya et al., CAplus Database Summary Sheet for Document No. 162:229476, Accession No. 2015:126147, CAplus on STN. (2015) (2 pages).
Konar et al., "Eculizumab treatment and impaired opsonophagocytic killing of meningococci by whole blood from immunized adults," Blood. 130(7):891-9 (2017).
Krauss, "Laboratory Diagnosis of Paroxysmal Nocturnal Hemoglobinuria," Annals of Clinical & Laboratory Science. 33(4):401-406 (2003).
Kuang et al., "Synthesis of (Z)-1-bromo-1-alkenes and terminal alkynes from anti-2,3-dibromoalkanoic acids by microwave-induced reaction," Tetrahedron. 61(16):4043-4052 (2005).
Lala et al., "Role of nitric oxide in tumor progression: lessons from experimental tumors," Cancer Metastasis Rev. 17(1):91-106 (1998).
Lassmann, "What drives disease in multiple sclerosis: Inflammation or neurodegeneration?" Clinical and Experimental Neuroimmunology. 1:2-11 (2010).
Layzer, "Degenerative Diseases of the Nervous System," *Cecil Textbook of Medicine, 20th Edition, vol. 2*. J. Claude Bennett and Fred Plum, p. 2050-2057 (1996) (9 pages).
Le et al., "A mechanistic pharmacokinetic/pharmacodynamic model of factor D inhibition in cynomolgus monkeys by lampalizumab for the treatment of geographic atrophy," J Pharmacol Exp Ther. 355(2):288-96 (2015).
MacKay et al., "Rapid Synthesis of the N-Methylwelwitindolinone Skeleton," Org Lett. 7(16):3421-4 (2005).
Mastellos et al., "Complement in paroxysmal nocturnal hemoglobinuria: exploiting our current knowledge to improve the treatment landscape," available in PMC Apr. 2, 2015, published in final edited form as: Expert Rev Hematol. 7(5):583-98 (2014) (26 pages).
Noris et al., "Overview of Complement Activation and Regulation," Semin Nephrol. 33(6):479-92 (2013).
Okutani et al., "Conversion of Bromoalkenes into Alkynes by Wet Tetra-n-butylammonium Fluoride," J Org Chem. 74(1):442-444 (2009).
Oseini et al., "Therapies in Non-Alcoholic Steatohepatitis (NASH)," available in PMC Jan. 1, 2018, published in final edited form as: Liver Int. 37(Suppl 1):97-103 (2017) (15 pages).
Oshima et al., "Correlation between improvement in visual acuity and QOL after Ranibizumab treatment for age-related macular degeneration patients: QUATRO study," BMC Ophthalmol. 21(1):58 (2021) (11 pages).
Pandya et al., "Complement System in Lung Disease," Am J Respir Cell Mol Biol. 51(4):467-473 (2014).
Parker, "Update on the diagnosis and management of paroxysmal nocturnal hemoglobinuria," Hematology Am Soc Hemtol Educ Program. 2016(1):208-16 (2016).
Patel et al., "In Vitro Combination Studies of ACH-4471 with Eculizumab to Assess a Potential 'Switch' Treatment Approach for Paroxysmal Nocturnal Hemoglobinuria," 59th American Society of Hematology Annual Meeting and Exposition, Dec. 9-12, Atlanta, Georgia. Poster Abstract 2198 (2017) (1 page).
Pearce et al., Chapter 18: Failure modes in anticancer drug discovery and development. *Cancer Drug Design and Discovery*. Stephen Neidle, 424-435 (2008).
Peifer et al., "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors," J Med Chem. 51(13):3814-3824 (2008).
Pugsley et al., "Inhibitors of the complement system currently in development for cardiovascular disease," Cardiovasc Toxicol. 3(1):43-69 (2003).
Qu et al., "Recent Developments in Low Molecular Weight Complement Inhibitors," available in PMC, Dec. 1, 2010, published in final edited form as: Mol Immunol. 47(2-3):185-195 (2009) (25 pages).

(56) References Cited

OTHER PUBLICATIONS

Quesada et al., "One-pot conversion of activated alcohols into terminal alkynes using manganese dioxide in combination with the Bestmann—Ohira reagent," Tetrahedron Letters. 46:6473-6476 (2005).
Ricklin et al., "Complement in immune and inflammatory disorders: pathophysiological mechanisms," J Immunol. 190(8):3831-3838 (2013) (9 pages).
Risitano et al., "Complement fraction 3 binding on erythrocytes as additional mechanism of disease in paroxysmal nocturnal hemoglobinuria patients treated by eculizumab," Blood. 113(17):4094-4100 (2009) (25 pages).
Risitano et al., "Peptide inhibitors of C3 activation as a novel strategy of complement inhibition for the treatment of paroxysmal nocturnal hemoglobinuria," Blood. 123(13):2094-101 (2014).
Risitano et al., "Safety and Pharmacokinetics of the Complement Inhibitor TT30 in a Phase I Trial for Untreated PNH Patients" Blood. 126(23): 2137 (2015) (Abstract Only) (7 pages).
Risitano et al., "Toward complement inhibition 2.0: Next generation anticomplement agents for paroxysmal nocturnal hemoglobinuria," Am J Hematol. 93(4):564-77 (2018).
Risitano, "Anti-Complement Treatment in Paroxysmal Nocturnal Hemoglobinuria: Where we Stand and Where we are Going," Transl Med UniSa. 8:43-52 (2014).
Risitano, "Paroxysmal nocturnal hemoglobinuria in the era of complement inhibition," Am J Hematol. 91(4):359-60 (2016).
Rohrer et al., "Eliminating complement factor D reduces photoreceptor susceptibility to light-induced damage," Invest Ophthalmol Vis Sci. 48(11):5282-9 (2007).
Roth et al., "Further Improvements of the Synthesis of Alkynes from Aldehydes," Synthesis. 1:59-62 (2004).
Ruiz-Gómez et al., "Structure—Activity Relationships for Substrate-Based Inhibitors of Human Complement Factor B," J Med Chem. 52(19):6042-6052 (2009).
Salifu, "Chronic Glomerulonephritis Medication," Medscape, <https://emedicine.medscape.com/article/239392-medication>, updated Feb. 1, 2017, retrieved on May 2, 2019 (1 page).
Segers et al., "Complement Alternative Pathway Activation in Human Nonalcoholic Steatohepatitis," PLoS ONE. 9(10):e110053 (2014) (9 pages).
Sica et al., "Eculizumab treatment: stochastic occurrence of C3 binding to individual PNH erythrocytes," J Hematol Oncol. 10(1):126 (2017) (10 pages).
Simone, "Oncology: Introduction," Cecil Textbook of Medicine, 20th Edition, vol. 1, pp. 1004-1010, (1996) (8 pages).
Stanton et al., "Complement Factor D in Age-Related Macular Degeneration," Invest Ophthalmol Vis Sci. 52(12):8828-8834 (2011) (15 pages).
Steinle et al., "Impact of Baseline Characteristics on Geographic Atrophy Progression in the FILLY Trial Evaluating the Complement C3 Inhibitor Pegcetacoplan," Am J Ophthalmol. DOI: https://doi.org/10.1016/j.ajo.2021.02.031 (Journal Pre-proof version) (2021) (19 pages).
Strobel et al., "Anti-factor B autoantibody in dense deposit disease," Mol Immunol. 47:1476-1483 (2010).
Tandon et al., "Substrate specificity of human prolyl-4-hydroxylase," Bioorg Med Chem Lett. 8(10):1139-1144 (1998).
Tang et al.,"Palladium-Catalyzed Carbonylative Sonogashira Coupling of Aryl Bromides via tert-Butyl Isocyanide Insertion," J Org Chem. 78(7):3170-3175 (2013).
Wehling et al., "Monitoring of complement activation biomarkers and eculizumab in complement-mediated renal disorders," Clin Exp Immunol. 187(2):304-15 (2017).
Written Opinion for International Application No. PCT/US20/24017, mailed Jun. 26, 2020 (6 pages).
Yonemoto-Kobayashi et al., "Carboxylation of alkynylsilanes with carbon dioxide mediated by cesium fluoride in DMSO," Org Biomol Chem. 11(23):3773-5 (2013).
Yuan et al., "Small-molecule Factor D Inhibitors Selectively Block the Alternative Pathway of Complement in Paroxysmal Nocturnal Hemoglobinuria and Atypical Hemolytic Uremic Syndrome," Haematologica. 102(3):466-75 (2017).

PHARMACEUTICAL COMPOUNDS FOR THE TREATMENT OF COMPLEMENT MEDIATED DISORDERS

STATEMENT OF RELATED APPLICATIONS

This application is the U.S. National Phase Application of PCT/US2020/024017, filed Mar. 20, 2020, and claims priority to, and the benefit of, U.S. Provisional Application No. 62/822,553, filed Mar. 22, 2019, and U.S. Provisional Application No. 62/951,669, filed Dec. 20, 2019, the entire contents of which are incorporated herein by reference.

FIELD OF THE DISCLOSURE

Herein are provided pharmaceutical compounds to treat medical disorders, such as complement-mediated disorders, including complement C1-mediated disorders.

BACKGROUND OF THE DISCLOSURE

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phagocytosis of antigens), chemotaxis (attracting macrophages and neutrophils), cell lysis (rupturing membranes of foreign cells), and agglutination (clustering and binding of pathogens together).

The complement system has three pathways: classical, alternative, and lectin. The classical pathway is triggered by antibody-antigen complexes with the antibody isotypes IgG and IgM. The antibody-antigen complex binds to C1 and this initiates the cleavage of C4 and C2 to generate C3 convertase that then splits C3 into C3a and C3b. C3a interacts with its C3a receptor to recruit leukocytes, while C3b binds to C3 convertase to form C5 convertase. C5 convertase cleaves C5 into C5a and C5b. Similarly to C3a, C5a interacts with its C5a receptor to recruit leukocytes, but C5b interacts with C6, C7, C8, and C8 and together these proteins form the cylindrical membrane attack complex (MAC) that causes the cell to swell and burst. These immune responses can be inhibited by preventing C1 from being able to bind the antibody-antigen complex.

Given the range of serious diseases mediated by a disfunction of the complement system, there is a clear medical need to provide pharmaceutically acceptable compounds, methods, compositions and methods of manufacture to inhibit the complement system in a patient in need thereof.

Therefore, it is an object of the present invention to provide compounds and their uses and compositions to treat disorders arising from or amplified by a disfunction of the complement system. It is another object of the invention to provide compounds, uses, compositions, combinations and processes of manufacture that inhibit C1s (complement 1 esterase) and thus can treat disorders mediated by that enzyme.

SUMMARY

This disclosure includes a compound of Formula I, II, III, IV, V, VI, VII, VIII, IX, X, XI, XII, XIII, XIV, XV, XVI, XVII, XVIII, XIX, or XX, or a pharmaceutically acceptable salt, prodrug, isotopic analog, N-oxide, or isolated isomer thereof, optionally in a pharmaceutically acceptable composition. In one embodiment, the compound or its salt or composition, as described herein is used to treat a medical disorder which is an inflammatory or immune condition, a disorder mediated by the complement cascade (including a dysfunctional cascade), a disorder or abnormality of a cell that adversely affects the ability of the cell to engage in or respond to normal complement activity including for example, the classical complement pathway, or an undesired complement-mediated response to a medical treatment, such as surgery or other medical procedure or a pharmaceutical or biopharmaceutical drug administration, a blood transfusion, or other allogenic tissue or fluid administration.

These compounds can be used to treat medical conditions in a host in need thereof, typically a human. The active compound may act as an inhibitor of the complement classical pathway by inhibiting complement C1s. In one embodiment, a method for the treatment of a disorder mediated by complement activity is provided that includes the administration of an effective amount of a compound of Formula I, II, III, IV, V, VI, VII, VIII, IX, X, XI, XII, XIII, XIV, XV, XVI, XVII, XVIII, XIX, or XX, or a pharmaceutically acceptable salt, prodrug, isotopic analog, N-oxide, or isolated isomer thereof, optionally in a pharmaceutically acceptable composition, as described in more detail below.

In one embodiment, the disorder is associated with the complement classical pathway and the compound inhibits the classical pathway. In yet another embodiment, the disorder is associated with the alternative complement cascade pathway. In a further embodiment, the disorder is associated with the complement lectin pathway. Alternatively, the active compound or its salt or prodrug may act through a different mechanism of action than the complement cascade to treat a disorder described herein. In another embodiment, the active compound, and/or its salt or prodrug, inhibits a combination of these pathways.

In another embodiment, a method is provided for treating a host, typically a human, with a disorder mediated by the complement system, that includes administration of a prophylactic antibiotic or vaccine to reduce the possibility of a bacterial infection during the treatment using one of the compounds described herein. In certain embodiments, the host, typically a human, is given a prophylactic vaccine prior to, during or after treatment with one of the compounds described herein. In certain embodiments, the host, typically a human, is given a prophylactic antibiotic prior to, during or after treatment with one of the compounds described herein. In some embodiments, the infection is a meningococcal infection (e.g., septicemia and/or meningitis), an *Aspergillus* infection, or an infection due to an encapsulated organism, for example, *Streptococcus pneumoniae* or *Haemophilus influenza* type b (Hib), especially in children. In other embodiments, the vaccine or antibiotic is administered to the patient after contracting an infection due to, or concommitant with, inhibition of the complement system.

In one aspect of the present disclosure, a compound of Formula I, II, III, IV, V, VI, VII, VIII, or IX is provided:

(I)
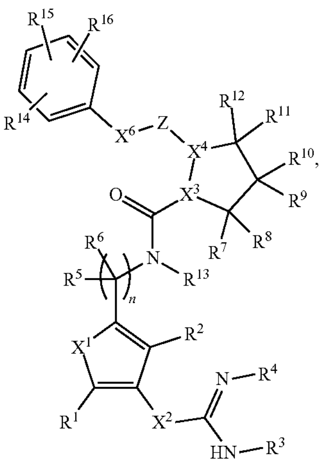
(II)
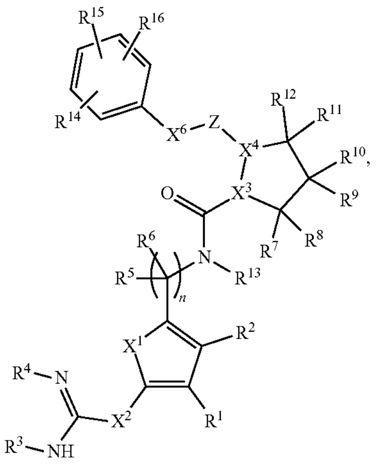
(III)
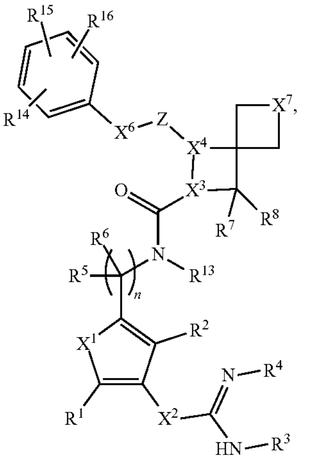
-continued
(IV)
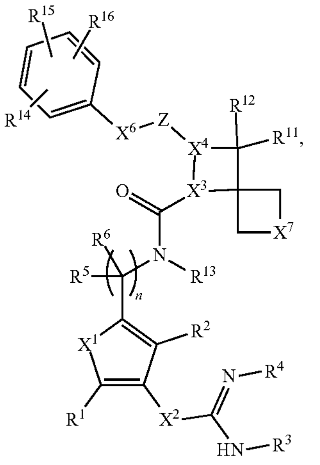
(V)
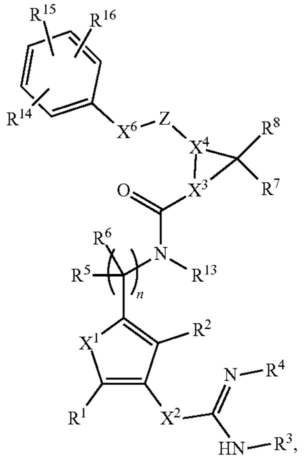
(VI)
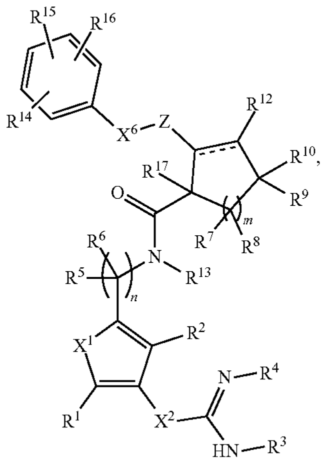

-continued (VII)

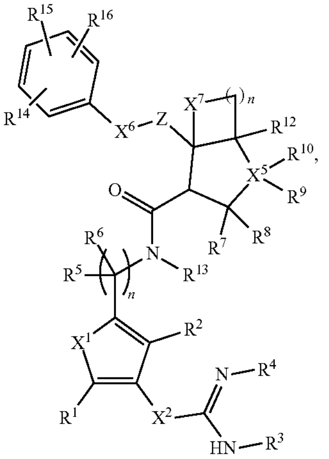

(VIII)

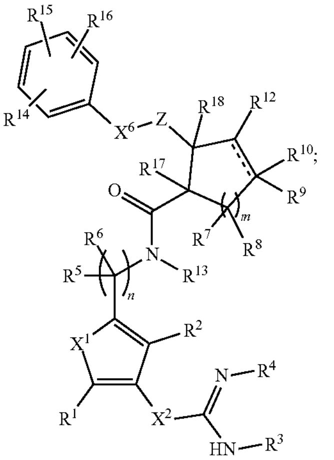

or (IX)

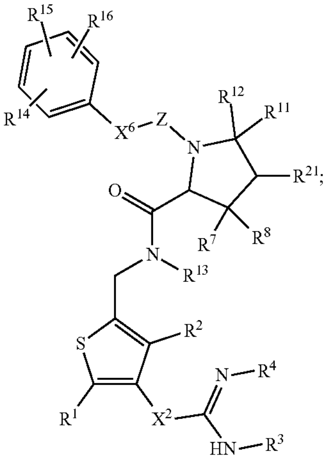

or a pharmaceutically acceptable salt, isotopic analog, prodrug, or isolated isomer thereof optionally in pharmaceutically acceptable carrier;

wherein:

each n is independently 1, 2, or 3;

each m is independently 0, 1, 2, or 3;

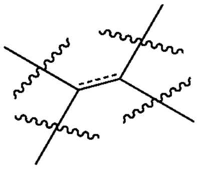

is either a single or a double bond;

Z is $CH_2$, $C(CH_2)$, or C(O);

$X^1$ is selected from S, O, and $N(R^{30})$;

$X^2$ is selected from bond, $N(R^{30})$, and —O—$N(R^{30})$—;

$X^3$ is selected from N and $C(R^{17})$;

$X^4$ is selected from N and $C(R^{18})$;

wherein only one of $X^3$ and $X^4$ can be N;

$X^5$ is C or Si;

$X^6$ is selected from

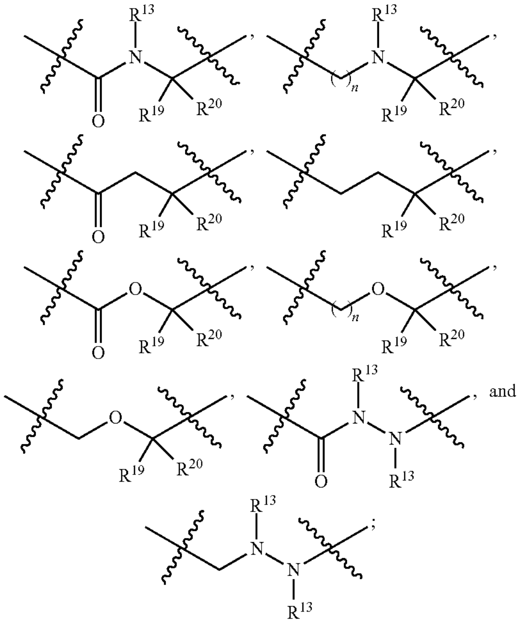

and $X^7$ is selected from O, S, $N(R^{30})$, and $CR^5R^6$;

$R^1$ and $R^2$ are independently selected from hydrogen, halogen, $C_1$-$C_6$ alkyl, $C_2$-$C_6$ alkenyl, $C_2$-$C_6$ alkynyl, $C_1$-$C_6$ haloalkyl, —$OR^{30}$, —$SR^{30}$, —$N(R^{30})_2$, —C(O)$R^{31}$, —S(O)$R^{31}$, —$S(O)_2R^{31}$, heterocycle, aryl, heteroaryl, cyano, and nitro; each of which $R^1$ and $R^2$ groups other than hydrogen, halogen, cyano, and nitro are optionally substituted with 1, 2, 3, or 4 substituents independently selected from $C_1$-$C_6$ alkyl, $C_2$-$C_6$ alkenyl, $C_2$-$C_6$ alkynyl, halogen, $C_1$-$C_6$ haloalkyl, —$OR^{30}$, —$SR^{30}$, —$N(R^{30})_2$, —C(O)$R^{31}$, —S(O)$R^{31}$, —$S(O)_2R^{31}$, heterocycle, aryl, heteroaryl, cyano, and nitro;

$R^3$ and $R^4$ are independently selected from hydrogen, C(O)$R^{31}$, —$SR^{30}$, and —$OR^{30}$;

or $R^3$ and $R^4$ are independently selected from hydrogen, CN, C(O)$R^{31}$, —$SR^{30}$, and —$OR^{30}$;

or $R^3$ and $R^4$ are instead combined to form an oxadiazole optionally substituted with 1, 2, or 3 substituents independently selected from $C_1$-$C_6$ alkyl, $C_1$-$C_6$ haloalkyl, —$OR^{30}$, and oxo, for example in this embodiment

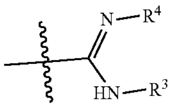

can be

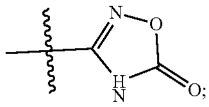 [SMILES: *c1noc(=O)[nH]1];

each $R^5$ and $R^6$ are independently selected from hydrogen, halogen, $C_1$-$C_6$ alkyl, $C_1$-$C_6$ haloalkyl, —$OR^{30}$, and —$N(R^{30})_2$, wherein when on carbons adjacent to each other a $R^5$ and a $R^6$ group may optionally be replaced by a carbon-carbon double bond, for example,

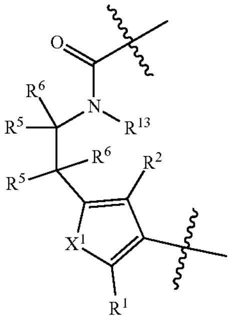

optionally includes

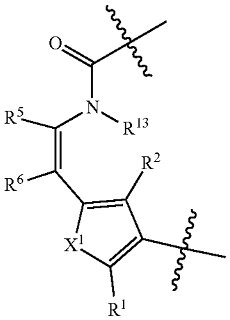

and

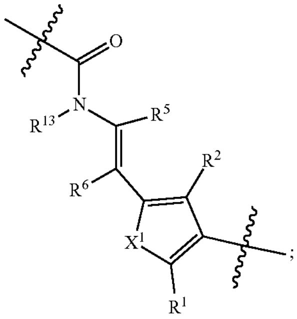;

$R^7$, $R^8$, $R^9$, $R^{10}$, $R^{11}$, and $R^{12}$ are independently selected from hydrogen, halogen, $C_1$-$C_6$ alkyl, $C_2$-$C_6$ alkenyl, $C_2$-$C_6$ alkynyl, $C_1$-$C_6$ haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, and heteroaryl, each of which $R^7$, $R^8$, $R^9$, $R^{10}$, $R^{11}$, and $R^{12}$ groups other than hydrogen and halogen are optionally substituted with 1, 2, 3, or 4 substituents independently selected from $C_1$-$C_6$ alkyl, $C_2$-$C_6$ alkenyl, $C_2$-$C_6$ alkynyl, halogen, $C_1$-$C_6$ haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

or $R^7$ and $R^8$ may be taken together with the carbon to which they are attached to form a 3- to 6-membered carbocyclic spiro ring or a 4- to 6-membered heterocyclic spiro ring containing 1 or 2 heteroatoms independently chosen from N, O, and S;

or $R^7$ and $R^8$ may be taken together with the carbon to which they are attached to form

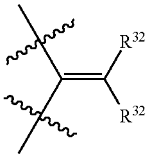

or carbonyl;

or $R^9$ and $R^{10}$ may be taken together with the atom to which they are attached to form a 3- to 6-membered carbocyclic spiro ring or a 4- to 6-membered heterocyclic spiro ring containing 1 or 2 heteroatoms independently chosen from N, O, and S;

or $R^9$ and $R^{10}$ may be taken together with the atom to which they are attached to form

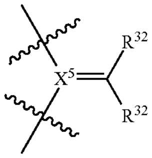

or carbonyl;

or $R^{11}$ and $R^{12}$ may be taken together with the carbon to which they are attached to form a 3- to 6-membered carbocyclic spiro ring or a 4- to 6-membered heterocyclic spiro ring containing 1 or 2 heteroatoms independently chosen from N, O, and S;

or $R^{11}$ and $R^{12}$ may be taken together with the carbon to which they are attached to form

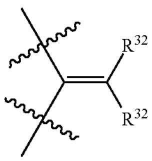

or carbonyl;

or $R^7$ and $R^9$ are taken together with the atoms to which they are attached to form a 3- to 8-membered carbocycle or a 4- to 8-membered heterocycle containing 1 or 2 heteroatoms independently chosen from N, O, and S;

or $R^9$ and $R^{11}$ are taken together with the atoms to which they are attached to form a 3- to 8-membered carbocycle or a 4- to 8-membered heterocycle containing 1 or 2 heteroatoms independently chosen from N, O, and S;

or $R^7$ and $R^{11}$ are taken together with the atoms to which they are attached to form a 1 or 2 carbon bridge, for example

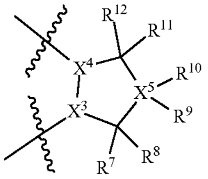

can optionally be

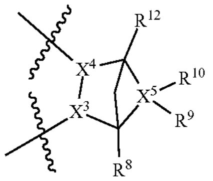 or 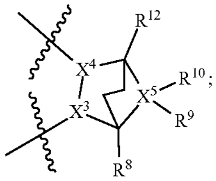;

each $R^{13}$ is independently selected from hydrogen or $C_1$-$C_6$ alkyl;

$R^{14}$, $R^{15}$, and $R^{16}$ are independently selected from hydrogen, halogen, $C_1$-$C_6$ alkyl, $C_2$-$C_6$ alkenyl, $C_2$-$C_6$ alkynyl, $C_1$-$C_6$ haloalkyl, —$C_1$-$C_6$ alkyl-aryl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro each of which $R^{14}$, $R^{15}$, and $R^{16}$ groups other than hydrogen, halogen, cyano, and nitro are optionally substituted with 1, 2, 3, or 4 substituents independently selected from $C_1$-$C_6$alkyl, $C_2$-$C_6$ alkenyl, $C_2$-$C_6$ alkynyl, halogen, $C_1$-$C_6$ haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

or $R^{14}$, $R^{15}$, and $R^{16}$ are independently selected from hydrogen, halogen, $SF_5$, $C_1$-$C_6$ alkyl, $C_2$-$C_6$ alkenyl, $C_2$-$C_6$ alkynyl, $C_1$-$C_6$ haloalkyl, —$C_1$-$C_6$ alkyl-aryl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro each of which $R^{14}$, $R^{15}$, and $R^{16}$ groups other than hydrogen, halogen, cyano, and nitro are optionally substituted with 1, 2, 3, or 4 substituents independently selected from $SF_5$, $C_1$-$C_6$ alkyl, $C_2$-$C_6$ alkenyl, $C_2$-$C_6$ alkynyl, halogen, $C_1$-$C_6$ haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

$R^{17}$ and $R^{18}$ are independently selected from hydrogen, halogen, $C_1$-$C_6$ alkyl, $C_1$-$C_6$ haloalkyl, —$OR^{30}$, and —$N(R^{30})_2$;

or $R^{17}$ and $R^{18}$ are taken together with the carbons to which they are attached to form a double bond;

$R^{19}$ and $R^{20}$ are independently selected from hydrogen, $C_1$-$C_6$alkyl, $C_5$-$C_{10}$ bicyclic carbocycle, $C_4$-$C_6$ heterocycle, halogen, $C_1$-$C_6$ haloalkyl, —$OR^{30}$, —$N(R^{30})_2$, —$(CH_2)_n$—$R^{33}$, and

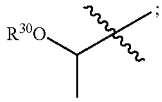;

$R^{21}$ is selected from $C_1$-$C_6$ alkyl and —O—$C_1$-$C_6$ alkyl;

or $R^{21}$ is selected from $C_1$-$C_6$ haloalkyl, —O—$C_1$-$C_6$ haloalkyl, $C_1$-$C_6$ alkyl, —O—$C_1$-$C_6$ alkyl, aryl, —O-aryl, heteroaryl, or —O-heteroaryl, each of which $R^{21}$ group is optionally substituted with 1, 2, 3, or 4 substituents independently selected from $SF_5$, $C_1$-$C_6$ alkyl, $C_2$-$C_6$ alkenyl, $C_2$-$C_6$ alkynyl, halogen, $C_1$-$C_6$ haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

each $R^{30}$ is independently selected from hydrogen, $C_1$-$C_6$ alkyl, $C_1$-$C_6$ haloalkyl, aryl, heteroaryl, heterocycle, and $C(O)R^{31}$;

each $R^{31}$ is independently selected from hydrogen, $C_1$-$C_6$ alkyl, $C_1$-$C_6$ haloalkyl, —$OR^{32}$, —$SR^{32}$, —$N(R^{32})_2$, heterocycle, aryl, and heteroaryl;

each $R^{32}$ is independently selected from hydrogen, $C_1$-$C_6$ alkyl, and $C_1$-$C_6$ haloalkyl;

each $R^{33}$ is independently selected from hydrogen, guanidine, heteroaryl, aryl, —$C_6H_5$—$OR^{30}$; —$OR^{30}$, —$SR^{30}$, —$SeR^{30}$, —$N(R^{30})_2$, and —$C(O)R^{31}$, wherein for compounds of Formula I and Formula II at least one of the following is satisfied:

a. $X^3$ is $C(R^{17})$ and $X^4$ is $C(R^{18})$;

b. $R^{17}$ is selected from halogen, $C_1$-$C_6$ alkyl, $C_1$-$C_6$ haloalkyl, —$OR^{30}$, and —$N(R^{30})_2$;

c. $X^5$ is Si;

d. Z is $C(CH_2)$;

e. Z is $CH_2$;

f. $R^7$ and $R^8$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

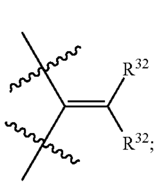;

or a carbonyl;

g. $R^9$ and $R^{10}$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

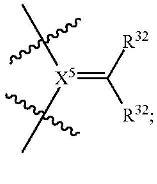;

or a carbonyl;

h. $R^{11}$ and $R^{12}$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

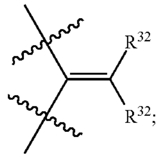

or a carbonyl;

i. $R^7$ and $R^9$ are taken together with the atoms to which they are attached to form a 3- to 8-membered carbocycle or a 4- to 8-membered heterocycle containing 1 or 2 heteroatoms independently chosen from N, O, and S; and $R^{10}$ or $R^{12}$ is not hydrogen;

j. $R^9$ and $R^{11}$ are taken together with the atoms to which they are attached to form a 3- to 8-membered carbocycle or a 4- to 8-membered heterocycle containing 1 or 2 heteroatoms independently chosen from N, O, and S; and $R^9$ or $R^{10}$ is not hydrogen;

k. $R^7$ and $R^{11}$ are taken together with the atoms to which they are attached to form a 1 or 2 carbon bridge;

l. $X^6$ is selected from

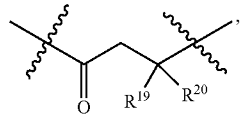,
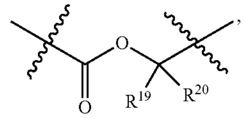,
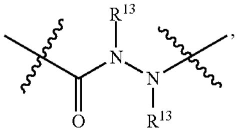, and
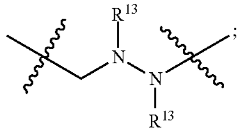;

m. at least one of $R^3$ and $R^4$ is CN, —$SR^{30}$ or $C(O)R^{31}$; or n. $R^3$ and $R^4$ are combined to form an oxadiazole optionally substituted with 1, 2, or 3 substituents independently selected from $C_1$-$C_6$ alkyl, $C_1$-$C_6$ haloalkyl, —$OR^{30}$, and oxo.

In one embodiment, the compound of Formula IX is:

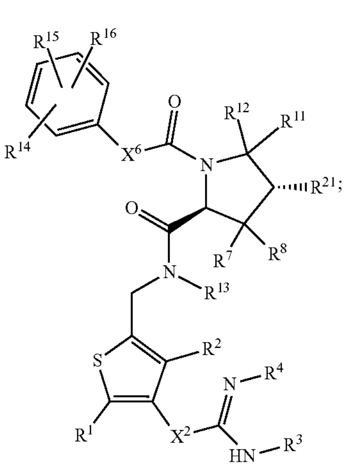

or a pharmaceutically acceptable salt thereof.

In another embodiment, the compound of Formula IX is:

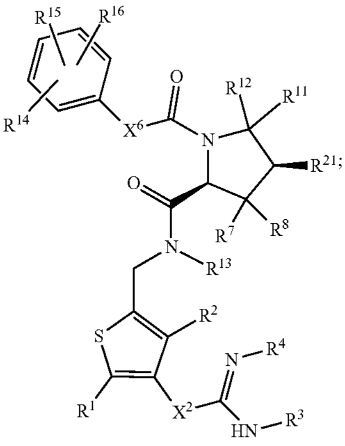

or a pharmaceutically acceptable salt thereof.

In an alternative embodiment, the compound of Formula IX is

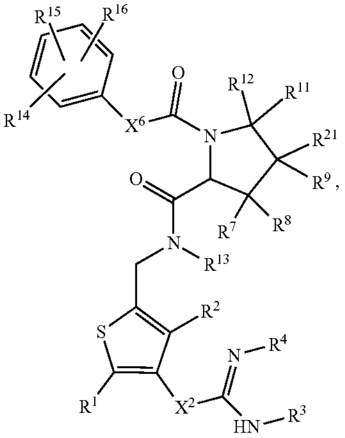

or

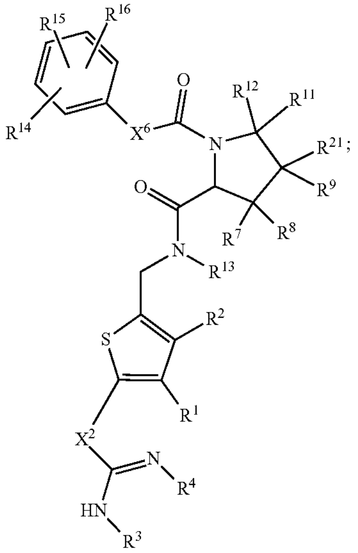

or a pharmaceutically acceptable salt thereof.

In another aspect, the compound of the present disclosure is of Formula X, XI, or XII:

(X)

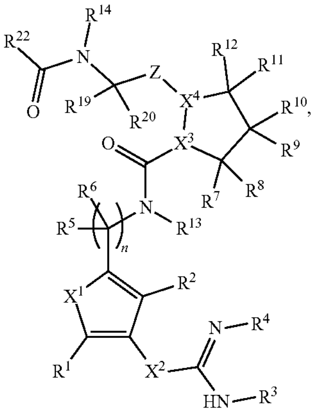

(XI)

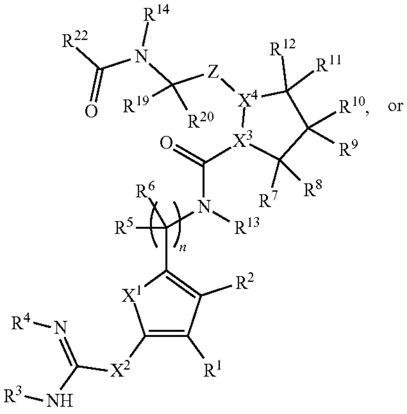

or (XII)

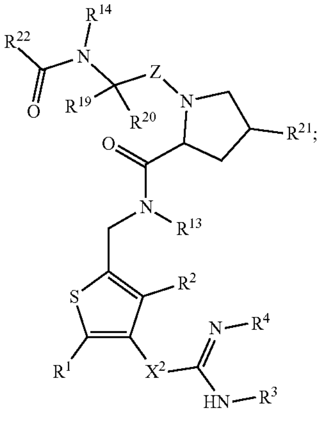

or a pharmaceutically acceptable salt, isotopic analog, prodrug, or isolated isomer thereof optionally in pharmaceutically acceptable carrier;

wherein:

$R^{22}$ is selected from —$C_1$-$C_6$ alkyl-$R^{23}$, —$C_2$-$C_6$ alkenyl-$R^{23}$, —$C_2$-$C_6$ alkynyl-$R^{23}$ and bicyclic cycloalkyl-$R^{23}$, each of which $R^{22}$ is optionally substituted with 1, 2, 3, or 4 substituents independently selected from $C_1$-$C_6$ alkyl, $C_2$-$C_6$ alkenyl, $C_2$-$C_6$ alkynyl, halogen, $C_1$-$C_6$ haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

$R^{23}$ is selected from hydrogen, sugar, —$OR^{30}$, —$SR^{30}$, —$N(R^{30})_2$, —$C(O)R^{31}$, —$S(O)R^{31}$, and —$S(O)_2R^{31}$; and all other variables are as defined herein;

wherein for compounds of Formula X and Formula XI at least one of the following is satisfied:

a. $X^3$ is $C(R^{17})$ and $X^4$ is $C(R^{18})$;

b. $R^{17}$ is selected from halogen, $C_1$-$C_6$ alkyl, $C_1$-$C_6$ haloalkyl, —$OR^{30}$, and —$N(R^{30})_2$;

c. $X^5$ is Si;

d. Z is $C(CH_2)$;

e. Z is $CH_2$;

f. $R^7$ and $R^8$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

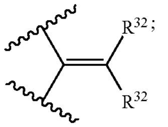

or a carbonyl;

g. $R^9$ and $R^{10}$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

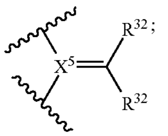

or a carbonyl;

h. $R^9$ and $R^{11}$ are taken together with the atoms to which they are attached to form a 3- to 8-membered carbocycle or a 4- to 8-membered heterocycle containing 1 or 2 heteroatoms independently chosen from N, O, and S; and $R^{10}$ is not hydrogen;

i. $R^{11}$ and $R^{12}$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

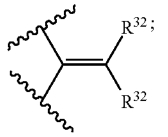

or a carbonyl;

j. $R^7$ and $R^9$ are taken together with the atoms to which they are attached to form a 3- to 8-membered carbocycle or a 4- to 8-membered heterocycle containing 1 or 2 heteroatoms independently chosen from N, O, and S; and $R^{10}$ is not hydrogen;

k. $R^7$ and $R^{11}$ are taken together with the atoms to which they are attached to form a 1 or 2 carbon bridge;

l. $R^{22}$ is substituted with at least three $OR^{30}$ groups;

m. $R^{23}$ is a sugar;

n. at least one of $R^3$ and $R^4$ is CN, —$SR^{30}$, or $C(O)R^{31}$; or o. $R^3$ and $R^4$ are combined to form an oxadiazole optionally substituted with 1, 2, or 3 substituents independently selected from $C_1$-$C_6$ alkyl, $C_1$-$C_6$ haloalkyl, —$OR^{30}$, and oxo.

In one embodiment $R^{23}$ is selected from hydrogen, —$OR^{30}$, —$SR^{30}$, —$N(R^{30})_2$, —$C(O)R^{31}$, —$S(O)R^{31}$, and —$S(O)_2R^{31}$.

In one embodiment, the compound of Formula X is selected from:

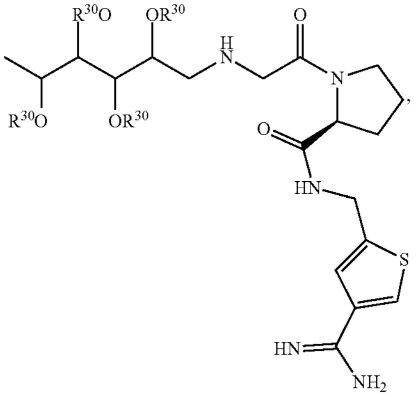

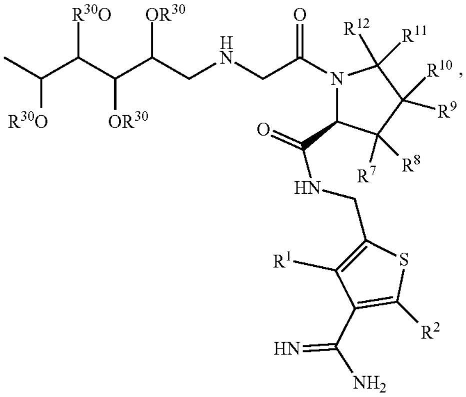

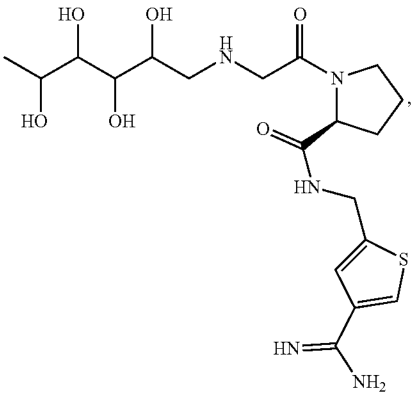

-continued

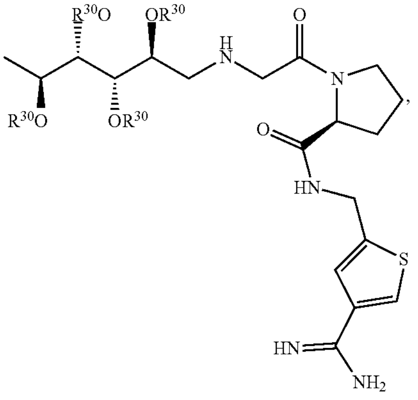

and

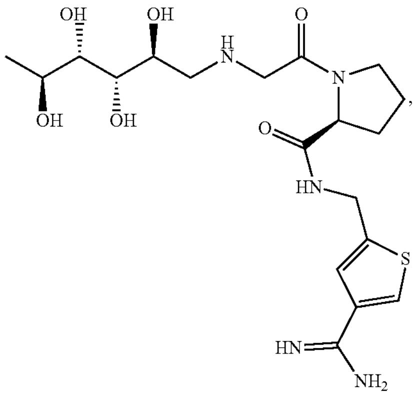

In one embodiment, $R^{23}$ is selected from —$OR^{30}$, —$SR^{30}$, —$N(R^{30})_2$, —$C(O)R^{31}$, —$S(O)R^{31}$, and —$S(O)_2R^{31}$.

In another aspect, the compound of Formula X, XI, or XII is selected from (X)

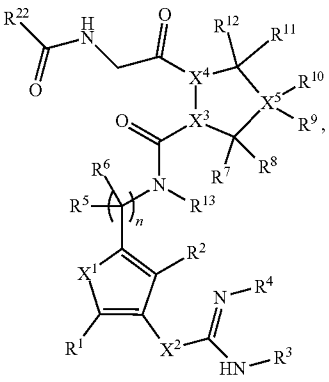

-continued (XI)

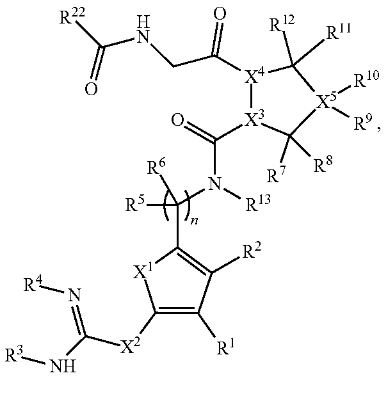

(XIIa)

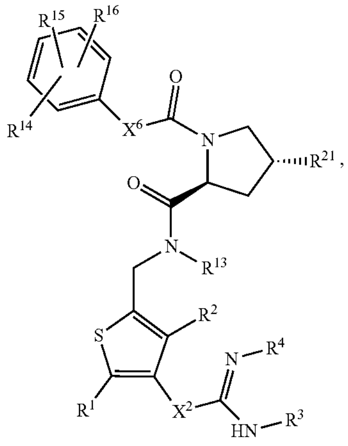

and (XIIb)

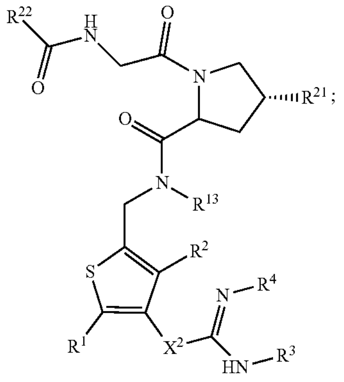

or a pharmaceutically acceptable salt, isotopic analog, prodrug, or isolated isomer thereof optionally in pharmaceutically acceptable carrier.

In an alternative embodiment, the compound of Formula XII is

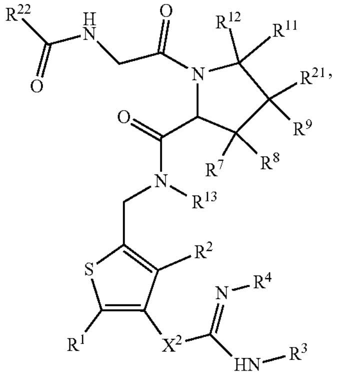

or

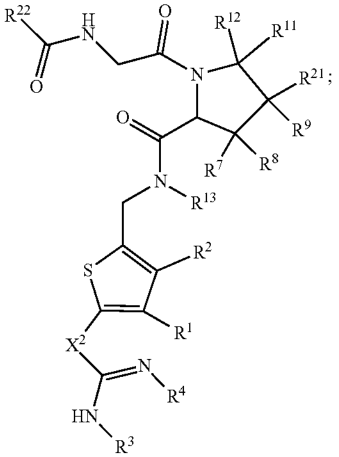

or a pharmaceutically acceptable salt thereof.

In another aspect, the compound of the present disclosure is of Formula XIII:

(XIII)

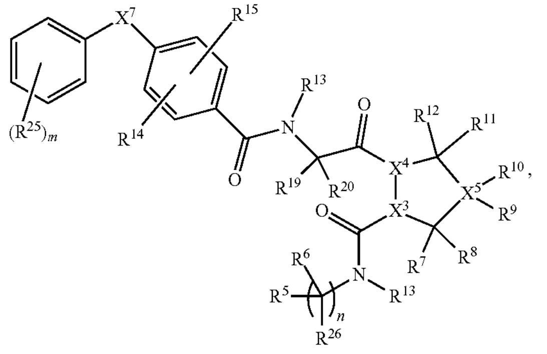

or a pharmaceutically acceptable salt, isotopic analog, prodrug, or isolated isomer thereof optionally in pharmaceutically acceptable carrier;

wherein:

$X^7$ is selected from O, S, $N(R^{30})$, and $CR^5R^6$;

o is 0, 1, or 2;

each $R^{25}$ is independently selected from hydrogen, halogen, $C_1$-$C_6$ alkyl, $C_2$-$C_6$ alkenyl, $C_2$-$C_6$ alkynyl, $C_1$-$C_6$ haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro; each of which $R^{25}$ groups other than hydrogen, halogen, cyano, and nitro are optionally substituted with 1, 2, 3, or 4 substituents independently selected from $C_1$-$C_6$ alkyl, $C_2$-$C_6$ alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro; or each $R^{25}$ is independently selected from hydrogen, $SF_5$, halogen, $C_1$-$C_6$ alkyl, $C_2$-$C_6$ alkenyl, $C_2$-$C_6$ alkynyl, $C_1$-$C_6$ haloalkyl, —$OR^{30}$, —$SR^{30}$, —$N(R^{30})_2$, —C(O) $R^{31}$, —$S(O)R^{31}$, —$S(O)_2R^{31}$, heterocycle, aryl, heteroaryl, cyano, and nitro; each of which $R^{25}$ groups other than hydrogen, halogen, cyano, and nitro are optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

$R^{26}$ is selected from

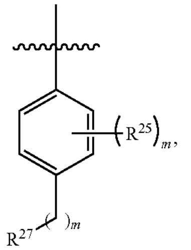
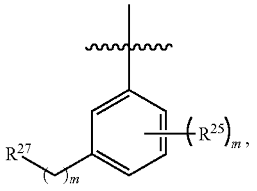
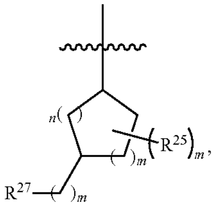
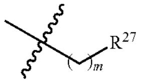
,
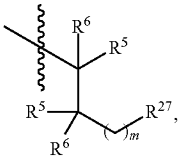
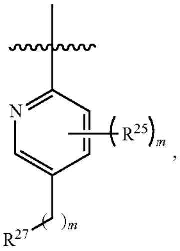
,
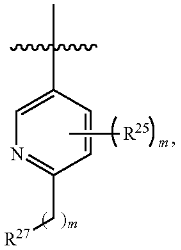
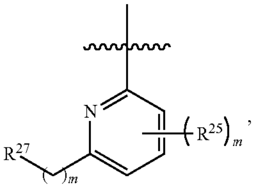
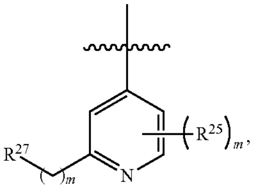
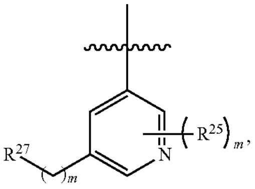

-continued

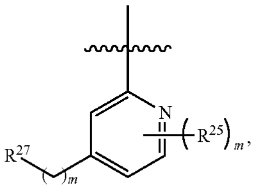
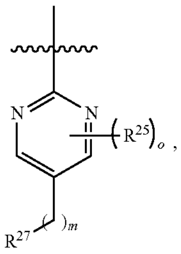
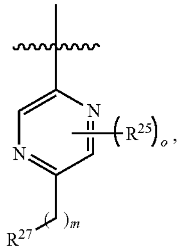
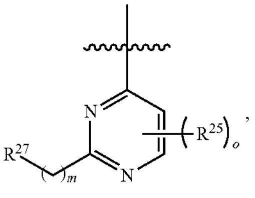
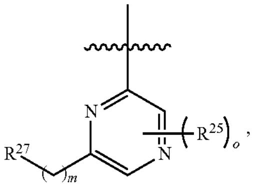
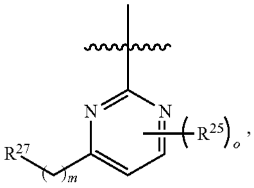
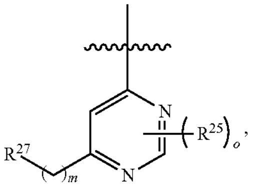
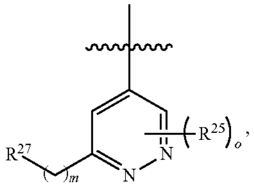
and
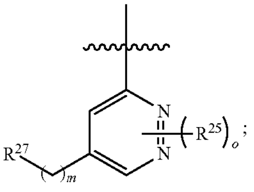

or $R^{26}$ is selected from

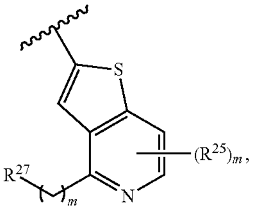
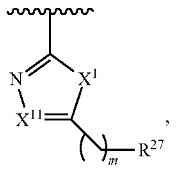
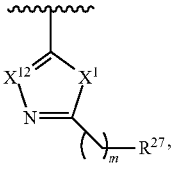
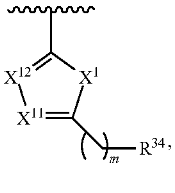
and

-continued

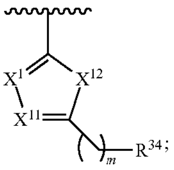

$R^{27}$ is selected from

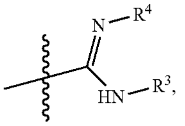

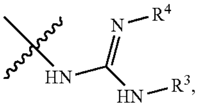

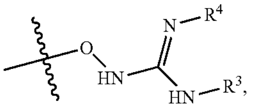

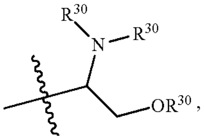

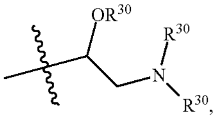

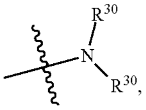

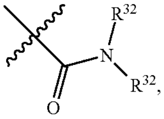

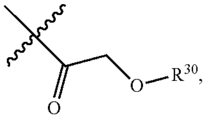

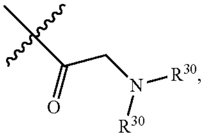

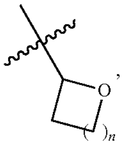

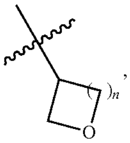

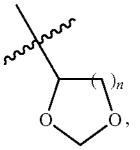

and

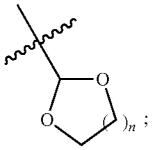

or $R^{27}$ is

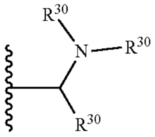

or

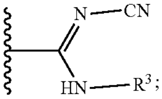

$R^{34}$ is selected from

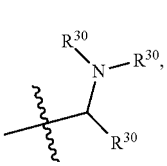

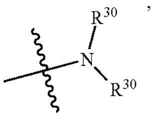

-continued

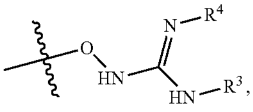

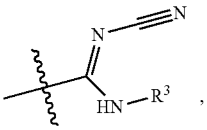

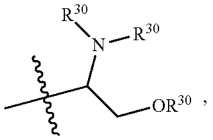

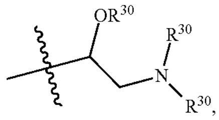

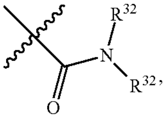

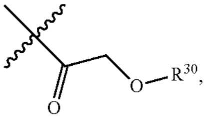

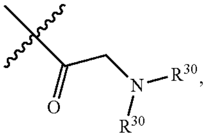

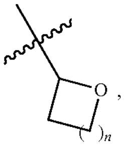

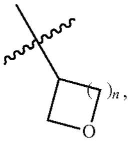

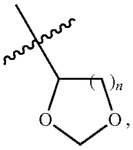

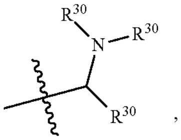

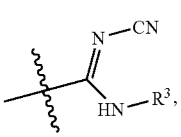

and

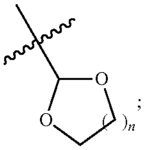

$X^{11}$ is selected from N and $CR^1$;

$X^{12}$ is selected from N and $CR^2$;

wherein each other variable is as defined herein.

In another aspect, the compound of the present disclosure is of Formula XIV:

(XIV)

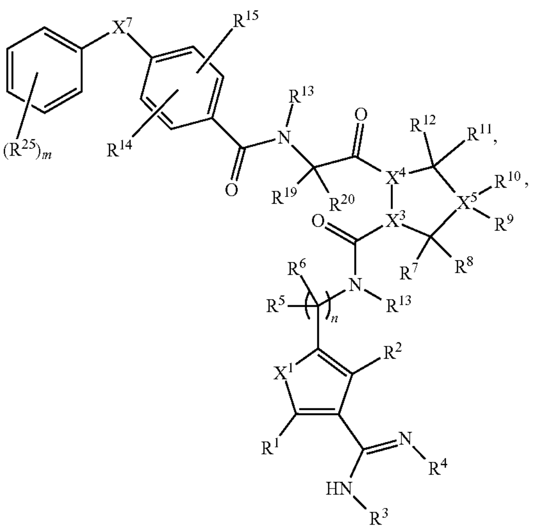

or a pharmaceutically acceptable salt, isotopic analog, prodrug, or isolated isomer thereof optionally in pharmaceutically acceptable carrier;

wherein the variables are as defined herein and for compounds of Formula XIV at least one of the following is satisfied:

a. $X^1$ is O or $N(R^{30})$;

b. $R^{14}$ is not hydrogen;

c. $R^1$ is not hydrogen;

d. $R^2$ is not hydrogen;

e. $R^3$ is not hydrogen; or f. $R^4$ is not hydrogen.

In another aspect the compound of Formula XIII or XIV is selected from

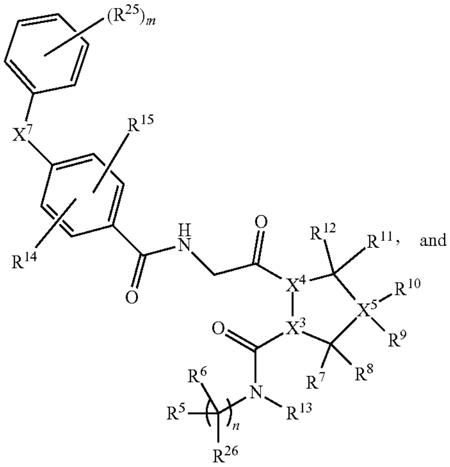

and

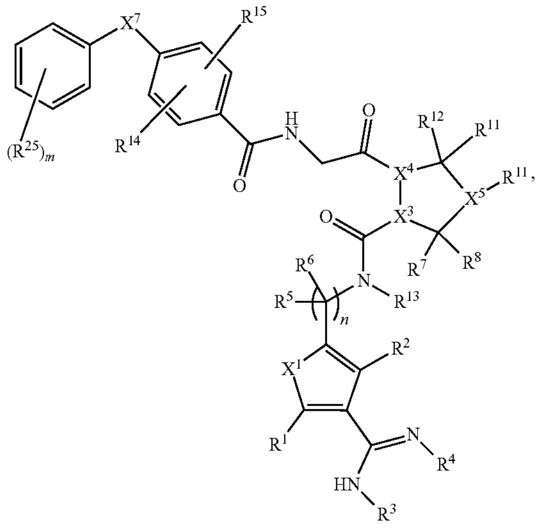

or a pharmaceutically acceptable salt, isotopic analog, prodrug, or isolated isomer thereof optionally in pharmaceutically acceptable carrier.

In another aspect, the compound of the present disclosure is of Formula XV:

(XV)

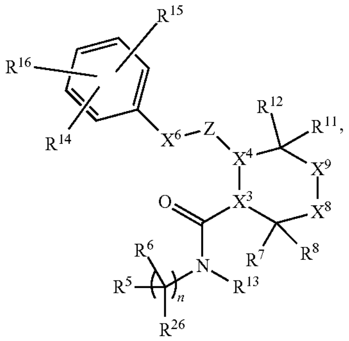

or a pharmaceutically acceptable salt, isotopic analog, prodrug, or isolated isomer thereof optionally in pharmaceutically acceptable carrier;

wherein:

each $X^8$ and $X^9$ is independently selected from O, S, $NR^{30}$, $CR^9R^{10}$, $CR^5R^6$, and $CH_2$; wherein $X^8$ and $X^9$ cannot both be the same group; and all other variables are as defined herein.

In an alternative embodiment

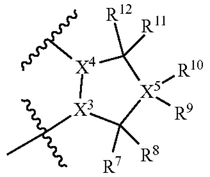

is replaced with

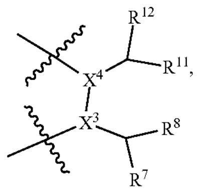

for example in this embodiment the compound of formula

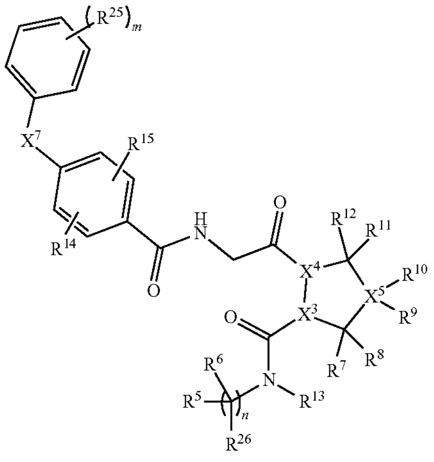

can be replaced with

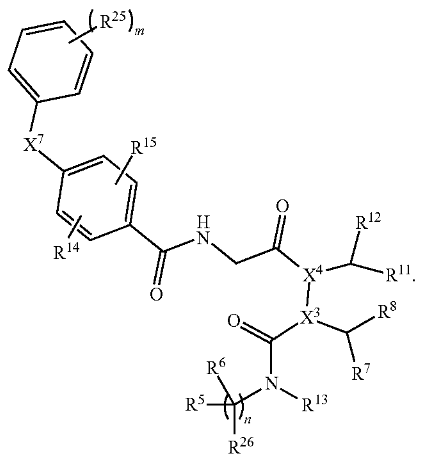

In another aspect, the compound of the present disclosure is of Formula XVI, XVII, or XVIII:

(XVI)

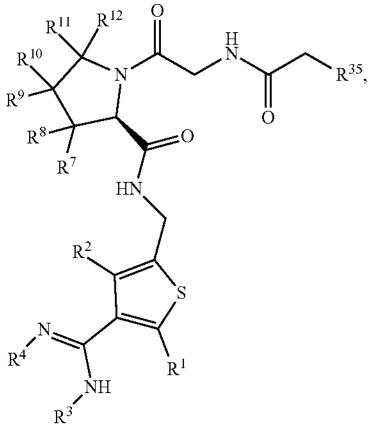

(XVII)

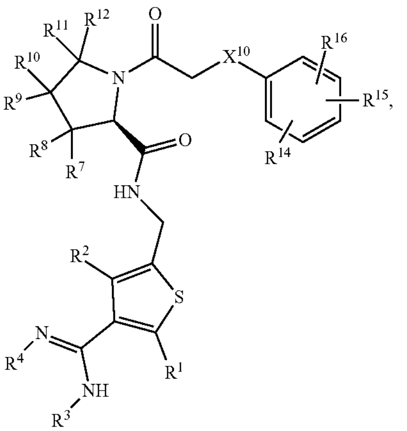

-continued (XVIII)

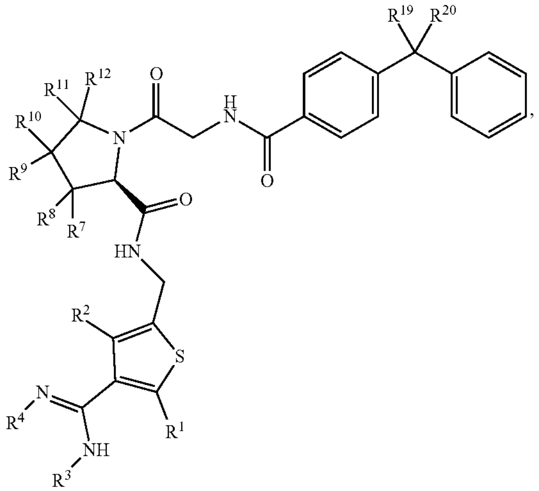

or a pharmaceutically acceptable salt, isotopic analog, prodrug, or isolated isomer thereof optionally in pharmaceutically acceptable carrier;

wherein:

$X^{10}$ is selected from

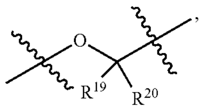
,
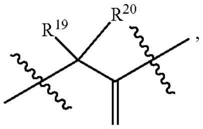
,
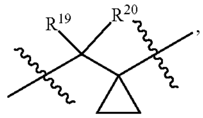
,
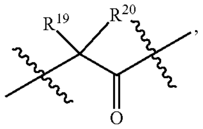
,
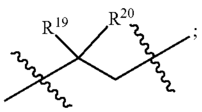
;

$R^{35}$ is selected from $C_3$-$C_{10}$alkyl or $C_3$-$C_{10}$haloalkyl; and all other variables are as defined herein.

In another aspect, the compound of the present disclosure is of Formula XIX or Formula XX:

(XIX)

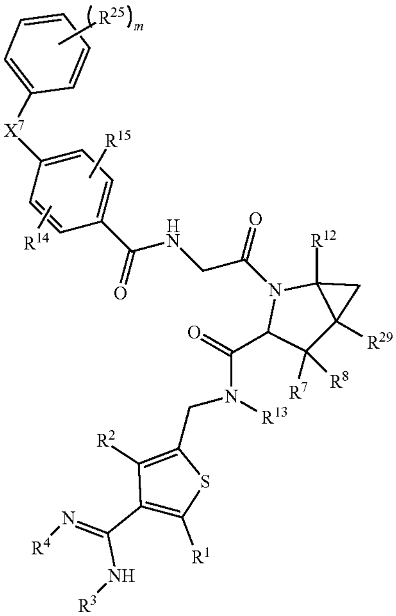

and (XX)

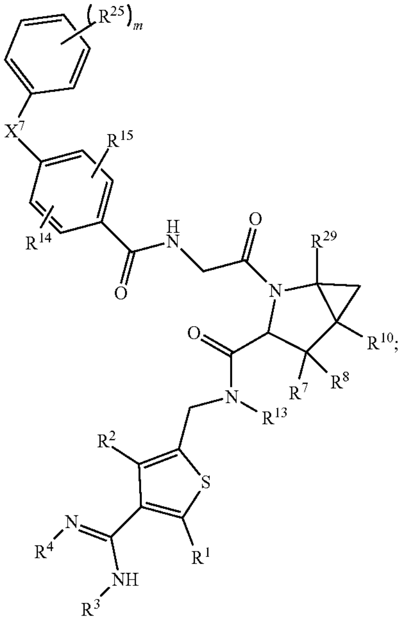

or a pharmaceutically acceptable salt, isotopic analog, prodrug, or isolated isomer thereof optionally in pharmaceutically acceptable carrier;

wherein:

$R^{29}$ is selected from halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, and heteroaryl, each of which $R^{29}$ groups other than hydrogen and halogen are optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro; and all other variables are as defined herein.

In an alternative embodiment $R^{29}$ is hydrogen.

Pharmaceutical compositions comprising a compound or salt of Formula I, II, III, IV, V, VI, VII, VIII, IX, X, XI, XII, XIII, XIV, XV, XVI, XVII, XVIII, XIX, or XX, together with a pharmaceutically acceptable carrier are also disclosed.

The present disclosure thus includes at least the following features:

a. a compound of the present disclosure or a pharmaceutically acceptable salt, prodrug, isotopic analog, N-oxide, or isolated isomer thereof, optionally in a pharmaceutically acceptable composition;

b. a compound of the present disclosure or a pharmaceutically acceptable salt, prodrug, isotopic analog, N-oxide, or isolated isomer thereof, optionally in a pharmaceutically acceptable composition, for use in treating or preventing a disorder including but not limited to the development of fatty liver and conditions stemming from fatty liver, such as nonalcoholic steatohepatitis (NASH), liver inflammation, cirrhosis, liver failure; dermatomyositis; amyotrophic lateral sclerosis; cytokine or inflammatory reactions in response to biotherapeutics (e.g. CAR T-cell therapy); hereditary angioedema (HAE), chronic immune thrombocytopenia (ITP), cold agglutinin disease, cold agglutinin syndrome, warm autoimmune hemolytic anemia, cryoglobulinemia, bullous pemphigoid, common variable immunodeficiency, endotoxemia, sepsis, multiple organ dysfunction syndrome, hemolytic uremic syndrome (HUS), atypical hemolytic uremic syndrome (aHUS), acute kidney injury, kidney transplantation, graft rejection, antibody-mediated rejection, delayed graft function, end-stage renal disease, myasthenia gravis, systemic lupus erythema (SLE), paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease; a disorder of the central nervous system or peripheral nervous system, ischaemic-reperfusion injury or stroke, traumatic brain injury (TBI) and spinal cord injury (SCI), Alzheimers diseases (AD), multiple sclerosis, neuromyelitis optica (NMO), amyotrophic lateral sclerosis (ALS), Parkinson's disease (PD), Huntington's disease (HD), demyelinating myelinoclastic diseases, demyelinating leukostrophic diseases, and neurological inflammatory disorders;

c. a pharmaceutically acceptable composition of a compound of the present disclosure or its pharmaceutically acceptable salt, prodrug, isotopic analog, N-oxide, or isolated isomer thereof in a pharmaceutically acceptable carrier;

d. a compound of the present disclosure or a pharmaceutically acceptable salt, prodrug, isotopic analog, N-oxide, or isolated isomer thereof, optionally in a pharmaceutically acceptable composition, for use in treating or preventing a disorder mediated by the complement pathway, and for example, the classical complement pathway;

e. use of a compound of the present disclosure as described herein, or a pharmaceutically acceptable salt, prodrug, isotopic analog, N-oxide, or isolated isomer thereof, optionally in a pharmaceutically acceptable composition, in the manufacture of a medicament for treating or preventing a disorder, including but not limited to the development of fatty liver and conditions stemming from fatty liver, such as nonalcoholic steatohepatitis (NASH), liver inflammation, cirrhosis, liver failure; dermatomyositis; amyotrophic lateral sclerosis; cytokine or inflammatory reactions in response to biotherapeutics (e.g. CAR T-cell therapy); hereditary angioedema (HAE), chronic immune thrombocytopenia (ITP), cold agglutinin disease, cold agglutinin syndrome, warm autoimmune hemolytic anemia, cryoglobulinemia, bullous pemphigoid, common variable immunodeficiency, endotoxemia, sepsis, multiple organ dysfunction syndrome, hemolytic uremic syndrome (HUS), atypical hemolytic uremic syndrome (aHUS), acute kidney injury, kidney transplantation, graft rejection, antibody-mediated rejection, delayed graft function, end-stage renal disease, myasthenia gravis, systemic lupus erythema (SLE), paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease; a disorder of the central nervous system or peripheral nervous system, ischaemic-reperfusion injury or stroke, traumatic brain injury (TBI) and spinal cord injury (SCI), Alzheimers diseases (AD), multiple sclerosis, neuromyelitis optica (NMO), amyotrophic lateral sclerosis (ALS), Parkinson's disease (PD), Huntington's disease (HD), demyelinating myelinoclastic diseases, demyelinating leukostrophic diseases, and neurological inflammatory disorders;

f. a process for manufacturing a medicament intended for the therapeutic use for treating or preventing a disorder, or generally for treating or preventing disorders mediated by the classical complement pathway, characterized in that a compound of the present disclosure or an embodiment of the active compound is used in the manufacture;

g. a compound of the present disclosure or a salt thereof as described herein in substantially pure form (e.g., at least 90 or 95%);

h. a compound of the present disclosure as described herein, or a pharmaceutically acceptable salt, prodrug, isotopic analog, N-oxide, or isolated isomer thereof, optionally in a carrier to form a pharmaceutically acceptable composition, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

i. For each of (a) through (h) above, and otherwise herein, each assembly of moieties and each active compound made therefrom or its use is considered and deemed specifically and individually disclosed, as such depiction is for convenience of space only and not intended to describe a only a genus or even a subgenus for such indication.

DETAILED DESCRIPTION

Terminology

Compounds are described using standard nomenclature. Unless defined otherwise, all technical and scientific terms used herein have the same meaning as is commonly understood by one of skill in the art to which the claimed invention belongs.

The compounds in any of the Formulas described herein include enantiomers, mixtures of enantiomers, diastereomers, tautomers, racemates and other isomers, such as rotamers, as if each is specifically described, unless otherwise indicated or otherwise excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely as a better illustration, and does not pose a limitation on the scope of the claimed invention, unless otherwise claimed.

The present disclosure includes compounds of Formula I, II, III, IV, V, VI, VII, VIII, IX, X, XI, XII, XIII, XIV, XV, XVI, XVII, XVIII, XIX, or XX, with at least one desired isotopic substitution of an atom, at an amount above the natural abundance of the isotope, i.e., enriched.

Examples of isotopes that can be incorporated into compounds of the disclosure include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{17}O$, $^{18}O$, $^{18}F$, $^{31}P$, $^{32}P$, $^{35}S$, $^{36}CI$, and $^{125}I$ respectively. In one embodiment, isotopically labelled compounds can be used in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^{2}H$) and tritium ($^{3}H$) may optionally be used anywhere in described structures that achieves the desired result. Alternatively or in addition, isotopes of carbon, e.g., $^{13}C$ and $^{14}C$, may be used. In one embodiment, the isotopic substitution is replacing hydrogen with a deuterium at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 80, 85, 90, 95 or 99% or more enriched in an isotope at any location of interest. In one embodiments deuterium is 80, 85, 90, 95 or 99% enriched at a desired location. Unless otherwise stated, the enrichment at any point is above natural abundance, and in an embodiment is enough to alter a detectable property of the drug in a human.

In one embodiment, the substitution of a hydrogen atom for a deuterium atom can be provided in any formula of the present disclosure. In one embodiment, the substitution of a hydrogen atom for a deuterium atom occurs within any R group. In one embodiment, the R group is selected from any of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{25}$, $R^{26}$, $R^{27}$, $R^{29}$, $R^{30}$, $R^{31}$, $R^{32}$, $R^{33}$, $R^{200}$, and $R^{201}$. For example, when any of R groups are, or contain for example through substitution, methyl, ethyl, or methoxy, the alkyl residue may be deuterated (in non-limiting embodiments, $CD_3$, $CH_2CD_3$, $CD_2CD_3$, $CDH_2$, $CD_2H$, $CD_3$, $CHDCH_2D$, $CH_2CD_3$, $CHDCHD_2$, $OCDH_2$, $OCD_2H$, or $OCD_3$ etc.). In certain other embodiments, an R group has a "'" or an "a" designation, which in one embodiment can be deuterated. In certain other embodiments, when two substituents of the central core ring are combined to form a cyclopropyl ring, the unsubstituted methylene carbon may be deuterated.

The compound of the present disclosure may form a solvate with solvents (including water). Therefore, in one embodiment, the disclosure includes a solvated form of the active compound. The term "solvate" refers to a molecular complex of a compound of the present disclosure (including a salt thereof) with one or more solvent molecules. Non-limiting examples of solvents are water, ethanol, dimethyl sulfoxide, acetone and other common organic solvents. The term "hydrate" refers to a molecular complex comprising a compound of the disclosure and water. Pharmaceutically acceptable solvates in accordance with the disclosure include those wherein the solvent of crystallization may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, $-(C{=}O)NH_2$ is attached through carbon of the keto (C=O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., =O) then two hydrogens on the atom are replaced. For example, a pyridyl group substituted by oxo is a pyridone. Combinations of substituents and/or variables are permissible only if such combinations result in stable compounds or useful synthetic intermediates.

A stable active compound refers to a compound that can be isolated and can be formulated into a dosage form with a shelf life of at least one month. A stable manufacturing intermediate or precursor to an active compound is stable if it does not degrade within the period needed for reaction or other use. A stable moiety or substituent group is one that does not degrade, react or fall apart within the period necessary for use. Non-limiting examples of unstable moieties are those that combine heteroatoms in an unstable arrangement, as typically known and identifiable to those of skill in the art.

Any suitable group may be present on a "substituted" or "optionally substituted" position that forms a stable molecule and meets the desired purpose of the disclosure and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl, including those having one or more thioether linkages; alkylsulfinyl; alkylsulfonyl groups, including those having one or more sulfonyl linkages; aryl (e.g., phenyl, biphenyl, naphthyl, or the like, each ring either substituted or unsubstituted); arylalkyl having, for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g., coumarine, quinoline, isoquinoline, quinazoline, pyridine, pyrazole, oxadiazole, triazole, pyrazine, pyrimidine, furan, pyrrole, thienyl, thiazole, triazine, oxazole, isoxazole, imidazole, indole, benzofuran, benzothiazole, tetrahydrofuran, tetrahydropyran, piperidine, morpholine, piperazine, and pyrrolidine. Such groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, $-CONH_2$, alkyl including $C_1$-$C_6$alkyl, alkenyl including $C_2$-$C_6$alkenyl, alkynyl including $C_2$-$C_6$alkynyl, $-C_1$-$C_6$alkoxy, alkanoyl including $C_2$-$C_6$alkanoyl, (mono- and di-$C_1$-$C_6$alkylamino)$C_0$-$C_2$alkyl, haloalkyl including $C_1$-$C_6$haloalkyl, hydoxy$C_1$-$C_6$alkyl, ester, carbamate, urea, sulfonamide, $-C_1$-$C_6$alkyl(heterocyclo), $C_1$-$C_6$alkyl(heteroaryl), $-C_1$-$C_6$alkyl($C_3$-$C_7$cycloalkyl), O—$C_1$-$C_6$alkyl($C_3$-$C_7$cycloalkyl), $B(OH)_2$, phosphate, phosphonate and haloalkoxy including $C_1$-$C_6$haloalkoxy.

"Alkyl" is a branched or straight chain saturated hydrocarbon group. In one embodiment, the alkyl contains from 1 to about 12 carbon atoms, more generally from 1 to about 6 carbon atoms or from 1 to about 4 carbon atoms. In one embodiment, the alkyl contains from 1 to about 8 carbon atoms. In certain embodiments, the alkyl is $C_1$-$C_2$, $C_1$-$C_3$, $C_1$-$C_4$, $C_1$-$C_5$ or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$cycloalkyl)$C_0$-$C_4$ alkyl, or $-C_0$-$C_4$alkyl($C_3$-$C_7$cycloalkyl), the indicated group, in this case cycloalkyl, is either directly bound by a single covalent bond ($C_0$alkyl), or attached by an alkyl chain in this case 1, 2, 3, or 4 carbon atoms. Alkyl groups can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, 2,3-dimethylbutane, and hexyl. Alkyl groups can be optionally substituted independently with one or more substituents described herein.

When a term is used that includes "alk" it should be understood that "cycloalkyl" or "carbocyclic" can be considered part of the definition, unless unambiguously excluded by the context. For example, and without limitation, the terms alkyl, alkenyl, alkynyl, alkoxy, alkanoyl, alkenyloxy, haloalkyl, etc., can all be considered to include the cyclic forms of alkyl, unless unambiguously excluded by context.

"Alkenyl" is a branched or straight chain aliphatic hydrocarbon group having one or more carbon-carbon double bonds that may occur at a stable point along the chain. Non-limiting examples are $C_2$-$C_8$alkenyl, $C_2$-$C_7$alkenyl, $C_2$-$C_6$alkenyl, $C_2$-$C_5$alkenyl and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl. Alkenyl groups can be optionally substituted independently with one or more substituents described herein.

"Alkynyl" is a branched or straight chain aliphatic hydrocarbon group having one or more carbon-carbon triple bonds that may occur at any stable point along the chain, for example, $C_2$-$C_8$alkynyl or $C_2$-$C_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. Alkynyl groups can be optionally substituted independently with one or more substituents described herein.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl. Haloalkyl groups can be optionally substituted independently with one or more substituents described herein.

"Halo" or "halogen" indicates independently, any of fluoro, chloro, bromo or iodo.

"Aryl" indicates an aromatic group containing only carbon in the aromatic ring or rings. In one embodiment, the aryl group contains 1 to 3 separate or fused rings and is 6 to 14 or 18 ring atoms, without heteroatoms as ring members. When indicated, such aryl groups may be further substituted with carbon or non-carbon atoms or groups. Such substitution may include fusion to a 4 to 7 or a 5 to 7-membered saturated or partially unsaturated cyclic group that optionally contains 1, 2 or 3 heteroatoms independently selected from N, O, B, P, Si and S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. Aryl groups can be optionally substituted independently with one or more substituents described herein.

The term "heterocycle" refers to saturated and partially saturated heteroatom-containing ring radicals, where the heteroatoms may be selected from N, S, and O. The term "heterocycle" includes monocyclic 3-12 membered rings, as well as bicyclic 5-16 membered ring systems (which can include fused, bridged, or spiro, bicyclic ring systems). It does not include rings containing —O—O—. —O—S—, or —S—S— portions. Examples of saturated heterocycle groups include saturated 4- to 7-membered monocyclic groups containing 1 to 4 nitrogen atoms [e.g., pyrrolidinyl, imidazolidinyl, piperidinyl, pyrrolinyl, azetidinyl, piperazinyl, and pyrazolidinyl]; saturated 4 to 6-membered monocyclic groups containing 1 to 2 oxygen atoms and 1 to 3 nitrogen atoms [e.g., morpholinyl]; saturated 3 to 6-membered heteromonocyclic group containing 1 to 2 sulfur atoms and 1 to 3 nitrogen atoms [e.g., thiazolidinyl]. Examples of partially saturated heterocycle radicals include but are not limited to, dihydrothienyl, dihydropyranyl, dihydrofuryl, and dihydrothiazolyl. Examples of partially saturated and saturated heterocycle groups include, but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydroquinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl. "Bicyclic heterocycle" includes groups wherein the heterocyclic radical is fused with an aryl radical wherein the point of attachment is the heterocycle ring. "Bicyclic heterocycle" also includes heterocyclic radicals that are fused with a carbocycle radical. For example, partially unsaturated condensed heterocyclic group containing 1 to 5 nitrogen atoms, for example, indoline, isoindoline, partially unsaturated condensed heterocyclic group containing 1 to 2 oxygen atoms and 1 to 3 nitrogen atoms, partially unsaturated condensed heterocyclic group containing 1 to 2 sulfur atoms and 1 to 3 nitrogen atoms, and saturated condensed heterocyclic group containing 1 to 2 oxygen or sulfur atoms are all encompassed. Heterocycle groups can be optionally substituted independently with one or more substituents described herein.

Non-limiting examples of bicyclic heterocycles include:

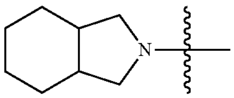,
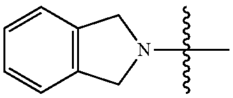,
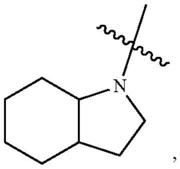,
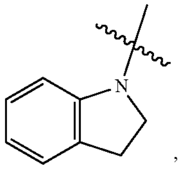,
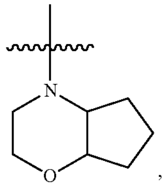,
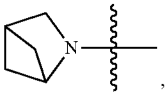,
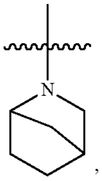,
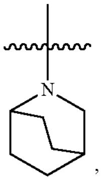,
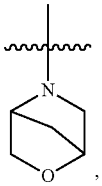,
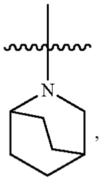, and
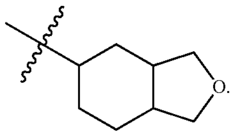.

Unless otherwise drawn or clear from the context, the term "bicyclic heterocycle" includes cis and trans diastereomers. Non-limiting examples of chiral bicyclic heterocycles include:

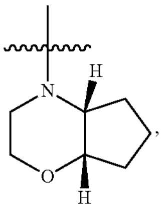, 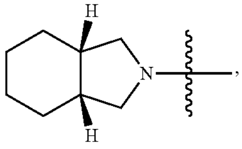,

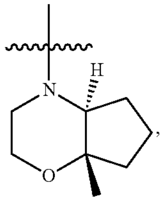, 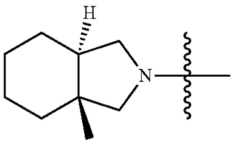

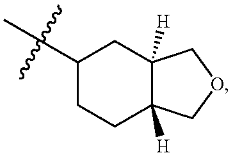, and 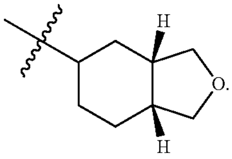.

"Heteroaryl" refers to a stable monocyclic, bicyclic, or multicyclic aromatic ring which contains from 1 to 3, or in some embodiments from 1, 2, or 3 heteroatoms selected from N, O, S, B, and P (and typically selected from N, O, and S) with remaining ring atoms being carbon, or a stable bicyclic or tricyclic system containing at least one 5, 6, or 7 membered aromatic ring which contains from 1 to 3, or in some embodiments from 1 to 2, heteroatoms selected from N, O, S, B or P with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5 or 6 ring atoms. In some embodiments, bicyclic heteroaryl groups are 8- to 10-membered heteroaryl groups, that is, groups containing 8 or 10 ring atoms in which one 5, 6, or 7 member aromatic ring is fused to a second aromatic or non-aromatic ring wherein the point of attachment is the aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. Heteroaryl groups can be optionally substituted independently with one or more substituents described herein.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

"Pharmaceutical compositions" are compositions comprising at least one active agent, and at least one other substance, such as a pharmaceutically acceptable carrier. "Pharmaceutical combinations" are combinations of at least two active agents which may be combined in a single dosage form or provided together in separate dosage forms with instructions that the active agents are to be used together to treat any disorder described herein.

A "pharmaceutically acceptable salt" is a derivative of the disclosed compound in which the parent compound is modified by making inorganic and organic, pharmaceutically acceptable, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include salts which are acceptable for human consumption and the quaternary ammonium salts of the parent compound formed, for example, from inorganic or organic acids. Examples of such salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_{1-4}$—COOH, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations according to the disclosure refers to a diluent, excipient, or vehicle with which an active compound is provided.

A "pharmaceutically acceptable excipient" or "pharmaceutically acceptable carrier" may be used interchangeably and mean an excipient that is useful in preparing a pharmaceutical composition/combination that is generally safe, acceptable for human consumption, and neither biologically nor otherwise inappropriate for administration to a host, typically a human. In one embodiment, an excipient is used that is acceptable for veterinary use. In one embodiment, an excipient is used that is acceptable for mammalian, particularly human, use.

A "patient" or "host" or "subject" is a human or non-human animal in need of treatment or prevention of any of the disorders as specifically described herein, including but not limited to by modulation of the classical complement pathway or with a condition that is treatable with one of the compounds described herein. Typically, the host is a human. A "patient" or "host" or "subject" also refers to for example, a mammal, primate (e.g., human), cows, sheep, goat, horse, dog, cat, rabbit, rat, mice, bird and the like.

A "prodrug" as used herein, means a compound which when administered to a host in vivo is converted into a parent drug. As used herein, the term "parent drug" means any of the presently described chemical compounds herein. Prodrugs can be used to achieve any desired effect, including to enhance properties of the parent drug or to improve the pharmaceutic or pharmacokinetic properties of the parent, including to increase the half-life of the drug in vivo. Prodrug strategies provide choices in modulating the conditions for in vivo generation of the parent drug. Non-limiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

"Providing a compound with at least one additional active agent," for example, in one embodiment can mean that the compound and the additional active agent(s) are provided simultaneously in a single dosage form, provided concomitantly in separate dosage forms, or provided in separate dosage forms for administration. In one embodiment, the compound administrations are separated by some amount of time that is within the time in which both the compound and the at least one additional active agent are within the blood stream of a patient. In certain embodiments, the compound and the additional active agent need not be prescribed for a patient by the same medical care worker. In certain embodiments, the additional active agent or agents need not require a prescription. Administration of the compound or the at least one additional active agent can occur via any appropriate route, for example, oral tablets, oral capsules, oral liquids, inhalation, injection, suppositories, parenteral, sublingual, buccal, intravenous, intraaortal, transdermal, polymeric controlled delivery, non-polymeric controlled delivery, nano or microparticles, liposomes, and/or topical contact. In one embodiment, the instructions for administration in a form of combination therapy is provided in the drug labeling.

A "therapeutically effective amount" of a pharmaceutical composition/combination of this disclosure means an amount effective, when administered to a host, to provide a therapeutic benefit, such as an amelioration of symptoms or reduction or dimunition of the disease itself. In one embodiment, a therapeutically effective amount is an amount sufficient to prevent a significant increase, or will significantly reduce, the detectable level of hemolysis in the patient's blood, serum, or tissues.

N-Oxides

In certain embodiments, any of the active compounds can be provided in its N-oxide form to a patient in need thereof. In one embodiment, an N-oxide of an active compound or a precursor of the active compound is used in a manufacturing scheme. In yet another embodiment, the N-oxide is a metabolite of administration of one of the active compounds herein, and may have independent activity. The N-oxide can be formed by treating the compound of interest with an oxidizing agent, for example, a suitable peroxyacid or peroxide, to generate an N-oxide compound. For example, a heteroaryl group, for example a pyridyl group, can be treated with an oxidizing agent such as sodium percarbonate in the presence of a rhenium-based catalyst under mild reaction conditions to generate an N-oxide compound. A person skilled in the art will understand that appropriate protecting groups may be necessary to carry out the chemistry. See Jain, S. L. et al., "Rhenium-Catalyzed Highly Efficient Oxidations of Tertiary Nitrogen Compounds to N-Oxides Using Sodium Percarbonate as Oxygen Source, *Synlett,* 2261-2663, 2006.

In other aspects of the present disclosure, any of the active compounds with a sulfur can be provided in its sulfoxide or sulfone form to a patient in need thereof. In a different embodiment, a sulfoxide or sulfone of one of the active compounds or a precursor of the active compound is used in a manufacturing scheme. A sulfur atom in a selected compound as described herein can be oxidized to form a sulfoxide

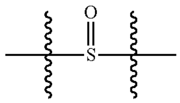

or a sulfone

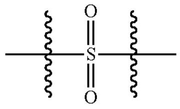 [SMILES: *S(*)(=O)=O]

using known methods. For example, the compound 1,3,5-triazo-2,4,6-triphosphorine-2,2,4,4,6,6-tetrachloride (TAPC) is an efficient promoter for the oxidation of sulfides to sulfoxides. See, Bahrami, M. et al., "TAPC-Promoted Oxidation of sulfides and Deoxygenation of Sulfoxides", J. Org. Chem., 75, 6208-6213 (2010). Oxidation of sulfides with 30% hydrogen peroxide catalyzed by tantalum carbide provides sulfoxides in high yields, see Kirihara, A., et al., "Tantalum Carbide or Niobium Carbide Catalyzed Oxidation of Sulfides with Hydrogen Peroxide: Highly Efficient and Chemoselective Syntheses of Sulfoxides and Sulfones", *Synlett,* 1557-1561 (2010). Sulfides can be oxidized to sulfones using, for example, niobium carbide as the catalyst, see Kirihara, A., et al., "Tantalum Cardide or Niobium Carbide Catalyzed Oxidation of Sulfides with Hydrogen Peroxide: Highly Efficient and Chemoselective Syntheses of Sulfoxides and Sulfones", *Synlett,* 1557-1561 (2010). Urea-hydrogen peroxide adduct is a stable inexpensive and easily handled reagent for the oxidation of sulfides to sulfones, see Varma, R. S. and Naicker, K. P., "The Urea-Hydrogen Peroxide Complex: Solid-State Oxidative Protocols for Hydroxylated Aldehydes and Ketones (Dakin Reaction), Nitriles, Sulfides, and Nitrogen Heterocycles", *Org. Lett.,* 1, 189-191 (1999). One skilled in the art will appreciate that other heteroatoms, such as nitrogen, may need to be protected and then deprotected while carrying out the oxidation of a sulfur atom to produce the desired compound.

Embodiments of "Alkyl"

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In one embodiment "alkyl" has one carbon.

In one embodiment "alkyl" has two carbons.

In one embodiment "alkyl" has three carbons.

In one embodiment "alkyl" has four carbons.

In one embodiment "alkyl" has five carbons.

In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

Embodiments of "Haloalkyl"

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.

In one embodiment "haloalkyl" has one carbon and one halogen.

In one embodiment "haloalkyl" has one carbon and two halogens.

In one embodiment "haloalkyl" has one carbon and three halogens.

In one embodiment "haloalkyl" has two carbons.

In one embodiment "haloalkyl" has three carbons.

In one embodiment "haloalkyl" has four carbons.

In one embodiment "haloalkyl" has five carbons.

In one embodiment "haloalkyl" has six carbons.

Non-limiting examples of "haloalkyl" include:

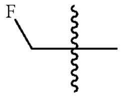, 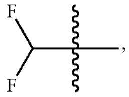, and 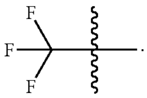.

Additional non-limiting examples of "haloalkyl" include:

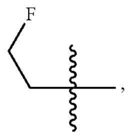, 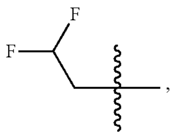, 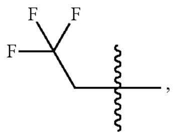,

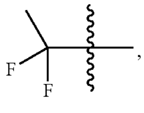, 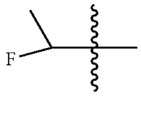, 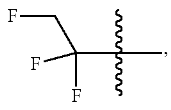,

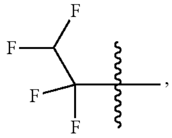, 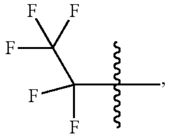,

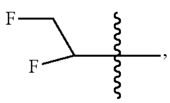, 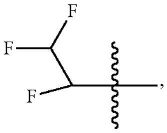, and

-continued

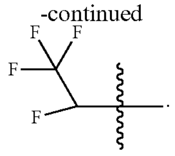.

Additional non-limiting examples of "haloalkyl" include:

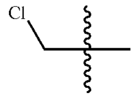, 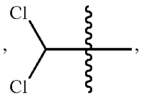, and 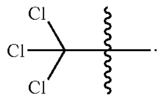.

Additional non-limiting examples of "haloalkyl" include:

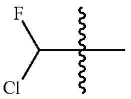, 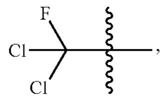, and 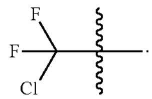.

Embodiments of "Aryl"

In one embodiment "aryl" is a 6 carbon aromatic group (phenyl)

In one embodiment "aryl" is a 10 carbon aromatic group (napthyl)

In one embodiment "aryl" is "substituted aryl".

Embodiments of "Heteroaryl"

In one embodiment "heteroaryl" is a 5 membered aromatic group containing 1, 2, or 3, nitrogen atoms.

Non-limiting examples of 5 membered "heteroaryl" groups include pyrrole, furan, thiophene, pyrazole, imidazole, triazole, isoxazole, oxazole, oxadiazole, oxatriazole, isothiazole, thiazole, thiadiazole, and thiatriazole.

Additional non-limiting examples of 5 membered "heteroaryl" groups include:

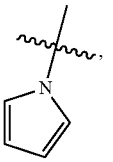, 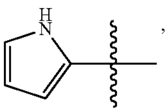, 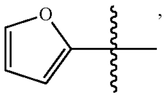,

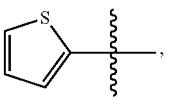, 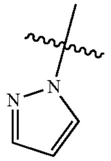, 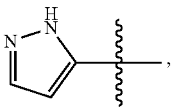,

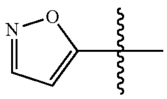, 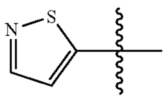, 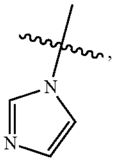,

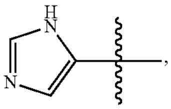, 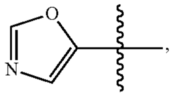, 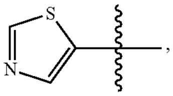,

-continued

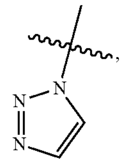, 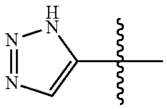, 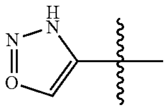,

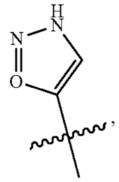 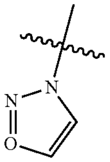, 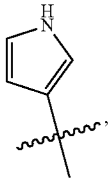

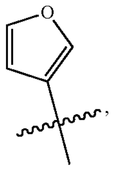 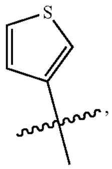 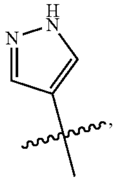

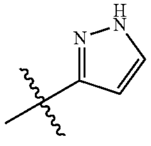, 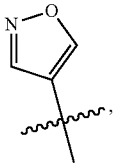 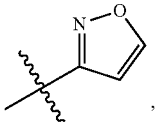,

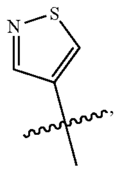 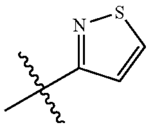, 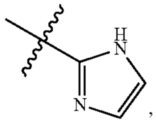,

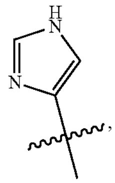 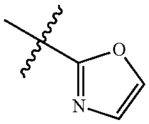, 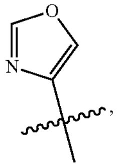

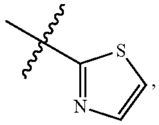 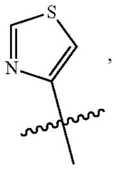, and 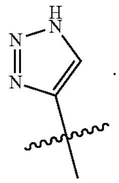.

In one embodiment, "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6-membered "heteroaryl" groups with 1 or 2 nitrogen atoms include:

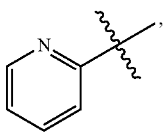 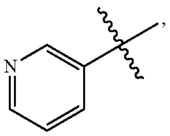

-continued

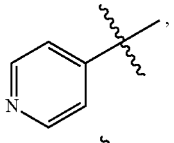 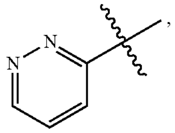

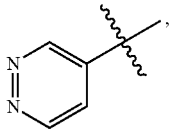 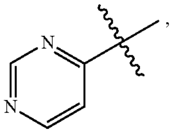

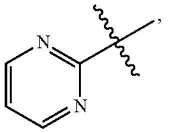 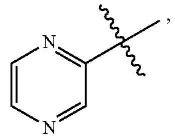

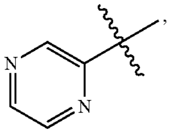 and 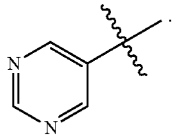

In one embodiment, "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

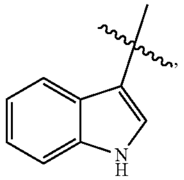 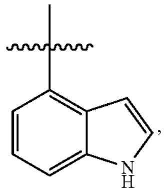

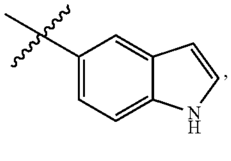 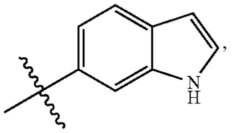

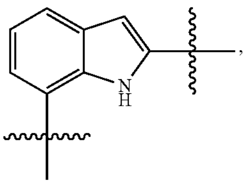 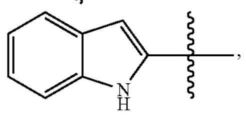 and

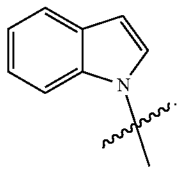

Additional non-limiting examples of "heteroaryl" groups that are bicyclic include:

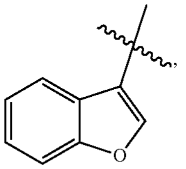,
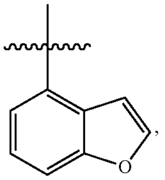,
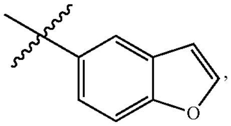,
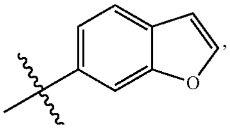,
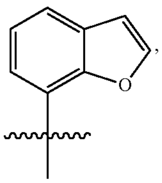, and
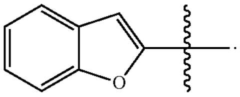.

Additional non-limiting examples of "heteroaryl" groups that are bicyclic include:

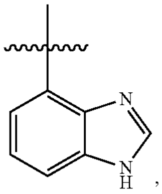,
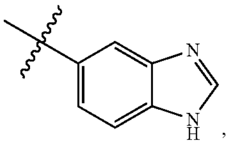,
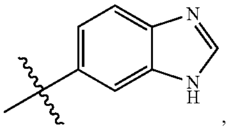,
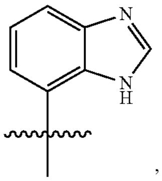,
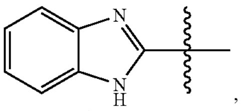, and
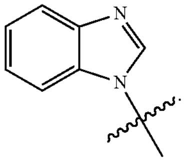.

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

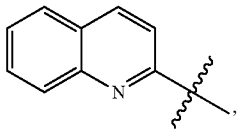,
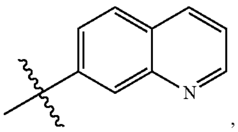,
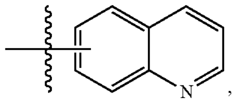,
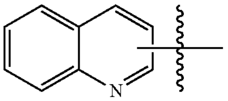,
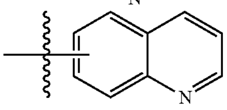, and
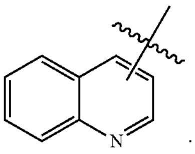.

In an alternative embodiment, heteroaryl is tetrazole.

Embodiments of "Cycloalkyl"

In one embodiment, "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In one embodiment, "cycloalkyl" has three carbons.

In one embodiment, "cycloalkyl" has four carbons.

In one embodiment, "cycloalkyl" has five carbons.

In one embodiment, "cycloalkyl" has six carbons.

In one embodiment, "cycloalkyl" has seven carbons.

In one embodiment, "cycloalkyl" has eight carbons.

In one embodiment, "cycloalkyl" has nine carbons.

In one embodiment, "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

Embodiments of "Heterocycle"

In one embodiment, "heterocycle" refers to a cyclic ring with one nitrogen and 3, 4, 5, 6, 7, or 8 carbon atoms.

In one embodiment, "heterocycle" refers to a cyclic ring with one nitrogen and one oxygen and 3, 4, 5, 6, 7, or 8 carbon atoms.

In one embodiment, "heterocycle" refers to a cyclic ring with two nitrogens and 3, 4, 5, 6, 7, or 8 carbon atoms.

In one embodiment, "heterocycle" refers to a cyclic ring with one oxygen and 3, 4, 5, 6, 7, or 8 carbon atoms.

In one embodiment, "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Non-limiting examples of "heterocycle" also include:

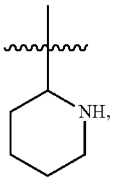 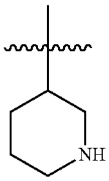 , 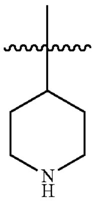 ,

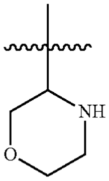 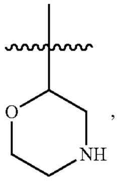 , 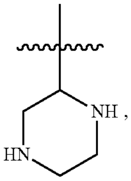

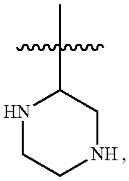 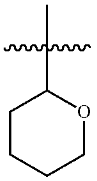 , 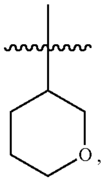 and

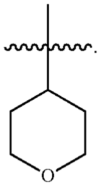

Additional non-limiting examples of "heterocycle" include:

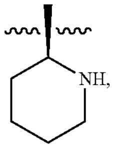

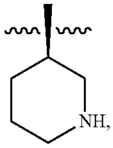

-continued

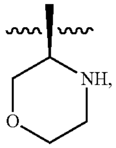

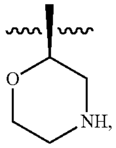

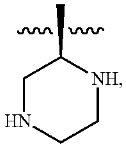

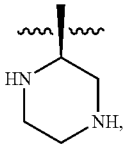

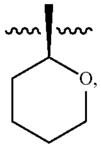 and

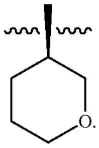

Additional non-limiting examples of "heterocycle" include:

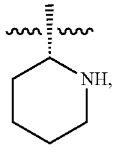

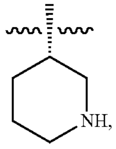

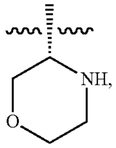

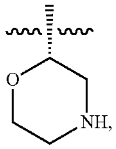

-continued
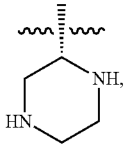
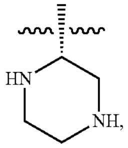
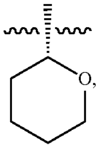
and
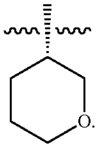
Non-limiting examples of “heterocycle” also include:
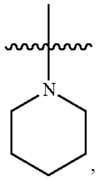
,
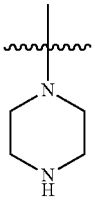
, and
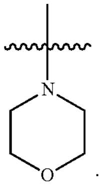
.
Non-limiting examples of “heterocycle” also include:
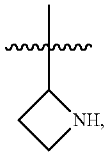
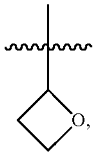
-continued
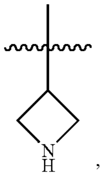
,
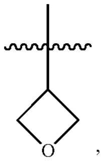
,
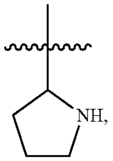
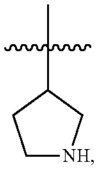
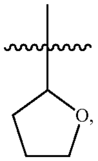
and
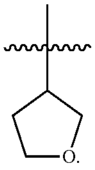
Additional non-limiting examples of “heterocycle” include:
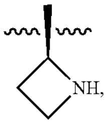
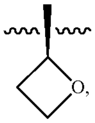
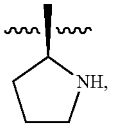
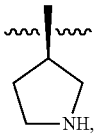

-continued
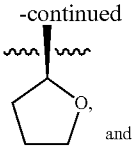
and
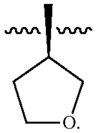
Additional non-limiting examples of "heterocycle" include:
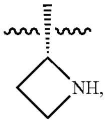
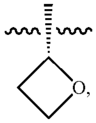
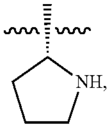
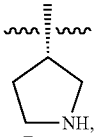
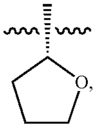
and
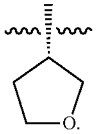
Embodiments of "Sugar"
In one embodiment, "sugar" refers to a compound of formula $C_3H_5O_3$, $C_4H_7O_4$, $C_5H_9O_5$, $C_6H_{11}O_6$, $C_7H_{13}O_7$, or $C_8H_{15}O_8$.
Non-limiting examples of sugar include
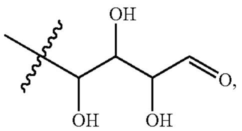
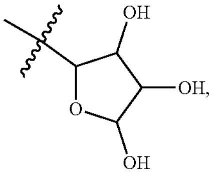
-continued
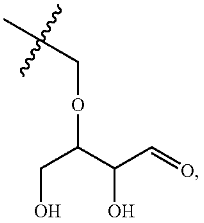
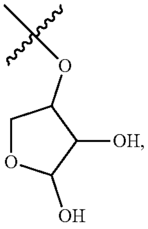
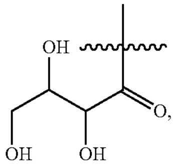
and
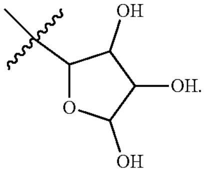
Additional Embodiments of the Present Disclosure
In one embodiment
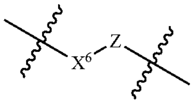
is selected from:
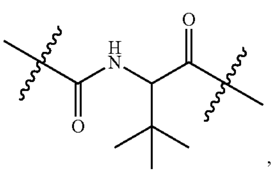
,
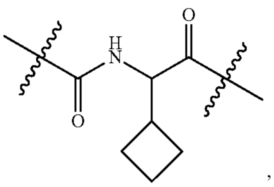
,
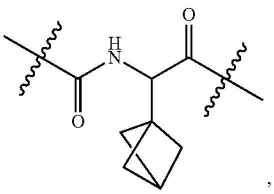
,
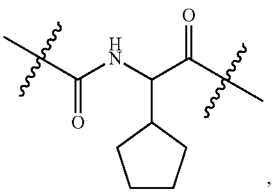
, -continued
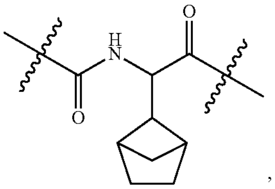,
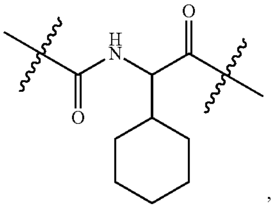,
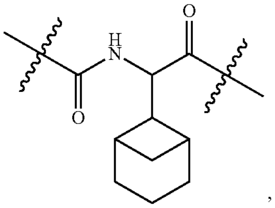,
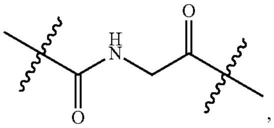,
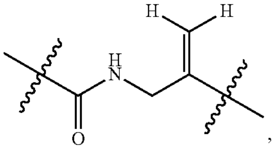,
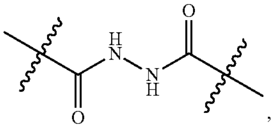,
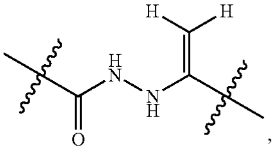,
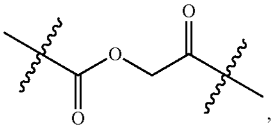,
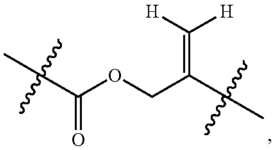,
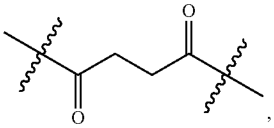,
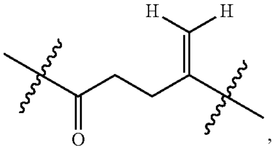,
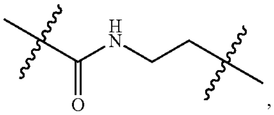,
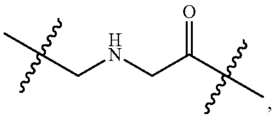,
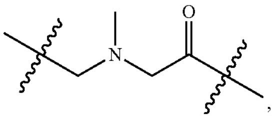,
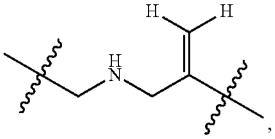,
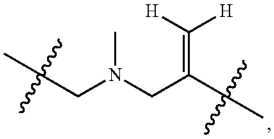,
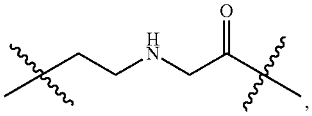,
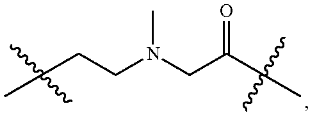,
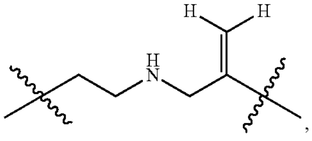,
-continued
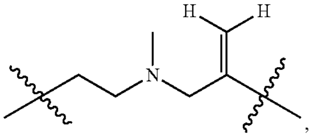,
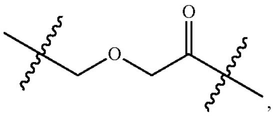,
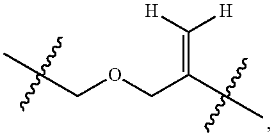,
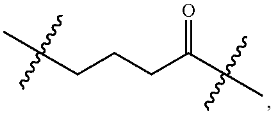,
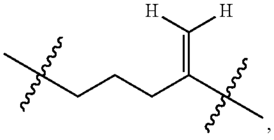,
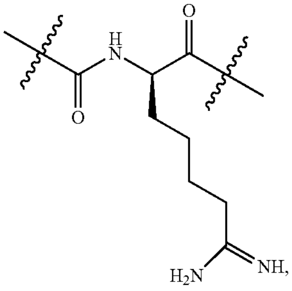,
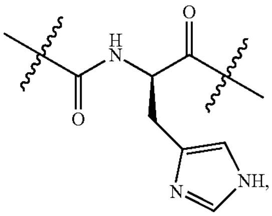,
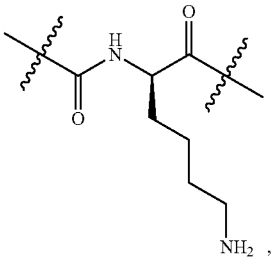,
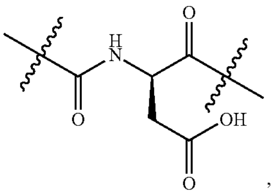,
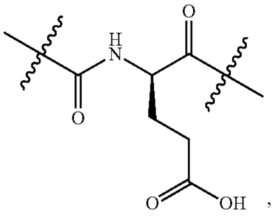,
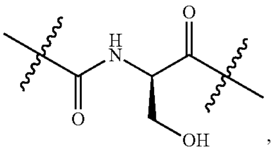,
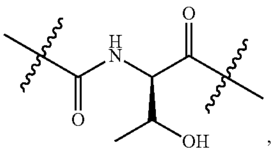,
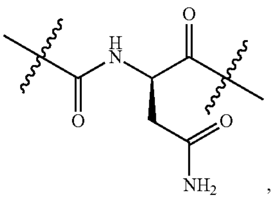,
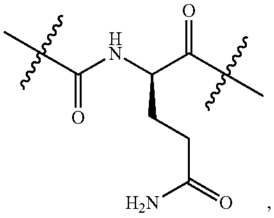,
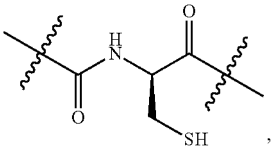, -continued
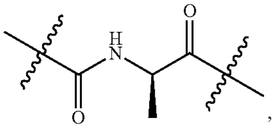,
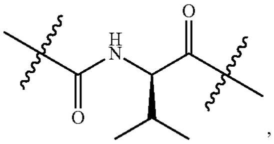,
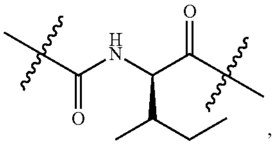,
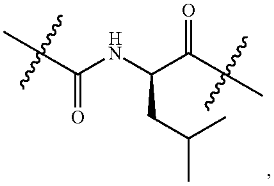,
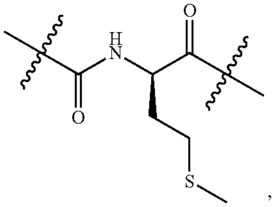,
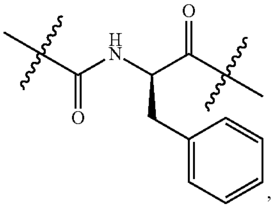,
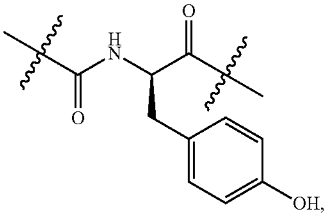
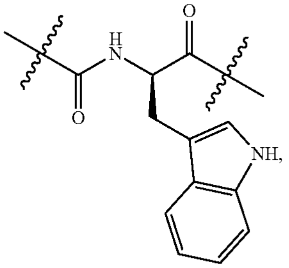
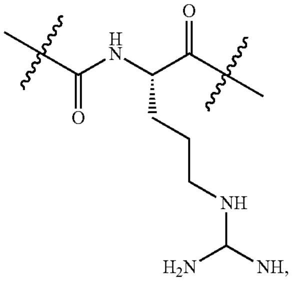
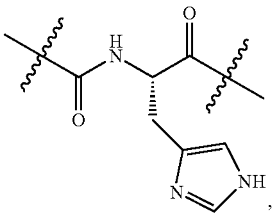,
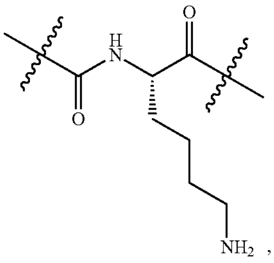,
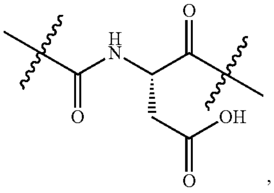,
-continued
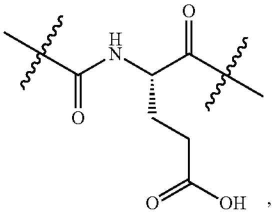,
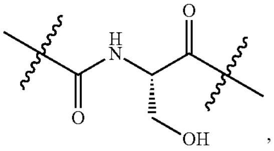,
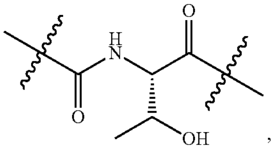,
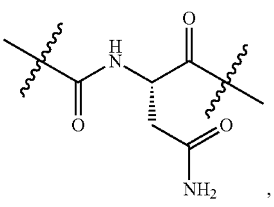,
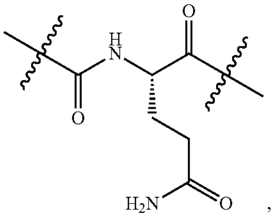,
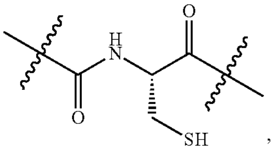,
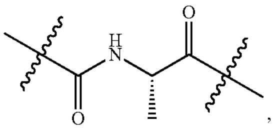,
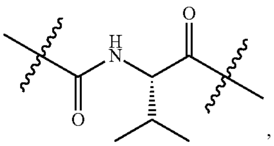,
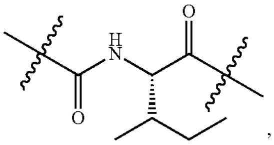,
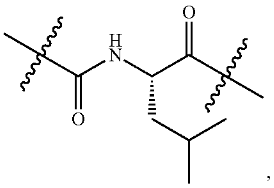,
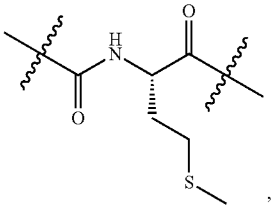,
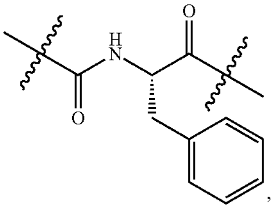,
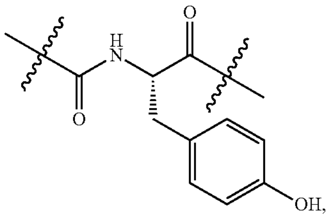 and
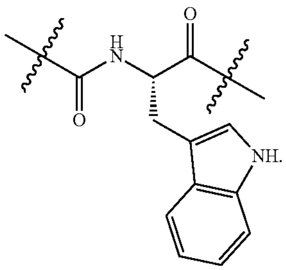

In one embodiment,
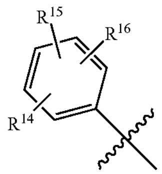
is selected from:
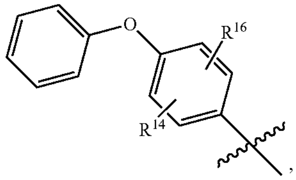,
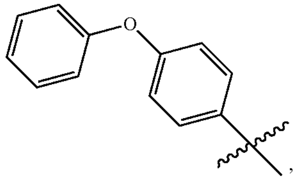,
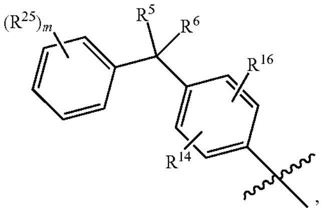,
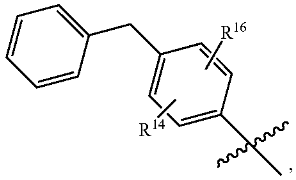,
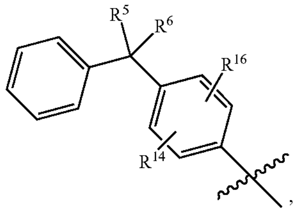,
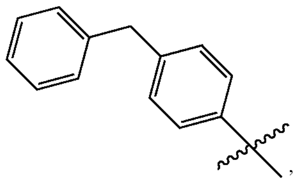,
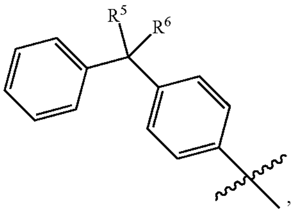,
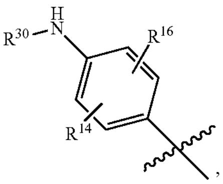,
-continued
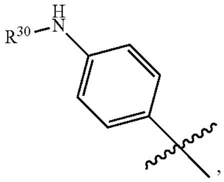,
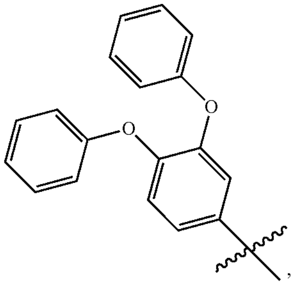,
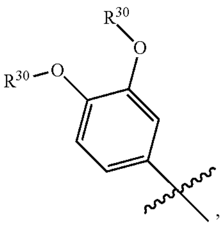,
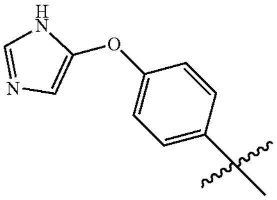,
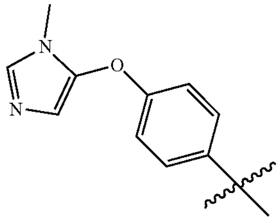,
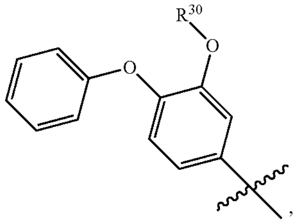,
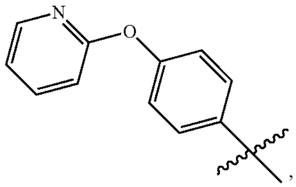,
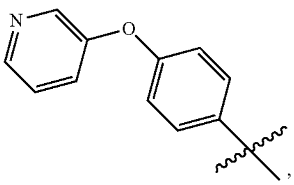, and
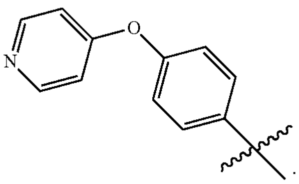.

In one embodiment, $R^{22}$ is selected from
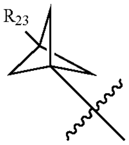,
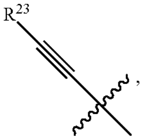,
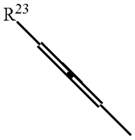,
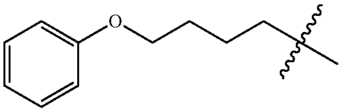,
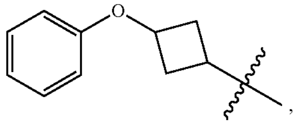,
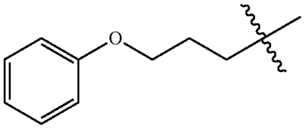
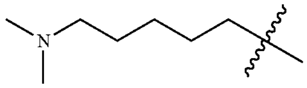,
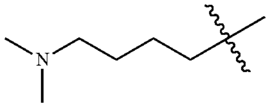,
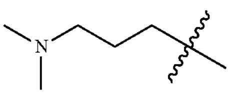,
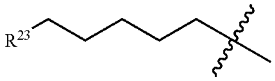,
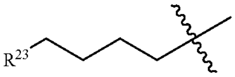, and 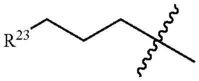.
In one embodiment, $R^{22}$ is selected from
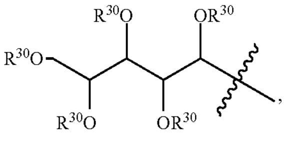,
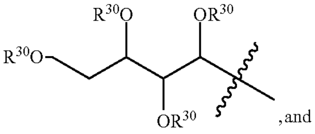, and
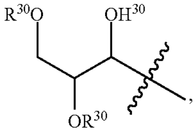,
In one embodiment,
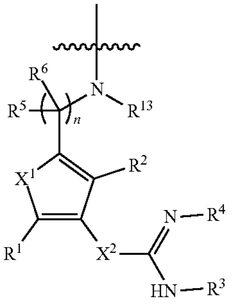
is selected from
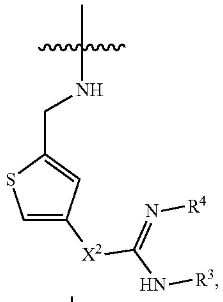,
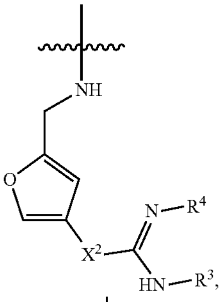,
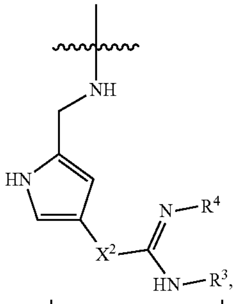,
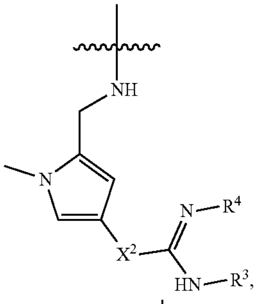,
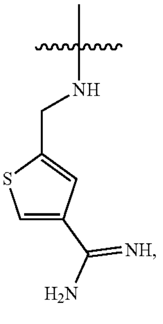,
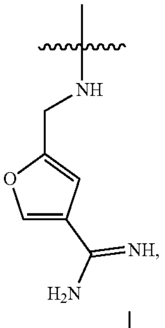,
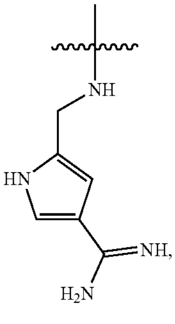, and
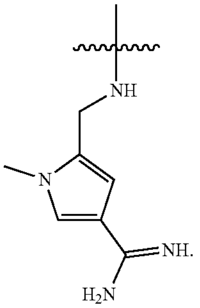.

In one embodiment,
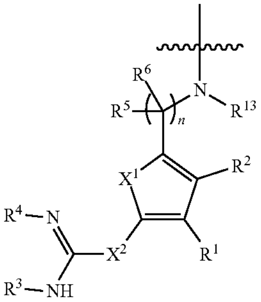
is selected from
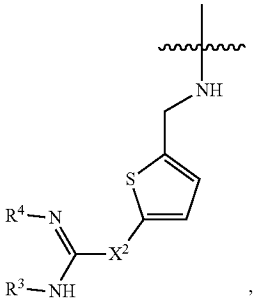
,
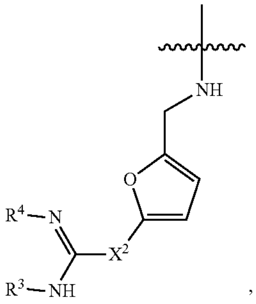
,
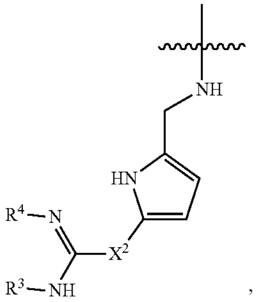
,
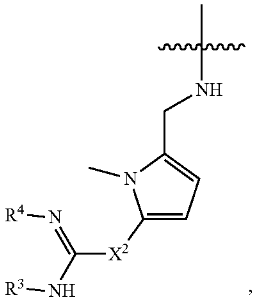
,
-continued
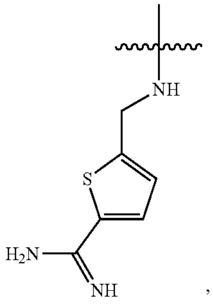
,
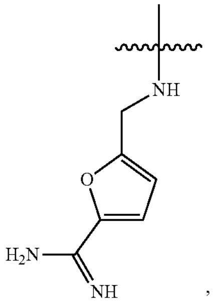
,
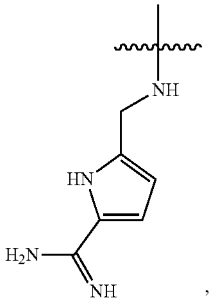
, and
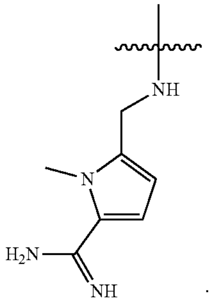
.
In one embodiment,
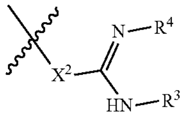

is selected from
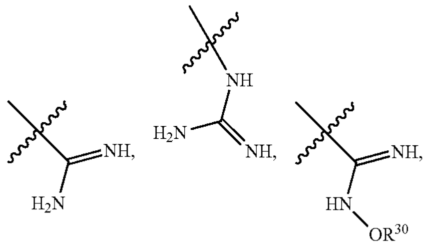
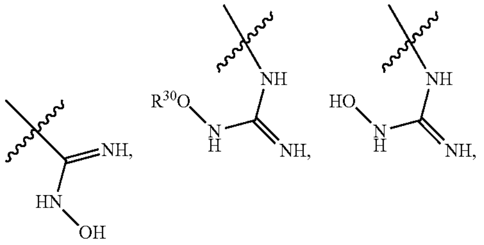
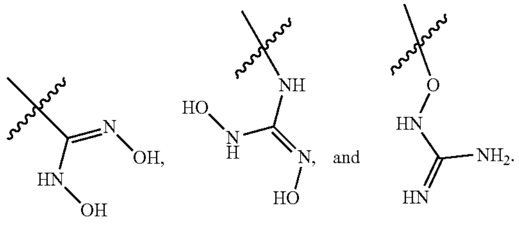
and
In another embodiment,
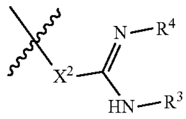
is selected from
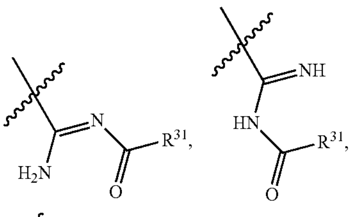
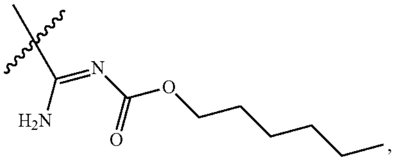
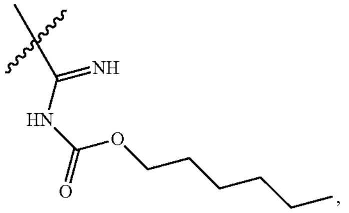
-continued
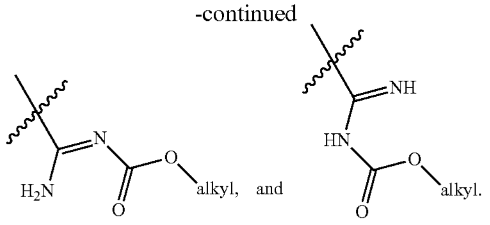
and
In another embodiment,
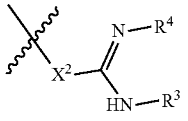
is selected from
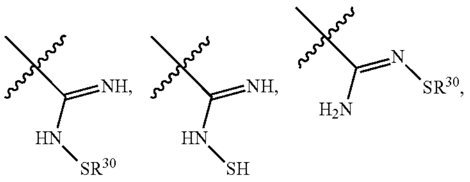
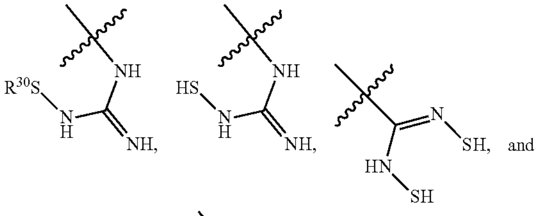
and
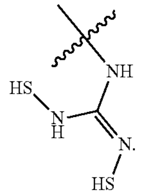
In another embodiment,
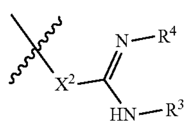
is
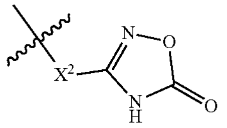
or
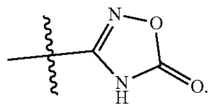
In another embodiment,
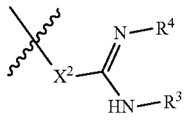
is
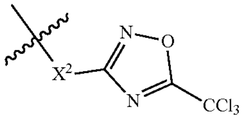
or -continued
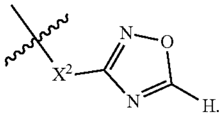
In one embodiment, $R^{26}$ is selected from
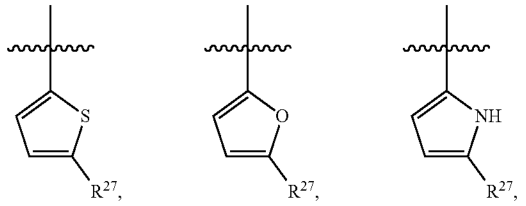
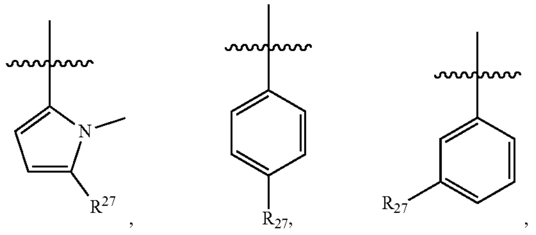
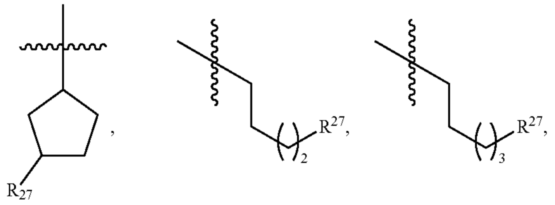
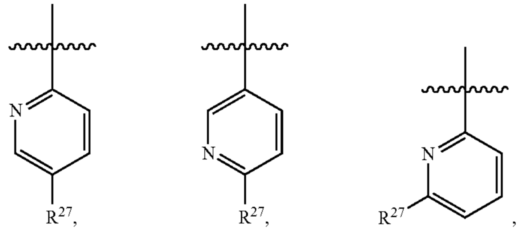
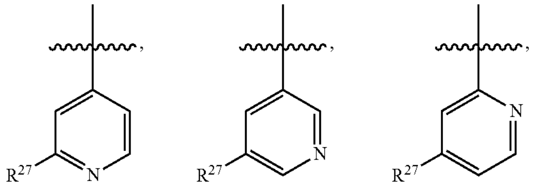
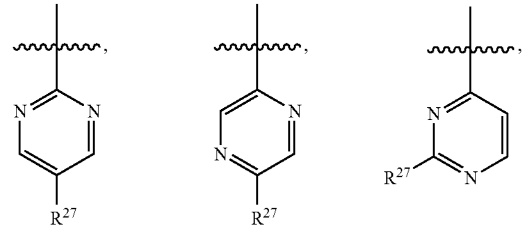
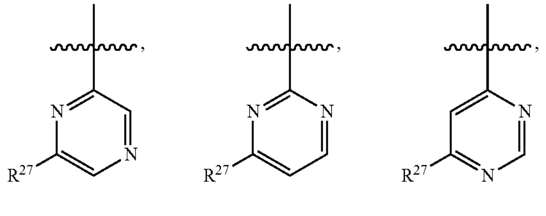
-continued
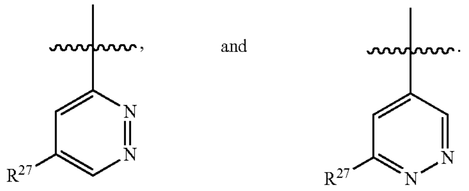
In one embodiment, $R^{27}$ is selected from
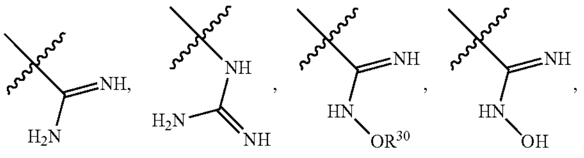
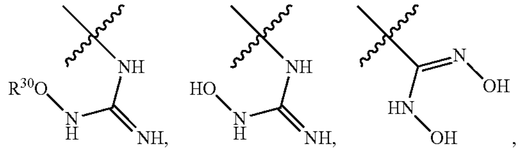
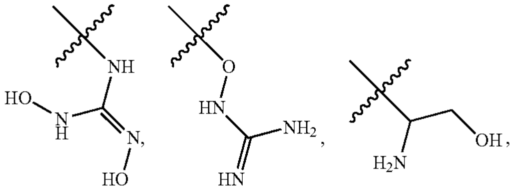
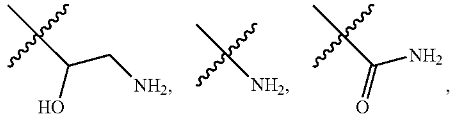
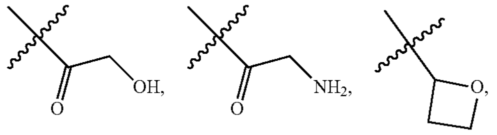
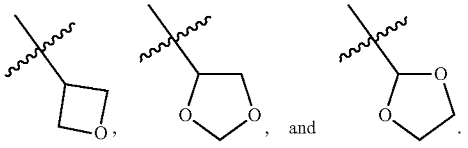
In one embodiment,
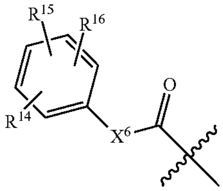

is selected from
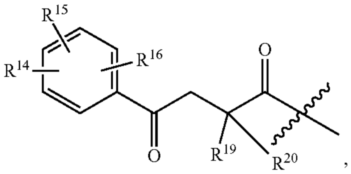
,
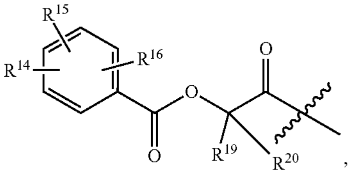
,
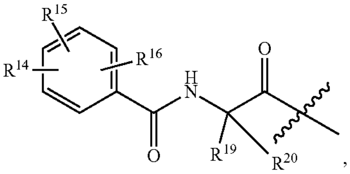
, and
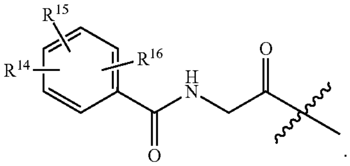
.
In one embodiment, $R^{21}$ is selected from:
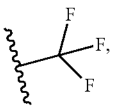
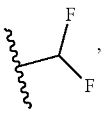
,
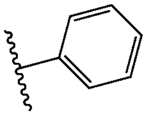
,
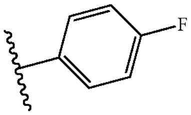
,
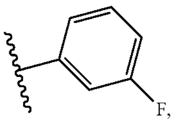
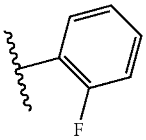
,
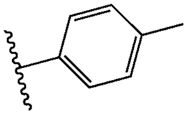
,
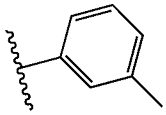
,
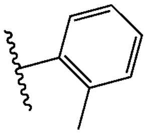
,
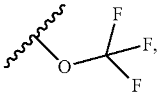
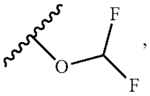
,
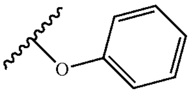
,
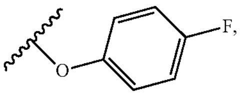
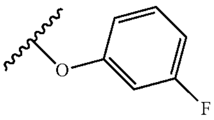
,
-continued
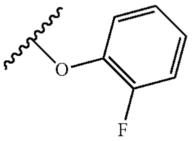
,
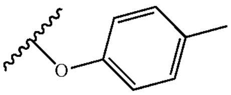
,
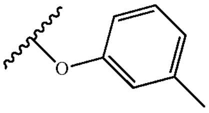
, and
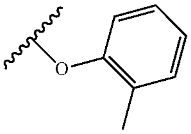
.
In one aspect, a compound of Formula I is provided selected from:
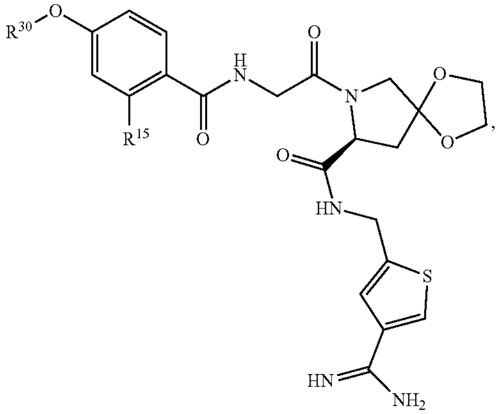
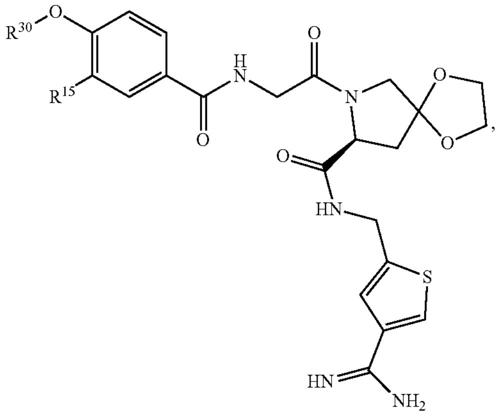
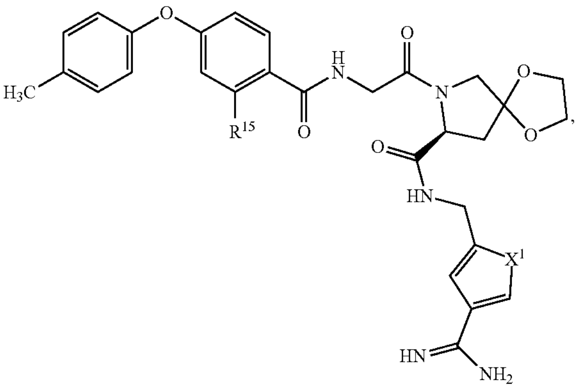

-continued
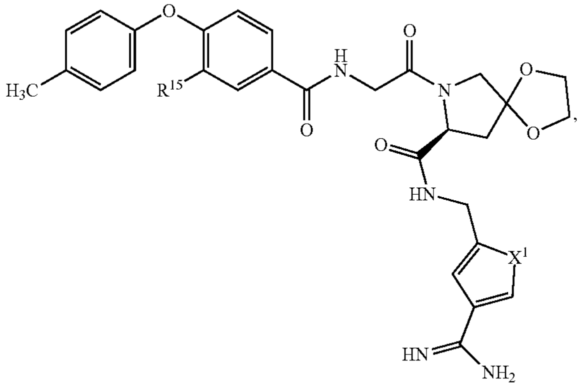
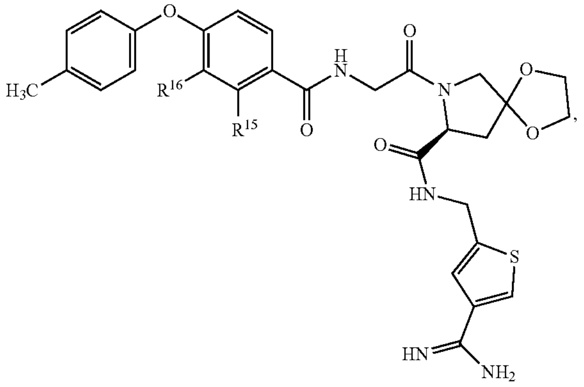
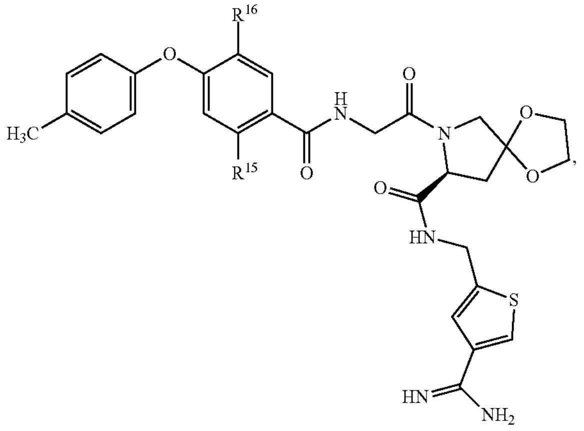
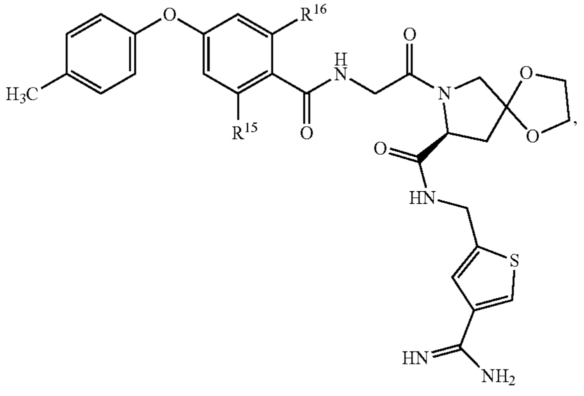
-continued
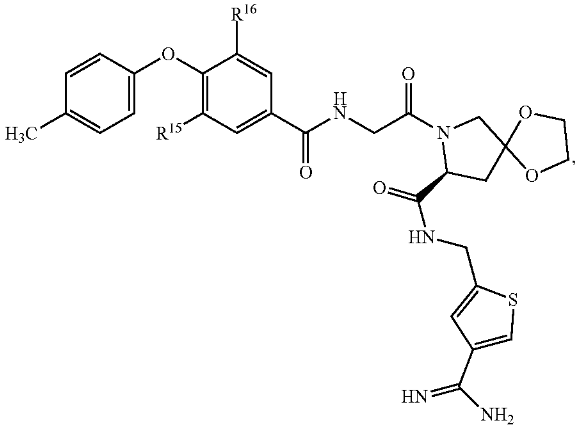
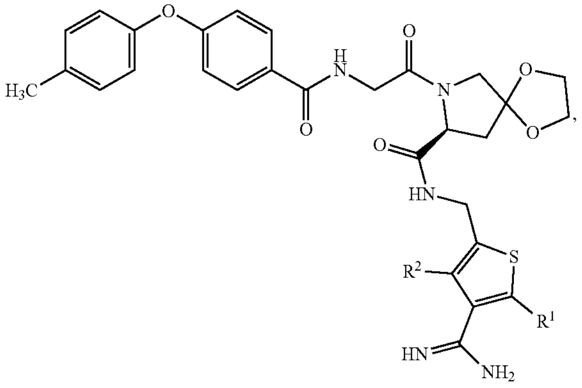
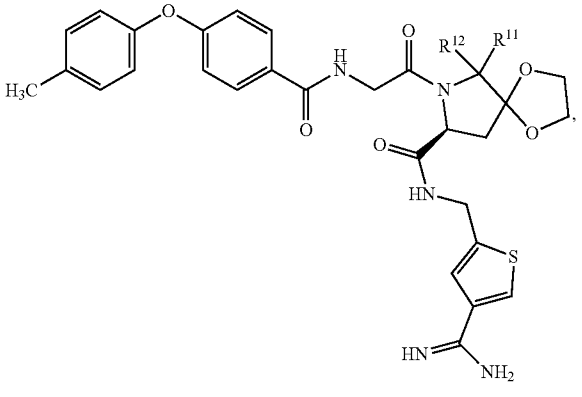
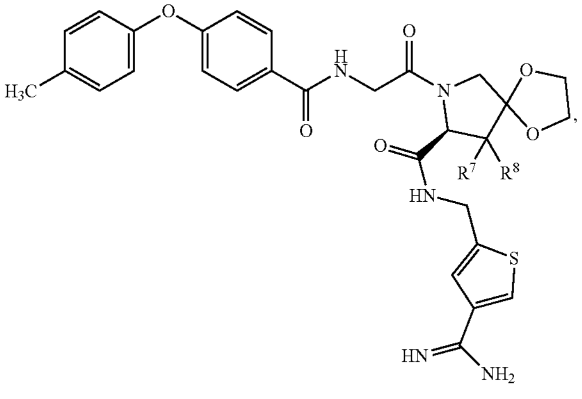

-continued
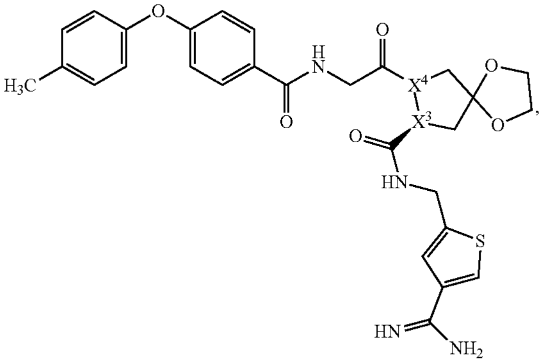
, and
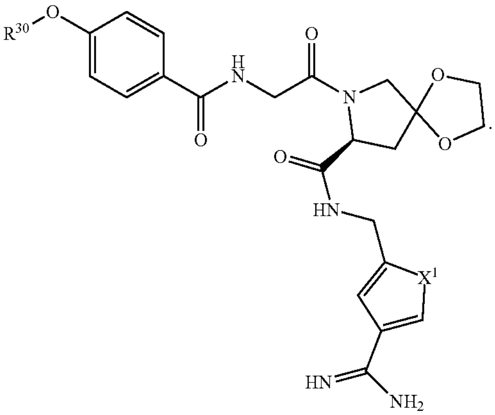
.
In one aspect, a compound of Formula I is provided selected from:
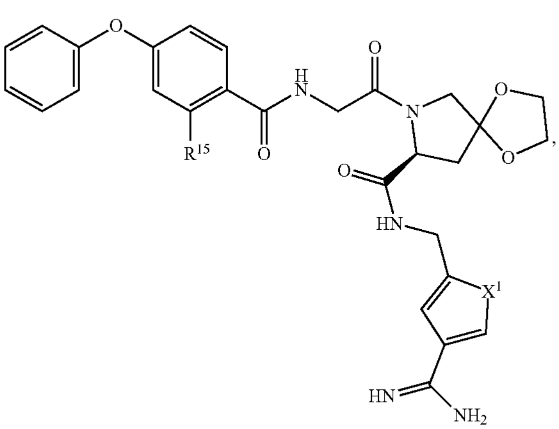
,
-continued
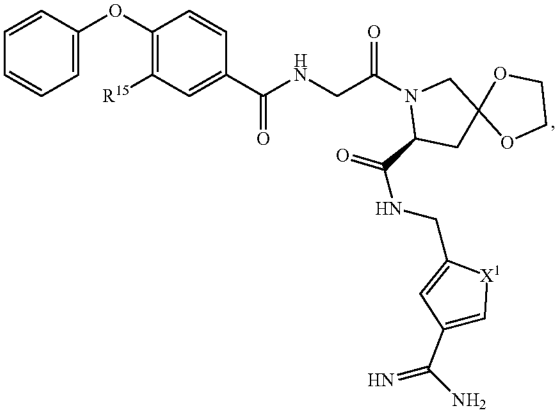
,
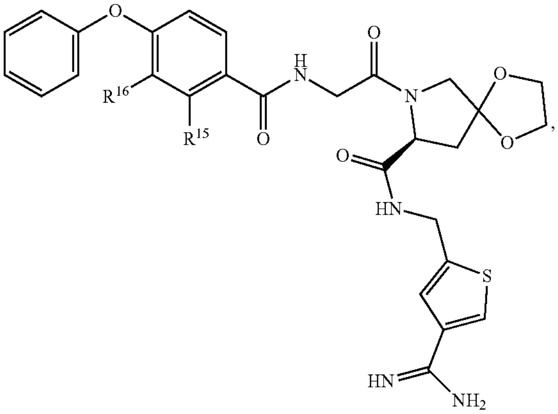
,
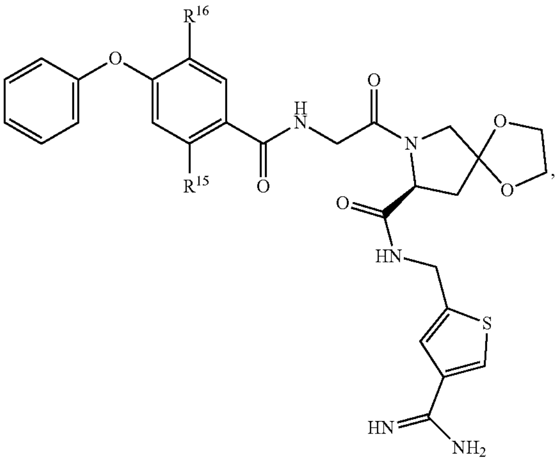
,
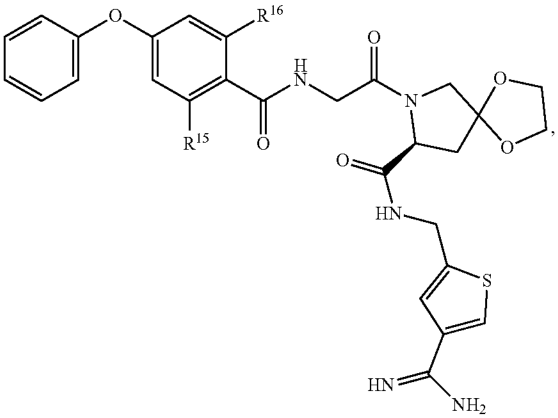
, -continued
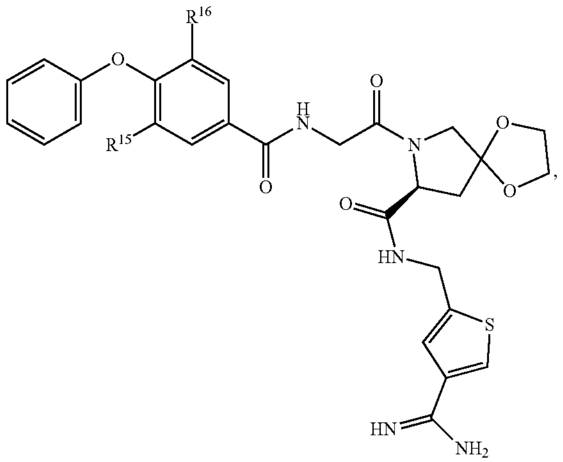
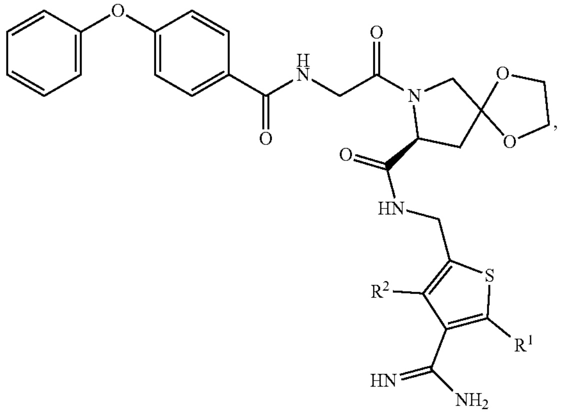
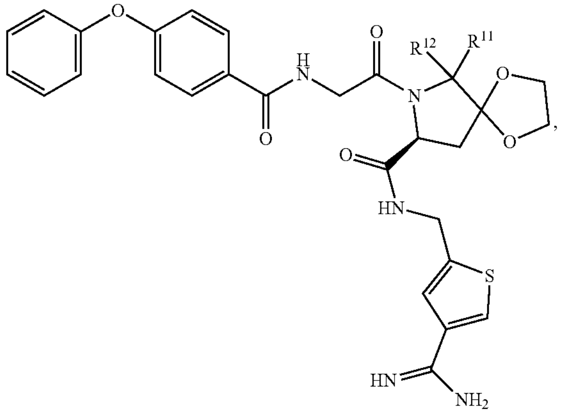
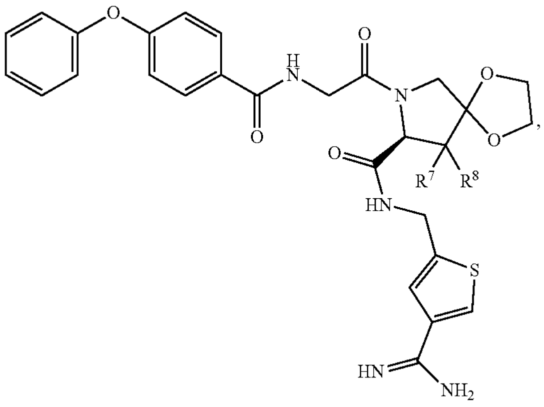
, and
-continued
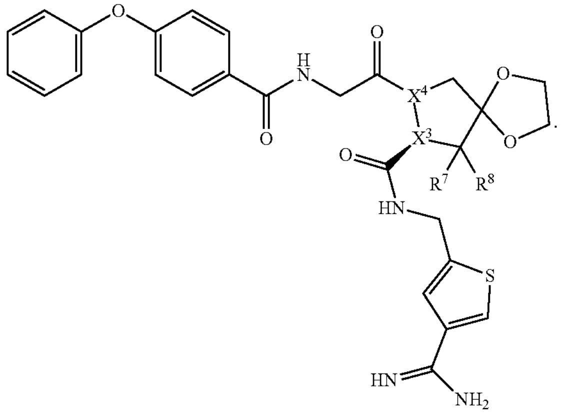
In one aspect, a compound of Formula I is provided selected from:
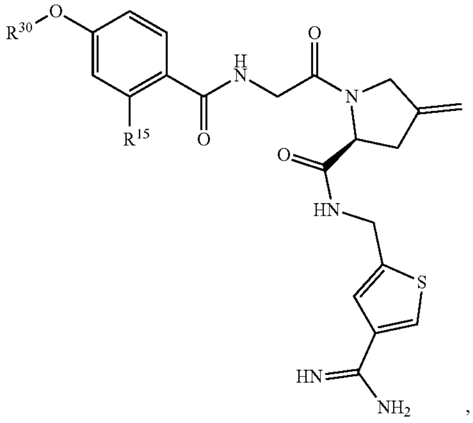
,
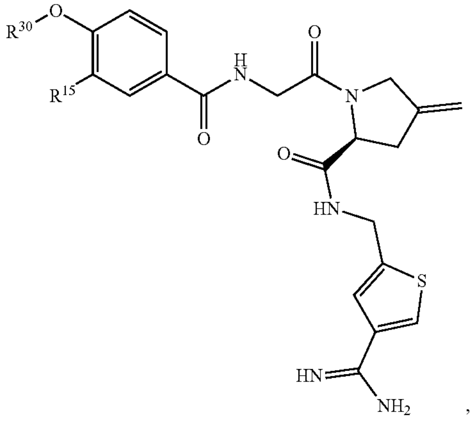
, -continued
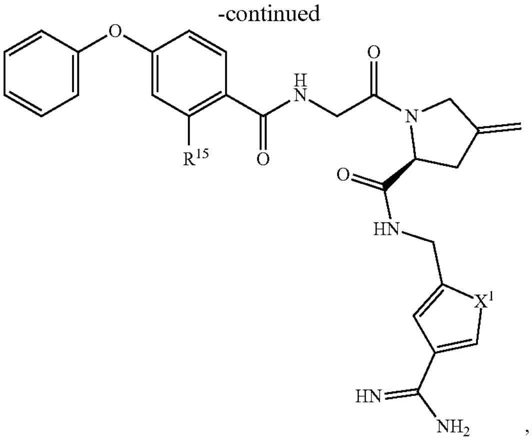
,
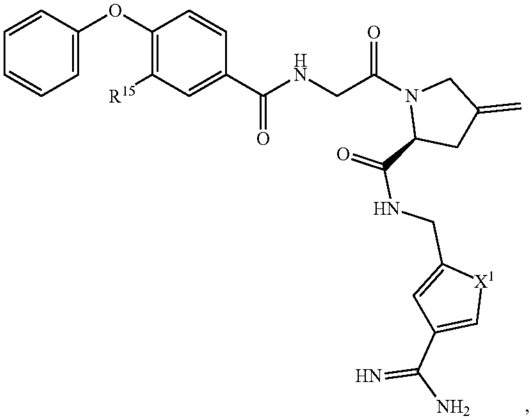
,
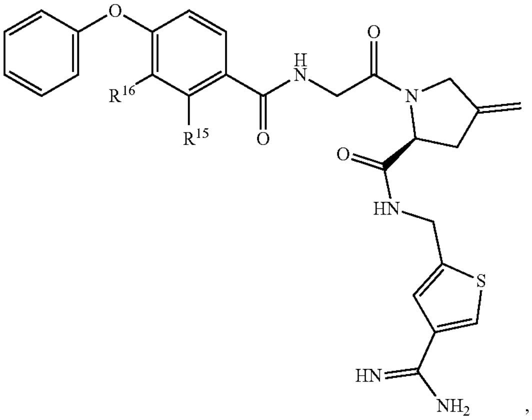
,
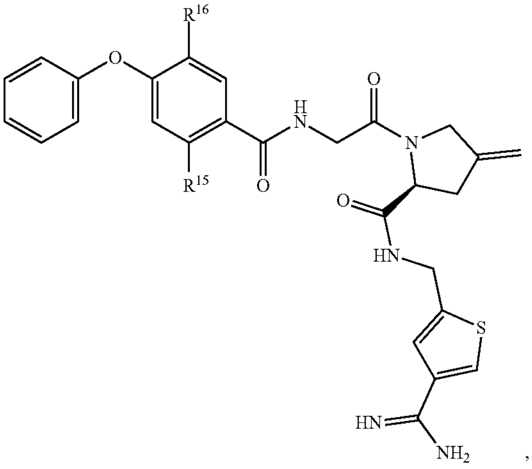
,
-continued
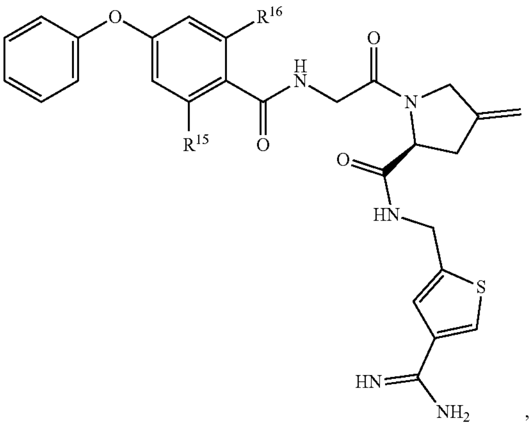
,
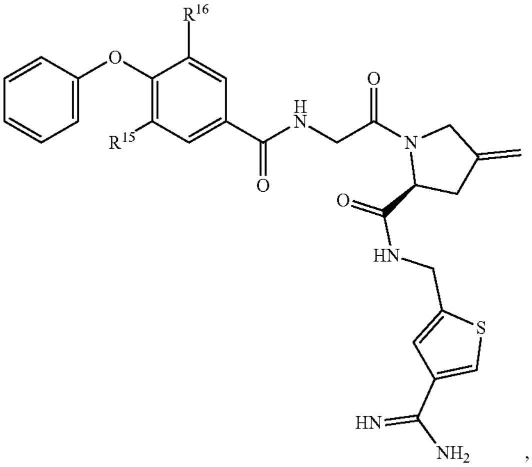
,
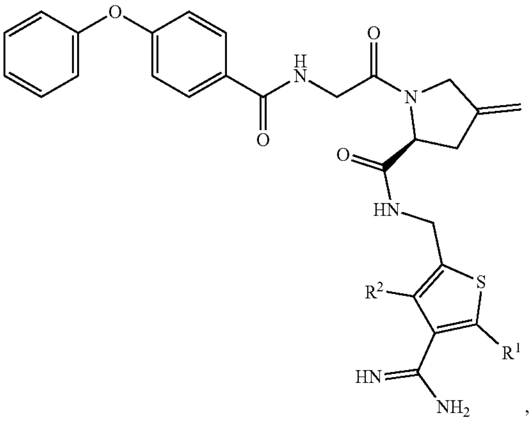
, -continued
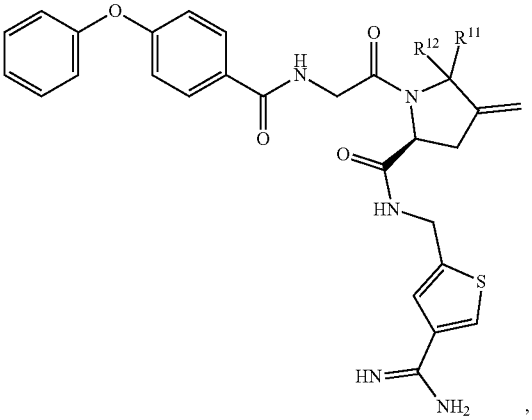
,
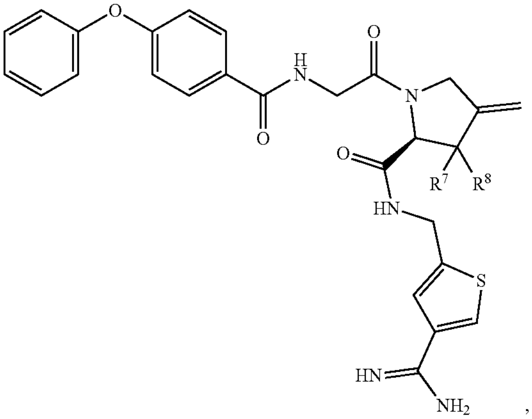
,
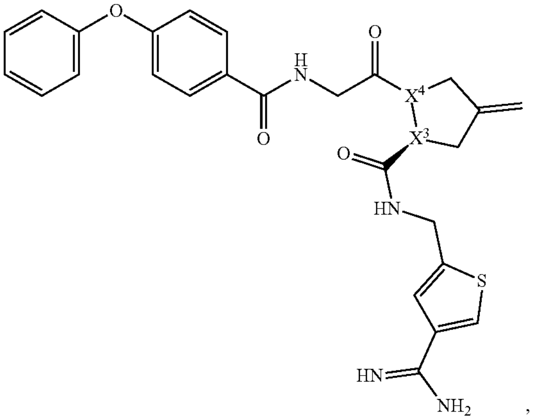
, and
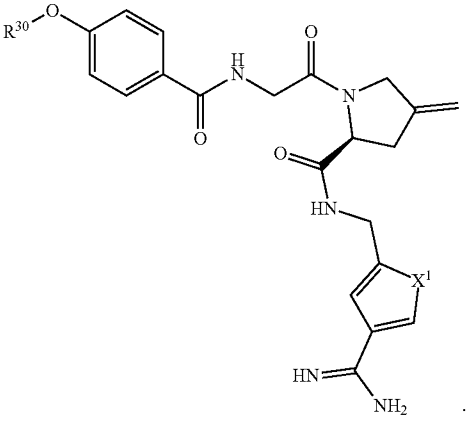
.
In one aspect, the compound of the present disclosure is selected from:
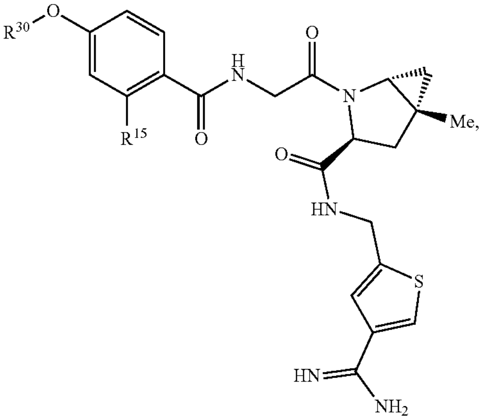
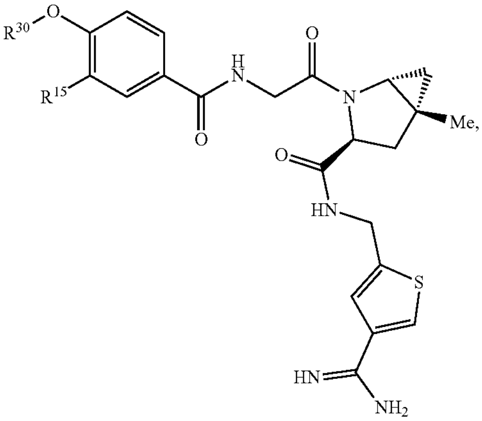
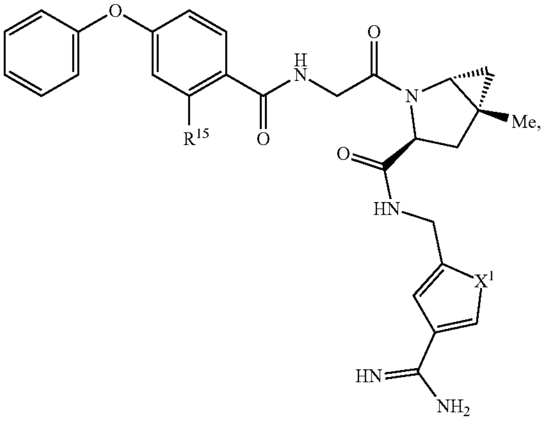

-continued
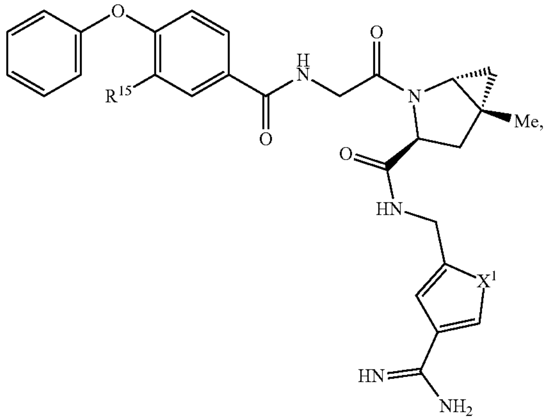
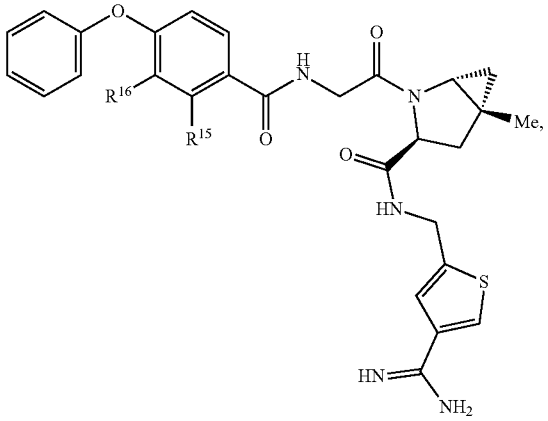
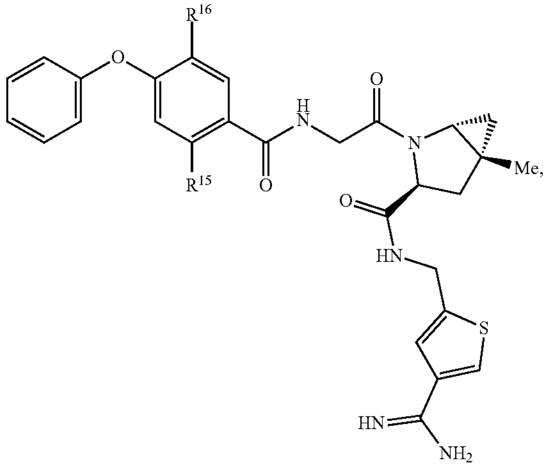
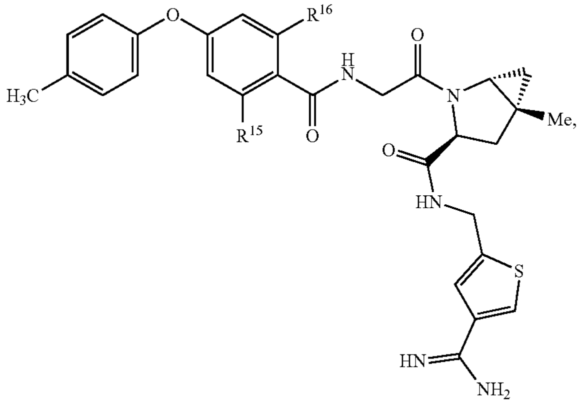
-continued
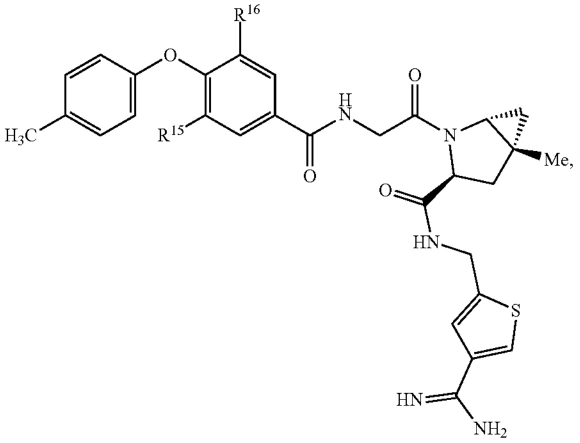
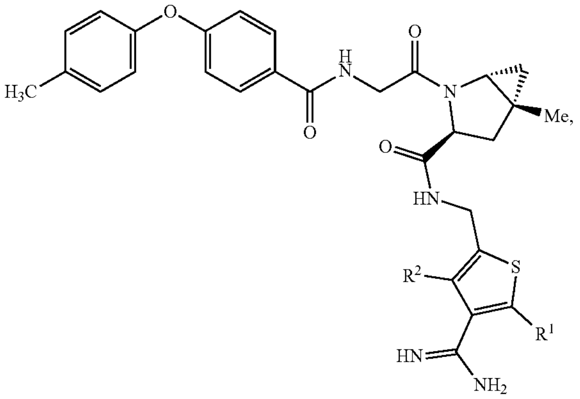
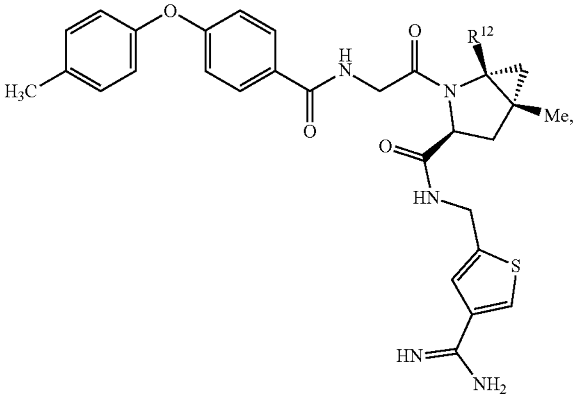
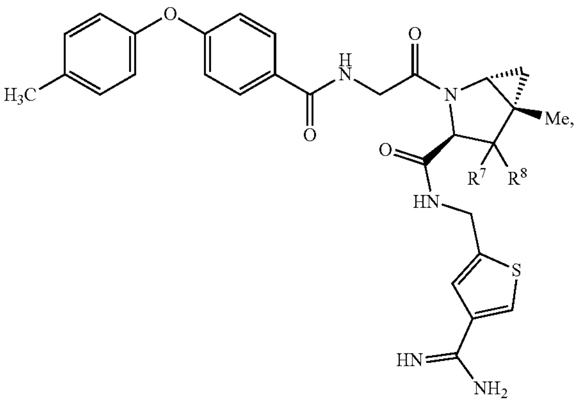

-continued
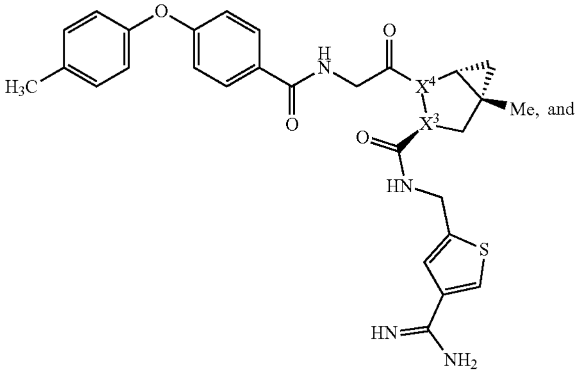
and
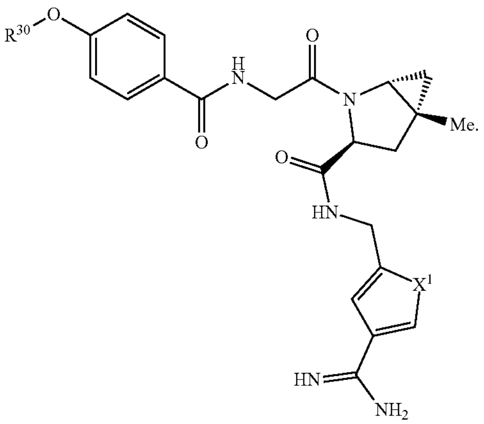
In one aspect, the compound of the present disclosure is selected from:
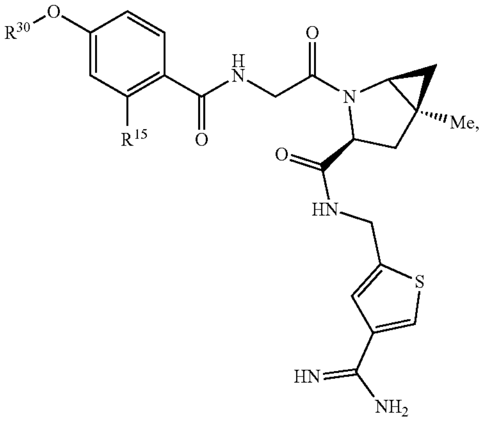
-continued
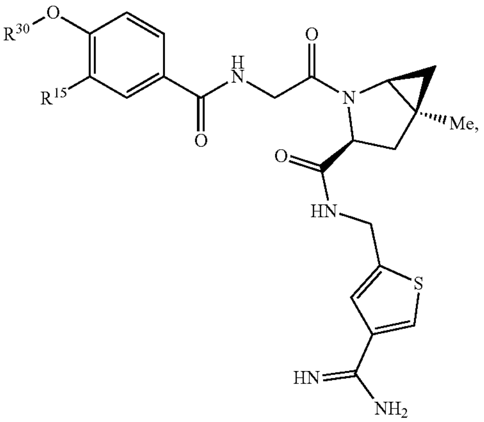
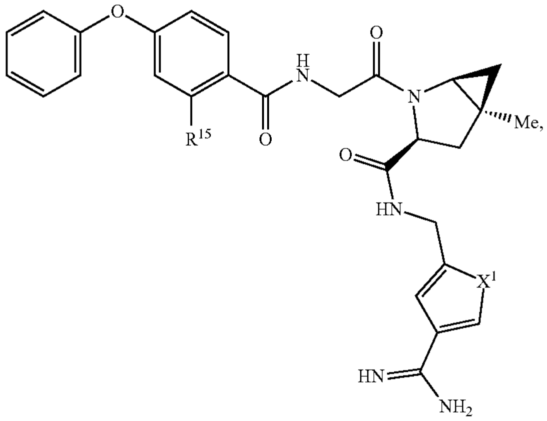
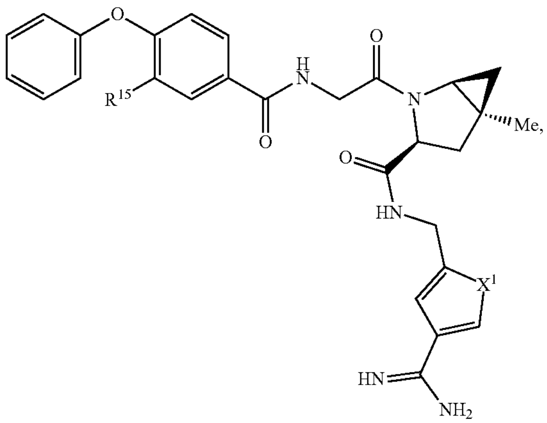
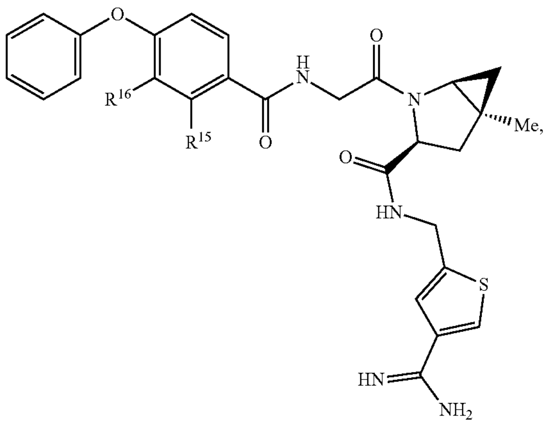

-continued
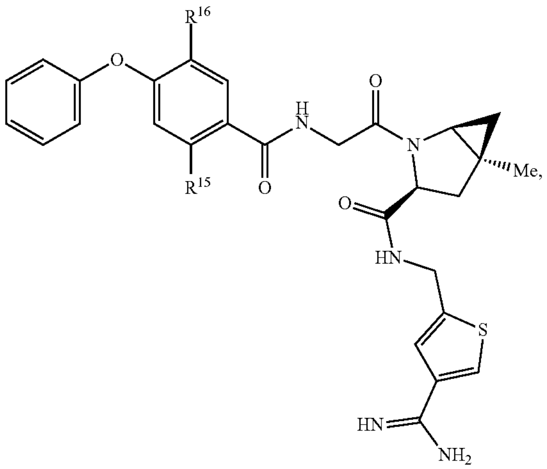
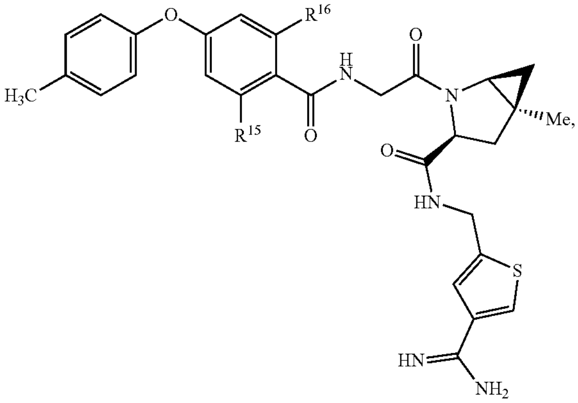
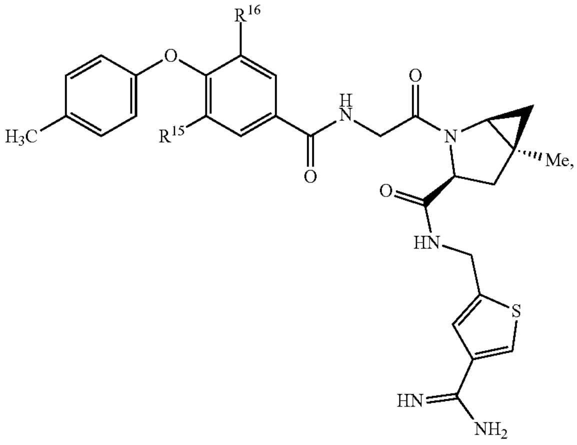
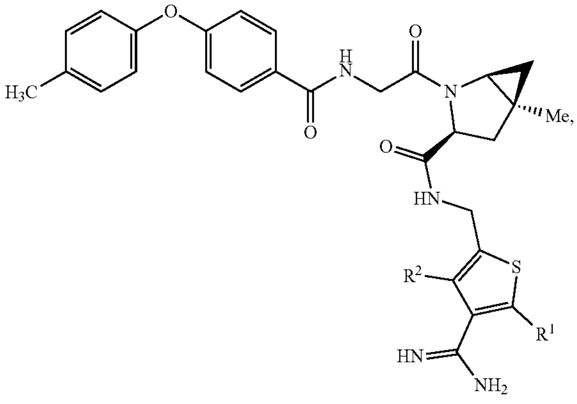
-continued
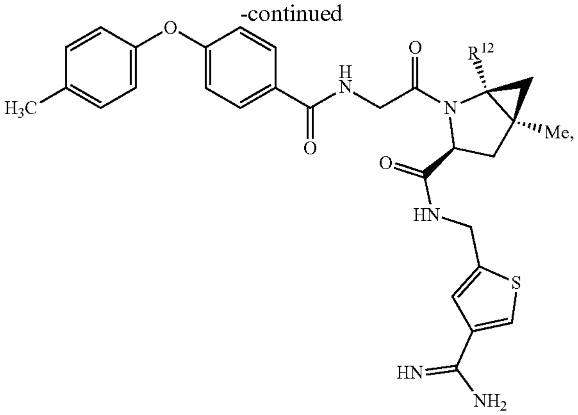
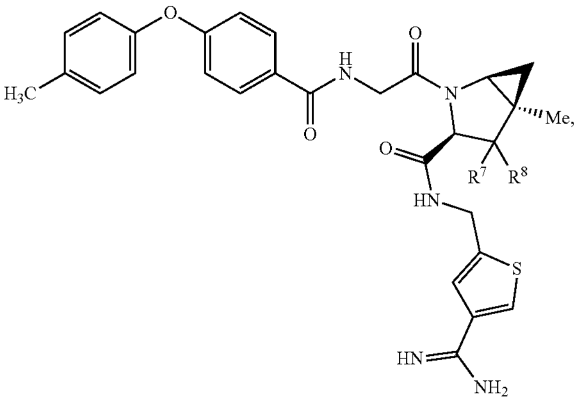
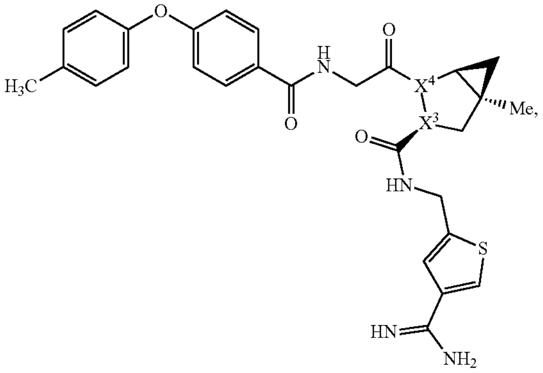
and
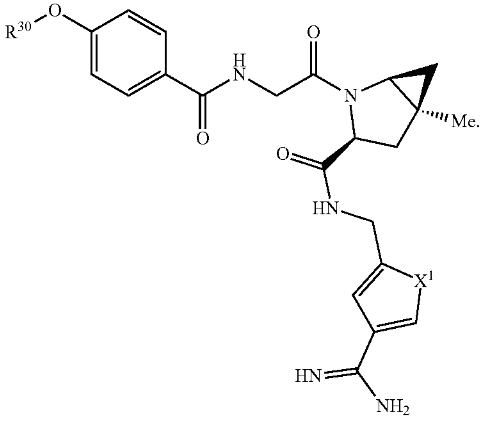
In one aspect, a compound of Formula I is provided selected from:

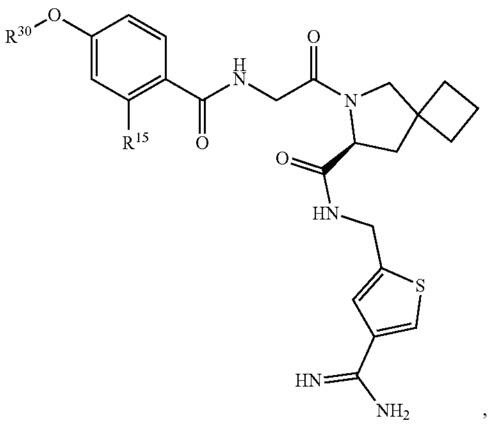
,
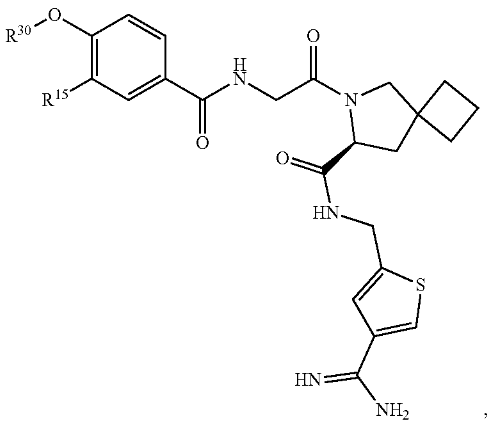
,
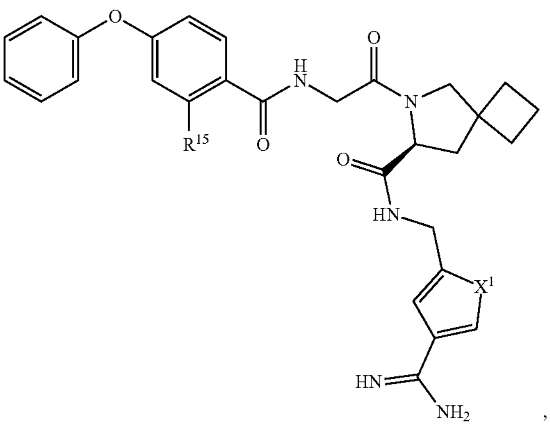
,
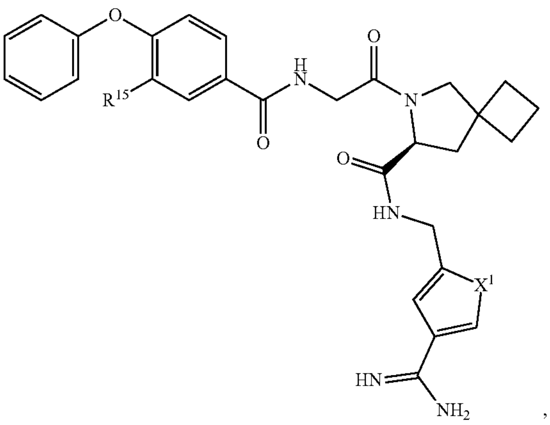
,
-continued
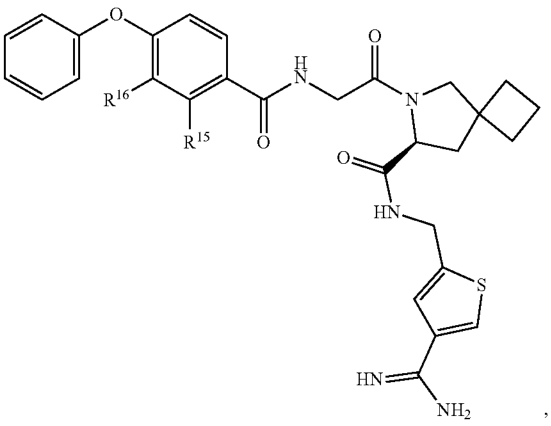
,
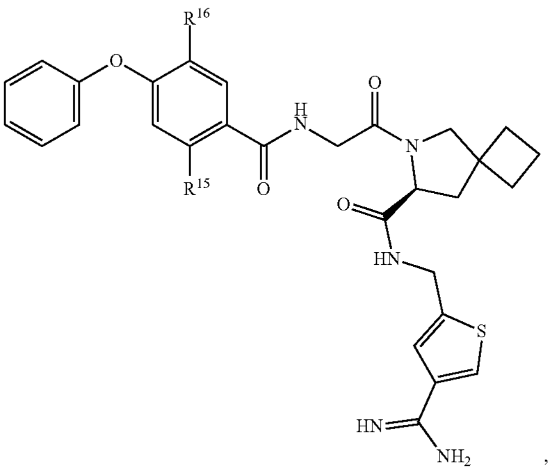
,
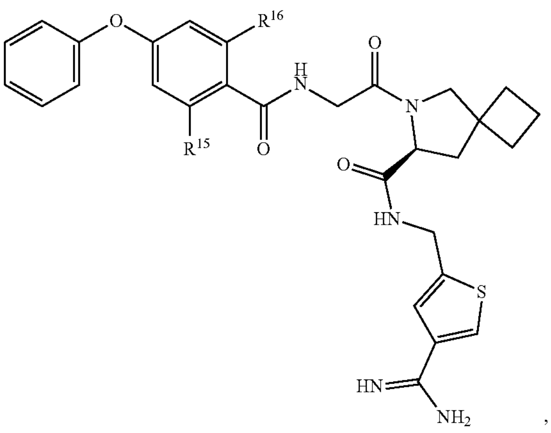
, -continued
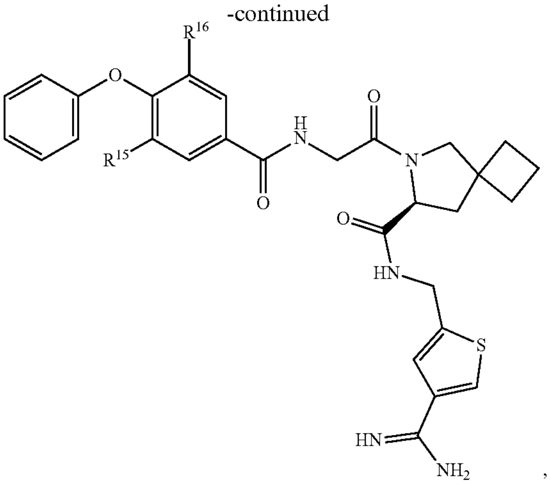
,
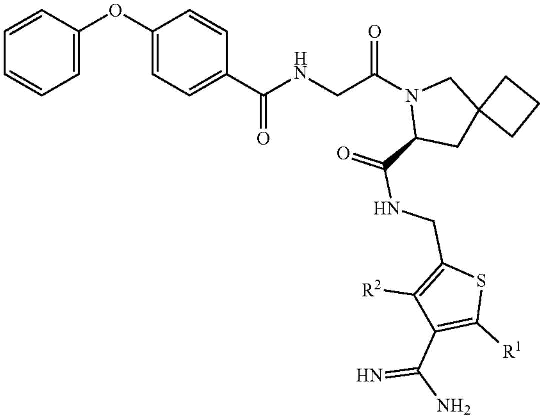
,
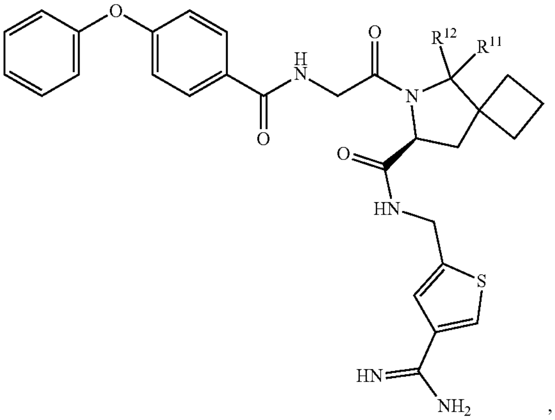
,
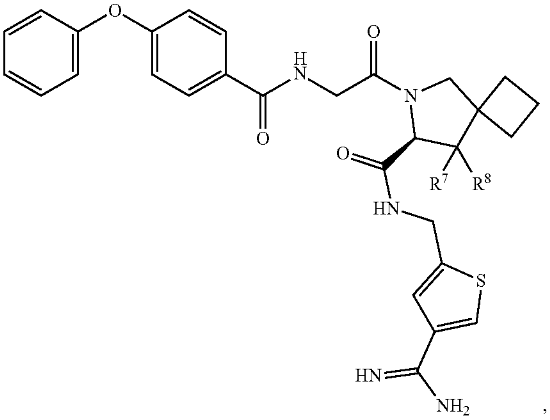
,
-continued
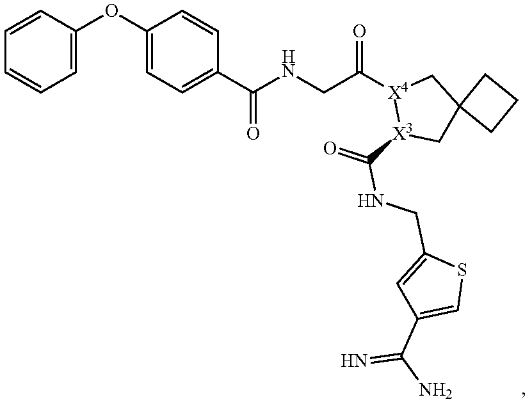
, and
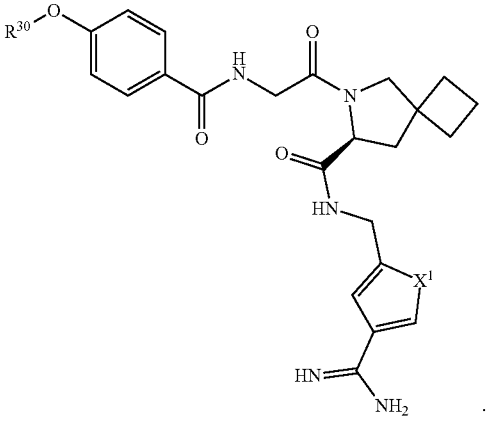
.
In one aspect, a compound of Formula I is provided selected from:
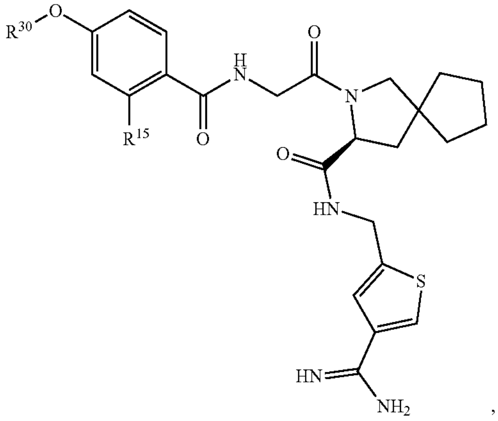
, -continued
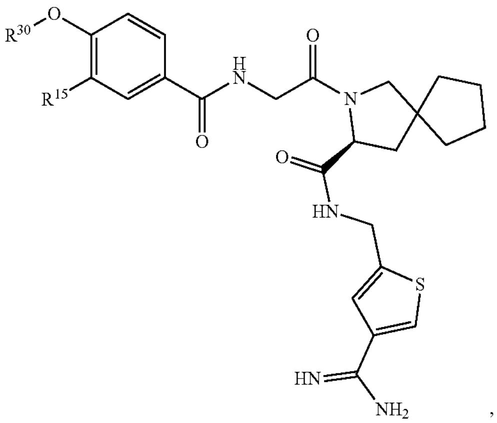
,
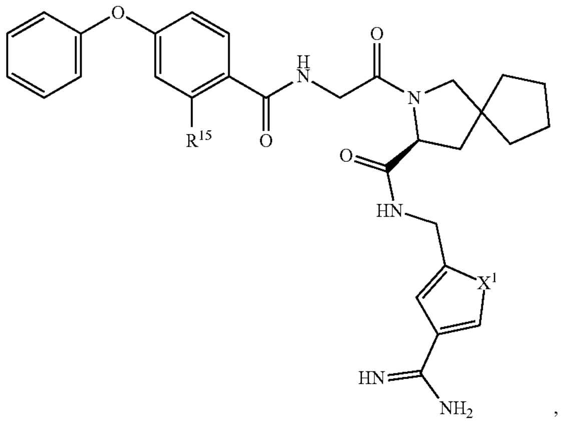
,
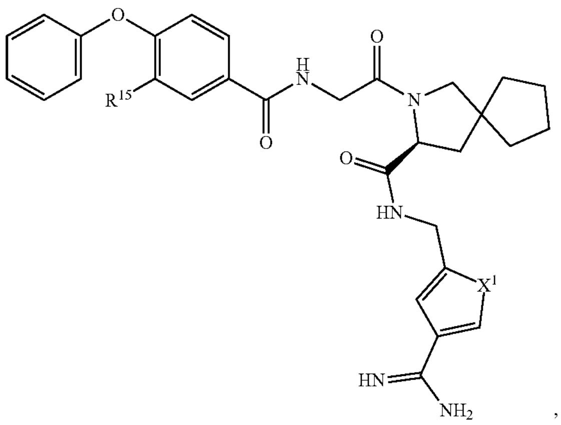
,
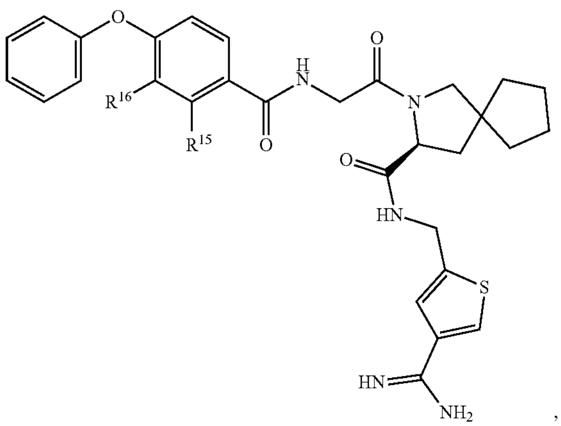
,
-continued
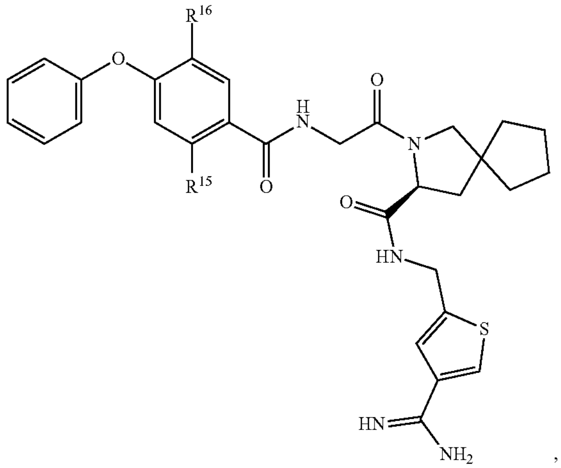
,
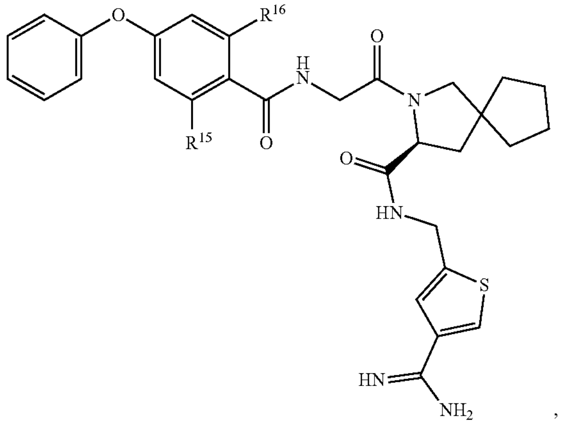
,
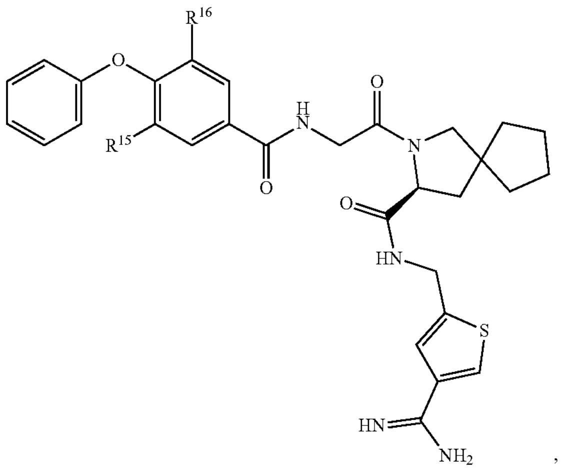
, -continued
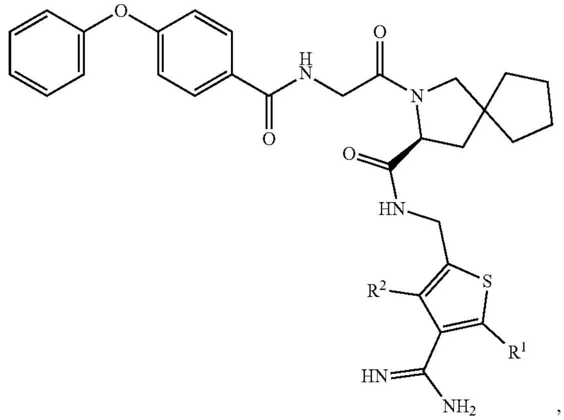
,
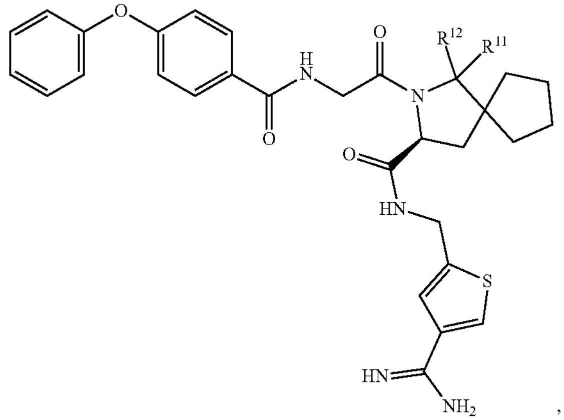
,
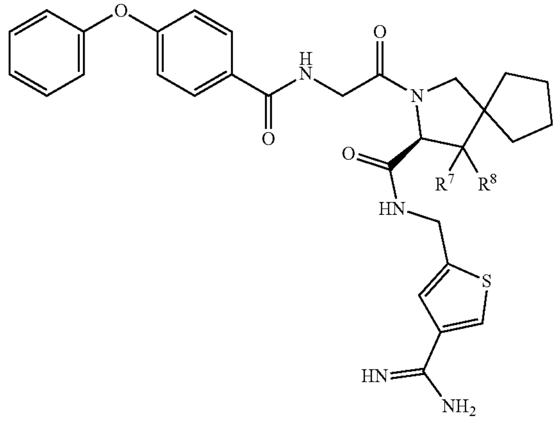
,
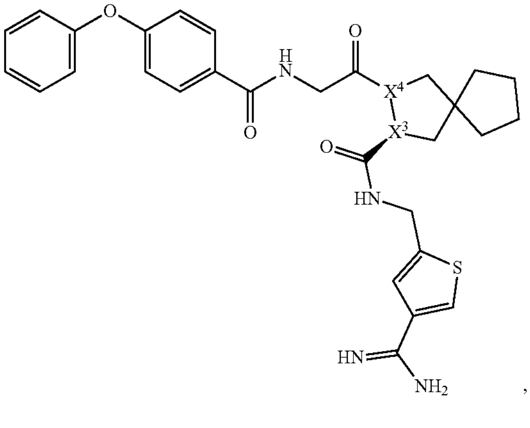
, and
-continued
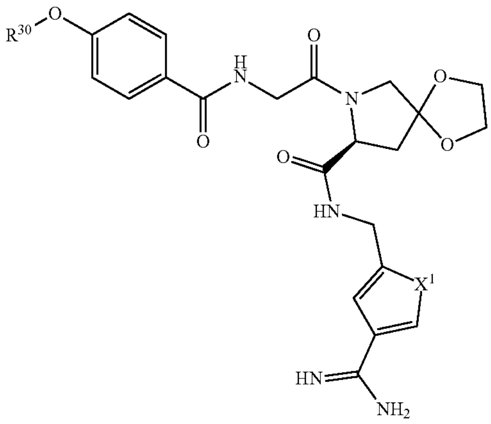
.
In one aspect, a compound of Formula I is provided selected from:
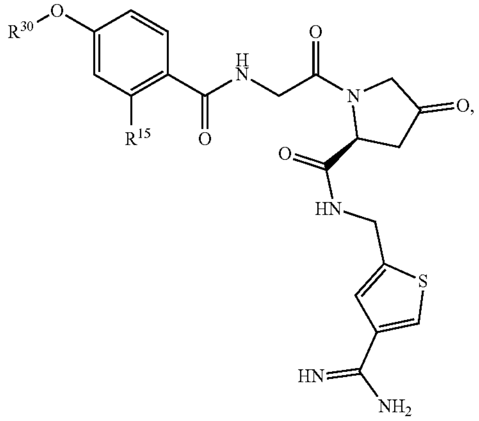
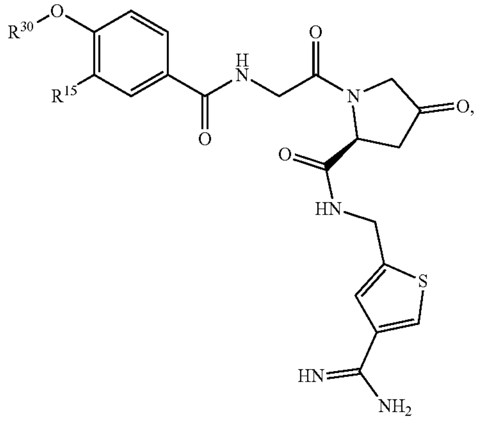

-continued
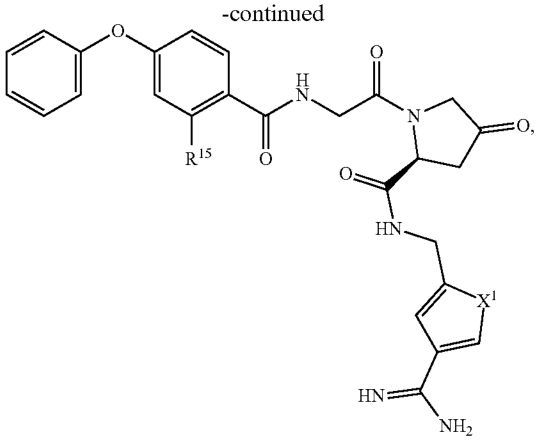
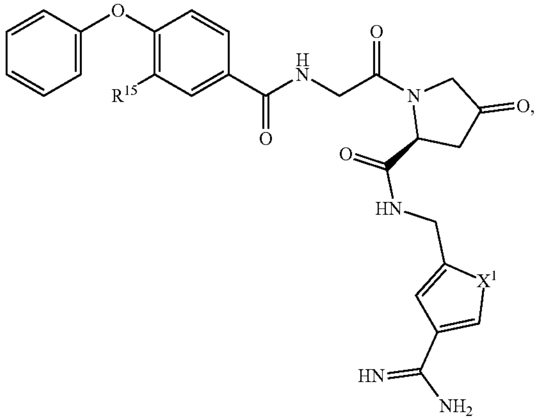
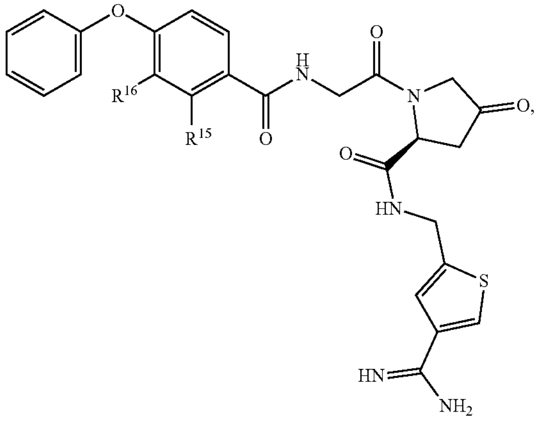
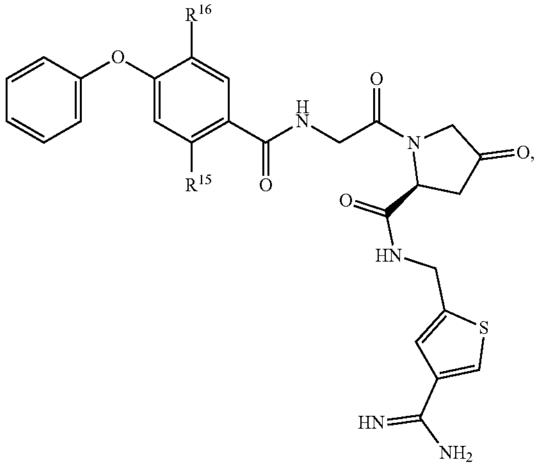
-continued
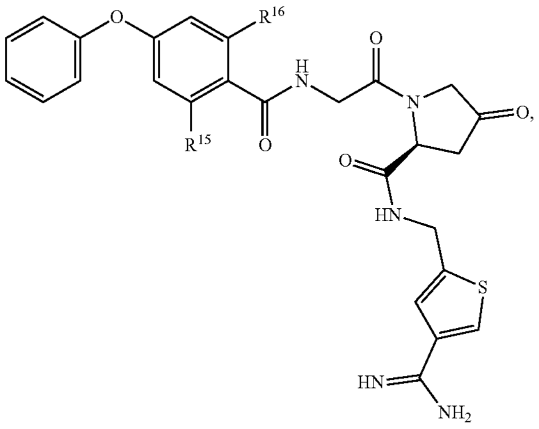
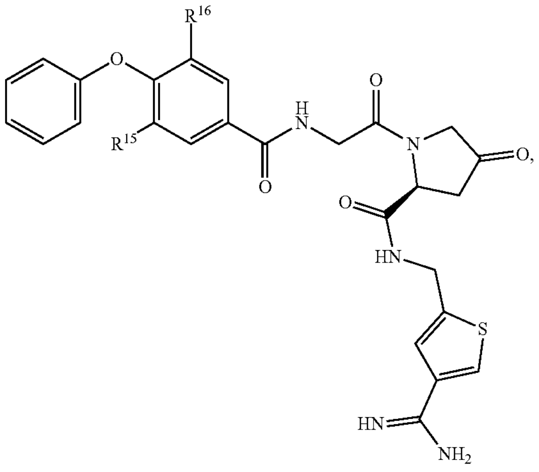
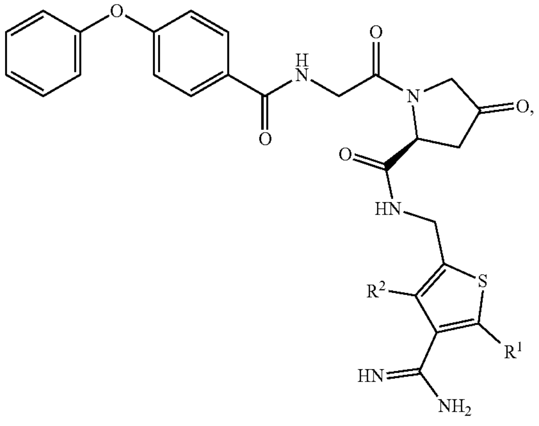

-continued
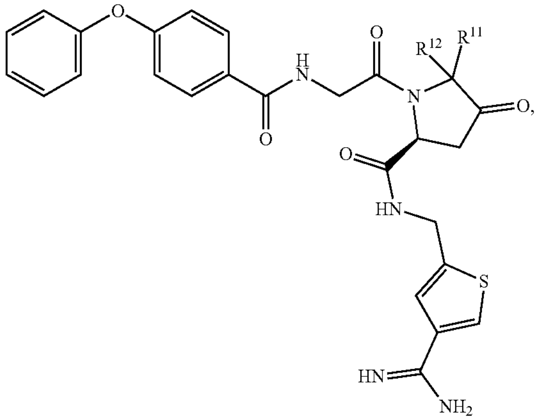
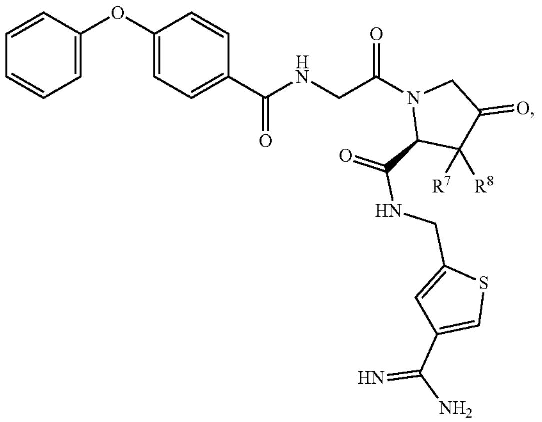
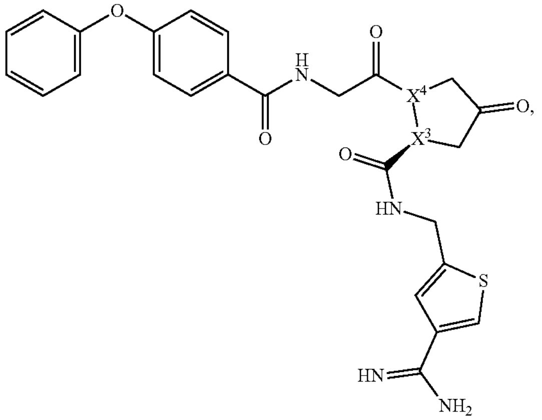
and
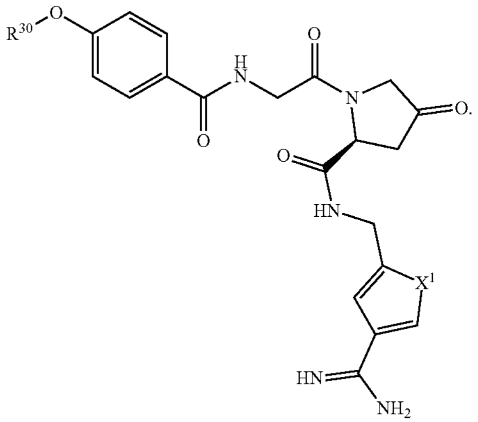
In one aspect, a compound of Formula I is provided selected from:
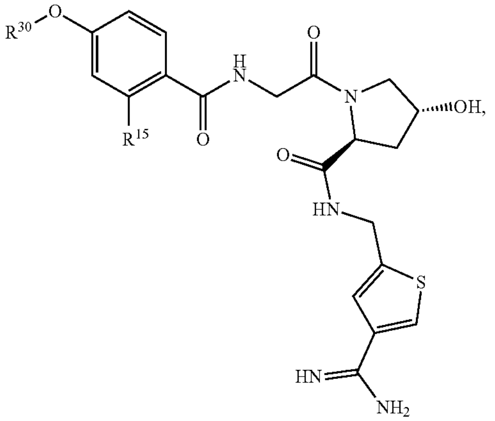
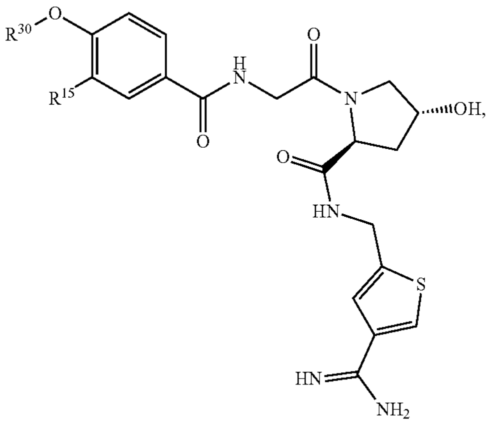
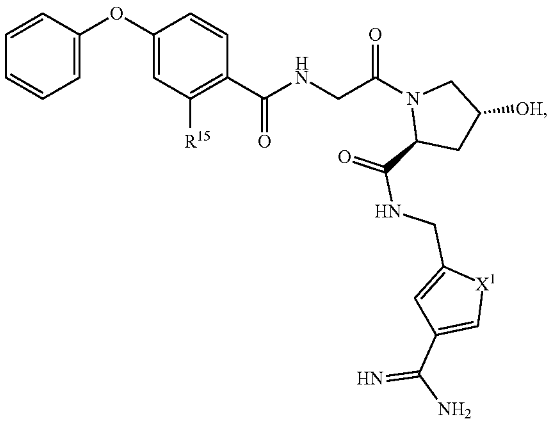

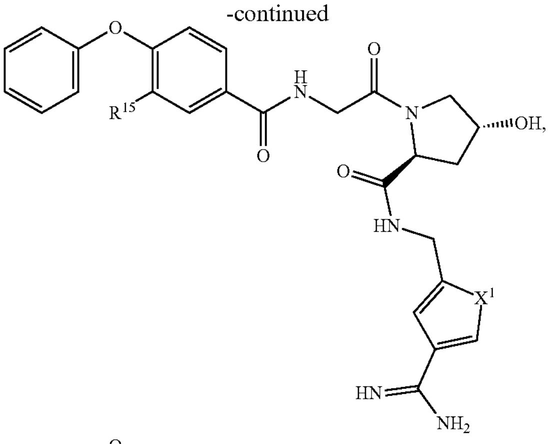
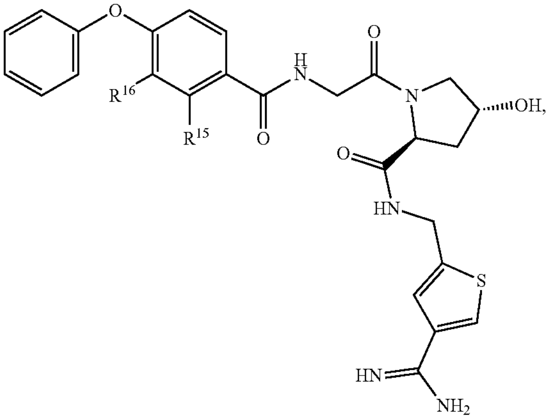
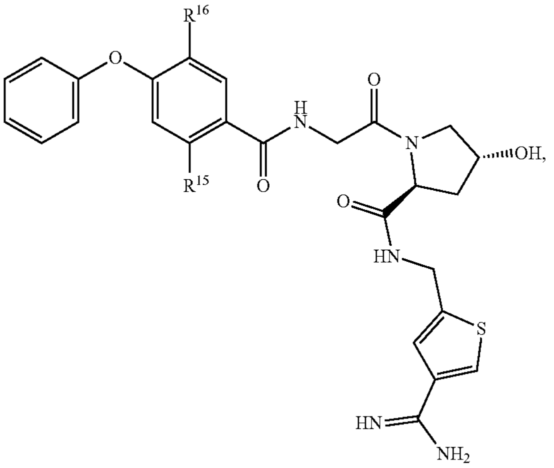
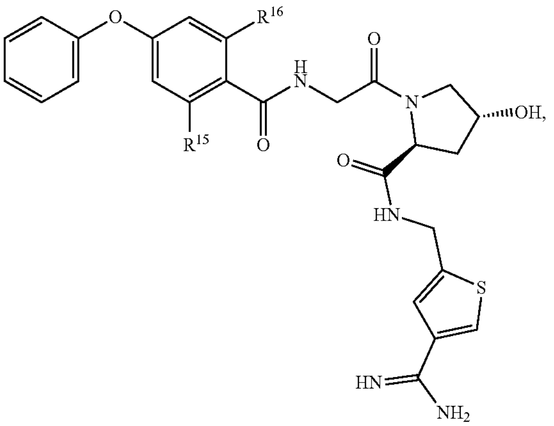
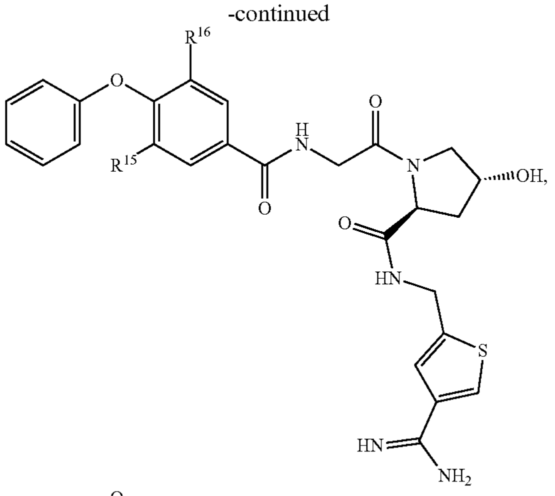
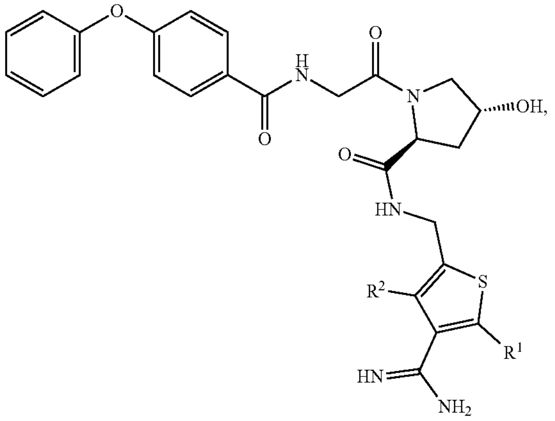
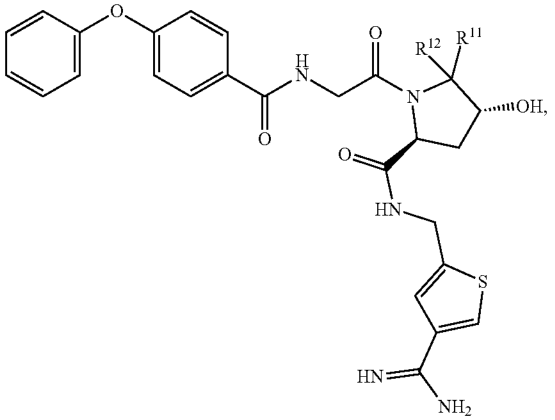
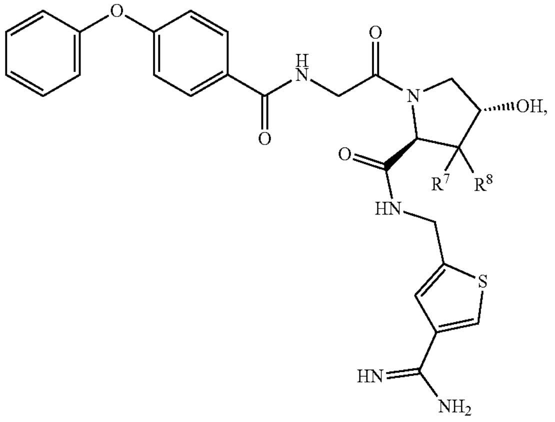

-continued
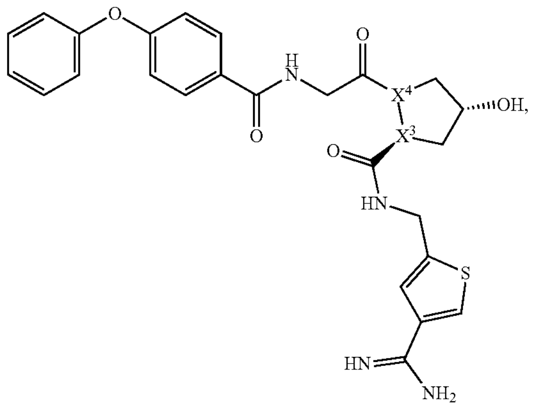
and
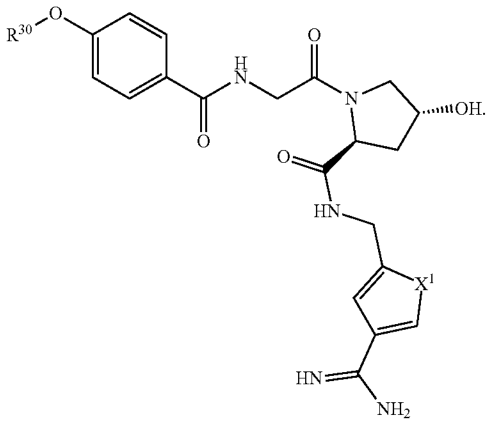
In one aspect, a compound of Formula I is provided selected from:
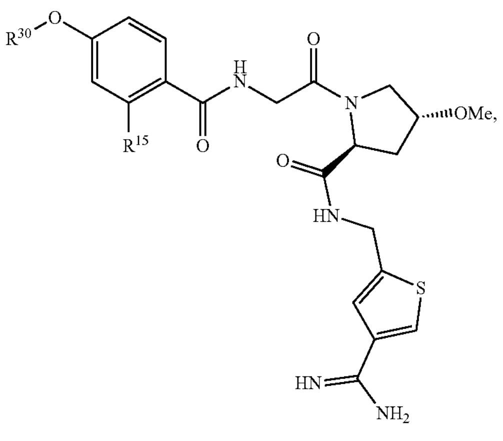
-continued
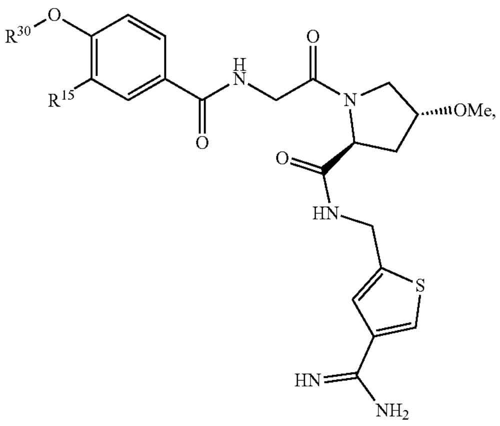
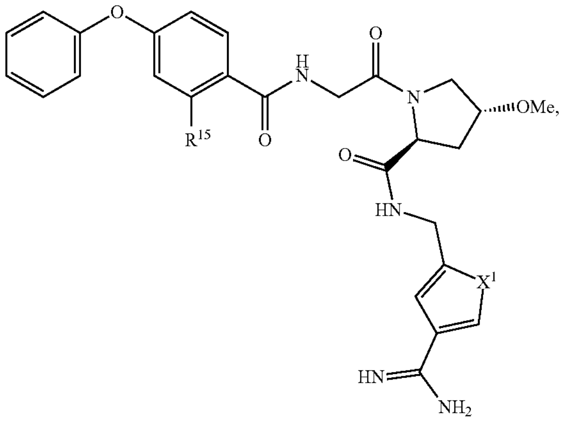
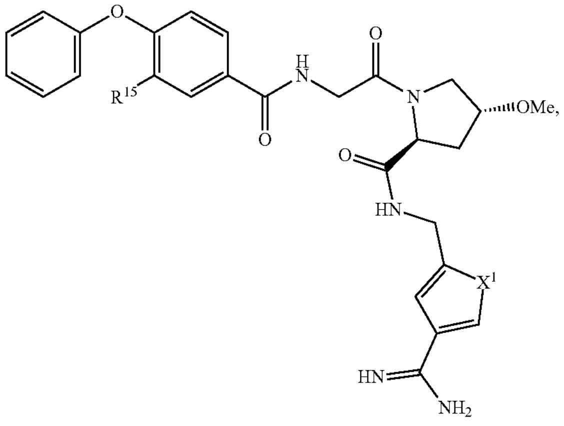
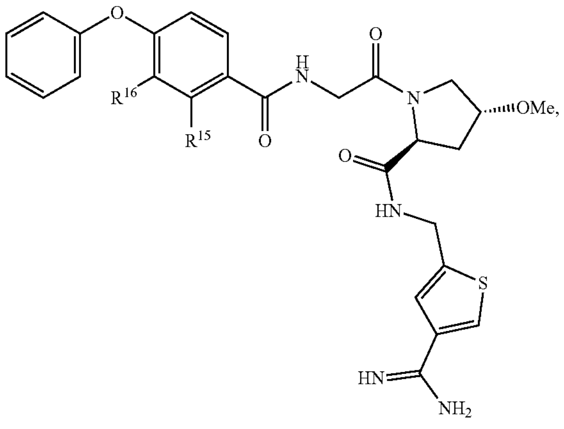

-continued
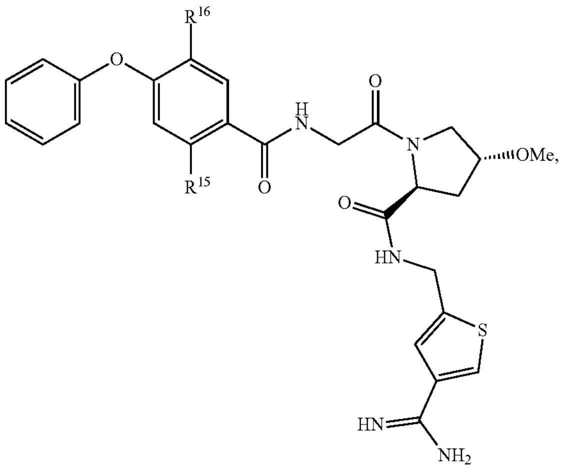
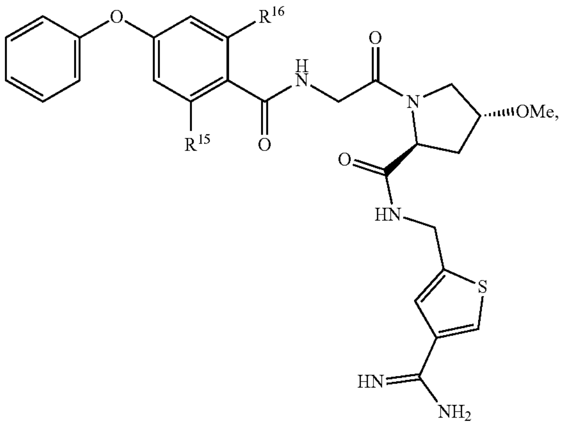
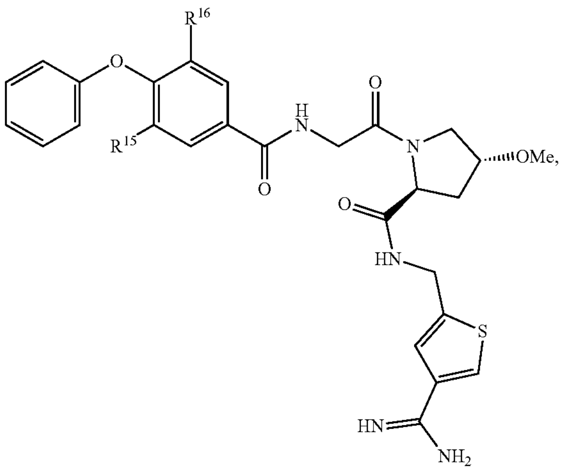
-continued
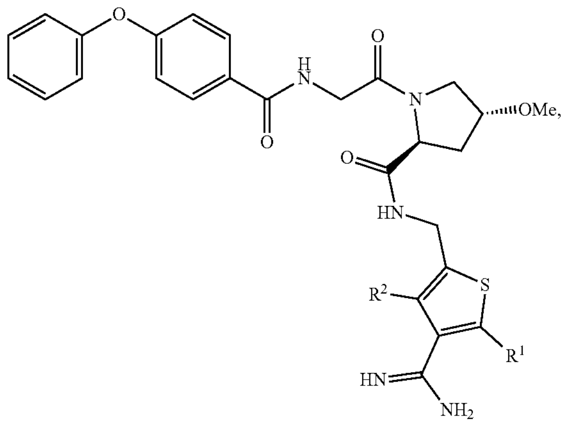
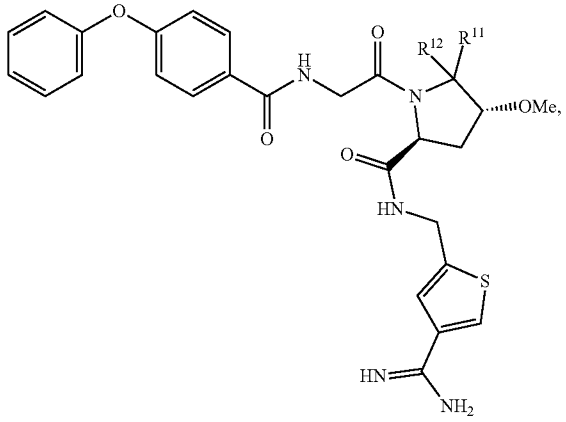
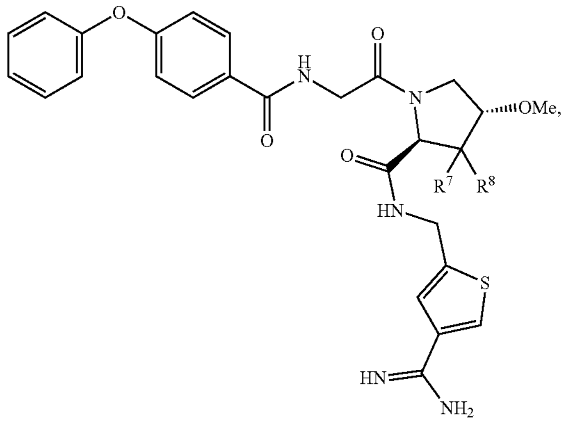
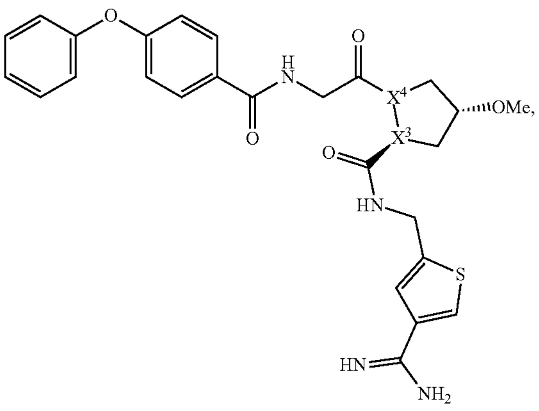
and -continued
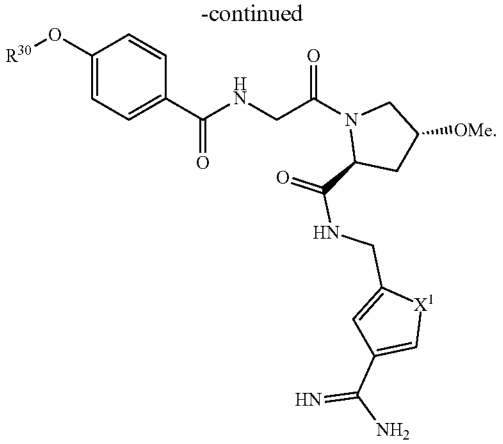
In one aspect, a compound of Formula IV is provided selected from:
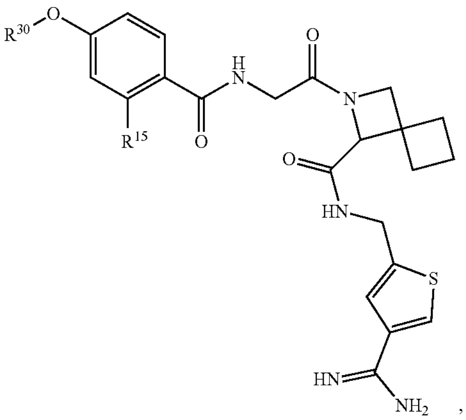
,
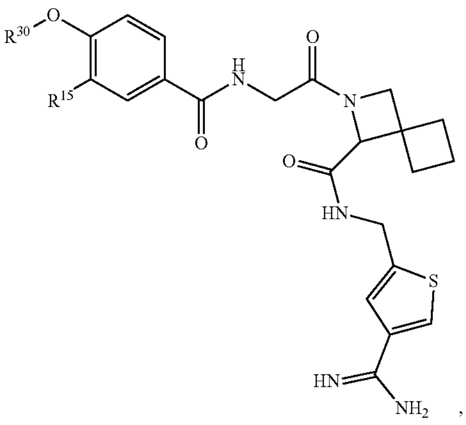
,
-continued
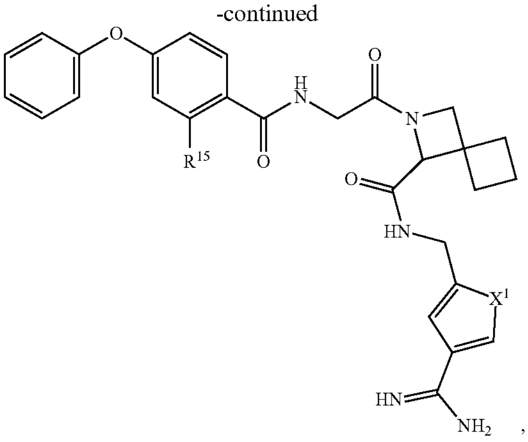
,
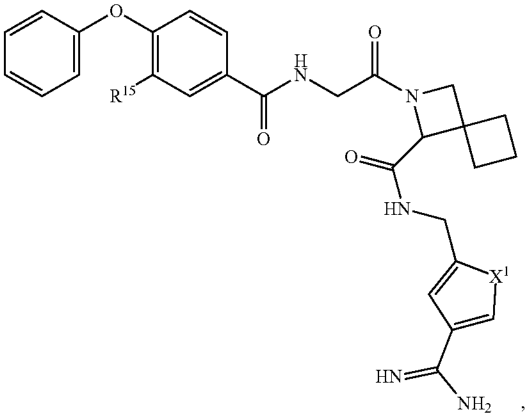
,
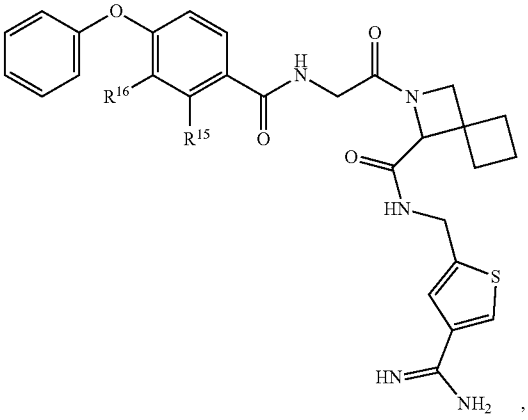
,
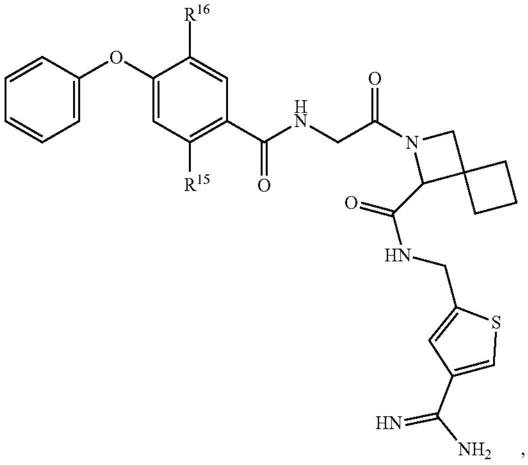
, -continued
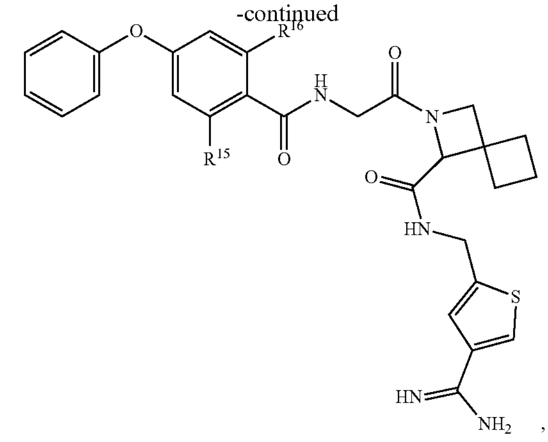
,
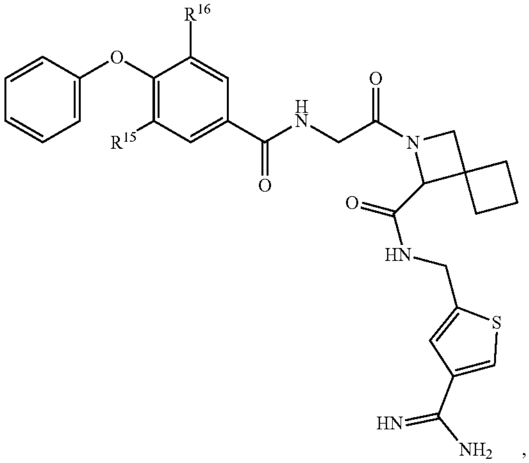
,
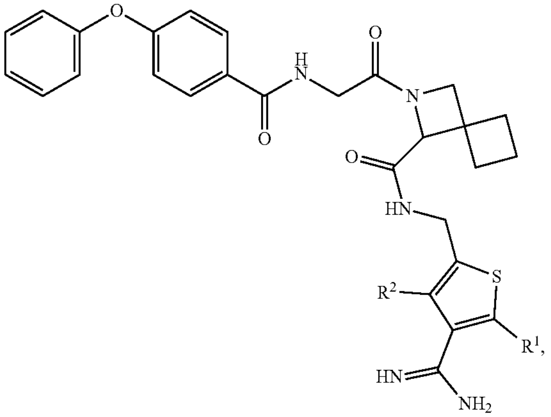
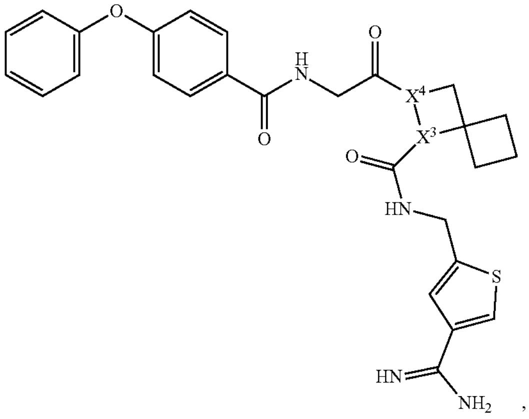
, and
-continued
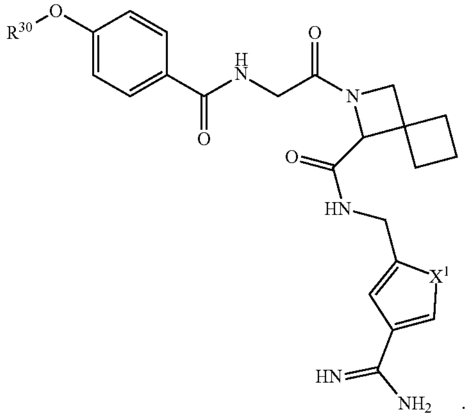
.
In one aspect, a compound of Formula V is provided selected from:
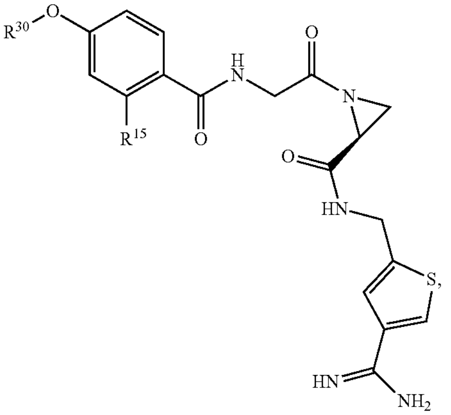
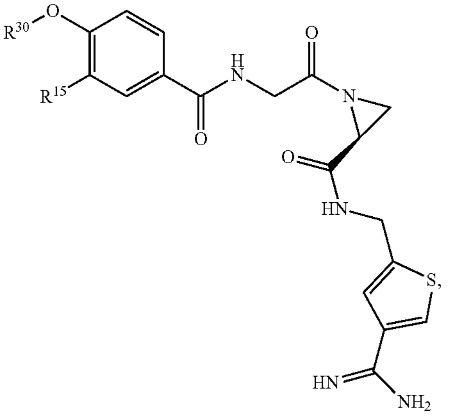

-continued
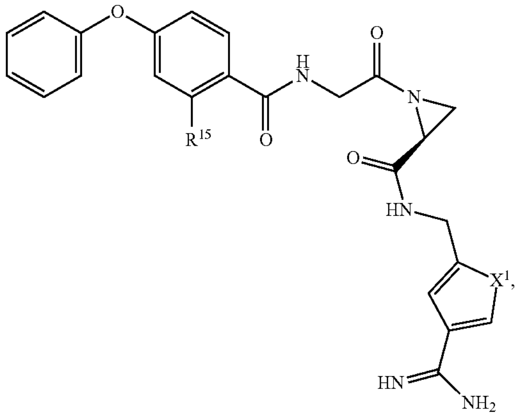
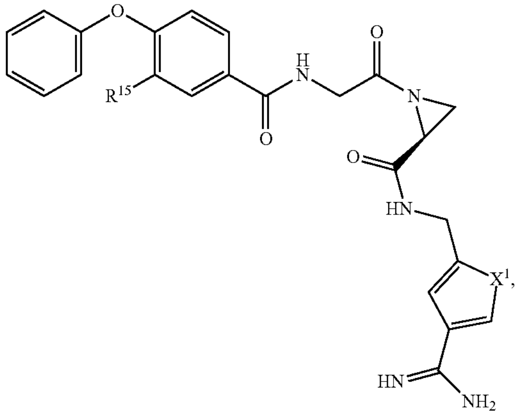
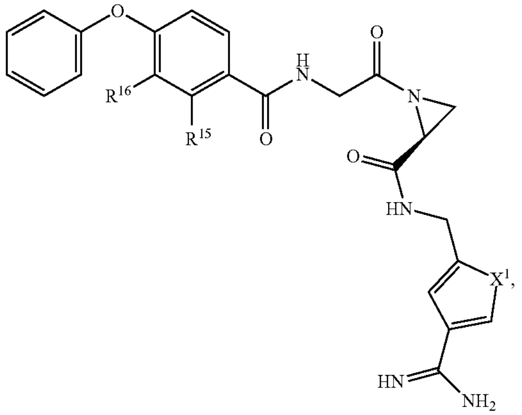
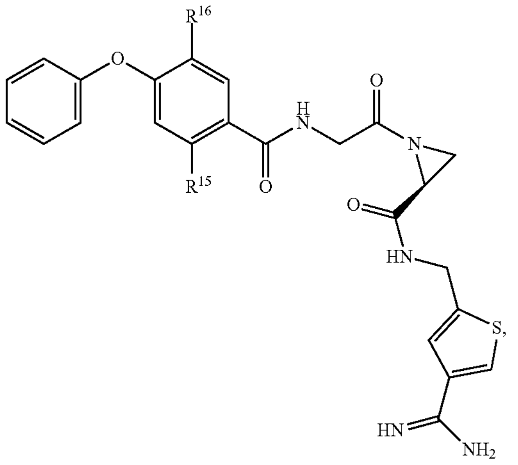
-continued
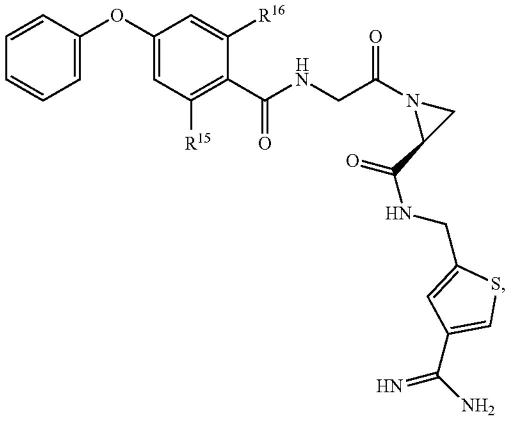
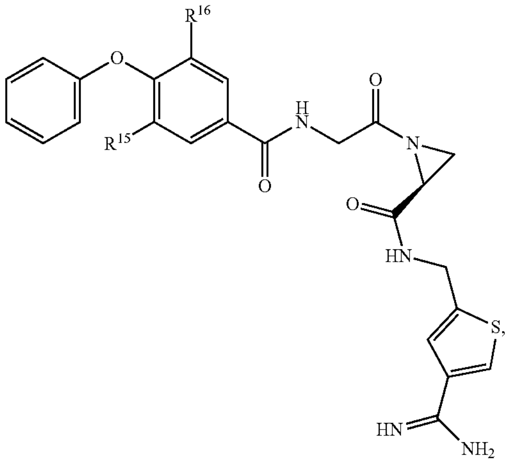
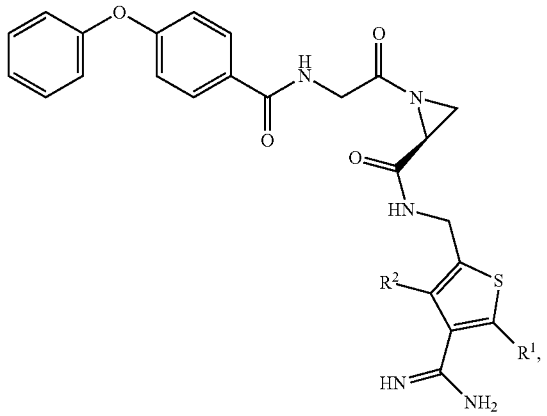
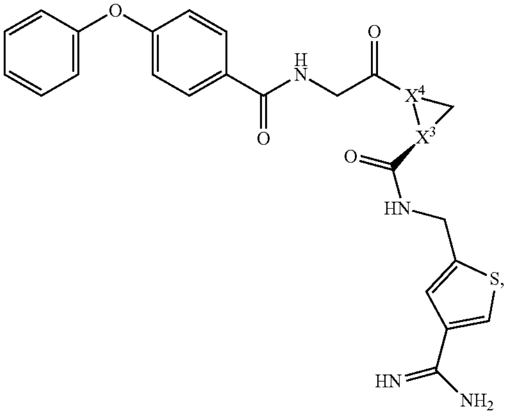
and -continued
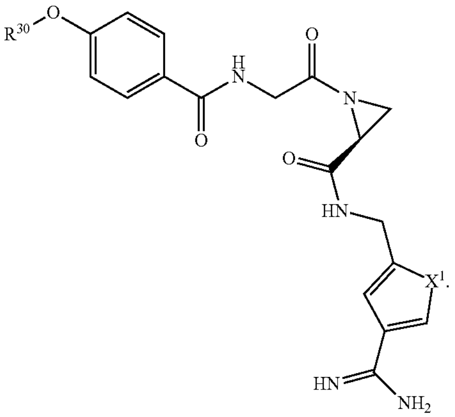
In another aspect, the compound of Formula I is selected from:
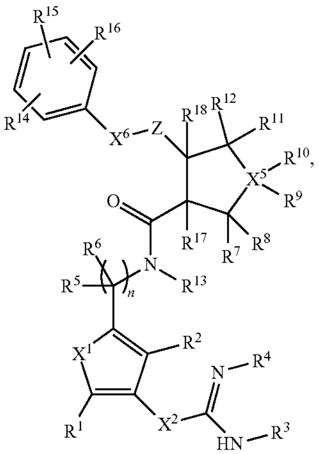
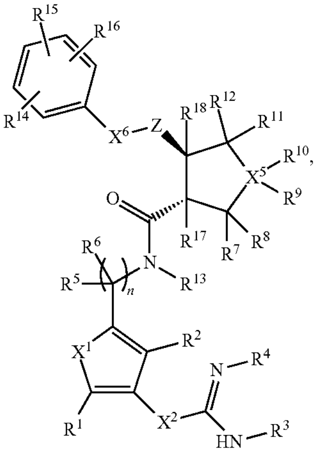
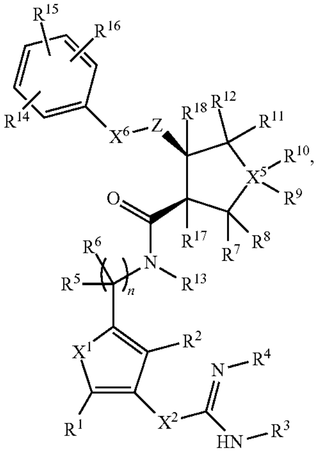
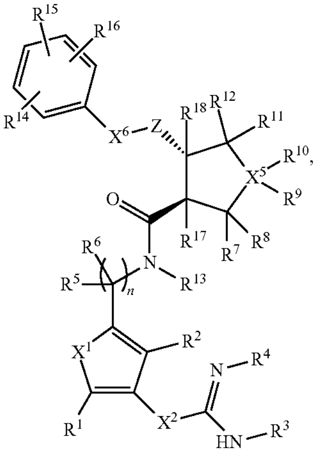
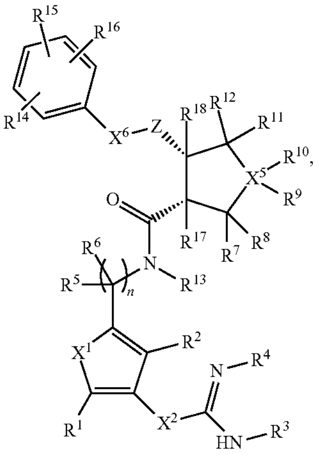

-continued
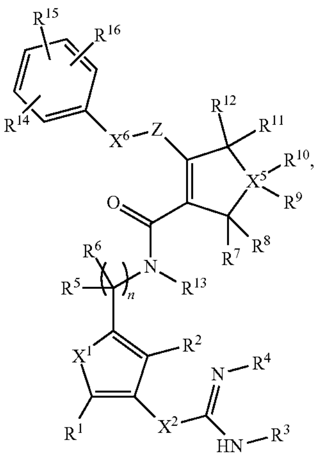
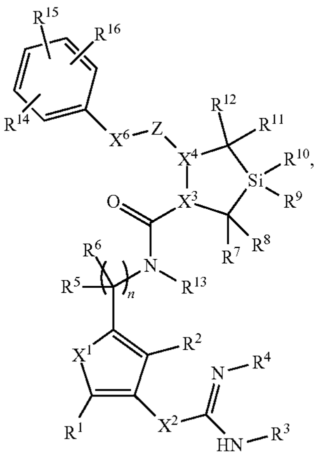
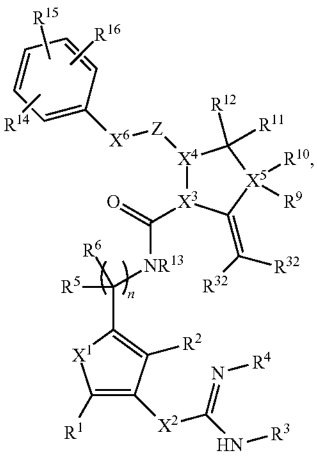
-continued
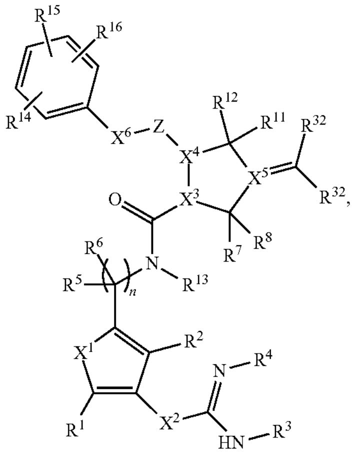
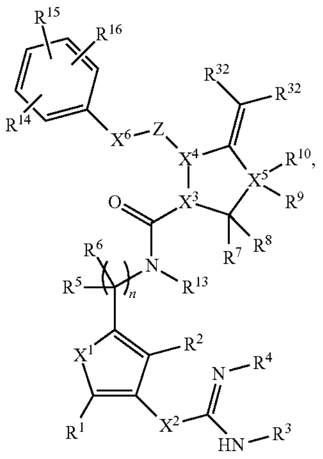
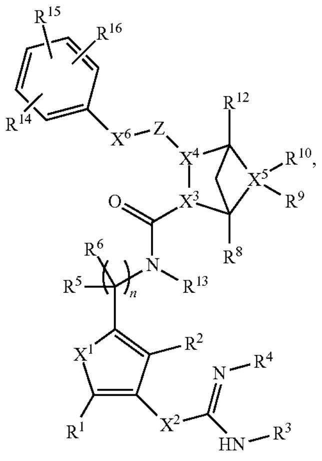
and -continued

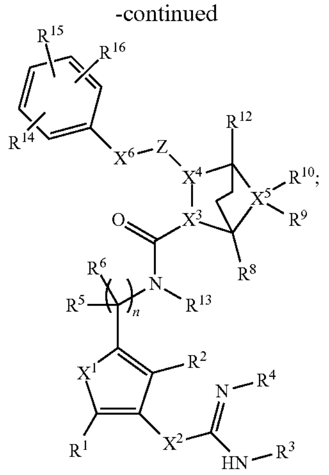

or a pharmaceutically acceptable salt, isotopic analog, prodrug, or isolated isomer thereof, optionally in pharmaceutically acceptable carrier; wherein all variables are as defined herein.

In another aspect, the compound of Formula I is selected from:

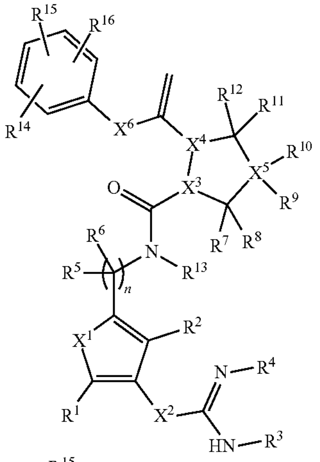

and

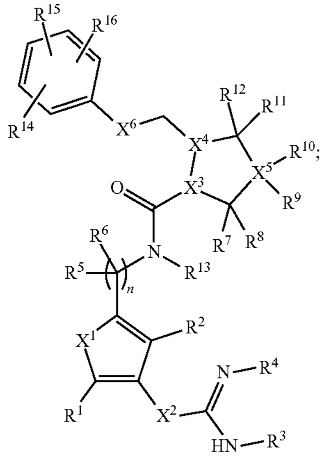

or a pharmaceutically acceptable salt, isotopic analog, prodrug, or isolated isomer thereof, optionally in pharmaceutically acceptable carrier; wherein all variables are as defined herein.

In another aspect the compound of Formula I is selected from:

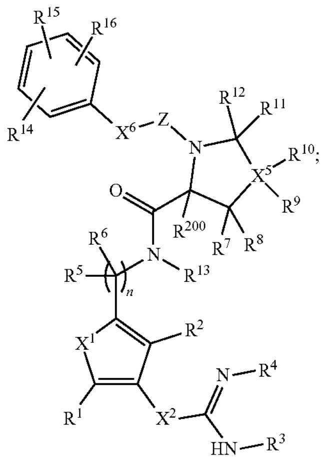

or a pharmaceutically acceptable salt, isotopic analog, prodrug, or isolated isomer thereof, optionally in pharmaceutically acceptable carrier;

wherein:

$R^{200}$ is selected from halogen, $C_1$-$C_6$alkyl, $C_1$-$C_6$haloalkyl, —$OR^{30}$, and —$N(R^{30})$; and all other variables are as defined herein.

In another aspect, the compound of Formula I is selected from:

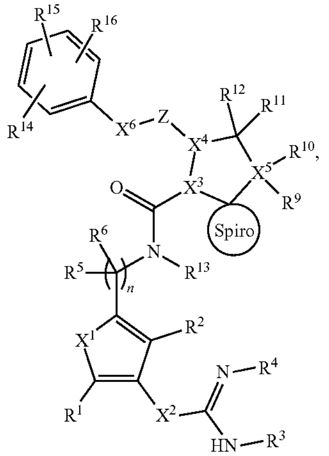

-continued
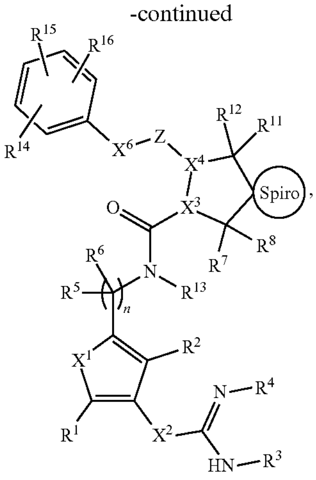
, and
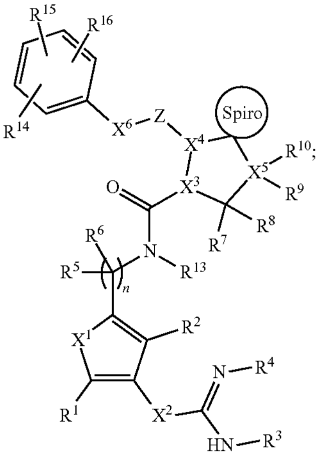
;
or a pharmaceutically acceptable salt, isotopic analog, prodrug, or isolated isomer thereof, optionally in pharmaceutically acceptable carrier;
wherein:
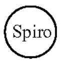
is selected from a 3- to 6-membered carbocyclic ring and a 4- to 6-membered heterocyclic ring containing 1 or 2 heteroatoms independently chosen from N, O, and S; for example
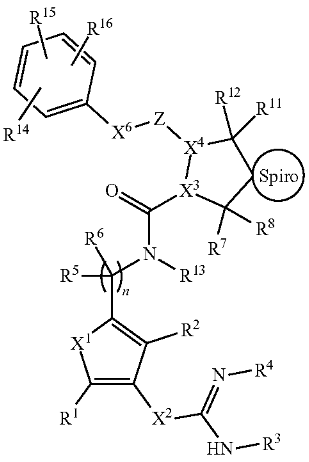
can be selected from
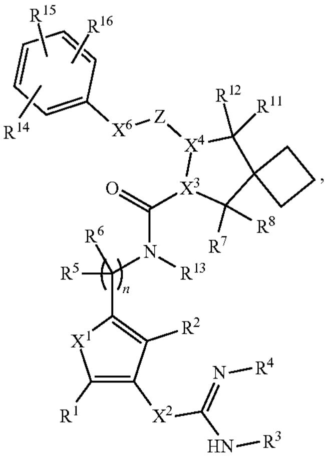
,
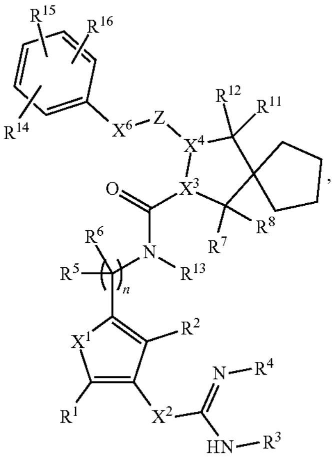
, and -continued

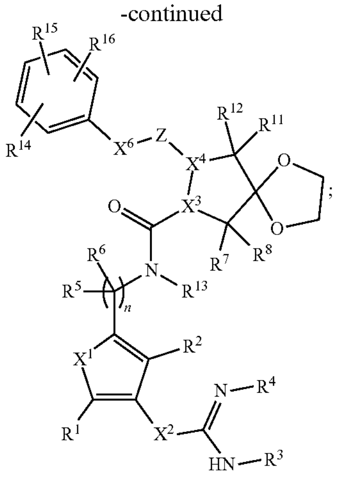

in an alternative embodiment

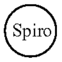

is optionally substituted with 1, 2, 3, or 4 substituents independently selected from halogen, $C_1$-$C_6$alkyl, $C_1$-$C_6$haloalkyl, —$OR^{30}$, and —$N(R^{30})_2$;

all other variables are as defined herein.

In another aspect, the compound of Formula I is selected from:

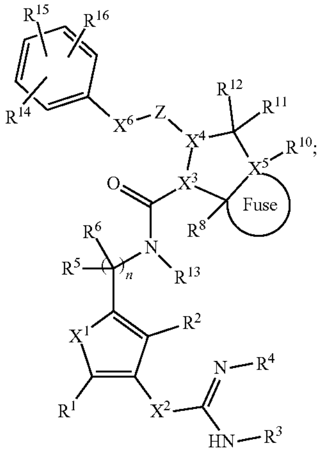

or a pharmaceutically acceptable salt, isotopic analog, prodrug, or isolated isomer thereof, optionally in pharmaceutically acceptable carrier;

wherein:

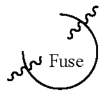

is a 3- to 8-membered carbocycle or a 4- to 8-membered heterocycle containing 1 or 2 heteroatoms independently chosen from N, O, and S; for example, in one embodiment,

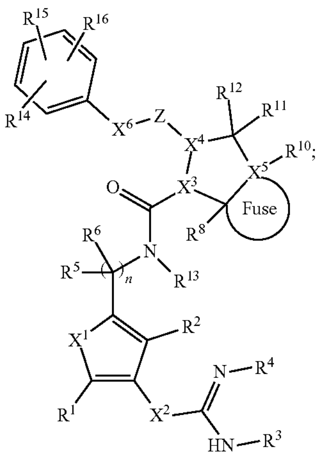

can be selected from

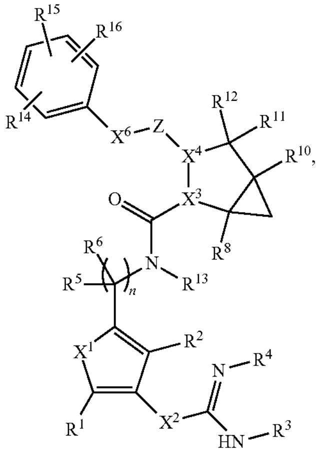

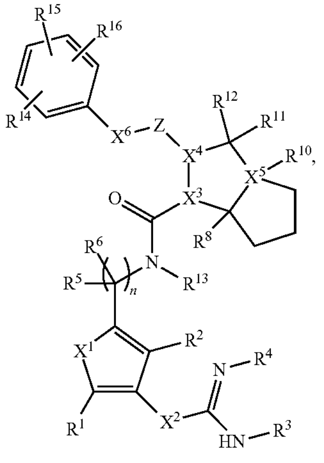

and

-continued

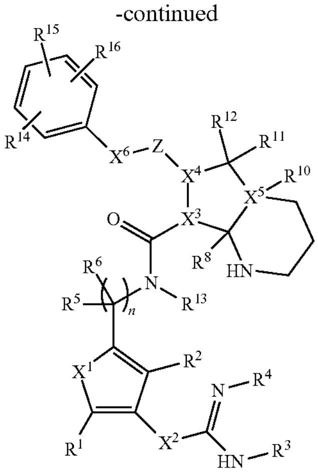

;

wherein in this aspect at least one of $R^8$ and $R^{10}$ is not hydrogen; and all other variables are as defined herein.

In another aspect, the compound of Formula I is selected from:

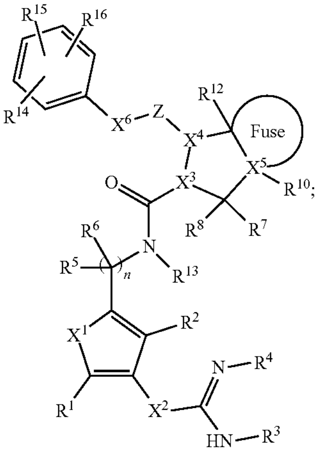

;

or a pharmaceutically acceptable salt, isotopic analog, prodrug, or isolated isomer thereof, optionally in pharmaceutically acceptable carrier;

wherein:

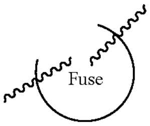

is a 3- to 8-membered carbocycle or a 4- to 8-membered heterocycle containing 1 or 2 heteroatoms independently chosen from N, O, and S; for example, in one embodiment;

wherein in this aspect at least one of $R^{10}$ and $R^{12}$ is not hydrogen; and all other variables are as defined herein.

In an alternative embodiment, the compound of the present disclosure is selected from:

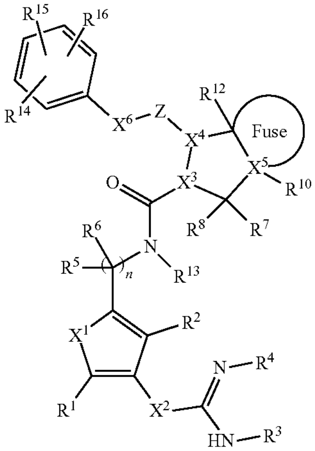

and

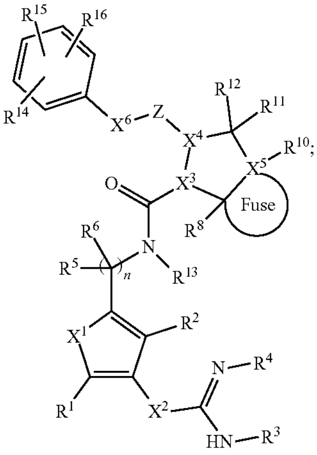

;

or a pharmaceutically acceptable salt, isotopic analog, prodrug, or isolated isomer thereof, optionally in pharmaceutically acceptable carrier;

wherein:

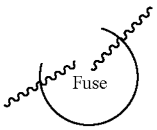

is a 3- to 8-membered carbocycle or a 4- to 8-membered heterocycle containing 1 or 2 heteroatoms independently chosen from N, O, and S, wherein

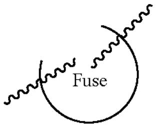

is substituted with 1, 2, 3, or 4 substituents selected from halogen, $C_1$-$C_6$alkyl, $C_1$-$C_6$haloalkyl, —$OR^{30}$, and —$N(R^{30})_2$; and all other variables are as defined herein.

In another aspect, the compound of Formula X is selected from:

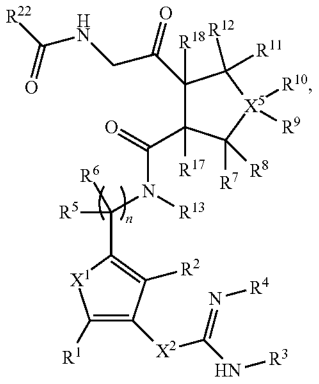
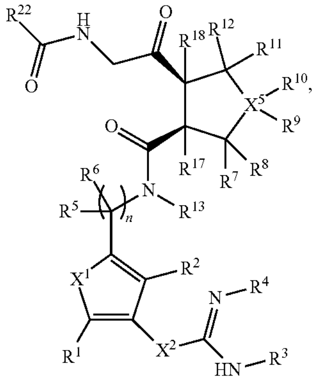
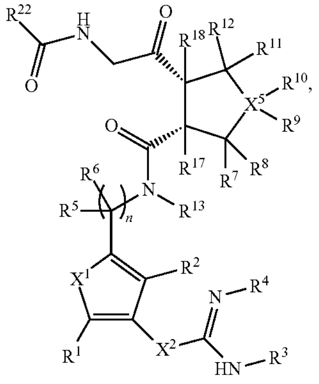
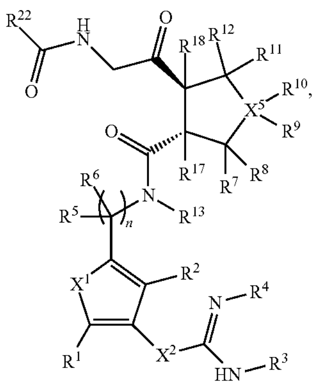
-continued
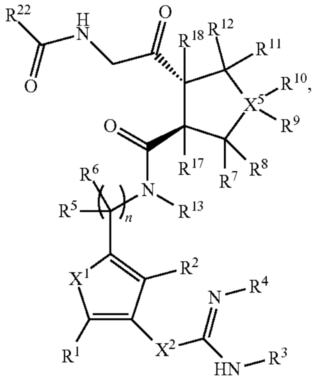
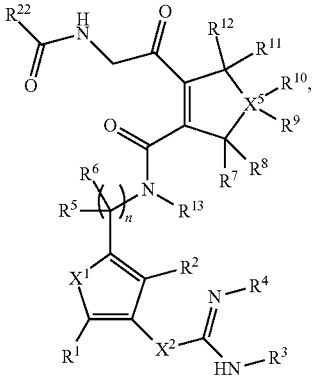
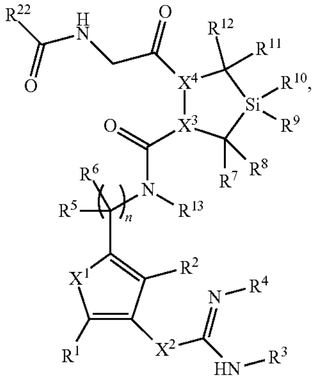
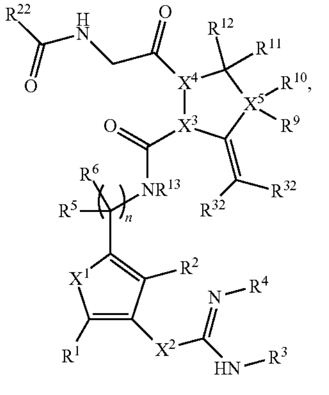

-continued

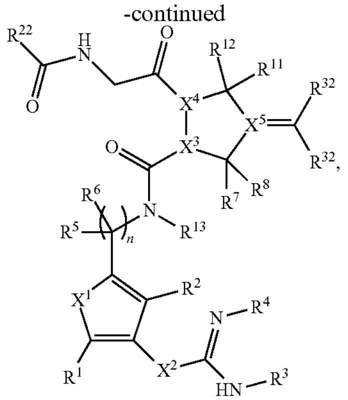

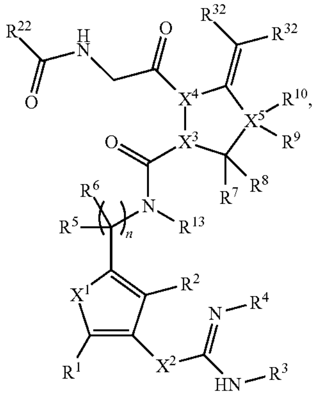

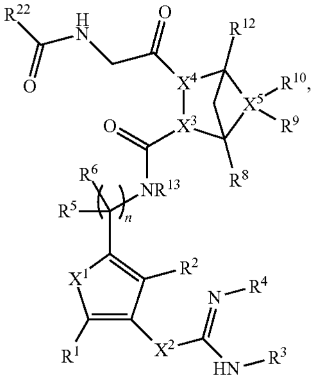

and

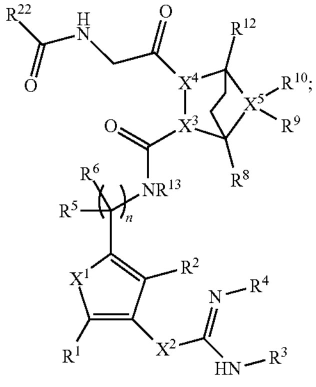

or a pharmaceutically acceptable salt, isotopic analog, prodrug, or isolated isomer thereof, optionally in pharmaceutically acceptable carrier; wherein all variables are as defined herein.

In another aspect, the compound of Formula X is selected from:

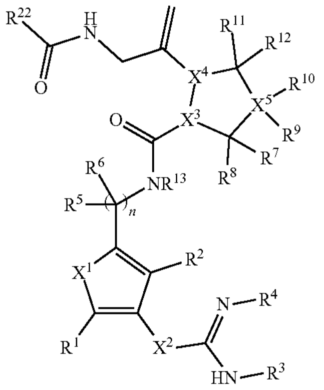

and

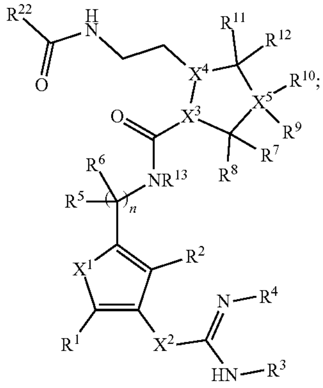

or a pharmaceutically acceptable salt, isotopic analog, prodrug, or isolated isomer thereof, optionally in pharmaceutically acceptable carrier; wherein all variables are as defined herein.

In another aspect, the compound of Formula X is selected from:

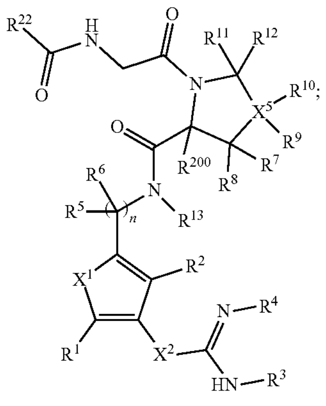

or a pharmaceutically acceptable salt, isotopic analog, prodrug, or isolated isomer thereof, optionally in pharmaceutically acceptable carrier;

wherein:

$R^{200}$ is selected from halogen, $C_1$-$C_6$alkyl, $C_1$-$C_6$haloalkyl, —$OR^{30}$, and —$N(R^{30})$ and all other variables are as defined herein.

In another aspect the compound of Formula X is selected from:

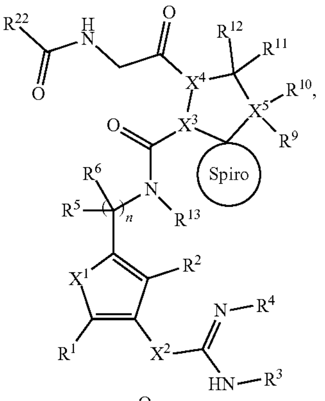

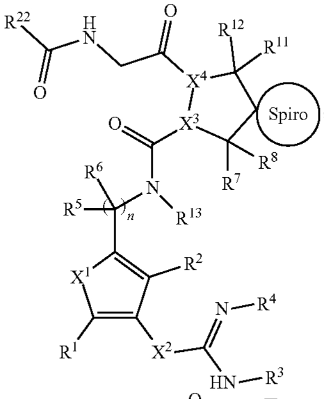

and

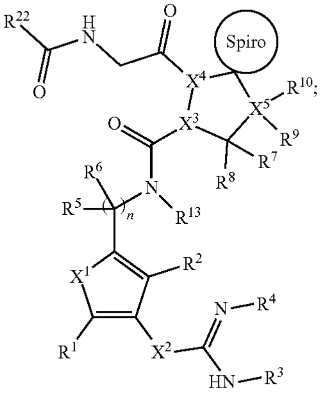

or a pharmaceutically acceptable salt, isotopic analog, prodrug, or isolated isomer thereof, optionally in pharmaceutically acceptable carrier;

wherein:

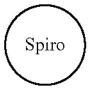

is selected from a 3- to 6-membered carbocyclic ring and a 4- to 6-membered heterocyclic ring containing 1 or 2 heteroatoms independently chosen from N, O, and S;

in an alternative embodiment,

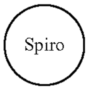

is optionally substituted with 1, 2, 3, or 4 substituents independently selected from halogen, $C_1$-$C_6$alkyl, $C_1$-$C_6$haloalkyl, —$OR^{30}$, and —$N(R^{30})_2$;

all other variables are as defined herein.

In another aspect, the compound of Formula X is selected from:

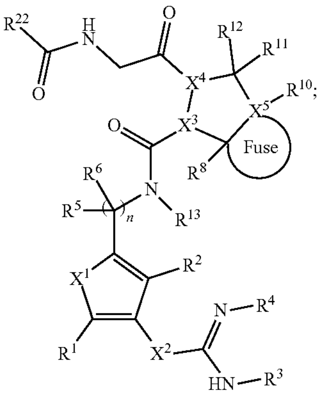

or a pharmaceutically acceptable salt, isotopic analog, prodrug, or isolated isomer thereof, optionally in pharmaceutically acceptable carrier;

wherein:

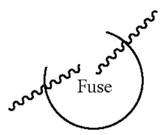

is a 3- to 8-membered carbocycle or a 4- to 8-membered heterocycle containing 1 or 2 heteroatoms independently chosen from N, O, and S;

wherein in this aspect at least one of $R^8$ and $R^{10}$ is not hydrogen; and all other variables are as defined herein.

In another aspect, the compound of Formula X is selected from:

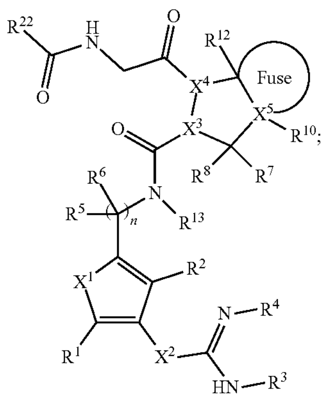

or a pharmaceutically acceptable salt, isotopic analog, prodrug, or isolated isomer thereof, optionally in pharmaceutically acceptable carrier;

wherein:

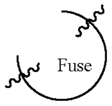

is a 3- to 8-membered carbocycle or a 4- to 8-membered heterocycle containing 1 or 2 heteroatoms independently chosen from N, O, and S; for example, in one embodiment wherein in this aspect at least one of $R^{10}$ and $R^{12}$ is not hydrogen; and all other variables are as defined herein.

In an alternative embodiment, the compound of the present disclosure is selected from:

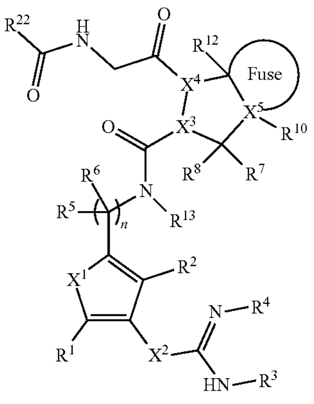

and

-continued

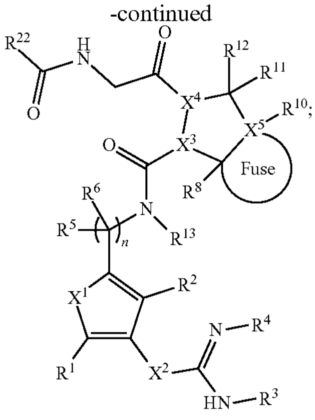

or a pharmaceutically acceptable salt, isotopic analog, prodrug, or isolated isomer thereof, optionally in pharmaceutically acceptable carrier;

wherein:

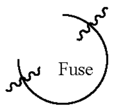

is a 3- to 8-membered carbocycle or a 4- to 8-membered heterocycle containing 1 or 2 heteroatoms independently chosen from N, O, and S, wherein

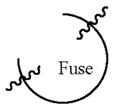

is substituted with 1, 2, 3, or 4 substituents selected from halogen, $C_1$-$C_6$alkyl, $C_1$-$C_6$haloalkyl, —$OR^{30}$, and —$N(R^{30})_2$; and all other variables are as defined herein.

In one embodiment, a 3- to 8-membered carbocycle is a 4- to 8-membered carbocycle. In another embodiment a 3- to 8-membered carbocycle is a 4- to 8-membered carbocycle.

In one embodiment, $R^7$ and $R^9$ are taken together with the atoms to which they are attached to form a 4- to 8-membered carbocycle or a 4- to 8-membered heterocycle containing 1 or 2 heteroatoms independently chosen from N, O, and S;

In one embodiment, $R^9$ and $R^{11}$ are taken together with the atoms to which they are attached to form a 4- to 8-membered carbocycle or a 4- to 8-membered heterocycle containing 1 or 2 heteroatoms independently chosen from N, O, and S;

In one embodiment,

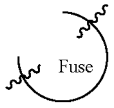

is a 4- to 8-membered carbocycle or a 4- to 8-membered heterocycle containing 1 or 2 heteroatoms independently chosen from N, O, and S;

In another aspect, the compound of Formula XIV is selected from:
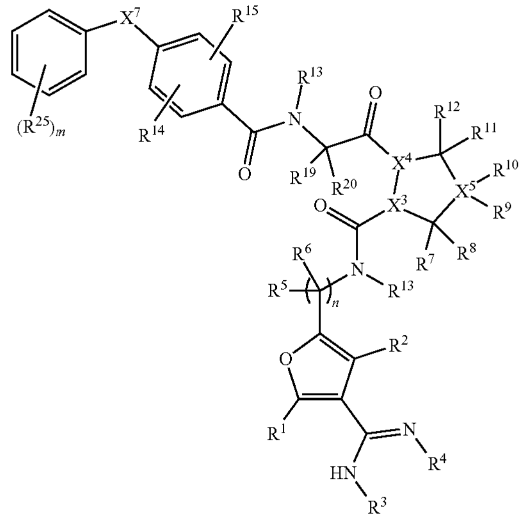
and
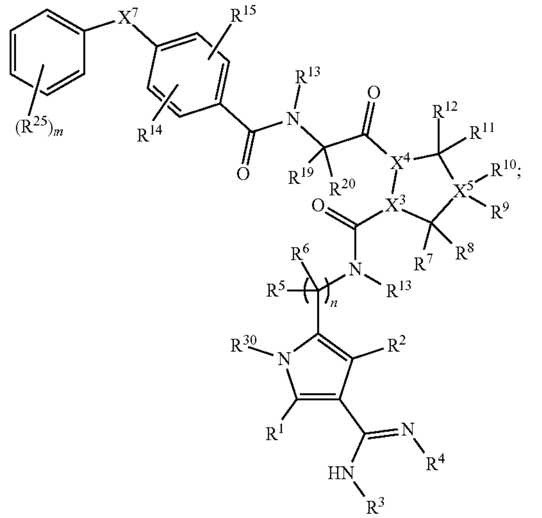
or a pharmaceutically acceptable salt, isotopic analog, prodrug, or isolated isomer thereof, optionally in pharmaceutically acceptable carrier; wherein all variables are as defined herein.
In another aspect, the compound of Formula XIV is selected from:
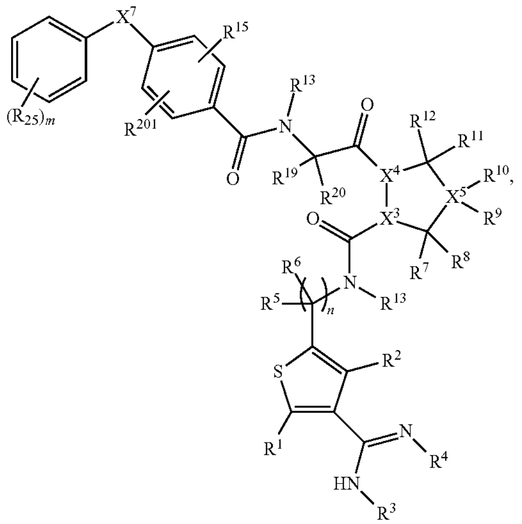
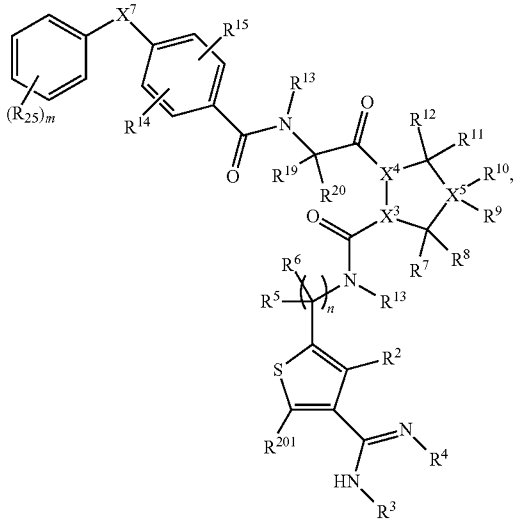
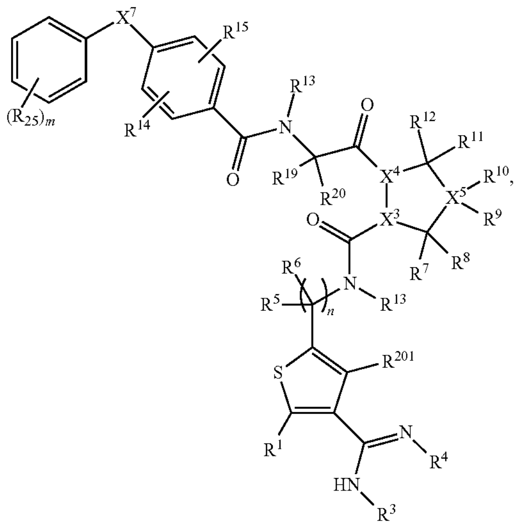

-continued

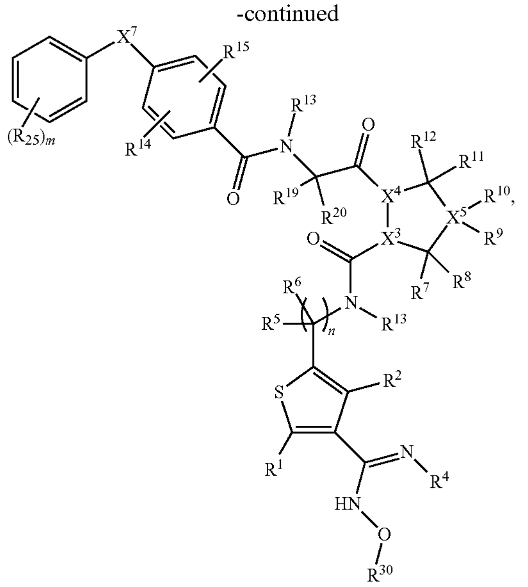

and

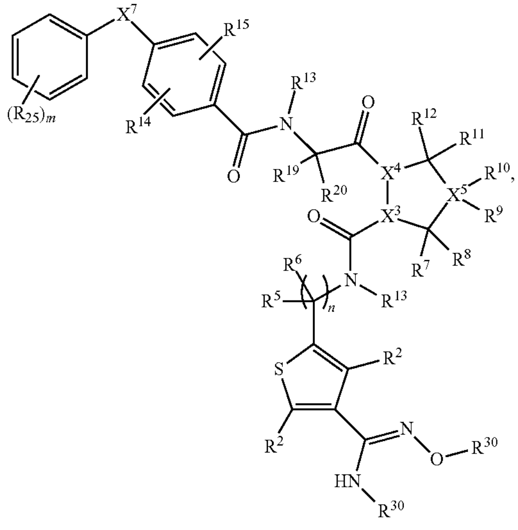

or a pharmaceutically acceptable salt, isotopic analog, prodrug, or isolated isomer thereof, optionally in pharmaceutically acceptable carrier;

wherein:

$R^{201}$ is selected from halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, and heteroaryl, each of which $R^{201}$ groups other than halogen are optionally substituted with 1, 2, 3, or 4 substituents independently selected from $C_1$-$C_6$alkyl, $CC_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro; and all other variables are as defined herein.

In certain aspects of the disclosure, $R^9$ and $R^{11}$ are taken together with the atoms to which they are attached to form a cyclopropane.

In one embodiment, the compound of the present disclosure is selected from:

(I')

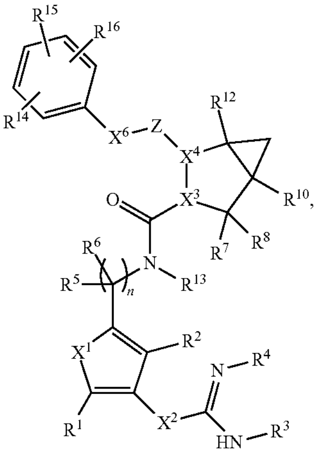

(II')

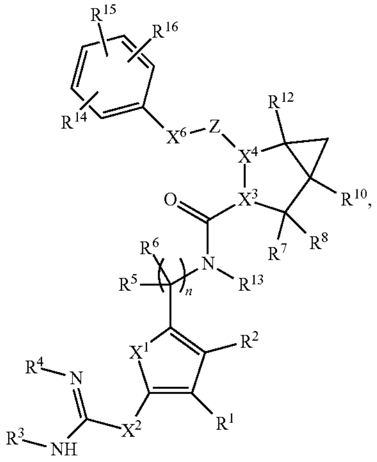

(X')

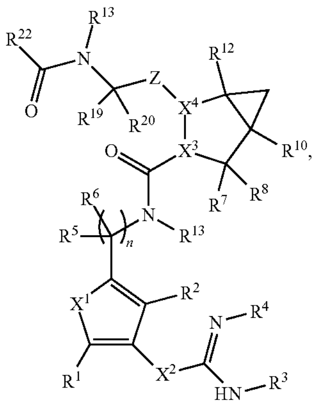

-continued
(XI')
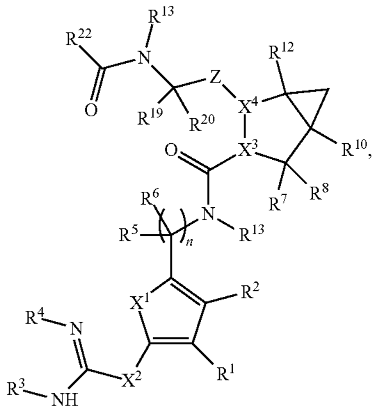
and
(XIII')
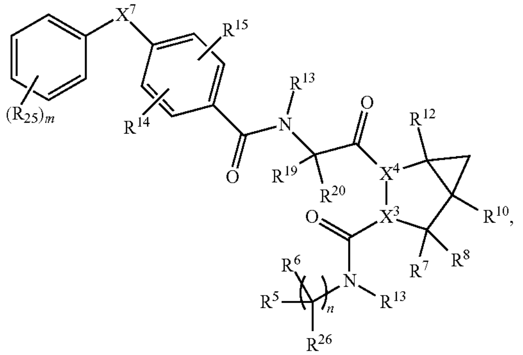
and
(XIV')
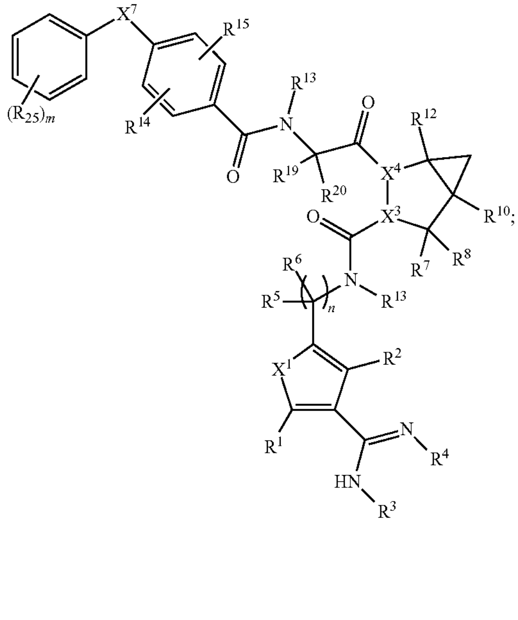
or a pharmaceutically acceptable salt thereof.
In certain embodiments, the compound of the present disclosure is selected from:
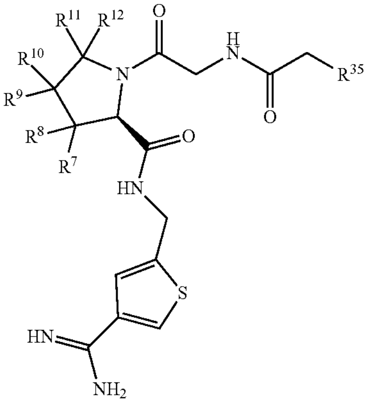
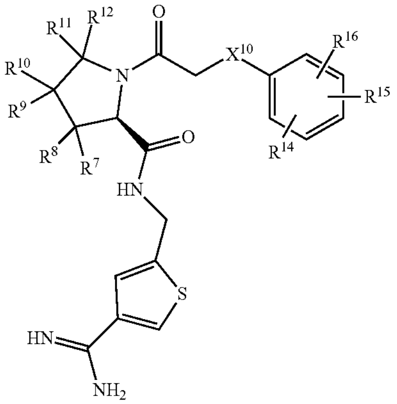
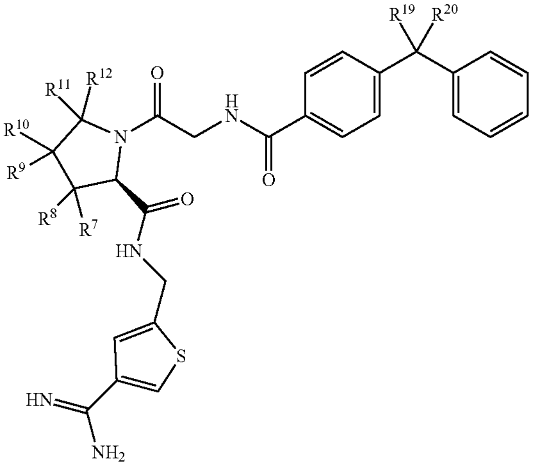
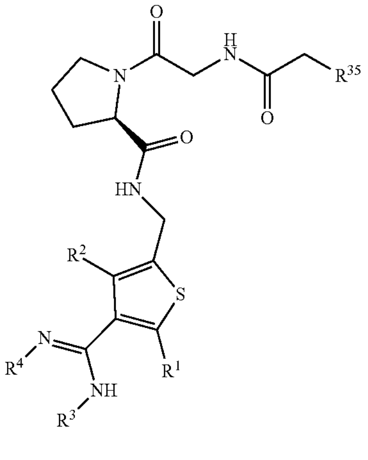

-continued
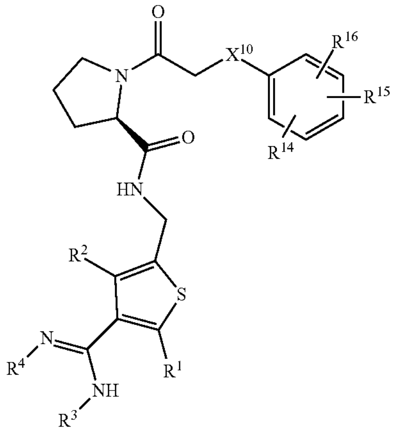
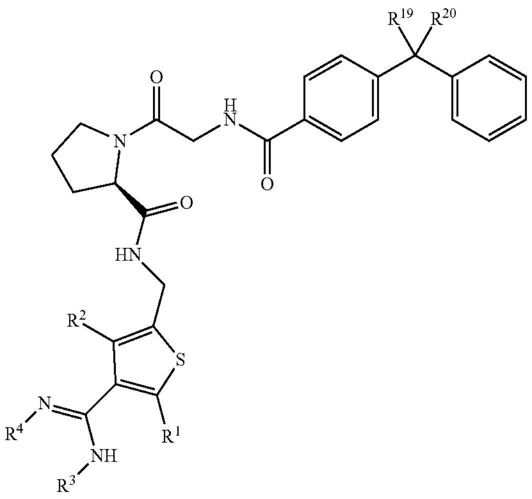
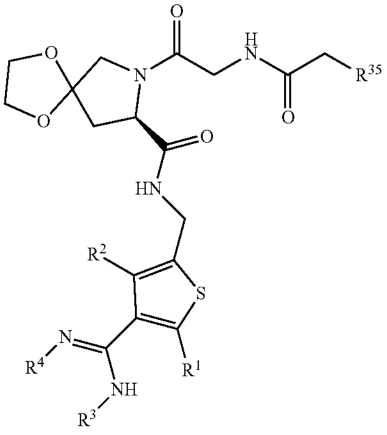
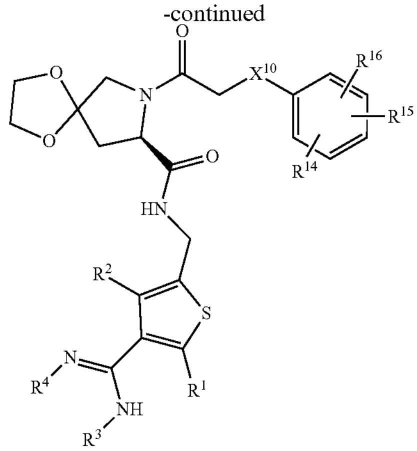
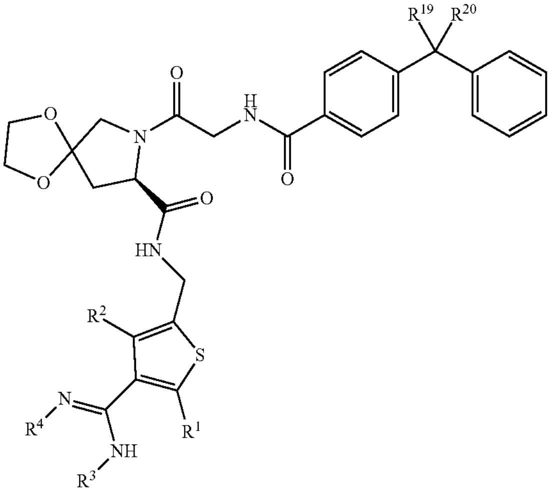
-continued
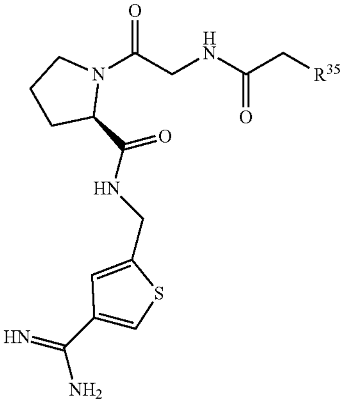
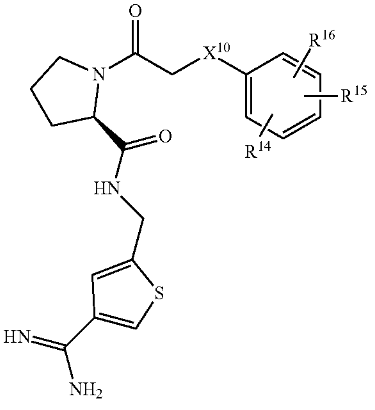
and -continued
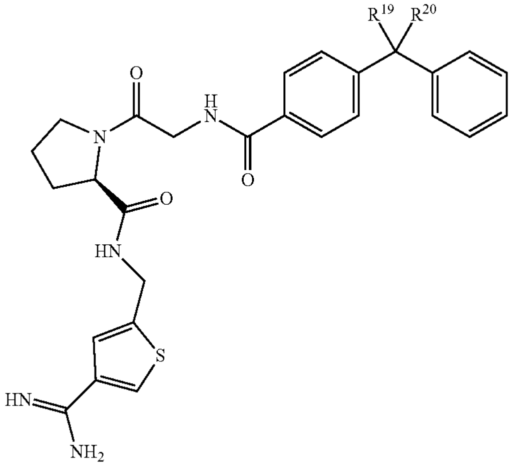
;
or a pharmaceutically acceptable salt thereof.
In certain embodiments, the compound of the present disclosure is selected from:
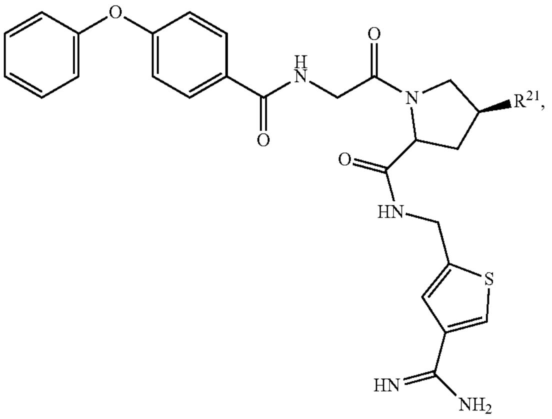
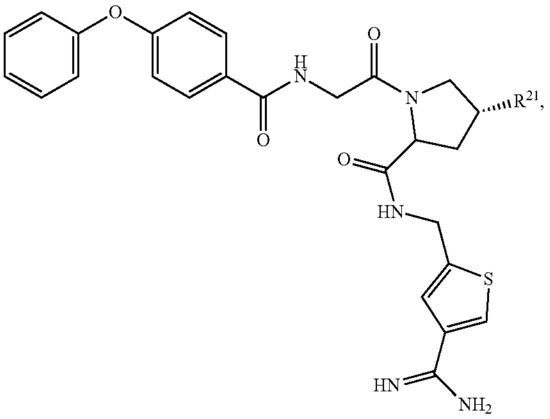
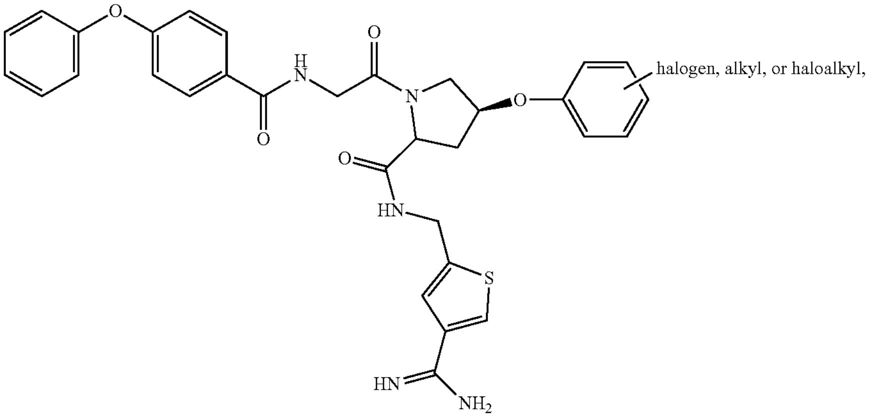

-continued
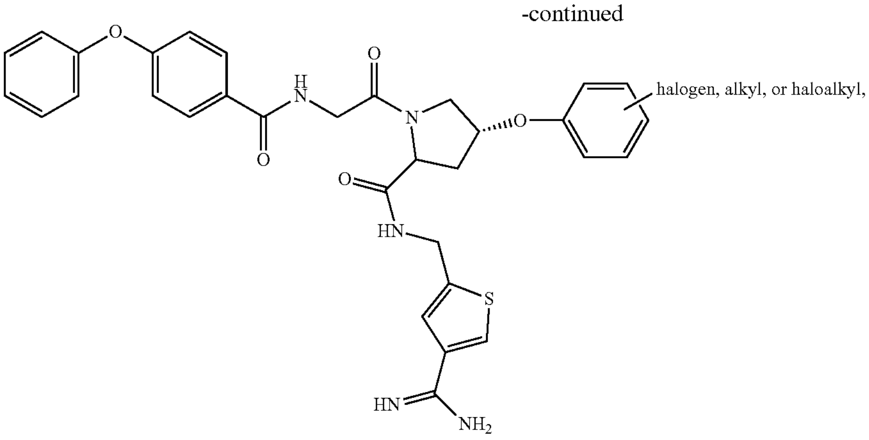
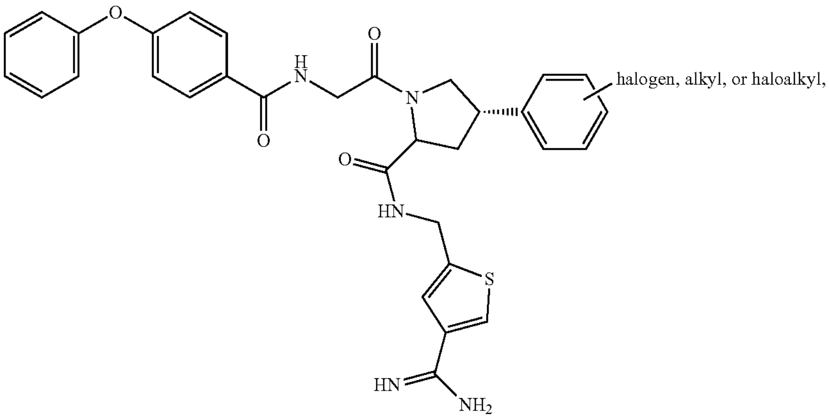
and
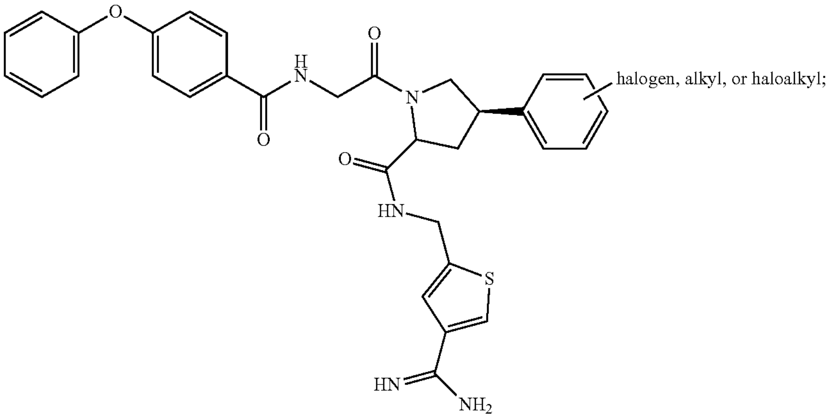
or a pharmaceutically acceptable salt thereof.
In certain embodiments, the compound of the present disclosure is selected from:

-continued
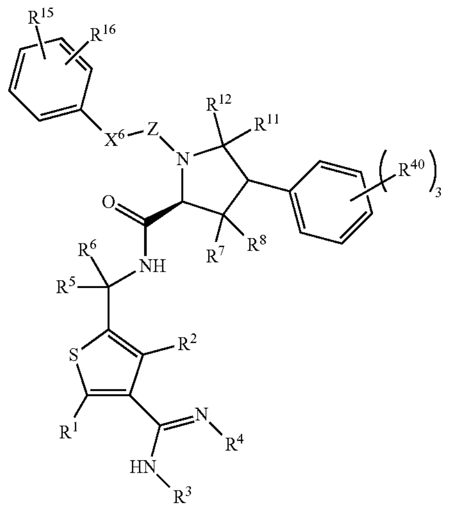
,
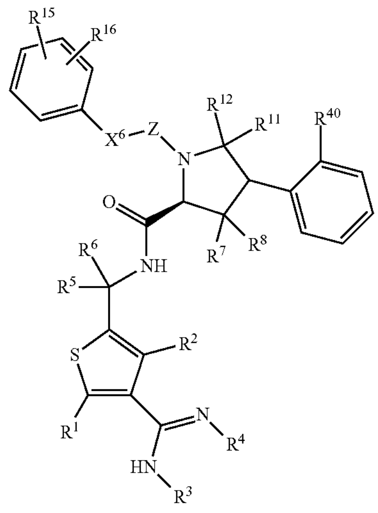
,
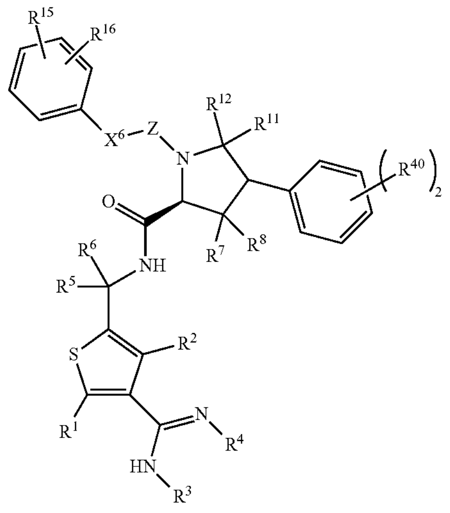
,
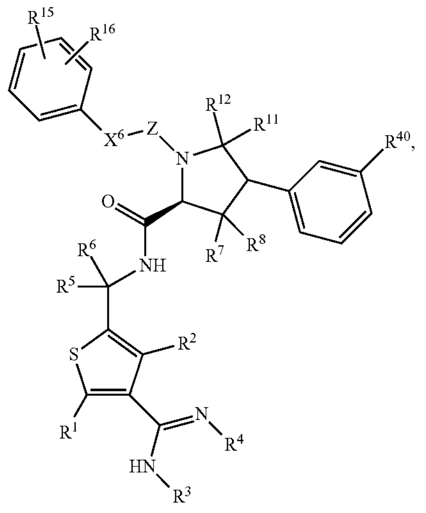
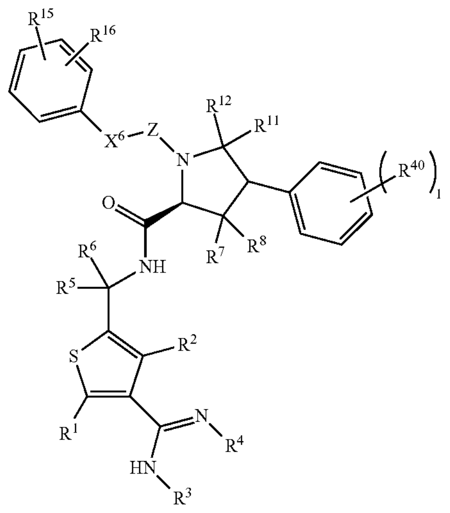
,
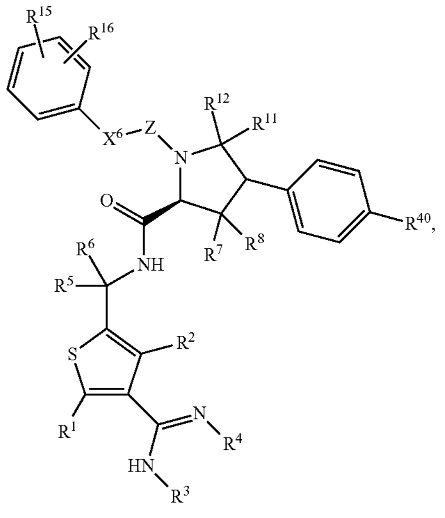

-continued

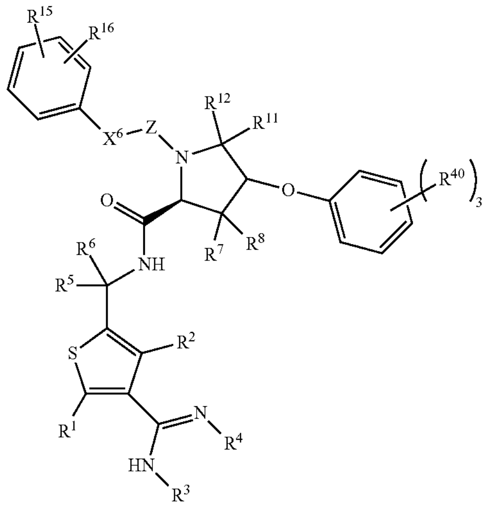

,

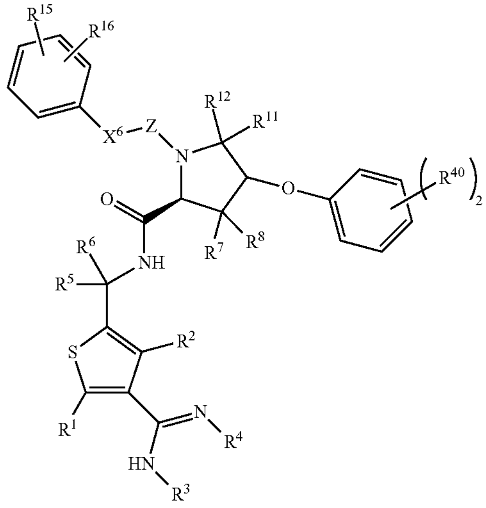

,

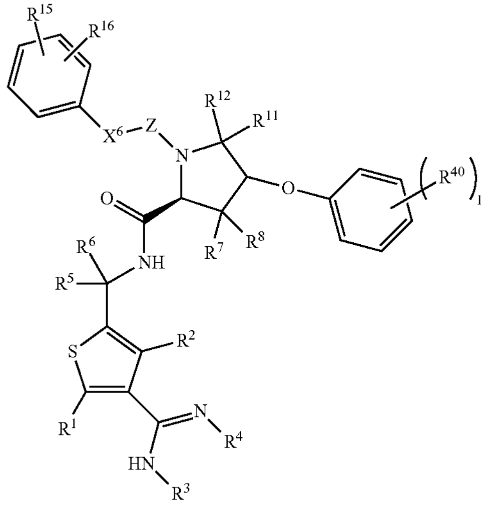

,

-continued

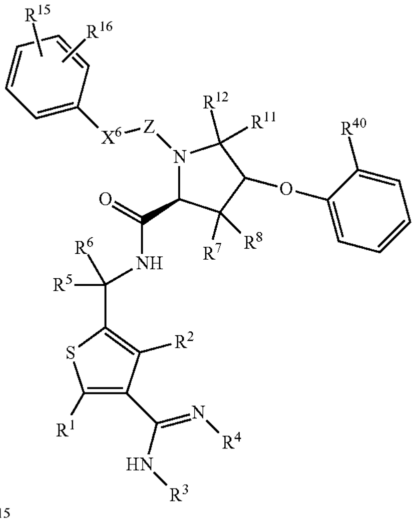

,

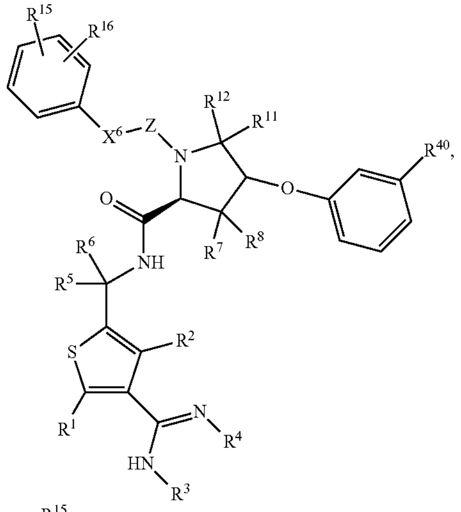

and

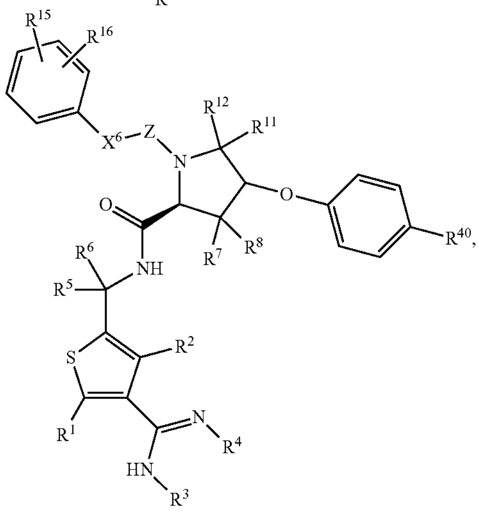

or a pharmaceutically acceptable salt thereof;

wherein each $R^{40}$ is independently selected from: $SF_5$, $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro.

In certain embodiments, the compound of the present disclosure is selected from:

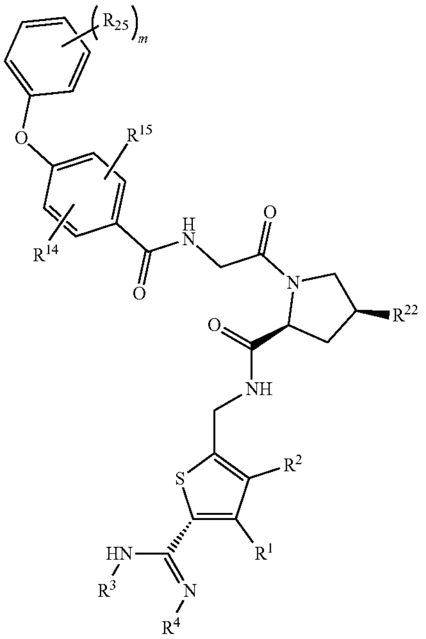
and
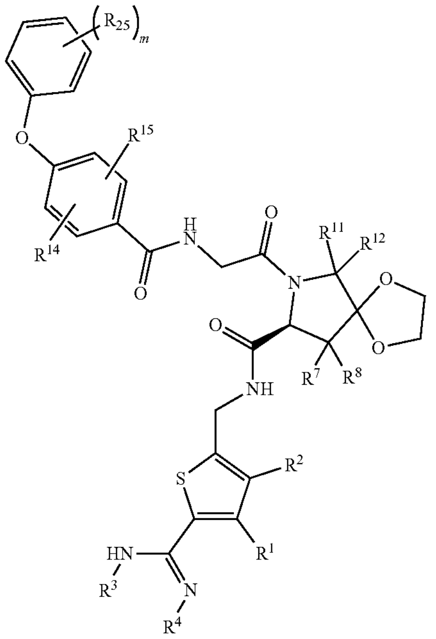
and
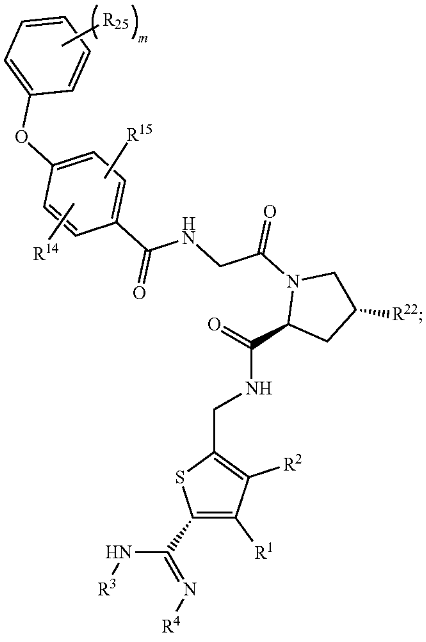
;
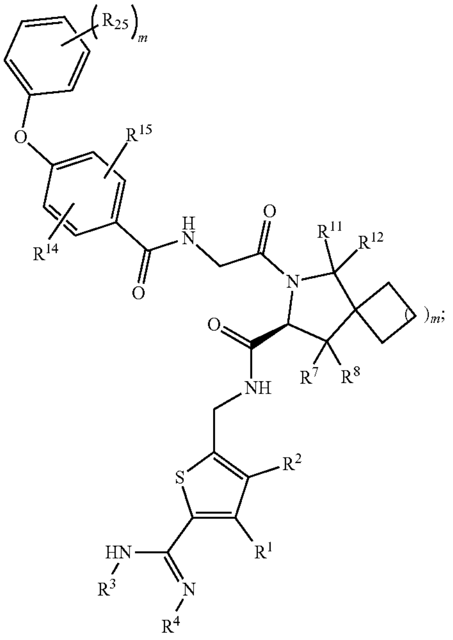
or a pharmaceutically acceptable salt thereof.
In certain embodiments, the compound of the present disclosure is selected from:
or a pharmaceutically acceptable salt thereof.
ADDITIONAL EMBODIMENTS
1. (Embodiment 1) In certain embodiments, the compound of the present disclosure is selected from:

(I)
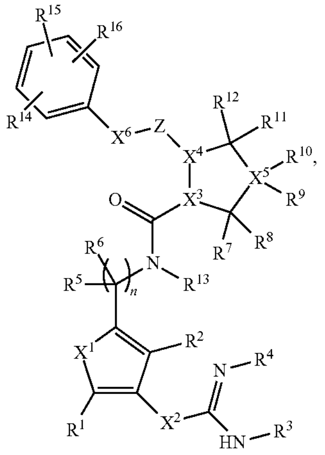
(II)
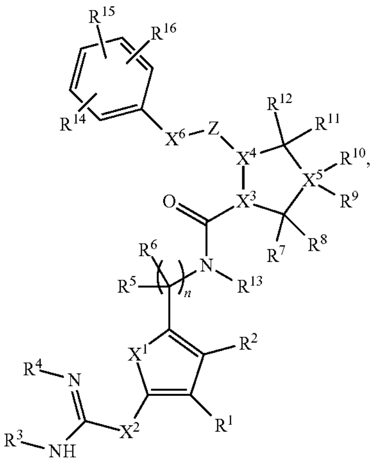
(III)
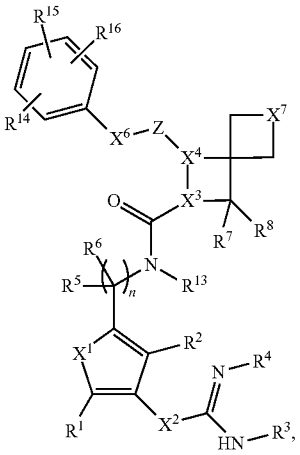
-continued
(IV)
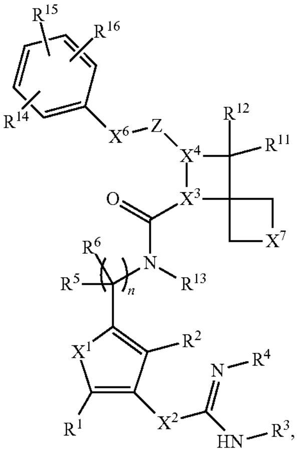
(V)
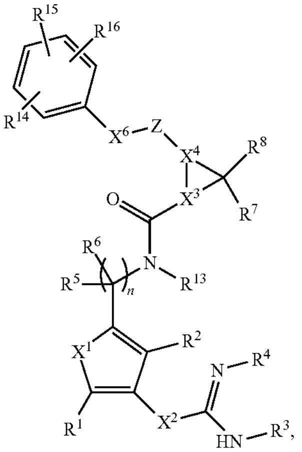
(VI)
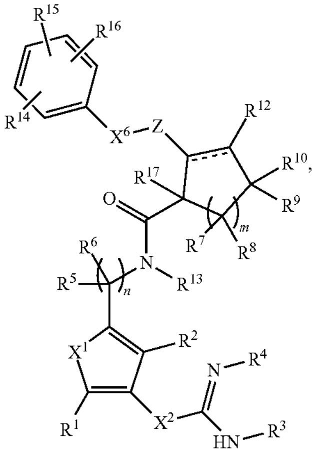

-continued
(VII)
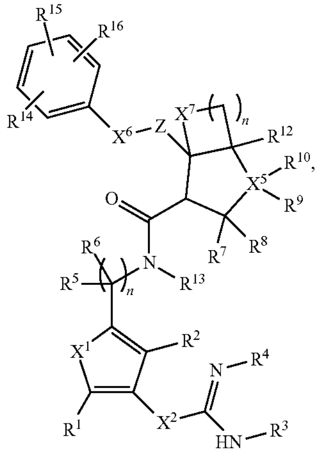
(VIII)
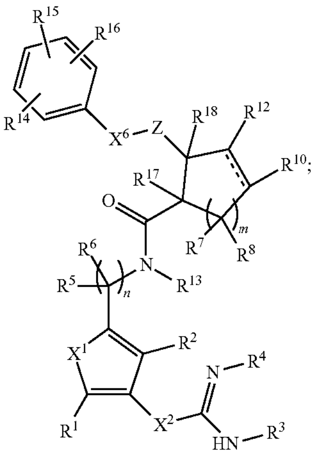
(IX)
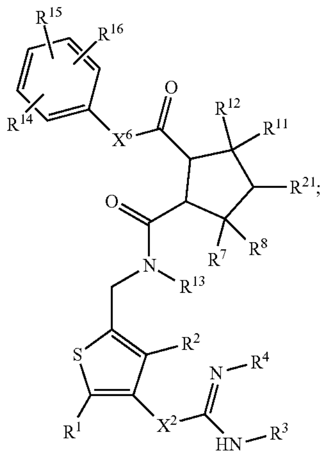
-continued
(X)
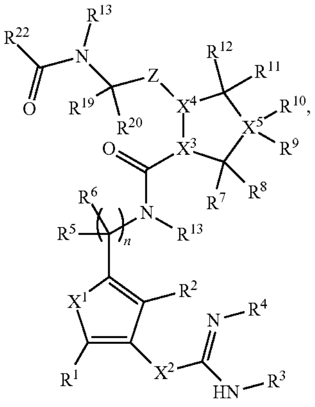
(XI)
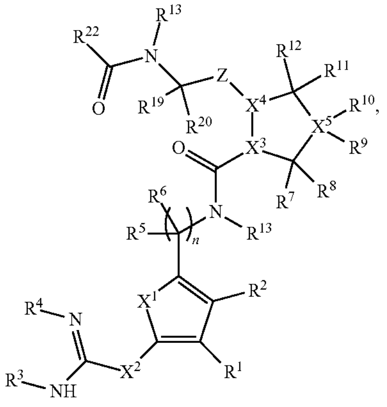
(XII)
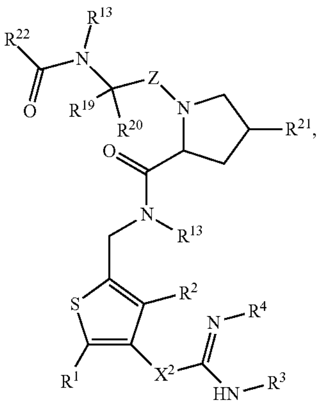
(XIII)
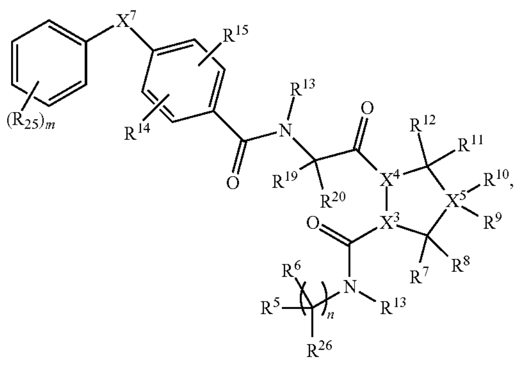

-continued
(XIV)
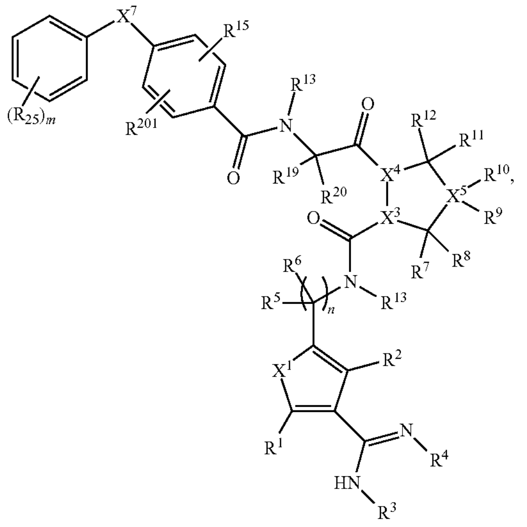
(XV)
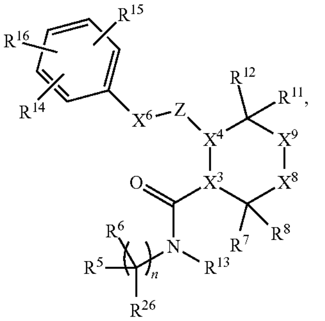
(XVI)
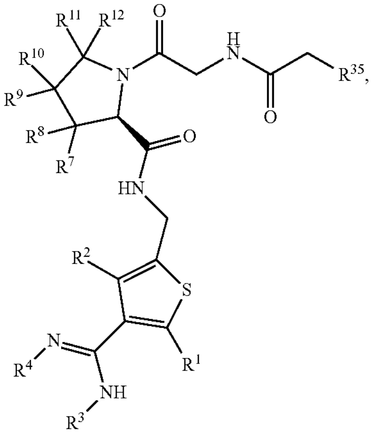
-continued
(XVII)
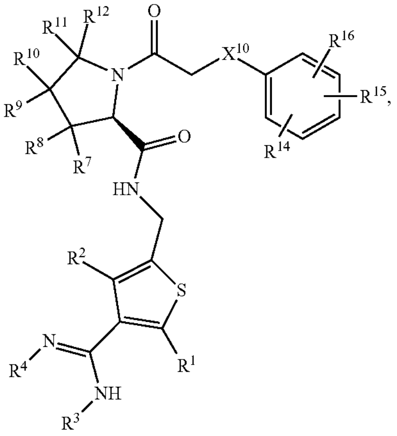
(XVIII)
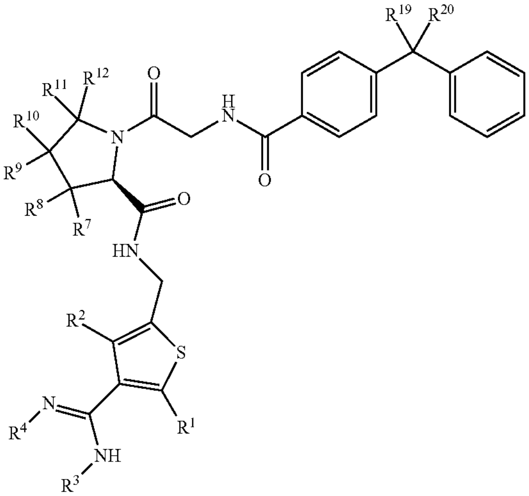
,
(XIX)
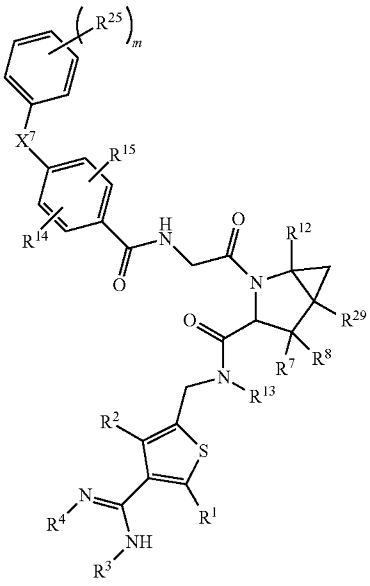
and -continued (XX)

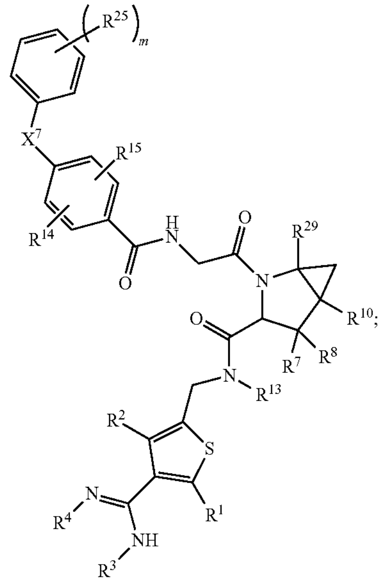

or a pharmaceutically acceptable salt, isotopic analog, prodrug, or isolated isomer thereof;

wherein:

each n is independently 1, 2, or 3;

each m is independently 0, 1, 2, or 3;

o is 0, 1, or 2;

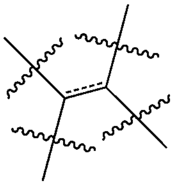

is either a single or a double bond;

Z is $CH_2$, $C(CH_2)$, or C(O);

$X^1$ is selected from S, O, and $N(R^{30})$;

$X^2$ is selected from bond, $N(R^{30})$, and —O—$N(R^{30})$—;

$X^3$ is selected from N and $C(R^{17})$;

$X^4$ is selected from N and $C(R^{18})$;

wherein only one of $X^3$ and $X^4$ can be N;

$X^5$ is C or Si;

$X^6$ is selected from

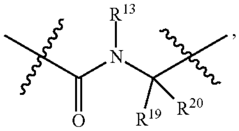, 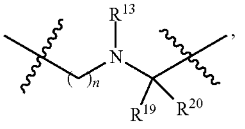, 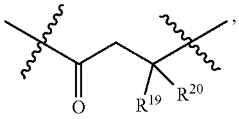, 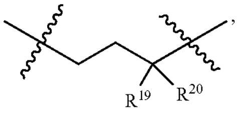, 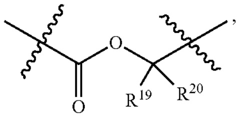, 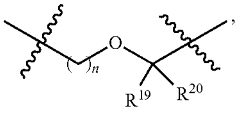,

-continued

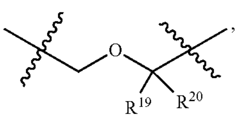, 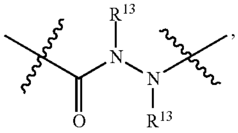, and 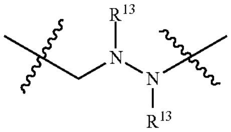;

$X^7$ is selected from O, S, $N(R^{30})$, and $CR^5R^6$;

each $X^8$ and $X^9$ is independently selected from O, S, $NR^{30}$, $CR^9R^{10}$, $CR^5R^6$. and $CH_2$; wherein $X^8$ and $X^9$ cannot both be the same group;

$X^{10}$ is selected from

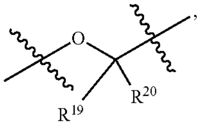, 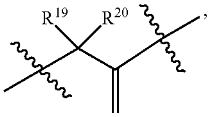, 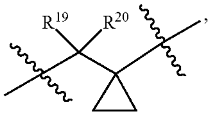, 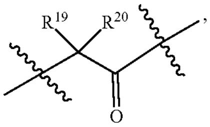, 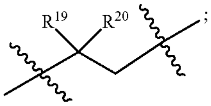;

$X^{11}$ is selected from N and $CR^1$;

$X^{12}$ is selected from N and $CR^2$;

$R^1$ and $R^2$ are independently selected from hydrogen, halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —C(O)$R^{31}$, —S(O)$R^{31}$, —$S(O)_2R^{31}$, heterocycle, aryl, heteroaryl, cyano, and nitro; each of which $R^1$ and $R^2$ groups other than hydrogen, halogen, cyano, and nitro are optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —C(O)$R^{31}$, —S(O)$R^{31}$, —$S(O)_2R^{31}$, heterocycle, aryl, heteroaryl, cyano, and nitro;

$R^3$ and $R^4$ are independently selected from hydrogen, CN, C(O)$R^{31}$, —$SR^{30}$, and —$OR^{30}$;

or $R^3$ and $R^4$ are instead combined to form an oxadiazole optionally substituted with 1, 2, or 3 substituents independently selected from $C_1$-$C_6$alkyl, $C_1$-$C_6$haloalkyl, —$OR^{30}$, and oxo;

each $R^5$ and $R^6$ are independently selected from hydrogen, halogen, $C_1$-$C_6$alkyl, $C_1$-$C_6$haloalkyl, —$OR^{30}$, and —$N(R^{30})_2$, wherein when on carbons adjacent to each other a $R^5$ and a $R^6$ group may optionally be replaced by a carbon-carbon double bond;

$R^7$, $R^8$, $R^9$, $R^{10}$, $R^{11}$, and $R^{12}$ are independently selected from hydrogen, halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —C(O)$R^{31}$, —S(O)$R^{31}$, —$S(O)_2R^{31}$, heterocycle, aryl, and heteroaryl, each of which $R^7$, $R^8$, $R^9$, $R^{10}$, $R^{11}$, and $R^{12}$ groups other than hydrogen and halogen are optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

or $R^7$ and $R^8$ may be taken together with the carbon to which they are attached to form a 3- to 6-membered carbocyclic spiro ring or a 4- to 6-membered heterocyclic spiro ring containing 1 or 2 heteroatoms independently chosen from N, O, and S;

or $R^7$ and $R^8$ may be taken together with the carbon to which they are attached to form

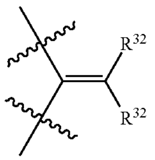

or carbonyl;

or $R^9$ and $R^{10}$ may be taken together with the atom to which they are attached to form a 3- to 6-membered carbocyclic spiro ring or a 4- to 6-membered heterocyclic spiro ring containing 1 or 2 heteroatoms independently chosen from N, O, and S;

or $R^9$ and $R^{10}$ may be taken together with the atom to which they are attached to form

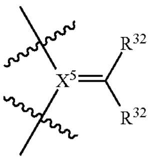

or carbonyl;

or $R^{11}$ and $R^{12}$ may be taken together with the carbon to which they are attached to form a 3- to 6-membered carbocyclic spiro ring or a 4- to 6-membered heterocyclic spiro ring containing 1 or 2 heteroatoms independently chosen from N, O, and S;

or $R^{11}$ and $R^{12}$ may be taken together with the carbon to which they are attached to form

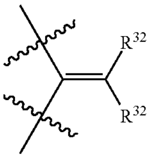

or carbonyl;

or $R^7$ and $R^9$ are taken together with the atoms to which they are attached to form a 3- to 8-membered carbocycle or a 4- to 8-membered heterocycle containing 1 or 2 heteroatoms independently chosen from N, O, and S;

or $R^9$ and $R^{11}$ are taken together with the atoms to which they are attached to form a 3- to 8-membered carbocycle or a 4- to 8-membered heterocycle containing 1 or 2 heteroatoms independently chosen from N, O, and S;

or $R^7$ and $R^{11}$ are taken together with the atoms to which they are attached to form a 1 or 2 carbon bridge;

each $R^{13}$ is independently selected from hydrogen or $C_1$-$C_6$alkyl;

$R^{14}$, $R^{15}$, and $R^{16}$ are independently selected from hydrogen, halogen, $SF_5$, $C_1$-$C_6$alkyl, $C_2$-$C_6$alkenyl, $C_2$-$C_6$alkynyl, $C_1$-$C_6$haloalkyl, —$C_1$-$C_6$alkyl-aryl. —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro each of which $R^{14}$, $R^{15}$, and $R^{16}$ groups other than hydrogen, halogen, cyano, and nitro are optionally substituted with 1, 2, 3, or 4 substituents independently selected from $SF_5$, $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

$R^{17}$ and $R^{18}$ are independently selected from hydrogen, halogen, $C_1$-$C_6$alkyl, $C_1$-$C_6$haloalkyl, —$OR^{30}$, and —$N(R^{30})_2$;

or $R^{17}$ and $R^{18}$ are taken together with the carbons to which they are attached to form a double bond;

$R^{19}$ and $R^{20}$ are independently selected from hydrogen, $C_1$-$C_6$alkyl, $C_5$-$C_{10}$ bicyclic carbocycle, $C_4$-$C_6$heterocycle, halogen, $C_1$-$C_6$haloalkyl, —$OR^{30}$, —$N(R^{30})_2$, —$(CH_2)_n$—$R^{33}$, and

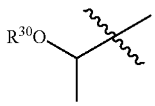

;

$R^{21}$ is selected from $C_1$-$C_6$haloalkyl, —O—$C_1$-$C_6$haloalkyl, $C_1$-$C_6$alkyl, —O—$C_1$-$C_6$alkyl, aryl, —O-aryl, heteroaryl, or —O-heteroaryl, each of which $R^{21}$ group is optionally substituted with 1, 2, 3, or 4 substituents independently selected from $SF_5$, $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

$R^{22}$ is selected from —$C_1$-$C_6$alkyl-$R^{23}$, —$C_2$-$C_6$alkenyl-$R^{23}$, —$C_2$-$C_6$alkynyl-$R^{23}$ and bicyclic cycloalkyl-$R^{23}$, each of which $R^{22}$ is optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

$R^{23}$ is selected from hydrogen, sugar, —$OR^{30}$, —$SR^{30}$, —$N(R^{30})_2$, —$C(O)R^{31}$, —$S(O)R^{31}$, and —$S(O)_2R^{31}$;

each $R^{25}$ is independently selected from hydrogen, $SF_5$, halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro; each of which $R^{25}$ groups other than hydrogen, halogen, cyano, and nitro are optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

$R^{26}$ is selected from
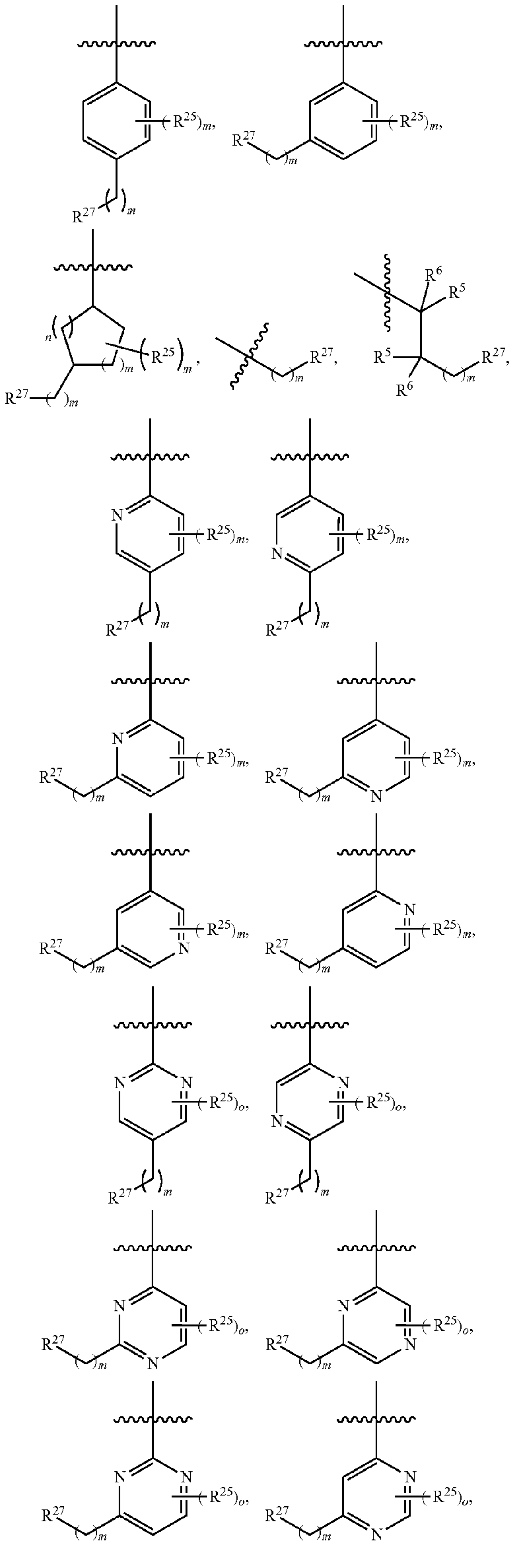
-continued
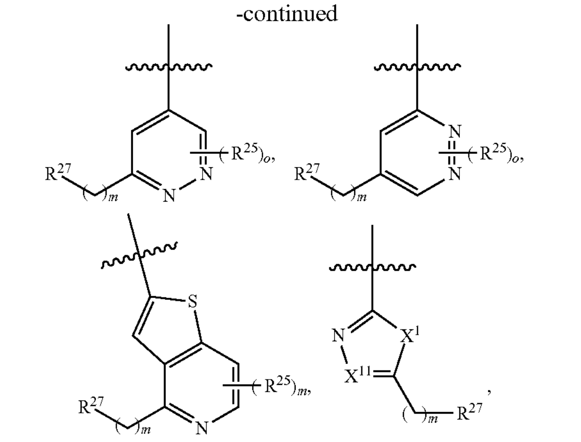
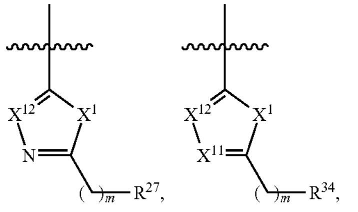
and
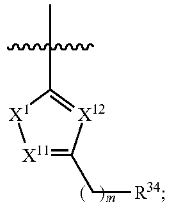
$R^{27}$ is selected from
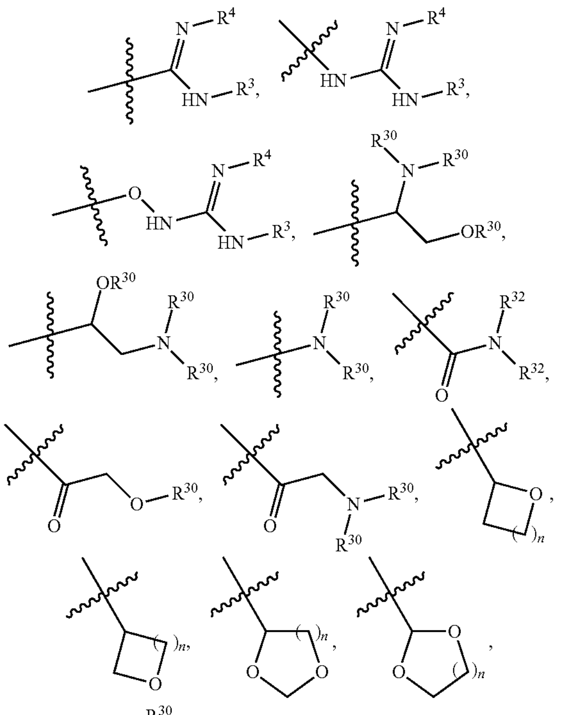
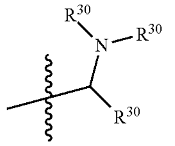
or
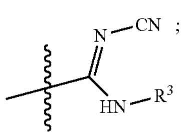
$R^{29}$ is selected from halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, and heteroaryl, each of which $R^{29}$ groups other than hydrogen and halogen are optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro.

each $R^{30}$ is independently selected from hydrogen, $C_1$-$C_6$alkyl, $C_1$-$C_6$haloalkyl, aryl, heteroaryl, heterocycle, and $C(O)R^{31}$;

each $R^{31}$ is independently selected from hydrogen, $C_1$-$C_6$alkyl, $C_1$-$C_6$haloalkyl, —$OR^{32}$, —$SR^{32}$, —$N(R^{32})_2$, heterocycle, aryl, and heteroaryl;

each $R^{32}$ is independently selected from hydrogen, $C_1$-$C_6$alkyl, and $C_1$-$C_6$haloalkyl;

each $R^{33}$ is independently selected from hydrogen, guanidine, heteroaryl, aryl, —$C_6H_5$—$OR^{30}$; —$OR^{30}$, —$SR^{30}$, —$SeR^{30}$, —$N(R^{30})_2$, and —$C(O)R^{31}$;

$R^{34}$ is selected from

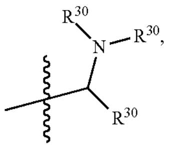 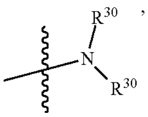 ,

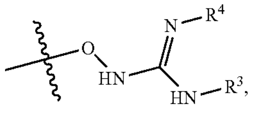 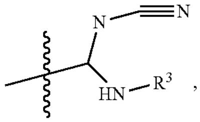 ,

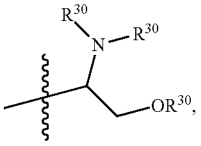 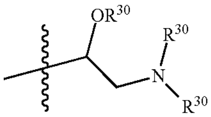 ,

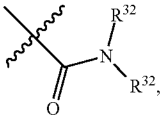 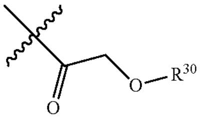 ,

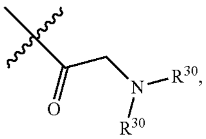 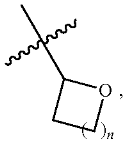 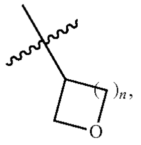

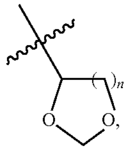 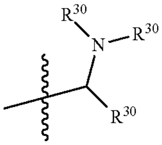 , 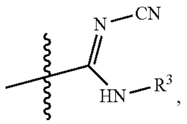 , and

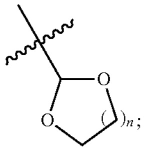

$R^{35}$ is selected from $C_3$-$C_{10}$alkyl or $C_3$-$C_{10}$haloalkyl;

wherein for compounds of Formula I and Formula II at least one of the following is satisfied:

a. $X^3$ is $C(R^{17})$ and $X^4$ is $C(R^{18})$;

b. $R^{17}$ is selected from halogen, $C_1$-$C_6$alkyl, $C_1$-$C_6$haloalkyl, —$OR^{30}$, and —$N(R^{30})_2$;

c. $X^5$ is Si;

d. Z is $C(CH_2)$;

e. Z is $CH_2$;

f. $R^7$ and $R^8$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

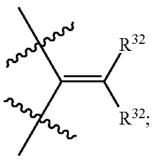

or a carbonyl;

g. $R^9$ and $R^{10}$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

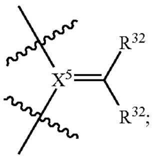

or a carbonyl;

h. $R^{11}$ and $R^{12}$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

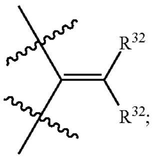

or a carbonyl;

i. $R^7$ and $R^9$ are taken together with the atoms to which they are attached to form a 3- to 8-membered carbocycle or a 4- to 8-membered heterocycle containing 1 or 2 heteroatoms independently chosen from N, O, and S; and $R^8$ or $R^{10}$ is not hydrogen;

j. $R^9$ and $R^{11}$ are taken together with the atoms to which they are attached to form a 3- to 8-membered carbocycle or a 4- to 8-membered heterocycle containing 1 or 2 heteroatoms independently chosen from N, O, and S; and $R^{10}$ or $R^{12}$ is not hydrogen;

k. $R^7$ and $R^{11}$ are taken together with the atoms to which they are attached to form a 1 or 2 carbon bridge;

l. $X^6$ is selected from

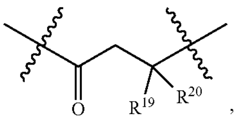 , 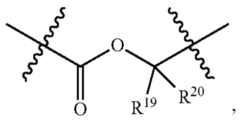 ,

-continued

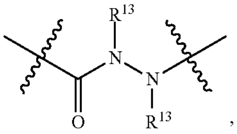
,
and
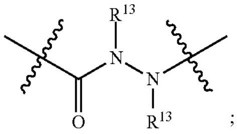
;

m. at least one of $R^3$ and $R^4$ is CN, —$SR^{30}$, or $C(O)R^{31}$; or n. $R^3$ and $R^4$ are combined to form an oxadiazole optionally substituted with 1, 2, or 3 substituents independently selected from $C_1$-$C_6$alkyl, $C_1$-$C_6$haloalkyl, —$OR^{30}$, and oxo;

wherein for compounds of Formula X and Formula XI at least one of the following is satisfied:

a. $X^3$ is $C(R^{17})$ and $X^4$ is $C(R^{18})$;

b. $R^{17}$ is selected from halogen, $C_1$-$C_6$alkyl, $C_1$-$C_6$haloalkyl, —$OR^{30}$, and —$N(R^{30})_2$;

c. $X^5$ is Si;

d. Z is $C(CH_2)$;

e. Z is $CH_2$;

f. $R^7$ and $R^8$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

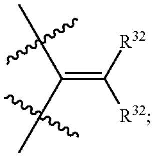

or a carbonyl;

g. $R^9$ and $R^{10}$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

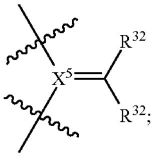

or a carbonyl;

h. $R^9$ and $R^{11}$ are taken together with the atoms to which they are attached to form a 3- to 8-membered carbocycle or a 4- to 8-membered heterocycle containing 1 or 2 heteroatoms independently chosen from N, O, and S; and $R^{10}$ is not hydrogen;

i. $R^{11}$ and $R^{12}$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

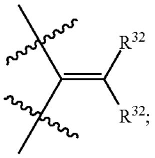

or a carbonyl;

j. $R^7$ and $R^9$ are taken together with the atoms to which they are attached to form a 3- to 8-membered carbocycle or a 4- to 8-membered heterocycle containing 1 or 2 heteroatoms independently chosen from N, O, and S; and $R^{10}$ is not hydrogen;

k. $R^7$ and $R^{11}$ are taken together with the atoms to which they are attached to form a 1 or 2 carbon bridge;

l. $R^{22}$ is substituted with at least three $OR^{30}$ groups;

m. $R^{23}$ is a sugar;

n. at least one of $R^3$ and $R^4$ is CN, —$SR^{30}$, or $C(O)R^{31}$; or o. $R^3$ and $R^4$ are combined to form an oxadiazole optionally substituted with 1, 2, or 3 substituents independently selected from $C_1$-$C_6$alkyl, $C_1$-$C_6$haloalkyl, —$OR^{30}$, and oxo;

wherein for compounds of Formula XIV at least one of the following is satisfied:

a. $X^1$ is O or $N(R^{30})$;

b. $R^{14}$ is not hydrogen;

c. $R^1$ is not hydrogen;

d. $R^2$ is not hydrogen;

e. $R^3$ is not hydrogen; or f. $R^4$ is not hydrogen.

2. The compound of embodiment 1, wherein the compound is selected from:

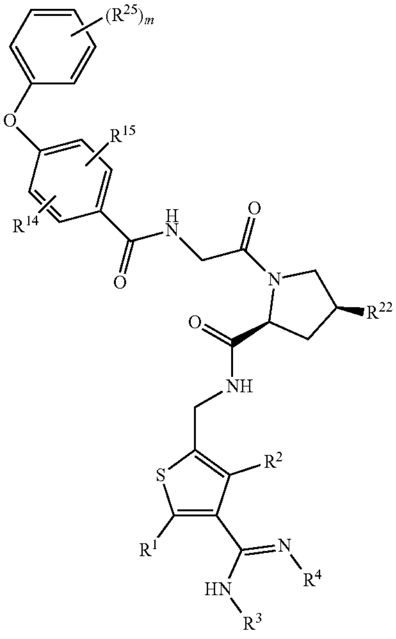
and

-continued
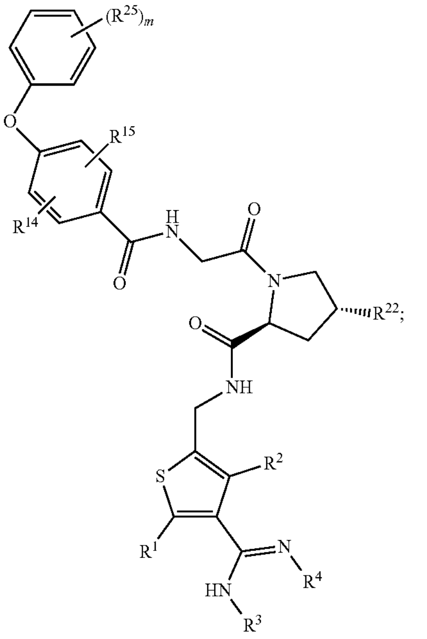
-continued
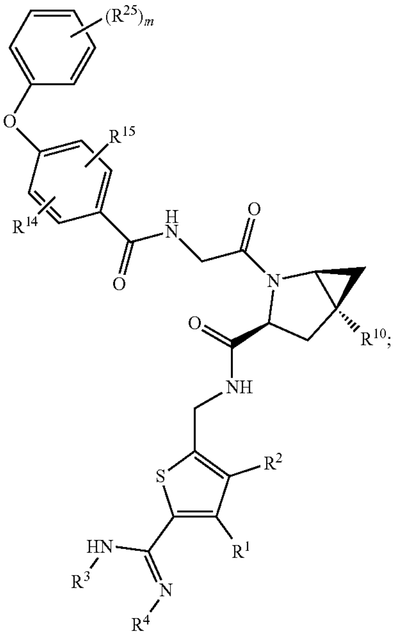
or a pharmaceutically acceptable salt, isotopic analog, prodrug, or isolated isomer thereof.
3. The compound of embodiment 1, wherein the compound is of formula:
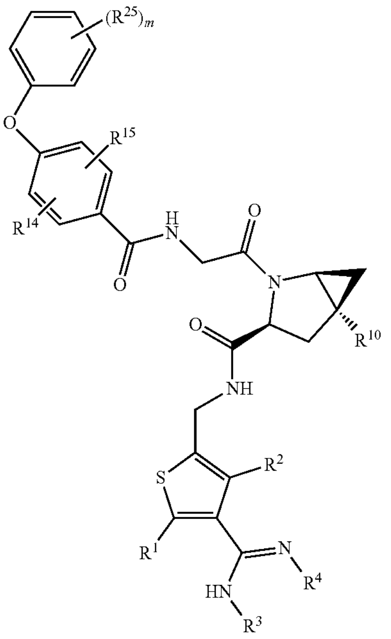
or
or a pharmaceutically acceptable salt, isotopic analog, prodrug, or isolated isomer thereof.
4. The compound of embodiment 1, of formula:
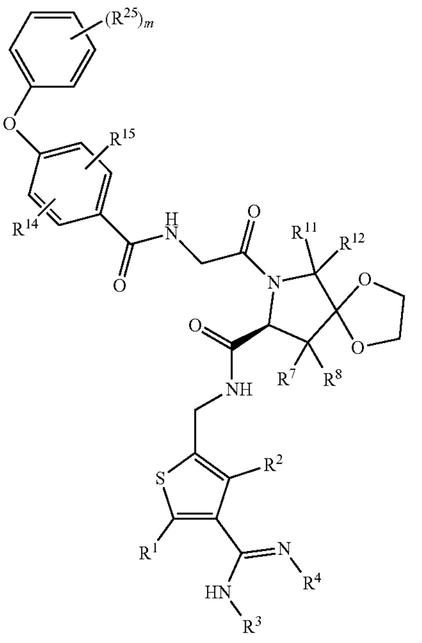
or -continued
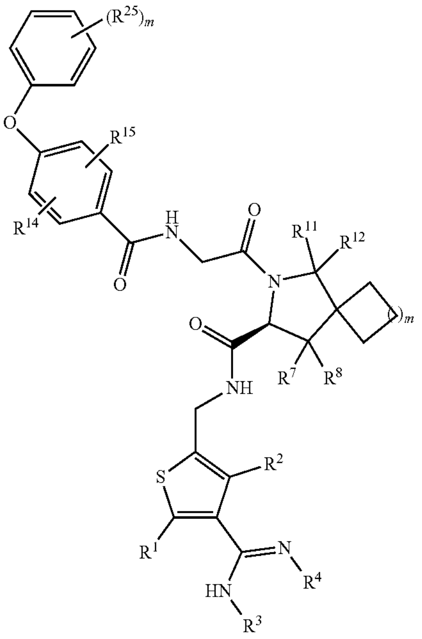
or a pharmaceutically acceptable salt, isotopic analog, prodrug, or isolated isomer thereof.
5. The compound of embodiment 1, selected from:
(I)
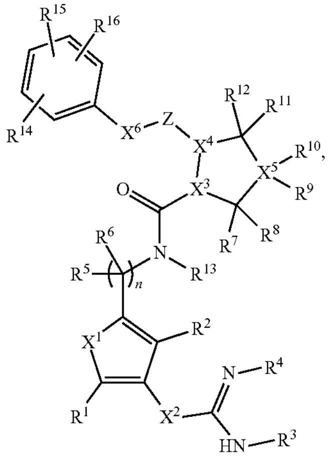
-continued
(II)
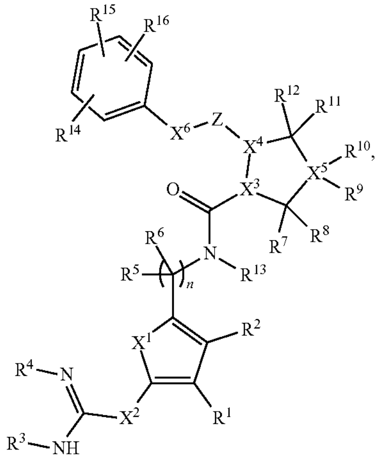
(III)
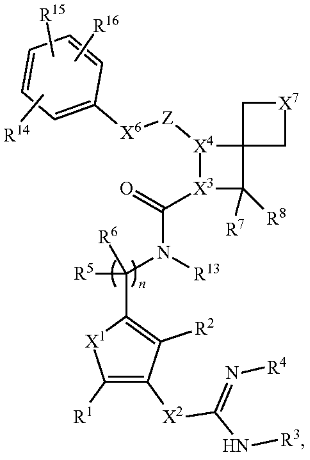
(IV)
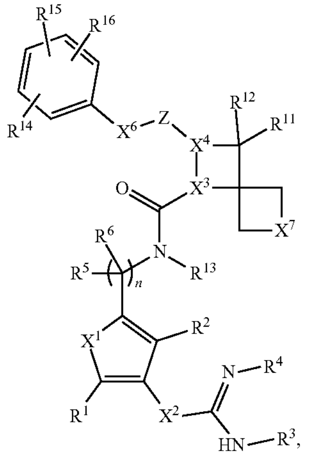

-continued
(V)
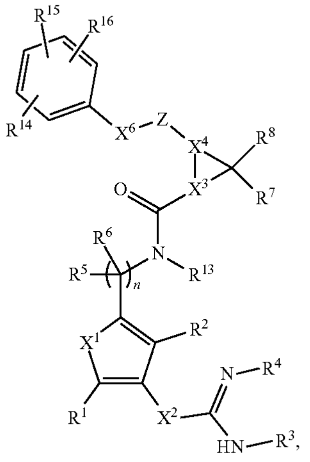
(VI)
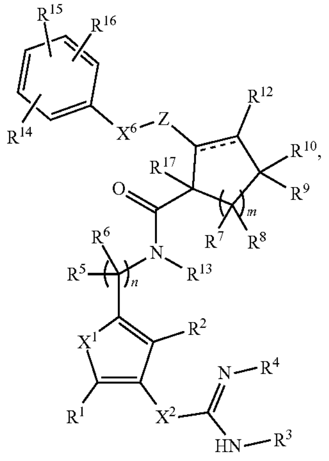
(VII)
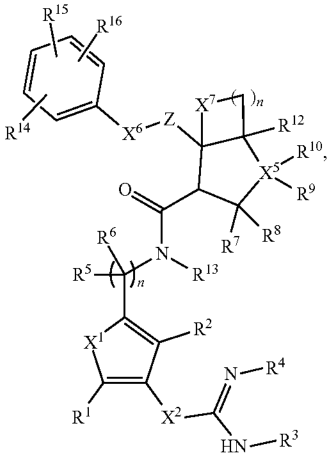
-continued
(VIII)
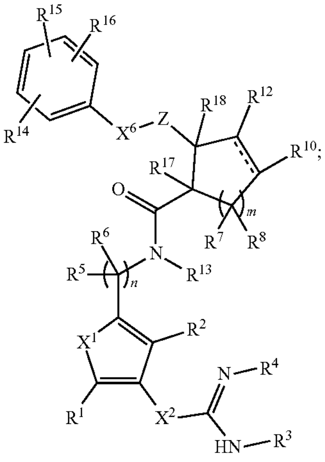
(IX)
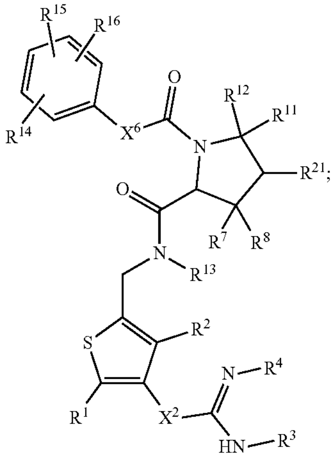
(X)
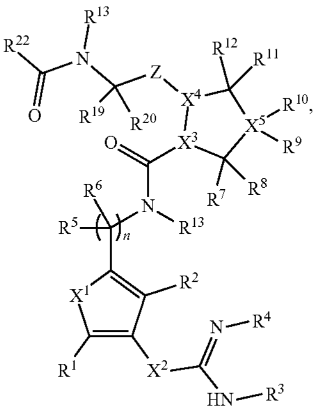

-continued
(XI)
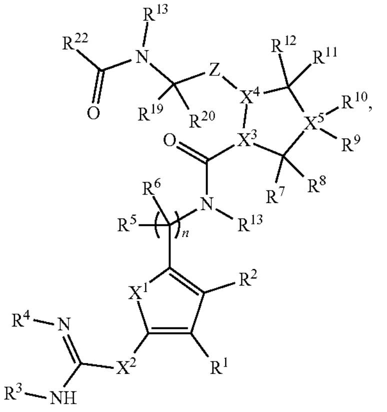
(XII)
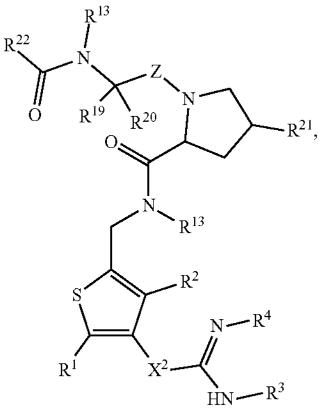
(XIII)
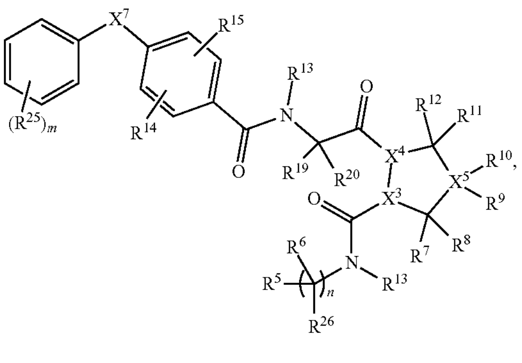
-continued
(XIV)
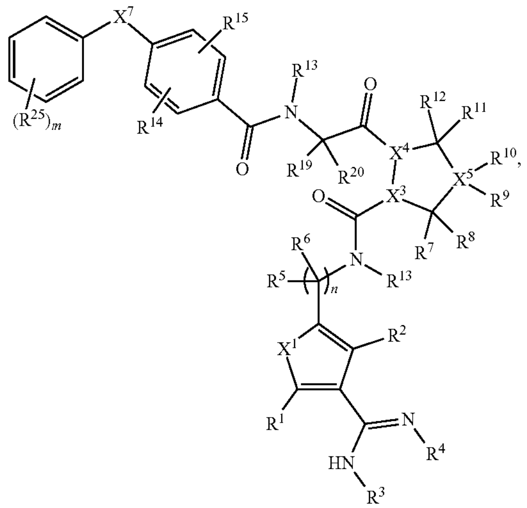
(XV)
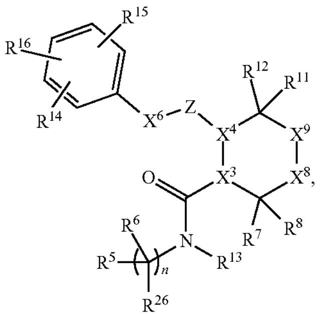
(XVI)
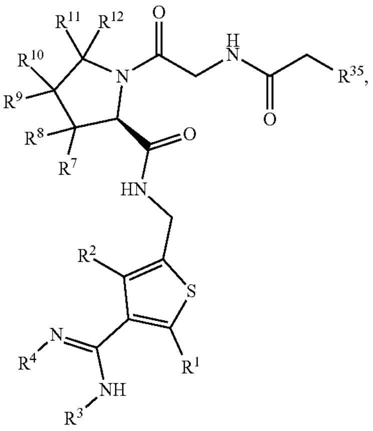

-continued (XVII)

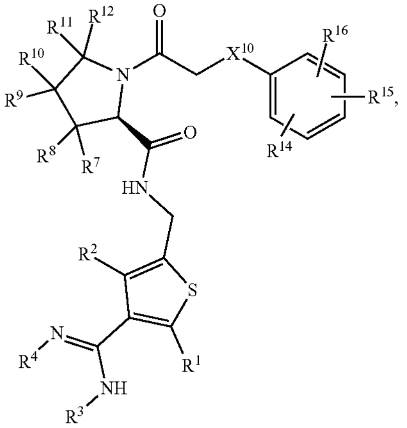

and (XVIII)

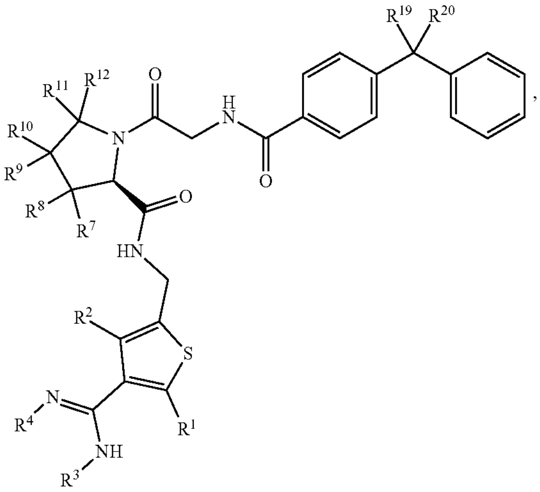

, wherein $R^{21}$ is selected from $C_1$-$C_6$alkyl and —O—$C_1$-$C_6$alkyl;

each $R^{25}$ is independently selected from hydrogen, halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —C(O)$R^{31}$, —S(O)$R^{31}$, —$S(O)_2R^{31}$, heterocycle, aryl, heteroaryl, cyano, and nitro; each of which $R^1$ and $R^2$ groups other than hydrogen, halogen, cyano, and nitro are optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —C(O)$R^{31}$, —S(O)$R^{31}$, —$S(O)_2R^{31}$, heterocycle, aryl, heteroaryl, cyano, and nitro;

$R^{14}$, $R^{15}$, and $R^{16}$ are independently selected from hydrogen, halogen, $C_1$-$C_6$alkyl, $C_2$-$C_6$alkenyl, $C_2$-$C_6$alkynyl, $C_1$-$C_6$haloalkyl, —$C_1$-$C_6$alkyl-aryl. —$OR^{30}$, —$SR^{30}$, —$N(R^{30})_2$, —C(O)$R^{31}$, —S(O)$R^{31}$, —$S(O)_2R^{31}$, heterocycle, aryl, heteroaryl, cyano, and nitro each of which $R^{14}$, $R^1$, and $R^{16}$ groups other than hydrogen, halogen, cyano, and nitro are optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —C(O)$R^{31}$, —S(O)$R^{31}$, —$S(O)_2R^{31}$, heterocycle, aryl, heteroaryl, cyano, and nitro;

6. In certain embodiments, the compound of the present disclosure is selected from:

(I)

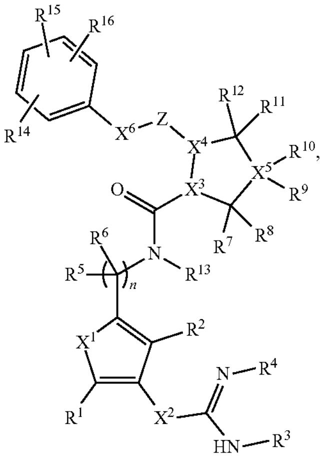

(II)

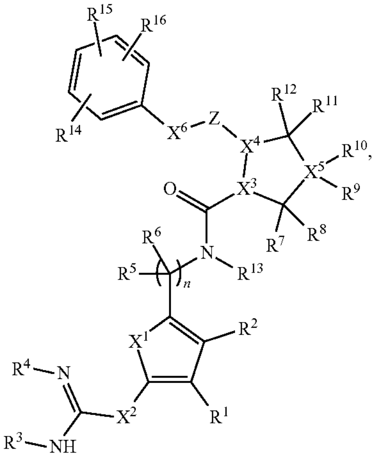

(III)

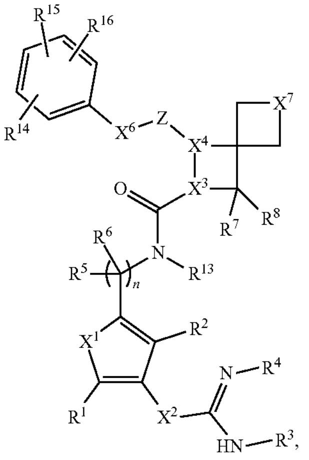

-continued
(IV)
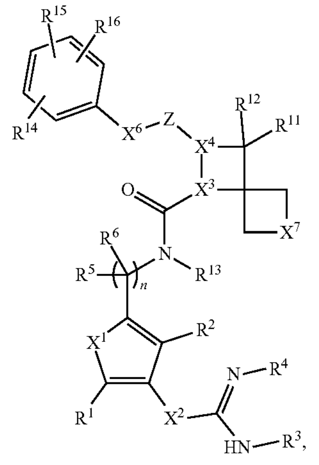
(V)
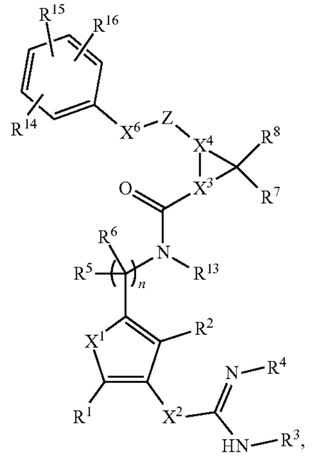
(VI)
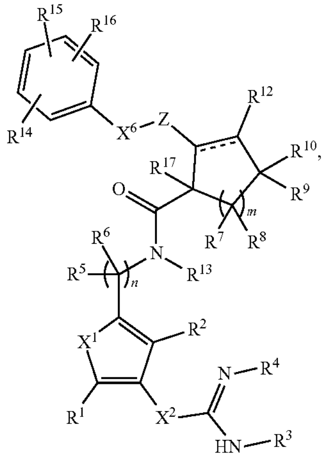
-continued
(VII)
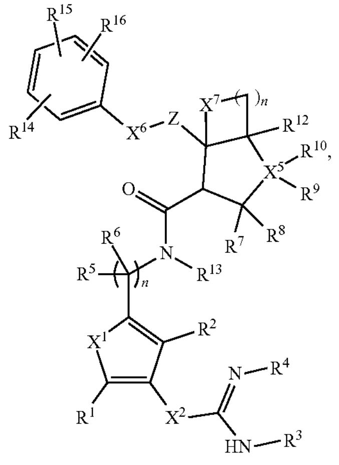
(VIII)
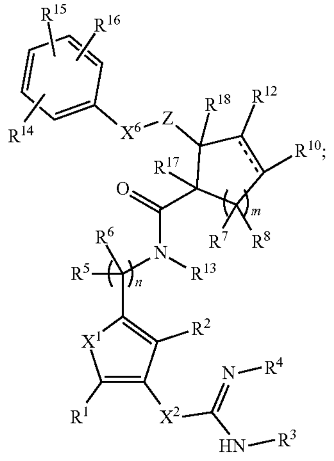
(IX)
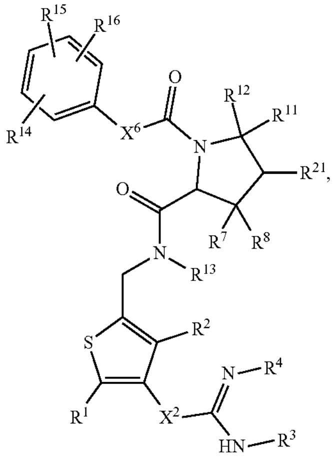

-continued (X)

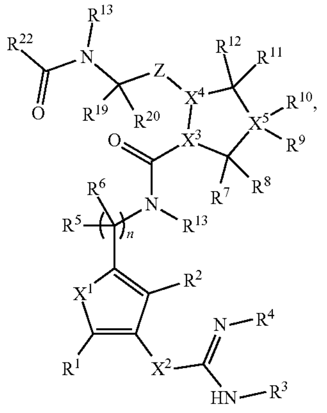

(XI)

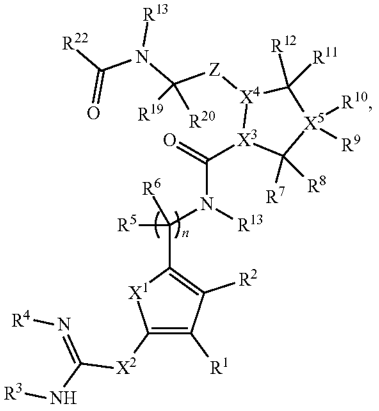

(XII)

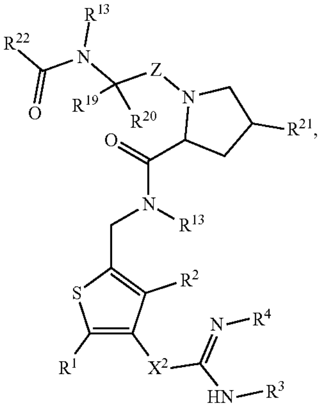

(XIII)

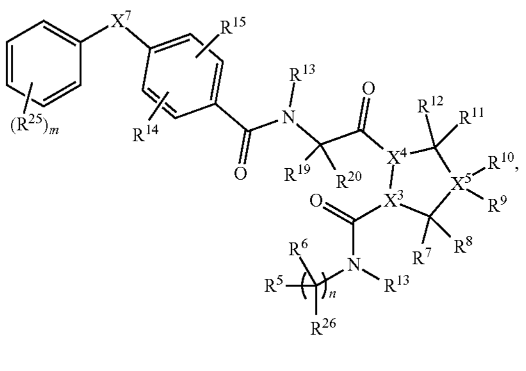

-continued (XIV)

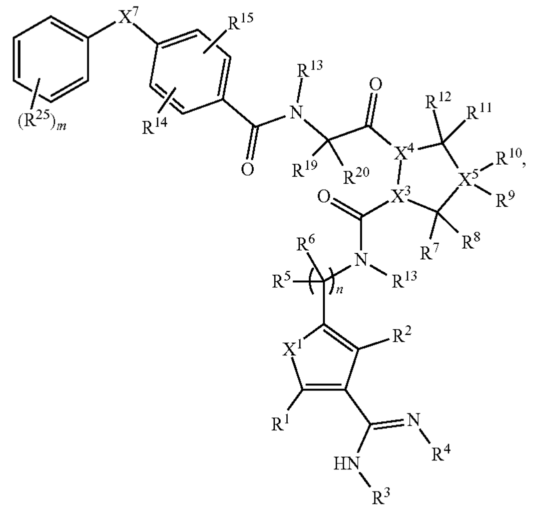

or (XV)

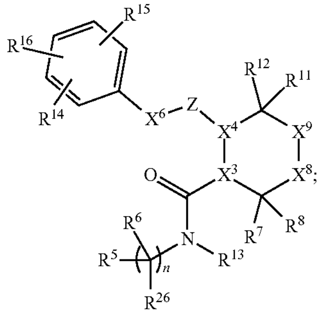

or a pharmaceutically acceptable salt, isotopic analog, prodrug, or isolated isomer thereof;

wherein:

each n is independently 1, 2, or 3;

each m is independently 0, 1, 2, or 3;

o is 0, 1, or 2;

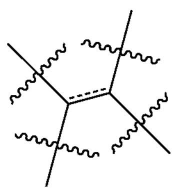

is either a single or a double bond;

Z is $CH_2$, $C(CH_2)$, or C(O);

$X^1$ is selected from S, O, and $N(R^{30})$;

$X^2$ is selected from bond, $N(R^{30})$, and —O—$N(R^{30})$—;

$X^3$ is selected from N and $C(R^{17})$;

$X^4$ is selected from N and $C(R^{18})$;

wherein only one of $X^3$ and $X^4$ can be N;

$X^5$ is C or Si;

$X^6$ is selected from

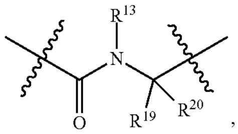 , 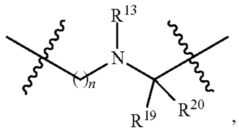 , 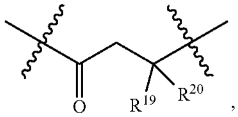 , 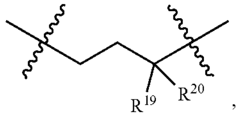 , 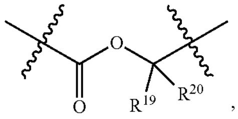 , 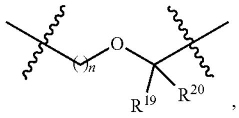 , 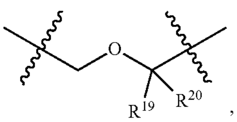 , 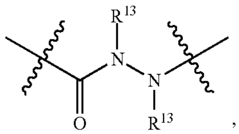 , and 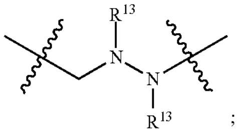 ;

$X^7$ is selected from O, S, $N(R^{30})$, and $CR^5R^6$;

each $X^8$ and $X^9$ is independently selected from O, S, $NR^{30}$, $CR^9R^{10}$, $CR^5R^6$. and $CH_2$; wherein $X^8$ and $X^9$ cannot both be the same group $X^{11}$ is selected from N and $CR^1$;

$X^{12}$ is selected from N and $CR^2$;

$R^1$ and $R^2$ are independently selected from hydrogen, halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro; each of which $R^1$ and $R^2$ groups other than hydrogen, halogen, cyano, and nitro are optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

$R^3$ and $R^4$ are independently selected from hydrogen, $C(O)R^{31}$, —$SR^{30}$, and —$OR^{30}$;

or $R^3$ and $R^4$ are instead combined to form an oxadiazole optionally substituted with 1, 2, or 3 substituents independently selected from $C_1$-$C_6$alkyl, $C_1$-$C_6$haloalkyl, —$OR^{30}$, and oxo;

each $R^5$ and $R^6$ are independently selected from hydrogen, halogen, $C_1$-$C_6$alkyl, $C_1$-$C_6$haloalkyl, —$OR^{30}$, and —$N(R^{30})_2$, wherein when on carbons adjacent to each other a $R^5$ and a $R^6$ group may optionally be replaced by a carbon-carbon double bond;

$R^7$, $R^8$, $R^9$, $R^{10}$, $R^{11}$, and $R^{12}$ are independently selected from hydrogen, halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, and heteroaryl, each of which $R^7$, $R^8$, $R^9$, $R^{10}$, $R^{11}$, and $R^{12}$ groups other than hydrogen and halogen are optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

or $R^7$ and $R^8$ may be taken together with the carbon to which they are attached to form a 3- to 6-membered carbocyclic spiro ring or a 4- to 6-membered heterocyclic spiro ring containing 1 or 2 heteroatoms independently chosen from N, O, and S;

or $R^7$ and $R^8$ may be taken together with the carbon to which they are attached to form

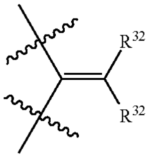

or carbonyl;

or $R^9$ and $R^{10}$ may be taken together with the atom to which they are attached to form a 3- to 6-membered carbocyclic spiro ring or a 4- to 6-membered heterocyclic spiro ring containing 1 or 2 heteroatoms independently chosen from N, O, and S;

or $R^9$ and $R^{10}$ may be taken together with the atom to which they are attached to form

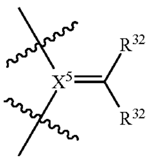

or carbonyl;

or $R^{11}$ and $R^{12}$ may be taken together with the carbon to which they are attached to form a 3- to 6-membered carbocyclic spiro ring or a 4- to 6-membered heterocyclic spiro ring containing 1 or 2 heteroatoms independently chosen from N, O, and S;

or $R^{11}$ and $R^{12}$ may be taken together with the carbon to which they are attached to form

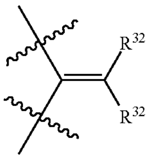

or carbonyl;

or $R^7$ and $R^9$ are taken together with the atoms to which they are attached to form a 4- to 8-membered carbocycle or a 4- to 8-membered heterocycle containing 1 or 2 heteroatoms independently chosen from N, O, and S;

or $R^9$ and $R^{11}$ are taken together with the atoms to which they are attached to form a 4- to 8-membered carbocycle or a 4- to 8-membered heterocycle containing 1 or 2 heteroatoms independently chosen from N, O, and S;

or $R^7$ and $R^{11}$ are taken together with the atoms to which they are attached to form a 1 or 2 carbon bridge;

each $R^{13}$ is independently selected from hydrogen or $C_1$-$C_6$alkyl;

$R^{14}$, $R^{15}$, and $R^{16}$ are independently selected from hydrogen, halogen, $C_1$-$C_6$alkyl, $C_2$-$C_6$alkenyl, $C_2$-$C_6$alkynyl, $C_1$-$C_6$haloalkyl, —$C_1$-$C_6$alkyl-aryl. —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro each of which $R^{14}$, $R^{15}$, and $R^{16}$ groups other than hydrogen, halogen, cyano, and nitro are optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

$R^{17}$ and $R^{18}$ are independently selected from hydrogen, halogen, $C_1$-$C_6$alkyl, $C_1$-$C_6$haloalkyl, —$OR^{30}$, and —$N(R^{30})_2$;

or $R^{17}$ and $R^{18}$ are taken together with the carbons to which they are attached to form a double bond;

$R^{19}$ and $R^{20}$ are independently selected from hydrogen, $C_1$-$C_6$alkyl, $C_5$-$C_{10}$ bicyclic carbocycle, $C_4$-$C_6$heterocycle, halogen, $C_1$-$C_6$haloalkyl, —$OR^{30}$, —$N(R^{30})_2$, —$(CH_2)_n$—$R^{33}$, and

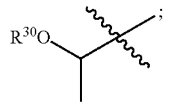

$R^{21}$ is selected from $C_1$-$C_6$ alkyl and —O—$C_1$-$C_6$ alkyl;

$R^{22}$ is selected from —$C_1$-$C_6$ alkyl-$R^{23}$, —$C_2$-$C_6$ alkenyl-$R^{23}$, —$C_2$-$C_6$ alkynyl-$R^{23}$ and bicyclic cycloalkyl-$R^{23}$, each of which $R^{22}$ is optionally substituted with 1, 2, 3, or 4 substituents independently selected from $C_1$-$C_6$ alkyl, $C_2$-$C_6$ alkenyl, $C_2$-$C_6$ alkynyl, halogen, $C_1$-$C_6$ haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

$R^{23}$ is selected from hydrogen, sugar, —$OR^{30}$, —$SR^{30}$, —$N(R^{30})_2$, —$C(O)R^{31}$, —$S(O)R^{31}$, and —$S(O)_2R^{31}$; and each $R^{25}$ is independently selected from hydrogen, halogen, $C_1$-$C_6$ alkyl, $C_2$-$C_6$ alkenyl, $C_2$-$C_6$ alkynyl, $C_1$-$C_6$ haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro; each of which $R^1$ and $R^2$ groups other than hydrogen, halogen, cyano, and nitro are optionally substituted with 1, 2, 3, or 4 substituents independently selected from $C_1$-$C_6$ alkyl, $C_2$-$C_6$ alkenyl, $C_2$-$C_6$ alkynyl, halogen, $C_1$-$C_6$ haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

$R^{26}$ is selected from

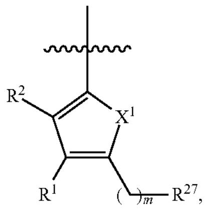
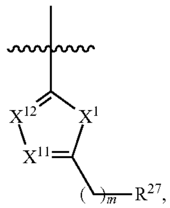
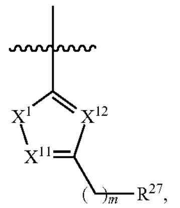

-continued

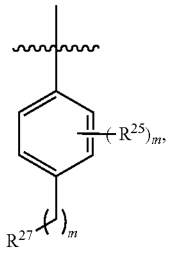
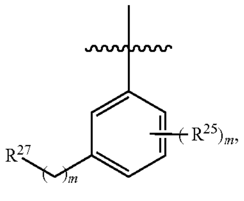
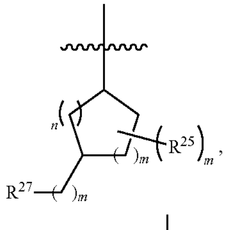
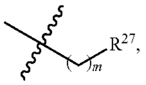
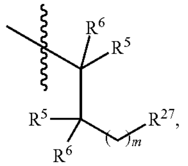
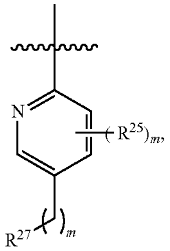
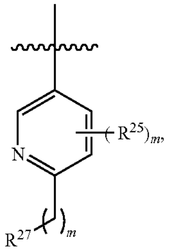
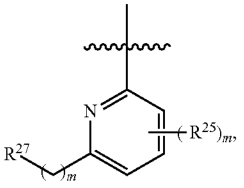
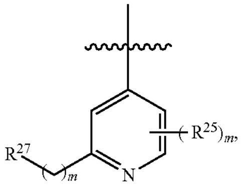
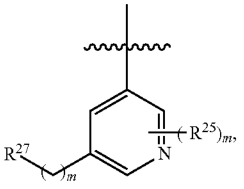
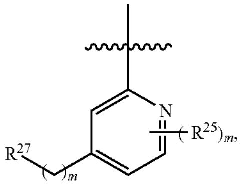
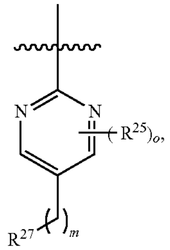
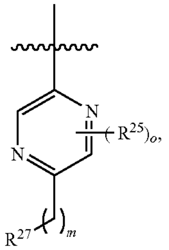
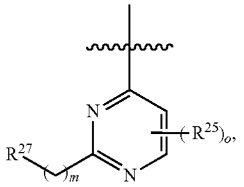
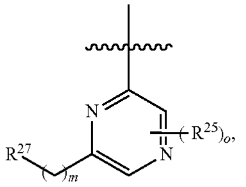
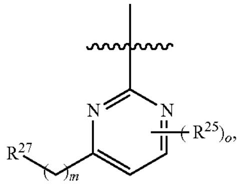
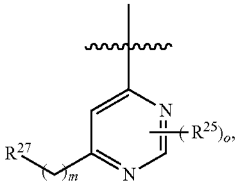

-continued

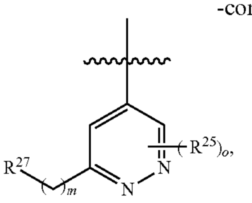 and 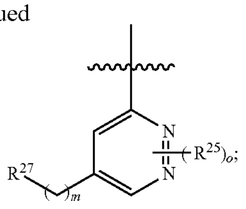

$R^{27}$ is selected from

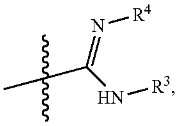 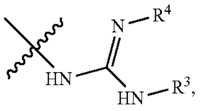

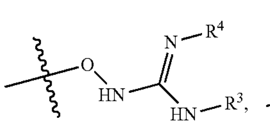 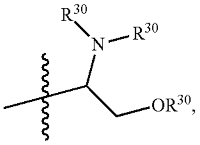

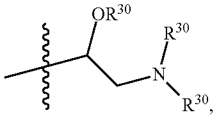 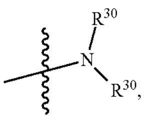 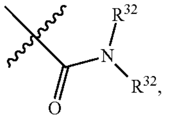

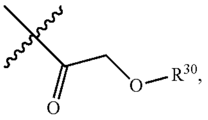 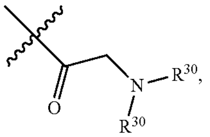 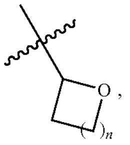

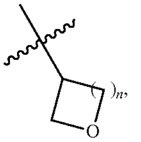 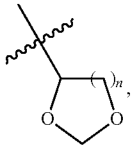 and 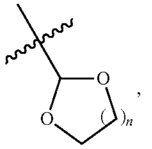

each $R^{30}$ is independently selected from hydrogen, $C_1$-$C_6$ alkyl, $C_1$-$C_6$ haloalkyl, aryl, heteroaryl, heterocycle, and $C(O)R^{31}$;

each $R^{31}$ is independently selected from hydrogen, $C_1$-$C_6$ alkyl, $C_1$-$C_6$ haloalkyl, —$OR^{32}$, —$SR^{32}$, —$N(R^{32})_2$, heterocycle, aryl, and heteroaryl;

each $R^{32}$ is independently selected from hydrogen, $C_1$-$C_6$ alkyl, and $C_1$-$C_6$ haloalkyl;

each $R^{33}$ is independently selected from hydrogen, guanidine, heteroaryl, aryl, —$C_6H_5$—$OR^{30}$; —$OR^{30}$, —$SR^{30}$, —$SeR^{30}$, —$N(R^{30})_2$, —$C(O)R^{31}$, wherein for compounds of Formula I and Formula II at least one of the following is satisfied:

a. $X^3$ is $C(R^{17})$ and $X^4$ is $C(R^{18})$;

b. $R^{17}$ is selected from halogen, $C_1$-$C_6$ alkyl, $C_1$-$C_6$ haloalkyl, —$OR^{30}$, and —$N(R^{30})_2$;

c. $X^5$ is Si;

d. Z is $C(CH_2)$;

e. Z is $CH_2$;

f. $R^7$ and $R^8$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

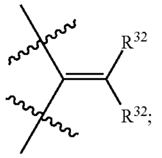

or a carbonyl;

g. $R^9$ and $R^{10}$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

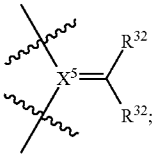

or a carbonyl;

h. $R^{11}$ and $R^{12}$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

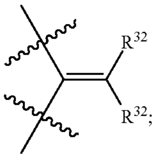

or a carbonyl;

i. $R^7$ and $R^9$ are taken together with the atoms to which they are attached to form a 4- to 8-membered carbocycle or a 4- to 8-membered heterocycle containing 1 or 2 heteroatoms independently chosen from N, O, and S; and $R^{10}$ or $R^{12}$ is not hydrogen;

j. $R^9$ and $R^{11}$ are taken together with the atoms to which they are attached to form a 4- to 8-membered carbocycle or a 4- to 8-membered heterocycle containing 1 or 2 heteroatoms independently chosen from N, O, and S; and $R^8$ or $R^{10}$ is not hydrogen;

k. $R^7$ and $R^{11}$ are taken together with the atoms to which they are attached to form a 1 or 2 carbon bridge;

l. $X^6$ is selected from

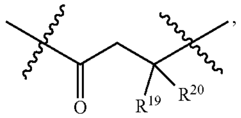 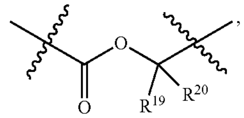

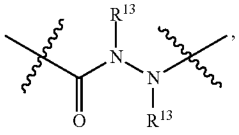 and 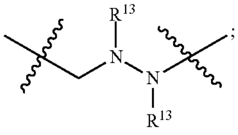

m. at least one of $R^3$ and $R^4$ is —$SR^{30}$ or $C(O)R^{31}$; or n. $R^3$ and $R^4$ are combined to form an oxadiazole optionally substituted with 1, 2, or 3 substituents independently selected from $C_1$-$C_6$ alkyl, $C_1$-$C_6$ haloalkyl, —$OR^{30}$, and oxo;

wherein for compounds of Formula X and Formula XI at least one of the following is satisfied:

a. $X^3$ is $C(R^{17})$ and $X^4$ is $C(R^{18})$;

b. $R^{17}$ is selected from halogen, $C_1$-$C_6$ alkyl, $C_1$-$C_6$ haloalkyl, —$OR^{30}$, and —$N(R^{30})_2$;

c. $X^5$ is Si;

d. Z is $C(CH_2)$;

e. Z is $CH_2$;

f. $R^7$ and $R^8$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

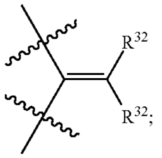

or a carbonyl;

g. $R^9$ and $R^{10}$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

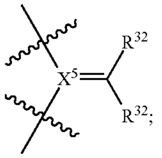

or a carbonyl;

h. $R^9$ and $R^{11}$ are taken together with the atoms to which they are attached to form a 4- to 8-membered carbocycle or a 4- to 8-membered heterocycle containing 1 or 2 heteroatoms independently chosen from N, O, and S; and $R^{10}$ is not hydrogen;

i. $R^{11}$ and $R^{12}$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

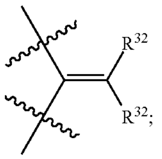

or a carbonyl;

j. $R^7$ and $R^9$ are taken together with the atoms to which they are attached to form a 4- to 8-membered carbocycle or a 4- to 8-membered heterocycle containing 1 or 2 heteroatoms independently chosen from N, O, and S; and $R^{10}$ is not hydrogen;

k. $R^7$ and $R^{11}$ are taken together with the atoms to which they are attached to form a 1 or 2 carbon bridge;

l. $R^{22}$ is substituted with at least three $OR^{30}$ groups;

m. $R^{23}$ is a sugar;

n. at least one of $R^3$ and $R^4$ is —$SR^{30}$ or $C(O)R^{31}$; or o. $R^3$ and $R^4$ are combined to form an oxadiazole optionally substituted with 1, 2, or 3 substituents independently selected from $C_1$-$C_6$alkyl, $C_1$-$C_6$haloalkyl, —$OR^{30}$, and oxo;

wherein for compounds of Formula XIV at least one of the following is satisfied:

a. $X^1$ is O or $N(R^{30})$;

b. $R^{14}$ is not hydrogen;

c. $R^1$ is not hydrogen;

d. $R^2$ is not hydrogen;

e. $R^3$ is not hydrogen; or f. $R^4$ is not hydrogen.

7. The compound of any one of embodiments 1-6, wherein n is 1.

8. The compound of any one of embodiments 1-7, wherein each m is independently 0 or 1.

9. The compound of any one of embodiments 1-8, wherein Z is C(O).

10. The compound of any one of embodiments 1-9, wherein $X^1$ is S.

11. The compound of any one of embodiments 1-10, wherein $X^2$ is bond.

12. The compound of any one of embodiments 1-11, wherein $X^3$ is $C(R^{17})$.

13. The compound of any one of embodiments 1-12, wherein $X^4$ is N.

14. The compound of any one of embodiments 1-13, wherein $X^5$ is C.

15. The compound of any one of embodiments 1-14, wherein $X^6$ is

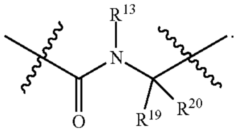

16. The compound of any one of embodiments 1-15, wherein $X^7$ is O.

17. The compound ofany one of embodiments 1-15, wherein $X^7$ is $CR^5R^6$.

18. The compound of any one of embodiments 1-15, wherein $X^7$ is S.

19. The compound of any one of embodiments 1-15, wherein $X^7$ is $N(R^3$.

20. The compound of any one of embodiments 1-19, wherein $X^8$ is CH and $X^9$ is N.

21. The compound of any one of embodiments 1-19, wherein $X^8$ is CH and $X^9$ is N.

22. The compound of any one of embodiments 1-21, wherein $X^{11}$ and $X^9$ are both CH.

23. The compound of any one of embodiments 1-21, wherein one of $X^{11}$ and $X^{12}$ is CH and the other is N.

24. The compound of any one of embodiments 1-23, wherein $R^1$ and $R^2$ are independently selected from hydrogen, halogen, —$OR^{30}$, —$SR^{30}$, —$N(R^{30})_2$, and $C_1$-$C_6$alkyl.

25. The compound of any one of embodiments 1-23, wherein $R^1$ and $R^2$ are independently selected from hydrogen, halogen, and $C_1$-$C_6$alkyl.
26. The compound of any one of embodiments 1-23, wherein $R^1$ and $R^2$ both hydrogen.
27. The compound of any one of embodiments 1-26, wherein $R^3$ and $R^4$ both hydrogen.
28. The compound of any one of embodiments 1-26, wherein $R^3$ is hydrogen and $R^4$ is hydroxyl.
29. The compound of any one of embodiments 1-26, wherein $R^3$ and $R^4$ are combined to form an oxadiazole optionally substituted with 1, 2, or 3 substituents independently selected from $C_1$-$C_6$alkyl, $C_1$-$C_6$haloalkyl, —$OR^{30}$, and oxo.
30. The compound of any one of embodiments 1-29, wherein $R^5$ and $R^6$ are both hydrogen,
31. The compound of any one of embodiments 1-30, wherein $R^7$ is hydrogen.
32. The compound of any one of embodiments 1-31, wherein $R^9$ is hydrogen.
33. The compound of any one of embodiments 1-30, wherein $R^7$ and $R^{11}$ are combined to form a 1 carbon bridge.
34. The compound of any one of embodiments 1-30, wherein $R^7$ and $R^{11}$ are combined to form a 2 carbon bridge.
35. The compound of any one of embodiments 1-31, wherein $R^{11}$ is hydrogen.
36. The compound of any one of embodiments 1-31, wherein $R^9$ and $R^{11}$ are combined to form a 4-8 membered carbocycle ring.
37. The compound of any one of embodiments 1-31, wherein $R^9$ and $R^{11}$ are combined to form a cyclopropyl ring.
38. The compound of any one of embodiments 1-35, wherein $R^{10}$ is hydrogen.
39. The compound of any one of embodiments 1-37, wherein $R^{10}$ is selected from halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —$C(O)R^{31}$, —$S(O)R^{31}$, and —$S(O)_2R^{31}$.
40. The compound of any one of embodiments 1-37, wherein $R^{10}$ is selected from aryl and heteroaryl each of which is optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro.
41. The compound of any one of embodiments 1-31, wherein $R^9$ and $R^{10}$ are combined to form a spirocycle.
42. The compound of any one of embodiments 1-31, wherein $R^9$ and $R^{10}$ are combined to form a 5-membered heterocycle spirocycle.
43. The compound of any one of embodiments 1-31, wherein $R^9$ and $R^{10}$ are combined to form a 5-membered carbocycle spirocycle.
44. The compound of any one of embodiments 1-40, wherein $R^{10}$ is methyl.
45. The compound of any one of embodiments 1-44, wherein $R^{12}$ is hydrogen.
46. The compound of any one of embodiments 1-45, wherein $R^8$ is hydrogen.
47. The compound of any one of embodiments 1-46, wherein $R^{13}$ is hydrogen.
48. The compound of any one of embodiments 1-46, wherein $R^{13}$ is $C_1$-$C_6$alkyl.
49. The compound of any one of embodiments 1-48, wherein $R^{14}$ is $C_1$-$C_6$alkyl.
50. The compound of any one of embodiments 1-48, wherein $R^{14}$ is hydrogen.
51. The compound of any one of embodiments 1-48, wherein $R^{14}$ is halogen.
52. The compound of any one of embodiments 1-48, wherein $R^{14}$ is haloalkyl.
53. The compound of any one of embodiments 1-48, wherein $R^{14}$ is $OR^{30}$.
54. The compound of any one of embodiments 1-48, wherein $R^{14}$ is —O-phenyl.
55. The compound of any one of embodiments 1-54, wherein $R^{15}$ is $C_1$-$C_6$alkyl.
56. The compound of any one of embodiments 1-54, wherein $R^{15}$ is hydrogen.
57. The compound of any one of embodiments 1-54, wherein $R^{15}$ is halogen.
58. The compound of any one of embodiments 1-54, wherein $R^{15}$ is haloalkyl.
59. The compound of any one of embodiments 1-54, wherein $R^{15}$ is $OR^{30}$.
60. The compound of any one of embodiments 1-54, wherein $R^{15}$ is —O-phenyl.
61. The compound of any one of embodiments 1-60, wherein $R^{16}$ is $C_1$-$C_6$alkyl.
62. The compound of any one of embodiments 1-60, wherein $R^{16}$ is hydrogen.
63. The compound of any one of embodiments 1-60, wherein $R^{16}$ is halogen.
64. The compound of any one of embodiments 1-60, wherein $R^{16}$ is haloalkyl.
65. The compound of any one of embodiments 1-60, wherein $R^{16}$ is $OR^{30}$.
66. The compound of any one of embodiments 1-60, wherein $R^{16}$ is —O-phenyl.
67. The compound of any one of embodiments 1-66, wherein $R^{11}$ is hydrogen.
68. The compound of any one of embodiments 1-67, wherein $R^{18}$ is hydrogen.
69. The compound of any one of embodiments 1-68, wherein $R^{19}$ is hydrogen.
70. The compound of any one of embodiments 1-68, wherein $R^{19}$ is selected from $C_1$-$C_6$alkyl, $C_5$-$C_{10}$ bicyclic carbocycle, $C_4$-$C_6$heterocycle, halogen, $C_1$-$C_6$haloalkyl, —$OR^{30}$, —$N(R^{30})_2$, —$(CH_2)_n$—$R^{33}$, and

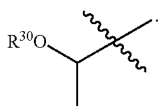

71. The compound of any one of embodiments 1-70, wherein $R^{20}$ is hydrogen.
72. The compound of any one of embodiments 1-70, wherein $R^{20}$ is selected from $C_1$-$C_6$alkyl, $C_5$-$C_{10}$ bicyclic carbocycle, $C_4$-$C_6$heterocycle, halogen, $C_1$-$C_6$haloalkyl, —$OR^{30}$, —$N(R^{30})_2$, —$(CH_2)_n$—$R^{33}$, and

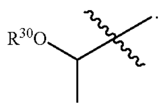

73. The compound of any one of embodiments 1-70, wherein $R^{20}$ is —$(CH_2)_n$—$R^{33}$.

74. The compound of any one of embodiments 1-73, wherein $R^{21}$ is $C_1$-$C_6$haloalkyl.

75. The compound of any one of embodiments 1-73, wherein $R^{21}$ is —O—$C_1$-$C_6$haloalkyl.

76. The compound of any one of embodiments 1-73, wherein $R^{21}$ is phenyl, optionally substituted with 1, 2, 3, or 4 substituents independently selected from $SF_5$, $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —C(O)$R^{31}$, —S(O)$R^{31}$, —$S(O)_2R^{31}$, heterocycle, aryl, heteroaryl, cyano, and nitro.

77. The compound of any one of embodiments 1-73, wherein $R^{21}$ is heteroaryl, optionally substituted with 1, 2, 3, or 4 substituents independently selected from $SF_5$, $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —C(O)$R^{31}$, —S(O)$R^{31}$, —$S(O)_2R^{31}$, heterocycle, aryl, heteroaryl, cyano, and nitro.

78. The compound of any one of embodiments 76-77, wherein $R^{21}$ is not substituted.

79. The compound of any one of embodiments 76-77, wherein $R^{21}$ is substituted with at least 1 halogen group.

80. The compound of any one of embodiments 76-77, wherein $R^{21}$ is substituted with at least 1 $C_1$-$C_6$alkyl group.

81. The compound of any one of embodiments 76-77, wherein $R^{21}$ is substituted with 1 fluoro group.

82. The compound of any one of embodiments 76-77, wherein $R^{21}$ is substituted with 1 methyl group.

83. The compound of any one of embodiments 1-82, wherein $R^{22}$ is —$C_1$-$C_6$alkyl-$R^{23}$ optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —C(O)$R^{31}$, —S(O)$R^{31}$, —$S(O)_2R^{31}$, heterocycle, aryl, heteroaryl, cyano, and nitro.

84. The compound of any one of embodiments 1-82, wherein $R^{22}$ is —$C_3$-$C_6$alkyl-$R^{23}$ optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —C(O)$R^{31}$, —S(O)$R^{31}$, —$S(O)_2R^{31}$, heterocycle, aryl, heteroaryl, cyano, and nitro.

85. The compound of any one of embodiments 1-82, wherein $R^{22}$ is bicyclic cycloalkyl-$R^{23}$ optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —C(O)$R^{31}$, —S(O)$R^{31}$, —$S(O)_2R^{31}$, heterocycle, aryl, heteroaryl, cyano, and nitro.

86. The compound of any one of embodiments 1-85, wherein $R^{23}$ is hydrogen.

87. The compound of any one of embodiments 1-85, wherein $R^{23}$ is sugar.

88. The compound of any one of embodiments 1-85, wherein $R^{23}$ is —$OR^{30}$.

89. The compound of any one of embodiments 1-85, wherein $R^{23}$ is $SR^{30}$, —$N(R^{30})_2$, —C(O)$R^{31}$, —S(O)$R^{31}$, or —$S(O)_2R^{31}$.

90. The compound of any one of embodiments 1-89, wherein $R^{25}$ is $C_1$-$C_6$alkyl.

91. The compound of any one of embodiments 1-89, wherein $R^{25}$ is hydrogen.

92. The compound of any one of embodiments 1-89, wherein $R^{25}$ is halogen.

93. The compound of any one of embodiments 1-89, wherein $R^{25}$ is haloalkyl.

94. The compound of any one of embodiments 1-89, wherein $R^{25}$ is $OR^{30}$.

95. The compound of any one of embodiments 1-89, wherein $R^{25}$ is —O-phenyl.

96. The compound of any one of embodiments 1-89, wherein $R^{25}$ is $SF_5$.

97. The compound ofany one of embodiments 1-96, wherein $R^{26}$ is

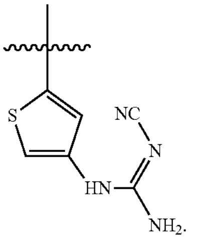 [SMILES: *c1cc(N/C(N)=N\C#N)cs1]

98. The compound of any one of embodiments 1-96, wherein $R^{26}$ is selected from.

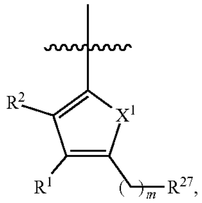

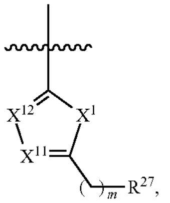

and

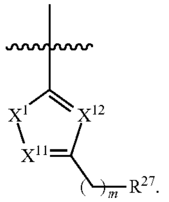

99. The compound of any one of embodiments 1-96, wherein $R^{26}$ is

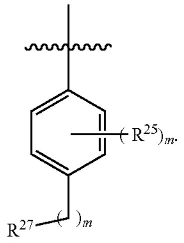

100. The compound of any one of embodiments 1-96, wherein $R^{26}$ is

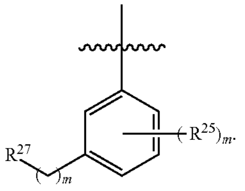

101. The compound of any one of embodiments 1-96, wherein $R^{26}$ is

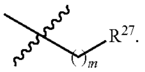

102. The compound of any one of embodiments 1-96, wherein $R^{26}$ is selected from:

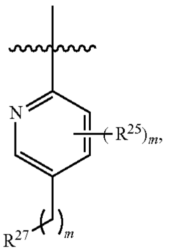

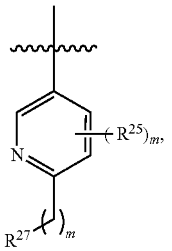

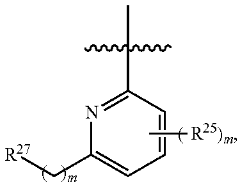

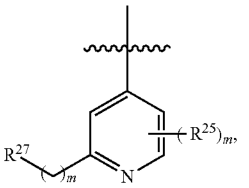

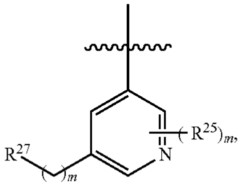

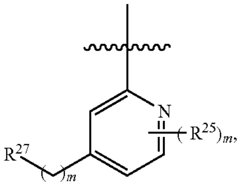

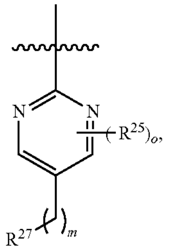

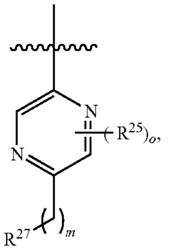

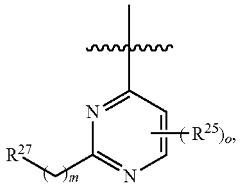

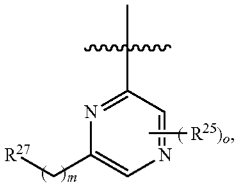

-continued

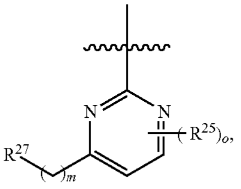

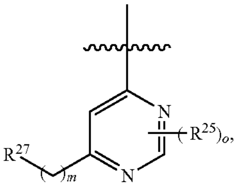

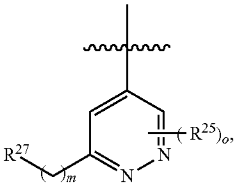

and

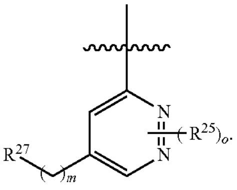

103. The compound of any one of embodiments 1-102, wherein $R^{27}$ is

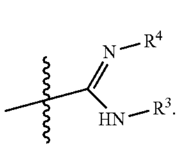

104. The compound of any one of embodiments 1-102, wherein $R^{27}$ is

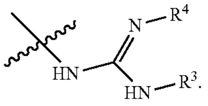

105. The compound of any one of embodiments 1-102, wherein $R^{27}$ is

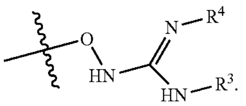

106. The compound of any one of embodiments 1-105, wherein $R^{30}$ is hydrogen.

107. The compound of any one of embodiments 1-105, wherein $R^{30}$ is $C_1$-$C_6$alkyl.

108. The compound of any one of embodiments 1-105, wherein $R^{30}$ is methyl.

109. The compound of any one of embodiments 1-105, wherein $R^{30}$ is $C_1$-$C_6$haloalkyl.

110. The compound of any one of embodiments 1-105, wherein $R^{30}$ is $CF_3$.

111. The compound of any one of embodiments 1-105, wherein $R^{30}$ is $C(O)R^{31}$.

112. The compound of any one of embodiments 1-111, wherein $R^{31}$ is hydrogen.

113. The compound of any one of embodiments 1-111, wherein $R^{31}$ is $C_1$-$C_6$alkyl.

114. The compound of any one of embodiments 1-111, wherein $R^{31}$ is methyl.

115. The compound of any one of embodiments 1-111, wherein $R^{31}$ is $C_1$-$C_6$haloalkyl.

116. The compound of any one of embodiments 1-111, wherein $R^{31}$ is $CF_3$.

117. The compound of any one of embodiments 1-111, wherein $R^{31}$ is —$OR^{32}$.

118. The compound of any one of embodiments 1-111, wherein $R^{31}$ is —$N(R^{32})_2$.

119. The compound of any one of embodiments 1-118, wherein $R^{32}$ is hydrogen.

120. The compound of any one of embodiments 1-118, wherein $R^{32}$ is $C_1$-$C_6$alkyl.

121. The compound of any one of embodiments 1-120, wherein $R^{33}$ is hydrogen.

122. The compound of any one of embodiments 1-120, wherein $R^{33}$ is independently selected from hydrogen, guanidine, heteroaryl, aryl, —$C_6H_5$—$OR^{30}$; —$OR^{30}$, —$SR^{30}$, —$SeR^{30}$, —$N(R^{30})_2$, and —$C(O)R^{31}$.

123. The compound of any one of embodiments 1-120, wherein $R^{33}$ is guanidine.

124. The compound of any one of embodiments 1-120, wherein $R^{33}$ is independently selected from hydrogen, guanidine, heteroaryl, aryl, —$C_6H_5$—$OR^{30}$; —$OR^{30}$, —$SR^{30}$, —$SeR^{30}$, —$N(R^{30})_2$, and —$C(O)R^{31}$.

125. The compound of any one of embodiments 1-124, wherein the compound is of formula:

(I)

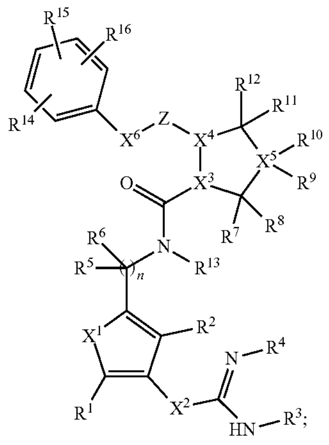

or a pharmaceutically acceptable salt thereof.

126. The compound of any one of embodiments 1-124, wherein the compound is of formula:

(II)

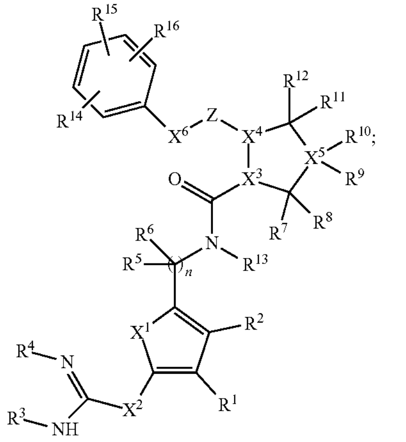

or a pharmaceutically acceptable salt thereof.

127. The compound of any one of embodiments 1-124, wherein the compound is of formula:

(III)

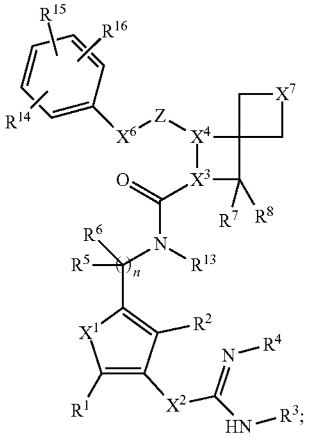

or a pharmaceutically acceptable salt thereof.

128. The compound of any one of embodiments 1-124, wherein the compound is of formula:

(IV)

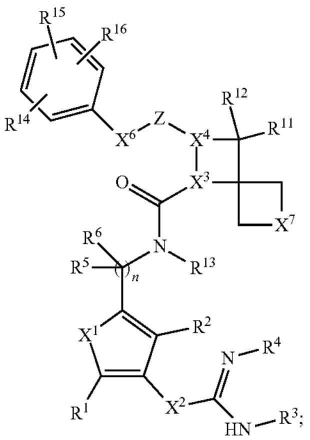

or a pharmaceutically acceptable salt thereof.

129. The compound of any one of embodiments 1-124, wherein the compound is of formula:

(V)

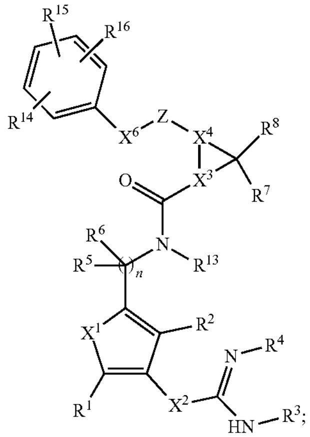

or a pharmaceutically acceptable salt thereof.

130. The compound of any one of embodiments 1-124, wherein the compound is of formula:

(VI)

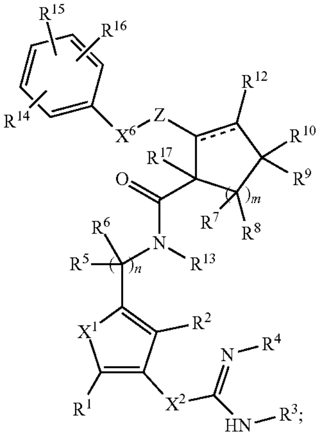

or a pharmaceutically acceptable salt thereof.

131. The compound of any one of embodiments 1-124, wherein the compound is of formula:

(VII)

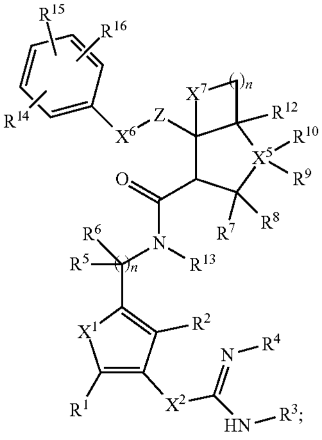

or a pharmaceutically acceptable salt thereof.

132. The compound of any one of embodiments 1-124, wherein the compound is of formula:

(VIII)

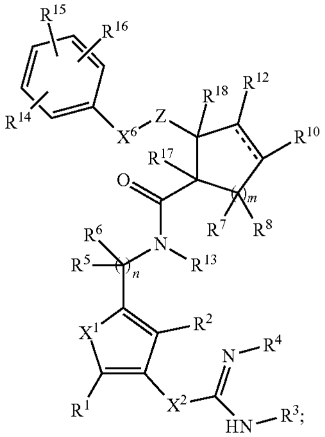

or a pharmaceutically acceptable salt thereof.

133. The compound of any one of embodiments 1-124, wherein the compound is of formula:

(IX)

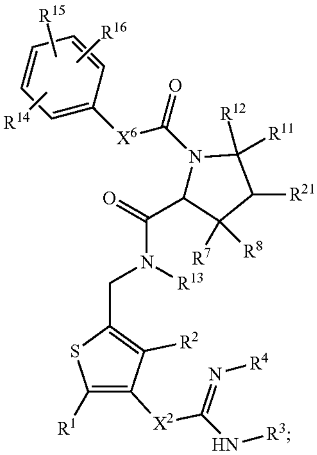

or a pharmaceutically acceptable salt thereof.

134. The compound of any one of embodiments 1-124, wherein the compound is of formula:

(X)

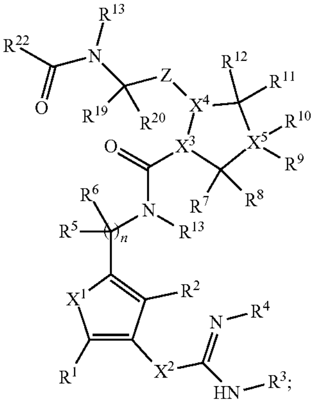

or a pharmaceutically acceptable salt thereof.

135. The compound of any one of embodiments 1-124, wherein the compound is of formula:

(XI)

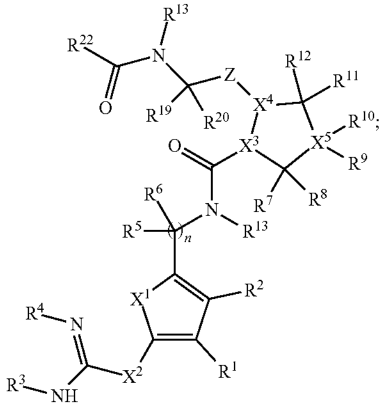

or a pharmaceutically acceptable salt thereof.

136. The compound of any one of embodiments 1-124, wherein the compound is of formula:

(XII)

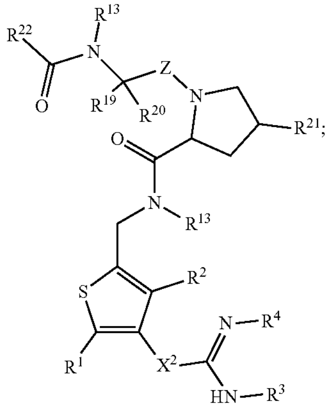

or a pharmaceutically acceptable salt thereof.

137. The compound of any one of embodiments 1-124, wherein the compound is of formula:

(XIII)

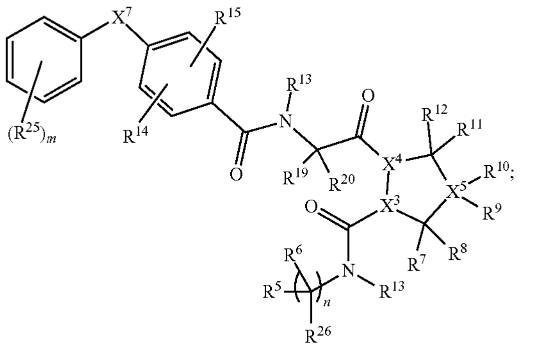

or a pharmaceutically acceptable salt thereof.

138. The compound of any one of embodiments 1-124, wherein the compound is of formula:

(XIV)

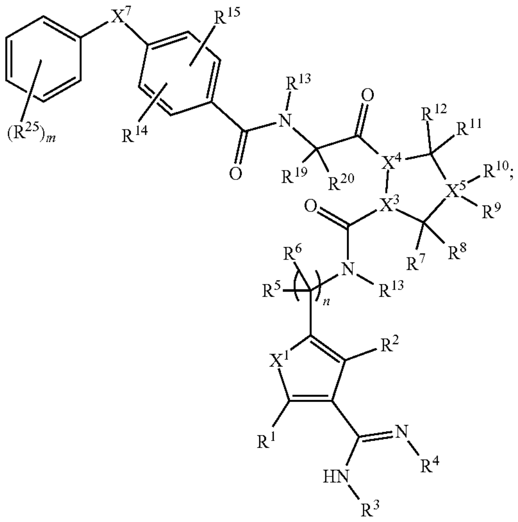

or a pharmaceutically acceptable salt thereof.

139. The compound of any one of embodiments 1-124, wherein the compound is of formula:

(XV)

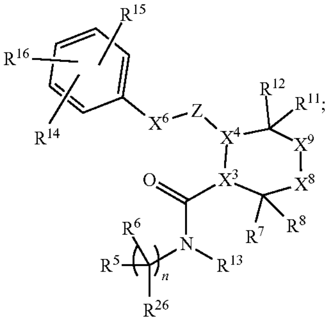

or a pharmaceutically acceptable salt thereof.

140. The compound of any one of embodiments 1-124, wherein the compound is of formula:

(XVI)

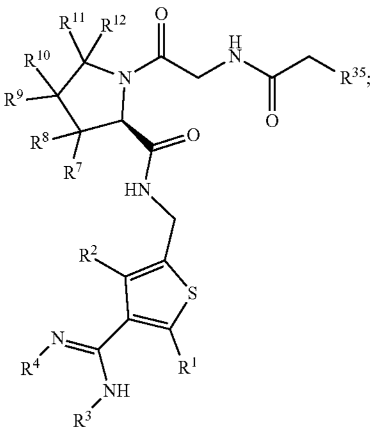

or a pharmaceutically acceptable salt thereof.

141. The compound of any one of embodiments 1-124, wherein the compound is of formula:

(XVII)

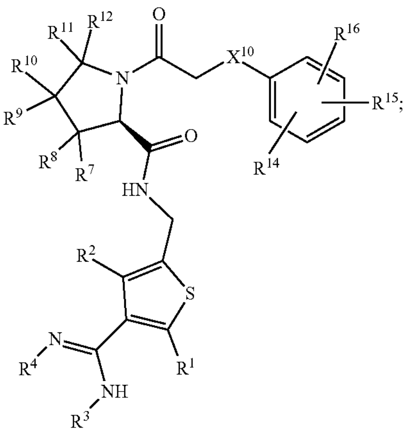

or a pharmaceutically acceptable salt thereof.

142. The compound of any one of embodiments 1-124, wherein the compound is of formula:

(XVIII)

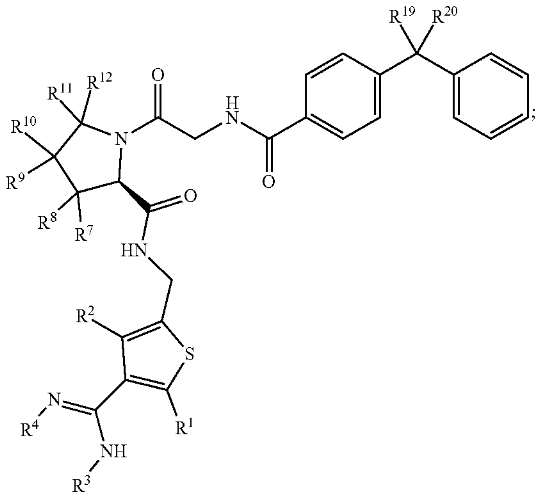

or a pharmaceutically acceptable salt thereof.

143. The compound of any one of embodiments 1-124, wherein the compound is of formula:

(XIX)

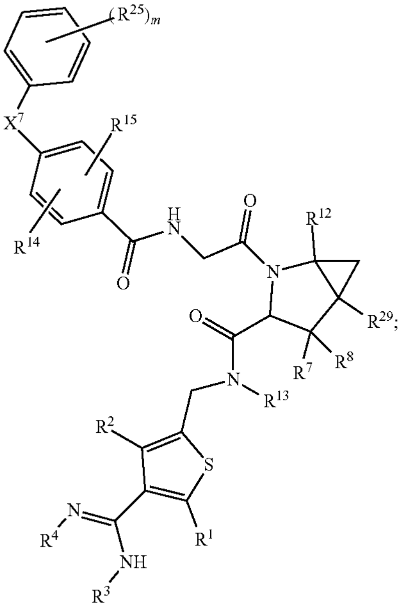

or a pharmaceutically acceptable salt thereof.

144. The compound of any one of embodiments 1-124, wherein the compound is of formula:

(XX)

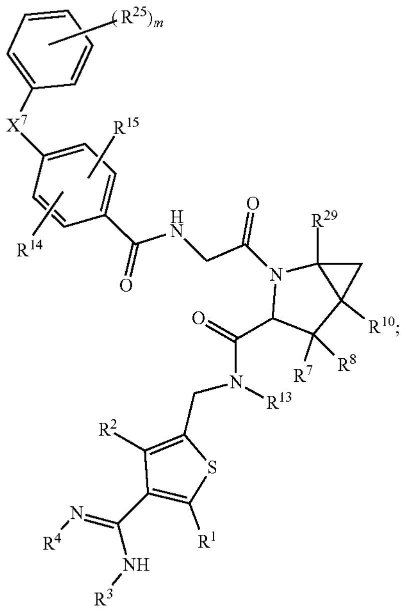

or a pharmaceutically acceptable salt thereof.

145. In certain embodiments, the compound of the present, is selected from:

-continued
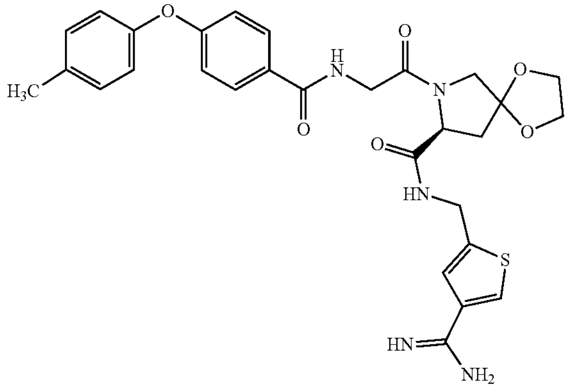
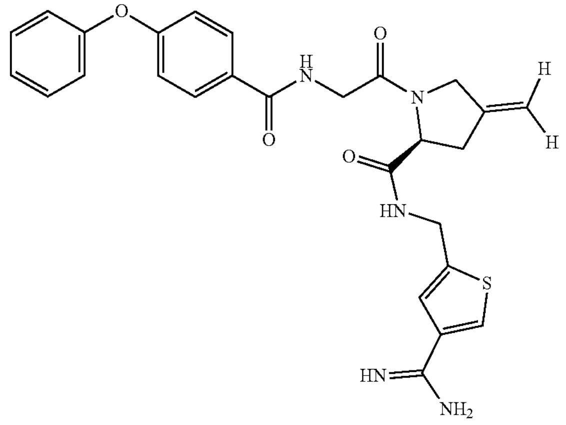
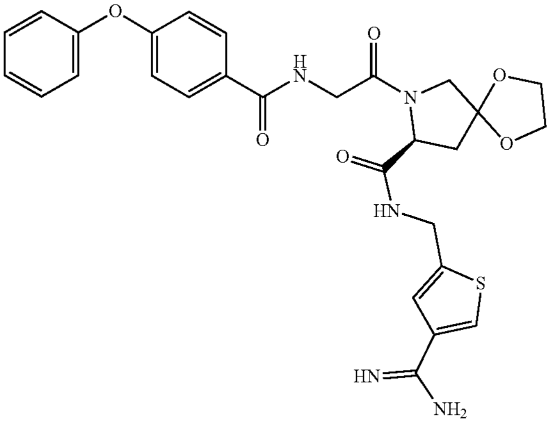
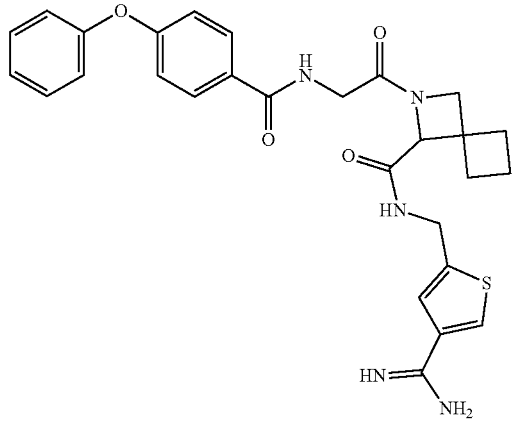
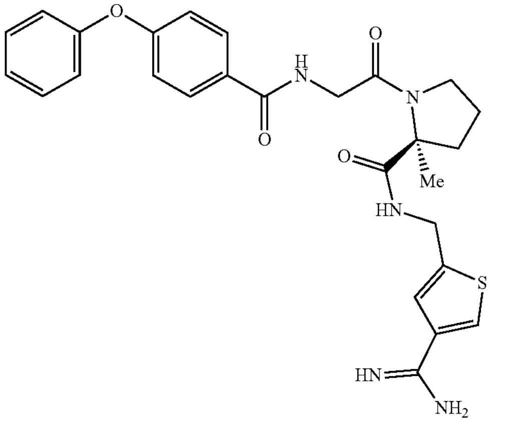
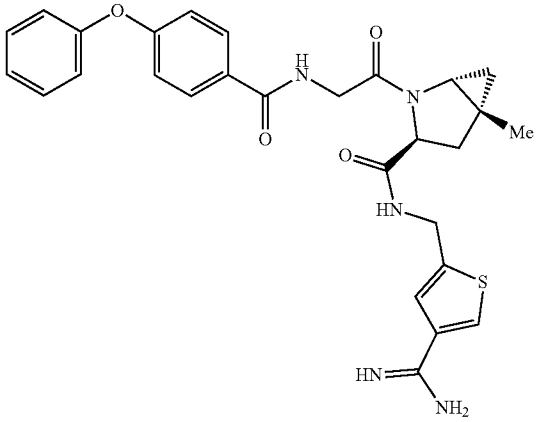
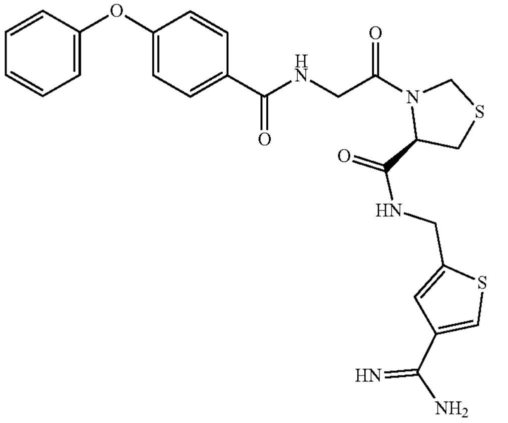
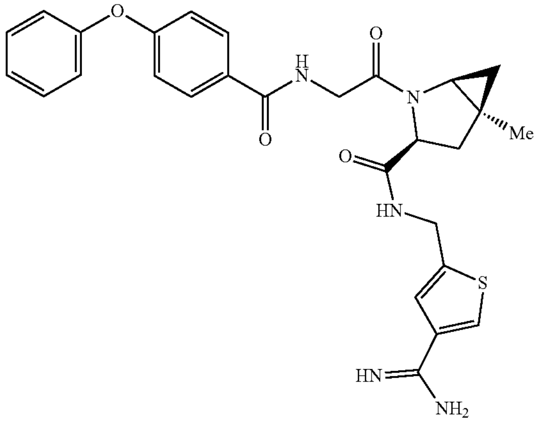

-continued
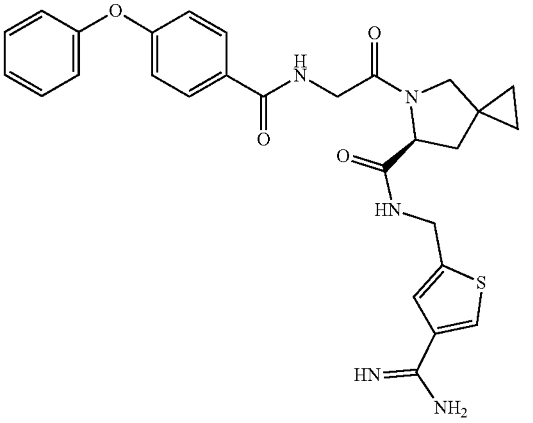
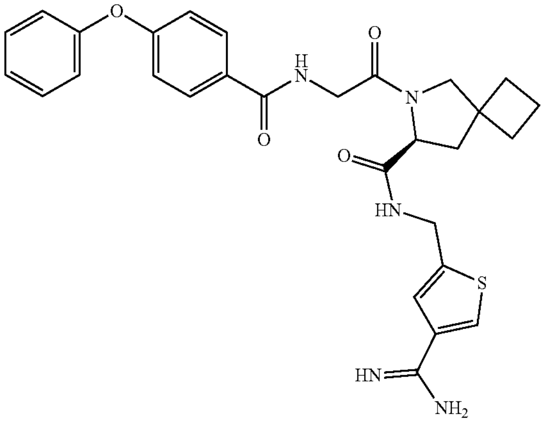
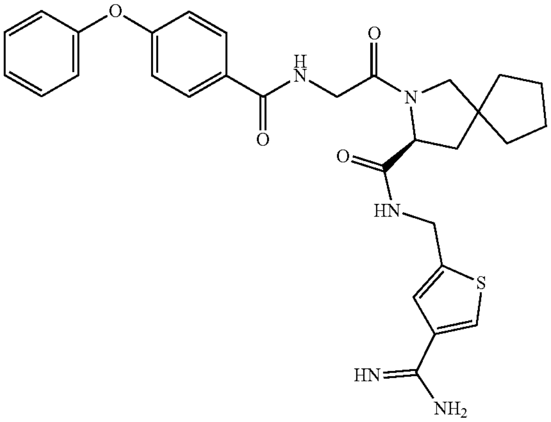
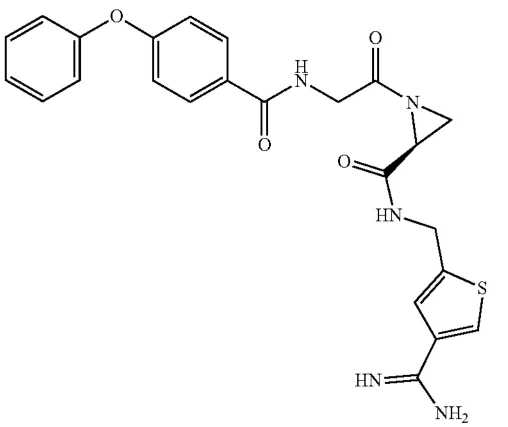
-continued
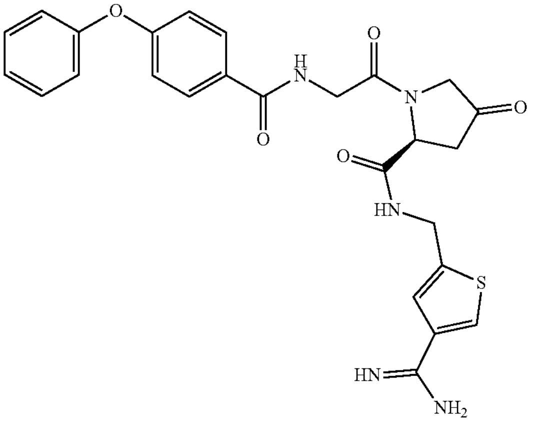
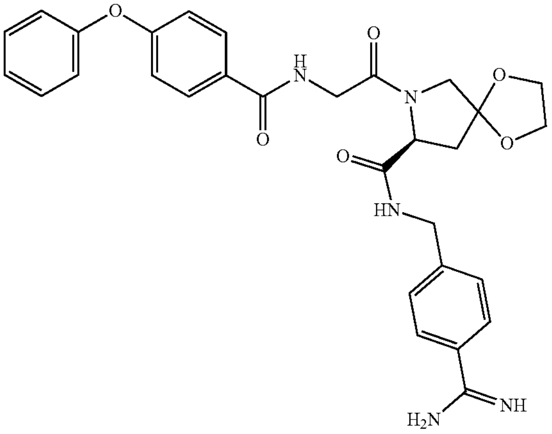
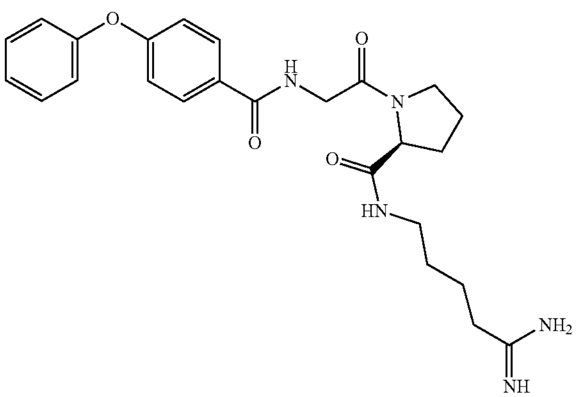
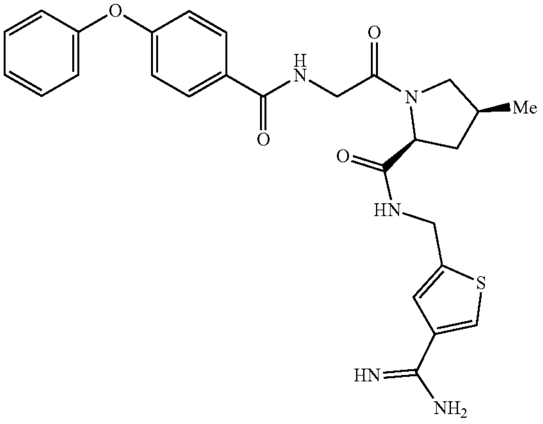

-continued
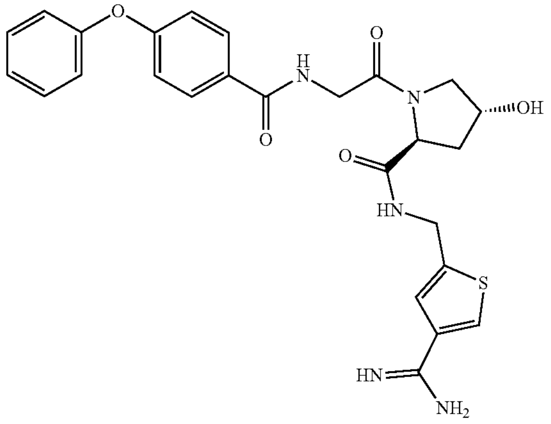
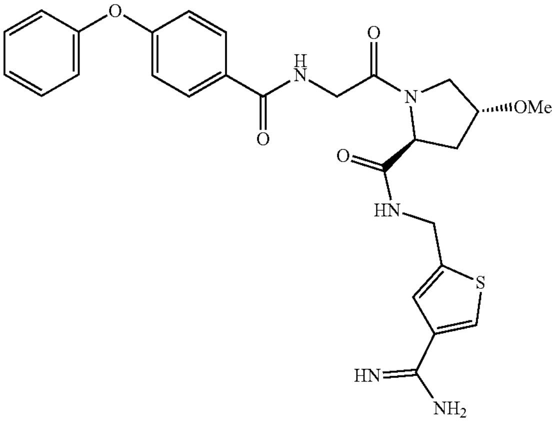
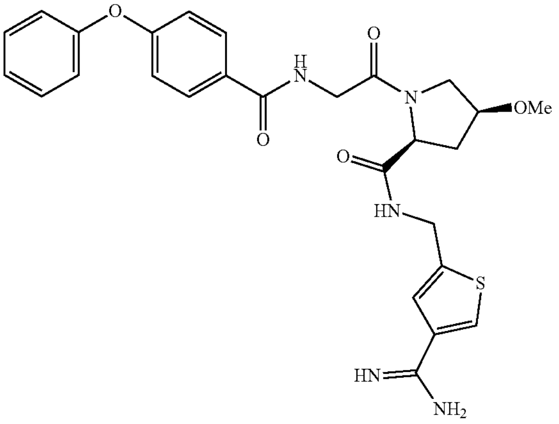
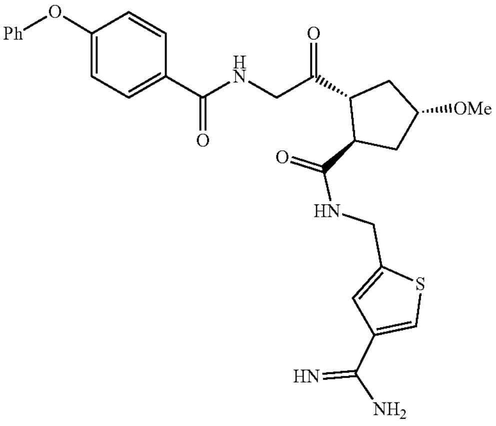
and
-continued
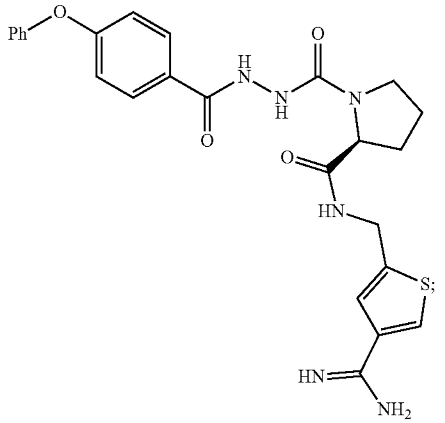 [SMILES: N=C(N)c1csc(CNC(=O)[C@@H]2CCCN2C(=O)NNC(=O)c2ccc(Oc3ccccc3)cc2)c1]
or a pharmaceutically acceptable salt thereof.
146. In certain embodiments, the compound of the present disclosure is selected from:
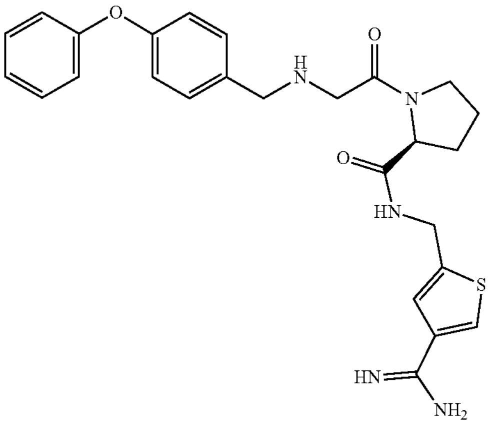
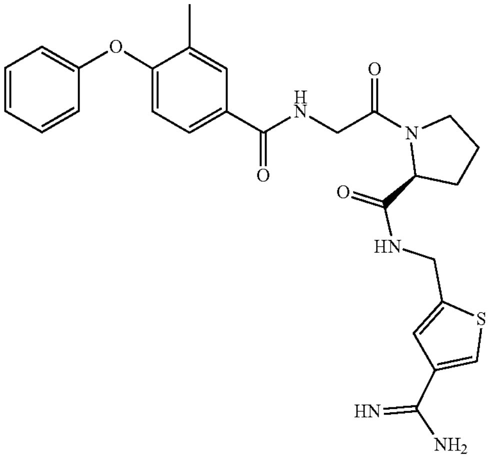

-continued
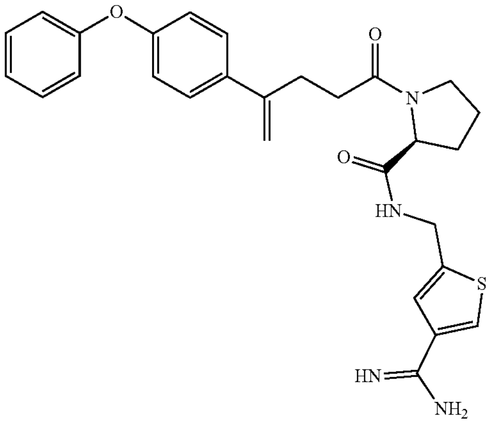
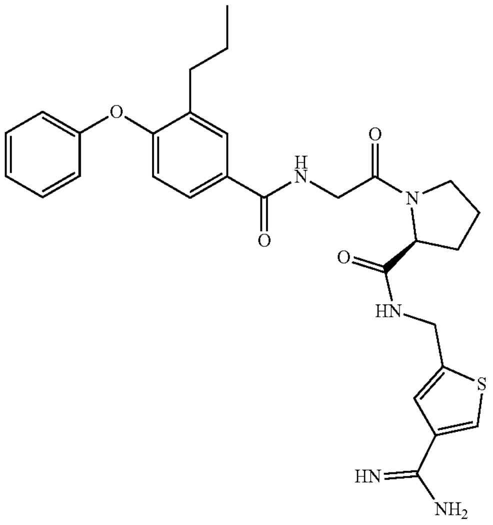
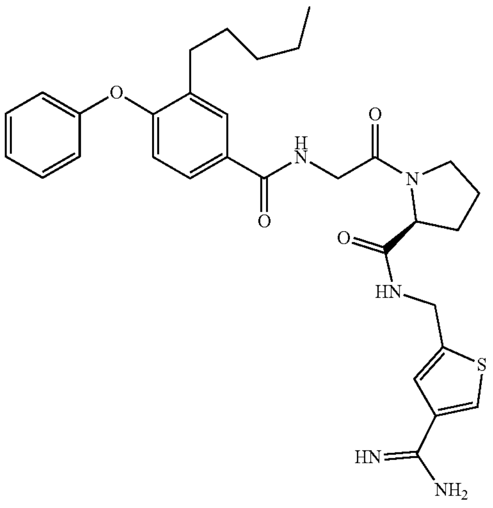
-continued
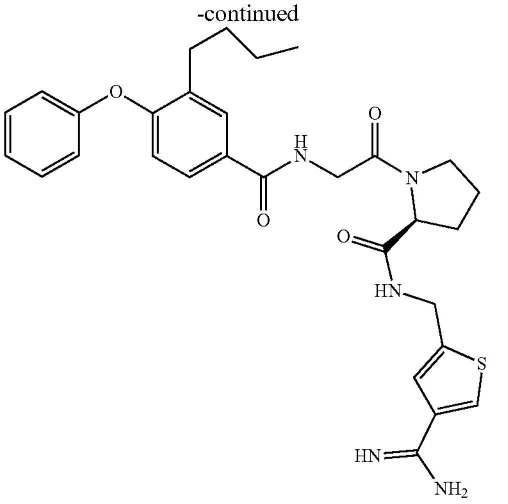
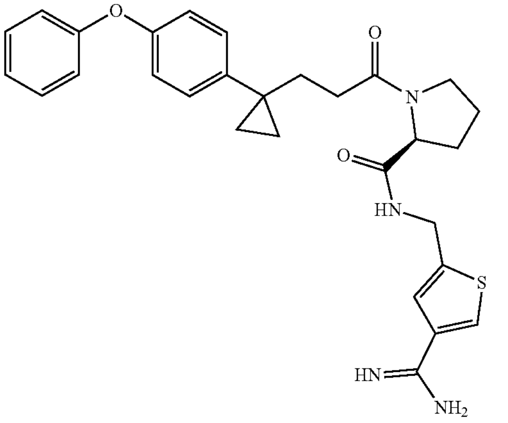
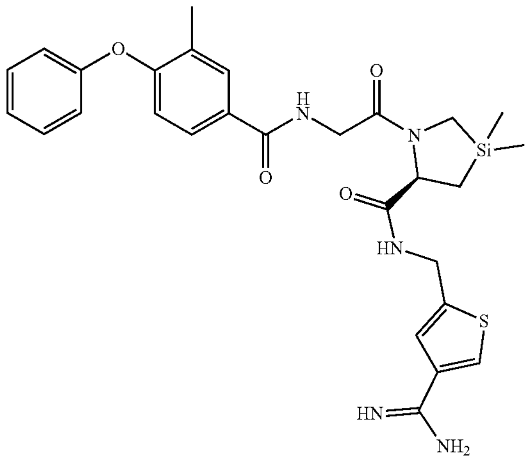

-continued
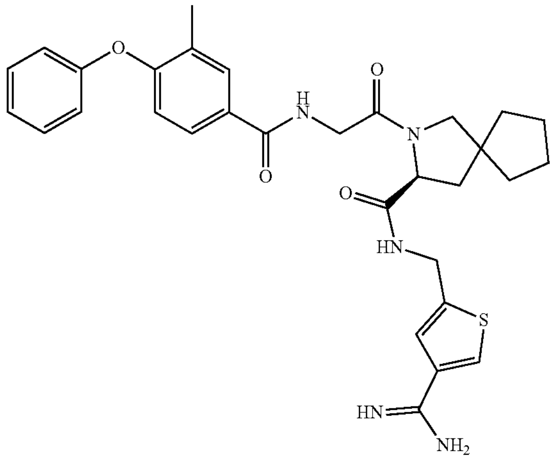
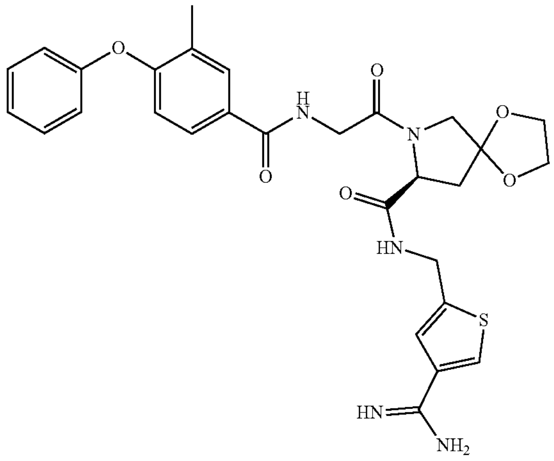
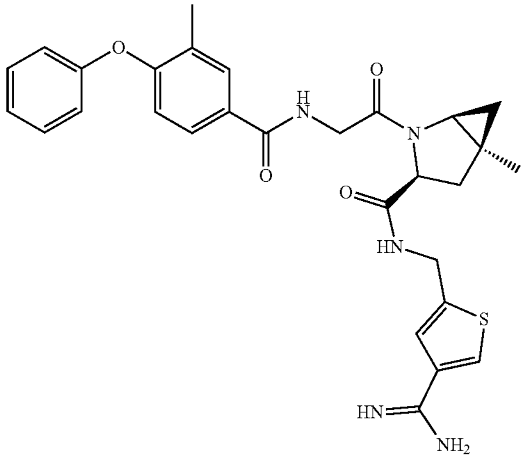
-continued
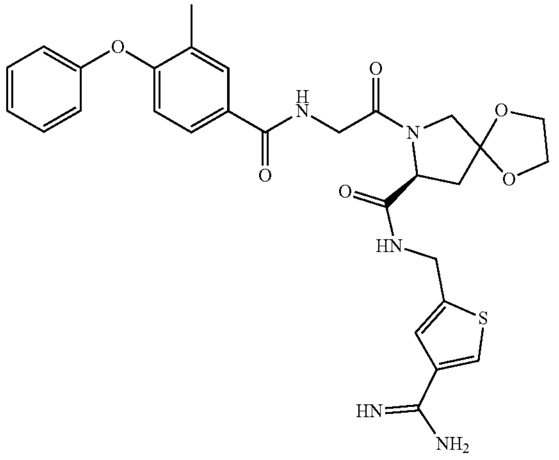
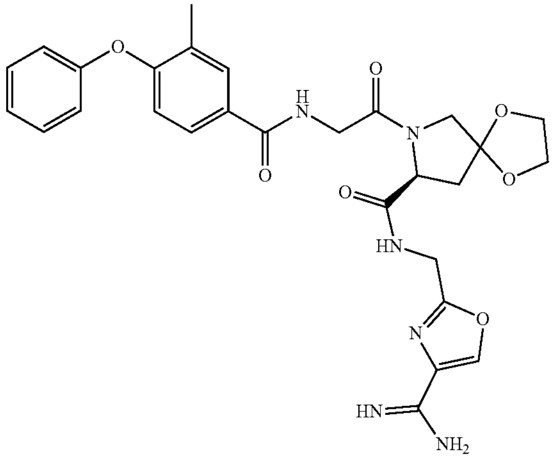
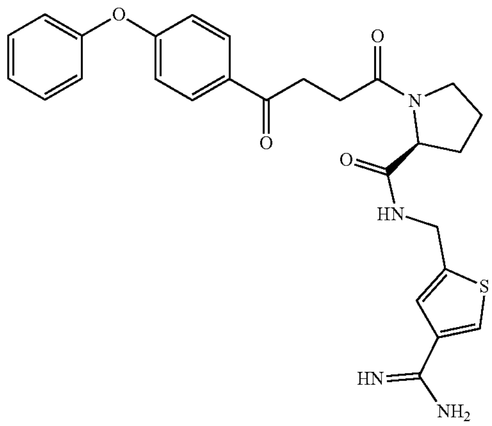
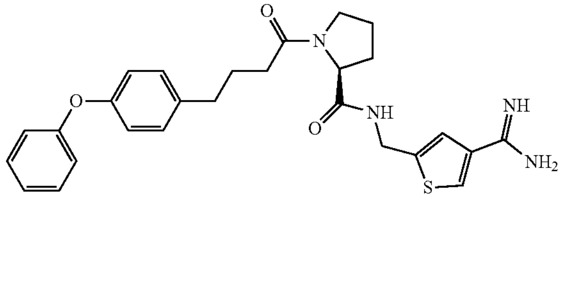

-continued
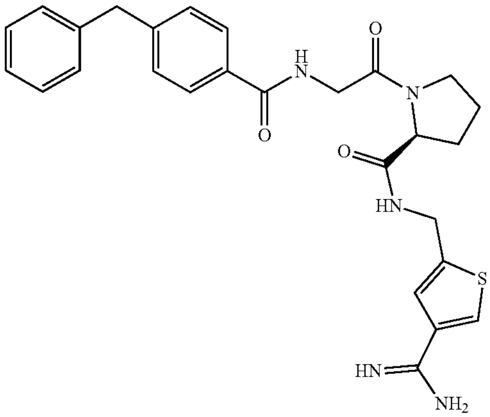
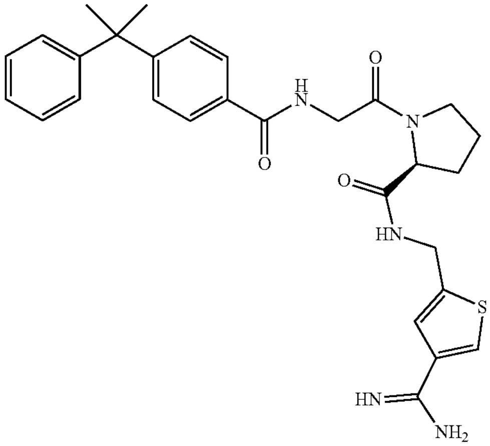
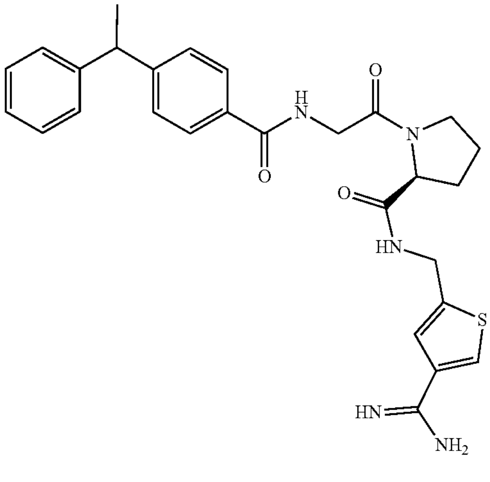
-continued
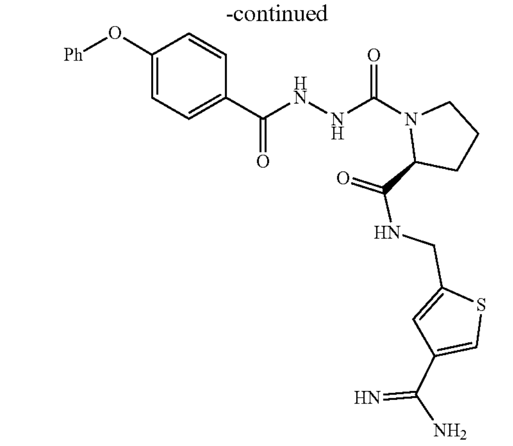
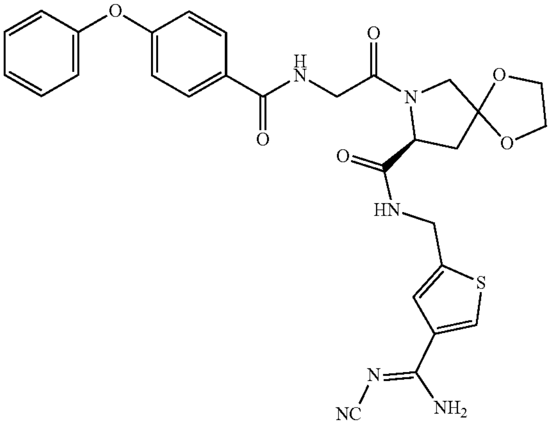
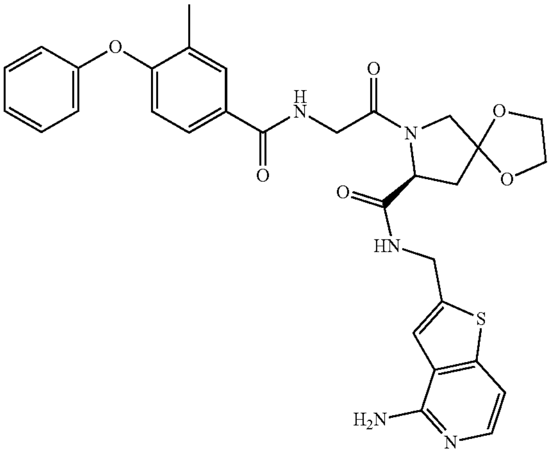
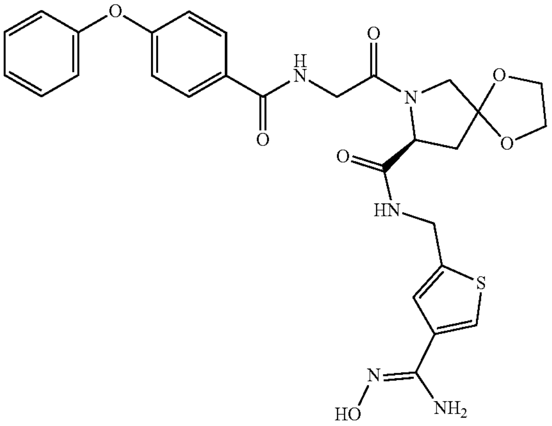

-continued
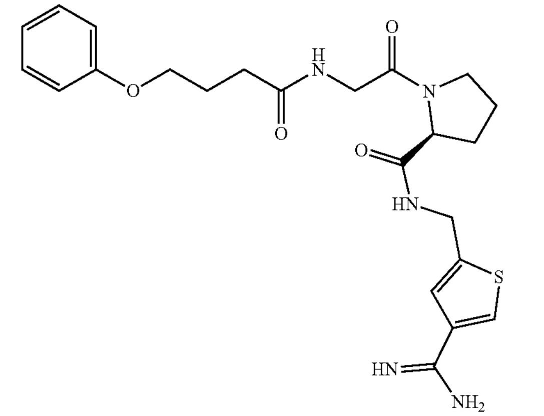
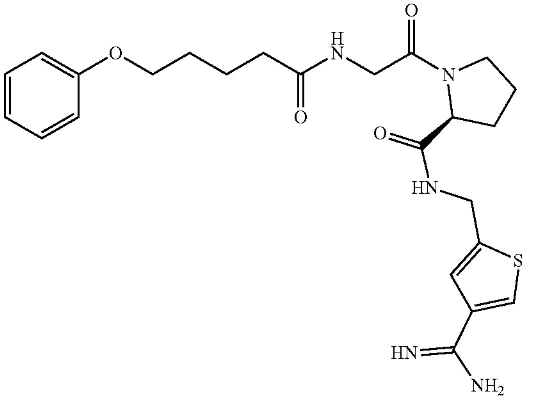
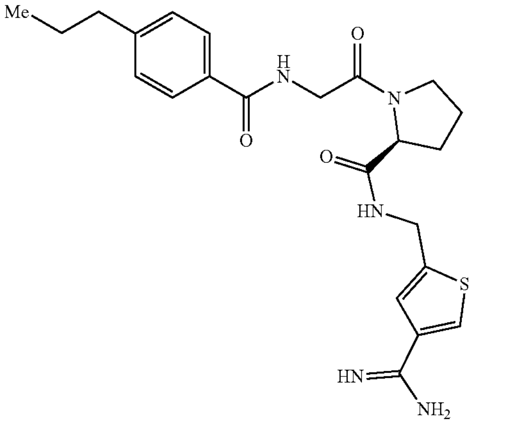
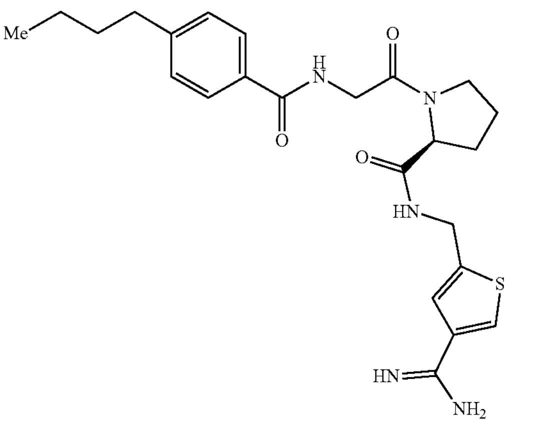
-continued
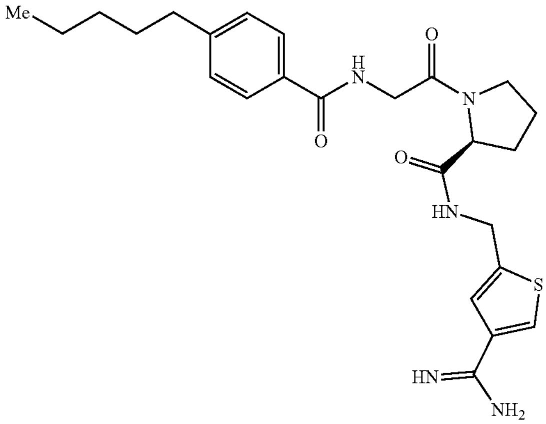
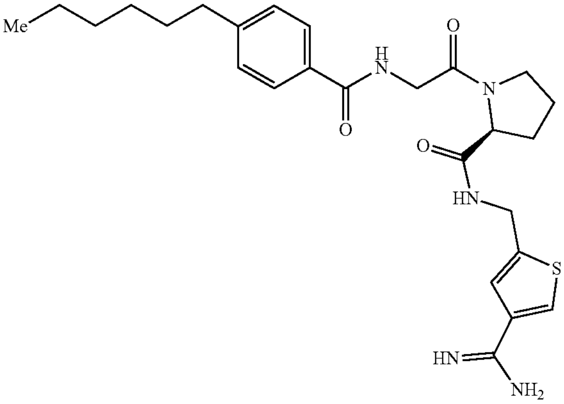
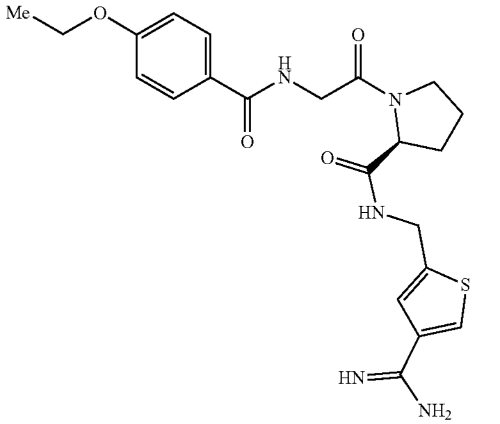
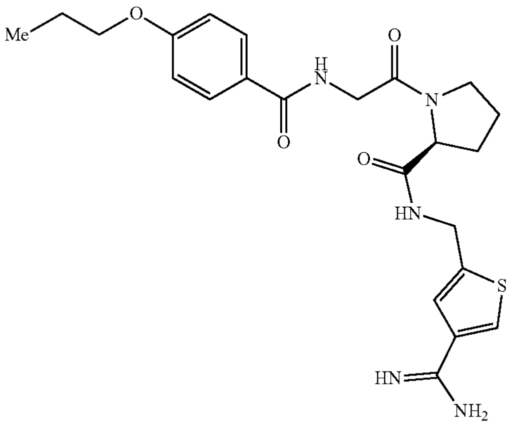

-continued
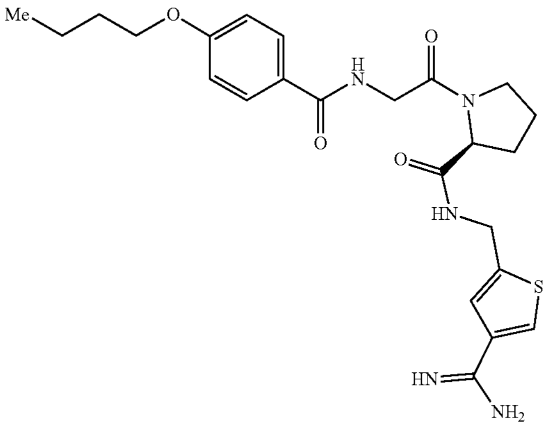
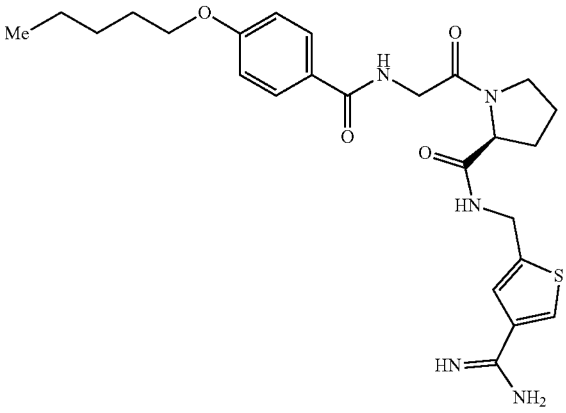
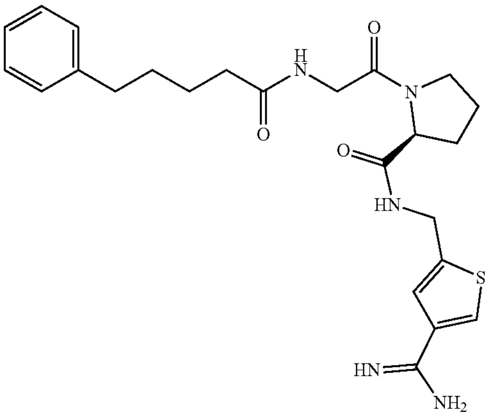
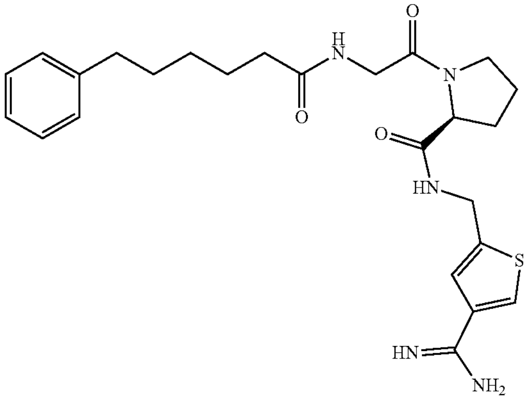
-continued
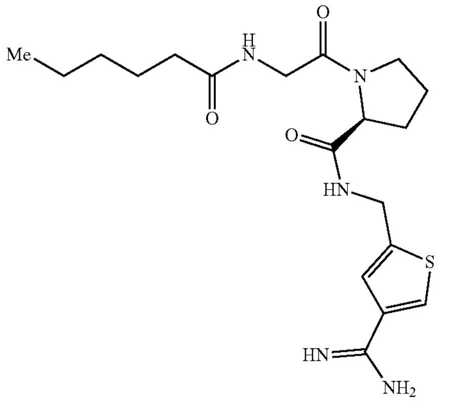
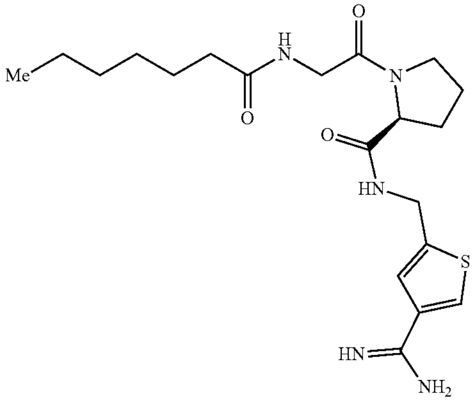
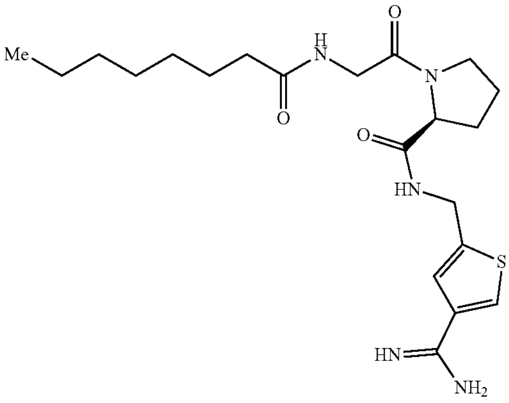
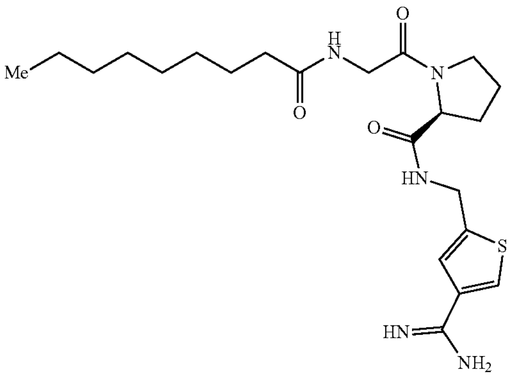
and -continued
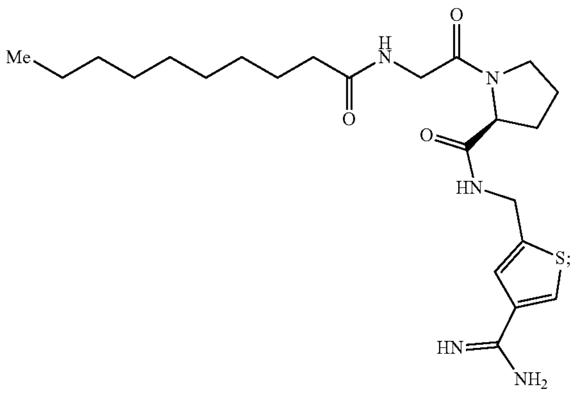
or a pharmaceutically acceptable salt thereof.
147. In certain embodiments, the compound of the present disclosure is selected from:
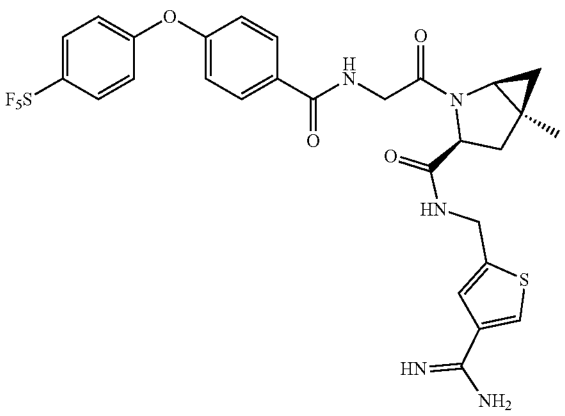
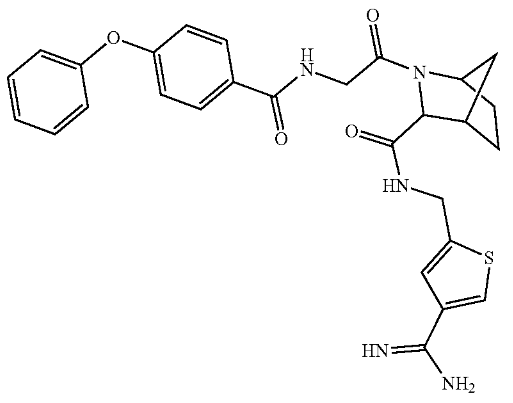
-continued
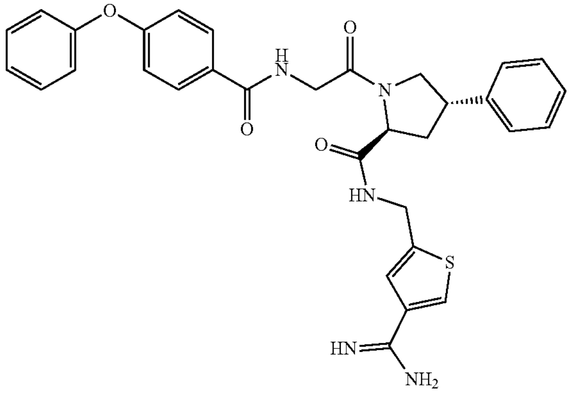
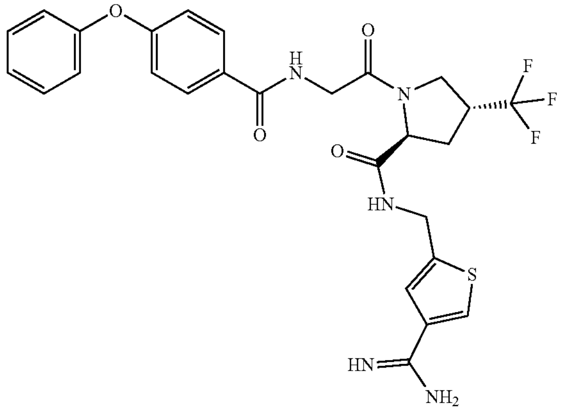
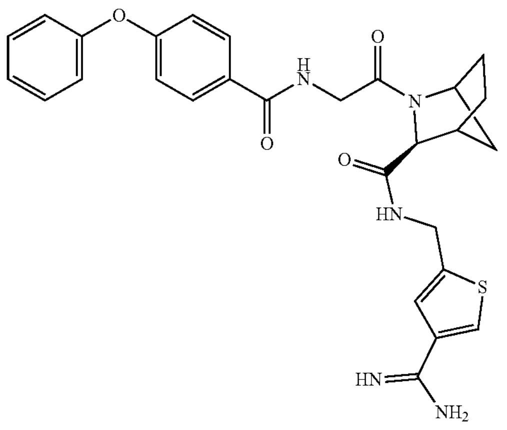
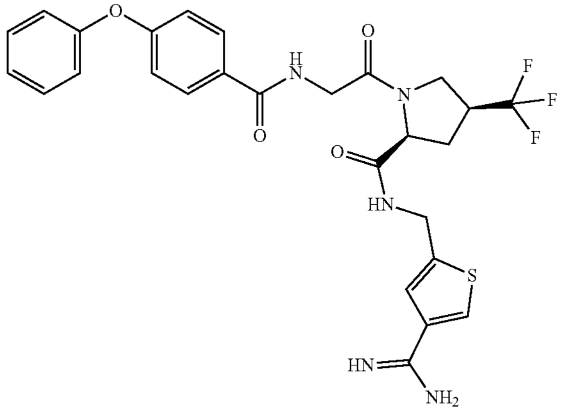

-continued

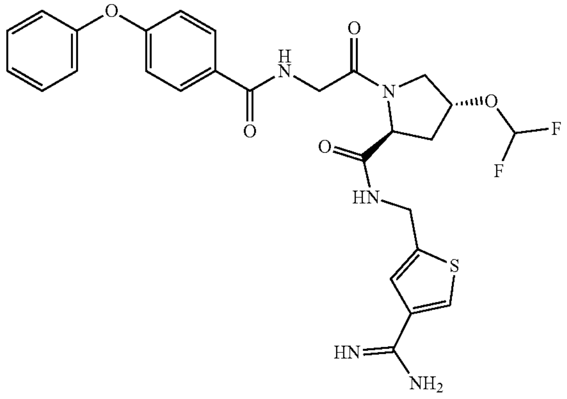

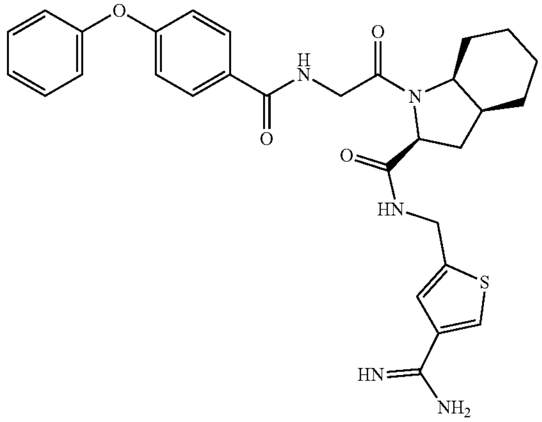

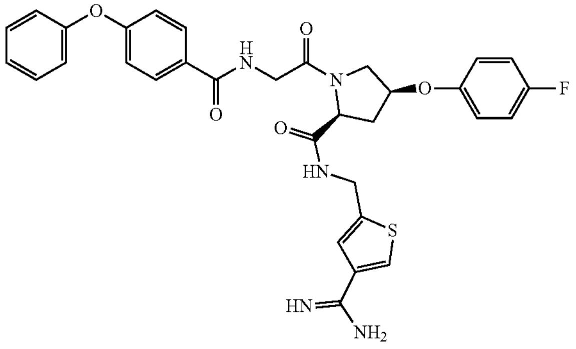

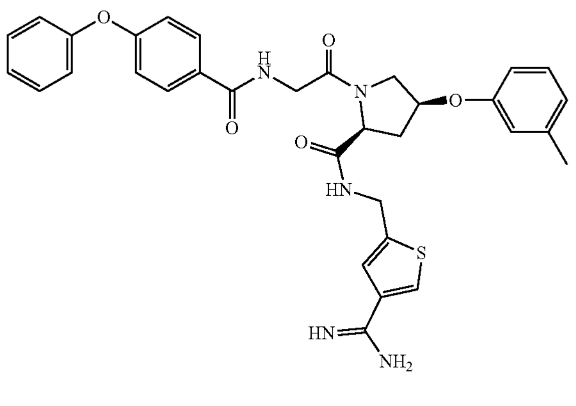

-continued

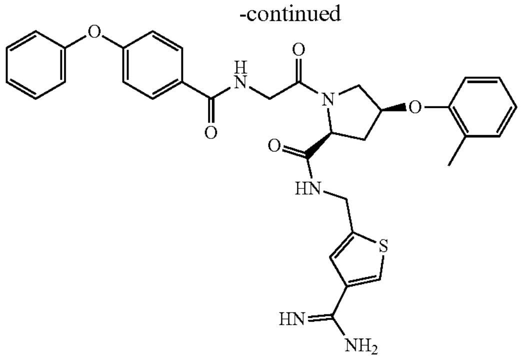

and

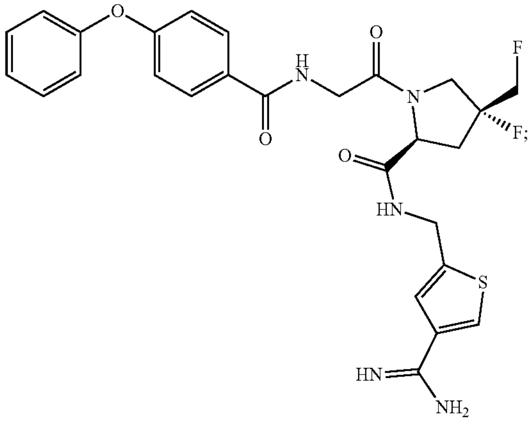

or a pharmaceutically acceptable salt thereof.

148. In certain embodiments, a pharmaceutical composition comprising a compound of any one of embodiments 1-147 and a pharmaceutically acceptable carrier is provided.

149. In certain embodiments, a method of treating a complement mediated disorder comprising administering to a subject in need thereof a therapeutically effective amount of a compound or pharmaceutical composition thereof according to any one of embodiments 1-148, or a pharmaceutically acceptable salt thereof, is provided.

150. The method of embodiment 149, wherein the subject is a human.

151. The method of embodiment 149 or 150, wherein the disorder is mediated by C1s.

152. The method of any one of embodiments 149-151, wherein the disorder is C3 glomerulopathy.

153. The method of any one of embodiments 149-151, wherein the disorder is an ophthalmic disorder.

154. The method of any one of embodiments 149-151, wherein the disorder is age-related macular degeneration (AMD).

155. The method of any one of embodiments 149-151, wherein the disorder is paroxysmal nocturnal hemoglobinuria (PNH).

156. The method of any one of embodiments 149-151, wherein the disorder is C3 glomerulonephritis.

157. The method of any one of embodiments 149-151, wherein the disorder is dense deposit disease.

158. The method of any one of embodiments 149-151, wherein the disorder is angioedema.

159. The method of any one of embodiments 149-151, wherein the disorder is hereditary angioedema.

160. The method of any one of embodiments 149-151, wherein the disorder is autoimmune hemolytic anemia.

161. The method of any one of embodiments 149-151, wherein the disorder is cold agglutinin disease.

162. The method of any one of embodiments 149-151, wherein the disorder is graft rejection.

163. The method of any one of embodiments 149-151, wherein the disorder is selected from hereditary angioedema type 1, hereditary angioedema type 2, trauma, inflammation, sepsis, multiple organ dysfunction syndrome, endotoxemia, end stage renal disease, kidney failure, delayed graft function, ischemic reperfusion injury, neuromyelitis optica, common variable immunodeficiency, antibody-mediated rejection, graft rejection, asthma, allergic asthma, angioneurotic edema, acute ACE-induced angioedema, kidney transplantation, and acute kidney injury.

164. In certain embodiments, a compound of pharmaceutically acceptable salt thereof according to any one of embodiments 1-147 or a pharmaceutical composition of embodiment 148 for use in the treatment of a complement mediated disorder is provided.

165. The compound or composition for use of embodiment 164, wherein the subject is a human.

166. The compound or composition for use of embodiment 164 or 165, wherein the disorder is mediated by C1s.

167. The compound or composition for use of any one of embodiments 164-166, wherein the disorder is C3 glomerulopathy.

168. The compound or composition for use of any one of embodiments 164-166, wherein the disorder is an ophthalmic disorder.

169. The compound or composition for use of any one of embodiments 164-166, wherein the disorder is age-related macular degeneration (AMD).

170. The compound or composition for use of any one of embodiments 164-166, wherein the disorder is paroxysmal nocturnal hemoglobinuria (PNH).

171. The compound or composition for use of any one of embodiments 164-166, wherein the disorder is C3 glomerulonephritis.

172. The compound or composition for use of any one of embodiments 164-166, wherein the disorder is dense deposit disease.

173. The compound or composition for use of any one of embodiments 164-166, wherein the disorder is angioedema.

174. The compound or composition for use of any one of embodiments 164-166, wherein the disorder is hereditary angioedema.

175. The compound or composition for use of any one of embodiments 164-166, wherein the disorder is autoimmune hemolytic anemia.

176. The compound or composition for use of any one of embodiments 164-166, wherein the disorder is cold agglutinin disease.

177. The compound or composition for use of any one of embodiments 164-166, wherein the disorder is graft rejection.

178. The compound or composition for use of any one of embodiments 164-166, wherein the disorder is selected from hereditary angioedema type 1, hereditary angioedema type 2, trauma, inflammation, sepsis, multiple organ dysfunction syndrome, endotoxemia, end stage renal disease, kidney failure, delayed graft function, ischemic reperfusion injury, neuromyelitis optica, common variable immunodeficiency, antibody-mediated rejection, graft rejection, asthma, allergic asthma, angioneurotic edema, acute ACE-induced angioedema, kidney transplantation, and acute kidney injury.

179. In certain embodiments a use of a compound of any one of embodiments 1-147 or its pharmaceutically acceptable salt in the manufacture of a medicament for the treatment of a complement mediated disorder is provided.

180. The use of embodiment 179, wherein the subject is a human.

181. The use of embodiment 179 or 180, wherein the disorder is mediated by C1s.

182. The use of any one of embodiments 179-181, wherein the disorder is C3 glomerulopathy.

183. The use of any one of embodiments 179-181, wherein the disorder is an ophthalmic disorder.

184. The use of any one of embodiments 179-181, wherein the disorder is age-related macular degeneration (AMD).

185. The use of any one of embodiments 179-181, wherein the disorder is paroxysmal nocturnal hemoglobinuria (PNH).

186. The use of any one of embodiments 179-181, wherein the disorder is C3 glomerulonephritis.

187. The use of any one of embodiments 179-181, wherein the disorder is dense deposit disease.

188. The use of any one of embodiments 179-181, wherein the disorder is angioedema.

189. The use of any one of embodiments 179-181, wherein the disorder is hereditary angioedema.

190. The use of any one of embodiments 179-181, wherein the disorder is autoimmune hemolytic anemia.

191. The use of any one of embodiments 179-181, wherein the disorder is cold agglutinin disease.

192. The use of any one of embodiments 179-181, wherein the disorder is graft rejection.

193. The use of any one of embodiments 179-181, wherein the disorder is selected from hereditary angioedema type 1, hereditary angioedema type 2, trauma, inflammation, sepsis, multiple organ dysfunction syndrome, endotoxemia, end stage renal disease, kidney failure, delayed graft function, ischemic reperfusion injury, neuromyelitis optica, common variable immunodeficiency, antibody-mediated rejection, graft rejection, asthma, allergic asthma, angioneurotic edema, acute ACE-induced angioedema, kidney transplantation, and acute kidney injury.

Pharmaceutical Preparations

Active compounds described herein can be administered to a host in need thereof as the neat chemical, but are more typically administered as a pharmaceutical composition that includes an effective amount for a host, typically a human, in need of such treatment of an active compound as described herein or its pharmaceutically acceptable salt, prodrug, isotopic analog, N-oxide, or isolated isomer thereof. Thus, in one embodiment, the disclosure provides pharmaceutical compositions comprising an effective amount of compound or pharmaceutically acceptable salt, prodrug, isotopic analog, N-oxide, or isolated isomer thereof together with at least one pharmaceutically acceptable carrier for any of the uses described herein. The pharmaceutical composition may contain a compound or salt as the only active agent, or, in an alternative embodiment, the compound and at least one additional active agent.

An effective amount of an active compound as described herein, or the active compound described herein in combination or alternation with, or preceded by, concomitant with or followed by another active agent, can be used in an amount sufficient to (a) inhibit the progression of a disorder mediated by the complement pathway, including an inflammatory, immune, including an autoimmune, disorder or complement related disorder; (b) cause a regression of an inflammatory, immune, including an autoimmune, disorder or complement related disorder; (c) cause a cure of an inflammatory, immune, including an autoimmune, disorder or complement related disorder; or inhibit or prevent the development of an inflammatory, immune, including an autoimmune, disorder or complement related disorder. Accordingly, an effective amount of an active compound or its salt or composition described herein will provide a sufficient amount of the active agent when administered to a patient to provide a clinical benefit.

The exact amount of the active compound or pharmaceutical composition described herein to be delivered to the host, typically a human, in need thereof, will be determined by the health care provider to achieve the desired clinical benefit.

In certain embodiments, the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.5, 1, 1.5, 2, 2.5, 3, 3.5, 4, 4.5, 5, 10, 15, 20, 25, 50, 75, 100, 150, 200, 250, 300, 350, 400, 450, 500, 550, 600, 650, 700, 750, 800, 900, 1000, 1100, 1200, 1250, 1300, 1400, 1500, or 1600 mg of active compound, or its salt, N-oxide, isotopic analog, or prodrug. In one embodiment, the dosage form has at least about 1 mg, 5 mg, 10 mg, 25 mg, 50 mg, 75 mg, 100 mg, 200 mg, 400 mg, 500 mg, 600 mg, 1000 mg, 1200 mg, or 1600 mg of active compound, N-oxide, isotopic analog, prodrug, or its salt. The amount of active compound in the dosage form is calculated without reference to the salt. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitoneal, subcutaneous, transnasal, sublingual, intrathecal, or rectal or by other means, in dosage unit formulations containing conventional pharmaceutically acceptable carriers. For ocular delivery, the compound can be administered, as desired, for example, as a solution, suspension, or other formulation via intravitreal, intrastromal, intracameral, subtenon, sub-retinal, retro-bulbar, peribulbar, suprachoroidal, subchoroidal, choroidal, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device, injection, or topically administered formulation, for example, a solution or suspension provided as an eye drop.

The pharmaceutical composition may be formulated as any pharmaceutically useful form, e.g., as an aerosol, a cream, a gel, a gel cap, a pill, a microparticle, a nanoparticle, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution or suspension. Some dosage forms, such as tablets and capsules, are subdivided into suitably sized unit doses containing appropriate quantities of the active components, e.g., an effective amount to achieve the desired purpose.

Pharmaceutical compositions, and methods of manufacturing such compositions, suitable for administration as contemplated herein are known in the art. Examples of known techniques include, for example, U.S. Pat. Nos. 4,983,593; 5,013,557; 5,456,923; 5,576,025; 5,723,269; 5,858,411; 6,254,889; 6,303,148; 6,395,302; 6,497,903; 7,060,296; 7,078,057; 7,404,828; 8,202,912; 8,257,741; 8,263,128; 8,337,899; 8,431,159; 9,028,870; 9,060,938; 9,211,261; 9,265,731; 9,358,478; and 9,387,252; incorporated by reference herein.

The pharmaceutical compositions contemplated here can optionally include a carrier. Carriers must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound. Classes of carriers include, but are not limited to binders, buffering agents, coloring agents, diluents, disintegrants, emulsifiers, fillers, flavorants, glidents, lubricants, pH modifiers, preservatives, stabilizers, surfactants, solubilizers, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils.

Examples of other matrix materials, fillers, or diluents include lactose, mannitol, xylitol, microcrystalline cellulose, calcium diphosphate, and starch. Examples of surface active agents include sodium lauryl sulfate and polysorbate 80.

Examples of drug complexing agents or solubilizers include the polyethylene glycols, caffeine, xanthene, gentisic acid and cylodextrins.

Examples of disintegrants include sodium starch glycolate, sodium alginate, carboxymethyl cellulose sodium, methyl cellulose, colloidal silicon dioxide, and croscarmellose sodium.

Examples of binders include methyl cellulose, microcrystalline cellulose, starch, and gums such as guar gum, and tragacanth.

Examples of lubricants include magnesium stearate and calcium stearate.

Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. Optional other active agents may be included in a pharmaceutical composition, which do not substantially interfere with the activity of the compound of the present disclosure.

In certain embodiments, the pharmaceutical composition for administration further includes a compound or salt of Formula I, II, III, IV, V, VI, VII, VIII, IX, X, XI, XII, XIII, XIV, XV, XVI, XVII, XVIII, XIX, or XX, and optionally comprises one or more of a phosphoglyceride; phosphatidylcholine; dipalmitoyl phosphatidylcholine (DPPC); dioleoylphosphatidyl ethanolamine (DOPE); dioleoyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (SPAN® 85) glycocholate; sorbitan monolaurate (SPAN® 20); polysorbate 20 (TWEEN® 20); polysorbate 60 (TWEEN® 60); polysorbate 65 (TWEEN® 65); polysorbate 80 (TWEEN® 80); polysorbate 85 (TWEEN® 85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl stearate; isopropyl myristate; tyloxapol; poly(ethylene glycol)5000-phosphatidylethanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellobiose, mannose, xylose, arabinose, glucoronic acid, galacturonic acid, mannuronic acid, glucosamine, galactosamine, and neuramic acid; pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucomannan, pustulan, heparin, hyaluronic acid, curdlan, and xanthan, mannitol, sorbitol, xylitol, erythritol, maltitol, and lactitol, a pluronic polymer, polyethylene, polycarbonate (e.g., poly(1,3-dioxan-2one)), polyanhydride (e.g., poly(sebacic anhydride)), polypropylfumerate, polyamide (e.g., polycaprolactam), polyacetal, polyether, polyester (e.g., polylactide, polyglycolide, polylactide-co-glycolide, polycaprolactone, polyhydroxyacid (e.g., poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), and hydroxypropylmethyl cellulose acetate succinate (HPMCAS).

In some embodiments, the pharmaceutical preparation may include polymers for controlled delivery of the described compounds, including, but not limited to pluronic polymers, polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers may be modified with polyethylene glycol (PEG), with a carbohydrate, and/or with acyclic polyacetals derived from polysaccharides. See, e.g., Papisov, 2001, *ACS Symposium Series,* 786:301, incorporated by reference herein.

The compounds of the present disclosure can be formulated as particles. In one embodiment the particles are, or include, microparticles. In an alternative embodiment, the particles are or include nanoparticles.

In an additional alternative embodiment, common techniques for preparing particles include, but are not limited to, solvent evaporation, solvent removal, spray drying, phase inversion, coacervation, and low temperature casting. Suitable methods of particle formulation are briefly described herein. Pharmaceutically acceptable excipients, including pH modifying agents, disintegrants, preservatives, and antioxidants, can optionally be incorporated into the particles during particle formation.

In one embodiment, the particles are derived through a solvent evaporation method. In this method, a compound described herein (or polymer matrix and one or more compounds described herein) is dissolved in a volatile organic solvent, such as methylene chloride. The organic solution containing a compound described herein is then suspended in an aqueous solution that contains a surface active agent such as poly(vinyl alcohol). The resulting emulsion is stirred until most of the organic solvent evaporated, leaving solid nanoparticles or microparticles. The resulting nanoparticles or microparticles are washed with water and dried overnight in a lyophilizer (under vacuum, with or without heat). Nanoparticles with different sizes and morphologies can be obtained by this method.

Pharmaceutical compositions which contain labile polymers, such as certain polyanhydrides, may degrade during the fabrication process due to the presence of water. For these polymers, methods which are performed in completely or substantially anhydrous organic solvents can be used to make the particles.

Solvent removal can also be used to prepare particles from a compound that is hydrolytically unstable. In this method, the compound (or polymer matrix and one or more compounds) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

In one embodiment, an active compound as described herein is administered to a patient in need thereof as particles formed by solvent removal. In another embodiment, the present disclosure provides particles formed by solvent removal comprising a compound of the present disclosure and one or more pharmaceutically acceptable excipients as defined herein. In another embodiment, the particles formed by solvent removal comprise a compound of the present disclosure and an additional therapeutic agent. In a further embodiment, the particles formed by solvent removal comprise a compound of the present disclosure, an additional therapeutic agent, and one or more pharmaceutically acceptable excipients. In another embodiment, any of the described particles formed by solvent removal can be formulated into a tablet, and then coated to form a coated tablet. In an alternative embodiment, the particles formed by solvent removal are formulated into a tablet but the tablet is uncoated.

In one embodiment, the particles are derived by spray drying. In this method, a compound (or polymer matrix and one or more compounds) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

In one embodiment, an active compound as described herein is administered to a patient in need thereof as a spray dried dispersion (SDD). In another embodiment, the present disclosure provides a spray dried dispersion (SDD) comprising a compound of the present disclosure and one or more pharmaceutically acceptable excipients as defined herein. In another embodiment, the SDD comprises a compound of the present disclosure and an additional therapeutic agent. In a further embodiment, the SDD comprises a compound of the present disclosure, an additional therapeutic agent, and one or more pharmaceutically acceptable excipients. In another embodiment, any of the described spray dried dispersions can be coated to form a coated tablet. In an alternative embodiment, the spray dried dispersion is formulated into a tablet but the tablet is uncoated.

Particles can be formed from the active compound as described herein using a phase inversion method. In this method, the compound (or polymer matrix and one or more active compounds) is dissolved in a suitable solvent, and the solution is poured into a strong non-solvent for the compound to spontaneously produce, under favorable conditions, microparticles or nanoparticles. The method can be used to produce nanoparticles in a wide range of sizes, including, for example, from nanoparticles to microparticles, typically possessing a narrow particle size distribution.

In one embodiment, an active compound as described herein is administered to a patient in need thereof as particles formed by phase inversion. In another embodiment, the present disclosure provides particles formed by phase inversion comprising a compound of the present disclosure and one or more pharmaceutically acceptable excipients as defined herein. In another embodiment the particles formed by phase inversion comprise a compound of the present disclosure and an additional therapeutic agent. In a further embodiment the particles formed by phase inversion comprise a compound of the present disclosure, an additional therapeutic agent, and one or more pharmaceutically acceptable excipients. In another embodiment, any of the described particles formed by phase inversion can be formulated into a tablet and then coated to form a coated tablet. In an alternative embodiment, the particles formed by phase inversion are formulated into a tablet, but the tablet is uncoated.

Techniques for particle formation using coacervation are known in the art, for example, as described in GB-B-929 406; GB-B-929 40 1; and U.S. Pat. Nos. 3,266,987; 4,794,000; and 4,460,563. Coacervation involves the separation of a compound (or polymer matrix and one or more compounds) solution into two immiscible liquid phases. One phase is a dense coacervate phase, which contains a high concentration of the compound, while the second phase contains a low concentration of the compound. Within the dense coacervate phase, the compound forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

In one embodiment, an active compound as described herein is administered to a patient in need thereof as particles formed by coacervation. In another embodiment, the present disclosure provides particles formed by coacervation comprising a compound of the present disclosure and one or more pharmaceutically acceptable excipients as defined herein. In another embodiment, the particles formed by coacervation comprise a compound of the present disclosure and an additional therapeutic agent. In a further embodiment, the particles formed by coacervation comprise a compound of the present disclosure, an additional therapeutic agent, and one or more pharmaceutically acceptable excipients. In another embodiment, any of the described particles formed by coacervation can be formulated into a tablet and then coated to form a coated tablet. In an alternative embodiment, the particles formed by coacervation are formulated into a tablet, but the tablet is uncoated.

Methods for very low temperature casting of controlled release microspheres are described in U.S. Pat. No. 5,019,400 to Gombotz et al. In this method, the compound is dissolved in a solvent. The mixture is then atomized into a vessel containing a liquid non-solvent at a temperature below the freezing point of the drug solution which freezes the compound droplets. As the droplets and non-solvent for the compound are warmed, the solvent in the droplets thaws and is extracted into the non-solvent, hardening the microspheres.

In one embodiment, a compound of the present disclosure is administered to a patient in need thereof as particles formed by low temperature casting. In another embodiment the present disclosure provides particles formed by low temperature casting comprising a compound of the present disclosure and one or more pharmaceutically acceptable excipients as defined herein. In another embodiment, the particles formed by low temperature casting comprise a compound of the present disclosure and an additional therapeutic agent. In a further embodiment, the particles formed by low temperature casting comprise a compound of the present disclosure, an additional therapeutic agent, and one or more pharmaceutically acceptable excipients. In another embodiment, any of the described particles formed by low temperature casting can be formulated into a tablet and then coated to form a coated tablet. In an alternative embodiment, the particles formed by low temperature casting are formulated into a tablet, but the tablet is uncoated.

In one aspect of the present disclosure, an effective amount of an active compound as described herein is incorporated into a nanoparticle, e.g., for convenience of delivery and/or extended release delivery. The use of materials in nanoscale provides one the ability to modify fundamental physical properties such as solubility, diffusivity, blood circulation half-life, drug release characteristics, and/or immunogenicity. A number of nanoparticle-based therapeutic and diagnostic agents have been developed for the treatment of cancer, diabetes, pain, asthma, allergy, and infections. These nanoscale agents may provide more effective and/or more convenient routes of administration, lower therapeutic toxicity, extend the product life cycle, and ultimately reduce health-care costs. As therapeutic delivery systems, nanoparticles can allow targeted delivery and controlled release.

In addition, nanoparticle-based compound delivery can be used to release compounds at a sustained rate and thus lower the frequency of administration, deliver drugs in a targeted manner to minimize systemic side effects, or deliver two or more drugs simultaneously for combination therapy to generate a synergistic effect and suppress drug resistance. A number of nanotechnology-based therapeutic products have been approved for clinical use. Among these products, liposomal drugs and polymer-based conjugates account for a large proportion of the products. See Zhang, L., et al., Nanoparticles in Medicine: Therapeutic Applications and Developments, *Clin. Pharm. and Ther.,* 83(5):761-769, 2008.

Methods for producing nanoparticles are known in the art. For example, see Muller, R. H., et al., Solid lipid nanoparticles (SLN) for controlled drug delivery—a review of the state of the art, *Eur. H. Pharm. Biopharm.,* 50:161-177, 2000; U.S. Pat. No. 8,691,750 to Consien et al.; WO 2012/145801 to Kanwar; U.S. Pat. No. 8,580,311 to Armes, S. et al.; Petros, R. A. and DeSimone, J. M., Strategies in the design of nanoparticles for therapeutic applications, *Nature Reviews/Drug Discovery*, vol. 9:615-627, 2010; U.S. Pat. Nos. 8,465,775; 8,444,899; 8,420,124; 8,263,129; 8,158,728; 8,268,446; Pellegrino et al., 2005, Small, 1:48; Murray et al., 2000, *Ann. Rev. Mat. Sci.,* 30:545; and Trindade et al., 2001, *Chem. Mat.,* 13:3843; all incorporated herein by reference. Additional methods have been described in the literature (see, e.g., Doubrow, Ed., "*Microcapsules and Nanoparticles in Medicine and Pharmacy*," CRC Press, Boca Raton, 1992; Mathiowitz et al., 1987, *J. Control. Release,* 5:13; Mathiowitz et al., 1987, *Reactive Polymers,* 6:275; and Mathiowitz et al., 1988, *J. Appl. Polymer Sci.,* 35:755; U.S. Pat. Nos. 5,578,325 and 6,007,845; P. Paolicelli et al., "Surface-modified PLGA-based Nanoparticles that can Efficiently Associate and Deliver Virus-like Particles" *Nanomedicine.* 5(6):843-853 (2010)), U.S. Pat. No. 5,543,158 to Gref et al., or WO publication WO2009/051837 by Von Andrian et al.; Zauner et al., 1998, *Adv. Drug Del. Rev.,* 30:97; and Kabanov et al., 1995, *Bioconjugate Chem.,* 6:7; (PEI; Boussif et al., 1995, Proc. Natl. Acad. Sci., USA, 1995, 92:7297), and poly(amidoamine) dendrimers (Kukowska-Latallo et al., 1996, *Proc. Natl. Acad. Sci., USA,* 93:4897; Tang et al., 1996, *Bioconjugate Chem.,* 7:703; and Haensler et al., 1993, *Bioconjugate Chem.,* 4:372; Putnam et al., 1999, *Macromolecules,* 32:3658; Barrera et al., 1993, *J. Am. Chem. Soc.,* 115:11010; Kwon et al., 1989, *Macromolecules,* 22:3250; Lim et al., 1999, *J. Am. Chem. Soc.,* 121:5633; and Zhou et al., 1990, *Macromolecules,* 23:3399). Examples of these polyesters include poly(L-lactide-co-L-lysine) (Barrera et al., 1993, *J. Am. Chem. Soc.,* 115:11010), poly(serine ester) (Zhou et al., 1990, *Macromolecules,* 23:3399), poly(4-hydroxy-L-proline ester) (Putnam et al., 1999, *Macromolecules,* 32:3658; and Lim et al., 1999, *J. Am. Chem. Soc.,* 121:5633), and poly(4-hydroxy-L-proline ester) (Putnam et al., 1999, *Macromolecules,* 32:3658; and Lim et al., 1999, *J. Am. Chem. Soc.,* 121:5633; U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, *J. Am. Chem. Soc.,* 123:9480; Lim et al., 2001, *J. Am. Chem. Soc.,* 123:2460; Langer, 2000, *Acc. Chem. Res.,* 33:94; Langer, 1999, *J. Control. Release,* 62:7; and Uhrich et al., 1999, *Chem. Rev.,* 99:3181*; Concise Encyclopedia of Polymer Science and Polymeric Amines and Ammonium Salts*, Ed. by Goethals, Pergamon Press, 1980*; Principles of Polymerization* by Odian, John Wiley & Sons, Fourth Edition, 2004*; Contemporary Polymer Chemistry* by Allcock et al., Prentice-Hall, 1981; Deming et al., 1997, *Nature,* 390:386; and in U.S. Pat. Nos. 6,506,577, 6,632,922, 6,686,446, and 6,818,732; C. Astete et al., "Synthesis and characterization of PLGA nanoparticles" *J. Biomater. Sci. Polymer Edn*, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" *Current Drug Delivery* 1:321-333 (2004); C. Reis et al., "Nanoencapsulation I. Methods for preparation of drug-loaded polymeric nanoparticles" *Nanomedicine* 2:8-21 (2006); P. Paolicelli et al., "Surface-modified PLGA-based Nanoparticles that can Efficiently Associate and Deliver Virus-like Particles" *Nanomedicine.* 5(6):843-853 (2010); and U.S. Pat. No. 6,632,671 to Unger Oct. 14, 2003, all incorporated herein by reference.

In one embodiment, the polymeric particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In one embodiment, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In some embodiments, a compound described herein may be covalently coupled to a polymer used in the nanoparticle, for example a polystyrene particle, PLGA particle, PLA particle, or other nanoparticle.

The pharmaceutical compositions according to the disclosure can be formulated for oral administration. These compositions can contain any amount of active compound that achieves the desired result, for example, between 0.1 and 99 weight % (wt. %) of the compound, and usually at least about 5 wt. % of the compound. Some embodiments contain at least about 10%, 15%, 20%, 25 wt. % to about 50 wt. % or from about 5 wt. % to about 75 wt. % of the compound.

Pharmaceutical compositions suitable for rectal administration are typically presented as unit dose suppositories. These may be prepared by admixing the active compound with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Pharmaceutical compositions suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Pharmaceutical compositions suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of inhalation drug delivery devices and methods include, for example, U.S. Pat. No. 7,383,837 titled "Inhalation Device" (SmithKline Beecham Corporation); WO/2006/033584 titled "Powder Inhaler" (Glaxo SmithKline Pharmaceuticals SA); WO/2005/044186 titled "Inhalable Pharmaceutical Formulations Employing Desiccating Agents and Methods of Administering the Same" (Glaxo Group Ltd and SmithKline Beecham Corporation); U.S. Pat. No. 9,095,670 titled "Inhalation Device and Method of Dispensing Medicament", U.S. Pat. No. 8,205,611 titled "Dry Powder Inhaler" (Astrazeneca AB); WO/2013/038170 titled "Inhaler" (Astrazeneca AB and Astrazeneca UK Ltd.); US/2014/0352690 titled "Inhalation Device with Feedback System", U.S. Pat. No. 8,910, 625 and US/2015/0165137 titled "Inhalation Device for Use in Aerosol Therapy" (Vectura GmbH); U.S. Pat. No. 6,948, 496 titled "Inhalers", US/2005/0152849 titled "Powders Comprising Anti-adherent Materials for Use in Dry Powder Inhalers", U.S. Pat. Nos. 6,582,678, 8,137,657, US/2003/ 0202944, and US/2010/0330188 titled "Carrier Particles for Use in Dry Powder Inhalers", U.S. Pat. No. 6,221,338 titled "Method of Producing Particles for Use in Dry Powder Inhalers", U.S. Pat. No. 6,989,155 titled "Powders", US/2007/0043030 titled "Pharmaceutical Compositions for Treating Premature Ejaculation by Pulmonary Inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of Making Particles for Use in a Pharmaceutical Composition", U.S. Pat. No. 7,541,022, US/2009/ 0269412, and US/2015/0050350 titled "Pharmaceutical Formulations for Dry Powder Inhalers" (Vectura Limited).

Many methods and devices for drug delivery to the eye are known in the art. Non-limiting examples are described in the following patents and patent applications (fully incorporated herein by reference): U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623, 395 titled "Implantable therapeutic device", WO/2014/ 160884 titled "Ophthalmic Implant for Delivering Therapeutic Substances", U.S. Pat. Nos. 8,399,006, 8,277,830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/ 141729 titled "Anterior Segment Drug Delivery", WO/2011/ 050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/ 040426 titled "Ocular Insert Apparatus and Methods", WO/2012/019136 titled "Injector Apparatus and Method for Drug Delivery", and WO/2013/040247 titled "Fluid Exchange Apparatus and Methods" (ForSight Vision4, Inc.).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/ 009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/ 065748 titled "Method for producing patterned materials", and WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/ 106702 and U.S. Pat. No. 8,889,193 titled "Sustained delivery of therapeutic agents to an eye compartment", WO2013/ 138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957, 034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion", WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", and U.S. Pat. No. 8,632,809 titled "Water insoluble polymer matrix for drug delivery" (Alcon, Inc.).

Additional non-limiting examples of drug delivery devices and methods include, for example, US 2009/0203709 titled "Pharmaceutical Dosage Form For Oral Administration Of Tyrosine Kinase Inhibitor" (Abbott Laboratories); US 2005/0009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US 2012/0052041 titled "Polymeric nanoparticles with enhanced drugloading and methods of use thereof" (The Brigham and Women's Hospital, Inc.); US 2014/0178475, US 2014/0248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers" (Massachusetts Institute of Technology); US 2004/0234611, US 2008/0305172, US 2012/0269894, and US20130122064 titled "Ophthalmic depot formulations for periocular or subconjunctival administration (Novartis Ag); U.S. Pat. No. 6,413,539 titled "Block polymer" (Poly-Med, Inc.); US 2007/0071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

Uses of Active Compounds for Treatment of Selected Disorders

In one aspect, an effective amount of an active compound or its salt or composition as described herein is used to treat a medical disorder which is an inflammatory or immune condition, a disorder mediated by the complement cascade (including a dysfunctional cascade) including a complement-related disorder or alternative complement pathway-related disorder, a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

A complement-mediated disease or disorder is a disease or disorder in which the amount or activity of complement is such as to cause disease or disorder in an individual.

In some embodiments, the complement-mediated disease or disorder is selected from the group consisting of autoimmune disease, cancer, hematological disease, infectious disease, inflammatory disease, ischemia-reperfusion injury, neurodegenerative disease, neurodegenerative disorder, ocular disease, renal disease, transplant rejection, vascular disease, and vasculitis disease.

In some embodiments, the complement-mediated disease or disorder is an autoimmune disease. In some embodiments, the complement-mediated disease or disorder is cancer.

In some embodiments, the complement-mediated disease or disorder is an infectious disease.

In some embodiments, the complement-mediated disease or disorder is an inflammatory disease.

In some embodiments, the complement-mediated disease or disorder is a hematological disease.

In some embodiments, the complement-mediated disease or disorder is an ischemia-reperfusion injury.

In some embodiments, the complement-mediated disease or disorder is ocular disease. In some embodiments, the complement-mediated disease or disorder is a renal disease.

In some embodiments, the complement-mediated disease or disorder is transplant rejection.

In some embodiments, the complement-mediated disease or disorder is antibody-mediated transplant rejection.

In some embodiments, the complement-mediated disease or disorder is a vascular disease.

In some embodiments, the complement-mediated disease or disorder is a vasculitis disorder.

In some embodiments, the complement-mediated disease or disorder is a neurodegenerative disease or disorder.

In some embodiments, the complement-mediated disease is a neurodegenerative disease.

In some embodiments, the complement-mediated disorder is a neurodegenerative disorder. In some embodiments, the complement-mediated disease or disorder is a tauopathy.

In certain aspects, an effective amount of an active compound described herein, or it pharmaceutically acceptable salt, is used to treat a medical disorder of the central nervous system (CNS) or peripheral nervous system disorders involving complement activation. In embodiments, the CNS disorder is an acquired brain or spinal cord injury, including, but not limited to ischaemic-reperfusion injury or stroke, traumatic brain injury (TBI) and spinal cord injury (SCI).

In embodiments, the disorder is a neurodegeneration disorder. In embodiments, the disorder is a neuroinflammation disorder.

In certain aspects, an active compound described herein, or a pharmaceutically acceptable salt thereof, is used to treat Alzheimer's disease (AD). AD is characterized by two hallmark pathologies; amyloid-β (Aβ) plaques and neurofibrillary tangles comprising hyperphosphorylated tau. Recent studies have implicated complement in AD pathogenesis, including genome-wide association studies identifying single nucleotide polymorphisms (SNPs) associated with risk of late-onset AD in genes encoding complement proteins Clusterin (CLU) and CR1 (CR1). See Carpanini et al., Therapeutic Inhibition of the Complement System in Diseases of the Central Nervous System, *Front. Immunol.,* 4 Mar. 2019. Biomarker studies have also identified complement proteins and activation products in plasma and/or CSF that distinguish AD from controls and predict risk of progression to AD. (Id.)

In certain aspects, an effective amount of active compound described herein, or a pharmaceutically acceptable salt thereof, is used to treat certain forms of frontotemporal dementia including, but not limited to, Pick's disease, sporadic Frontotemporal dementia and Frontotemporal dementia with Parkinsonism linked to chromosome 17, Progressive supranuclear palsy (PSP), Corticobasal degeneration (CBD), and Subacute sclerosing panencephalitis.

In certain aspects, an effective amount of active compound described herein, or a pharmaceutically acceptable salt thereof, is used to treat multiple sclerosis (MS). Multiple sclerosis (MS) is the most common cause of neurological disability in young adults in northern European-Caucasian populations, with an approximate lifetime risk of one in 400. C3 has been shown to be deposited in the brains of MS patients. T-cell clone (TCC) has been shown to be in association with capillary endothelial cells, predominantly within plaques and adjacent white matter. Localization of C activation to areas of active myelin destruction has also been shown, with TCC deposited exclusively in such areas. C3d has been shown to be deposited in association with short segments of disrupted myelin in plaques with low-grade active demyelination and provides evidence for a C contribution to disease progression as well as acute inflammation. See Ingram et al., Complement in multiple sclerosis: its role in disease and potential as a biomarker. *Clin Exp Immunol.* 2009 February; 155(2):128-39.

In certain aspects, an effective amount of an active compound described herein, or a pharmaceutically acceptable salt thereof, is used to treat neuromyelitis optica (NMO). Neuromyelitis optica (NMO) is an inflammatory demyelinating disease affecting predominantly the optic nerves and spinal cord. Traditionally seen as a variant of MS, it has been redefined recently according to new criteria using a combination of phenotypic subtyping along with a newly developed biomarker of disease, NMO-immunoglobulin G (IgG) (reported sensitivity of 58-76% and specificity of 85-99% for NMO). NMO patients have higher levels of C3a and anti-C1q antibodies than healthy controls. C3a levels correlated with disease activity, neurological disability and aquaporin-4 IgG. Nytrova et al., Complement activation in patients with neuromyelitis optica. *J Neuroimmunol.* 2014 Sep. 15; 274(1-2):185-91.

In certain aspects, an effective amount of an active compound as described herein, or a pharmaceutically acceptable salt thereof, is used to treat amyotrophic lateral sclerosis (ALS). ALS is caused by progressive loss of upper and lower (a) motor neurons resulting in denervation of neuromuscular junctions in the peripheral nervous system, progressive muscle weakness, atrophy, spasticity, respiratory failure, and ultimately paralysis and death. Recent studies have shown increased C1q protein in motor cortex and spinal cord of ALS post-mortem tissue; C3 activation fragments and TCC in areas of pathology; C4d and TCC staining of degenerating neurons and glia in ALS motor cortex and spinal cord, and C5aR1 upregulation in areas of pathology. C3d and C4d have been found on oligodendroglia and degenerating neurites, surrounded by CR4-positive microglia, in spinal cord and motor cortex, and C1q, C3, and TCC have been shown to be present on motor end-plates in intercostal muscles in ALS donors even early in the disease process. See Carpanini et al., Therapeutic Inhibition of the Complement System in Diseases of the Central Nervous System, *Front. Immunol.,* 4 Mar. 2019.

In certain aspects, an effective amount of an active compound described herein, or a pharmaceutically acceptable salt thereof, is used to treat Parkinson's disease (PD). PD is characterized by loss of dopaminergic neurons in the substantia nigra and deposits of the protein α-synuclein that form the pathological hallmarks of the disease, Lewy bodies. Patients present with resting tremor, bradykinesia, and rigidity. Complement activation has been associated with α-synuclein and Lewy bodies in Parkinson's disease; in vitro studies have demonstrated that the disease-associated splice variant α-synuclein 112, but not the full-length protein, cause activation of complement. In vivo, C3d, C4d, C7 and C9 localization in Lewy bodies has been reported. More recently, deposition of iC3b and C9 in Lewy bodies and melanized neurons has been reported, and iC3b immunoreactivity has been shown to be increased with normal ageing and was further elevated in PD vs. age-matched controls. Furthermore, correlation between the ratios of C3/Aβ42 or FH/Aβ42 in CSF and severity of Parkinson's disease motor and cognitive symptoms has been shown. See Carpanini et al., Therapeutic Inhibition of the Complement System in Diseases of the Central Nervous System, *Front. Immunol.,* 4 Mar. 2019. In some embodiments, the subject to be treated suffers from Parkinson's Disease with dementia (PDD).

In certain aspects, an effective amount of an active compound described herein, or a pharmaceutically acceptable salt thereof, is used to treat Huntington's disease (HD). HD is an autosomal dominant, inherited neurodegenerative disease characterized by progressive motor symptoms, psychiatric disturbances, and dementia. It is caused by expansion of a three-base-pair (CAG) repeat (39-121 repeats vs. normal range 8-39 repeats) in exon 1 of the HTT gene that translates into a polyglutamine tract at the N-terminus of the protein. This results in a polyglutamine length-dependent misfolding and accumulation of huntingtin protein in the striatum and cortex (layers 3, 5, and 6) followed by neuronal loss in these areas which spreads to the hippocampus. It has been shown that neurons, astrocytes, and myelin sheaths in the HD caudate and striatum were immunoreactive for C1q, C4, C3 and neo-epitopes in iC3b and TCC. Expression of mRNA encoding early complement components C1q (c-chain), C1r, C3, and C4, complement regulators C1INH, Clusterin, MCP, DAF and CD59, and complement receptors C3a and C5a, have been shown to be upregulated in the HD striatum, see Carpanini et al., Therapeutic Inhibition of the Complement System in Diseases of the Central Nervous System, *Front. Immunol.,* 4 Mar. 2019.

In certain aspects, an effective amount of an active compound described herein, or a pharmaceutically acceptable salt thereof, is used to treat argyrophilic grain dementia, British type amyloid angiopathy, cerebral amyloid angiopathy, Creutzfeldt-Jakob disease, dementia pugilistica, diffuse neurofibrillary tangles with calcification, Down's syndrome, frontotemporal lobar degeneration, Gerstmann-Straussler-Scheinker disease, Hallervorden-Spatz disease, inclusion body myositis, multiple system atrophy (MSA), myotonic dystrophy, Niemann-Pick disease type C, non-Guamanian motor neuron disease with neurofibrillary tangles, postencephalitic parkinsonism, prion protein cerebral amyloid angiopathy, progressive subcortical gliosis, progressive supranuclear palsy, subacute sclerosing panencephalitis, Tangle only dementia, multi-infarct dementia, ischemic stroke, chronic traumatic encephalopathy (CTE), traumatic brain injury (TBI), and stroke.

In certain aspects, an effective amount of an active compound described herein, or a pharmaceutically acceptable salt thereof, is used to treat a hereditary motor and sensory neuropathy (HMSN).

In some embodiments, the hereditary and sensory neuropathy is Charcot-Marie-Tooth (CMT) disease.

In some embodiments, the HSMN is Charcot-Marie-Tooth disease type 1A or type 1B.

In some embodiments, the HSMN is Charcot-Marie-Tooth disease type 2.

In some embodiments, the HSMN is Dejerine-Sottas disease (Charcot-Marie-Tooth type 3).

In some embodiments, the HSMN is Refsum disease.

In some embodiments, the HSMN is Charcot-Marie-Tooth with pyramidal features. In some embodiments, the HSMN is Charcot-Marie-Tooth type 6. In some embodiments, the HSMN is HMSN+retinitis pigmentosa.

In some embodiments, an effective amount of an active compound described herein, or a pharmaceutically acceptable salt thereof, is used to treat Churg-Strauss syndrome.

In some embodiments, an effective amount of an active compound described herein, or a pharmaceutically acceptable salt thereof, is used to treat a peripheral artery disease (PAD).

In certain aspects, an effective amount of an active compound described herein, or a pharmaceutically acceptable salt thereof, is used to treat myasthenia gravis with CNS involvement.

In certain aspects, an effective amount of an active compound described herein, or a pharmaceutically acceptable salt thereof, is used to treat dementia with Lewy bodies.

In certain aspects, an effective amount of an active compound described herein, or a pharmaceutically acceptable salt thereof, is used to treat an individual suffering from prion disease.

In certain aspects, an effective amount of an active compound described herein, or a pharmaceutically acceptable salt thereof, is used to treat Behcet's Disease.

In certain aspects, an effective amount of an active compound described herein, or a pharmaceutically acceptable salt thereof, is used to treat congenital myasthenia.

In certain aspects, an effective amount of an active compound described herein, or a pharmaceutically acceptable salt thereof, is used to treat subacute sclerosing panencephalitis (SSPE).

In certain aspects, an effective amount of an active compound described herein, or a pharmaceutically acceptable salt thereof, is used to treat Guillain-Barré syndrome.

In certain aspects, the CNS disorder to be treated is a demyelinating disease, including, but not limited to, demyelinating myelinoclastic diseases and demyelinating leukostrophic disease.

In certain aspects, the disorder to be treated is a demyelinating myelonoclastic disease including, but not limited to, multiple sclerosis, neuromyelitis optica, neuromyelitis optica spectrum of disorders (NMOSD), idiopathic inflammatory demyelinating diseases (IIDD), anti-NMDA receptor encephalitis, acute disseminated encephalomyelitis, anti-MOG autoimmune encephalomyelitis, chronic relapsing inflammatory optic neuritis (CRION), acute disseminated encephalomyelitis (ADEM), immune-mediated encephalomyelitis, progressive multifocal leukoencephalopathy (PML); McDonalds-positive multiple sclerosis, acute hemorrhagic leukoencephalitis, Rasmussen's Encephalitis, Marburg multiple sclerosis, pseudotumefactive and tumefactive multiple sclerosis, Balo concentric sclerosis, diffuse myelinoclastic sclerosis, solitary sclerosis, multiple sclerosis with cavitary lesions, myelocortical multiple sclerosis (MCMS), atypical optic-spinal multiple sclerosis, pure spinal multiple sclerosis, HLA DRB3*02:02 multiple sclerosis, autoimmune GFAP astrocytopathy, Chronic inflammatory demyelinating polyneuropathy (CIDP), Guillain-Barré syndrome, progressive inflammatory neuropathy, Lewis-Sumner Syndrome, combined central and peripheral demyelination (CCPD), Bickerstaff brainstem encephalitis, Fisher syndrome, trigeminal neuralgia, N/DAR anti-NN/DA receptor encephalitis, primary progressive MS (PPMS), OPA1 variant multiple sclerosis, KIR4.1 multiple sclerosis, aquaporine-related multiple sclerosis, chronic cerebrospinal venous insufficiency (CCSVI or CCVI), diffuse sclerosis, and Schilder's disease.

In certain aspects, the disorder to be treated is a demyelinating leukostrophic disease including, but not limited to, myelitis, central pontine myelinolysis (CPM), extrapontine myelinolysis, tabes dorsalis, progressive multifocal leukoencephalopathy, leukoencephalopathy with vanishing white matter, leukoencephalopathy with neuroaxonal spheroids, reversible posterior leukoencephalopathy syndrome, megalencephalic leukoencephalopathy with subcortical cysts, megalencephalic leukoencephalopathy with subcortical cysts 1, hypertensive leukoencephalopathy, Metachromatic leukodystrophy, Krabbe disease, Canavan disease, X-linked adrenoleukodystrophy, Alexander disease, cerebrotendineous xanthomatosis, Pelizaeus-Merzbacher disease, and Refsum disease.

In some embodiments, an effective amount of an active compound described herein, or a pharmaceutically acceptable salt thereof, is used to treat Buerger's disease, also known as thromboangiitis obliterans.

In some embodiments, an effective amount of an active compound described herein, or a pharmaceutically acceptable salt thereof, is used to treat giant cell arteritis.

In some embodiments, an effective amount of an active compound described herein, or a pharmaceutically acceptable salt thereof, is used to treat Raynaud's disease.

In certain aspects, the disorder to be treated is a demyelinating disease of the peripheral nervous system, including, but not limited to, Guillain-Barré syndrome and its chronic counterpart, chronic inflammatory demyelinating polyneuropathy, anti-MAG peripheral neuropathy, Charcot-Marie-Tooth disease and its counterpart Hereditary neuropathy with liability to pressure palsy, Copper deficiency-associated conditions (peripheral neuropathy, myelopathy, and rarely optic neuropathy), and progressive inflammatory neuropathy.

In certain aspects, the disorder to be treated is a neurological inflammatory disorder. In certain embodiments, the disorder to be treated includes, but is not limited to, cranial arteritis; giant cell arteritis; Holmes-Adie syndrome; inclusion body myositis (IBM); meningitis; neurologic paraneoplastic syndrome including, but not limited to, Lambert-Eaton myasthenic syndrome, stiff-person syndrome, encephalomyelitis (inflammation of the brain and spinal cord), myasthenia gravis, cerebellar degeneration, limbic and/or brainstem encephalitis, neuromyotonia, and opsoclonus (involving eye movement) and sensory neuropathy; polymyositis; transverse myelitis; vasculitis including temporal arteritis; arachnoiditis; Kinsbourne syndrome or opsoclonus myoclonus syndrome (OMS); or Saint Vitus Dance or sydenham chorea (SD) disease.

In some embodiments, an effective amount of an active compound described herein, or a pharmaceutically acceptable salt thereof, is used to treat transverse myelitis.

In certain aspects, the disorder to be treated is a peripheral neuropathy. In some embodiments, the peripheral neuropathy is a mononeuropathy. In some embodiments, the neuropathy is a polyneuropathy. In some embodiments, the polyneuropathy is distal axonopathy, diabetic neuropathy, a demyelinating polyneuropathy, small fiber peripheral neuropathy, mononeuritis multiplex, polyneuritis multiplex, autonomic neuropathy, or neuritis.

In some embodiments, an effective amount of an active compound described herein, or a pharmaceutically acceptable salt thereof, is used to treat an autoimmune vascular disease. In some embodiments, the autoimmune vascular disease is vasculitis. In some embodiments, the vasculitis includes, but is not limited to, autoimmune inflammatory vasculitis, Cutaneous small-vessel vasculitis, Granulomatosis with polyangiitis, Eosinophilic granulomatosis with polyangiitis, Behçet's disease, Kawasaki disease, Buerger's disease, and "Limited" granulomatosis with polyangiitis vasculitis.

In some embodiments, an active compound or its salt or composition as described herein is used to treat an arteritis. Is some embodiments, the arteritis includes, but is not limited to, giant cell arteritis, Takayasu arteritis, temporal arteritis, and polyarteritis nodosa.

In some embodiments, a method for the treatment of a glomerulonephritis is provided. In some embodiment, the glomerulonephritis is membranoproliferative glomerulonephritis (MPGN). In some embodiments, the MPGN is MPGN Type I. In some embodiments, the MPGN is MPGN Type II. In some embodiments, the MPGN is MPGN Type III. In some embodiments, the MPGN is C3 glomerulonephritis (C3G). In some embodiments, the MPGN is dense deposit disease (DDD). In some embodiments, the MPGN is a C4 deposition disorder.

In some embodiments, the glomerulonephritis is IC-MPGN. In some embodiments, the glomerulonephritis is a membranous glomerulonephritis. In some embodiments, the glomerulonephritis is IgA nephropathy. In some embodiments, the glomerulonephritis is Post-infectious glomerulonephritis. In some embodiments, the glomerulonephritis is a rapidly progressive glomerulonephritis, for example Type I (Goodpasture syndrome), Type II, or Type III rapidly progressive glomerulonephritis.

In some embodiments, a method for the treatment of paroxysmal nocturnal hemoglobinuria (PNH) is provided that includes the administration of an effective amount of a compound to a host of Formula I, II, III, IV, V, VI, VII, VIII, IX, X, XI, XII, XIII, XIV, XV, XVI, XVII, XVIII, XIX, or XX or a pharmaceutically acceptable salt, prodrug, isotopic analog, N-oxide, or isolated isomer thereof, optionally in a pharmaceutically acceptable composition.

In some embodiments, a method for the treatment of hereditary angioedema (HAE) is provided that includes the administration of an effective amount of a compound to a host of Formula I, II, III, IV, V, VI, VII, VIII, IX, X, XI, XII, XIII, XIV, XV, XVI, XVII, XVIII, XIX, or XX, or a pharmaceutically acceptable salt, prodrug, isotopic analog, N-oxide, or isolated isomer thereof, optionally in a pharmaceutically acceptable composition. Mutations in the SERPING1 gene cause hereditary angioedema type I and type II. Hereditary angioedema is a disorder characterized by recurrent episodes of severe swelling (angioedema). The most common areas of the body to develop swelling are the limbs, face, intestinal tract, and airway. The SERPING1 gene provides instructions for making the C1 inhibitor protein, which is important for controlling inflammation. C1 inhibitor blocks the activity of certain proteins that promote inflammation. Mutations that cause hereditary angioedema type I lead to reduced levels of C1 inhibitor in the blood, while mutations that cause type II result in the production of a C1 inhibitor that functions abnormally. Without the proper levels of functional C1 inhibitor, excessive amounts of a protein fragment (peptide) called bradykinin are generated. Bradykinin promotes inflammation by increasing the leakage of fluid through the walls of blood vessels into body tissues. Excessive accumulation of fluids in body tissues causes the episodes of swelling seen in individuals with hereditary angioedema type I and type II.

In some embodiments, a method for the treatment of cold agglutinin disease (CAD) is provided that includes the administration of an effective amount of a compound to a host of Formula I, II, III, IV, V, VI, VII, VIII, IX, X, XI, XII, XIII, XIV, XV, XVI, XVII, XVIII, XIX, or XX, or a pharmaceutically acceptable salt, prodrug, isotopic analog, N-oxide, or isolated isomer thereof, optionally in a pharmaceutically acceptable composition. CAD is a rare autoimmune hemolytic condition with potentially serious acute and chronic consequences that are driven by C1 activation of the classical complement pathway.

In some embodiments, a method for the treatment of atypical hemolytic uremic syndrome (aHUS) is provided that includes the administration of an effective amount of a compound to a host of Formula I, II, III, IV, V, VI, VII, VIII, IX, X, XI, XII, XIII, XIV, XV, XVI, XVII, XVIII, XIX, or XX, or a pharmaceutically acceptable salt, prodrug, isotopic analog, N-oxide, or isolated isomer thereof, optionally in a pharmaceutically acceptable composition. Atypical hemolytic-uremic syndrome is a disease that primarily affects kidney function. Atypical hemolytic uremic syndrome, which can occur at any age, causes abnormal blood clots (thrombi) to form in small blood vessels in the kidneys. These clots can cause serious medical problems if they restrict or block blood flow. Atypical hemolytic-uremic syndrome is characterized by three major features related to abnormal clotting: hemolytic anemia, thrombocytopenia, and kidney failure.

In another embodiment, a method for the treatment of wet or dry age-related macular degeneration (AMD) in a host is provided that includes the administration of an effective amount of a compound of Formula I, II, III, IV, V, VI, VII, VIII, IX, X, XI, XII, XIII, XIV, XV, XVI, XVII, XVIII, XIX, or XX, or a pharmaceutically acceptable salt, prodrug, isotopic analog, N-oxide, or isolated isomer thereof, optionally in a pharmaceutically acceptable composition. In another embodiment, a method for the treatment of rheumatoid arthritis in a host is provided that includes the administration of an effective amount of a compound of Formula I, II, III, IV, V, VI, VII, VIII, IX, X, XI, XII, XIII, XIV, XV, XVI, XVII, XVIII, XIX, or XX, or a pharmaceutically acceptable salt, prodrug, isotopic analog, N-oxide, or isolated isomer thereof, optionally in a pharmaceutically acceptable composition.

In another embodiment, a method for the treatment of multiple sclerosis in a host is provided that includes the administration of an effective amount of a compound of Formula I, II, III, IV, V, VI, VII, VIII, IX, X, XI, XII, XIII, XIV, XV, XVI, XVII, XVIII, XIX, or XX, or a pharmaceutically acceptable salt, prodrug, isotopic analog, N-oxide, or isolated isomer thereof, optionally in a pharmaceutically acceptable composition.

The active compounds, or pharmaceutically acceptable salt, prodrug, isotopic analog, N-oxide, or isolated isomer thereof, optionally in a pharmaceutically acceptable composition, as disclosed herein, are also useful for administration in combination (in the same or a different dosage form) or alternation with a second pharmaceutical agent for use in ameliorating or reducing a side effect of the second pharmaceutical agent.

For example, in some embodiments, the active compound may be used in combination with an adoptive cell-transfer therapy to reduce an inflammatory response associated with such therapy, for example, a cytokine mediated response such as cytokine response syndrome.

In some embodiments, the adoptive cell-transfer therapy is a chimeric antigen receptor T-Cell (CAR T) or a dendritic cell used to treat a hematologic or solid tumor, for example, a B-cell related hematologic cancer.

In some embodiments, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19.

In some embodiments, the adoptive cell-transfer therapy is a non-engineered T-cell therapy, wherein the T-cells have been activated and/or expanded to one or more viral or tumor antigens. In some embodiments, the associated inflammatory response is a cytokine mediated response.

In some embodiments, the second pharmaceutical agent is a cell that has been transformed to express a protein, wherein the protein in the host is mutated or otherwise has impaired function. In some embodiments, the transformed cell includes a CRISPR gene.

Another embodiment is provided that includes the administration of an effective amount of an active compound, or a pharmaceutically acceptable salt, prodrug, isotopic analog, N-oxide, or isolated isomer thereof, optionally in a pharmaceutically acceptable composition to a host to treat an ocular, pulmonary, gastrointestinal, or other disorder.

Any of the compounds described herein (e.g. Formula I, II, III, IV, V, VI, VII, VIII, IX, X, XI, XII, XIII, XIV, XV, XVI, XVII, XVIII, XIX, or XX) can be administered to the eye in any desired form of administration, including via intravitreal, intrastromal, intracameral, sub-tenon, sub-retinal, retro-bulbar, peribulbar, suprachoroidal, choroidal, subchoroidal, conjunctival, subconjunctival, episcleral, posterior juxtascleral, scleral, circumcorneal, and tear duct injections, or through a mucus, mucin, or a mucosal barrier, in an immediate or controlled release fashion. In certain embodiments, the active compound includes a lipophilic group, such as a lipophilic acyl group, which is delivered to the eye in a polymeric drug delivery system such as polylactic acid, polylactide-co-glycolide, polyglycolide or other erodible polymer, or a combination thereof, or in another type of lipophilic material for ocular delivery. In some embodiments, the lipophilic active molecule is more soluble in the polymeric or other form of delivery system than in ocular fluid.

In other embodiments of the disclosure, an active compound provided herein can be used to treat or prevent a disorder in a host mediated by complement. As examples, the disclosure includes methods to treat or prevent complement associated disorders that are induced by antibody-antigen interactions, a component of an immune or autoimmune disorder or by ischemic injury. The disclosure also provides methods to decrease inflammation or an immune response, including an autoimmune response, where mediated or affected by the classical complement pathway.

In some embodiments, the disorder is selected from fatty liver and conditions stemming from fatty liver, such as nonalcoholic steatohepatitis (NASH), liver inflammation, cirrhosis and liver failure. In some embodiments of the present disclosure, a method is provided for treating fatty liver disease in a host by administering an effective amount of an active compound or its salt or composition as described herein.

In another embodiment, an active compound or its salt or composition as described herein is used to modulate an immune response prior to or during surgery or other medical procedure. One non-limiting example is use in connection with acute or chronic graft versus host disease, which is a common complication as a result of organ transplantation, allogeneic tissue transplant, and can also occur as a result of a blood transfusion.

In some embodiments, the present disclosure provides a method of treating or preventing dermatomyositis by administering to a subject in need thereof an effective amount of an active compound or its salt or composition as described herein.

In some embodiments, the present disclosure provides a method of treating or preventing amyotrophic lateral sclerosis by administering to a subject in need thereof an effective amount of an active compound or its salt or composition as described herein.

In some embodiments, the present disclosure provides a method of treating or preventing abdominal aortic aneurysm, hemodialysis complications, hemolytic anemia, or hemodialysis by administering to a subject in need thereof an effective amount of an active compound or its salt or composition as described herein.

In another embodiment, a method is provided for the treatment or prevention of cytokine or inflammatory reactions in response to the administration of pharmaceutical or biotherapeutic (e.g., CAR T-cell therapy or monoclonal antibody therapy) in a host by administering an effective amount of an active compound or its salt or composition as described herein. Various types of cytokine or inflammatory reactions may occur in response to a number of factors, such as the administrations of biotherapeutics.

In some embodiments, the cytokine or inflammatory reaction is cytokine release syndrome. In some embodiments, the cytokine or inflammatory reaction is tumor lysis syndrome (which also leads to cytokine release). Symptoms of cytokine release syndrome range from fever, headache, and skin rashes to bronchospasm, hypotension and even cardiac arrest. Severe cytokine release syndrome is described as a cytokine storm, and can be fatal.

Fatal cytokine storms have been observed in response to infusion with several monoclonal antibody therapeutics. See, Abramowicz D, et al. "Release of tumor necrosis factor, interleukin-2, and gamma-interferon in serum after injection of OKT3 monoclonal antibody in kidney transplant recipients" *Transplantation* (1989) 47(4):606-8; Chatenoud L, et al. "In vivo cell activation following OKT3 administration. Systemic cytokine release and modulation by corticosteroids" *Transplantation* (1990) 49(4):697-702; and Lim L C, Koh L P, and Tan P. "Fatal cytokine release syndrome with chimeric anti-CD20 monoclonal antibody rituximab in a 71-year-old patient with chronic lymphocytic leukemia" *J. Clin Oncol*. (1999) 17(6):1962-3.

Also contemplated herein, is the use of an active compound or its salt or composition as described herein to mediate an adverse immune response in patients receiving bi-specific T-cell engagers (BiTE). A bi-specific T-cell engager directs T-cells to target and bind with a specific antigen on the surface of a cancer cell. For example, Blinatumomab (Amgen), a BiTE has recently been approved as a second line therapy in Philadelphia chromosome-negative relapsed or refractory acute lymphoblastic leukemia. Blinatumomab is given by continuous intravenous infusion in 4-week cycles. The use of BiTE agents has been associated with adverse immune responses, including cytokine release syndrome. The most significantly elevated cytokines in the CRS associated with ACT include IL-10, IL-6, and IFN-γ (Klinger et al., Immunopharmacologic response of patients with B-lineage acute lymphoblastic leukemia to continuous infusion of T cell-engaging CD19/CD3-bispecific BiTE antibody blinatumomab. *Blood* (2012) 119:6226-6233).

In another embodiment, the disorder is episcleritis, idiopathic episcleritis, anterior episcleritis, or posterior episcleritis. In some embodiments, the disorder is idiopathic anterior uveitis, HLA-B27 related uveitis, herpetic keratouveitis, Posner Schlossman syndrome, Fuch's heterochronic iridocyclitis, or cytomegalovirus anterior uveitis.

In some embodiments, the present disclosure provides a method of treating or preventing a IC-MPGN by administering to a subject in need thereof an effective amount of an active compound or its salt or composition as described herein.

In some embodiments, the present disclosure provides a method of treating or preventing a paroxysmal nocturnal hemoglobinuria (PNH) by administering to a subject in need thereof an effective amount of an active compound or its salt or composition as described herein.

In some embodiments, the present disclosure provides a method of treating or preventing a hereditary angioedema (HAE) by administering to a subject in need thereof an effective amount of an active compound or its salt or composition as described herein.

In some embodiments, the present disclosure provides a method of treating or preventing cold agglutinin disease (CAD) by administering to a subject in need thereof an effective amount of an active compound or its salt or composition as described herein.

In some embodiments, the present disclosure provides a method of treating or preventing atypical hemolytic syndrome (aHUS) by administering to a subject in need thereof an effective amount of an active compound or its salt or composition as described herein.

In some embodiments, the present disclosure provides a method of treating or preventing age-related macular degeneration (AMD) by administering to a subject in need thereof an effective amount of an active compound or its salt or composition as described herein.

In some embodiments, the present disclosure provides a method of treating or preventing rheumatoid arthritis by administering to a subject in need thereof an effective amount of an active compound or its salt or composition as described herein.

In some embodiments, the present disclosure provides a method of treating or preventing multiple sclerosis by administering to a subject in need thereof an effective amount of an active compound or its salt or composition as described herein.

In some embodiments, the present disclosure provides a method of treating or preventing myasthenia gravis by administering to a subject in need thereof an effective amount of an active compound or its salt or composition as described herein.

In some embodiments, the present disclosure provides a method of treating or preventing atypical hemolytic uremic syndrome (aHUS) by administering to a subject in need thereof an effective amount of an active compound or its salt or composition as described herein.

In yet another embodiment, the present disclosure provides a method of treating or preventing a disorder as described below by administering to a subject in need thereof an effective amount of an active compound or its salt or composition as described herein, including: vitritis, sarcoidosis, syphilis, tuberculosis, or Lyme disease; retinal vasculitis, Eales disease, tuberculosis, syphilis, or toxoplasmosis; neuroretinitis, viral retinitis, or acute retinal necrosis; varicella zoster virus, herpes simplex virus, cytomegalovirus, Epstein-Barr virus, lichen planus, or Dengue-associated disease (e.g., hemorraghic Dengue Fever); Masquerade syndrome, contact dermatitis, trauma induced inflammation, UVB induced inflammation, eczema, granuloma annulare, or acne.

In an additional embodiment, the disorder is selected from: acute myocardial infarction, aneurysm, cardiopulmonary bypass, dilated cardiomyopathy, complement activation during cardiopulmonary bypass operations, coronary artery disease, restenosis following stent placement, or percutaneous transluminal coronary angioplasty (PTCA); antibody-mediated transplant rejection, anaphylactic shock, anaphylaxis, allogenic transplant, humoral and vascular transplant rejection, graft dysfunction, graft-versus-host disease, Graves' disease, adverse drug reactions, or chronic graft vasculopathy; allergic bronchopulmonary aspergillosis, allergic neuritis, drug allergy, radiation-induced lung injury, eosinophilic pneumonia, radiographic contrast media allergy, bronchiolitis obliterans, or interstitial pneumonia; parkinsonism-dementia complex, sporadic frontotemporal dementia, frontotemporal dementia with Parkinsonism linked to chromosome 17, frontotemporal lobar degeneration, tangle only dementia, cerebral amyloid angiopathy, cerebrovascular disorder, certain forms of frontotemporal dementia, chronic traumatic encephalopathy (CTE), Parkinson's Disease with dementia (PDD), argyrophilic grain dementia, dementia pugilistica, dementia with Lewy Bodies (DLB), or multi-infarct dementia; Creutzfeldt-Jakob disease, Huntington's disease, multifocal motor neuropathy (MMN), prion protein cerebral amyloid angiopathy, polymyositis, postencephalitic parkinsonism, subacute sclerosing panencephalitis, non-Guamanian motor neuron disease with neurofibrillary tangles, neural regeneration, and diffuse neurofibrillary tangles with calcification.

In some embodiments, the disorder is selected from: atopic dermatitis, dermatitis, dermatomyositis bullous pemphigoid, scleroderma, sclerodermatomyositis, psoriatic arthritis, pemphigus vulgaris, Discoid lupus erythematosus, cutaneous lupus, chilblain lupus erythematosus, or lupus erythematosus-lichen planus overlap syndrome; cryoglobulinemic vasculitis, mesenteric/enteric vascular disorder, peripheral vascular disorder, antineutrophil cytoplasm antibody (ANCA)-associated vasculitis (AAV), IL-2 induced vascular leakage syndrome, or immune complex vasculitis; angioedema, low platelets (HELLP) syndrome, sickle cell disease, platelet refractoriness, red cell casts, or typical or infectious hemolytic uremic syndrome (tHUS); hematuria, hemorrhagic shock, drug-induced thrombocytopenia, autoimmune hemolytic anemia (AIHA), azotemia, blood vessel and/or lymph vessel inflammation, rotational atherectomy, or delayed hemolytic transfusion reaction; British type amyloid angiopathy, Buerger's disease, bullous pemphigoid, C1q nephropathy, cancer, and catastrophic antiphospholipid syndrome.

In another embodiment, the disorder is selected from: wet (exudative) AMD, dry (non-exudative) AMD, chorioretinal degeneration, choroidal neovascularization (CNV), choroiditis, loss of RPE function, loss of vision (including loss of visual acuity or visual field), loss of vision from AMD, retinal damage in response to light exposure, retinal degeneration, retinal detachment, retinal dysfunction, retinal neovascularization (RNV), retinopathy of prematurity, pathological myopia, or RPE degeneration; pseudophakic bullous keratopathy, symptomatic macular degeneration related disorder, optic nerve degeneration, photoreceptor degeneration, cone degeneration, loss of photoreceptor cells, pars planitis, scleritis, proliferative vitreoretinopathy, or formation of ocular drusen; chronic urticaria, Churg-Strauss syndrome, cold agglutinin disease (CAD), corticobasal degeneration (CBD), cryoglobulinemia, cyclitis, damage of the Bruch's membrane, Degos disease, diabetic angiopathy, elevated liver enzymes, endotoxemia, epidermolysis bullosa, or epidermolysis bullosa acquisita; essential mixed cryoglobulinemia, excessive blood urea nitrogen-BUN, focal segmental glomerulosclerosis, Gerstmann-Straussler-Scheinker disease, giant cell arteritis, gout, Hallervorden-Spatz disease, Hashimoto's thyroiditis, Henoch-Schonlein purpura nephritis, or abnormal urinary sediments; hepatitis, hepatitis A, hepatitis B, hepatitis C or human immunodeficiency virus (HIV), a viral infection more generally, for example selected from Flaviviridae, Retroviruses, Coronaviridae, Poxviridae, Adenoviridae, Herpesviridae, Caliciviridae, Reoviridae, Picornaviridae, Togaviridae, Orthomyxoviridae, Rhabdoviridae, or Hepadnaviridae; *Neisseria meningitidis*, shiga toxin *E. coli*-related hemolytic uremic syndrome (STEC-HUS), hemolytic uremic syndrome (HUS); *Streptococcus*, and poststreptococcal glomerulonephritis.

In a further embodiment, the disorder is selected from: hyperlipidemia, hypertension, hypoalbuminemia, hypobolemic shock, hypocomplementemic urticarial vasculitis syndrome, hypophosphastasis, hypovolemic shock, idiopathic pneumonia syndrome, or idiopathic pulmonary fibrosis; inclusion body myositis, intestinal ischemia, iridocyclitis, iritis, juvenile chronic arthritis, Kawasaki's disease (arteritis), or lipiduria; membranoproliferative glomerulonephritis (MPGN) I, microscopic polyangiitis, mixed cryoglobulinemia, molybdenum cofactor deficiency (MoCD) type A, pancreatitis, panniculitis, Pick's disease, polyarteritis nodosa (PAN), progressive subcortical gliosis, proteinuria, reduced glomerular filtration rate (GFR), or renovascular disorder; multiple organ failure, multiple system atrophy (MSA), myotonic dystrophy, Niemann-Pick disease type C, chronic demyelinating diseases, or progressive supranuclear palsy; spinal cord injury, spinal muscular atrophy, spondyloarthropathies, Reiter's syndrome, spontaneous fetal loss, recurrent fetal loss, pre-eclampsia, synucleinopathy, Takayasu's arteritis, post-partum thyroiditis, thyroiditis, Type I cryoglobulinemia, Type II mixed cryoglobulinemia, Type III mixed cryoglobulinemia, ulcerative colitis, uremia, urticaria, venous gas embolus (VGE), or Wegener's granulomatosis; von Hippel-Lindau disease, histoplasmosis of the eye, hard drusen, soft drusen, pigment clumping, and photoreceptor and/or retinal pigmented epithelia (RPE) loss.

In some embodiments, an active compound or its salt or composition as described herein is useful for treating or preventing a disorder selected from autoimmune oophoritis, endometriosis, autoimmune orchitis, Ord's thyroiditis, autoimmune enteropathy, coeliac disease, Hashimoto's encephalopathy, antiphospholipid syndrome (APLS) (Hughes syndrome), aplastic anemia, autoimmune lymphoproliferative syndrome (Canale-Smith syndrome), autoimmune neutropenia, Evans syndrome, pernicious anemia, pure red cell aplasia, thrombocytopenia, adipose dolorosa (Dercum's disease), adult onset Still's disease, ankylosing spondylitis, CREST syndrome, drug-induced lupus, eosinophilic fasciitis (Shulman's syndrome), Felty syndrome, IgG4-related disease, mixed connective tissue disease (MCTD), palindromic rheumatism (Hench-Rosenberg syndrome), Parry-Romberg syndrome, Parsonage-Turner syndrome, relapsing polychondritis (Meyenburg-Altherr-Uehlinger syndrome), retroperitoneal fibrosis, rheumatic fever, Schnitzler syndrome, fibromyalgia, neuromyotonia (Isaac's disease), paraneoplastic degeneration, autoimmune inner ear disease, Meniere's disease, interstitial cystitis, autoimmune pancreatitis, zika virus-related disorders, chikungunya virus-related disorders, subacute bacterial endocarditis (SBE), IgA nephropathy, IgA vasculitis, polymyalgia rheumatic, rheumatoid vasculitis, alopecia areata, autoimmune progesterone dermatitis, dermatitis herpetiformis, erythema nodosum, gestational pemphigoid, hidradenitis suppurativa, lichen sclerosus, linear IgA disease (LAD), morphea, myositis, *Pityriasis lichenoides* et varioliformis *acuta*, vitiligo post-myocardial infarction syndrome (Dressler's syndrome), post-pericardiotomy syndrome, autoimmune retinopathy, Cogan syndrome, Graves opthalmopathy, ligneous conjunctivitis, Mooren's ulcer, opsoclonus myoclonus syndrome, optic neuritis, retinocochleocerebral vasculopathy (Susac's syndrome), sympathetic opthalmia, Tolosa-Hunt syndrome, interstitial lung disease, antisynthetase syndrome, Addison's disease, autoimmune polyendocrine syndrome (APS) type I, autoimmune polyendocrine syndrome (APS) type II, autoimmune polyendocrine syndrome (APS) type III, disseminated sclerosis (multiple sclerosis, pattern II), rapidly progressing glomerulonephritis (RPGN), juvenile rheumatoid arthritis, enthesitis-related arthritis, reactive arthritis (Reiter's syndrome), autoimmune hepatitis or lupoid hepatitis, primary biliary cirrhosis (PBS), primary sclerosing cholangitis, microscopic colitis, latent lupus (undifferentiated connective tissue disease (UCTD)), acute disseminated encephalomyelitis (ADEM), acute motor axonal neuropathy, anti-n-methyl-D-aspartate receptor encephalitis, Balo concentric sclerosis (Schilders disease), Bickerstaff's encephalitis, chronic inflammatory demyelinating polyneuropathy, idiopathic inflammatory demyelinating disease, Lambert-Eaton mysathenic syndrome, Oshtoran syndrome, pediatric autoimmune neuropsychiatric disorder associated with *Streptococcus* (PANDAS), progressive inflammatory neuropathy, restless leg syndrome, stiff person syndrome, Sydenhem syndrome, transverse myelitis, lupus vasculitis, leukocytoclastic vasculitis, Microscopic Polyangiitis, polymyositis, and ischemic-reperfusion injury of the eye.

Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma, and combinations thereof.

In a further embodiment, the disorder is selected from glaucoma, diabetic retinopathy, blistering cutaneous diseases (including bullous pemphigoid, pemphigus, and epidermolysis bullosa), ocular cicatrical pemphigoid, uveitis, adult macular degeneration, diabetic retinopa retinitis pigmentosa, macular edema, diabetic macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, postoperative inflammation, and retinal vein occlusion, and central retinal vein occlusion (CVRO).

In some embodiments, complement mediated diseases include ophthalmic diseases (including early or neovascular age-related macular degeneration and geographic atrophy), autoimmune diseases (including arthritis, rheumatoid arthritis), respiratory diseases, and cardiovascular diseases. In other embodiments, the compounds of the disclosure are suitable for use in the treatment of diseases and disorders associated with fatty acid metabolism, including obesity and other metabolic disorders.

Disorders that may be treated or prevented by an active compound or its salt or composition as described herein also include, but are not limited to: hereditary angioedema, capillary leak syndrome, hemolytic uremic syndrome (HUS), neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome; inflammatory effects of sepsis, systemic inflammatory response syndrome (SIRS), disorders of inappropriate or undesirable complement activation, interleukin-2 induced toxicity during IL-2 therapy, inflammatory disorders, inflammation of autoimmune diseases, systemic lupus erythematosus (SLE), lupus nephritides, arthritis, immune complex disorders and autoimmune diseases, systemic lupus, or lupus erythematosus; ischemia/reperfusion injury (I/R injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes; Alzheimer's dementia, stroke, schizophrenia, traumatic brain injury, trauma, Parkinson's disease, epilepsy, transplant rejection, prevention of fetal loss, biomaterial reactions (e.g. in hemodialysis, implants), hyperacute allograft rejection, xenograft rejection, transplantation, psoriasis, burn injury, thermal injury including burns or frostbite, or crush injury; asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, and immune complex-associated inflammation.

In some embodiments, a method for the treatment of sickle cell in a host is provided that includes the administration of an effective amount of an active compound or its salt or composition as described herein.

In some embodiments, a method for the treatment of immune thrombocytopenic purpura (ITP), thrombotic thrombocytopenic purpura (TTP), or idiopathic thrombocytopenic purpura (ITP) in a host is provided that includes the administration of an effective amount of an active compound or its salt or composition as described herein.

In some embodiments, a method for the treatment of ANCA-vasculitis in a host is provided that includes the administration of an effective amount of an active compound or its salt or composition as described herein.

In some embodiments, a method for the treatment of IgA nephropathy in a host is provided that includes the administration of an effective amount of an active compound or its salt or composition as described herein.

In some embodiments, a method for the treatment of rapidly progressing glomerulonephritis (RPGN), in a host is provided that includes the administration of an effective amount of an active compound or its salt or composition as described herein.

In some embodiments, a method for the treatment of lupus nephritis, in a host is provided that includes the administration of an effective amount of an active compound or its salt or composition as described herein.

In some embodiments, a method for the treatment of hemorraghic dengue fever, in a host is provided that includes the administration of an effective amount of an active compound or its salt or composition as described herein.

In an additional alternative embodiment, an active compound or its salt or composition as described herein is used in the treatment of an autoimmune disorder. The complement pathway enhances the ability of antibodies and phagocytic cells to clear microbes and damaged cells from the body. It is part of the innate immune system and in healthy individuals is an essential process. Inhibiting the complement pathway will decrease the body's immune system response. Therefore, it is an object of the present disclosure to treat autoimmune disorders by administering an effective does of an active compound or its salt or composition as described herein to a subject in need thereof.

In some embodiments, the autoimmune disorder is caused by activity of the complement system. In some embodiments the autoimmune disorder is caused by activity of the alternative complement pathway. In some embodiments the autoimmune disorder is caused by activity of the classical complement pathway. In another embodiment the autoimmune disorder is caused by a mechanism of action that is not directly related to the complement system, such as the over-proliferation of T-lymphocytes or the over-production of cytokines.

Non-limiting examples of autoimmune disorders include: lupus, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), diabetes, multiple sclerosis, pernicious anemia, psoriasis, rheumatoid arthritis, sarcoidosis, and scleroderma.

In some embodiments, an active compound or its salt or composition as described herein is used in the treatment of lupus. Non-limiting examples of lupus include lupus erythematosus, cutaneous lupus, discoid lupus erythematosus, chilblain lupus erythematosus, and lupus erythematosus-lichen planus overlap syndrome.

Lupus erythematosus is a general category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Diabetes can refer to either type 1 or type 2 diabetes. In some embodiments an active compound or its salt or composition as described herein is provided at an effective dose to treat a patient with type 1 diabetes. In some embodiments an active compound or its salt or composition as described herein is provided at an effective dose to treat a patient with type 2 diabetes. Type 1 diabetes is an autoimmune disease. An autoimmune disease results when the body's system for fighting infection (the immune system) attacks a part of the body. In the case of diabetes type 1, the pancreas then produces little or no insulin.

In some embodiments, the complement-mediated disease or disorder comprises transplant rejection. In some embodiments, the complement-mediated disease or disorder is antibody-mediated transplant rejection.

In certain aspects, an active compound or its salt or composition as described herein is used to treat a proliferative disorder, including, but not limited to, cancer. Targeted cancers suitable for administration of an active compound or its salt described herein include, but are not limited to, estrogen-receptor positive cancer, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, adenocarcinoma of the colon, adenocarcinoma of the rectum, central nervous system germ cell tumors, teratomas, estrogen receptor-negative breast cancer, estrogen receptor-positive breast cancer, familial testicular germ cell tumors, HER2-negative breast cancer, HER2-positive breast cancer, male breast cancer, ovarian immature teratomas, ovarian mature teratoma, ovarian monodermal and highly specialized teratomas, progesterone receptor-negative breast cancer, progesterone receptor-positive breast cancer, recurrent breast cancer, recurrent colon cancer, recurrent extragonadal germ cell tumors, recurrent extragonadal non-seminomatous germ cell tumor, recurrent extragonadal seminomas, recurrent malignant testicular germ cell tumors, recurrent melanomas, recurrent ovarian germ cell tumors, recurrent rectal cancer, stage III extragonadal non-seminomatous germ cell tumors, stage III extragonadal seminomas, stage III malignant testicular germ cell tumors, stage III ovarian germ cell tumors, stage IV breast cancers, stage IV colon cancers, stage IV extragonadal non-seminomatous germ cell tumors, stage IV extragonadal seminoma, stage IV melanomas, stage IV ovarian germ cell tumors, stage IV rectal cancers, testicular immature teratomas, testicular mature teratomas. In particular embodiments, the targeted cancers included estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, metastatic colorectal cancer, metastatic melanoma with CDK4 mutation or amplification, or cisplatin-refractory, unresectable germ cell tumors, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, fibrosarcoma, myxosarcoma, chondrosarcoma, osteosarcoma, chordoma, malignant fibrous histiocytoma, hemangiosarcoma, angiosarcoma, lymphangiosarcoma, Mesothelioma, leiomyosarcoma, rhabdomyosarcoma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, bladder cancer, and Wilms tumor, a blood disorder or a hematologic malignancy, including, but not limited to, myeloid disorder, lymphoid disorder, leukemia, lymphoma, myelodysplastic syndrome (MDS), myeloproliferative disease (MPD), mast cell disorder, and myeloma (e.g., multiple myeloma), among others, T-cell or NK-cell lymphoma, for example, but not limited to: peripheral T-cell lymphoma; anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In some embodiments, the methods described herein can be used to treat a host, for example a human, with a lymphoma or lymphocytic or myelocytic proliferation disorder or abnormality. For example, the methods as described herein can be administered to a host with a Hodgkin Lymphoma or a Non-Hodgkin Lymphoma. For example, the host can have a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia, a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL, a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma, a leukemia, for example, an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); large granular lymphocytic leukemia; or Adult T-cell chronic leukemia. In some embodiments, the patient has an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7), small cell lung cancer, retinoblastoma, HPV positive malignancies like cervical cancer and certain head and neck cancers, MYC amplified tumors such as Burkitts' Lymphoma, and triple negative breast cancer; certain classes of sarcoma, certain classes of non-small cell lung carcinoma, certain classes of melanoma, certain classes of pancreatic cancer, certain classes of leukemia, certain classes of lymphoma, certain classes of brain cancer, certain classes of colon cancer, certain classes of prostate cancer, certain classes of ovarian cancer, certain classes of uterine cancer, certain classes of thyroid and other endocrine tissue cancers, certain classes of salivary cancers, certain classes of thymic carcinomas, certain classes of kidney cancers, certain classes of bladder cancers, and certain classes of testicular cancers.

In certain aspects, an active compound or its salt as described herein can be used to preserve or prevent damage to an organ or blood product. For example, an active compound or its salt described herein can be used to prevent damage to an organ, tissue, cell product, or blood product, that has been harvested for transplantation. In some embodiments, the organ is the heart, kidney, pancreas, lung, liver, or intestine. In some embodiments, the tissue is derived from the cornea, bone, tendon, muscle, heart valve, nerve, artery or vein, or the skin. In some embodiments, the blood product is whole blood, plasma, red blood cells or reticulocytes.

In some embodiments, an active compound or its salt or composition as described herein prevents or delays the onset of at least one symptom of a complement-mediated disease or disorder in an individual. In some embodiments, an active compound or its salt or composition as described herein reduces or eliminates at least one symptom of a complement-mediated disease or disorder in an individual. Examples of symptoms include, but are not limited to, symptoms associated with autoimmune disease, cancer, hematological disease, infectious disease, inflammatory disease, ischemia-reperfusion injury, neurodegenerative disease, neurodegenerative disorder, renal disease, transplant rejection, ocular disease, vascular disease, or a vasculitis disorder. The symptom can be a neurological symptom, for example, impaired cognitive function, memory impairment, loss of motor function, etc. The symptom can also be the activity of C1s protein in a cell, tissue, or fluid of an individual. The symptom can also be the extent of complement activation in a cell, tissue, or fluid of an individual.

In some embodiments, administering an active compound or its salt or composition as described herein to an individual modulates complement activation in a cell, tissue, or fluid of an individual. In some embodiments, administration of an active compound or its salt or composition as described herein to an individual inhibits complement activation in a cell, tissue, or fluid of an individual. For example, in some embodiments, an active compound or its salt or composition as described herein, when administered in one or more doses as monotherapy or in combination therapy to an individual having a complement-mediated disease or disorder, inhibits complement activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to complement activation in the individual before treatment with the compounds described herein.

In some embodiments, an active compound or its salt or composition as described herein reduces C3 deposition onto red blood cells; for example, in some embodiments, an active compound or its salt or composition as described herein reduces deposition of C3b, iC3b, etc., onto RBCs. In some embodiments, an active compound or its salt or composition as described herein inhibits complement-mediated red blood cell lysis.

In some embodiments, an active compound or its salt or composition as described herein reduces C3 deposition onto platelets; for example, in some embodiments, an active compound or its salt or composition as described herein reduces deposition of C3b, iC3b, etc., onto platelets.

In some embodiments, administering an active compound or its salt or composition as described herein results in an outcome selected from the group consisting of: (a) a reduction in complement activation; (b) an improvement in cognitive function; (c) a reduction in neuron loss; (d) a reduction in phospho-Tau levels in neurons; (e) a reduction in glial cell activation; (f) a reduction in lymphocyte infiltration; (g) a reduction in macrophage infiltration; (h) a reduction in antibody deposition, (i) a reduction in glial cell loss; (j) a reduction in oligodendrocyte loss; (k) a reduction in dendritic cell infiltration; (l) a reduction in neutrophil infiltration; (m) a reduction in red blood cell lysis; (n) a reduction in red blood cell phagocytosis; (o) a reduction in platelet phagocytosis; (p) a reduction in platelet lysis; (q) an improvement in transplant graft survival; (r) a reduction in macrophage mediated phagocytosis; (s) an improvement in vision; (t) an improvement in motor control; (u) an improvement in thrombus formation; (v) an improvement in clotting; (w) an improvement in kidney function; (x) a reduction in antibody mediated complement activation; (y) a reduction in autoantibody mediated complement activation; (z) an improvement in anemia; (aa) reduction of demyelination; (ab) reduction of eosinophilia; (ac) a reduction of C3 deposition on red blood cells (e.g., a reduction of deposition of C3b, iC3b, etc., onto RBCs); and (ad) a reduction in C3 deposition on platelets (e.g., a reduction of deposition of C3b, iC3b, etc., onto platelets); and (ae) a reduction of anaphylatoxin toxin production; (af) a reduction in autoantibody mediated blister formation; (ag) a reduction in autoantibody induced pruritis; (ah) a reduction in autoantibody induced erythematosus; (ai) a reduction in autoantibody mediated skin erosion; (aj) a reduction in red blood cell destruction due to transfusion reactions; (ak) a reduction in red blood cell lysis due to alloantibodies; (al) a reduction in hemolysis due to transfusion reactions; (am) a reduction in allo-antibody mediated platelet lysis; (an) a reduction in platelet lysis due to transfusion reactions; (ao) a reduction in mast cell activation; (ap) a reduction in mast cell histamine release; (aq) a reduction in vascular permeability; (ar) a reduction in edema; (as) a reduction in complement deposition on transplant graft endothelium; (at) a reduction of anaphylatoxin generation in transplant graft endothelium; (au) a reduction in the separation of the dermal-epidermal junction; (av) a reduction in the generation of anaphylatoxins in the dermal-epidermal junction; (aw) a reduction in alloantibody mediated complement activation in transplant graft endothelium; (ax) a reduction in antibody mediated loss of the neuromuscular junction; (ay) a reduction in complement activation at the neuromuscular junction; (az) a reduction in anaphylatoxin generation at the neuromuscular junction; (ba) a reduction in complement deposition at the neuromuscular junction; (bb) a reduction in paralysis; (bc) a reduction in numbness; (bd) increased bladder control; (be) increased bowel control; (bf) a reduction in mortality associated with autoantibodies; and (bg) a reduction in morbidity associated with autoantibodies.

In some embodiments, an active compound or its salt or composition as described herein, when administered in one or more doses as monotherapy or in combination therapy to an individual having a complement-mediated disease or disorder, is effect to achieve a reduction of at least about 10%, at least about 15%, at least about 20%, at least about 25%, at least about 30%, at least about 40%, at least about 50%, at least about 60%, at least about 70%, at least about 80%, at least about 90%, or more than 90%, of one or more of the following outcomes: (a) complement activation; (b) decline in cognitive function; (c) neuron loss; (d) phospho-Tau levels in neurons; (e) glial cell activation; (f) lymphocyte infiltration; (g) macrophage infiltration; (h) antibody deposition, (i) glial cell loss; (j) oligodendrocyte loss; (k) dendritic cell infiltration; (l) neutrophil infiltration; (m) red blood cell lysis; (n) red blood cell phagocytosis; (o) platelet phagocytosis; (p) platelet lysis; (q) transplant graft rejection;

(r) macrophage mediated phagocytosis; (s) vision loss; (t) antibody mediated complement activation; (u) autoantibody mediated complement activation; (v) demyelination; (w) eosinophilia; compared to the level or degree of the outcome in the individual before treatment with the active compound.

In some embodiments, an active compound or its salt or composition as described herein, when administered in one or more doses as monotherapy or in combination therapy to an individual having a complement-mediated disease or disorder, is effect to achieve an improvement of at least about 10%, at least about 15%, at least about 20%, at least about 25%, at least about 30%, at least about 40%, at least about 50%, at least about 60%, at least about 70%, at least about 80%, at least about 90%, or more than 90%, of one or more of the following outcomes: a) cognitive function; b) transplant graft survival; c) vision; d) motor control; e) thrombus formation; f) clotting; g) kidney function; and h) hematocrit (red blood cell count), compared to the level or degree of the outcome in the individual before treatment with the active compound.

In some embodiments, administering an active compound or its salt or composition as described herein to an individual reduces complement activation in the individual. For example, in some embodiments, an active compound or its salt or composition as described herein, when administered in one or more doses as monotherapy or in combination therapy to an individual having a complement-mediated disease or disorder, reduces complement activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to complement activation in the individual before treatment with the active compound or its salt.

In some embodiments, administering an active compound or its salt or composition as described herein improves cognitive function in the individual. For example, in some embodiments, an active compound described herein, when administered in one or more doses as monotherapy or in combination therapy to an individual having a complement-mediated disease or disorder, improves cognitive function in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the cognitive function in the individual before treatment with the active compound.

In some embodiments, administering an active compound or its salt or composition as described herein reduces the rate of decline in cognitive function in the individual. For example, in some embodiments, an active compound or its salt, when administered in one or more doses as monotherapy or in combination therapy to an individual having a complement-mediated disease or disorder, reduces the rate of decline of cognitive function in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the rate of decline in cognitive function in the individual before treatment with the active compound or its salt.

In some embodiments, administering an active compound or its salt or composition as described herein to an individual reduces neuron loss in the individual. For example, in some embodiments, an active compound or its salt, when administered in one or more doses as monotherapy or in combination therapy to an individual having a complement-mediated disease or disorder, reduces neuron loss in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to neuron loss in the individual before treatment with the active compound.

In some embodiments, administering an active compound or its salt or composition as described herein to an individual reduces phospho-Tau levels in the individual. For example, in some embodiments, an active compound or its salt, when administered in one or more doses as monotherapy or in combination therapy to an individual having a complement-mediated disease or disorder, reduces phospho-Tau in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the phospho-Tau level in the individual before treatment with the active compound or its salt.

In some embodiments, administering an active compound or its salt or composition as described herein to an individual reduces glial cell activation in the individual. For example, in some embodiments, an active compound or its salt, when administered in one or more doses as monotherapy or in combination therapy to an individual having a complement-mediated disease or disorder, reduces glial activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to glial cell activation in the individual before treatment with the active compound or its salt. In some embodiments, the glial cells are astrocytes or microglia.

In some embodiments, administering an active compound or its salt or composition as described herein to an individual reduces lymphocyte infiltration in the individual. For example, in some embodiments, an active compound or its salt, when administered in one or more doses as monotherapy or in combination therapy to an individual having a complement-mediated disease or disorder, reduces lymphocyte infiltration in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to lymphocyte infiltration in the individual before treatment with the active compound or its salt.

In some embodiments, administering an active compound or its salt or composition as described herein to an individual reduces macrophage infiltration in the individual. For example, in some embodiments, an active compound or its salt, when administered in one or more doses as monotherapy or in combination therapy to an individual having a complement-mediated disease or disorder, reduces macrophage infiltration in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to macrophage infiltration in the individual before treatment with the active compound or its salt.

In some embodiments, administering an active compound or its salt or composition as described herein to an individual reduces antibody deposition in the individual. For example, in some embodiments, an active compound or its salt, when administered in one or more doses as monotherapy or in combination therapy to an individual having a complement-mediated disease or disorder, reduces antibody deposition in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to antibody deposition in the individual before treatment with the active compound or its salt.

In some embodiments, administering an active compound or its salt or composition as described herein to an individual reduces anaphylatoxin (e.g., C3a, C4a, C5a) production in an individual. For example, in some embodiments, an active compound or its salt, when administered in one or more doses as monotherapy or in combination therapy to an individual having a complement-mediated disease or disorder, reduces anaphylatoxin production in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the level of anaphylatoxin production in the individual before treatment with the active compound or its salt.

The present disclosure provides for use of an active compound or its salt of the present disclosure or a pharmaceutical composition comprising an active compound or its salt of the present disclosure and a pharmaceutically acceptable excipient to treat an individual having a complement-mediated disease or disorder. In some embodiments, the present disclosure provides for use of an active compound or its salt of the present disclosure to treat an individual having a complement-mediated disease or disorder. In some embodiments, the present disclosure provides for use of a pharmaceutical composition comprising an active compound or its salt of the present disclosure and a pharmaceutically acceptable excipient to treat an individual having a complement-mediated disease or disorder.

Combination Therapy

In one aspect of the present disclosure, an active compound or its salt or composition as described herein may be provided in combination or alternation with or preceded by, concomitant with or followed by, an effective amount of at least one additional therapeutic agent, for example, for treatment of a disorder listed herein. Non-limiting examples of second active agents for such combination therapy are provided as follows.

In some embodiments, an active compound or its salt or composition as described herein may be provided in combination or alternation with at least one additional inhibitor of the complement system or a second active compound with a different biological mechanism of action. In the description below and herein generally, whenever any of the terms referring to an active compound or its salt or composition as described herein are used, it should be understood that pharmaceutically acceptable salts, prodrugs or compositions are considered included, unless otherwise stated or inconsistent with the text.

In non-limiting embodiments, an active compound or its salt or composition as described herein may be provided together with a protease inhibitor, a soluble complement regulator, a therapeutic antibody (monoclonal or polyclonal), complement component inhibitor, receptor agonist, chemotherapeutic agent, or siRNA.

In other embodiments, an active compound described herein is administered in combination or alternation with an antibody against tumor necrosis factor (TNF), including but not limited to infliximab (REMICADE®), adalimumab (HUMIRA®), certolizumab (CIMZIA®), golimumab (SIMPONI®), or a receptor fusion protein such as etanercept (ENBREL®). In some embodiments, the agent for combination therapy is a biosimilar of any agent named above, including, but not limited to, REMISMA® (infliximab biosimilar), FLIXABI® (infliximab biosimilar), AMGEVITA® (adalimumab biosimilar), IMRALDI® (adalimumab biosimilar), CYTELZO® (adalimumab biosimilar), BENEPALI® (etanercept biosimilar), and ERELZI® (etanercept biosimilar).

In another embodiment, an active compound as described herein can be administered in combination or alternation with an anti-CD20 antibody, including but not limited to rituximab (RITUXAN®), ofatumumab (ARZERRA®), tositumomab (BEXXAR®), obinutuzumab (GAZYVA®), ibritumomab (ZEVALIN®), ocrelizumab (OCREVUS®), or veltuzumab. In some embodiments, the agent for combination therapy is a biosimilar of any agent named above, including, but not limited to, TRUXIMA® (rituximab biosimilar).

In an alternative embodiment, an active compound as described herein can be administered in combination or alternation with an anti-IL6 antibody, including but not limited to tocilizumab (ACTEMRA®), siltuximab (SYLVANT®), sarilumab (KEVZARA®), sirukumab, clazakizumab, vobarilizumab, olokizumab, and WBP216 (MEDI5117). In some embodiments, the agent for combination therapy is a biosimilar of any agent named above, including, but not limited to, BAT1806 (tocilizumab biosimilar).

In an alternative embodiment, an active compound as described herein can be administered in combination or alternation with an IL17 inhibitor, including but not limited to secukinumab (Cosentyx), ixekizumab (TALTZ®), brodalumab (SILIQ®), bimekizumab, ALX-0761, CJM112, CNTO6785, LY3074828, SCH-900117, and MSB0010841. In some embodiments, the agent for combination therapy is a biosimilar of any agent named above.

In an alternative embodiment, an active compound as described herein can be administered in combination or alternation with a p40 (IL12/IL23) inhibitor, including but not limited to ustekinumab (STELARA®) and briakinumab (ABT874). In some embodiments, the agent for combination therapy is a biosimilar of any agent named above, including, but not limited to, FYB202 (ustekinumab biosimilar) and Neulara® (ustekinumab biosimilar).

In an alternative embodiment, an active compound as described herein can be administered in combination or alteration with an IL23 inhibitor, including but not limited to risankizumab (SKYRIZI®), tildrakizumab (ILUMYA®), guselkumab (TREMFYA®), mirakizumab and brazikumab. In some embodiments, the agent for combination therapy is a biosimilar of any agent named above.

In an alternative embodiment, an active compound as described herein can be administered in combination or alteration with an anti-interferon α antibody, for example but not limited to sifalimumab, anifrolumab, and rontalizumab. In some embodiments, the agent for combination therapy is a biosimilar of any agent named above.

In an alternative embodiment, an active compound as described herein can be administered in combination or alteration with a kinase inhibitor, for example but not limited to a JAK1/JAK3 inhibitor, for example but not limited to tofacitinib (XELJANZ®). In an alternative embodiment, an active compound as described herein can be administered in combination or alteration with a JAK1/JAK2 inhibitor, for example but not limited to baracitinib (OLUMIANT®) and ruxolitinib (JAKAFI®).

In an alternative embodiment, an active compound as described herein can be administered in combination or alteration with an anti-VEGF agent, for example but not limited to: aflibercept (EYLEA®; Regeneron Pharmaceuticals); ranibizumab (LUCENTIS®: Genentech and Novartis); pegaptanib (MACUGEN®; OSI Pharmaceuticals and Pfizer); bevacizumab (AVASTIN®; Genentech/Roche) and ziv-aflibercept (ZALTRAP®).

In an alternative embodiment, an active compound as described herein can be administered in combination or alternation with a tyrosine kinase inhibitor, for example but not limited to: lapatinib (TYKERB®); sunitinib (SUTENT®); axitinib (INLYTA®); pazopanib; sorafenib (NEXAVAR®); ponatinib (INCLUSIG®); regorafenib (STIVARGA®); cabozantinib (ABOMETYX®; COMETRIQ®); vendetanib (CAPRELSA®); ramucirumab (CYRAMZA®); lenvatinib (LENVIMA®); cediranib (RECENTIN®); anecortane acetate, squalamine lactate, and corticosteroids.

In another embodiment, an active compound as described herein can be administered in combination or alternation with an immune checkpoint inhibitor. Non-limiting examples of checkpoint inhibitors include anti-PD-1 or anti-PDL1 antibodies, for example, nivolumab (OPDIVO®), pembrolizumab (KEYTRUDA®), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.), atezolizumab (TECENTRIQ®), durvalumab (IMFINZI®), and KN035, or anti-CTLA4 antibodies, for example Ipilimumab (YERVOY®), Tremelimumab, AGEN1884 and AGEN2041 (Agenus).

Non-limiting examples of active agents that can be used in combination with active compounds described herein include, but are not limited to:

- Protease inhibitors: plasma-derived C1-INH concentrates, for example CETOR® (Sanquin), BERINERT-P® (CSL Behring, Lev Pharma), HAEGARDA® (CSL Bering), CINRYZE®; recombinant human C1-inhibitors, for example RHUCIN®; ritonavir (NORVIR®, Abbvie, Inc.);
- Soluble complement regulators: Soluble complement receptor 1 (TP10) (Avant Immunotherapeutics); sCR1-sLe$^X$/TP-20 (Avant Immunotherapeutics); MLN-2222/CAB-2 (Millenium Pharmaceuticals); Mirococept (Inflazyme Pharmaceuticals);
- Therapeutic antibodies: Eculizumab/SOLIRIS® (Alexion Pharmaceuticals); Pexelizumab (Alexion Pharmaceuticals); Ravulizumab/ULTOMIRIS® (Alexion Pharmaceuticals); BCD-148 (Biocad); ABP-959 (Amgen); SB-12 (Samsung Bioepsis); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-CD38 (Genmab A/S); Anti-properdin compounds from WO 2018/140956 (Alexion Pharmaceuticals);
- Complement component inhibitors: Compstatin/POT-4 (Potentia Pharmaceuticals); ARC1905 (Archemix); 4(1MEW)APL-1, APL-2 (Apellis); CP40/AMY-101, PEG-Cp40 (Amyndas); eculizumab/SOLIRIS® (Alexion Pharmaceuticals); Pexelizumab (Alexion Pharmaceuticals); ravulizumab/ULTOMIRIS® (Alexion Pharmaceuticals);
- Multiple kinase inhibitors: Sorafenib Tosylate (NEXAVAR®); Imatinib Mesylate (GLEEVEC®); Sunitinib Malate (SUTENT®); Ponatinib (ICLUSIG®); Axitinib (INLYTA®); Nintedanib (OFEV®); Pazopanib HCl (VOTRIENT®); Dovitinib (TKI-258, Oncology Ventures); gilteritinib (XOSPATA®); Linifanib (ABT-869); Crenolanib (CP-868596); Masitinib (AB1010); Tivozanib (FOTIVDA®); Motesanib Diphosphate (AMG-706); Amuvatinib (MP-470); TSU-68 (SU6668, Orantinib); CP-673451; Ki8751; Telatinib (BAY 57-9352); PP121; KRN 633; MK-2461; Tyrphostin (AG 1296); Sennoside B; AZD2932; and Trapidil;
- Anti-factor H or anti-factor B agents: Anti-FB siRNA (Alnylam); FCFD4514S (Genentech/Roche) SOMAmers for CFB and CFD (SomaLogic); TA106 (Alexion Pharmaceuticals); 5C6, NM8074 (Novelmed) and AMY-301 (Amyndas);
- Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH; Anti-CR3, anti-MASP2, anti-MASP3, anti C1s, and anti-C1n molecules: CINRYZE® (Takeda); TNT003 (Bioverativ/Sanofi); BIVV009 (fka TNT009; Bioverativ/Sanofi); BIVV020 (Bioverativ/Sanofi); OMS721 (Omeros); and OMS906 (Omeros);
- Factor B and Factor Bb inhibitors: IONIS-FB-LRx (Ionis Pharmaceuticals); for example, as described in US Patent Publication 20190071492 to Allergan, International Publication WO2017176651 to True North Therapeutics (now Sanofi), U.S. Pat. No. 9,243,070 (Novelmed); NM8074 (Novelmed); and as further described below;
- Plasma kallikrein inhibitors: KALBITOR® and TAKHZYRO®;
- Bradykinin receptor antagonists: FIRAZYR®;
- Factor D inhibitors, as further described below.
- Receptor agonists: PMX-53 (Peptech Ltd.); JPE-137 (Jerini); JSM-7717 (Jerini);
- Others: Recombinant human MBL (rhMBL; Enzon Pharmaceuticals); Imides and glutarimide derivatives such as thalidomide, lenalidomide, pomalidomide; Additional non-limiting examples that can be used in combination or alternation with an active compound or its salt or composition as described herein include the following.

Non-limiting examples for combination therapy

| Name | Target | Company | Class of Molecule |
|---|---|---|---|
| LFG316 | C5 | Novartis/Morphosys | Monoclonal antibody |
| SB12 | C5 | Samsung Bioepsis | Monoclonal antibody |

-continued

| Non-limiting examples for combination therapy | | | |
|---|---|---|---|
| Name | Target | Company | Class of Molecule |
| IONIS-FB-LRx | CFB | Ionis Pharmaceuticals | Antisense Inhibitor |
| 4(1MEW)APL-1, APL-2 | C3/C3b | Apellis | Compstatin Family |
| 4(1MeW)POT-4 | C3/C3b | Potentia | Compstatin Family |
| ALN-CC5/cemdisiran | C5 | Alnylam | SiRNA |
| Anti-FB siRNA | CFB | Alnylam | SiRNA |
| ARC1005 | C5 | Novo Nordisk | Aptamers |
| ATA | C5 | N.A. | Chemical |
| BIVV009 | C1s | Bioverativ/Sanofi | Monoclonal antibody |
| BERINERT ® | C1n/C1s | CSL Bering | Human purified protein |
| CCX168 (avocopan) | C5 | ChemoCentryx | Ligand |
| Coversin (nomacopan) | C5 | Akari Therapeutics | recombinant small protein |
| CP40/AMY-101, PEG-Cp40 | C3/C3b | Amyndas | Compstatin Family |
| CRIg/CFH | CAP C3 convertase | NA | CFH-based protein |
| CINRYZE ® | C1n/C1s | Takeda | Human purified protein |
| FCFD4514S | CFD | Genentech/Roche | Monoclonal antibody |
| FIRAZYR ® | Bradykinin | Takeda Pharmaceuticals | peptidomimetic |
| H17 | C3 (C3b/iC3b) | EluSys Therapeutics | Monoclonal antibody |
| IFX-1 (CaCP29) | C5a | InflaRx | Monoclonal antibody |
| KALBITOR ® | kallikrein | Shire Pharmaceuticals | polypeptide |
| Mini-CFH | CAP C3 convertase | Amyndas | CFH-based protein |
| Mirococept (APT070) | CAP and CCP C3 | NA | CR1-based protein |
| Mubodine | C5 | Adienne | Monoclonal antibody |
| RA101348 (zilucoplan) | C5 | Ra Pharma | Small molecule |
| RUCONEST ® | C1n/C1s | Pharming | Recombinant human protein |
| sCR1 (CDX-1135) | CAP and CP C3 | Celldex | CR1-based protein |
| SOBI002 | C5 | Swedish Orphan Biovitrum | Affibody |
| SOMAmers | C5 | SomaLogic | Aptamers |
| SOMAmers | CFB and CFD | SomaLogic | Aptamers |
| TAKHZYRO ® | kallakrein | Shire Pharmaceuticals | Monoclonal antibody |
| TA106 | CFB | Alexion Pharmaceuticals | Monoclonal antibody |
| TNT003 | C1s | Bioverativ/Sanofi | Monoclonal antibody |
| TT30 (CR2/CFH) | CAP C3 convertase | Alexion Pharmaceuticals | CFH-based protein |
| TT32 (CR2/CR1) | CAP and CCP C3 | Alexion Pharmaceuticals | CR1-based protein |
| Nafamostat (FUT-175, Futhan) | C1s, CFD, other proteases | Torri Pharmaceuticals | Small molecule |
| OMS721 | MASP-2 | Omeros | Monoclonal antibody |
| OMS906 | MASP-3 | Omeros | Monoclonal antibody |
| NM8074 | CFB | Novelmed | Monoclonal antibody |
| Bikaciomab, NM9308 | CFB | Novelmed | Monoclonal antibody |
| NM9401 | Properdin | Novelmed | Monoclonal antibody |
| CVF, HC-1496 | C3 | InCode | Recombinant peptide |
| ALXN1102/ALXN1103 (TT30) | C3-conv, C3b | Alexion Pharmaceuticals | Regulator |
| rFH | C3-conv, C3b | Optherion | Regulator |
| 5C6, AMY-301 | CFH | Amyndas | Regulator |
| Erdigna | C5 | Adienne Pharma | Antibody |
| ARC1905 | C5 | Ophthotech | Monoclonal Antibody |
| MEDI7814 | C5/C5a | MedImmune | Monoclonal Antibody |
| NOX-D19 | C5a | Noxxon | Aptamer (Spiegelmer) |
| PMX53, PMX205 | C5aR | Cephalon, Teva | Peptidomimetic |
| CCX168 | C5aR | ChemoCentryx | Small molecule |
| ADC-1004 | C5aR | Alligator Bioscience | Small molecule |
| Anti-C5aR-151, NN8209; Anti-C5aR-215, NN8210 | C5aR | Novo Nordisk | Monoclonal Antibody |
| Imprime PGG | CR3 | Biothera | Soluble beta-glucan |
| ANX005; ANX007 | C1q | Annexon | Monoclonal Antibody |
| LNP023 | fB | Novartis | Small molecule |
| Lampalizumab | fD | Roche | Monoclonal Antibody |
| avacincaptad pegol | C5 | Ophthotech | Aptamer |
| Regenemab | C6 | Regenesance | Monoclonal Antibody |
| BIVV020 | C1s | Bioverativ | Monoclonal Antibody |
| PRO-02 | C2 | Broteio/Argen-x | Monoclonal Antibody |
| 5C6, compsorbin | fH | Amyndas | Peptide |
| SOBI005 | C5 | Sobi | Protein |

-continued

| Non-limiting examples for combination therapy | | | |
|---|---|---|---|
| Name | Target | Company | Class of Molecule |
| ISU305 | C5 | ISU ABXIS | Monoclonal Antibody |
| IFX-2, IFX-3 | C5a | InflaRx | Monoclonal Antibody |
| ALS-205 | C5aR1 | Alsonex | Peptide |
| DF2593A | C5aR1 | Dompé | Small Molecule |
| IPH5401 | C5aR1 | Innate Pharma | Monoclonal Antibody |
| C6-LNA | C6 | Regenesance | Oligonucleotide |
| Pozelimab (REGN3918) | C5 | Regeneron | Monoclonal Antibody |
| SKY59 (crovalimab) | C5 | Roche/Chugai | Monoclonal Antibody |
| Aptamers to Factor D | fD | Vitrisa Therapeutics | Aptamer |
| CLG561 | Properdin | Novartis | Monoclonal Antibody |
| Tesidolumab; LFG316 | C5 | Novartis and MorphoSys | Monoclonal Antibody |

In some embodiments, the agent for combination therapy is a biosimilar of any agent named above.

In some embodiments, an active compound or its salt or composition as described herein may be provided together with a compound that inhibits an enzyme that metabolizes an administered protease inhibitor. In some embodiments, a compound or salt may be provided together with ritonavir.

In some embodiments, an active compound or its salt or composition as described herein may be provided in combination with a terminal complement inhibitor, for example a complement C5 inhibitor or C5 convertase inhibitor. In another embodiment, an active compound or its salt or composition as described herein may be provided in combination with eculizumab, a monoclonal antibody directed to the complement factor C5 and manufactured and marketed by Alexion Pharmaceuticals under the tradename SOLIRIS®. Eculizumab has been approved by the U.S. FDA for the treatment of PNH and aHUS. In another embodiment, an active compound or its salt or composition as described herein may be provided in combination with revulizumab, a monoclonal antibody directed to the complement factor C5 and manufactured and marketed by Alexion Pharmaceuticals under the tradename ULTOMIRIS®. Revulizumab has been approved by the U.S. FDA for the treatment of PNH. Additional C5 and C5 convertase inhibitors include, but are not limited to, cemdisiran (Alnylam); prozelimab (Regeneron); BCD-148 (Biocad); ABP-959 (Amgen); SB-12 (Samsung Bioepis Co., Ltd.); LFG316 (Novartis); coversin (nomacopan; Akari)); zilucoplan (Ra Pharma); crovalimab (SKY59; Roche/Chugai); and mubodina (Adienne Pharma).

In some embodiments, an active compound or its salt or composition as described herein is administered in combination with an anti-inflammatory drug, antimicrobial agent, anti-angiogenesis agent, immunosuppressant, antibody, steroid, ocular antihypertensive drug or combinations thereof. Examples of such agents include amikacin, anecortane acetate, anthracenedione, anthracycline, an azole, amphotericin B, bevacizumab, camptothecin, cefuroxime, chloramphenicol, chlorhexidine, chlorhexidine digluconate, clotrimazole, a clotrimazole cephalosporin, corticosteroids, dexamethasone, desamethazone, econazole, eftazidime, epipodophyllotoxin, fluconazole, flucytosine, fluoropyrimidines, fluoroquinolones, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogs, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluoromethalone, rimexolone, anecortave, cyclosporine, methotrexate, tacrolimus, anti-PDGFR molecule, and combinations thereof.

In some embodiments of the present disclosure, an active compound or its salt or composition as described herein can be administered in combination or alternation with at least one immunosuppressive agent. The immunosuppressive agent as non-limiting examples, may be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analog thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, ELIDEl®), CTLA4lg (Abatacept), belatacept, LFA3lg, etanercept (sold as ENBREL® by Immunex), adalimumab (HUMIRA®), infliximab (REMICADE®), an anti-LFA-1 antibody, natalizumab (ANTEGREN®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, tocilizumab (Actemra), siltuximab (Sylvant), secukibumab (Cosentyx), ustekinumab (Stelara), risankizumab, sifalimumab, aspirin and ibuprofen.

Examples of anti-inflammatory agents include methotrexate, dexamethasone, dexamethasone alcohol, dexamethasone sodium phosphate, fluoromethalone acetate, fluoromethalone alcohol, lotoprendol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flurbiprofen, naproxen, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucocorticoids, diclofenac, and any combination thereof. In some embodiments, an active compound or its salt or composition as described herein is combined with one or more non-steroidal anti-inflammatory drugs (NSAIDs) selected from naproxen sodium (Anaprox), celecoxib (Celebrex), sulindac (Clinoril), oxaprozin (Daypro), salsalate (Disalcid), diflunisal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

In some embodiments, an active compound or its salt or composition as described herein is administered in combination or alteration with an omega-3 fatty acid or a peroxisome proliferator-activated receptor (PPARs) agonist. Omega-3 fatty acids are known to reduce serum triglycerides by inhibiting DGAT and by stimulating peroxisomal and mitochondrial beta oxidation. Two omega-3 fatty acids, eicosapentaenoic acid (EPA) and docosahexaenoic acid (DHA), have been found to have high affinity for both PPAR-alpha and PPAR-gamma. Marine oils, e.g., fish oils, are a good source of EPA and DHA, which have been found to regulate lipid metabolism. Omega-3 fatty acids have been found to have beneficial effects on the risk factors for cardiovascular diseases, especially mild hypertension, hypertriglyceridemia and on the coagulation factor VII phospholipid complex activity. Omega-3 fatty acids lower serum triglycerides, increase serum HDL-cholesterol, lower systolic and diastolic blood pressure and the pulse rate, and lower the activity of the blood coagulation factor VII-phospholipid complex. Further, omega-3 fatty acids seem to be well tolerated, without giving rise to any severe side effects. One such form of omega-3 fatty acid is a concentrate of omega-3, long chain, polyunsaturated fatty acids from fish oil containing DHA and EPA and is sold under the trademark OMACOR®. Such a form of omega-3 fatty acid is described, for example, in U.S. Pat. Nos. 5,502,077, 5,656,667 and 5,698,594, the disclosures of which are incorporated herein by reference.

Peroxisome proliferator-activated receptors (PPARs) are members of the nuclear hormone receptor superfamily ligand-activated transcription factors that are related to retinoid, steroid and thyroid hormone receptors. There are three distinct PPAR subtypes that are the products of different genes and are commonly designated PPAR-alpha, PPAR-beta/delta (or merely, delta) and PPAR-gamma. General classes of pharmacological agents that stimulate peroxisomal activity are known as PPAR agonists, e.g., PPAR-alpha agonists, PPAR-gamma agonists and PPAR-delta agonists. Some pharmacological agents are combinations of PPAR agonists, such as alpha/gamma agonists, etc., and some other pharmacological agents have dual agonist/antagonist activity. Fibrates such as fenofibrate, bezafibrate, clofibrate and gemfibrozil, are PPAR-alpha agonists and are used in patients to decrease lipoproteins rich in triglycerides, to increase HDL and to decrease atherogenic-dense LDL. Fibrates are typically orally administered to such patients. Fenofibrate or 2-[4-(4-chlorobenzoyl)phenoxy]-2-methyl-propanoic acid, 1-methylethyl ester, has been known for many years as a medicinally active principle because of its efficacy in lowering blood triglyceride and cholesterol levels.

In some embodiments, the present disclosure provides a method of treating or preventing age-related macular degeneration (AMD) by administering to a subject in need thereof an effective amount of an active compound or its salt or composition as described herein in combination with an anti-VEGF agent. Non-limiting examples of anti-VEGF agents include, but are not limited to, aflibercept (EYLEA®; Regeneron Pharmaceuticals); ranibizumab (LUCENTIS®: Genentech and Novartis); pegaptanib (MACUGEN®; OSI Pharmaceuticals and Pfizer); bevacizumab (Avastin; Genentech/Roche); lapatinib (TYKERB®); sunitinib (SUTENT®); axitinib (INLYTA®); pazopanib; sorafenib (NEXAVAR®); ponatinib (INCLUSIG®); regorafenib (STIVARGA®); Cabozantinib (Abometyx; COMETRIQ®); vendetanib (CAPRELSA®); ramucirumab (CYRAMZA®); lenvatinib (LENVIMA®); ziv-aflibercept (ZALTRAP®); cediranib (RECENTIN®); anecortane acetate, squalamine lactate, and corticosteroids, including, but not limited to, triamcinolone acetonide.

In some embodiments, the disclosure provides a method of treating or preventing age-related macular degeneration (AMD) by administering to a subject in need thereof an effective amount of an active compound or its salt or composition as described herein in combination with a complement C5 inhibitor, for example, a complement C5 inhibitor described herein and in the table above titled Non-limiting examples of potential therapeutics for combination therapy, including, but not limited to, eculizumab (Alexion Pharmaceuticals); ravulizumab (Alexion Pharmaceuticals); LFG316 (Novartis/Morphosys); cemdisiran, cemdisiran/ALN-CC5 (Alnylam); ARC1005 (Novo Nordisk); Coversin (Akari Therapeutics); Mubodine (Adienne Pharma); RA101348 (Ra Pharma); SOBI002 (Swedish Orphan Biovitrum); SOMAmers (SomaLogic); Erdigna (Adienne Pharma); ARC1905 (Ophthotech); MEDI7814 (MedImmune); NOX-D19 (Noxxon); IFX-1, CaCP29 (InflaRx); PMX53, PMX205 (Cephalon, Teva); CCX168 (ChemoCentryx); ADC-1004 (Alligator Bioscience); and Anti-C5aR-151, NN8209; Anti-C5aR-215, NN8210 (Novo Nordisk); prozelimab (Regeneron); BCD-148 (Biocad); ABP-959 (Amgen); SB-12 (Samsung Bioepis Co., Ltd.); zilucoplan (Ra Pharma); and crovalimab (SKY59; Roche/Chugal).

In some embodiments, the present disclosure provides a method of treating or preventing age-related macular degeneration (AMD) by administering to a subject in need thereof an effective amount of an active compound or its salt or composition as described herein in combination with anti-properidin agent, for example, an anti-properidin agent as described above, including but not limited to NM9401 (Novelmed).

In some embodiments, the present disclosure provides a method of treating or preventing age-related macular degeneration (AMD) by administering to a subject in need thereof an effective amount of an active compound or its salt or composition as described herein in combination with a complement C3 inhibitor for example, a complement C3 inhibitor described above, including, but not limited to, a compstatin or compstatin analog, for example Compstatin/POT-4 (Potentia Pharmaceuticals); ARC1905 (Archemix); 4(1MEW)APL-1, APL-2 (Apellis); CP40/AMY-101, PEG-Cp40 (Amyndas) Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals);

rFH (Optherion); H17 C3 (C3b/iC3b) (EluSys Therapeutics); Mini-CFH (Amyndas) Mirococept (APT070); sCR1 (CDX-1135) (Celldex); and CRIg/CFH.

In some embodiments, the present disclosure provides a method of treating or preventing age-related macular degeneration (AMD) by administering to a subject in need thereof an effective amount of an active compound or its salt or composition as described herein in combination with an anti-factor H or anti-factor B agent selected from Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas).

In some embodiments, the present disclosure provides a method of treating or preventing age-related macular degeneration (AMD) by administering to a subject in need thereof an effective amount of an active compound or its salt or composition as described herein in combination with an anti-MASP2, anti-C1s or anti-CR3 molecules, for example, but not limited to: Cynryze (ViroPharma/Baxter); TNT003 (True North); OMS721 (Omeros); OMS906 (Omeros); and Imprime PGG (Biothera).

In some embodiments, the disclosure provides a method of treating or preventing age-related macular degeneration (AMD) by administering to a subject in need thereof an effective amount of an active compound or its salt or composition as described herein in combination with a multiple kinase inhibitor, for example as described herein including but not limited to Sorafenib Tosylate (NEXAVAR®); Imatinib Mesylate (GLEEVEC®); Sunitinib Malate (SUTENT®); Ponatinib (ICLUSIG®); Axitinib (INLYTA®); Nintedanib (OFEV®); Pazopanib HCl (VOTRIENT®); Dovitinib (TKI-258, Oncology Ventures); gilteritnib (XOSPATA®); Linifanib (ABT-869); Crenolanib (CP-868596); Masitinib (AB1010); Tivozanib (FOTIVDA®); Motesanib Diphosphate (AMG-706); Amuvatinib (MP-470); TSU-68 (SU6668, Orantinib); CP-673451; Ki8751; Telatinib (BAY 57-9352); PP121; KRN 633; MK-2461; Tyrphostin (AG 1296); Sennoside B; AZD2932; and Trapidil.

In some embodiments, the disclosure provides a method of treating or preventing cold agglutinin disease (CAD) by administering to a subject in need thereof an effective amount of an active compound or its salt or composition as described herein in combination with a complement C5 inhibitor, for example, a complement C5 inhibitor described herein and in the table above titled Non-limiting examples of potential therapeutics for combination therapy, including, but not limited to, eculizumab (Alexion Pharmaceuticals); ravulizumab (Alexion Pharmaceuticals); LFG316 (Novartis/Morphosys); cemdisiran, cemdisiran/ALN-CC5 (Alnylam); ARC1005 (Novo Nordisk); Coversin (Akari Therapeutics); Mubodine (Adienne Pharma); RA101348 (Ra Pharma); SOBI002 (Swedish Orphan Biovitrum); SOMAmers (SomaLogic); Erdigna (Adienne Pharma); ARC1905 (Ophthotech); MEDI7814 (MedImmune); NOX-D19 (Noxxon); IFX-1, CaCP29 (InflaRx); PMX53, PMX205 (Cephalon, Teva); CCX168 (ChemoCentryx); ADC-1004 (Alligator Bioscience); and Anti-C5aR-151, NN8209; Anti-C5aR-215, NN8210 (Novo Nordisk); prozelimab (Regeneron); BCD-148 (Biocad); ABP-959 (Amgen); SB-12 (Samsung Bioepis Co., Ltd.); zilucoplan (Ra Pharma); and crovalimab (SKY59; Roche/Chugal).

In some embodiments, the disclosure provides a method of treating or preventing cold agglutinin disease (CAD) by administering to a subject in need thereof an effective amount of an active compound or its salt or composition as described herein in combination with anti-properdin agent, for example, an anti-properdin agent as described above, including but not limited to NM9401 (Novelmed).

In some embodiments, the disclosure provides a method of treating or preventing cold agglutinin disease (CAD) by administering to a subject in need thereof an effective amount of an active compound or its salt or composition as described herein in combination with a complement C3 inhibitor for example, a complement C3 inhibitor described above, including, but not limited to, a compstatin or compstatin analog, for example Compstatin/POT-4 (Potentia Pharmaceuticals); ARC1905 (Archemix); 4(1MEW)APL-1, APL-2 (Apellis); CP40/AMY-101, PEG-Cp40 (Amyndas) Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); and CRIg/CFH.

In some embodiments, the disclosure provides a method of treating or preventing cold agglutinin disease (CAD) by administering to a subject in need thereof an effective amount of an active compound or its salt or composition as described herein in combination with an anti-factor H or anti-factor B agent selected from IONIS-FB-LRx (Ionis Pharmaceuticals); Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas).

In some embodiments, the disclosure provides a method of treating or preventing cold agglutinin disease (CAD) by administering to a subject in need thereof an effective amount of an active compound or its salt or composition as described herein in combination with an anti-MASP2, anti C1s, or anti-C1n molecule, for example but not limited to Cinryze® (Takeda); Berinert® (Bering CSL), Ruconest® (Pharming), Haegarda® (Bering CSL); TNT003 (Bioverativ/Sanofi); BIVV009 (Bioverativ/Sanofi); BIVV020 (Bioverativ/Sanofi); OMS721 (Omeros); OMS906 (Omeros); and Imprime PGG (Biothera)

In some embodiments, the disclosure provides a method of treating or preventing cold agglutinin disease (CAD) by administering to a subject in need thereof an effective amount of an active compound or its salt or composition as described herein in combination with a multiple kinase inhibitor, for example as described herein including but not limited to Sorafenib Tosylate (NEXAVAR®); Imatinib Mesylate (GLEEVEC®); Sunitinib Malate (SUTENT®); Ponatinib (ICLUSIG®); Axitinib (INLYTA®); Nintedanib (OFEV®); Pazopanib HCl (VOTRIENT®); Dovitinib (TKI-258, Oncology Ventures); gilteritinib (XOSPATA®); Linifanib (ABT-869); Crenolanib (CP-868596); Masitinib (AB1010); Tivozanib (FOTIVDA®); Motesanib Diphosphate (AMG-706); Amuvatinib (MP-470); TSU-68 (SU6668, Orantinib); CP-673451; Ki8751; Telatinib (BAY 57-9352); PP121; KRN 633; MK-2461; Tyrphostin (AG 1296); Sennoside B; AZD2932; and Trapidil.

In some embodiments, the present disclosure provides a method of treating or preventing paroxysmal nocturnal hemoglobinuria (PNH) by administering to a subject in need thereof an effective amount of an active compound or its salt or composition as described herein with an additional inhibitor of the complement system or another active compound with a different biological mechanism of action. In another embodiment, the present disclosure provides a method of treating or preventing paroxysmal nocturnal hemoglobinuria (PNH) by administering to a subject in need thereof an effective amount of an active compound or its salt or composition as described herein in combination or alternation with eculizumab or ravulizumab.

In another embodiment, the present disclosure provides a method of treating or preventing paroxysmal nocturnal hemoglobinuria (PNH) by administering to a subject in need thereof an effective amount of an active compound or its salt or composition as described herein in combination or alternation with CP40.

In some embodiments, the additional agent is PEGylated-CP40. CP40 is a peptide inhibitor that shows a strong binding affinity for C3b and inhibits hemolysis of paroxysmal nocturnal hemoglobinuria (PNH) erythrocytes. In some embodiments, the additional agent is a complement component inhibitor, for example but not limited to Compstatin/POT-4 (Potentia Pharmaceuticals); ARC1905 (Archemix); 4(1MEW)APL-1, APL-2 (Apellis); CP40/AMY-101, PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cinryze (Takeda); TNT003 (True North); OMS721 (Omeros); OMS906 (Omeros); and Imprime PGG (Biothera)

In some embodiments, the present disclosure provides a method of treating or preventing rheumatoid arthritis by administering to a subject in need thereof an effective amount of a composition comprising an active compound or its salt or composition as described herein in combination or alternation with an additional inhibitor of the complement system, or an active agent that functions through a different mechanism of action.

In another embodiment, the present disclosure provides a method of treating or preventing rheumatoid arthritis by administering to a subject in need thereof an effective amount of an active compound or its salt or composition as described herein in combination or alternation with methotrexate.

In certain embodiments, an active compound or its salt or composition as described herein is administered in combination or alternation with at least one additional therapeutic agent selected from: salicylates including aspirin (ANACIN®, ASCRIPTIN®, BAYER ASPIRIN®, ECOTRIN®) and salsalate (MONO-GESIC®, SALGESIC®); nonsteroidal anti-inflammatory drugs (NSAIDs); nonselective inhibitors of the cyclo-oxygenase (COX-1 and COX-2) enzymes, including diclofenac (CATAFLAM®, VOLTAREN®), ibuprofen (ADVIL®, MOTRIN®), ketoprofen (ORUDIS®), naproxen (ALEVE®, NAPROSYN®), piroxicam (Feldene), etodolac (LODINE®), indomethacin, oxaprozin (DAYPRO®), nabumetone (RELAFEN®), and meloxicam (MOBIC®); selective cyclo-oxygenase-2 (COX-2) inhibitors including Celecoxib (CELEBREX®); disease-modifying antirheumatic drugs (DMARDs), including azathioprine (IMURAN®), cyclosporine (Sandimmune, NEORAL®), gold salts (RIDAURA®, SOLGANAL®, AUROLATE®, MYOCHRYSINE®), hydroxychloroquine (PLAQUENIL®), leflunomide (ARAVA®), methotrexate (RHEUMATREX®), penicillamine (CUPRIMINE®), and sulfasalazine (AZULFIDINE®); biologic drugs including abatacept (ORENCIA®), etanercept (ENBREL®), infliximab (REMICADE®), adalimumab (HUMIRA®), and anakinra (KINERET®); corticosteroids including betamethasone (CELESTONE® SOLUSPAN®), cortisone (CORTONE®), dexamethasone (DECADRON®), methylprednisolone (SOLUMEDROL®, DEPOMEDROL®), prednisolone (DELTA-CORTEF®), prednisone (DELTASONE®, ORASONE®), and triamcinolone (Aristocort); gold salts, including Auranofin (RIDAURA®); Aurothioglucose (SOLGANAL®); Aurolate; Myochrysine; or any combination thereof.

In some embodiments, the present disclosure provides a method of treating or preventing multiple sclerosis by administering to a subject in need thereof an effective amount of an active compound or its salt or composition as described herein in combination or alternation with an additional inhibitor of the complement system, or an active agent that functions through a different mechanism of action.

In another embodiment, the present disclosure provides a method of treating or preventing multiple sclerosis by administering to a subject in need thereof an effective amount of an active compound or its salt or composition as described herein in combination or alternation with a corticosteroid.

Examples of corticosteroids include, but are not limited to, prednisone, dexamethasone, solumedrol, and methylprednisolone. In some embodiments, an active compound or its salt or composition as described herein is combined with at least one anti-multiple sclerosis drug, for example, selected from: AUBAGIO® (teriflunomide), AVONEX® (interferon beta-1a), BETASERON® (interferon beta-1b), COPAXONE® (glatiramer acetate), EXTAVIA® (interferon beta-1b), GILENYA® (fingolimod), LEMTRADA® (alemtuzumab), Novantrone (mitoxantrone), PLEGRIDY® (peginterferon beta-1a), REBIF® (interferon beta-1a), TECFIDERA® (dimethyl fumarate), TYSABRI® (natalizumab), SOLU-MEDROL® (methylprednisolone), High-dose oral DELTASONE® (prednisone), H.P. ACTHAR GEL® (ACTH), or a combination thereof.

In some embodiments, an active compound or its salt or composition as described herein is useful in a combination with another pharmaceutical agent to ameliorate or reduce a side effect of the agent. For example, in some embodiments, an active compound or its salt or composition as described herein may be used in combination with adoptive cell transfer therapies to reduce an associated inflammatory response associated with such therapies, for example, a cytokine mediated response such as cytokine release syndrome. In some embodiments, the adoptive cell transfer therapy includes the use of a chimeric antigen receptor T-Cell (CAR T). In some embodiments, the adoptive cell transfer therapy includes the use of a chimeric antigen receptor T-Cell (CAR T) or a dendritic cell to treat a hematologic or solid tumor, for example, a B-cell related hematologic cancer. In some embodiments, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19.

In an additional alternative embodiment, an active compound or its salt or composition as described herein may be provided in combination with eculizumab or ravulizumab for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In some embodiments, an active compound or its salt or composition as described herein may be provided in combination with compstatin or a compstatin derivative for the treatment of PNH, aHUSs, STEC-HUS, ANCA-vasculitis, AMD, CAD, C3 glomerulopathy, for example DDD or C3GN, chronic hemolysis, neuromyelitis optica, neuromyelitis optica spectrum disorder in adults who are anti-aquaporin-4 (AQP4) antibody positive, myasthenia gravis, generalized myasthenia gravis, or transplantation rejection. In some embodiments, the additional agent is a complement component inhibitor, for example but not limited to Compstatin/POT-4 (Potentia Pharmaceuticals); ARC1905 (Archemix); 4(1MEW)APL-1, APL-2 (Apellis); CP40/AMY-101, PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cinryze (Takeda); TNT003 (True North); OMS721 (Omeros); OMS906 (Omeros); and Imprime PGG (Biothera).

In some embodiments, an active compound or its salt or composition as described herein may be provided in combination with rituxan for the treatment of a complement mediated disorder. In some embodiments, the complement mediated disorder is, for example, rheumatoid arthritis, Granulomatosis with Polyangiitis (GPA) (Wegener's Granulomatosis), and Microscopic Polyangiitis (MPA). In some embodiments, the disorder is Lupus.

In some embodiments, an active compound or its salt or composition as described herein may be provided in combination with cyclophosphamide for the treatment of a complement mediated disorder. In some embodiments, the disorder is an autoimmune disease. In some embodiments, the complement mediated disorder is, for example, rheumatoid arthritis, Granulomatosis with Polyangiitis (GPA) (Wegener's Granulomatosis), and Microscopic Polyangiitis (MPA). In some embodiments, the disorder is Lupus.

In some embodiments, an active compound or its salt or composition as described herein is dosed in combination with a conventional DLE treatment for the treatment of lupus to a subject in need thereof.

Examples of conventional DLE treatments include topical corticosteroid ointments or creams, such as triamcinolone acetonide, fluocinolone, flurandrenolide, betamethasone valerate, or betamethasone dipropionate. Resistant plaques can be injected with an intradermal corticosteroid. Other potential DLE treatments include calcineurin inhibitors such as pimecrolimus cream or tacrolimus ointment. Particularly resistant cases can be treated with systemic antimalarial drugs, such as hydroxychloroquine (PLAQUENIL).

In some embodiments, an active compound or its salt or composition as described herein may be provided in combination with methotrexate for the treatment of Lupus.

In some embodiments, an active compound or its salt or composition as described herein may be provided in combination with azathioprine for the treatment of Lupus.

In some embodiments, an active compound or its salt or composition as described herein may be provided in combination with a non-steroidal anti-inflammatory drug for the treatment of Lupus.

In some embodiments, an active compound or its salt or composition as described herein may be provided in combination with a corticosteroid for the treatment of Lupus.

In some embodiments, an active compound or its salt or composition as described herein may be provided in combination with a belimumab (Benlysta) for the treatment of Lupus.

In some embodiments, an active compound or its salt or composition as described herein may be provided in combination with hydroxychloroquine (Plaquenil) for the treatment of Lupus.

In some embodiments, an active compound or its salt or composition as described herein may be provided in combination with sifalimumab for the treatment of Lupus.

In some embodiments, an active compound or its salt or composition as described herein may be provided in combination with OMS721 (Omeros) for the treatment of a complement mediated disorder. In some embodiments, an active compound or its salt or composition as described herein may be provided in combination with OMS906 (Omeros) for the treatment of a complement mediated disorder. In some embodiments, the complement mediated disorder is, for example, thrombotic thrombocytopenic purpura (TTP) or aHUS.

In some embodiments, an active compound or its salt or composition as described herein may be provided in combination with an anti-inflammatory agent, immunosuppressive agent, or anti-cytokine agent for the treatment or prevention of cytokine or inflammatory reactions in response to the administration of pharmaceuticals or biotherapeutics (e.g. adoptive T-cell therapy (ACT) such as CAR T-cell therapy, or monoclonal antibody therapy).

In some embodiments, an active compound or its salt or composition as described herein may be provided in combination with a corticosteroid, for example prednisone, dexamethasone, solumedrol, and methylprednisolone, and/or anti-cytokine compounds targeting, e.g., IL-4, IL-10, IL-11, IL-13 and TGFβ.

In some embodiments, an active compound or its salt or composition as described herein may be provided in combination with an anti-cytokine inhibitor including, but are not limited to, adalimumab, infliximab, etanercept, protopic, efalizumab, alefacept, anakinra, siltuximab, secukinumab, ustekinumab, golimumab, and tocilizumab, or a combination thereof.

Additional anti-inflammatory agents that can be used in combination with an active compound or its salt or composition as described herein include, but are not limited to, non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline); DAB 486-IL-2 and/or DAB 389-IL-2 (IL-2 fusion proteins; Seragen); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein); R973401 (phosphodiesterase Type IV inhibitor); MK-966 (COX-2 Inhibitor); Iloprost, leflunomide (anti-inflammatory and cytokine inhibition); tranexamic acid (inhibitor of plasminogen activation); T-614 (cytokine inhibitor); prostaglandin E1; Tenidap (non-steroidal anti-inflammatory drug); Naproxen (non-steroidal anti-inflammatory drug); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine; Azathioprine; ICE inhibitor (inhibitor of the enzyme interleukin-1β converting enzyme); zap-70 and/or lck inhibitor (inhibitor of the tyrosine kinase zap-70 or lck); TNF-convertase inhibitors; anti-IL-12 antibodies; anti-IL-18 antibodies; interleukin-11; interleukin-13; interleukin-17 inhibitors; gold; penicillamine; chloroquine; chlorambucil; hydroxychloroquine; cyclosporine; cyclophosphamide; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine).

In a specific embodiment, an active compound or its salt or composition as described herein may be provided in combination with a corticosteroid for the treatment or prevention of cytokine or inflammatory reactions in response to the administration of pharmaceuticals or biotherapeutics.

In another embodiment, an active compound or its salt or composition as described herein may be provided in combination with etanercept for the treatment or prevention of cytokine or inflammatory reactions in response to the administration of pharmaceuticals or biotherapeutics.

In another embodiment, an active compound or its salt or composition as described herein may be provided in combination with tocilizumab for the treatment or prevention of cytokine or inflammatory reactions in response to the administration of pharmaceuticals or biotherapeutics.

In another embodiment, an active compound or its salt or composition as described herein may be provided in combination with etanercept and tocilizumab for the treatment or prevention of cytokine or inflammatory reactions in response to the administration of pharmaceuticals or biotherapeutics.

In another embodiment, an active compound or its salt or composition as described herein may be provided in combination with infliximab for the treatment or prevention of cytokine or inflammatory reactions in response to the administration of pharmaceuticals or biotherapeutics.

In another embodiment, an active compound or its salt or composition as described herein may be provided in combination with golimumab for the treatment or prevention of cytokine or inflammatory reactions in response to the administration of pharmaceuticals or biotherapeutics.

In a specific embodiment, an active compound or its salt or composition as described herein may be provided in combination with methylprednisolone, azathioprine, mycophenolate, rituximab, methotrexate, an oral corticosteroid, mitoxantrone, tocilizumab, or a C5 inhibitor such as eculizumab or ravulizumab, or a combination thereof, for the treatment of NMO.

In a specific embodiment, an active compound or its salt or composition as described herein may be provided in combination with Carbidopa-levodopa, a Dopamine agonists including, but not limited to pramipexole (Mirapex), ropinirole (Requip) and rotigotine (Neupro, given as a patch). Apomorphine (Apokyn), an MAO B inhibitors, for example selegiline (Eldepryl, Zelapar), rasagiline (Azilect) and safinamide (Xadago), a Catechol O-methyltransferase (COMT) inhibitor, for example Entacapone (Comtan) and Tolcapone (Tasmar), an Anticholinergics, for example benztropine (Cogentin) or trihexyphenidyl, or Amantadine, or a combination thereof, for the treatment of Parkinson's Disease.

In a specific embodiment, an active compound or its salt or composition as described herein may be provided in combination with a cholinesterase inhibitor, Namenda, risperidone (Risperdal), olanzapine (Zyprexa), and quetiapine (Seroquel), vitamin E, sertraline (Zoloft), bupropion (Wellbutrin), citalopram (Celexa), paroxetine (Paxil), or venlafaxine (Effexor), or a combination thereof, for the treatment of Alzheimer's Disease.

In a specific embodiment, an active compound or its salt or composition as described herein may be provided in combination with Riluzole (Rilutek), Edaravone (Radicava), or a combination thereof, for the treatment of ALS.

In one aspect, an active compound or its salt or composition as described herein may be provided in combination with an immune modulator for the treatment of cancer, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

Immune checkpoint inhibitors for use in the methods described herein include, but are not limited to PD-1 inhibitors, PD-L1 inhibitors, PD-L2 inhibitors, CTLA-4 inhibitors, LAG-3 inhibitors, TIM-3 inhibitors, and V-domain Ig suppressor of T-cell activation (VISTA) inhibitors, or combinations thereof.

In some embodiments, the immune checkpoint inhibitor is a PD-1 inhibitor that blocks the interaction of PD-1 and PD-L1 by binding to the PD-1 receptor, and in turn inhibits immune suppression. In some embodiments, the immune checkpoint inhibitor is a PD-1 immune checkpoint inhibitor selected from nivolumab (Opdivo®), pembrolizumab (Keytruda®), pidilizumab, AMP-224 (AstraZeneca and MedImmune), PF-06801591 (Pfizer), MEDI0680 (AstraZeneca), PDR001 (Novartis), REGN2810 (Regeneron), MGA012 (MacroGenics), BGB-A317 (BeiGene) SHR-12-1 (Jiangsu Hengrui Medicine Company and Incyte Corporation), TSR-042 (Tesaro), and the PD-L1/VISTA inhibitor CA-170 (Curis Inc.).

In some embodiments, the immune checkpoint inhibitor is the PD-1 immune checkpoint inhibitor nivolumab (Opdivo®) administered in an effective amount for the treatment of Hodgkin lymphoma, melanoma, non-small cell lung cancer, hepatocellular carcinoma, or ovarian cancer. Nivolumab has been approved by the FDA for the use of metastatic melanoma, non-small cell lung cancer, and renal cell carcinoma.

In another aspect of this embodiment, the immune checkpoint inhibitor is the PD-1 immune checkpoint inhibitor pembrolizumab (Keytruda®) administered in an effective amount for the treatment of melanoma, non-small cell lung cancer, small cell lung cancer, head and neck cancer, or urothelial cancer.

In an additional aspect of this embodiment, the immune checkpoint inhibitor is the PD-1 immune checkpoint inhibitor pidilizumab (Medivation) administered in an effective amount for refractory diffuse large B-cell lymphoma (DLBCL) or metastatic melanoma.

In some embodiments, the immune checkpoint inhibitor is a PD-L1 inhibitor that blocks the interaction of PD-1 and PD-L1 by binding to the PD-L1 receptor, and in turn inhibits immune suppression. PD-L1 inhibitors include, but are not limited to, atezolizumab, durvalumab, KN035CA-170 (Curis Inc.), and LY3300054 (Eli Lilly). In some embodiments, the PD-L1 inhibitor is atezolizumab. In some embodiments, the PD-L1 inhibitor blocks the interaction between PD-L1 and CD80 to inhibit immune suppression.

In some embodiments, the immune checkpoint inhibitor is the PD-L1 immune checkpoint inhibitor atezolizumab (Tecentriq®) administered in an effective amount for the treatment of metastatic bladder cancer, metastatic melanoma, metastatic non-small cell lung cancer, or metastatic renal cell carcinoma.

In another aspect of this embodiment, the immune checkpoint inhibitor is durvalumab (AstraZeneca and MedImmune) administered in an effective amount for the treatment of non-small cell lung cancer or bladder cancer.

In yet another aspect of the embodiment, the immune checkpoint inhibitor is KN035 (Alphamab) administered in an effective amount for the treatment of PD-L1 positive solid tumors. An additional example of a PD-L1 immune checkpoint inhibitor is BMS-936559 (Bristol-Myers Squibb), although clinical trials with this inhibitor have been suspended as of 2015.

In one aspect, the immune checkpoint inhibitor is a CTLA-4 immune checkpoint inhibitor that binds to CTLA-4 and inhibits immune suppression. CTLA-4 inhibitors include, but are not limited to, ipilimumab, tremelimumab (AstraZeneca and MedImmune), AGEN1884 and AGEN2041 (Agenus).

In some embodiments, the CTLA-4 immune checkpoint inhibitor is ipilimumab (Yervoy®) administered in an effective amount for the treatment of metastatic melanoma, adjuvant melanoma, or non-small cell lung cancer.

In another embodiment, the immune checkpoint inhibitor is a LAG-3 immune checkpoint inhibitor. Examples of LAG-3 immune checkpoint inhibitors include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). In yet another aspect of this embodiment, the immune checkpoint inhibitor is a TIM-3 immune checkpoint inhibitor. A specific TIM-3 inhibitor includes, but is not limited to, TSR-022 (Tesaro).

Other immune checkpoint inhibitors for use in combination with the active compounds described herein for the treatment of cancer include, but are not limited to, B7-H3/CD276 immune checkpoint inhibitors such as MGA217, indoleamine 2,3-dioxygenase (IDO) immune checkpoint inhibitors such as Indoximod and INCB024360, killer immunoglobulin-like receptors (KIRs) immune checkpoint inhibitors such as Lirilumab (BMS-986015), carcinoembryonic antigen cell adhesion molecule (CEACAM) inhibitors (e.g., CEACAM-1, -3 and/or -5). Exemplary anti-CEACAM-1 antibodies are described in WO 2010/125571, WO 2013/082366 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. PLoS One. 2010 Sep. 2; 5(9). pii: e12529 (DOI:10:1371/journal.pone.0021146), or cross-reacts with CEACAM-1 and CEACAM-5 as described in, e.g., WO 2013/054331 and US 2014/0271618. Still other checkpoint inhibitors can be molecules directed to B and T lymphocyte attenuator molecule (BTLA), for example as described in Zhang et al., Monoclonal antibodies to B and T lymphocyte attenuator (BTLA) have no effect on in vitro B cell proliferation and act to inhibit in vitro T cell proliferation when presented in a cis, but not trans, format relative to the activating stimulus, Clin Exp Immunol. 2011 January; 163(1): 77-87.

As contemplated herein, the active compounds described herein, or a pharmaceutically acceptable salt thereof, is administered in an oral dosage form and can be in combination with any standard chemotherapeutic agent treatment modality for the treatment of cancer. In some embodiments the chemotherapeutic agent inhibits cell growth. In some embodiments, the chemotherapeutic agent administered is a DNA damaging chemotherapeutic agent. In some embodiments, the chemotherapeutic agent is a protein synthesis inhibitor, a DNA-damaging chemotherapeutic, an alkylating agent, a topoisomerase inhibitor, an RNA synthesis inhibitor, a DNA complex binder, a thiolate alkylating agent, a guanine alkylating agent, a tubulin binder, DNA polymerase inhibitor, an anticancer enzyme, RAC1 inhibitor, thymidylate synthase inhibitor, oxazophosphorine compound, integrin inhibitor such as cilengitide, camptothecin or homocamptothecin, antifolate or a folate antimetabolite.

In some embodiments, the additional therapeutic agent is trastuzumab. In some embodiments, the additional therapeutic agent is lapatinib.

In some embodiments, the additional therapeutic agent is osimertinib. In some embodiments, the additional therapeutic agent is alectinib.

In some embodiments, the additional therapeutic agent is a MEK inhibitor.

In some embodiments, the additional therapeutic agent is an Androgen Receptor ligand.

In some embodiments, the additional therapeutic agent is a BTK inhibitor.

In some embodiments, the additional therapeutic agents are a MEK inhibitor and a RAF inhibitor.

In some embodiments, the additional therapeutic agent is a RAF inhibitor. In some embodiments, the additional therapeutic agent is regorafenib.

In some embodiments, the MEK inhibitor is Binimetinib, Selumetinib, Cl-040, PD-325901, PD035901, or TAK-733.

In another embodiment the MEK inhibitor is Tramatenib, U0126-EtOH, PD98059, Pimasertib, BIX 02188, AZD8330, PD318088, SL-327, Refametinib, Myricetin, BI-847325, Cobimetinib, APS-2-79 HCl, or GDC-0623.

In some embodiments, the RAF inhibitor is PLX-4720, Dabrafenib, GDC-0879, Lifrafenib, CCT196969, RAF265, AZ 628, NVP-BHG712, SB590885, ZM 336372, Sorafenib, GW5074, TAK-632, CEP-32496, Encorafenib, PLX7904, LY3009120, RO5126766, or MLN2480.

In some embodiments, the BTK inhibitor is CC-292, CNX-774, RN486, LFM-A13, ONO-4059, ibrutinib, Acalabrutinib, or CGI746.

In some embodiments, the Androgen Receptor ligand is MK-2866, Apalutamide, Andarine, Boldenone, testosterone enanthate, dihydrotestosterone, Galertone, dehydroepiandrosterone, cyproterone acetate, megestrol acetate, epiandrosterone, AZD3514, spironolactone, chloromadinone acetate, ODM-201, EPI-001.

In some embodiments, the EGFR inhibitor is Lapatinib, Afatinib, Neratinib, Catertinib, AG-490, CP-724714, Dacomitinib, WZ4002, Sapitinib, CUDC-101, AG-1478, PD153035 HCl, Pelitinib, AC480, AEE788, AP26113, OSI-420, WZ3146, WZ8040, AST-1306, Rociletinib, Genisten, Varlitinib, Icotinib, TAK-285, WHI-P154, Daphnetin, PD168393, Tyrphostin 9, CNX-2006, AG-18, Cetuximab, Nazartinib, NSC228155, AZ5104, Poziotnib, AZD3759, Lifirafenib, Olmutinib, Erlotinib, Naquotinib, EAI045, or CL-387785.

In some embodiments, an active compound described herein is combined with a DNA-damaging chemotherapeutic agent for the treatment of cancer. As used herein the term "DNA-damaging" chemotherapy or chemotherapeutic agent refers to treatment with a cytostatic or cytotoxic agent (i.e., a compound) to reduce or eliminate the growth or proliferation of undesirable cells, for example cancer cells, wherein the cytotoxic effect of the agent can be the result of one or more of nucleic acid intercalation or binding, DNA or RNA alkylation, inhibition of RNA or DNA synthesis, the inhibition of another nucleic acid-related activity (e.g., protein synthesis), or any other cytotoxic effect. Such compounds include, but are not limited to, DNA damaging compounds that can kill cells. "DNA damaging" chemotherapeutic agents include, but are not limited to, alkylating agents, DNA intercalators, protein synthesis inhibitors, inhibitors of DNA or RNA synthesis, DNA base analogs, topoisomerase inhibitors, telomerase inhibitors, and telomeric DNA binding compounds.

For example, alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylol melamine; nitrogen mustards such as chlorambucil, chlornaphazine, cyclophosphamide, estramustine, mechlorethamine, mechlorethamine oxide hydrochloride, melphalan, novembichine, phenesterine, prednimustine, trofosfamide, and uracil mustard; and nitroso ureas, such as carmustine, chlorozotocin, fotemustine, lomustine, nimustine, and ranimustine.

Other DNA-damaging chemotherapeutic agents include daunorubicin, doxorubicin, idarubicin, epirubicin, mitomycin, and streptozocin. Chemotherapeutic antimetabolites include gemcitabine, mercaptopurine, thioguanine, cladribine, fludarabine phosphate, fluorouracil (5-FU), floxuridine, cytarabine, pentostatin, methotrexate, azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors that may be combined with the active compounds described herein include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim.

Inhibitors of DNA synthesis that may be combined with the active compounds described herein include alkylating agents such as dimethyl sulfate, nitrogen and sulfur mustards; intercalating agents, such as acridine dyes, actinomycins, anthracenes, benzopyrene, ethidium bromide, propidium diiodide-intertwining; and other agents, such as distamycin and netropsin. Topoisomerase inhibitors, such as irinotecan, teniposide, coumermycin, nalidixic acid, novobiocin, and oxolinic acid; inhibitors of cell division, including colcemide, mitoxantrone, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be used as the DNA damaging compound.

In some embodiments, the chemotherapeutic agent that may be combined with the active compounds described herein for the treatment of cancer is a DNA complex binder such as camptothecin, or etoposide; a thiolate alkylating agent such as nitrosourea, BCNU, CCNU, ACNU, or fotesmustine; a guanine alkylating agent such as temozolomide, a tubulin binder such as vinblastine, vincristine, vinorelbine, vinflunine, cryptophycin 52, halichondrins, such as halichondrin B, dolastatins, such as dolastatin 10 and dolastatin 15, hemiasterlins, such as hemiasterlin A and hemiasterlin B, colchicine, combrestatins, 2-methoxyestradiol, E7010, paclitaxel, docetaxel, epothilone, discodermolide; a DNA polymerase inhibitor such as cytarabine; an anticancer enzyme such as asparaginase; a Rac1 inhibitor such as 6-thioguanine; a thymidylate synthase inhibitor such as capecitabine or 5-FU; a oxazophosphorine compound such as Cytoxan; a integrin inhibitor such as cilengitide; an antifolate such as pralatrexate; a folate antimetabolite such as pemetrexed; or a camptothecin or homocamptothecin such as diflomotecan.

In some embodiments the topoisomerase inhibitor is a type I inhibitor. In another embodiment the topoisomerase inhibitor is a type II inhibitor.

Other DNA-damaging chemotherapeutic agents that may be combined with the active compounds described herein for the treatment of cancer include, but are not limited to, cisplatin, hydrogen peroxide, carboplatin, procarbazine, ifosfamide, bleomycin, plicamycin, taxol, transplatinum, thiotepa, oxaliplatin, and the like, and similar acting-type agents. In some embodiments, the DNA damaging chemotherapeutic agent is selected from the group consisting of cisplatin, carboplatin, camptothecin, and etoposide.

Other suitable chemotherapeutic agents that may be combined with the active compounds described herein include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®), liposomal vincristine (Marqibo®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Prednisone, and Dexamethasone (Decadron). Examples of additional suitable chemotherapeutic agents include but are not limited to 5-fluorouracil, dacarbazine, alkylating agents, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), bleomycin sulfate, calicheamicin, cytochalasin B, dactinomycin (formerly actinomycin), daunorubicin HCl, daunorubicin citrate, denileukin diftitox, dihydroxy anthracin dione, Docetaxel, doxorubicin HCl, *E. coli* L-asparaginase, Erwinia L-asparaginase, etoposide citrovorum factor, etoposide phosphate, gemcitabine HCl, idarubicin HCl, interferon α-2b, irinotecan HCl, maytansinoid, mechlorethamine HCl, melphalan HCl, mithramycin, mitomycin C, mitotane, polifeprosan 20 with carmustine implant, procarbazine HCl, streptozotocin, teniposide, thiotepa, topotecan HCl, valrubicin, vinblastine sulfate, vincristine sulfate, and vinorelbine tartrate.

Additional cytotoxic chemotherapeutic agents for use with the present disclosure include: epirubicin, abraxane, taxotere, epothilone, tafluposide, vismodegib, azacytidine, doxifluridine, vindesine, and vinorelbine.

In some embodiments, the chemotherapeutic agent that may be combined with the active compounds described herein for the treatment of cancer is a DNA complex binder. In some embodiments, the chemotherapeutic agent is a tubulin binder. In some embodiments, the chemotherapeutic agent is an alkylating agent. In some embodiments, the chemotherapeutic agent is a thiolate alkylating agent.

Additional chemotherapeutic agents that may be combined with the active compounds described herein for the treatment of cancer may include 2-methoxyestradiol or 2ME2, finasunate, etaracizumab (MEDI-522), HLL1, huN901-DM1, atiprimod, saquinavir mesylate, ritonavir, nelfinavir mesylate, indinavir sulfate, plitidepsin, P276-00, tipifarnib, lenalidomide, thalidomide, pomalidomide, simvastatin, and celecoxib. Chemotherapeutic agents useful in the present disclosure include, but are not limited to, Trastuzumab (HERCEPTIN®), Pertuzumab (PERJETA™), Lapatinib (TYKERB®), Gefitinib (IRESSA®), Erlotinib (TARCEVA®), Cetuximab (ERBITUX®), Panitumumab (VECTIBIX®), Vandetanib (CAPRELSA®), Vemurafenib (ZELBORAF®), Vorinostat (ZOLINZA®), Romidepsin (ISTODAX®), Bexarotene (TARGRETIN®), Alitretinoin (Panretin®), Tretinoin (VESANOID®), Carfilzomib (Kyprolis™), Pralatrexate (FOLOTYN®), Bevacizumab (AVASTIN®), Ziv-aflibercept (ZALTRAP®), Sorafenib (NEXAVAR®), Sunitinib (SUTENT®), Pazopanib (VOTRIENT®), Regorafenib (STIVARGA®), and Cabozantinib (Cometriq™).

Additional chemotherapeutic agents that may be combined with the active compounds described herein for the treatment of cancer include, but are not limited to, a calcineurin inhibitor, e.g. a cyclosporin or an ascomycin, e.g. Cyclosporin A (Neoral®), FK506 (tacrolimus), pimecrolimus, a mTOR inhibitor, e.g. rapamycin or a derivative thereof, e.g. Sirolimus (Rapamune®), Everolimus (Certican®), temsirolimus, zotarolimus, biolimus-7, biolimus-9, a rapalog, e.g. ridaforolimus, campath 1H, a S1P receptor modulator, a dual mTORC1 and mTORC2 inhibitor, eg. Vistusertib (AZD2014), e.g. fingolimod or an analogue thereof, an anti IL-8 antibody, mycophenolic acid or a salt thereof, e.g. sodium salt, or a prodrug thereof, e.g. Mycophenolate Mofetil (CellCept®), OKT3 (Orthoclone OKT3®), Prednisone, ATGAM®, Thymoglobulin®, Brequinar Sodium, OKT4, T10B9.A-3A, 33B3.1, 15-deoxyspergualin, tresperimus, Leflunomide Arava®, anti-CD25, anti-IL2R, Basiliximab (Simulect®), Daclizumab (Zenapax®), mizoribine, dexamethasone, ISAtx-247, SDZ ASM 981 (pimecrolimus, Elidel®), Abatacept, belatacept, LFA3lg, etanercept (sold as ENBREL® by ImmuneXcite), adalimumab (HUMIRA®), infliximab (REMICADE®), an anti-LFA-1 antibody, natalizumab (ANTEGREN®), Enlimomab, gavilimomab, Golimumab, antithymocyte immunoglobulin, siplizumab, Alefacept, efalizumab, Pentasa, mesalazine, asacol, codeine phosphate, benorylate, fenbufen, naprosyn, diclofenac, etodolac, indomethacin, dasatinib (SPRYCEL®) nilotinib (TASIGNA®), bosutinib (BOSULIF®), Imatinib mesylate (GLEEVEC®) and ponatinib (ICLUSIG™) amifostine, dolasetron mesylate, dronabinol, epoetin-α, etidronate, filgrastim, fluconazole, goserelin acetate, gramicidin D, granisetron, leucovorin calcium, lidocaine, Mesna, ondansetron HCl, pilocarpine HCl, porfimer sodium, vatalanib, 1-dehydrotestosterone, allopurinol sodium, Betamethasone, sodium phosphate and betamethasone acetate, calcium leucovorin, conjugated estrogens, Dexrazoxane, Dibromomannitol, esterified estrogens, estradiol, estramustine phosphate sodium, ethinyl estradiol, flutamide, folinic acid, glucocorticoids, leuprolide acetate, levamisole HCl, medroxyprogesterone acetate, megestrol acetate, methyltestosterone, nilutamide, octreotide acetate, pamidronate disodium, procaine, propranolol, testolactone, tetracaine, toremifene citrate, and sargramostim.

In some embodiments, the chemotherapeutic agent that may be combined with the active compounds described herein for the treatment of cancer is an estrogen receptor ligands such as tamoxifen, raloxifene, fulvestrant, anordrin, bazedoxifene, broparoestrol, chlorotrianisene, clomiphene citrate, cyclofenil, lasofoxifene, ormeloxifene, or toremifene; an androgen receptor ligand such as bicalutamide, enzalutamide, apalutamide, cyproterone acetate, chlormadinone acetate, spironolactone, canrenone, drospirenone, ketoconazole, topilutamide, abiraterone acetate, or cimetidine; an aromatase inhibitor such as letrozole, anastrozole, or exemestane; an anti-inflammatory such as prednisone; an oxidase inhibitor such as allopurinol; an anticancer antibody; an anticancer monoclonal antibody; an antibody against CD40 such as lucatumumab or dacetuzumab; an antibody against CD20 such as rituximab; an antibody that binds CD52 such as alemtuzumab; an antibody that binds integrin such as volociximab or natalizumab; an antibody against interleukin-6 receptor such as tocilizumab; an interleukin-2 memetic such as aldesleukin; an antibody that targets IGF1 like figitumumab; an antibody that targets DR4 such as mapatumumab; an antibody that targets TRAIL-R2 such as lexatumumab or dulanermin; a fusion protein such as atacicept; a B cell inhibitor such as atacicept; a proteasome inhibitor such as carfilzomib, bortezomib, or marizomib; a HSP90 inhibitor such as tanespimycin; a HDAC inhibitor such as vorinostat, belinostat or panobinostat; a MAPK ligand such as talmapimod; a PKC inhibitor such as enzastaurin; a HER2 receptor ligand such as trastuzumab, lapatinib, or pertuzumab; an EGFR inhibitor such as gefitinib, erlotinib, cetuximab, panitumumab, or vandetanib; a natural product such as romidepsin; a retinoid such as bexarotene, tretinoin, or alitretinoin; a receptor tyrosine kinase (RTK) inhibitor such as sunitinib, regorafenib, or pazopanib; or a VEGF inhibitor such as zivaflibercept, bevacizumab or dovitinib.

Additional chemotherapeutic agents that may be combined with the active compounds described herein for the treatment of cancer, particularly in the treatment of abnormal tissue of the female reproductive system such as breast, ovarian, endometrial, or uterine cancer include an estrogen inhibitor including but not limited to a SERM (selective estrogen receptor modulator), a SERD (selective estrogen receptor degrader), a complete estrogen receptor degrader, or another form of partial or complete estrogen antagonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth.

In contrast, fulvestrant, a complete anti-estrogen, is free of estrogen-like action on the uterus and is effective in tamoxifen-resistant tumors. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703,810, as well as US 2015/0005286, WO 2014/205136, and WO 2014/205138.

Additional non-limiting examples of anti-estrogen compounds include: SERMS such as anordrin, bazedoxifene, broparestriol, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, delmadinone acetate, dydrogesterone, medroxyprogesterone acetate, megestrol acetate, nomegestrol acetate, norethisterone acetate, progesterone, and spironolactone.

Additional chemotherapeutic agents that may be combined with the active compounds described herein for the treatment of cancer, particularly in the treatment of abnormal tissue of the male reproductive system such as prostate or testicular cancer, include, but are not limited to, an androgen (such as testosterone) inhibitor including but not limited to a selective androgen receptor modulator, a selective androgen receptor degrader, a complete androgen receptor degrader, or another form of partial or complete androgen antagonist.

In some embodiments, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: chlormadinone acetate, spironolactone, canrenone, drospirenone, ketoconazole, topilutamide, abiraterone acetate, and cimetidine.

The chemotherapeutic agent that may be combined with the active compounds described herein for the treatment of cancer may include a kinase inhibitor, including but not limited to a phosphoinositide 3-kinase (PI3K) inhibitor, a Bruton's tyrosine kinase (BTK) inhibitor, or a spleen tyrosine kinase (Syk) inhibitor, or a combination thereof.

PI3k inhibitors are well known. Examples of PI3 kinase inhibitors include, but are not limited to, Wortmannin, demethoxyviridin, perifosine, idelalisib, pictilisib, Palomid 529, ZSTK474, PWT33597, CUDC-907, and AEZS-136, duvelisib, GS-9820, GDC-0032 (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d]pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4, 5h]isochromen-10-yl] acetate (also known as sonolisib)), and the structure described in WO2014/071109.

BTK inhibitors are well known. Examples of BTK inhibitors include ibrutinib (also known as PCI-32765) (Imbruvica™) (1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g]quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino)pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), BGB-3111, and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors are well known, and include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (Gleevec; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, *J. Med. Chem.* 2012, 55, 3614-3643 incorporated in its entirety herein), luteolin (see Singh et al. Discovery and Development of Spleen Tyrosine Kinase (SYK) Inhibitors, *J. Med. Chem.* 2012, 55, 3614-3643 incorporated in its entirety herein), apigenin (see Singh et al. Discovery and Development of Spleen Tyrosine Kinase (SYK) Inhibitors, *J. Med. Chem.* 2012, 55, 3614-3643 incorporated in its entirety herein), quercetin (see Singh et al. Discovery and Development of Spleen Tyrosine Kinase (SYK) Inhibitors, *J. Med. Chem.* 2012, 55, 3614-3643 incorporated in its entirety herein), fisetin (see Singh et al. Discovery and Development of Spleen Tyrosine Kinase (SYK) Inhibitors, *J. Med. Chem.* 2012, 55, 3614-3643 incorporated in its entirety herein), myricetin (see Singh et al. Discovery and Development of Spleen Tyrosine Kinase (SYK) Inhibitors, *J. Med. Chem.* 2012, 55, 3614-3643 incorporated in its entirety herein), morin (see Singh et al. Discovery and Development of Spleen Tyrosine Kinase (SYK) Inhibitors, *J. Med. Chem.* 2012, 55, 3614-3643 incorporated in its entirety herein).

The chemotherapeutic agent that may be combined with the active compounds described herein for the treatment of cancer can also be a B-cell lymphoma 2 (Bcl-2) protein inhibitor. BCL-2 inhibitors are known in the art, and include, for example, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), or G3139 (Oblimersen).

Additional chemotherapeutic agents that may be combined with the active compounds described herein for the treatment of cancer for use in the methods contemplated herein include, but are not limited to, midazolam, MEK inhibitors, RAS inhibitors, ERK inhibitors, ALK inhibitors, HSP inhibitors (for example, HSP70 and HSP90 inhibitors, or a combination thereof), RAF inhibitors, apoptotic compounds, topoisomerase inhibitors, AKT inhibitors, including but not limited to, MK-2206, GSK690693, Perifosine, (KRX-0401), GDC-0068, Triciribine, AZD5363, Honokiol, PF-04691502, and Miltefosine, or FLT-3 inhibitors, including but not limited to, P406, Dovitinib, Quizartinib (AC220), Amuvatinib (MP-470), Tandutinib (MLN518), ENMD-2076, and KW-2449, or combinations thereof. Examples of MEK inhibitors include but are not limited to trametinib/GSKl120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEAl19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide). Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol.

Known ERK inhibitors include SCH772984 (Merck/Schering-Plough), VTX-11e (Vertex), DEL-22379, Ulixertinib (BVD-523, VRT752271), GDC-0994, FR 180204, XMD8-92, and ERK5-IN-1.

Raf inhibitors are well known, and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide;
4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), and Sorafenib N-Oxide (4-[4-[[[[4-Chloro-3(trifluoroMethyl)phenyl]aMino]carbonyl]aMino]phenoxy]-N-Methyl-2pyridinecarboxaMide 1-Oxide).

Known topoisomerase I inhibitors useful in the present disclosure include (S)-10-[(dimethylamino)methyl]-4-ethyl-4,9-dihydroxy-1H-pyrano[3',4':6,7]indolizino[1,2-b]quinoline-3,14(4H,12H)-dione monohydrochloride (topotecan), (S)-4-ethyl-4-hydroxy-1H-pyrano[3',4':6,7]indolizino[1,2-b]quinoline-3,14-(4H,12H)-dione (camptothecin), (1S,9S)-1-Amino-9-ethyl-5-fluoro-1,2,3,9,12,15-hexahydro-9-hydroxy-4-methyl-10H,13H-benzo(de)pyrano(3',4':6,7)indolizino(1,2-b)quinoline-10,13-dione (exatecan), (7-(4-methylpiperazinomethylene)-10,11-ethylenedioxy-20(S)-camptothecin (lurtotecan), or (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate (irinotecan), (R)-5-ethyl-9,10-difluoro-5-hydroxy-4,5-dihydrooxepino[3',4': 6,7]indolizino[1,2-b]quinoline-3,15(1H,13H)-dione (diflomotecan), (4S)-11-((E)-((1,1-Dimethylethoxy)imino)methyl)-4-ethyl-4-hydroxy-1,12-dihydro-14H-pyrano(3',4':6,7)indolizino(1,2-b)quinoline-3,14(4H)-dione (gimatecan), (S)-8-ethyl-8-hydroxy-15-((4-methylpiperazin-1-yl)methyl)-11,14-dihydro-2H-[1,4]dioxino[2,3-g]pyrano[3',4':6,7]indolizino[1,2-b]quinoline-9,12(3H,8H)-dione (lurtotecan), (4S)-4-Ethyl-4-hydroxy-11-[2-[(1-methylethyl)amino]ethyl]-1H-pyrano[3,4:6,7]indolizino[1,2-b]quinoline-3,14(4H,12H)-dione (belotecan), 6-((1,3-dihydroxypropan-2-yl)amino)-2,10-dihydroxy-12-((2R,3R,4S,5S,6R)-3,4,5-trihydroxy-6-(hydroxymethyl)tetrahydro-2H-pyran-2-yl)-12,13-dihydro-5H-indolo[2,3-a]pyrrolo[3,4-c]carbazole-5,7(6H)-dione (edotecarin), 8,9-dimethoxy-5-(2-N,N-dimethylamino-ethyl)-2,3-methylenedioxy-5H-dibenzo(c,h)(1,6)naphthyridin-6-one (topovale), benzo[6,7]indolizino[1,2-b]quinolin-11(13H)-one (rosettacin), (S)-4-ethyl-4-hydroxy-11-(2-(trimethylsilyl)ethyl)-1H-pyrano[3',4':6,7]indolizino[1,2-b]quinoline-3,14(4H,12H)-dione (cositecan), tetrakis{(4S)-9-[([1,4'-bipiperidinyl]-1'-carbonyl)oxy]-4,11-diethyl-3,14-dioxo-3,4,12,14-tetrahydro-1H-pyrano[3',4':6,7]indolizino[1,2-b]quinolin-4-yl} N,N',N'',N'''-{methanetetrayltetrakis[methylenepoly(oxyethylene)oxy(1-oxoethylene)]}tetraglycinate tetrahydrochloride (etirinotecan pegol), 10-hydroxy-camptothecin (HOCPT), 9-nitrocamptothecin (rubitecan), SN38 (7-ethyl-10-hydroxycamptothecin), and 10-hydroxy-9-nitrocamptothecin (CPT109), (R)-9-chloro-5-ethyl-5-hydroxy-10-methyl-12-((4-methylpiperidin-1-yl)methyl)-4,5-dihydrooxepino[3',4':6,7]indolizino[1,2-b]quinoline-3,15(1H,13H)-dione (elmotecan).

C5 Inhibitor Combinations

Provided herein are methods for a treating a complement mediated disorder in a subject comprising administering to the subject an effective amount of a C5 inhibitor in combination or alternation with an effective amount of an active compound as described herein.

C5 inhibitors are known in the art. In some embodiments, the C5 inhibitor is a monoclonal antibody targeting C5. In some embodiments, the C5 inhibitor is eculizumab (SOLIRIS® Alexion Pharmaceuticals, Boston, MA, see, e.g., U.S. Pat. No. 9,352,035), or a biosimilar molecule thereof. In some embodiments, the C5 inhibitor is ravulizumab (ULTOMIRIS® Alexion Pharmaceuticals, Boston, MA, see, e.g., U.S. Pat. Nos. 9,371,377; 9,079,949 and 9,633,574), or a biosimilar thereof.

In some embodiments, the C5 inhibitor may be, but is not limited to: a recombinant human minibody, for example Mubodina® (monoclonal antibody, Adienne Pharma and Biotech, Bergamo, Italy; see U.S. Pat. No. 7,999,081); coversin (nomacopan, Akari Therapeutics, London, England; see e.g., Penabad et al. Lupus, 2012, 23(12):1324-6); LFG316 (monoclonal antibody, Novartis, Basel, Switzerland, and Morphosys, Planegg, Germany; see U.S. Pat. Nos. 8,241,628 and 8,883,158); ARC-1905 (pegylated RNA aptamer, Ophthotech, Princeton, NJ and New York, NY; see Keefe et al., Nature Reviews Drug Discovery, 9, 537-550); RA101348 and zilucoplan (macrocyclic peptides, Ra Pharmaceuticals, Cambridge, MA); SOBI002 (affibody, Swedish Orphan Biovitrum, Stockholm, Sweden); cemdisiran (SiRNA, Alnylam Pharmaceuticals, Cambridge, MA); ARC1005 (aptamers, Novo Nordisk, Bagsvaerd, Denmark); SOMAmers (aptamers, SomaLogic, Boulder, Co); SSL7 (bacterial protein toxin, see, e.g., Laursen et al. *Proc. Natl. Acad. Sci. U.S.A.,* 107(8):3681-6); MEDI7814 (monoclonal antibody, MedImmune, Gaithersburg, MD); aurin tricarboxylic acid; aurin tricarboxylic acid derivatives (Aurin Biotech, Vancouver, BC, see U.S. Patent Appl. Pub. 2013/003592); crovalimab (RG6107/SKY59; anti-C5 recycling antibody, Roche Pharmaceuticals, Basel, Switzerland); ALXN1210 and ALXN5500 (monoclonal antibodies, Alexion Pharmaceuticals, Boston, MA); TT30 (fusion protein, Alexion Pharmaceuticals, Boston, MA); REGN3918 (monoclonal antibody, Regeneron, Tarrytown, NY); ABP959 (eculizumab biosimilar, Amgen, Thousand Oaks, CA); BCD-148 (Biocad); and SB-12 (Samsung Bioepis Co., Ltd.); or combinations thereof.

In some embodiments, the C5 inhibitor is a recombinant human minibody, for example Mubodina®. Mubodina® is a fully human recombinant antibody C5 developed by Adienne Pharma and Biotech. Mubodina® is described in U.S. Pat. No. 7,999,081.

In some embodiments, the C5 inhibitor is coversin. Coversin is a recombinant protein derived from a protein discovered in the saliva of the *Ornithodoros moubata* tick currently developed as a recombinant protein by Akari Therapeutics (also known as nomacopan). Coversin is described in Penabad et al. *Lupus* 2012, 23(12):1324-6.

In some embodiments, the C5 inhibitor is Tesidolumab/LFG316. Tesidolumab is a monoclonal antibody developed by Novartis and Morphosys. Tesidolumab is described in U.S. Pat. Nos. 8,241,628 and 8,883,158.

In some embodiments, the C5 inhibitor is ARC-1905. ARC-1905 is a pegylated RNA aptamer developed by Ophthotech. ARC-1905 is described in Keefe et al. *Nature Reviews Drug Discovery,* 9:537-550.

In some embodiments, the C5 inhibitor is RA101348. RA101348 is a macrocyclic peptide developed by Ra Pharmaceuticals.

In some embodiments, the C5 inhibitor is RA101495. RA101495, also known as zilucoplan, is a macrocyclic peptide developed by Ra Pharmaceuticals.

In some embodiments, the C5 inhibitor is SOBI002. SOBI002 is an affibody developed by the Swedish Orphan Biovitrum.

In some embodiments, the C5 inhibitor is ARC1005. ARC1005 is an aptamer developed by Novo Nordisk.

In some embodiments, the C5 inhibitor is SOMAmers for C5. SOMAmers are aptamers developed by SomaLogic.

In some embodiments, the C5 inhibitor is SSL7. SSL7 is a bacterial protein toxin described in Laursen et al. *Proc. Natl. Acad. Sci. U.S.A.,* 107(8):3681-6.

In some embodiments, the C5 inhibitor is MEDI7814. MEDI7814 is a monoclonal antibody developed by MedImmune.

In some embodiments, the C5 inhibitor is aurin tricarboxylic acid. In another embodiment, the C5 inhibitor is an aurin tricarboxylic acid derivative. These aurin derivatives were developed by Aurin Biotech and are further described in U.S. Patent Appl. Pub. No. 2013/003592).

In some embodiments, the C5 inhibitor is RG6107/SKY59. RG6107/SKY59 is an anti-C5 recycling antibody developed by Roche Pharmaceuticals.

In some embodiments, the C5 inhibitor is ravulizumab (ULTOMIRIS®). In another embodiment, the C5 inhibitor is ALXN5500. Ravulizumab and ALXN5500 are monoclonal antibodies developed by Alexion Pharmaceuticals.

In some embodiments, the C5 inhibitor is TT30. TT30 is a fusion protein licensed by Alexion Pharmaceuticals.

In some embodiments, the C5 inhibitor is ABP959. ABP959 is an eculizamab biosimilar monoclonal antibody developed by Amgen.

In some embodiments, the C5 inhibitor is Anti-C5 siRNA cemdisiran. Anti-C5 siRNA was developed by Alnylam Pharmaceuticals.

In some embodiments, the C5 inhibitor is Erdigna®. Erdigna® is an antibody developed by Adienne Pharma.

In some embodiments, the C5 inhibitor is avacincaptad pegol/Zimura®. Avacincaptad pegol is in aptamer developed by Ophthotech.

In some embodiments, the C5 inhibitor is SOBI005. SOBI005 is a protein in developed by the Swedish Orphan Biovitrum.

In some embodiments, the C5 inhibitor is ISU305. ISU305 is a monoclonal antibody developed by ISU ABXIS.

In some embodiments, the C5 inhibitor is REGN3918. REGN3918 is a monoclonal antibody developed by Regeneron.

In some embodiments, the C5 inhibitor is BCD-148. BCD is an eculizumab biosimilar being developed by Biocad.

In some embodiments, the C5 inhibitor is SB-12. SB-12 is an eculizumab biosimilar being developed by Samsung Bioepis Co., Ltd.

C3 Inhibitor Combinations

Provided herein are methods for treating a complement-mediated disorder in a subject comprising administering to the subject an effective amount of a C3 inhibitor in combination or alternation with an effective amount of an active compound described herein.

C3 inhibitors are known in the art. In some embodiments, a compound of the present disclosure is administered in combination or alternation with compstatin and/or a compstatin analog. Compstatin and compastin analogs are known and are found to be useful inhibitors of C3, see U.S. Pat. Nos. 9,056,076; 8,168,584; 9,421,240; 9,291,622; 8,580,735; 9,371,365; 9,169,307; 8,946,145; 7,989,589; 7,888,323; 6,319,897; and US Patent Appl. Pub. Nos. 2016/0060297; 2016/0015810; 2016/0215022; 2016/0215020; 2016/0194359; 2014/0371133; 2014/0323407; 2014/0050739; 2013/0324482; and 2015/0158915.

In some embodiments, the compstatin analog having the amino acid sequence ICVVQDWGHHCRT (SEQ. ID. NO. 1).

In another embodiment, the C3 inhibitor is a compstatin analog. In some embodiments, the compstatin analog is 4(1MeW)/APL-1 of the sequence Ac-ICV(1-mW)QDW-GAHRCT (SEQ. ID. NO. 2), wherein Ac is acetyl and 1-mW is 1-methyltryptophan.

In another embodiment, the compstatin analog is Cp40/AMY-101, which has an amino acid sequence yICV(1mW)QDW-Sar-AHRC-mI (SEQ. ID. NO. 3), wherein y is D-tyrosine, 1mW is 1-methyltryptophan, Sar is sarcosine, and mI is N-methylisoleucine.

In yet another embodiment, the compstatin analog is PEG-Cp40, having the amino acid sequence PEG-yICV(1mW)QDW-Sar-AHRC-mI (SEQ. ID. NO. 4), wherein PEG is polyethyleneglycol (40 kDa), y is D-tyrosine, 1mW is 1-methyltryptophan, Sar is sarcosine, and mI is N-methylisoleucine.

In yet another embodiment, the compstatin analog is 4(1MeW)POT-4. 4(1MeW)POT-4 was developed by Potentia.

In yet another embodiment, the compstatin analog is AMY-201. AMY-201 was developed by Amyndas Pharmaceuticals.

In some embodiments, a compound of the present disclosure can be combined with C3 inhibitors that include, but are not limited to: H17 (monoclonal antibody, EluSys Therapeutics, Pine Brook, NJ); mirococept (CR1-based protein); sCR1 (CR1-based protein, Celldex, Hampton, NJ); TT32 (CR-1 based protein, Alexion Pharmaceuticals, Boston, MA); HC-1496 (recombinant peptide); CB 2782 (enzyme, Catalyst Biosciences, South San Francisco, CA); APL-2 (pegylated synthetic cyclic peptide, Apellis Pharmaceuticals, Crestwood, KY); or combinations thereof.

In some embodiments, the C3 inhibitor is H17. H17 is a humanized monoclonal antibody in development by EluSys Therapeutics. H17 is described in Paixao-Cavalcante et al. J. Immunol. 2014, 192(10):4844-4851.

In some embodiments, the C3 inhibitor is mirococept. Mirococept is a CR1-based protein developed by Inflazyme Pharmaceuticals.

In some embodiments, the C3 inhibitor is sCR1. sCR1 is a soluble form of the CR1 protein developed by Celldex.

In some embodiments, the C3 inhibitor is TT32. TT32 is a CR-1 based protein licensed by Alexion Pharmaceuticals.

In some embodiments, the C3 inhibitor is HC-1496. HC-1496 is a recombinant peptide developed by InCode.

In some embodiments, the C3 inhibitor is CB 2782. CB 2782 is novel protease derived from human membrane type serine protease 1 (MTSP-1) that was developed by Catalyst Biosciences.

In some embodiments, the C3 inhibitor is APL-2. APL-2 is a pegylated version of APL-1 developed by Apellis Pharmaceuticals.

Complement Factor B (CFB) Inhibitor Combinations

Provided herein are methods for treating complement mediated disorder comprising administering a CFB inhibitor in combination or alternation with an active compound of the present disclosure. CFB inhibitors are known in the art.

In some embodiments, a compound of the present disclosure can be combined with CFB inhibitors that include, but are not limited to: anti-FB SiRNA (Alnylam Pharmaceuticals, Cambridge, MA); TA106 (monoclonal antibody, Alexion Pharmaceuticals, Boston, MA); LNP023 (small molecule, Novartis, Basel, Switzerland); SOMAmers (aptamers, SomaLogic, Boulder, CO); bikaciomab (Novelmed Therapeutics, Cleveland, OH); complin (see, Kadam et al., J. Immunol. 2010, DOI:10.409/jimmunol.10000200); Ionis-FB-$L_{Rx}$ (ligand conjugated antisense drug, Ionis Pharmaceuticals, Carlsbad, CA); or a combination thereof.

In another embodiment, CFB inhibitors that can be combined with a compound of the present disclosure include those disclosed in PCT/US17/39587.

In another embodiment, CFB inhibitors that can be combined with a compound of the present disclosure as described herein include those disclosed in PCT/US17/014458.

In another embodiment, CFB inhibitors that can be combined with a compound of the present disclosure as described herein include those disclosed in U.S. Patent Appl. Pub. No. 2016/0024079; PCT Int. Appl. WO 2013/192345; PCT Int. Appl. WO 2013/164802; PCT Int. Appl. WO 2015/066241; PCT Int. Appl. WO 2015/009616 (assigned to Novartis AG).

In some embodiments, the CFB inhibitor is

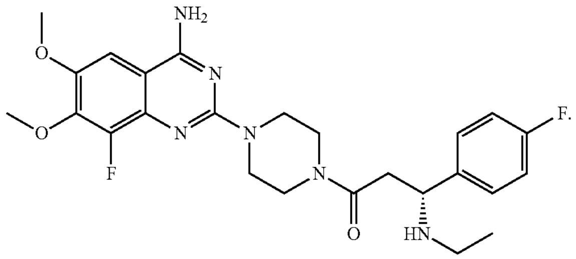 [SMILES: CCN[C@H](CC(=O)N1CCN(c2nc(N)c3cc(OC)c(OC)c(F)c3n2)CC1)c1ccc(F)cc1]

In another embodiment, the CFB inhibitor is

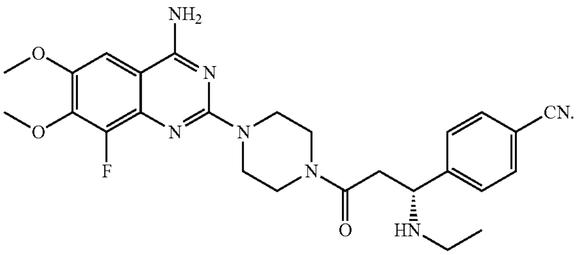 [SMILES: CCN[C@H](CC(=O)N1CCN(c2nc(N)c3cc(OC)c(OC)c(F)c3n2)CC1)c1ccc(C#N)cc1]

In another embodiment, the CFB inhibitor is

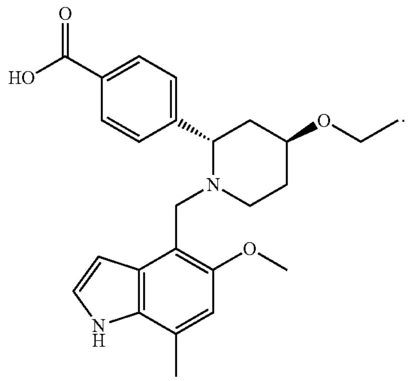 [SMILES: CCO[C@H]1CCN(Cc2c(OC)cc(C)c3[nH]ccc23)[C@H](c2ccc(C(=O)O)cc2)C1]

In some embodiments, the CFB inhibitor is anti-FB siRNA. Anti-FB siRNA was developed by Alnylam Pharmaceuticals.

In some embodiments, the CFB inhibitor is TA106. TA106 is a monoclonal antibody developed by Alexion Pharmaceuticals.

In some embodiments, the CFB inhibitor is LNP023. LNP023 is a small molecule inhibitor of CFB developed by Novartis.

In some embodiments, the CFB inhibitor is complin. Complin is a peptide inhibitor that is described in Kadam et al. *J. Immunol.* 2010 184(12):7116-24.

In some embodiments, the CFB inhibitor is IONIS-FB-LRx. IONIS-FB-LRx was developed by Ionis Pharmaceuticals.

Complement Factor D (CFD) Inhibitor Combinations

Provided herein are methods for treating complement mediated disorder comprising administering a CFD inhibitor in combination or alternation with an active compound of the present disclosure.

In some embodiments, a fD inhibitor may be used as described by BioCryst Pharmaceuticals in U.S. Pat. No. 6,653,340 title "Compounds useful in the complement, coagulate and kallikrein pathways and methods for their preparation" which described fused bicyclic ring compounds that are potent inhibitors of Factor D.

In some embodiments, a fD inhibitor may be used as described by Novartis in PCT Patent Publication No. WO 2012/093101 titled "Indole compounds or analogues thereof useful for the treatment of age-related macular degeneration". In another embodiment, a fD inhibitor may be used as described in Novartis PCT Patent Publication Nos. WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, or WO2015/066241.

In some embodiments, a fD inhibitor may be used as described by Bristol-Myers Squibb in PCT Patent Publication No. WO2004/045518 titled "Open chain prolyl urea-related modulators of androgen receptor function".

In some embodiments, a fD inhibitor may be used as described by Japan Tobacco Inc. in PCT Patent Publication No. WO1999/048492 title "Amide derivatives and nociceptin antagonists".

In some embodiments, a fD inhibitor may be used as described by Ferring B. V. and Yamanouchi Pharmaceutical Co. LTD. in PCT Patent Publication No. WO 1993/020099 titled "CCK and/or gastrin receptor ligands".

In some embodiments, the fD inhibitor is the monoclonal antibody FCFD4515S as developed by Genentech/Roche.

In some embodiments, the fD inhibitor is Nafamostat (FUT-175, Futhan) as developed by Torri Pharmaceuticals.

In some embodiments, the fD inhibitor is aptamers (SOMAmers) to Factor D as developed by SomaLogic.

In some embodiments, the fD inhibitor is the monoclonal antibody lampalizumab as developed by Roche.

In some embodiments, the fD inhibitor is aptamers to Factor D as developed by Vitrisa Therapeutics.

In some embodiments, the fD inhibitor is a fD inhibitor as developed by Ra Pharmaceuticals.

In some embodiments, the fD inhibitor comprises a drug disclosed in PCT/US17/014458.

In some embodiments, a fD inhibitor may be used as described by Alexion Pharmaceuticals in PCT Patent Publication No. WO1995/029697 title "Methods and compositions for the treatment of glomerulonephritis and other inflammatory diseases".

In some embodiments, the fD inhibitor for use in combination with the compound of the disclosure is selected among those described by Achillion Pharmaceuticals in WO2015/130784; WO2015/130795; WO2015/130806; WO2015/130830; WO2015/130838; WO2015/130842; WO2015/130845; WO2015/130854; WO2016/044243; WO2017/035348; WO2017/035349; WO2017/035351; WO2017/035352; WO2017/035353; WO2017/035355; WO2017/035357; WO2017/035360; WO2017/035361; WO2017/035362; WO2017/035401; WO2017/035405; WO2017/035408; WO2017/035409; WO2017/035411; WO2017/035413; WO2017/035415; WO2017/035417; WO2017/035418; WO2018/160889; WO2018/160891; WO2018/160892; WO2019/028284; WO2019/028284; WO2019/227102; WO2020/041301; WO2020/051532; or WO2020/051538.

In some embodiments the fD inhibitor is a compound of Formula:

(fD-I)

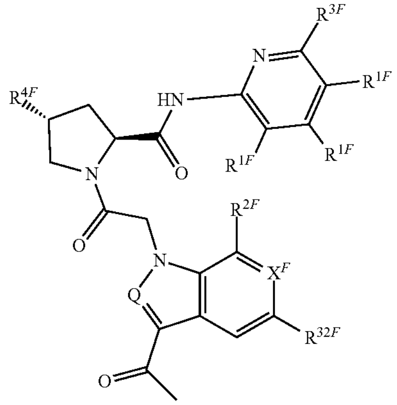

or (fD-II)

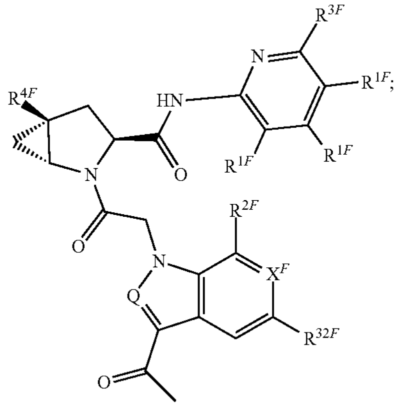

;

or a pharmaceutically acceptable salt thereof.

wherein:

Q is CH or N.

$X^F$ is selected from N and CH;

each $R^{1F}$ is independently selected from hydrogen, $C_1$-$C_3$ alkyl (e.g., methyl), and halogen (e.g., bromo, chloro, or fluoro);

$R^{2F}$ is selected from hydrogen and $C_1$-$C_3$ alkyl (e.g., methyl);

$R^{3F}$ is selected from $C_1$-$C_3$ alkyl (e.g., methyl), $C_1$-$C_3$ haloalkyl, and halogen (e.g., bromo, chloro, or fluoro);

$R^{4F}$ is selected from hydrogen, $C_1$-$C_3$ alkyl (e.g., methyl), and halogen (e.g., bromo, chloro, or fluoro);

$R^{5F}$ is selected from hydrogen, $C_1$-$C_3$ alkyl (e.g., methyl), halogen (e.g., bromo, chloro, or fluoro), -alkyl-OH, and cyano; and $R^{32F}$ is selected from
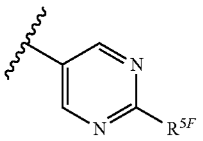
and
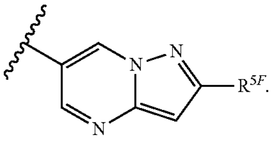
In some embodiments the fD inhibitor is selected from:
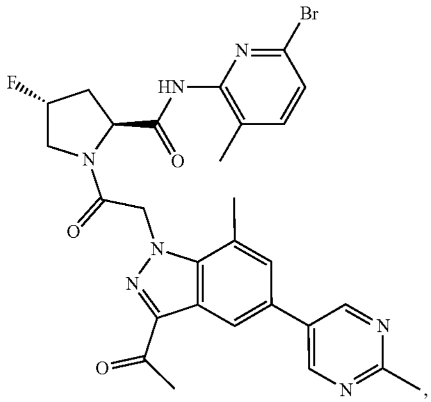
,
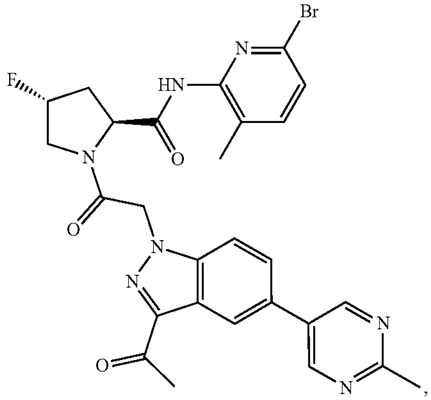
,
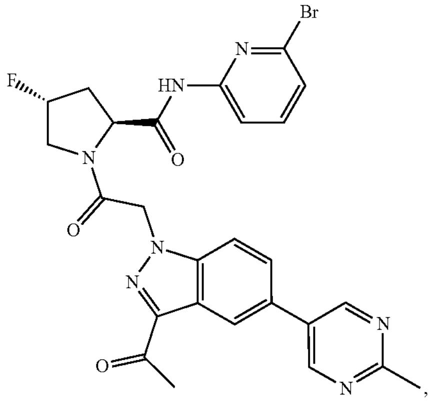
,
-continued
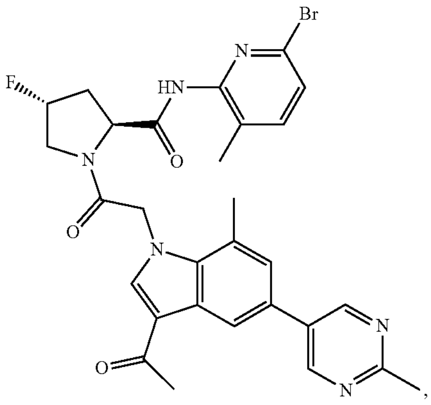
,
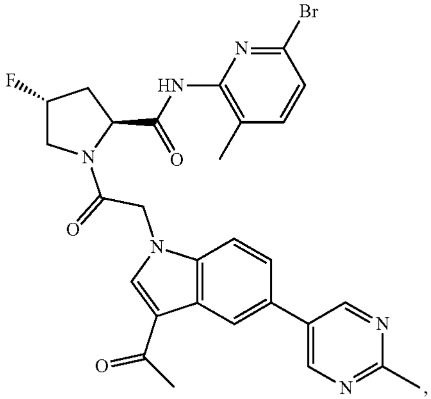
,
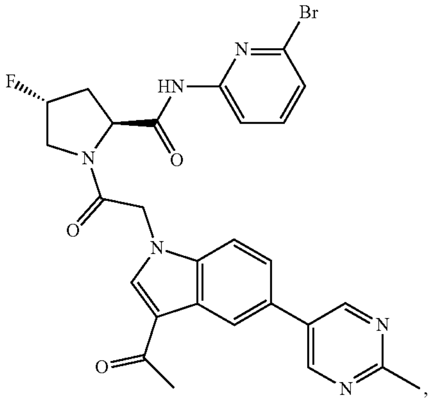
,
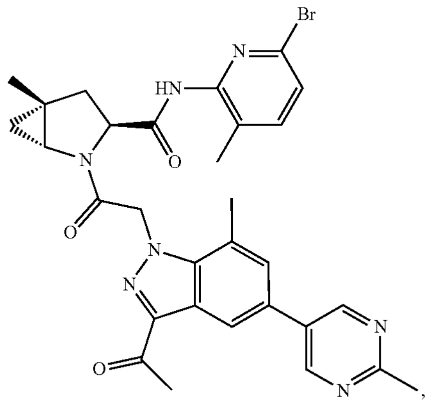
, -continued
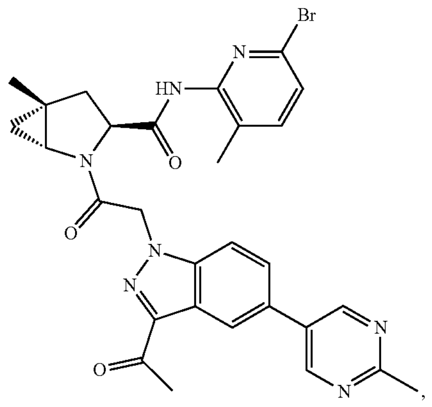
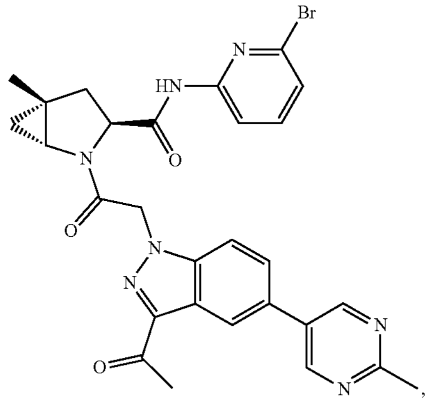
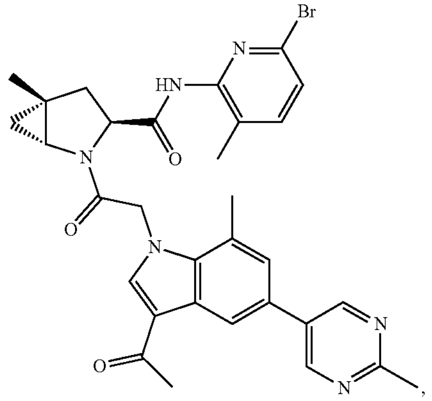
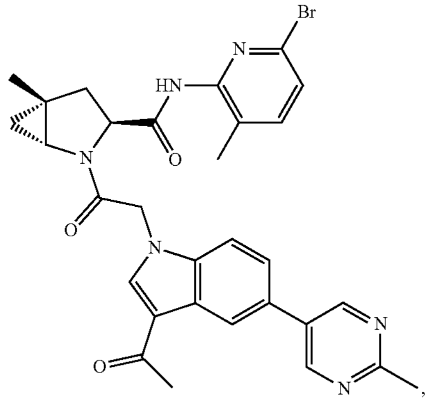
-continued
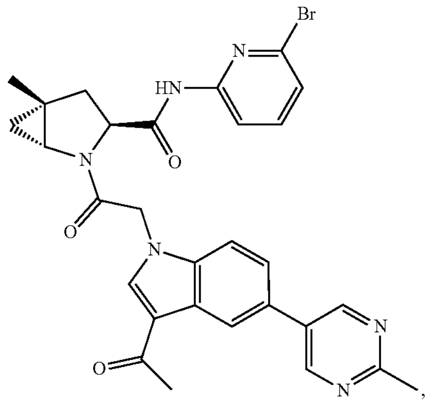
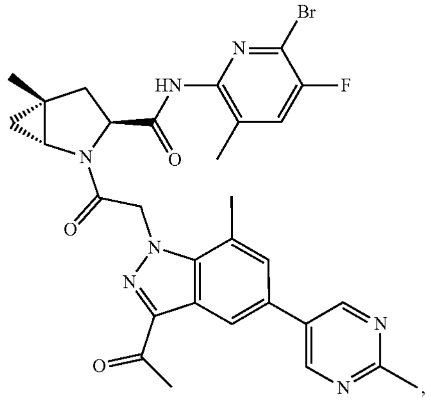
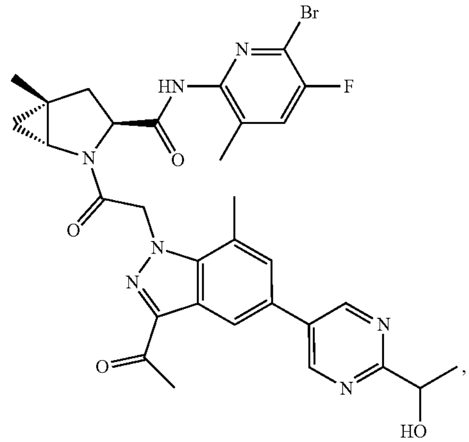
and
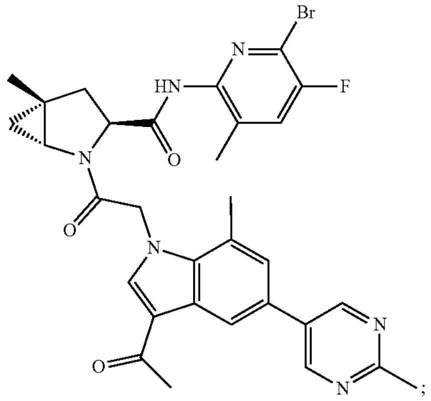
or a pharmaceutically acceptable salt thereof.

In some embodiments the fD inhibitor is selected from:

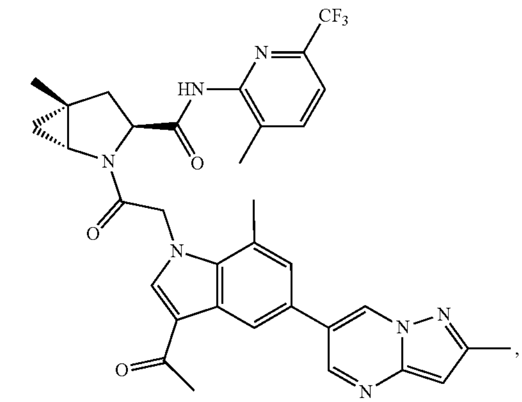

,

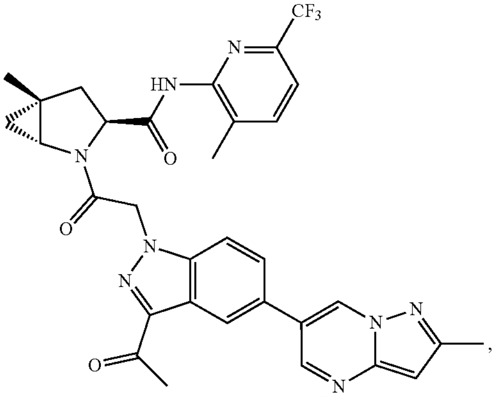

, and

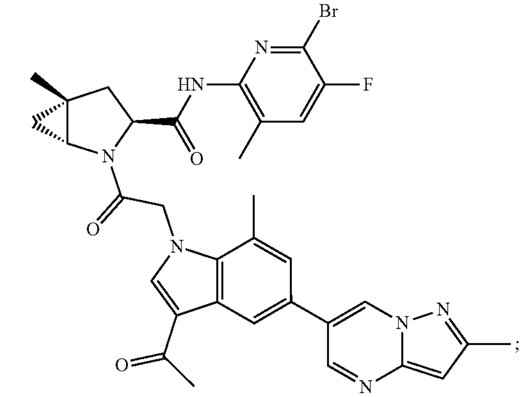

;

or a pharmaceutically acceptable salt thereof.

Pan-Inhibitors of Complement Components

Provided herein are methods for treating a complement mediated disorder comprising administering a pan-inhibitor of complement components in combination or alternation with a compound of the present disclosure. Pan-inhibitors of complement components are known in the art. In some embodiments, the inhibitor is FUT-175.

Combinations for Prophylactic or Concommitant Anti-Bacterial Therapy

In one aspect of the present disclosure, a method is provided for treating a host in need thereof that comprises administering an effective amount of a prophylactic anti-bacterial vaccine prior to administration of an active compound or its salt or composition for any of the disorders described herein. In another aspect of the present disclosure, a method is provided for treating a host in need thereof that comprises administering an effective amount of a prophylactic anti-bacterial drug, such as a pharmaceutical drug, prior to administration of an active compound or its salt or composition for any of the disorders described herein. In one aspect of the present disclosure, a method is provided for treating a host in need thereof that comprises administering an effective amount of an anti-bacterial vaccine after administration of an active compound or its salt or composition for any of the disorders described herein. In another aspect of the present disclosure, a method is provided for treating a host in need thereof that comprises administering an effective amount of an anti-bacterial drug, such as a pharmaceutical drug, after administration of an active compound or its salt or composition for any of the disorders described herein. In one embodiment, the disorder is PNH, C3G, or aHUS. In one embodiment, the host has received an organ or other tissue or biological fluid transplant. In one embodiment, the host is also administered a C5 inhibitor, for example, eculizumab.

In one aspect of the present disclosure, an active compound or its salt or composition as described herein is administered to a host concomitantly to a subject following the prophylactic administration of a vaccine against a bacterial infection. In some embodiments, the complement-mediated disease or disorder is selected from the group consisting of autoimmune disease, cancer, hematological disease, infectious disease, inflammatory disease, ischemia-reperfusion injury, neurodegenerative disease, neurodegenerative disorder, ocular disease, renal disease, transplant rejection, vascular disease, and vasculitis disease. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present disclosure, an active compound or its salt or composition as described herein is administered to a subject concomitantly with the prophylactic administration of a vaccine against a bacterial infection. In some embodiments, the complement-mediated disease or disorder is selected from the group consisting of autoimmune disease, cancer, hematological disease, infectious disease, inflammatory disease, ischemia-reperfusion injury, neurodegenerative disease, neurodegenerative disorder, ocular disease, renal disease, transplant rejection, vascular disease, and vasculitis disease. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present disclosure, an active compound or its salt or composition as described herein is administered to a subject and, during the administration period of the compound or salt, a vaccine against a bacterial infection is administered to the subject. In some embodiments, the complement-mediated disease or disorder is selected from the group consisting of autoimmune disease, cancer, hematological disease, infectious disease, inflammatory disease, ischemia-reperfusion injury, neurodegenerative disease, neurodegenerative disorder, ocular disease, renal disease, transplant rejection, vascular disease, and vasculitis disease. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present disclosure, the subject is administered an active compound or its salt or composition as described herein in combination with an antibiotic compound for the duration of active compound administration. In some embodiments, the complement-mediated disease or disorder is selected from the group consisting of autoimmune disease, cancer, hematological disease, infectious disease, inflammatory disease, ischemia-reperfusion injury, neurodegenerative disease, neurodegenerative disorder, ocular disease, renal disease, transplant rejection, vascular disease, and vasculitis disease. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present disclosure, an active compound or its salt or composition as described herein is administered to a subject following the prophylactic administration of a vaccine against a bacterial infection, and in combination with an antibiotic compound for the duration of active compound administration. In some embodiments, the complement-mediated disease or disorder is selected from the group consisting of autoimmune disease, cancer, hematological disease, infectious disease, inflammatory disease, ischemia-reperfusion injury, neurodegenerative disease, neurodegenerative disorder, ocular disease, renal disease, transplant rejection, vascular disease, and vasculitis disease. In one embodiment, the complement mediated disorder is PNH or aHUS. In one embodiment, the subject has received an organ or other tissue or biological fluid transplant. In one embodiment, the subject is also administered eculizumab. In one embodiment, the subject, prior to receiving an active compound or its salt or composition as described herein, is vaccinated against a bacterial infection caused by the bacterium *Neisseria meningitidis*. In one embodiment, the subject is vaccinated against a bacterial infection caused by the bacterium *Haemophilus influenzae*. In one embodiment, the *Haemophilus influenzae* is *Haemophilus influenzae* serotype B (Hib).

In one embodiment, the subject is vaccinated against a bacterial infection caused by *Streptococcus pneumoniae*.

In one embodiment, the subject is vaccinated against a bacterial infection caused by the bacterium *Neisseria meningitidis, Haemophilus influenzae*, or *Streptococcus pneumoniae*, or a combination of one or more of *Neisseria meningitidis, Haemophilus influenzae*, or *Streptococcus pneumoniae*.

In one embodiment, the subject is vaccinated against a bacterial infection caused by the bacterium *Neisseria meningitidis, Haemophilus influenzae*, and *Streptococcus pneumoniae*.

In other embodiments, the subject is vaccinated against a bacterial infection caused by a bacterium selected from a Gram-negative bacterium.

In one embodiment, the subject is vaccinated against a bacterial infection caused by a bacterium selected from a Gram-positive bacterium.

In one embodiment, the subject is vaccinated against a bacterial infection caused by the bacterium *Neisseria meningitidis, Haemophilus influenzae*, or *Streptococcus pneumoniae*, or a combination of one or more of *Neisseria meningitidis, Haemophilus influenzae*, or *Streptococcus pneumoniae*, and one or more of, but not limited to, *Bacillus anthracis, Bordetella pertussis, Clostridium tetani, Corynebacterium diphtheria, Coxiella burnetii, Mycobacterium tuberculosis, Salmonella typhi, Vibrio cholerae, Anaplasma phagocytophilum, Ehrlichia ewingii, Ehrlichia chaffeensis, Ehrlichia canis, Neorickettsia sennetsu, Mycobacterium leprae, Borrelia burgdorferi, Borrelia mayonii, Borrelia afzelii, Borrelia garinii, Mycobacterium bovis, Staphylococcus aureus, Streptococcus pyogenes, Treponema pallidum, Francisella tularensis*, and *Yersinia pestis*.

In one embodiment, the subject is vaccinated with one or more vaccines selected from, but not limited to, typhoid vaccine, live (Vivotif Berna Vaccine, PaxVax), typhoid Vi polysaccharide vaccine (Typhim Vi, Sanofi), pneumococcal 23-polyvalent vaccine, PCV13 (Pneumovax 23, Merck), pneumococcal 7-valent vaccine, PCV7 (Prevnar, Pfizer), pneumococcal 13-valent vaccine, PCV13 (Prevnar 13, Pfizer), *Haemophilus* b conjugate (prp-t) vaccine (ActHIB, Sanofi; Hibrix, GSK), *Haemophilus* b conjugate (hboc) vaccine (HibTITER, Neuron Biotech), *Haemophilus* b conjugate (prp-omp) vaccine (PedvaxHIB, Merck), *Haemophilus* b conjugate (prp-t) vaccine/meningococcal conjugate vaccine (MenHibrix, GSK), *Haemophilus* b conjugate (prp-t) vaccine/meningococcal conjugate vaccine/Hepatitis B vaccine (Comvax, Merck), meningococcal polysaccharide vaccine (Menomune A/C/Y/W-135, Sanofi), meningococcal conjugate vaccine/diphtheria CRM197 conjugate (Menveo, GSK; Menactra, Sanofi), meningococcal group B vaccine (Bexsero, GSK; Trumenba, Pfizer), anthrax vaccine adsorbed (Biothrax, Emergent Biosolutions), tetanus toxoid (Te Anatoxal Berna, Hendricks Regional Health), *Bacillus* Calmette and Guérin, live, intravesical (TheraCys, Sanofi; Tice BCG, Organon), cholera vaccine, live, oral (Vachora, Sanofi; Dukoral, SBL Vaccines; ShanChol, Shantha Biotec; Micromedex, Truven Health), tetanus toxoids and diphtheria absorbed (Tdap; Decavac, Sanofi; Tenivac, Sanofi; td, Massachusetts Biological Labs), diphtheria and tetanus toxois and pertussis (DTap; Daptacel, Sanofi; Infanrix, GSK; Tripedia, Sanofi), diphtheria and tetanus toxois and pertussis/polio (Kinrix, GSK; Quadracel, Sanofi), diphtheria and tetanus toxois and pertussis tetanus/hepatitis B/polio (Pediarix, GSK), diphtheria and tetanus toxois and pertussis/polio, *Haemophilus* influenza tybe b (Pentacel, Sanofi), and/or diphtheria, and pertussis (Tdap; Boostrix, GSK; Adacel, Sanofi), or a combination thereof.

As described above, a subject receiving a compound of the present disclosure to treat a disorder is prophylactically administered an antibiotic compound in addition to a compound described herein.

In one embodiment, the subject is administered an antibiotic compound for the duration of administration of the active compound to reduce the development of a bacterial infection.

Antibiotic compounds for concomitant administration with a compound described herein can be any antibiotic useful in preventing or reducing the effect of a bacterial infection. Antibiotics are well known in the art and include, but are not limited to, amikacin (Amikin), gentamicin (Garamycin), kanamycin (Kantrex), neomycin (Neo-Fradin), netilmicin (Netromycin), tobramycin (Nebcin), paromomycin (Humatin), streptomycin, spectinomycin (Trobicin), geldanamycin, herbimycin, rifaximin (Xifaxan), loracarbef (Lorabid), ertapenem (Invanz), doripenem (Doribax), imipenem/cilastatin (Primaxin), meropenem (Merrem), cefadroxil (Duricef), cefazolin (Ancef), cefalotin/cefalothin (Keflin), cephalexin (Keflex), cefaclor (Distaclor), cefamandole (Mandol), cefoxitin (Mefoxin), cefprozil (Cefzil), cefuroxime (Ceftin, Zinnat), cefixime (Cefspan), cefdinir (Omnicef, Cefdiel), cefditoren (Spectracef, Meiact), cefoperazone (Cefobid), cefotaxime (Claforan), cefpodoxime (Vantin) ceftazidime (Fortaz), ceftibuten (Cedax), ceftizoxime (Cefizox), ceftriaxone (Rocephin), cefepime (Maxipime), ceftaroline fosamil (Teflaro), ceftobiprole (Zeftera), teicoplanin (Targocid), vancomycin (Vancocin), telavancin (Vibativ), dalbavancin (Dalvance), oritavancin (Orbactiv), clindamycin (Cleocin), lincomycin (Lincocin), daptomycin (Cubicin), azithromycin (Zithromax, Sumamed, Xithrone), clarithromycin (Biaxin), dirithromycin (Dynabac), erythromycin (Erythocin, Erythroped), roxithromycin, troleandomycin (Tao), telithromycin (Ketek), spiramycin (Rovamycine), aztreonam (Azactam), furazolidone (Furoxone), nitrofurantoin (Macrodantin, Macrobid), linezolid (Zyvox), posizolid, radezolid, torezolid, amoxicillin (Novamox, Amoxil), ampicillin (Principen), azlocillin, carbenicillin (Geocillin), cloxacillin (Tegopen), dicloxacillin (Dynapen), flucloxacillin (Floxapen), mezlocillin (Mezlin), methicillin (Staphcillin), nafcillin (Unipen), oxacillin (Prostaphlin), penicillin G (Pentids), penicillin V (Veetids (Pen-Vee-K), piperacillin (Pipracil), penicillin G (Pfizerpen), temocillin (Negaban), ticarcillin (Ticar), amoxicillin/clavulanate (Augmentin), ampicillin/sulbactam (Unasyn), piperacillin/tazobactam (Zosyn), ticarcillin/clavulanate (Timentin), bacitracin, colistin (Coly-Mycin-S), polymyxin B, ciprofloxacin (Cipro, Ciproxin, Ciprobay), enoxacin (Penetrex), gatifloxacin (Tequin), gemifloxacin (Factive), levofloxacin (Levaquin), lomefloxacin (Maxaquin), moxifloxacin (Avelox), nalidixic acid (NegGram), norfloxacin (Noroxin), ofloxacin (Floxin, Ocuflox), trovafloxacin (Trovan), grepafloxacin (Raxar), sparfloxacin (Zagam), temafloxacin (Omniflox), mafenide (Sulfamylon), sulfacetamide (Sulamyd, Bleph-10), sulfadiazine (Micro-Sulfon), silver sulfadiazine (Silvadene), sulfadimethoxine (Di-Methox, Albon), sulfamethizole (Thiosulfil Forte), sulfamethoxazole (Gantanol), sulfanilamide, sulfasalazine (Azulfidine), sulfisoxazole (Gantrisin), trimethoprim-sulfamethoxazole (Co-trimoxazole) (TMP-SMX) (Bactrim, Septra), sulfonamidochrysoidine (Prontosil), demeclocycline (Declomycin), doxycycline (Vibramycin), minocycline (Minocin), oxytetracycline (Terramycin), tetracycline (Sumycin, Achromycin V, Steclin), clofazimine (Lamprene), dapsone (Avlosulfon), capreomycin (Capastat), cycloserine (Seromycin), ethambutol (Myambutol), ethionamide (Trecator), isoniazid (I.N.H.), pyrazinamide (Aldinamide), rifampicin (Rifadin, Rimactane), rifabutin (Mycobutin), rifapentine (Priftin), streptomycin, arsphenamine (Salvarsan), chloramphenicol (Chloromycetin), fosfomycin (Monurol, Monuril), fusidic acid (Fucidin), metronidazole (Flagyl), mupirocin (Bactroban), platensimycin, quinupristin/dalfopristin (Synercid), thiamphenicol, tigecycline (Tigacyl), tinidazole (Tindamax Fasigyn), trimethoprim (Proloprim, Trimpex), and/or teixobactin, or a combination thereof.

In one embodiment, the subject is administered a prophylactic antibiotic selected from cephalosporin, for example, ceftriaxone or cefotaxime, ampicillin-sulbactam, Penicillin G, ampicillin, chloramphenicol, fluoroquinolone, aztreonam, levofloxacin, moxifloxacin, gemifloxacin, vancomycin, clindamycin, cefazolin, azithromycin, meropenem, ceftaroline, tigecycline, clarithromycin, moxifloxacin, trimethoprim/sulfamethoxazole, cefuroxime, axetil, ciprofloxacin, rifampin, minocycline, spiramycin, and cefixime, or a combination of two or more thereof.

Process of Preparation of Compounds of the Present Disclosure

Abbreviations

ACN Acetonitrile
Ac Acetyl
$Ac_2O$ Acetic anhydride
AcOEt, EtOAc ethyl acetate
AcOH Acetic acid
AcONa Sodium acetate
$AlCl_3$ Aluminum chloride
$BH_3$ borane
$Boc_2O$ di-tert-butyl dicarbonate
$Boc_2NH$ Di-tert-butyl-iminodicarboxylate
BnBr Benzyl bromide
BnOH Benzyl alcohol
Bu Butyl
$Bu_4NHSO_4$ Tetrabutylammonium bisulfate
CAN Ceric ammonium nitrate
$CBr_4$ Carbon tetrabromide
CBz Carboxybenzyl
CDI Carbonyldiimidazole
$CH_3OH$, MeOH Methanol
$CH_3PPh_3Br$ Methyltriphenylphosphonium bromide
$CCl_3Br$ Bromotrichloromethane
$(CoCl)_2$ oxalylchloride
$ClCO_2Et$ ethyl chloroformate
CNBr cyanogen bromide
CsF Cesium fluoride
CuI Cuprous iodide
DAST Diethylaminosulfur trifluoride
DBU 1,8-Diazabicyclo[5.4.0]undec-7-ene,
DCM, $CH_2Cl_2$ Dichloromethane
DIBAL-H Diisobutylaluminium hydride
DIAD Diisopropyl azodicarboxylate
DIEA, DIPEA N,N-diisopropylethylamine
DMA N,N-dimethylacetamide
DMAP 4-Dimethylaminopyridine
$DMBNH_2$ 3,5-Dimethoxybenzylamine
DMF N,N-dimethylformamide
DMS Dimethyl sulfide
DMSO Dimethylsulfoxide
DPPA Diphenyl phosphoryl azide
EDCI 1-Ethyl-3-(3-dimethylaminopropyl)carbodiimide
EEDQ N-Ethoxycarbonyl-2-ethoxy-1,2-dihydroquinoline
Et Ethyl
$Et_3N$, TEA Triethylamine
EtOAc Ethylacetate
EtOH Ethanol
FA Formic acid
HATU 1-[Bis(dimethylamino)methylene]-1H-1,2,3-triazolo[4,5-b]pyridinium3-oxide hexafluorophosphate
$H_2SO_4$ Sulfuric acid
$HBF_4$ Fluoroboric acid
HBr—AcOH Acetic acid hydrogen bromide
HCl Hydrochloric acid
HOBT Hydroxybenzotriazole
iBu, i-Bu, isoBu Isobutyl
iPr, i-Pr, isoPr Isopropyl
${}^{i}Pr_2NEt$ N,N-diisopropylethylamine
$KH_2PO_4$ Potassium dihydrogen phosphate
$K_2CO_3$ Potassium carbonate
KI Potassium iodide
$KMnO_4$ Potassium permanganate
$Li_2CO_3$ Lithium carbonate
LiOH Lithium hydroxide
LiHMDS Lithium bis(trimethylsilyl)amide
Me Methyl
MeCN Acetonitrile
MeI Methyl iodide
Ms Mesyl
MsCl Mesylchloride
MTBE Methyl ${}^{t}$butylether
n-BuLi n-Butyllithium
$NaBH_4$ sodium borohydride
$NaBH_3CN$ Sodium cyanoborohydride
$Na_2SO_4$ Sodium sulfate NaCl Sodium chloride
NaClO Sodium hypochlorite
NaH Sodium hydride
$NaHCO_3$Sodium bicarbonate
NaI Sodium iodide
NaOH Sodium hydroxide
NBS N-bromo succinimide
NCS N-chloro succinimide
$NEt_3$ Trimethylamine
$NH_2SO_3H$ Sulfamic acid
$NH_2OH$ Hydroxylamine
$NH_4OH$ Ammonium hydroxide
$NH_4OAc$ Ammonium acetate
Ni nickel
NMP N-Methyl-2-pyrrolidone
PCC Pyridinium chlorochromate
Pd $(OAc)_2$ Palladium acetate
Pd(dppf)$Cl_2$ [1,1'-Bis(diphenylphosphino) ferrocene]dichloropalladium(II)
$Pd(PPh_3)_2Cl_2$ Bis(triphenylphosphine)palladium(II) dichloride
$Pd(PPh_3)_4$ Tetrakis(triphenylphosphine)palladium(O)
Pd/C Palladium on carbon
$Pd_2$ $(dba)_3$ Tris(dibenzylideneacetone)dipalladium(O)
PMB 4-Methoxybenzyl ether
$PPh_3$ Triphenylphosphine
Pr Propyl
$PtO_2$ Platinum oxide
PTSA p-Toluenesulfonic acid
Py, py Pyridine
PyBOP benzotriazol-1-yl-oxytripyrrolidinophosphonium hexafluorophosphate
RT Room temperature
T3P Propane phosphonic acid anhydride
TBAB Tetra-n-butylammonium bromide
TBAF Tetra-n-butylammonium fluoride
TBAT Tetrabutylammonium difluorotriphenylsilicate
tBu, t-Bu tertbutyl
tBuOK Potassium tert-butoxide
TEA Trimethylamine
TES Tris(hydroxymethyl)methyl]-2-aminoethanesulfonic acid
$Tf_2O$ Trifluoromethanesulfonic anhydride
TFA Trifluoroacetic acid
TFAA Trifluoroacetic anhydride
THF Tetrahydrofuran
$TiCl_4$ Titanium tetrachloride
TMS Trimethylsilane
TMSBr Bromotrimethylsilane
$TMSCHN_2$ Trimethylsilyldiazomethane
tol. toluene
$t_R$ Retention time
Troc 2,2,2-Trichlorethoxycarbonyl chloride
Zn $(CN)_2$ Zinc cyanide General Methods All nonaqueous reactions were performed under an atmosphere of dry argon or nitrogen gas using anhydrous solvents. The progress of reactions and the purity of target compounds were determined using one of the two liquid chromatography (LC) methods A or B disclosed herein. The structure of starting materials, intermediates, and final products was confirmed by standard analytical techniques, including NMR spectroscopy and mass spectrometry.

LC Method A

Instrument: Waters Acquity Ultra Performance LC
Column: ACQUITY UPLC BEH C18 2.1×50 mm, 1.7 μm
Column Temperature: 40° C.
Mobile Phase: Solvent A: $H_2O$+0.05% FA; Solvent B: $CH_3CN$+0.05% FA
Flow Rate: 0.8 mL/min
Gradient: 0.24 min @ 15% B, 3.5 min gradient (15-85% B), then 0.5 min @ 85% B.
Detection: UV (210-410 nm) and MS (SQ in ES+ mode)

LC Method B

Instrument: Shimadzu LC-2010A HT
Column: Athena, C18-WP, 50×4.6 mm, 5 μm
Column Temperature: 40° C.
Mobile Phase: Solvent A: $H_2O/CH_3OH$/FA=90/10/0.05; Solvent B: $H_2O/CH_3OH$/FA=10/90/0.05
Flow Rate: 3 mL/min
Gradient: 0.4 min @ 30% B, 3.4 min gradient (30-100% B), then 0.8 min @ 100% B
Detection: UV (220/254 nm)

Example 1. Non-Limiting Synthetic Examples of Compounds of the Present Disclosure The below schemes are non-limiting examples of methods to make compounds of the present disclosure. The skilled artisan will recognize that there are various modifications that can be performed to make analogs or prepare compounds in other ways.

Scheme 1.
Synthesis of (8S)-N-[(4-Carbamimidoylthiophen-2-yl)methyl]-7-(2-{[4-(4-methylphenoxy)phenyl]-formamido}acetyl)-1,4-dioxa-7-azaspiro[4,4]nonane-8-carboxamide (Compound 1)

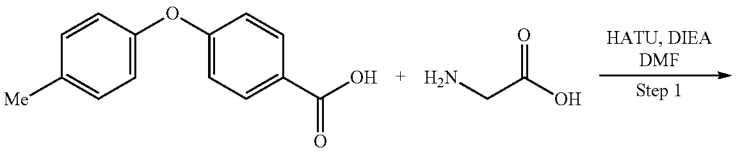

-continued

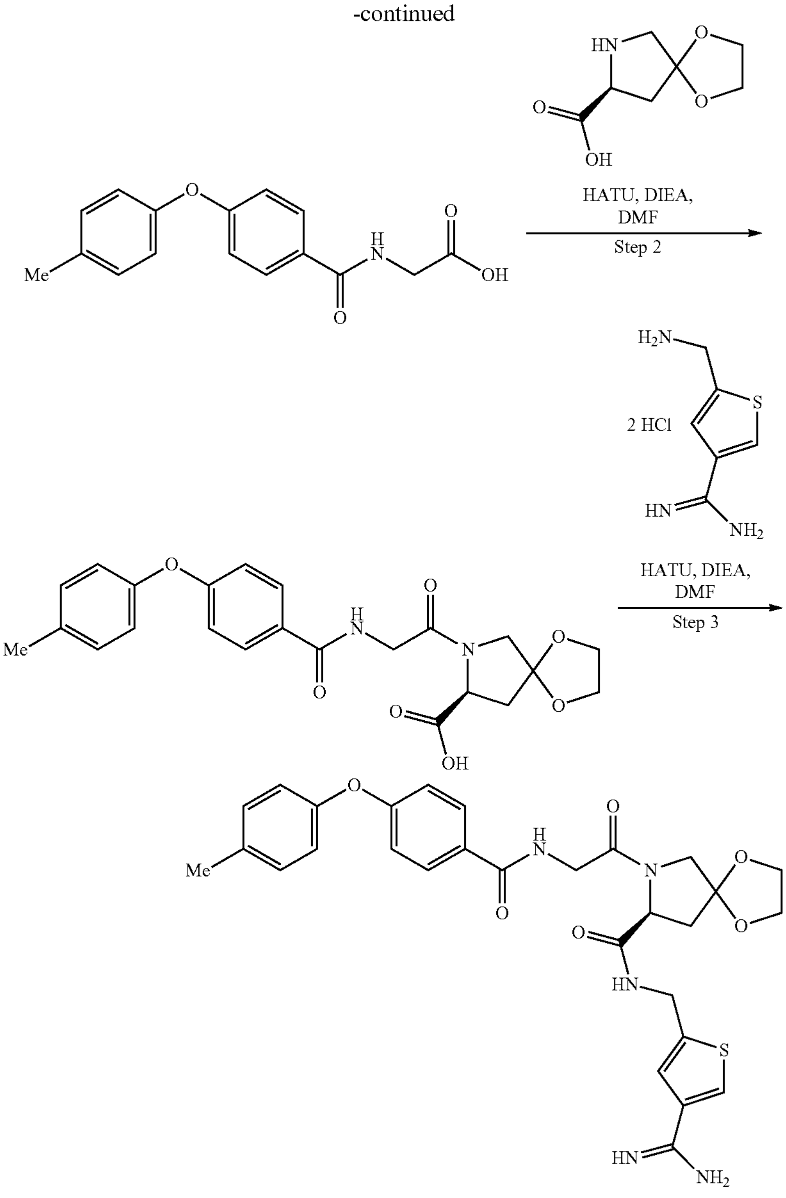

Step 1: 1-[Bis(dimethylamino)methylene]-1H-1,2,3-triazolo[4,5-b]pyridinium 3-oxid hexafluoro phosphate (0.34 g, 0.90 mmol, 1.1 equiv) was added to a stirring solution of 4-(4-methylphenoxy)benzoic acid (0.18 g, 0.81 mmol, 1.0 equiv) in DMF (8.0 mL, 0.1 M, 44 vols) at room temperature. Next, diisopropylethylamine (0.42 mL, 2.4 mmol, 3 equiv) was added. The mixture was stirred at room temperature for 90 minutes. After 90 minutes of stirring, glycine (0.061 g, 0.81 mmol, 1.0 equiv) was added in a single portion. This mixture was stirred at room temperature for 1 hour. The reaction mixture was directly purified via reverse phase HPLC to isolate {[4-(4-methylphenoxy)-phenyl]formamido}acetic acid (22 mg, 0.077 mmol, yield 9.6%).

Step 2 and Step 3: 1-[Bis(dimethylamino)methylene]-1H-1,2,3-triazolo[4,5-b]pyridinium 3-oxid hexafluorophosphate (0.016 g, 0.042 mmol, 1 equiv) and {[4-(4-methylphenoxy)phenyl]formamido}acetic acid (12 mg, 0.042 mmol, 1 equiv) were combined in a reaction vessel, and the vessel was evacuated and charged with argon. The mixture was taken up in DMF (1.0 mL, 0.042 M, 83 vols) and Hunig's Base (0.022 g, 0.029 mL, 0.17 mmol, 4 equiv) was added. The amber colored solution was evaluated by LCMS. Conversion to the ester was confirmed via LCMS. After 15 minutes of stirring at room temperature, (8S)-1,4-dioxa-7-azaspiro[4.4]nonane-8-carboxylic acid (0.007 g, 0.042 mmol, 1.0 equiv) was added and the mixture was stirred for 1 hour at which point LCMS showed conversion to the desired coupled product.

To this stirring mixture was added 1-[bis(dimethylamino)methylene]-1H-1,2,3-triazolo[4,5-b]pyridinium 3-oxid hexafluorophosphate (0.016 g, 0.042 mmol, 1 equiv) and 5-(aminomethyl)thiophene-3-carboximidamide dihydrochloride (0.010 g, 0.042 mmol, 1 equiv) in one single combined portion. After 30 minutes, LCMS confirmed conversion to the amidine product. The mixture was immediately purified via reverse phase HPLC to afford (8S)—N-[(4-carbamimidoylthiophen-2-yl)methyl]-7-(2-{[4-(4-methylphenoxy)phenyl]formamido}acetyl)-1,4-dioxa-7-azaspiro[4.4]nonane-8-carboxamide (4.5 mg, 0.008 mmol, yield 19%) $^1$H NMR (400 MHz, Methanol-d4) δ 8.70 (t, J=6.0 Hz, 1H), 8.23-8.19 (m, 1H), 7.89-7.79 (m, 2H), 7.43 (d, J=1.5 Hz, 1H), 7.25 (d, J=8.1 Hz, 2H), 7.03-6.93 (m, 4H), 4.69-4.52 (m, 3H), 4.23 (dd, J=16.7, 4.4 Hz, 1H), 4.17-4.05 (m, 1H), 4.06-3.93 (m, 4H), 3.80-3.65 (m, 2H), 2.45 (dd, J=13.2, 9.2 Hz, 1H), 2.37 (s, 3H), 2.24 (dd, J=13.3, 5.5 Hz, 1H).

Scheme 2.
Synthesis of (8S)-N-[(4-Carbamimidoylthiophen-2-yl)methyl]-7-{2-[(4-phenoxyphenyl)-formamido]acetyl}-1,4-dioxa-7-azaspiro[4,4]nonane-8-carboxamide (Compound 2)

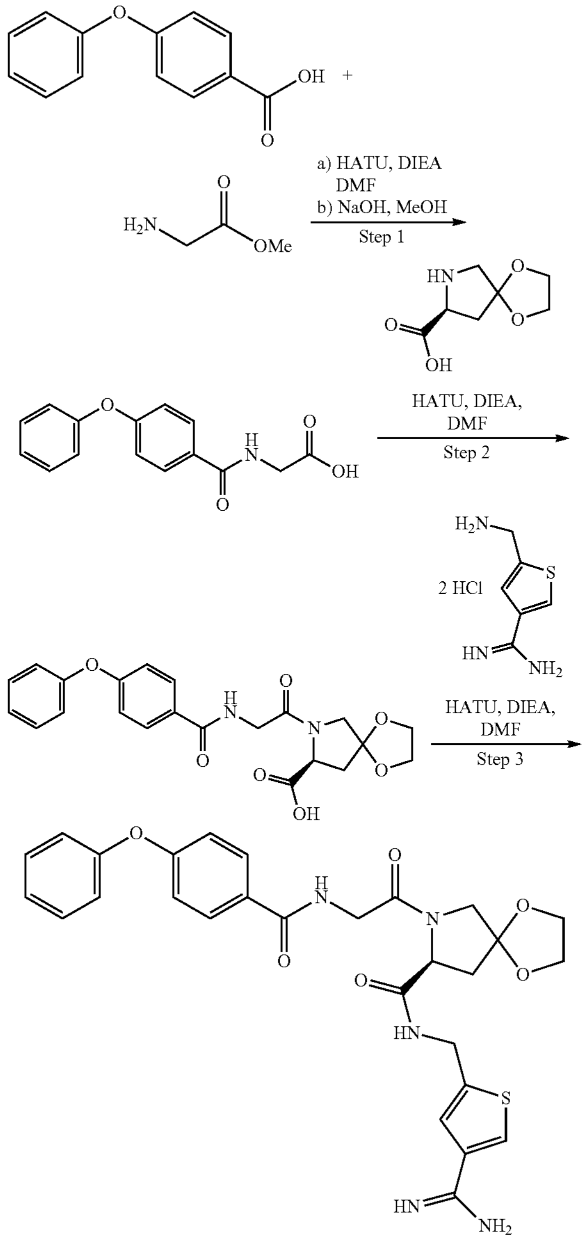

Step 1: 1-[Bis(dimethylamino)methylene]-1H-1,2,3-triazolo[4,5-b]pyridinium 3-oxid hexafluoro phosphate (3.7 g, 9.8 mmol, 1.0 equiv) was added to a stirring solution of p-phenoxybenzoic acid (2.0 g, 9.3 mmol, 1.0 equiv) in DMF (93 mL, 0.1 M, 46 vols) at room temperature. Next, diisopropylethylamine (3.0 g, 4.1 mL, 23 mmol, 2.5 equiv) added. The mixture was stirred at room temperature for 90 minutes before methyl 2-aminoacetate (0.83 g, 9.3 mmol, 1.0 equiv) was added in a single portion. This mixture was stirred at room temperature for 1 hour. The reaction mixture was concentrated to afford a crude brown residue that was adsorbed into Celite and purified via silica gel column chromatography eluting with 2:1 hexanes:EtOAc to afford methyl 2-[(4-phenoxyphenyl)formamido]acetate (1.8 g, 6.3 mmol, yield 68%) as a white solid.

Methyl 2-[(4-phenoxyphenyl)formamido]acetate (1.8 g, 6.3 mmol, 1.0 equiv) was taken up in methanol (50 mL, 0.13 M, 28 vols) and lithium hydroxide 1M aqueous solution (0.30 g, 13 mL, 13 mmol, 2.0 equiv) was added. The solution was stirred at room temperature for 2 hours at which point LCMS showed quantitative conversion to the acid. The mixture was then acidified with the addition of HCl in MeOH until pH was acidic. The mixture was concentrated to a dry solid that was suspended in EtOAc (50 mL) and stirred vigorously for 30 minutes. The EtOAc was decanted off and the process was repeated once more. The combined organic supernatant was dried over $Na_2SO_4$, filtered and concentrated to afford [(4-phenoxyphenyl)formamido]acetic acid (1.7 g, 6.3 mmol, yield 99%) as a white solid.

Step 2 and Step 3: 1-[Bis(dimethylamino)methylene]-1H-1,2,3-triazolo[4,5-b]pyridinium 3-oxid hexafluorophosphate (0.010 g, 0.026 mmol, 1.0 equiv) and [(4-phenoxyphenyl) formamido]acetic acid (7 mg, 0.026 mmol, 1.0 equiv) were combined in a reaction vessel that was evacuated and charged with argon. The mixture was taken up in DMF (1.0 mL, 0.026 M, 140 vols) and Hunig's Base (0.013 g, 0.018 mL, 0.10 mmol, 4.0 equiv) was added. The amber colored solution was evaluated by LCMS. LCMS confirmed conversion to the ester. After 15 minutes of stirring at room temperature, (8S)-1,4-dioxa-7-azaspiro[4.4]nonane-8-carboxylic acid (0.004 g, 0.026 mmol, 1.0 equiv) was added and the mixture was stirred for 1 hour. LCMS showed conversion to the desired coupled product.

Subsequently to the same reaction vessel was added 1-[bis(dimethylamino)methylene]-1H-1,2,3-triazolo[4,5-b] pyridinium 3-oxid hexafluorophosphate (0.010 g, 0.026 mmol, 1 equiv) and 5-(aminomethyl)thiophene-3-carboximidamide dihydrochloride (0.0060 g, 0.026 mmol, 1.0 equiv) in one single combined portion. LCMS after 30 minutes showed conversion to the amidine product. The mixture was directly purified via reverse phase HPLC to afford (8S)—N-[(4-carbamimidoylthiophen-2-yl)methyl]-7-{2-[(4-phenoxyphenyl)formamido]acetyl}-1,4-dioxa-7-azaspiro[4.4]nonane-8-carboxamide (7.0 mg, 0.012 mmol, yield 48%) as a white solid. $^1$H NMR (400 MHz, Methanol-d4) δ 8.74-8.63 (m, 1H), 8.22 (d, J=1.6 Hz, 1H), 7.94-7.81 (m, 2H), 7.48-7.39 (m, 3H), 7.22 (t, J=7.4 Hz, 1H), 7.12-6.98 (m, 4H), 4.69-4.53 (m, 3H), 4.23 (d, J=16.6 Hz, 1H), 4.18-4.04 (m, 1H), 4.06-3.92 (m, 4H), 3.81-3.76 (m, 2H), 2.45 (dd, J=13.3, 9.2 Hz, 1H), 2.24 (dd, J=13.2, 5.4 Hz, 1H).

Scheme 3. Synthesis of Compound 3 - Compound 15

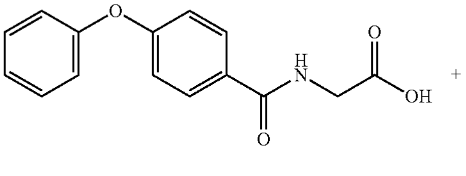

-continued

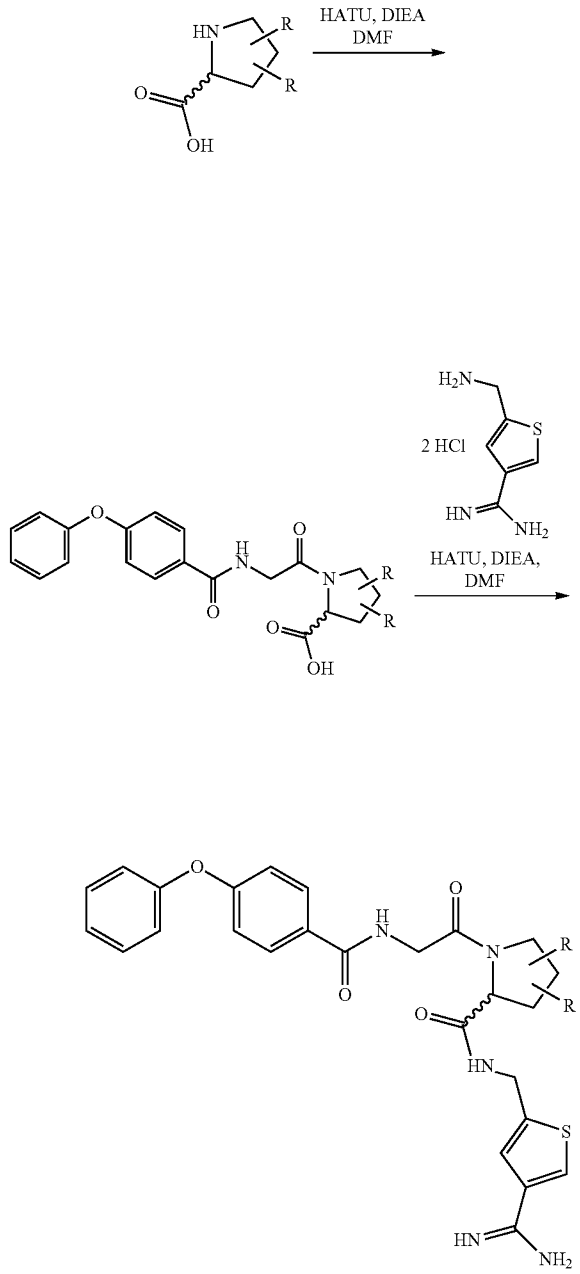

1-[Bis(dimethylamino)methylene]-1H-1,2,3-triazolo[4,5-b]pyridinium 3-oxid hexafluorophosphate (1.0 equiv) and [(4-phenoxyphenyl)formamido]acetic acid (1.0 equiv) were combined in a reaction vessel that was evacuated and charged with argon gas. The mixture was taken up in DMF (140 vols) and Hunig's base (4.0 equiv) was added. After 60 minutes of stirring at room temperature, the corresponding amino acid (1.0 equiv) was added and the mixture was stirred for 1 hour. Following this period of stirring, to the same reaction vessel, was added another aliquot of 1-[bis(dimethylamino)methylene]-1H-1,2,3-triazolo[4,5-b]pyridinium 3-oxid hexafluorophosphate (1.0 equiv) and 5-(aminomethyl)thiophene-3-carboximidamide dihydrochloride (1.0 equiv) in a single combined portion. After 30 minutes of stirring, the mixture was directly purified via reverse phase HPLC to afford the amidine product.

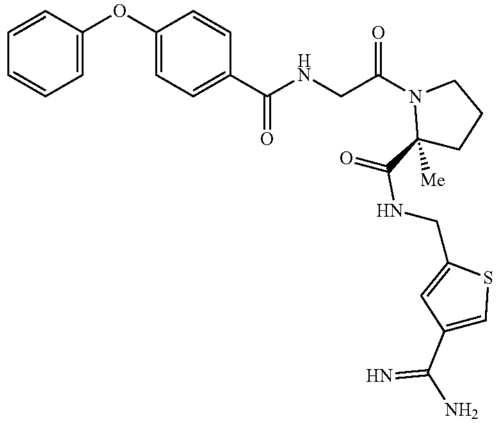 [SMILES: C[C@@]1(C(=O)NCc2cc(C(=N)N)cs2)CCCN1C(=O)CNC(=O)c1ccc(Oc2ccccc2)cc1]

(2S)—N-[(4-Carbamimidoylthiophen-2-yl)methyl]-2-methyl-1-{2-[(4-phenoxyphenyl)formamido]acetyl}pyrrolidine-2-carboxamide (Compound 3): (2S)—N-[(4-Carbamimidoylthiophen-2-yl)methyl]-2-methyl-1-{2-[(4-phenoxyphenyl)formamido]acetyl}pyrrolidine-2-carboxamide was prepared according to Scheme 3 with the use of (2S)-2-methylpyrrolidine-2-carboxylic acid as the central amino acid. $^{1}$H NMR (400 MHz, Methanol-d4) δ 8.75 (dd, J=4.4, 1.3 Hz, 1H), 8.44 (ddd, J=10.0, 7.3, 3.6 Hz, 2H), 8.17 (d, J=1.6 Hz, 1H), 7.88-7.79 (m, 2H), 7.54 (dd, J=8.4, 4.4 Hz, 1H), 7.48-7.38 (m, 3H), 7.27-7.18 (m, 1H), 7.12-6.97 (m, 4H), 4.66-4.49 (m, 2H), 4.30 (d, J=16.6 Hz, 1H), 4.02 (d, J=16.5 Hz, 1H), 3.88 (dt, J=10.0, 6.7 Hz, 1H), 3.83-3.67 (m, 3H), 2.21 (dd, J=11.7, 6.5 Hz, 1H), 2.18-1.93 (m, 3H), 1.65 (s, 3H).

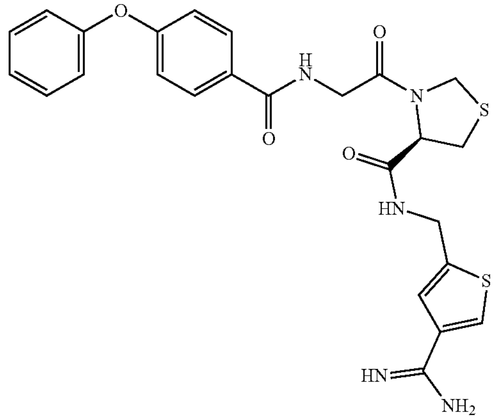 [SMILES: N=C(N)c1csc(CNC(=O)[C@@H]2CSCN2C(=O)CNC(=O)c2ccc(Oc3ccccc3)cc2)c1]

(4R)—N-[(4-Carbamimidoylthiophen-2-yl)methyl]-3-{2-[(4-phenoxyphenyl)formamido]acetyl}-1,3-thiazolidine-4-carboxamide (Compound 4): (4R)—N-[(4-Carbamimidoylthiophen-2-yl)methyl]-3-{2-[(4-phenoxyphenyl)formamido]acetyl}-1,3-thiazolidine-4-carboxamide was prepared according to Scheme 3 with the use of thioproline as the central amino acid. $^{1}$H NMR (400 MHz, Methanol-d4) δ 8.76 (s, 1H), 8.28-8.19 (m, 1H), 7.91-7.82 (m, 2H), 7.49-7.39 (m, 3H), 7.27-7.18 (m, 1H), 7.13-6.99 (m, 4H), 5.04-4.93 (m, 1H), 4.87 (d, J=8.6 Hz, 1H), 4.79 (s, 1H), 4.62 (q, J=16.0, 13.5 Hz, 2H), 4.39 (d, J=16.6 Hz, 1H), 4.24-4.11 (m, 1H), 3.39 (dd, J=12.0, 7.0 Hz, 1H), 3.25 (dd, J=11.9, 3.4 Hz, 1H).

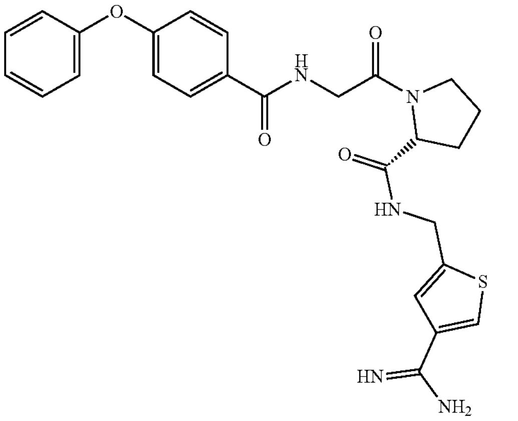

(2R)—N-[(4-Carbamimidoylthiophen-2-yl)methyl]-1-{2-[(4-phenoxyphenyl)-formamido]acetyl}pyrrolidine-2-carboxamide (Compound 5): (2R)—N-[(4-Carbamimidoylthiophen-2-yl)methyl]-1-{2-[(4-phenoxyphenyl)-formamido]acetyl}pyrrolidine-2-carboxamide was prepared according to Scheme 3 with the use of D-proline as the central amino acid. $^1$H NMR (400 MHz, Methanol-d4) δ 8.68 (m, 1H), 8.29-8.18 (m, 1H), 7.92-7.81 (m, 2H), 7.54-7.38 (m, 3H), 7.22 (t, J=7.4 Hz, 1H), 7.11-7.03 (m, 2H), 7.06-6.97 (m, 2H), 4.59 (d, J=5.0 Hz, 1H), 4.59-4.47 (m, 4H), 4.28-4.17 (m, 1H), 3.70 (t, J=8.5 Hz, 1H), 2.18-2.01 (m 4H).

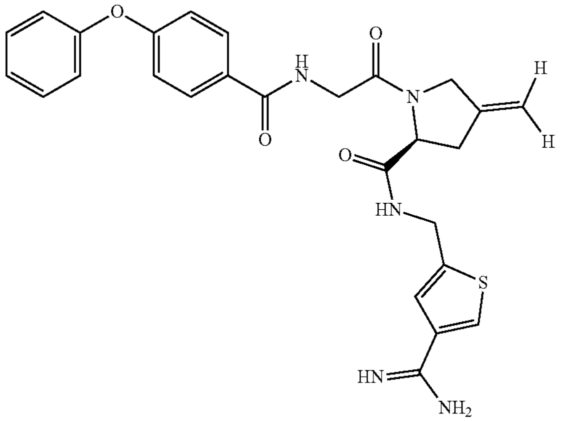 [SMILES: C=C1C[C@@H](C(=O)NCc2cc(C(=N)N)cs2)N(C(=O)CNC(=O)c2ccc(Oc3ccccc3)cc2)C1]

(2S)—N-[(4-Carbamimidoylthiophen-2-yl)methyl]-4-methylidene-1-{2-[(4-phenoxyphenyl)formamido]acetyl}pyrrolidine-2-carboxamide (Compound 6): (2S)—N-[(4-Carbamimidoylthiophen-2-yl)methyl]-4-methylidene-1-{2-[(4-phenoxyphenyl)formamido]acetyl}pyrrolidine-2-carboxamide was prepared according to Scheme 3 with the use of methylidenepyrrolidine-2-carboxylic acid as the central amino acid. $^1$H NMR (400 MHz, Methanol-d4) δ 8.81 (s, 1H), 8.30-8.22 (m, 2H), 7.88-7.81 (m, 2H), 7.53 (br s, 1H), 7.49-7.38 (m, 3H), 7.22 (t, J=7.4 Hz, 1H), 7.12-6.98 (m, 4H), 4.88 (s, 0H), 4.74-4.57 (m, 2H), 4.37-4.24 (m, 1H), 4.04-3.89 (m, 2H), 2.35 (qd, J=14.3, 9.4, 7.4 Hz, 2H), 2.13 (q, J=8.6, 8.1 Hz, 1H), 2.05-1.95 (m, 1H), 1.88 (p, J=7.5 Hz, 2H).

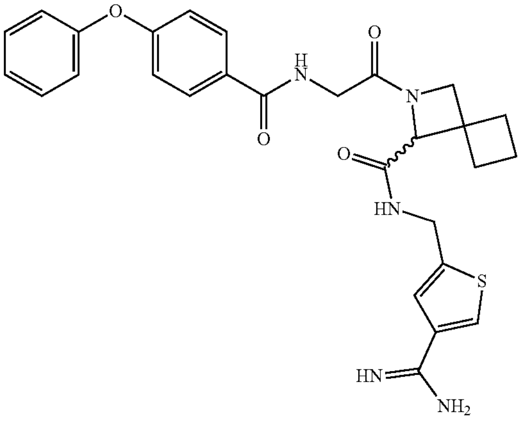 [SMILES: N=C(N)c1csc(CNC(=O)C2N(C(=O)CNC(=O)c3ccc(Oc4ccccc4)cc3)CC23CCC3)c1]

N-[(4-Carbamimidoylthiophen-2-yl)methyl]-2-{2-[(4-phenoxyphenyl)formamido]acetyl}-2-azaspiro[3.3]heptane-1-carboxamide (Compound 7): N-[(4-Carbamimidoylthiophen-2-yl)methyl]-2-{2-[(4-phenoxyphenyl)formamido]acetyl}-2-azaspiro[3.3]heptane-1-carboxamide was prepared according to Scheme 3 with the use of 2-azaspiro[3.3]heptane-1-carboxylic acid as the central amino acid. $^1$H NMR (400 MHz, Methanol-d4) δ 8.81 (br s, 1H), 8.30-8.22 (m, 1H), 7.88-7.81 (m, 2H), 7.53-7.38 (m, 3H), 7.22 (t, J=7.4 Hz, 1H), 7.12-6.98 (m, 4H), 4.91-4.75 (m, 1H), 4.74-4.57 (m, 3H), 4.37-4.24 (m, 1H), 4.05 (d, J=15.7 Hz, 1H), 4.04-3.89 (m, 1H), 2.35 (qd, J=14.3, 9.4, 7.4 Hz, 2H), 2.13 (q, J=8.6, 8.1 Hz, 1H), 2.00 (d, J=16.1 Hz, 1H), 1.88 (p, J=7.5 Hz, 2H).

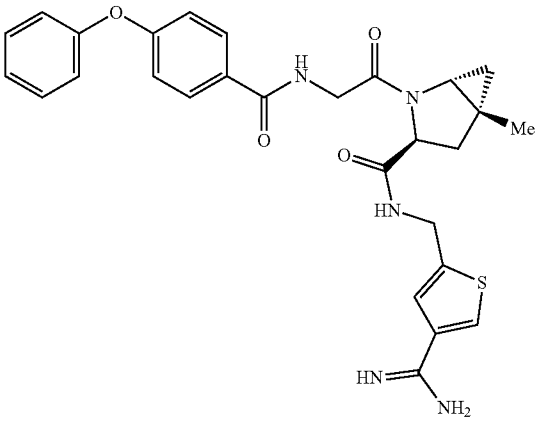 [SMILES: C[C@@]12C[C@@H](C(=O)NCc3cc(C(=N)N)cs3)N(C(=O)CNC(=O)c3ccc(Oc4ccccc4)cc3)[C@@H]1C2]

(1R,3S,5R)—N-[(4-Carbamimidoylthiophen-2-yl)methyl]-5-methyl-2-{2-[(4-phenoxyphenyl)formamido]acetyl}-2-azabicyclo[3.1.0]hexane-3-carboxamide (Compound 8): (1R,3S,5R)—N-[(4-Carbamimidoylthiophen-2-yl)methyl]-5-methyl-2-{2-[(4-phenoxyphenyl)formamido]acetyl}-2-azabicyclo[3.1.0]hexane-3-carboxamide was prepared according to Scheme 3 with the use of (1R,3S,5R)-5-methyl-2-{2-[(4-phenoxyphenyl)formamido]acetyl}-2-azabicyclo[3.1.0]hexane-3-carboxylic acid as the central amino acid. $^1$H NMR (400 MHz, Methanol-d4) δ 8.72 (t, J=6.0 Hz, 1H), 8.30-8.21 (m, 1H), 7.93-7.83 (m, 2H), 7.46-7.38 (m, 3H), 7.22 (t, J=7.5 Hz, 1H), 7.05 (ddd, J=20.7, 7.7, 1.7 Hz, 4H), 4.64-4.57 (m, 2H), 4.45 (d, J=16.8 Hz, 1H), 4.39 (dd, J=9.4, 5.0 Hz, 1H), 4.31 (d, J=16.8 Hz, 1H), 3.39-3.33 (m, 1H), 2.51 (dd, J=13.4, 9.4 Hz, 1H), 2.15-2.05 (m, 1H), 1.32 (s, 3H), 1.03 (t, J=5.4 Hz, 1H), 0.88 (dd, J=5.5, 2.4 Hz, 1H).

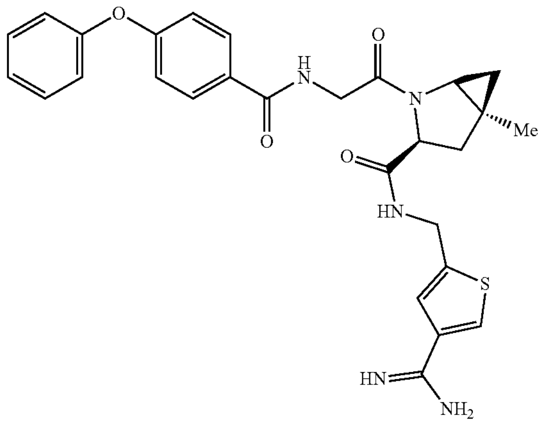

(1S,3S,5S)—N-[(4-Carbamimidoylthiophen-2-yl)methyl]-5-methyl-2-{2-[(4-phenoxyphenyl)formamido]acetyl}-2-azabicyclo[3.1.0]hexane-3-carboxamide (Compound 9): (1 S,3S,5S)—N-[(4-Carbamimidoylthiophen-2-yl)methyl]-5-methyl-2-{2-[(4-phenoxyphenyl)formamido]acetyl}-2-azabicyclo[3.1.0]hexane-3-carboxamide was prepared according to Scheme 3 with the use of (1S,3S,5S)-5-methyl-2-azabicyclo[3.1.0]hexane-3-carboxylic acid as the central amino acid. $^{1}$H NMR (400 MHz, Methanol-d4) δ 8.23 (s, 1H), 7.94-7.81 (m, 2H), 7.52-7.39 (m, 3H), 7.27-7.18 (m, 1H), 7.12-6.98 (m, 4H), 4.88 (d, J=3.4 Hz, 1H), 4.66-4.50 (m, 2H), 4.36 (d, J=2.9 Hz, 2H), 3.43 (dd, J=6.0, 2.5 Hz, 1H), 2.43 (td, J=12.3, 11.1, 1.6 Hz, 1H), 2.20 (dd, J=13.4, 3.4 Hz, 1H), 1.32 (s, 3H), 1.15 (dd, J=5.8, 2.5 Hz, 1H), 0.86-0.78 (m, 1H).

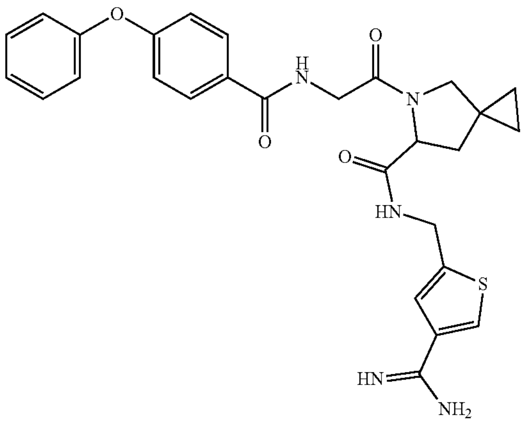 [SMILES: N=C(N)c1csc(CNC(=O)C2CC3(CC3)CN2C(=O)CNC(=O)c2ccc(Oc3ccccc3)cc2)c1]

N-[(4-Carbamimidoylthiophen-2-yl)methyl]-5-{2-[(4-phenoxyphenyl)formamido]acetyl}-5-azaspiro[2.4]heptane-6-carboxamide (Compound 10): N-[(4-Carbamimidoylthiophen-2-yl)methyl]-5-{2-[(4-phenoxyphenyl)formamido]acetyl}-5-azaspiro[2.4]heptane-6-carboxamide can be prepared according to Scheme 3. $^{1}$H NMR (400 MHz, Methanol-d4) δ 8.52-8.50 (br, s, 1H), 8.29-8.27 (m, 1H), 7.94-7.87 (m, 2H), 7.46-7.40 (m, 3H), 7.25-7.20 (m, 3H), 7.12-7.00 (m, 4H), 4.62-4.50 (m, 3H), 3.87-3.73 (m, 2H), 2.75-4.73 (m, 1H), 2.63-4.61 (m, 1H), 4.27-4.07 (m, 2H) 0.85-0.70 (m, 4H).

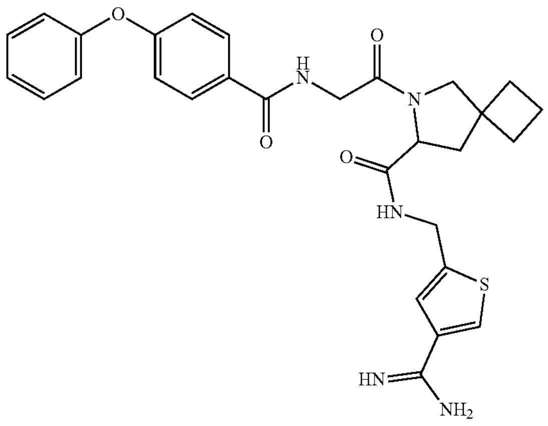 [SMILES: N=C(N)c1csc(CNC(=O)C2CC3(CCC3)CN2C(=O)CNC(=O)c2ccc(Oc3ccccc3)cc2)c1]

N-[(4-Carbamimidoylthiophen-2-yl)methyl]-6-{2-[(4-phenoxyphenyl)formamido]acetyl}-6-azaspiro[3.4]octane-7-carboxamide (Compound 11): N-[(4-Carbamimidoylthiophen-2-yl)methyl]-6-{2-[(4-phenoxyphenyl)formamido]acetyl}-6-azaspiro[3.4]octane-7-carboxamide was prepared according to Scheme 3 with the use of 6-azaspiro[3.4]octane-7-carboxylic acid as the central amino acid. $^{1}$H NMR (400 MHz, Methanol-d4) δ 8.50 (s, 1H), 8.21 (m, 1H), 7.90-7.82 (m, 2H), 7.48-7.39 (m, 3H), 7.27-7.18 (m, 1H), 7.12-6.98 (m, 4H), 4.66-4.51 (m, 2H), 4.47 (dd, J=8.5, 5.6 Hz, 1H), 4.26-4.17 (m, 2H), 3.78-3.60 (m, 2H), 2.32 (dd, J=12.7, 8.5 Hz, 1H), 2.18-1.88 (m, 7H).

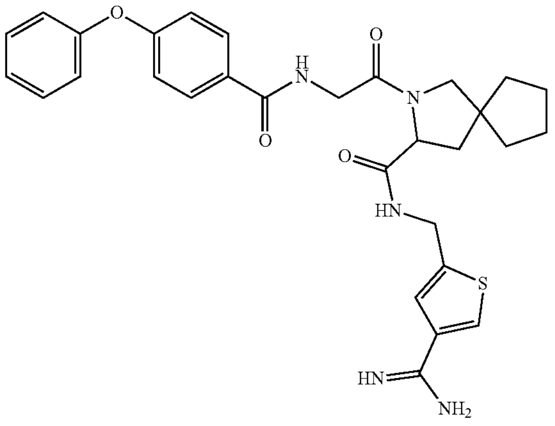 [SMILES: N=C(N)c1csc(CNC(=O)C2CC3(CCCC3)CN2C(=O)CNC(=O)c2ccc(Oc3ccccc3)cc2)c1]

(3S)—N-[(4-Carbamimidoylthiophen-2-yl)methyl]-2-{2-[(4-phenoxyphenyl)formamido]acetyl}-2-azaspiro[4.4]nonane-3-carboxamide (Compound 12): (3S)—N-[(4-Carbamimidoylthiophen-2-yl)methyl]-2-{2-[(4-phenoxyphenyl)formamido]acetyl}-2-azaspiro[4.4]nonane-3-carboxamide was prepared according to Scheme 3 with the use of 2-azaspiro[4.4]nonane-3-carboxylic acid as the central amino acid. $^{1}$H NMR (400 MHz, Methanol-d4) δ 8.57 (s, 1H), 8.22 (m, 1H), 7.90-7.82 (m, 2H), 7.48-7.39 (m, 3H), 7.27-7.18 (m, 1H), 7.12-6.98 (m, 4H), 4.59 (s, 2H), 4.47 (t, J=7.9 Hz, 1H), 4.27-4.04 (m, 2H), 3.75-3.55 (m, 2H), 2.23 (dd, J=12.5, 8.2 Hz, 1H), 1.95 (dd, J=12.6, 7.7 Hz, 1H), 1.78-1.52 (m, 8H).

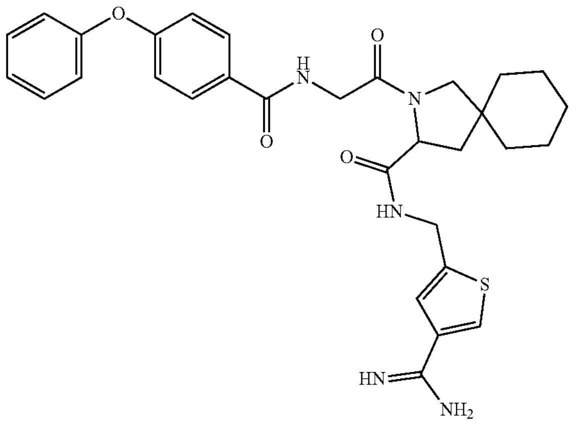 [SMILES: N=C(N)c1csc(CNC(=O)C2CC3(CCCCC3)CN2C(=O)CNC(=O)c2ccc(Oc3ccccc3)cc2)c1]

(3S)—N-[(4-Carbamimidoylthiophen-2-yl)methyl]-2-{2-[(4-phenoxyphenyl)formamido]acetyl}-2-azaspiro[4.5]decane-3-carboxamide (Compound 13): (3S)—N-[(4-Carbamimidoylthiophen-2-yl)methyl]-2-{2-[(4-phenoxyphenyl)formamido]acetyl}-2-azaspiro[4.5]decane-3-carboxamide was prepared according to Scheme 3 with the use of 2-azaspiro[4.5]decane-3-carboxylic acid as the central amino acid. $^{1}$H NMR (400 MHz, Methanol-d4) δ 8.55 (br s, 1H), 8.29 (dd, J=3.6, 1.6 Hz, 1H), 7.93-7.86 (m, 2H), 7.50-7.38 (m, 3H), 7.27-7.17 (m, 1H), 7.13-6.99 (m, 4H), 4.72-4.59 (m, 1H), 4.56 (dd, J=15.5, 6.1 Hz, 1H), 4.26 (dd, J=20.6, 16.7 Hz, 1H), 4.12 (dd, J=16.7, 6.0 Hz, 1H), 3.91-3.61 (m, 2H), 3.60 (d, J=4.3 Hz, 1H), 3.52 (s, 1H), 2.85 (dd, J=7.2, 4.5 Hz, 1H), 2.75 (dd, J=7.1, 4.0 Hz, 1H), 1.59-1.29 (m, 10H).

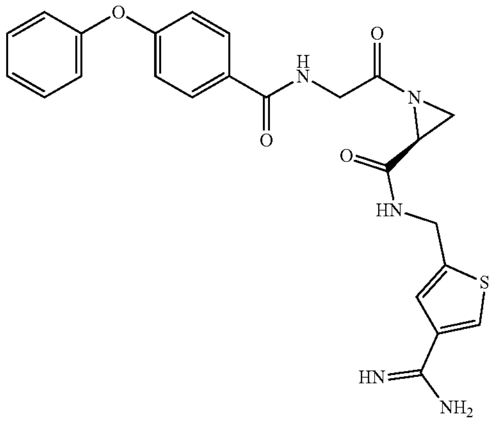 [SMILES: N=C(N)c1csc(CNC(=O)[C@@H]2CN2C(=O)CNC(=O)c2ccc(Oc3ccccc3)cc2)c1]

(2S)—N-[(4-Carbamimidoylthiophen-2-yl)methyl]-1-{2-[(4-phenoxyphenyl)formamido]acetyl}aziridine-2-carboxamide (Compound 14): (2S)—N-[(4-Carbamimidoylthiophen-2-yl)methyl]-1-{2-[(4-phenoxyphenyl)formamido]acetyl}aziridine-2-carboxamide was prepared according to Scheme 3 with the use of lithio (2S)-aziridine-2-carboxylate as the central amino acid. $^{1}$H NMR (400 MHz, Methanol-d4) δ 8.33 (br s, 1H), 8.25-8.23 (m, 1H), 7.91-7.85 (m, 2H), 7.50-7.39 (m, 3H), 7.27-7.18 (m, 1H), 7.12-7.00 (m, 4H), 4.64-4.49 (m, 2H), 4.23 (d, J=3.2 Hz, 2H), 4.06 (s, 1H), 2.74-2.65 (m, 1H), 2.50 (dd, J=3.2, 1.5 Hz, 1H).

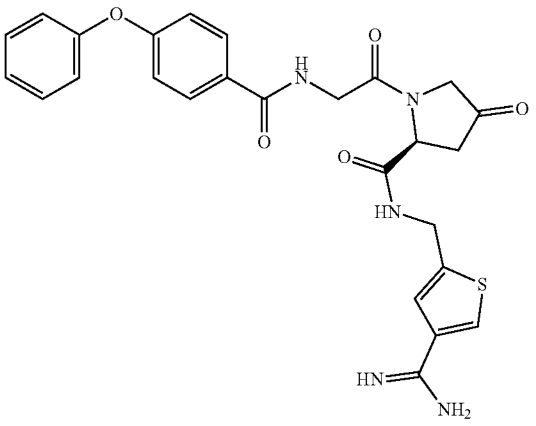 [SMILES: N=C(N)c1csc(CNC(=O)[C@@H]2CC(=O)CN2C(=O)CNC(=O)c2ccc(Oc3ccccc3)cc2)c1]

(2S)—N-[(4-Carbamimidoylthiophen-2-yl)methyl]-4-oxo-1-{2-[(4-phenoxyphenyl)formamido]acetyl}pyrrolidine-2-carboxamide (Compound 15): (2S)—N-[(4-Carbamimidoylthiophen-2-yl)methyl]-4-oxo-1-{2-[(4-phenoxyphenyl)formamido]acetyl}pyrrolidine-2-carboxamide was prepared according to Scheme 3 with the use of 4-oxoproline as the central amino acid. $^{1}$H NMR (400 MHz, Methanol-d4) δ 8.50 (br s, 1H), 8.28-8.19 (m, 1H), 7.94-7.81 (m, 2H), 7.47-7.41 (m, 3H), 7.23 (t, J=7.2 Hz, 1H), 7.12-6.99 (m, 4H), 5.06-5.01 (m, 1H), 4.64-4.53 (m, 3H), 4.33-4.04 (m, 4H), 3.76-3.74 (m, 1H).

Scheme 4. Synthesis of Compound 16 - Compound 27

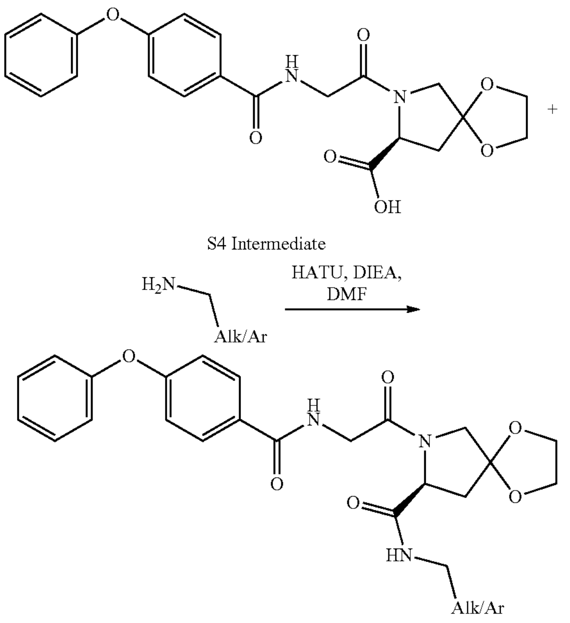

To a stirring mixture of the in situ generated GlyPro peptide (S4 Intermediate) in DMF (140 vols) (containing excess Hünigs base) was added 1-[bis(dimethylamino)methylene]-1H-1,2,3-triazolo[4,5-b]pyridinium 3-oxid hexafluoro phosphate (1.0 equiv) and an amine nucleophile (1.0 equiv) in a single combined portion. The mixture was allowed to stir at room temperature for 1 hour. The mixture was directly purified via reverse phase HPLC to afford the desired coupled product after concentration of the appropriate fractions.

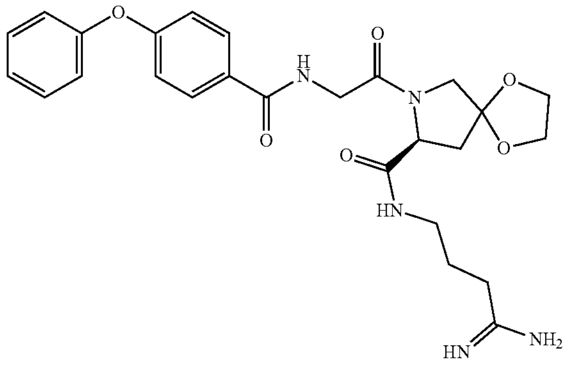 [SMILES: N=C(N)CCCNC(=O)[C@@H]1CC2(CN1C(=O)CNC(=O)c1ccc(Oc3ccccc3)cc1)OCCO2]

(8S)—N-(3-Carbamimidoylpropyl)-7-{2-[(4-phenoxyphenyl)formamido]acetyl}-1,4-dioxa-7-azaspiro[4.4]nonane-8-carboxamide (Compound 16): (8S)—N-(3-Carbamimidoylpropyl)-7-{2-[(4-phenoxyphenyl)formamido]acetyl}-1,4-dioxa-7-azaspiro[4.4]nonane-8-carboxamide was prepared according to Scheme 4 with the use of 4-aminobutanimidamide dihydrochloride as the amine nucleophile. $^{1}$H NMR (400 MHz, Methanol-d4) δ 7.94-7.84 (m, 2H), 7.49-7.39 (m, 2H), 7.23 (t, J=7.5 Hz, 1H), 7.12-6.99 (m, 4H), 4.51 (dd, J=8.9, 6.2 Hz, 1H), 4.26 (d, J=16.7 Hz, 1H), 4.09 (d, J=16.7 Hz, 1H), 4.03 (s, 4H), 3.96-4.02 (m, 1H), 3.86-3.77 (m, 2H), 3.30-3.28 (m, 1H), 2.61-2.34 (m, 3H), 2.21 (dd, J=13.1, 6.3 Hz, 1H), 1.94-1.87 (m, 2H).

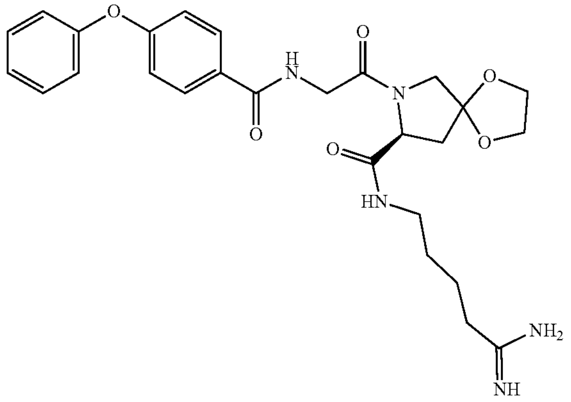 [SMILES: N=C(N)CCCCNC(=O)[C@@H]1CC2(CN1C(=O)CNC(=O)c1ccc(Oc3ccccc3)cc1)OCCO2]

(8S)—N-(4-Carbamimidoylbutyl)-7-{2-[(4-phenoxyphenyl)formamido]acetyl}-1,4-dioxa-7-azaspiro[4.4]nonane-8-carboxamide (Compound 17): (8S)—N-(4-Carbamimidoylbutyl)-7-{2-[(4-phenoxyphenyl)formamido]acetyl}-1,4-dioxa-7-azaspiro[4.4]nonane-8-carboxamide was prepared according to Scheme 4 with the use of 4-aminopentanimidamide dihydrochloride as the amine nucleophile. $^{1}$H NMR (400 MHz, Methanol-d4) δ 8.06 (t, J=6.0 Hz, 1H), 7.93-7.84 (m, 2H), 7.49-7.39 (m, 2H), 7.22 (t, J=7.5 Hz, 1H), 7.06 (ddd, J=16.6, 7.7, 1.6 Hz, 4H), 4.52 (dd, J=9.0, 5.9 Hz, 1H), 4.24 (d, J=16.6 Hz, 1H), 4.11 (d, J=16.6 Hz, 1H), 4.07-3.89 (m, 5H), 3.80 (s, 2H), 3.29 (q, J=5.8 Hz, 1H), 2.53-2.41 (m, 1H), 2.46-2.30 (m, 2H), 2.20 (dd, J=13.2, 6.0 Hz, 1H), 1.77-1.25 (m, 4H).

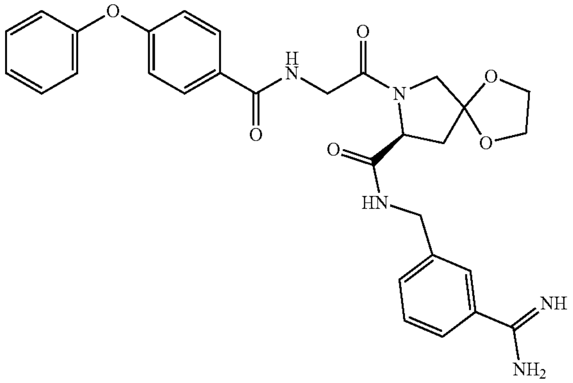 [SMILES: N=C(N)c1cccc(CNC(=O)[C@@H]2CC3(CN2C(=O)CNC(=O)c2ccc(Oc4ccccc4)cc2)OCCO3)c1]

(8S)—N-[(3-Carbamimidoylphenyl)methyl]-7-{2-[(4-phenoxyphenyl)formamido]acetyl}-1,4-dioxa-7-azaspiro[4.4]nonane-8-carboxamide (Compound 18): (8S)—N-[(3-Carbamimidoylphenyl)methyl]-7-{2-[(4-phenoxyphenyl)formamido]acetyl}-1,4-dioxa-7-azaspiro[4.4]nonane-8-carboxamide was prepared according to Scheme 4 with the use of 3-(aminomethyl)benzenecarboximidamide dihydrochloride as the amine nucleophile. $^{1}$H NMR (400 MHz, Methanol-d4) δ 8.63 (br s, 1H), 7.92-6.96 (m, 1H), 7.81-7.73 (m, 3H), 7.69 (d, J=7.7 Hz, 1H), 7.61 (d, J=7.9 Hz, 1H), 7.52 (t, J=7.7 Hz, 1H), 7.49-7.40 (m, 2H), 7.28-7.19 (m, 1H), 7.12-6.96 (m, 4H), 4.68-4.57 (m, 2H), 4.46 (d, J=15.8 Hz, 1H), 4.23 (d, J=16.6 Hz, 1H), 4.07 (d, J=16.5 Hz, 1H), 4.03 (s, 4H), 3.91-3.80 (m, 2H), 2.50 (dd, J=13.2, 9.2 Hz, 1H), 2.26 (dd, J=13.2, 5.7 Hz, 1H).

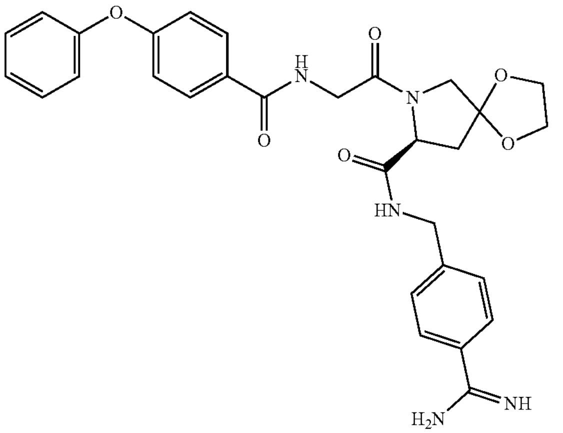 [SMILES: N=C(N)c1ccc(CNC(=O)[C@@H]2CC3(CN2C(=O)CNC(=O)c2ccc(Oc4ccccc4)cc2)OCCO3)cc1]

(8S)—N-[(4-Carbamimidoylphenyl)methyl]-7-{2-[(4-phenoxyphenyl)formamido]acetyl}-1,4-dioxa-7-azaspiro[4.4]nonane-8-carboxamide (Compound 19): (8S)—N-[(4-Carbamimidoylphenyl)methyl]-7-{2-[(4-phenoxyphenyl)formamido]acetyl}-1,4-dioxa-7-azaspiro[4.4]nonane-8-carboxamide was prepared according to Scheme 4 with the use of 4-(aminomethyl)benzenecarboximidamide dihydrochloride as the amine nucleophile. $^{1}$H NMR (400 MHz, Methanol-d4) δ 8.64 (t, J=6.1 Hz, 1H), 7.95-7.82 (m, 3H), 7.78-7.69 (m, 3H), 7.67-7.54 (m, 2H), 7.44 (dd, J=8.6, 7.3 Hz, 2H), 7.23 (t, J=7.5 Hz, 1H), 7.12-6.98 (m, 4H), 4.69-4.62 (m, 1H), 4.57-4.62 (m, 1H), 4.25 (d, J=16.7 Hz, 1H), 4.13 (d, J=16.6 Hz, 1H), 4.04 (s, 4H), 3.83 (s, 2H), 3.08-2.96 (m, 1H), 2.48 (dd, J=13.2, 9.3 Hz, 1H), 2.31-2.13 (m, 1H).

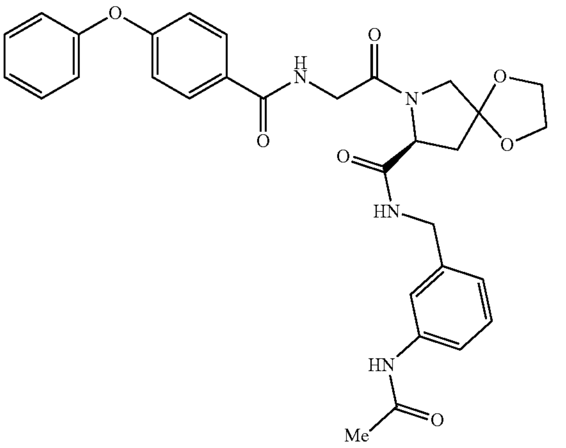 [SMILES: CC(=O)Nc1cccc(CNC(=O)[C@@H]2CC3(CN2C(=O)CNC(=O)c2ccc(Oc4ccccc4)cc2)OCCO3)c1]

(8S)—N-[(3-Acetamidophenyl)methyl]-7-{2-[(4-phenoxyphenyl)formamido]acetyl}-1,4-dioxa-7-azaspiro[4.4]nonane-8-carboxamide (Compound 20): (8S)—N-[(3-Acetamidophenyl)methyl]-7-{2-[(4-phenoxyphenyl)formamido]acetyl}-1,4-dioxa-7-azaspiro[4.4]nonane-8-carboxamide was prepared according to Scheme 4 with the use of N-[3-(aminomethyl)phenyl]acetamide hydrochloride as the amine nucleophile. $^{1}$H NMR (400 MHz, Methanol-d4) δ 8.48 (t, J=5.9 Hz, 1H), 7.94-7.79 (m, 3H), 7.49 (dd, J=8.0, 6.1 Hz, 1H), 7.48-7.35 (m, 3H), 7.32-7.17 (m, 3H), 7.14-6.95 (m, 5H), 4.63 (dd, J=9.1, 5.7 Hz, 1H), 4.42 (d, J=4.6 Hz, 2H), 4.27-4.07 (m, 2H), 4.05-3.97 (m, 4H), 3.97-3.98 (m, 1H), 3.80 (s, 2H), 2.51-2.41 (m, 1H), 2.26 (dd, J=13.2, 5.7 Hz, 1H), 2.06 (m, 3H).

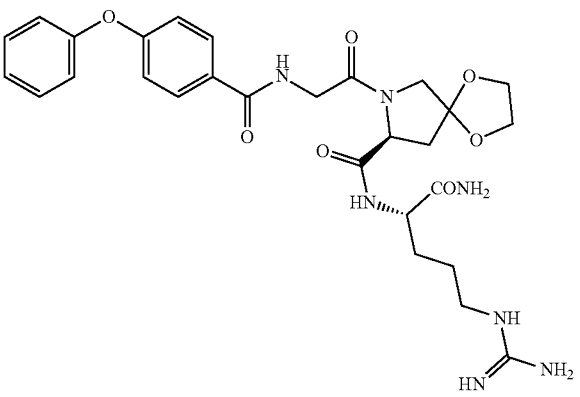

N-{2-[(8S)-8-{[(1S)-4-Carbamimidamido-1-carbamoylbutyl]carbamoyl}-1,4-dioxa-7-azaspiro[4.4]nonan-7-yl]-2-oxoethyl}-4-phenoxybenzamide (Compound 22): N-{2-[(8S)-8-{[(1S)-4-Carbamimidamido-1-carbamoylbutyl]carbamoyl}-1,4-dioxa-7-azaspiro[4.4]nonan-7-yl]-2-oxoethyl}-4-phenoxybenzamide was prepared according to Scheme 4 with the use of (2S)-2-amino-5-carbamimidamidopentanamide dihydrochlorideas the amine nucleophile. $^{1}$H NMR (400 MHz, Methanol-d4) δ 8.50 (s, 1H), 7.93-7.83 (m, 2H), 7.49-7.38 (m, 2H), 7.27-7.18 (m, 1H), 7.12-6.99 (m, 4H), 4.61 (dd, J=9.3, 5.2 Hz, 1H), 4.38 (dd, J=10.1, 4.2 Hz, 1H), 4.25 (d, J=16.4 Hz, 1H), 4.15-3.96 (m, 5H), 3.89 (d, J=10.7 Hz, 1H), 3.82 (d, J=10.7 Hz, 1H), 3.22 (td, J=6.8, 4.4 Hz, 2H), 2.50 (dd, J=13.3, 9.4 Hz, 1H), 2.23 (dd, J=13.3, 5.2 Hz, 1H), 1.90-1.64 (m, 2H).

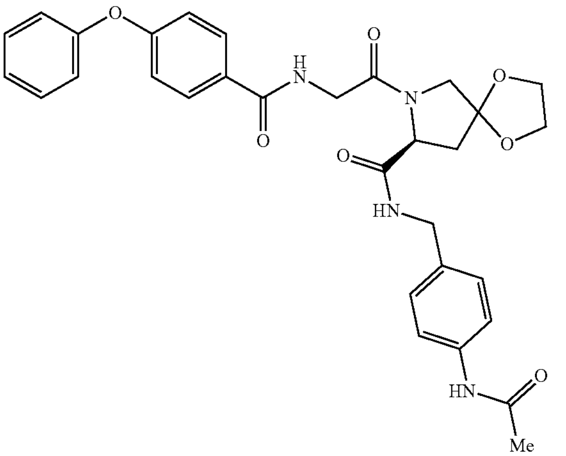 [SMILES: CC(=O)Nc1ccc(CNC(=O)[C@@H]2CC3(CN2C(=O)CNC(=O)c2ccc(Oc4ccccc4)cc2)OCCO3)cc1]

(8S)—N-[(4-Acetamidophenyl)methyl]-7-{2-[(4-phenoxyphenyl)formamido]acetyl}-1,4-dioxa-7-azaspiro[4.4]nonane-8-carboxamide (Compound 21): (8S)—N-[(4-Acetamidophenyl)methyl]-7-{2-[(4-phenoxyphenyl)formamido]acetyl}-1,4-dioxa-7-azaspiro[4.4]nonane-8-carboxamide was prepared according to Scheme 4 with the use of N-[4-(aminomethyl)phenyl]acetamide as the amine nucleophile. $^{1}$H NMR (400 MHz, Methanol-d4) δ 7.93-7.79 (m, 3H), 7.50-7.38 (m, 4H), 7.34-7.17 (m, 4H), 7.14-7.04 (m, 3H), 7.07-6.96 (m, 3H), 4.62 (dt, J=8.9, 4.4 Hz, 1H), 4.47-4.28 (m, 2H), 4.16 (s, 2H), 4.01 (s, 4H), 4.04-3.93 (m, 1H), 3.79 (s, 2H), 2.51-2.39 (m, 1H), 2.24 (dd, J=13.2, 5.4 Hz, 1H), 2.11 (s, 3H).

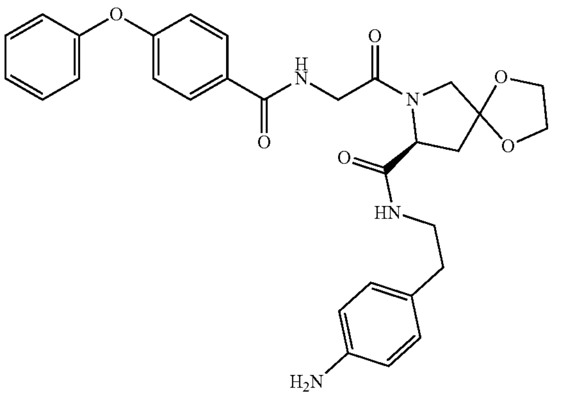 [SMILES: Nc1ccc(CCNC(=O)[C@@H]2CC3(CN2C(=O)CNC(=O)c2ccc(Oc4ccccc4)cc2)OCCO3)cc1]

(8S)—N-[2-(4-Aminophenyl)ethyl]-7-{2-[(4-phenoxyphenyl)formamido]acetyl}-1,4-dioxa-7-azaspiro[4.4]nonane-8-carboxamide (Compound 23): (8S)—N-[2-(4-Aminophenyl)ethyl]-7-{2-[(4-phenoxyphenyl)formamido]acetyl}-1,4-dioxa-7-azaspiro[4.4]nonane-8-carboxamide was prepared according to Scheme 4 with the use of 4-(2-aminoethyl)aniline as the amine nucleophile. $^{1}$H NMR (400 MHz, Methanol-d4) δ 8.13 (s, 1H), 8.00 (t, J=5.9 Hz, 1H), 7.89 (dd, J=9.0, 2.8 Hz, 2H), 7.48-7.37 (m, 2H), 7.21 (t, J=7.4 Hz, 1H), 7.12-6.98 (m, 6H), 6.75 (t, J=8.3 Hz, 2H), 4.51 (dd, J=9.0, 6.0 Hz, 1H), 4.24-4.06 (m, 2H), 4.04-3.89 (m, 4H), 3.75 (q, J=10.8 Hz, 2H), 3.39-3.32 (m, 1H), 2.80-2.66 (m, 1H), 2.42-2.33 (m, 1H), 2.15 (dd, J=13.2, 6.1 Hz, 1H).

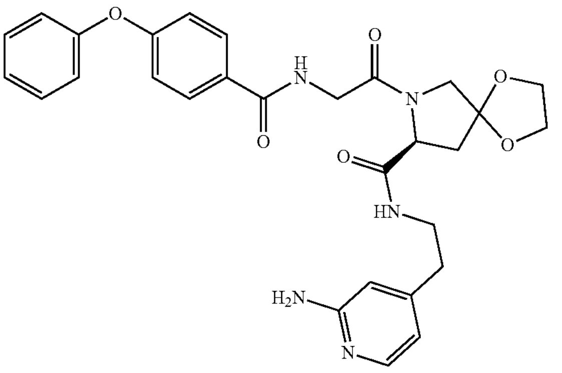 [SMILES: Nc1cc(CCNC(=O)[C@@H]2CC3(CN2C(=O)CNC(=O)c2ccc(Oc4ccccc4)cc2)OCCO3)ccn1]

(8S)—N-[2-(2-Aminopyridin-4-yl)ethyl]-7-{2-[(4-phenoxyphenyl)formamido]acetyl}-1,4-dioxa-7-azaspiro[4.4]nonane-8-carboxamide (Compound 24): (8S)—N-[2-(2-Aminopyridin-4-yl)ethyl]-7-{2-[(4-phenoxyphenyl)formamido]acetyl}-1,4-dioxa-7-azaspiro[4.4]nonane-8-carboxamide was prepared according to Scheme 4 with the use of 4-(2-aminoethyl)pyridin-2-amine as the amine nucleophile. $^1$H NMR (400 MHz, Methanol-d4) δ 8.52 (s, 1H), 7.93-7.84 (m, 2H), 7.74 (s, 1H), 7.48-7.34 (m, 2H), 7.26-7.17 (m, 1H), 7.12-6.98 (m, 4H), 6.73 (s, 2H), 4.52 (dd, J=9.1, 5.7 Hz, 1H), 4.20 (d, J=16.7 Hz, 1H), 4.18-4.05 (m, 1H), 4.04-3.85 (m, 4H), 3.83-3.71 (m, 2H), 3.64-3.40 (m, 2H), 2.81-2.75 (m, 2H), 2.44-2.26 (m, 1H), 2.16 (dd, J=13.2, 5.7 Hz, 1H).

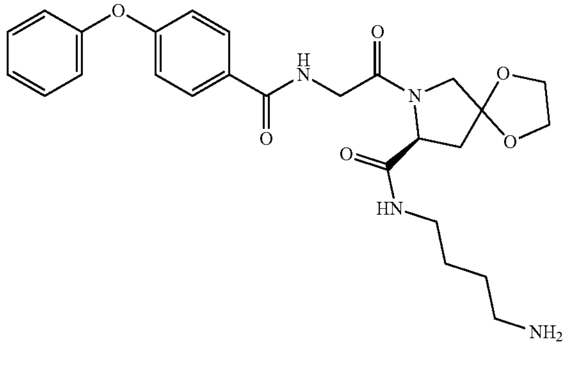 [SMILES: NCCCCNC(=O)[C@@H]1CC2(CN1C(=O)CNC(=O)c1ccc(Oc3ccccc3)cc1)OCCO2]

(8S)—N-(4-Aminobutyl)-7-{2-[(4-phenoxyphenyl)formamido]acetyl}-1,4-dioxa-7-azaspiro[4.4]nonane-8-carboxamide (Compound 25): (8S)—N-(4-Aminobutyl)-7-{2-[(4-phenoxyphenyl)formamido]acetyl}-1,4-dioxa-7-azaspiro[4.4]nonane-8-carboxamide was prepared according to Scheme 4 with the use of putrescine as the amine nucleophile. $^1$H NMR (400 MHz, Methanol-d4) δ 8.56 (br s, 1H), 7.94-7.85 (m, 2H), 7.49-7.38 (m, 2H), 7.27-7.18 (m, 1H), 7.12-6.99 (m, 4H), 4.51 (dd, J=9.0, 6.1 Hz, 1H), 4.24 (d, J=16.7 Hz, 1H), 4.15-4.06 (m, 1H), 4.02 (s, 4H), 4.04-3.95 (m, 1H), 3.79 (s, 2H), 3.28 (t, J=6.1 Hz, 1H), 2.95-2.86 (m, 2H), 2.48-2.36 (m, 1H), 2.20 (dd, J=13.2, 6.1 Hz, 1H), 1.76-1.57 (m, 4H).

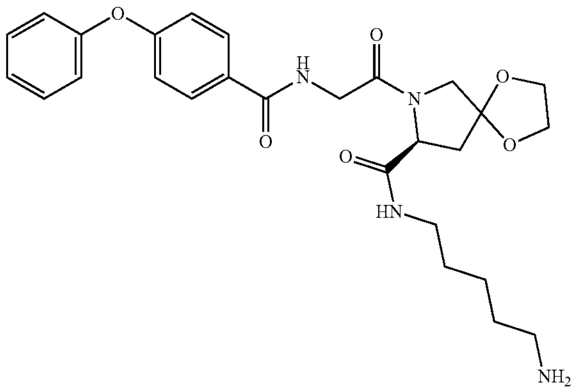 [SMILES: NCCCCCNC(=O)[C@@H]1CC2(CN1C(=O)CNC(=O)c1ccc(Oc3ccccc3)cc1)OCCO2]

(8S)—N-(5-Aminopentyl)-7-{2-[(4-phenoxyphenyl)formamido]acetyl}-1,4-dioxa-7-azaspiro[4.4]nonane-8-carboxamide (Compound 26): (8S)—N-(5-Aminopentyl)-7-{2-[(4-phenoxyphenyl)formamido]acetyl}-1,4-dioxa-7-azaspiro[4.4]nonane-8-carboxamide was prepared according to Scheme 4 with the use of cadaverine as the amine nucleophile. $^1$H NMR (400 MHz, Methanol-d4) δ 8.53 (s, 1H), 7.94-7.85 (m, 2H), 7.48-7.38 (m, 2H), 7.27-7.18 (m, 1H), 7.12-6.99 (m, 4H), 4.52 (dd, J=9.1, 5.9 Hz, 1H), 4.22 (d, J=16.6 Hz, 1H), 4.12 (d, J=16.7 Hz, 1H), 4.08-3.98 (m, 4H), 4.01-3.94 (m, 1H), 3.81-3.77 (m, 2H), 3.25 (td, J=6.6, 1.6 Hz, 1H), 2.9 (t, J=7.5 Hz, 2H), 2.39 (ddd, J=23.1, 13.2, 8.9 Hz, 1H), 2.20 (dd, J=13.2, 5.9 Hz, 1H), 1.64 (dtt, J=27.5, 14.1, 7.2 Hz, 4H), 1.42 (qd, J=9.8, 9.0, 6.4 Hz, 2H).

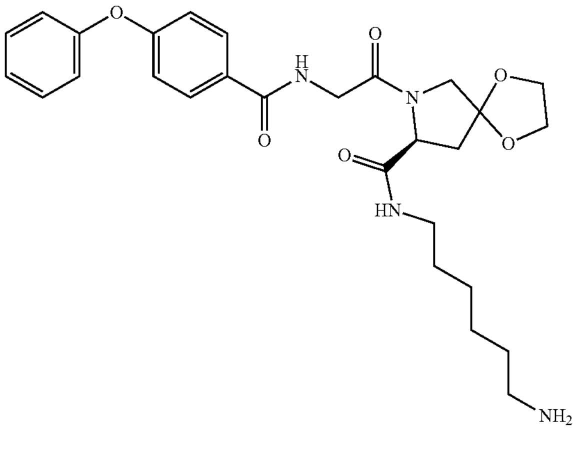 [SMILES: NCCCCCCNC(=O)[C@@H]1CC2(CN1C(=O)CNC(=O)c1ccc(Oc3ccccc3)cc1)OCCO2]

(8S)—N-(6-Aminohexyl)-7-{2-[(4-phenoxyphenyl)formamido]acetyl}-1,4-dioxa-7-azaspiro[4.4]nonane-8-carboxamide (Compound 27): (8S)—N-(6-Aminohexyl)-7-{2-[(4-phenoxyphenyl)formamido]acetyl}-1,4-dioxa-7-azaspiro[4.4]nonane-8-carboxamide was prepared according to Scheme 4 with the use of 1,6-diaminohexane as the amine nucleophile. $^1$H NMR (400 MHz, Methanol-d4) δ 8.55 (br s, 1H), 7.94-7.87 (m, 2H), 7.48-7.39 (m, 2H), 7.22 (t, J=7.5 Hz, 1H), 7.08 (d, J=17.5, Hz, 2H), 7.04 (d, J=17.5, Hz, 2H), 4.52 (dd, J=9.0, 5.9 Hz, 1H), 4.23 (d, J=16.7 Hz, 1H), 4.11 (d, J=16.6 Hz, 1H), 4.01 (s, 3H), 4.03-3.95 (m, 1H), 3.79 (d, J=1.7 Hz, 2H), 3.32-3.14 (m, 1H), 2.92 (t, J=7.4 Hz, 2H), 2.47-2.29 (m, 1H), 2.19 (dd, J=13.2, 5.9 Hz, 1H), 1.66-1.52 (m, 4H), 1.48-1.36 (m, 4H).

Scheme 5. Synthesis of Compound 30- Compound 33.

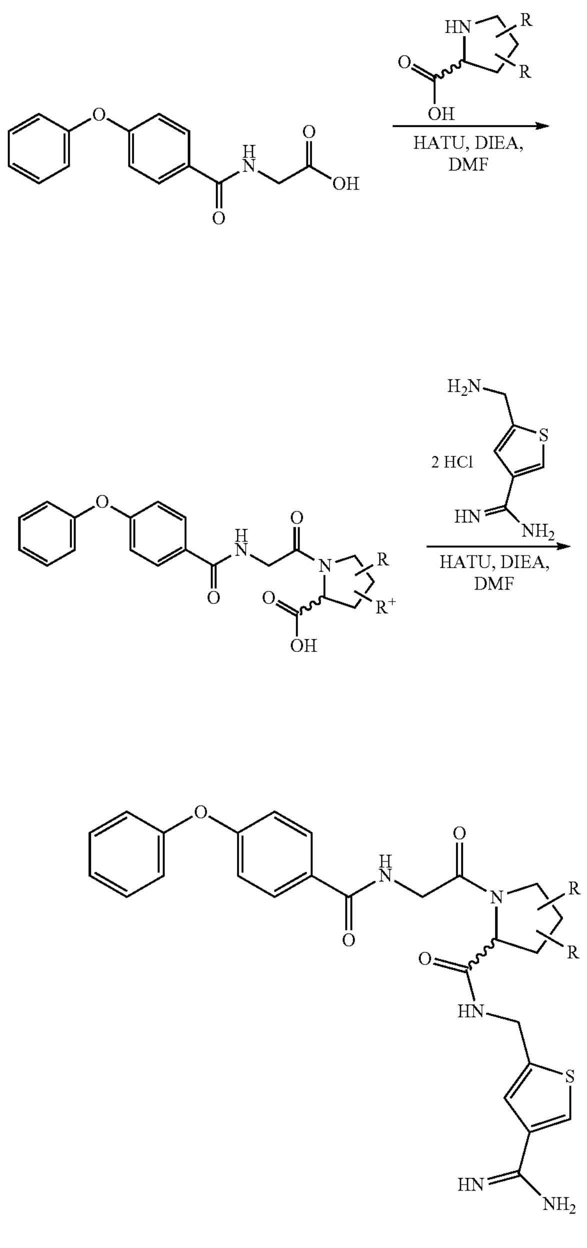

1-[Bis(dimethylamino)methylene]-1H-1,2,3-triazolo[4,5-b]pyridinium 3-oxid hexafluorophosphate (1.0 equiv) and [(4-phenoxyphenyl)formamido]acetic acid (1.0 equiv) were combined in a reaction vessel, the vessel was evacuated and the mixture was charged with Ar gas. The mixture was taken up in DMF (140 Vols) and Hunig's base (4.0 equiv) was added. After 60 min of stirring at RT, the corresponding amino acid (1.0 equiv) was added and the mixture was stirred for 1 h. Following this period of stirring, to the same reaction vessel, was added another aliquot of 1-[Bis(dimethylamino)methylene]-1H-1,2,3-triazolo[4,5-b]pyridinium 3-oxid hexafluorophosphate (1.0 equiv) and 5-(aminomethyl)thiophene-3-carboximidamide dihydrochloride (1.0 equiv) in a single combined portion. After 30 min of stirring, the mixture was directly purified via reverse phase HPLC to give the desired amidine product after concentration of the appropriate fractions.

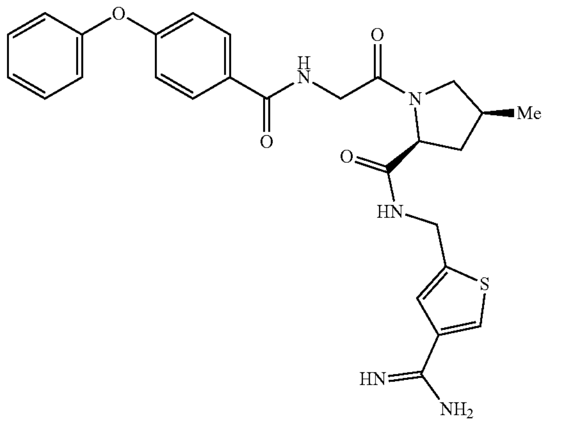 [SMILES: C[C@H]1C[C@@H](C(=O)NCc2cc(C(=N)N)cs2)N(C(=O)CNC(=O)c2ccc(Oc3ccccc3)cc2)C1]

(2S,4S)—N-[(4-carbamimidoylthiophen-2-yl)methyl]-4-methyl-1-{2-[(4-phenoxyphenyl)formamido]acetyl}pyrrolidine-2-carboxamide (COMPOUND 30): (2S,4S)—N-[(4-carbamimidoylthiophen-2-yl)methyl]-4-methyl-1-{2-[(4-phenoxyphenyl)formamido]acetyl}pyrrolidine-2-carboxamide was prepared according to Scheme 5 with the use (2S,4S)-4-methylpyrrolidine-2-carboxylic acid as the central amino acid. $^{1}$H NMR (400 MHz, Methanol-d4) δ 8.50 (s, 1H), 8.22 (d, J=1.6 Hz, 1H), 7.94-7.82 (m, 2H), 7.53 (s, 1H), 7.44 (td, J=7.4, 1.8 Hz, 3H), 7.22 (t, J=7.5 Hz, 1H), 7.12-6.98 (m, 4H), 4.59 (br s, 2H), 4.47-4.38 (m, 1H), 4.26 (d, J=16.7 Hz, 1H), 4.17 (d, J=16.7 Hz, 1H), 4.02-3.93 (m, 1H), 3.23 (t, J=9.7 Hz, 1H), 2.54-2.39 (m, 1H), 1.57 (q, J=10.0 Hz, 1H), 1.12 (dd, J=18.7, 6.4 Hz, 3H), 0.92 (s, 1H).

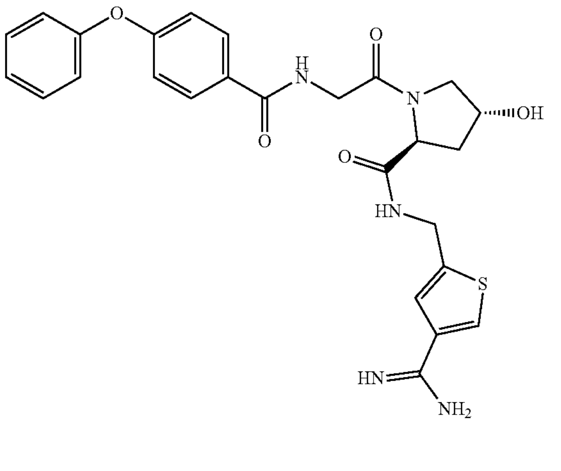 [SMILES: N=C(N)c1csc(CNC(=O)[C@@H]2C[C@@H](O)CN2C(=O)CNC(=O)c2ccc(Oc3ccccc3)cc2)c1]

(2S,4R)—N-[(4-carbamimidoylthiophen-2-yl)methyl]-4-hydroxy-1-{2-[(4-phenoxyphenyl)formamido]acetyl}pyrrolidine-2-carboxamide (COMPOUND 31): (2S,4R)—N-[(4-carbamimidoylthiophen-2-yl)methyl]-4-hydroxy-1-{2-[(4-phenoxyphenyl)formamido]acetyl}pyrrolidine-2-carboxamide was prepared according to Scheme 5 with the use (2S,4R)-4-hydroxypyrrolidine-2-carboxylic acid as the central amino acid. $^{1}$H NMR (400 MHz, Methanol-$d_4$) δ 8.31-8.19 (m, 2H), 7.91-7.82 (m, 2H), 7.48-7.39 (m, 3H), 7.23 (t, J=7.4 Hz, 1H), 7.12-6.99 (m, 4H), 4.65-4.52 (m, 4H), 4.22 (d, J=1.5 Hz, 2H), 3.85 (dd, J=10.9, 4.3 Hz, 1H), 3.66 (d, J=11.1 Hz, 1H), 2.29 (t, J=10.7 Hz, 1H), 2.09 (ddd, J=13.1, 8.1, 4.7 Hz, 1H).

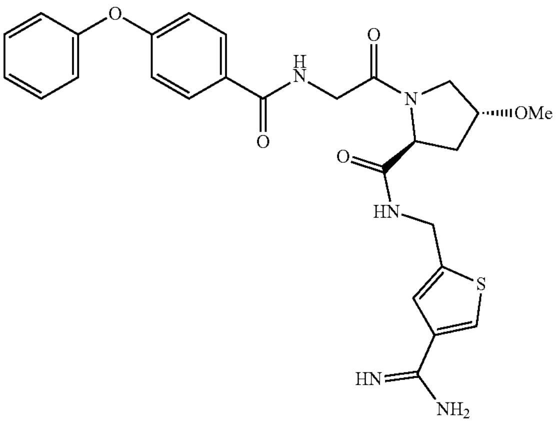 [SMILES: CO[C@@H]1C[C@@H](C(=O)NCc2cc(C(=N)N)cs2)N(C(=O)CNC(=O)c2ccc(Oc3ccccc3)cc2)C1]

(2S,4R)—N-[(4-carbamimidoylthiophen-2-yl)methyl]-4-methoxy-1-{2-[(4-phenoxyphenyl)formamido]acetyl}pyrrolidine-2-carboxamide (COMPOUND 32): (2S,4R)—N-[(4-carbamimidoylthiophen-2-yl)methyl]-4-methoxy-1-{2-[(4-phenoxyphenyl)formamido]acetyl}pyrrolidine-2-carboxamide was prepared according to Scheme 5 with the use (2S,4R)-4-methoxypyrrolidine-2-carboxylic acid as the central amino acid. $^1$H NMR (400 MHz, Methanol-$d_4$) δ 8.54 (s, 1H), 8.22 (d, J=1.6 Hz, 1H), 7.91-7.82 (m, 2H), 7.48-7.38 (m, 4H), 7.27-7.18 (m, 1H), 7.12-6.98 (m, 4H), 4.59 (s, 2H), 4.50 (t, J=8.1 Hz, 1H), 4.23 (s, 2H), 4.11-3.91 (m, 2H), 3.83 (d, J=3.5 Hz, 2H), 3.39 (s, 3H), 2.47-2.36 (m, 1H), 2.08 (ddd, J=13.2, 8.2, 4.8 Hz, 1H).

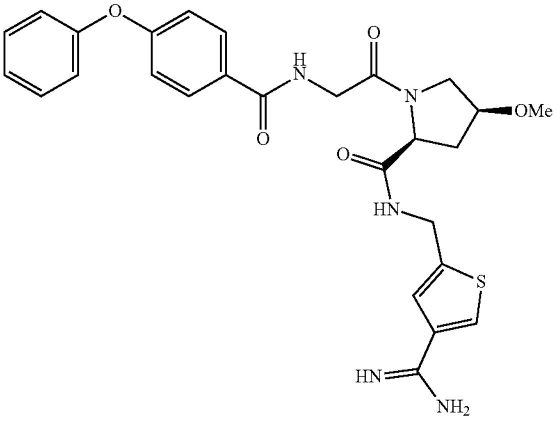 [SMILES: CO[C@H]1C[C@@H](C(=O)NCc2cc(C(=N)N)cs2)N(C(=O)CNC(=O)c2ccc(Oc3ccccc3)cc2)C1]

(2S,4S)—N-[(4-carbamimidoylthiophen-2-yl)methyl]-4-methoxy-1-{2-[(4-phenoxyphenyl)formamido]acetyl}pyrrolidine-2-carboxamide (COMPOUND 33): (2S,4S)—N-[(4-carbamimidoylthiophen-2-yl)methyl]-4-methoxy-1-{2-[(4-phenoxyphenyl)formamido]acetyl}pyrrolidine-2-carboxamide was prepared according to Scheme 5 with the use (2S,4S)-4-methoxypyrrolidine-2-carboxylic acid as the central amino acid. $^1$H NMR (400 MHz, Methanol-$d_4$) δ 8.43 (s, 1H), 8.21 (d, J=1.7 Hz, 1H), 7.94-7.81 (m, 2H), 7.54-7.38 (m, 3H), 7.30-7.18 (m, 1H), 7.12-6.98 (m, 4H), 4.71-4.58 (m, 1H), 4.62-4.51 (m, 2H), 4.15-4.04 (m, 2H), 4.03 (d, J=18.7 Hz, 1H), 3.85 (d, J=3.1 Hz, 2H), 3.25 (s, 3H), 2.44-2.24 (m, 2H).

Example 2. Additional Non-Limiting Synthetic Examples of Compounds of the Present Disclosure Scheme 6. Synthesis of N-(2-((1S,2R,4S)-2-(((4-carbamimidoylthiophen-2-yl)methyl)carbamoyl)-4-methoxycyclopentyl)-2-oxoethyl)-4-phenoxybenzamide (Compound 34)

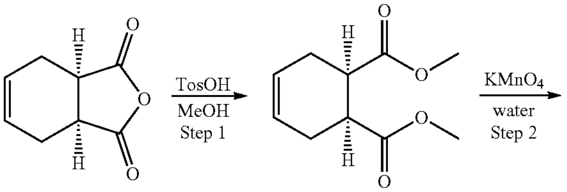

1 2

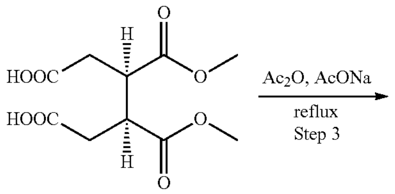

3

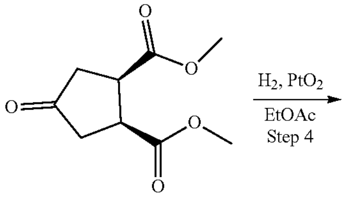

4

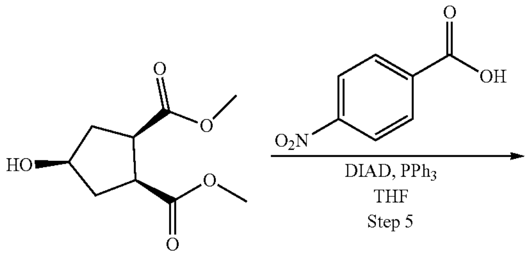

5

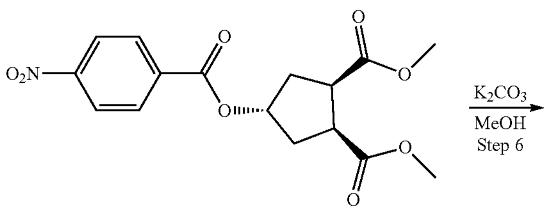

6

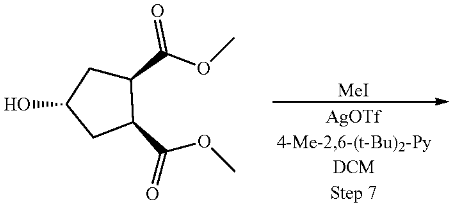

7

-continued

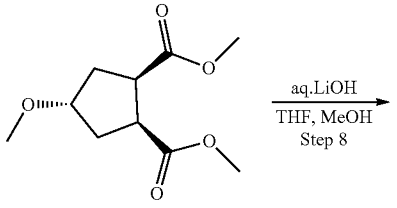

8

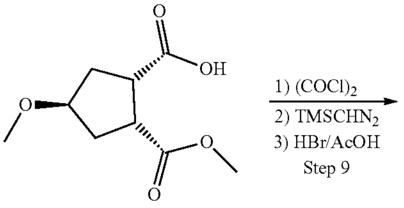

9

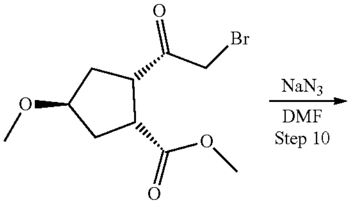

10

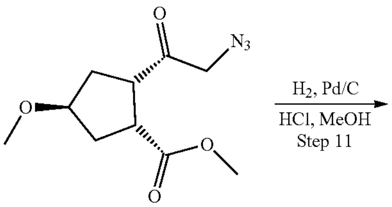

11

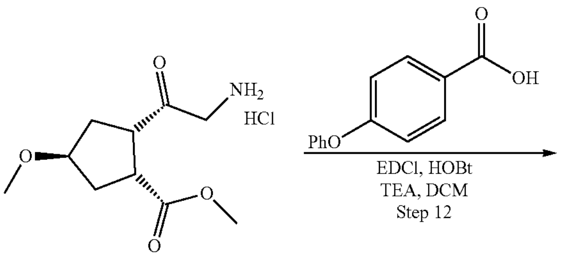

12

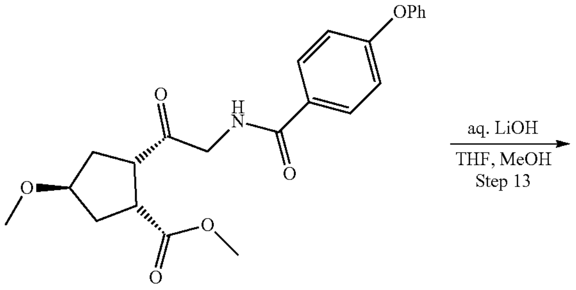

13

-continued

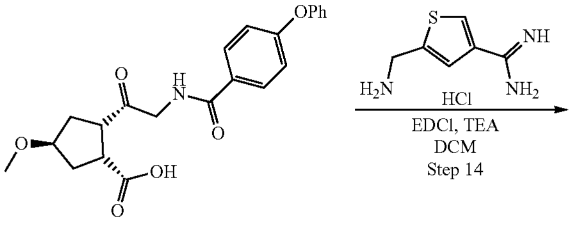

14

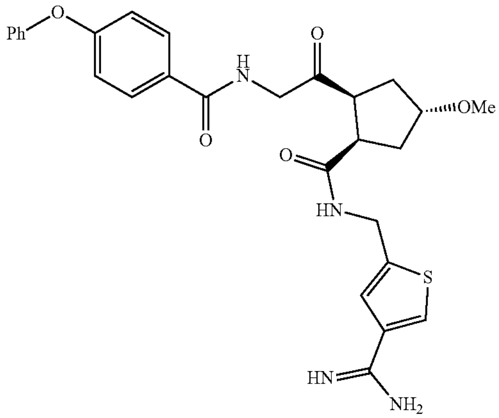

COMPOUND 34

In Step 1, intermediate 1 (25 g) was subjected to ring-opening conditions using TosOH in MeOH to afford intermediate 2 (13 g). In Step 2, Intermediate 2 (5 g) was oxidized to intermediate 3 in the presence of $KMNO_4$ to afford intermediate 3 (6.5) that was refluxed with acetic anhydride and sodium acetate to afford intermediate 4 in Step 3. In Step 4, intermediate 4 undergoes hydrogenation conditions to afford hydroxyl-compound 5 that is then coupled to 4-nitrobenzoic acid via Mitsunobu reaction conditions in Step 5 to afford intermediate 6. The nitrobenzyl group is removed in Step 6 using $K_2CO_3$ in MeOH to afford intermediate 7 that is methylated in Step 7 to afford intermediate 8. In Step 8, intermediate 8 undergoes hydrolysis using LiOH in THF and MeOH to afford racemic intermediate 9. In Step 9, intermediate 8 is converted to the acid chloride using $(COCl)_2$ and then subjected to diazoketone formation and subsequent bromomethyl ketone formation to afford racemic intermediate 10. In Step 10, intermediate 10 is reacted with $NaN_3$ to afford intermediate 11 and in Step 11, the azide intermediate 11 is converted to amine-containing intermediate 12 via hydrogenation. In Step 12, intermediate 12 is coupled to 4-phenoxybenzoic acid to afford intermediate 13 that undergoes hydrolysis conditions in Step 13 to afford intermediate 14. In Step 14, intermediate 14 is then coupled to 5-(aminomethyl)thiophene-3-carboximidamide to afford COMPOUND 34.

Scheme 7. Synthesis of N-(2-((1R,2R,4S)-2-(((4-carbamimidoylthiophen-2-yl)methyl)carbamoyl)-4-methoxycyclophentyl)-2-oxoethyl)-4-phenoxybenzamide (COMPOUND 35)
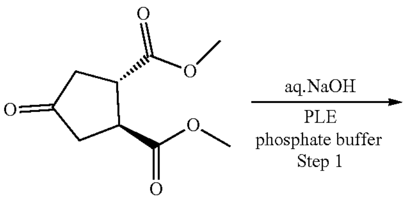
1
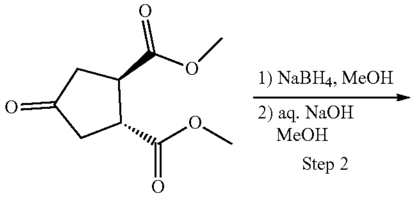
2
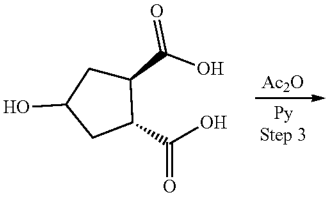
3
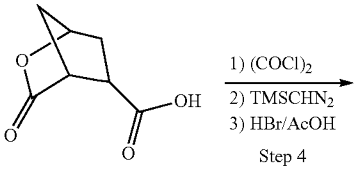
4
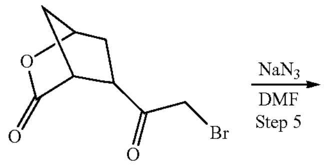
5
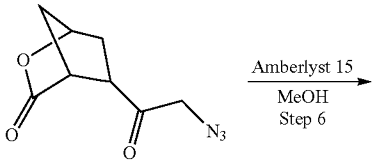
6
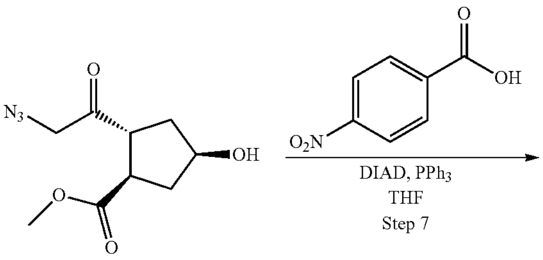
7
-continued
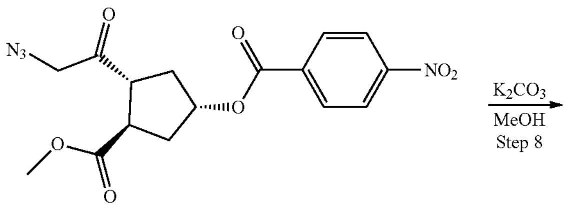
8
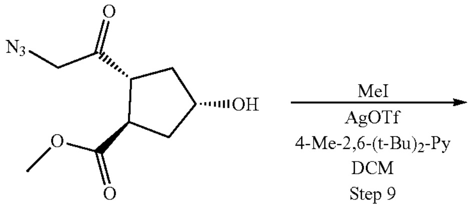
9
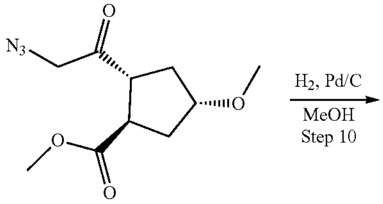
10
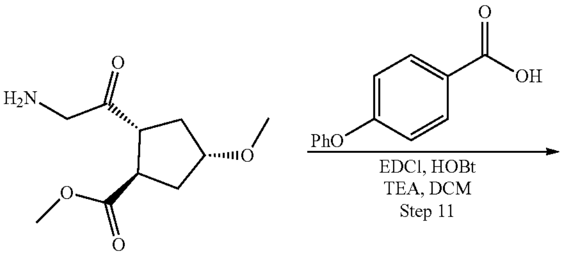
11
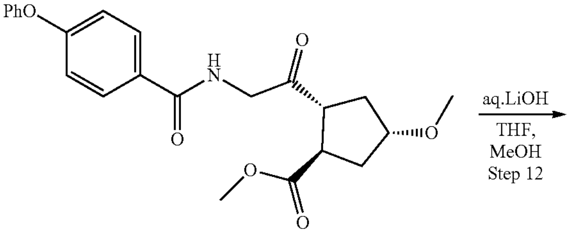
12
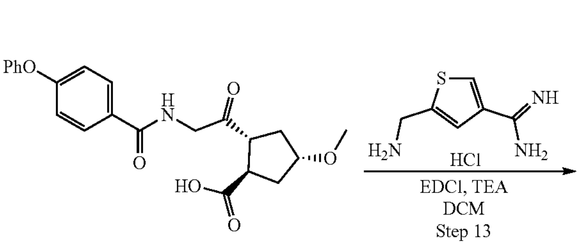
13

-continued

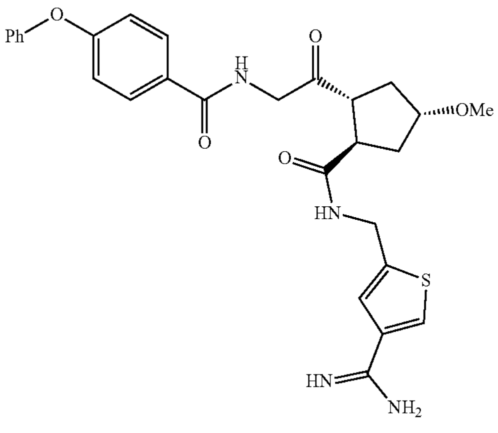

COMPOUND 35

In Step 1, racemic intermediate 1 is subjected to stereoselective hydrolysis using pig liver enzyme in phosphate buffer to afford intermediate 2. In Step 2, intermediate 2 is reduced to intermediate 3 using hydrolysis conditions and in Step 3, intermediate 3 is cyclized to intermediate 4 using acetic anhydride. In Step 4, intermediate 4 is converted to the acid chloride using $(COCl)_2$ and then subjected to diazoketone formation and subsequent bromomethyl ketone formation to afford intermediate 5. In Step 5, intermediate 5 is reacted with $NaN_3$ to afford intermediate 6. In step 6, intermediate 6 is subjected to ring-opening conditions using Amberlyst 15 and in Step 7, intermediate 7 is coupled to 4-nitrobenzoic acid via Mitsunobu reaction conditions to afford intermediate 8. The nitrobenzyl group is removed in Step 8 using $K_2CO_3$ in MeOH to afford intermediate 9 that is methylated in Step 9 to afford intermediate 10. In Step 10, azide intermediate 10 is converted to amine-containing intermediate 11 via hydrogenation. In Step 11, intermediate 11 is coupled to 4-phenoxybenzoic acid to afford intermediate 12 that undergoes hydrolysis conditions in Step 12 to afford intermediate 13. In Step 13, intermediate 13 is then coupled to 5-(aminomethyl)thiophene-3-carboximidamide to afford COMPOUND 35.

Scheme 8. Synthesis of (S)-N-((4-carbamimidoylthiophen-2-yl)methyl)-1-(2-(4-phenoxybenzoyl)hydrazine-1-carbonyl)pyrrolidine-2-carboxamide (COMPOUND 36)

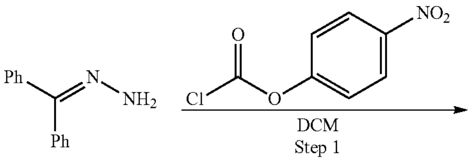

1

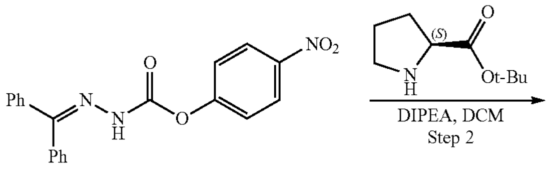

2

-continued

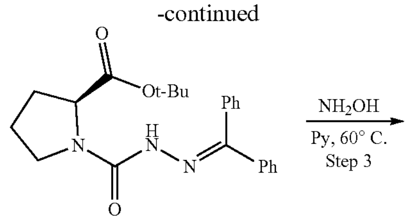

3

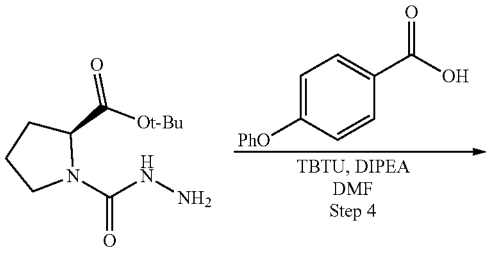

4

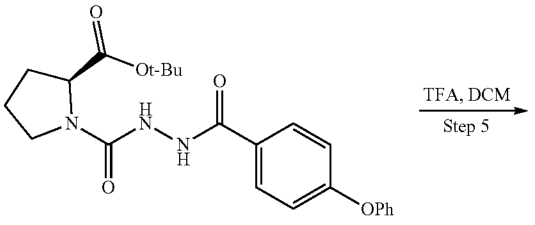

5

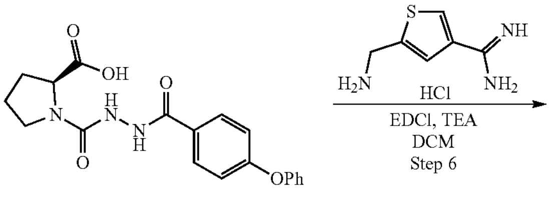

5

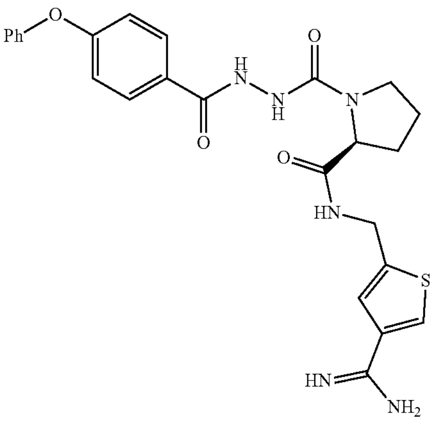

COMPOUND 36

In Step 1, compound 1 is coupled to 4-nitrophenyl chloroformate to afford intermediate 2 and in Step 2, intermediate 2 is reacted with tert-butyl L-prolinate to afford intermediate 3. In Step 3, intermediate 3 is converted to intermediate 4 in the presence of hydroxylamine to afford intermediate 4. In Step 4, intermediate 4 is coupled to 4-phenoxybenzoic acid to afford intermediate 5 that undergoes hydrolysis conditions using TFA in Step 5 to afford intermediate 6. In Step 6, intermediate 6 is then coupled to 5-(aminomethyl)thiophene-3-carboximidamide to afford COMPOUND 36.

Scheme 9: Synthesis of (S)-N-((4-carbamimidoylthiophen-2-yl) methyl)-1-(4-(4-phenoxyphenyl)butanoyl)pyrrolidine-2-carboxamide (COMPOUND 37)

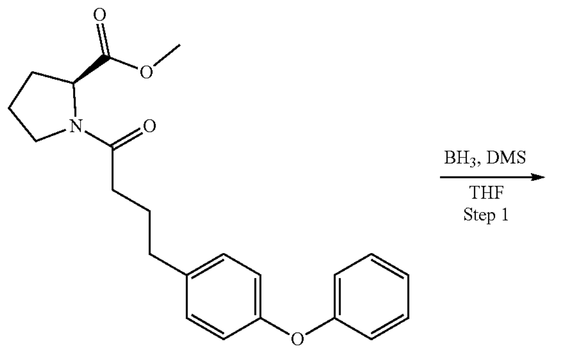

1

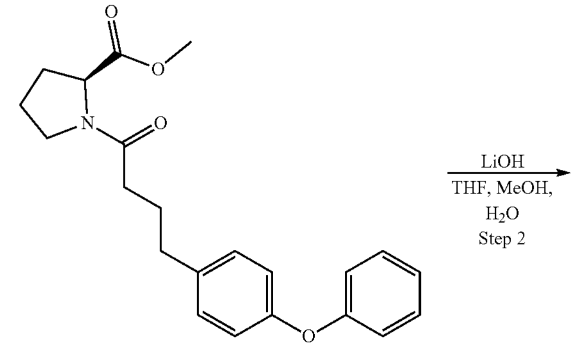

2

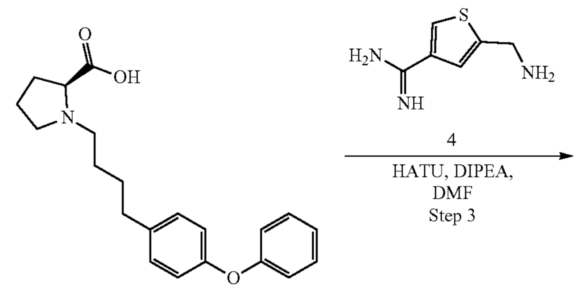

3

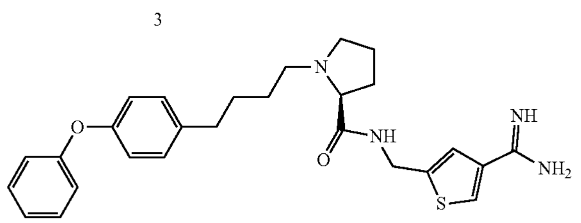

COMPOUND 37

Step 1: a solution of starting material 1 (0.4 g, 1.08 mmol) in THF (4.0 mL) was added borane methylsulfide solution (1.6 mL, 3.2 mmol, 1M in THF) drop-wise at 0° C. The mixture was stirred at 25° C. for 12 hours before poured into ice water and extracted with EtOAc twice. The combined organic layers were washed with brine, dried over anhydrous $Na_2SO_4$, filtered and concentrated to dryness. The residue was purified by chromatography on silica gel (DCM:MeOH=20:1) to give intermediate 2 (0.20 g, yield 52.1%) as light yellow oil. LC/MS (ESI) (m/z): 354 $(M+H)^+$.

Step 2: a solution of intermediate 2 (0.2 g, 0.565 mmol) in MeOH (2 mL), THF (2 mL) and water (2 mL) was added to lithium hydroxide monohydrate (40 mg, 1.695 mmol). The mixture was stirred at room temperature for 2 hours before concentrated to ⅓ volume, diluted with water and washed with MTBE twice. The aqueous layer was acidified with 1N aq.HCl to pH~3 and extracted with DCM twice. The combined organic layers were washed with brine, dried over anhydrous $Na_2SO_4$, filtered and concentrated under reduced pressure to dryness. The residue was purified by chromatography on silica gel (DCM:MeOH=30:1) to give intermediate 3 (0.18 g, yield 94.7%) as white solid. LC/MS (ESI) (m/z): 340 $(M+H)^+$.

Step 3: a mixture of intermediate 3 (80 mg, 0.24 mmol) and 5-(aminomethyl)thiophene-3-carboximidamide (92 mg, 0.35 mmol) in DMF (4 mL) was added to DIPEA (121 mg, 0.96 mmol) and HATU (161 mg, 0.43 mmol) at 0° C. The mixture was stirred at room temperature under $N_2$ atmosphere for 12 hours before diluted with EtOAc and washed with saturated aq.$NH_4Cl$ solution and brine, dried over anhydrous $Na_2SO_4$, filtered and concentrated to dryness. The residue was purified by prep-HPLC to afford COMPOUND 37 (13 mg, yield 11.3%) as white solid. $^1$H-NMR (400 MHz, $CD_3OD$) δ 8.41 (s, 2H), 8.26 (d, J=1.3 Hz, 1H), 7.44 (s, 1H), 7.32 (dd, J=8.4, 7.6 Hz, 2H), 7.14 (d, J=8.5 Hz, 2H), 7.07 (t, J=7.4 Hz, 1H), 6.98-6.83 (m, 4H), 4.61 (q, J=15.5 Hz, 2H), 3.58 (dd, J=9.3, 5.3 Hz, 1H), 3.45 (td, J=7.2, 4.0 Hz, 1H), 2.82 (ddd, J=28.0, 17.9, 7.0 Hz, 3H), 2.58 (t, J=7.0 Hz, 2H), 2.39-2.27 (m, 1H), 1.94 (ddd, J=13.4, 7.1, 4.4 Hz, 3H), 1.77-1.49 (m, 4H); LC/MS (ESI) m/z: 477 $(M+H)^+$.

Scheme 10: Synthesis of (2S)-N-[(4-carbamimidoylthiophen-2-yl)methyl]-1-{2-[(4-phenoxyphenyl)methoxy]acetyl}pyrrolidine-2-carboxamide (COMPOUND 38)

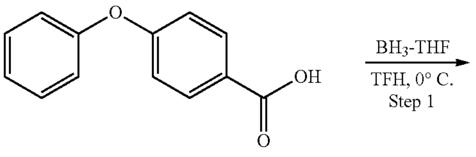

1

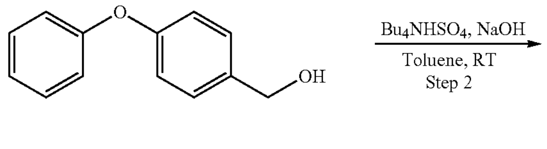

2

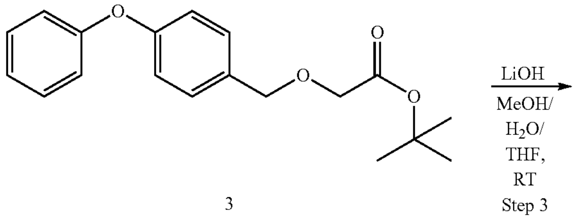

3

-continued

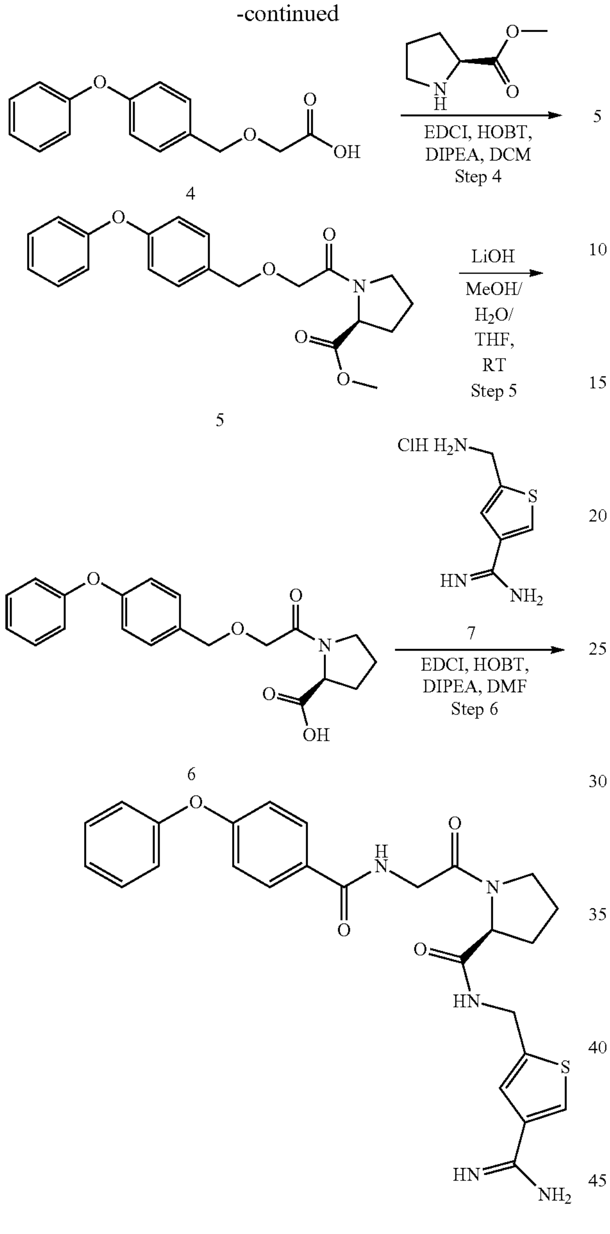

4

5

6

COMPOUND 38

Step 1: a solution of starting material 1 (1 g, 4.67 mmol.) in THF (15 mL) was added to $BH_3$-THF solution (4.67 mL, 1 M in THF) at 0° C. The mixture was stirred at same temperature for 2 hours. MeOH (5 mL) was drop-wise added and the mixture was stirred for another 0.5 hour before aq.1M HCl solution was added and extracted with EtOAc twice. The combined organic layers were washed with water and brine, dried over anhydrous $Na_2SO_4$, filtered and concentrated to dryness. The residue was purified by chromatography on silica gel (PE:EtOAc=1:1) to give intermediate 2 (800 mg, yield 86.0%) as yellow solid. $^1$H-NMR (400 MHz, $CDCl_3$) δ 7.30-7.23 (m, 4H), 7.03 (t, J=7.4 Hz, 1H), 6.93 (dd, J=8.6, 1.8 Hz, 4H), 4.60 (d, J=5.7 Hz, 2H), 1.59 (t, J=5.8 Hz, 1H).

Step 2: a stirred mixture of NaOH (2.15 g, 53.94 mmol) in water (5 mL) and toluene (5 mL) at 20° C. was charged with $Bu_4NHSO_4$ (61 mg, 0.18 mmol), followed by intermediate 2 (360 mg, 1.79 mmol). The mixture was stirred at 20° C. for 1 hour, and then cooled to 5° C. Tert-butyl 2-bromoacetate (0.29 mL, 2.34 mmol) was added drop-wisely. The reaction mixture was stirred at room temperature overnight and extracted with EtOAc twice. The combined organic layers were dried over anhydrous $Na_2SO_4$, concentrated under reduced pressure. The residue was washed with (PE:EtOAc=3:1) to give intermediate 3 (360 mg, yield 64%) as colorless oil.

Step 3: a solution of intermediate 3 (200 mg, 0.64 mmol) in THF (2 mL), MeOH (2 mL) and water (2 mL) was added LiOH (80 mg, 1.9 mmol.) at 0° C. The mixture was stirred at room temperature for 2 hours before concentrated to dryness under reduced pressure. The residue was diluted with water and washed with MTBE twice and the aqueous layer was acidified with 1N aq.HCl to pH~3 and extracted with DCM twice. The combined organic layers were washed with brine, dried over anhydrous $Na_2SO_4$, and concentrated to dryness under reduced pressure to give intermediate 4 (100 mg, yield 61%) as yellow oil.

Step 4: a mixture of intermediate 4 (200 mg, 0.78 mmol) and methyl (2S)-pyrrolidine-2-carboxylate (250.3 mg, 1.94 mmol) in DCM was added HOBt (530.7 mg, 1.4 mmol) and EDCI followed by DIPEA (355 mg, 1.5 mmol) at 0° C. The mixture was stirred overnight before diluted with DCM and washed with water and brine, dried over anhydrous $Na_2SO_4$, filtered and concentrated to dryness under reduced pressure. The residue was purified by chromatography on silica gel (PE:EtOAc=5:1) to give intermediate 5 (100 mg, yield 35%) as yellow oil. LC/MS (ESI) m/z: 370 $(M+H)^+$.

Step 5: a solution of intermediate 5 (100 mg, 0.28 mmol) in THF (2 mL), water (2 mL) and MeOH (2 mL) was added LiOH (19.5 mg, 0.8 mmol) at room temperature (RT). The mixture was stirred at room temperature for 2 hours before concentrated to ⅕ volume, diluted with water and washed with MTBE twice. The aqueous layer was acidified with 1N aq.HCl to pH~3 and extracted with DCM twice. The combined organic layers were washed with brine, dried over anhydrous $Na_2SO_4$, and concentrated to dryness under reduced pressure to give intermediate 6 (60 mg, yield 63%) as yellow oil. LC/MS (ESI) m/z: 356 $(M+H)^+$.

Step 6: a mixture of intermediate 6 (50 mg, 0.14 mmol) in DMF (3 mL) was added to EDCI (48 mg, 0.25 mmol), HOBt (28 mg, 0.21 mmol) and DIPEA (72 mg, 0.56 mmol), followed by 5-(aminomethyl)thiophene-3-carboximidamide hydrochloride (40 mg, 0.21 mmol) at 0° C. The resulting mixture was stirred at room temperature overnight before diluted with EtOAc and washed with saturated aq.$NH_4Cl$ solution and brine, dried over anhydrous $Na_2SO_4$, filtered and concentrated to dryness under reduced pressure. The residue was purified by prep-HPLC to afford COMPOUND 38 (22.8 mg, yield 32.9%) as light yellow solid. $^1$H-NMR (400 MHz, $CD_3OD$) δ 8.54 (s, 1H), 8.23 (dd, J=5.2, 5.2 Hz, 1H), 7.47 (d, J=1.6 Hz, 1H), 7.39-7.28 (m, 5H), 7.13-7.09 (m, 1H), 7.01-6.92 (m, 5H), 4.63-4.53 (m, 4H), 4.45-4.42 (m, 1H), 4.23 (s, 2H), 3.60-3.52 (m, 2H), 2.24-2.16 (m, 1H), 2.08-1.94 (m, 3H); LC/MS (ESI) m/z: 493 $(M+H)^+$.

Scheme 11: Synthesis of (S)-N-((4-carbamimidoylthiophen-2-yl)methyl)-1-(2-(3-methyl-4-phenoxybenzamido)acetyl)pyrrolidine-2-carboxamide (COMPOUND 39)

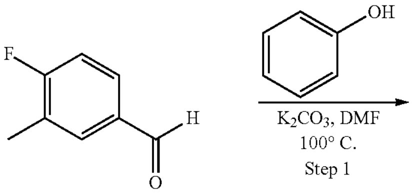

1

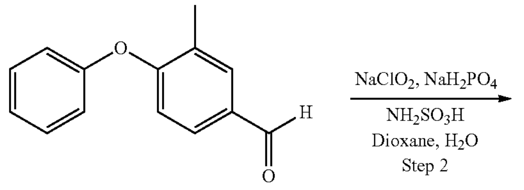

2

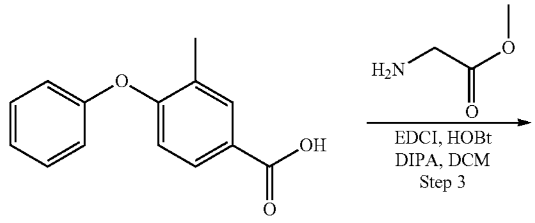

3

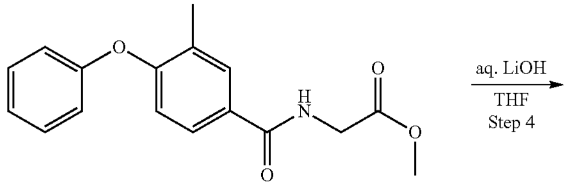

4

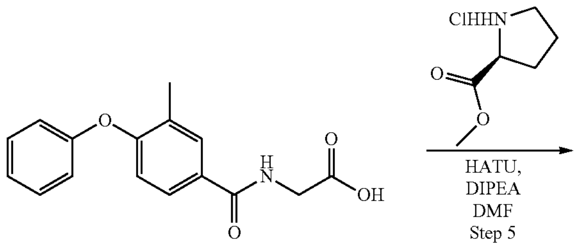

5

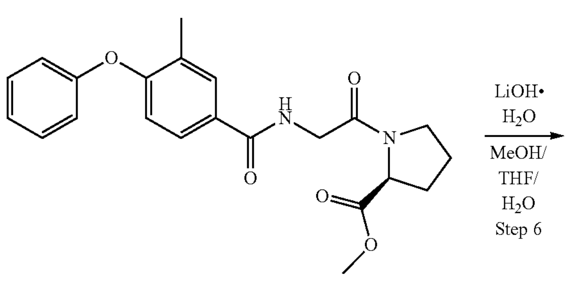

6

-continued

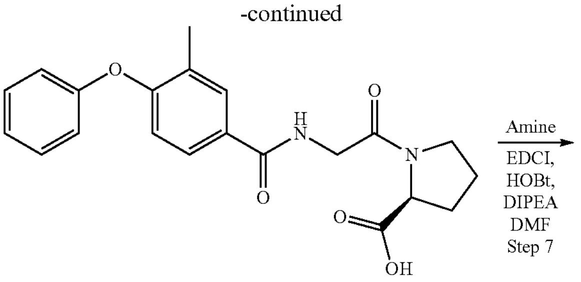

7

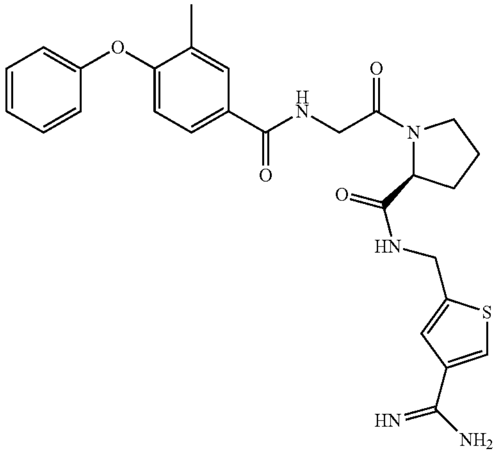

COMPOUND 39

Step 1: a mixture of starting material 1 (2.0 g, 14.49 mmol) and phenol (1.63 g, 17.39 mmol) in DMF (20 mL) was added $K_2CO_3$ (2.0 g, 14.49 mmol) and the mixture was stirred at 120° C. for 16 hours. The mixture was diluted with water and extracted with EtOAc twice. The combined organic layers were washed with aq.$NH_4Cl$ solution and brine, dried over anhydrous $Na_2SO_4$, filtered and concentrated to dryness. The residue was purified by column chromatography on silica gel (PE:EtOAc=100:1) to give intermediate 2 (2.3 g, yield 74.9%) as yellow oil. LC/MS (ESI) m/z: 213 $(M+H)^+$.

Step 2: A mixture of sodium phosphate monobasic (3.61 g, 30.11 mmol) and sulfamic acid (1.28 g, 13.15 mmol) in water (27 mL) was added a solution of intermediate 2 (0.9 g, 4.24 mmol) in 1,4-dioxane (90 mL) at 0° C. Sodium chlorite (1.1 g, 12.13 mmol) in water (27 mL) was added drop-wisely to the mixture. The mixture was stirred at 0° C. for half an hour before diluted with EtOAc and washed with water and brine, dried over anhydrous $Na_2SO_4$, filtered and concentrated to give the residue. The residue was purified by column chromatography on silica gel (PE:EtOAc=20:1 to 1:1) to give intermediate 3 (0.95 g, yield 98.2%) as yellow oil. LC/MS (ESI) m/z: 229 $(M+H)^+$.

Step 3: a mixture of intermediate 3 (515 mg, 2.26 mmol) and methyl 2-aminoacetate hydrochloride (567 mg, 4.52 mmol) in DMF (7 mL) was added EDCI (780 mg, 4.07 mmol), HOBt (458 mg, 3.39 mmol) followed by DIPEA (1.17 g, 9.04 mmol) at 0° C. The mixture was stirred at 25° C. for 16 hours before diluted with DCM and washed with water and brine, dried over anhydrous $Na_2SO_4$, filtered and concentrated to dryness under reduced pressure. The residue was purified by chromatography on silica gel (PE: EtOAc=100:1 to 1:1) to give intermediate 4 (510 mg, yield 75.4%) as light oil. LC/MS (ESI) (m/z): 300 $(M+H)^+$.

Step 4: a solution of intermediate 4 (510 mg, 1.71 mmol) in MeOH (4 mL) and THF (2 mL) was added a solution of lithium hydroxide hydrate (358 mg, 8.53 mmol) in water (2 mL) at 0° C. and the mixture was stirred at room temperature for 1 hour. The mixture was diluted with water and washed with diethyl ether twice. The aqueous layer was acidified with 0.5 M aq.HCl solution and extracted with DCM twice. The combined organic layers were washed with brine, dried over anhydrous $Na_2SO_4$, filtered and concentrated to dryness to give intermediate 5 (485 mg, yield 99.8%) as white solid. LC/MS (ESI) m/z: 286 $(M+H)^+$.

Step 5: a mixture of intermediate 5 (160 mg, 0.56 mmol) and (S)-methyl pyrrolidine-2-carboxylate hydrochloride (92 mg, 0.56 mmol) in DMF (3 mL) was added to DIPEA (303 mg, 2.35 mmol) and HATU (314 mg, 0.84 mmol) at 0° C., and the mixture was stirred at room temperature under $N_2$ atmosphere for 1 hour. The mixture was diluted with EtOAc and washed with saturated aq. $NH_4Cl$ solution and brine, dried over anhydrous $Na_2SO_4$, filtered and concentrated under reduced pressure to give intermediate 6 (217 mg, yield 97.7%) as yellow oil. LC/MS (ESI) (m/z): 397 $(M+H)^+$.

Step 6: a solution of intermediate 6 (217 mg, 0.55 mmol) in MeOH (4 mL) and THF (2 mL) was added a solution of lithium hydroxide hydrate (115 mg, 2.74 mmol) in water (2 mL) at 0° C. The mixture was stirred at room temperature for 1 hour before diluted with water and washed with diethyl ether. The aqueous layer was acidified with 0.5 M aq.HCl solution and extracted with DCM twice. The combined organic layers were washed with brine, dried over anhydrous $Na_2SO_4$, filtered and concentrated to dryness to give intermediate 7 (150 mg, yield 71.4%) as light oil. LC/MS (ESI) m/z: 383 $(M+H)^+$.

Step 7: a mixture of intermediate 7 (80 mg, 0.21 mmol) and 5-(aminomethyl)thiophene-3-carboximidamide hydrochloride (44 mg, 0.23 mmol) in DMF (3 mL) was added to EDCI (72 mg, 0.38 mmol), and HOBt (43 mg, 0.32 mmol), followed by DIPEA (108 mg, 0.84 mmol) at 0° C. The mixture was stirred at 25° C. for 16 hours before diluted with DCM and washed with water and brine, dried over anhydrous $Na_2SO_4$, filtered and concentrated to dryness under reduced pressure. The residue was purified by prep-HPLC to give COMPOUND 39 (6.2 mg, yield 5.7%) as white solid. $^1$H-NMR (400 MHz, DMSO-$d_6$) δ 8.65-8.49 (m, 2H), 8.46 (d, J=1.6 Hz, 1H), 8.32 (t, J=5.8 Hz, 1H), 7.86 (t, J=4.2 Hz, 1H), 7.71 (dd, J=8.4, 8.4 Hz, 1H), 7.48-7.36 (m, 4H), 7.16 (t, J=7.4 Hz, 1H), 7.02-6.95 (m, 3H), 6.88 (d, J=8.4 Hz, 1H), 4.61-4.43 (m, 2H), 4.46-4.29 (m, 4H), 4.22-3.99 (m, 2H), 3.72-3.53 (m, 3H), 2.26 (s, 4H), 2.13-2.00 (m, 1H), 2.00-1.80 (m, 5H); LC/MS (ESI) (m/z): 520 $(M+H)^+$.

Scheme 12: Synthesis of (S)-N-((4-carbamimidoylthiophen-2-yl)methyl)-1-(4-(4-phenoxyphenyl)pent-4-enoyl)pyrrolidine-2-carboxamide (COMPOUND 40)

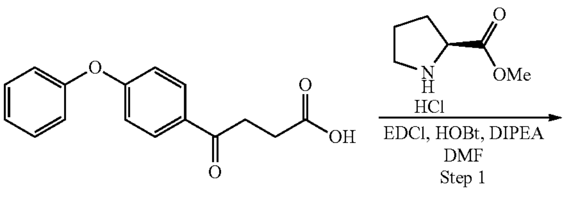

1

-continued

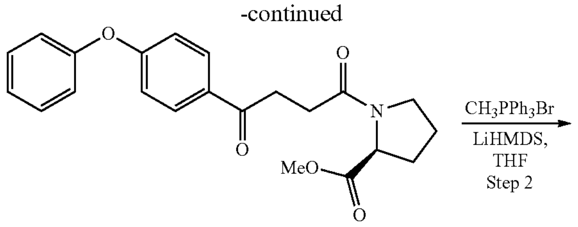

2

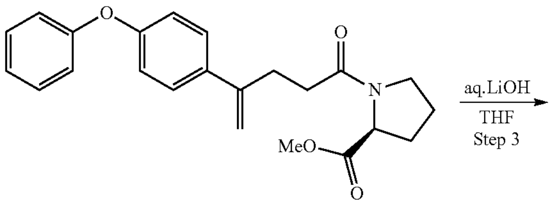

3

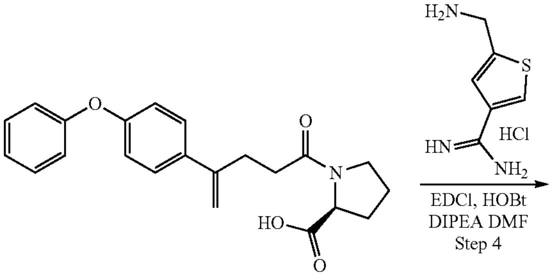

4

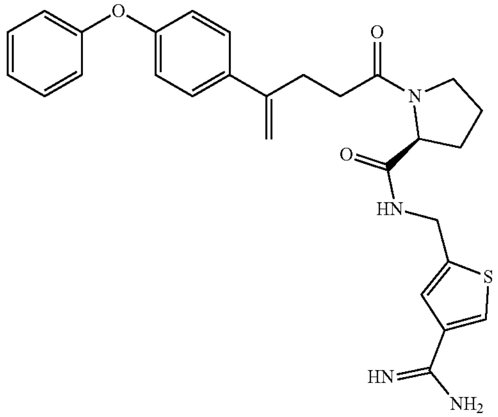

COMPOUND 40

Step 1: a mixture of starting material 1 (2 g, 7.4 mmol), methyl L-prolinate hydrochloride (1.83 g, 11.1 mmol) in DMF was added to DIPEA (5.09 mL, 29.6 mmol), EDCI (2.12 g, 11.1 mmol) and HOBt (1.20 g, 8.88 mmol) at 0° C. The resulting mixture was stirred at room temperature for 16 hours before diluted with EtOAc and washed with saturated aq.$NH_4Cl$ solution and brine, dried over anhydrous $Na_2SO_4$, filtered and concentrated to dryness. The residue was purified by column chromatography on silica gel (eluted with PE:EtOAc=5:1) to give intermediate 2 (1.7 g, yield 60.3%) as yellow oil. LC/MS (ESI) m/z: 382 $(M+H)^+$.

Step 2: a mixture of methyltriphenylphosphonium bromide (300 mg, 0.84 mmol) in THF (5 mL) was added n-butyllithium (0.49 mL, 0.78 mmol, 1.6 M in hexane) drop-wisely at 0° C. The reaction was stirred at 0° C. for 1 hour before cooled to −78° C., and a solution of intermediate 2 (200 mg, 0.52 mmol) in THF (1 mL) was added. After addition, the mixture was stirred at 25° C. for 2 hours before poured into saturated aq.$NH_4Cl$ solution and extracted with EtOAc twice. The combined organic layers were washed with brine, dried over anhydrous $Na_2SO_4$, filtered and concentrated to dryness. The residue was purified by column chromatography on silica gel (eluted with PE:EtOAc=6:1) to give intermediate 3 (80 mg, yield 40.4%) as yellow oil. LC/MS (ESI) m/z: 380 $(M+H)^+$.

Step 3: a solution of intermediate 3 (50 mg, 0.13 mmol) in THF (1 mL), MeOH (1 mL) and water (1 mL) was added LiOH (16.6 mg, 0.40 mmol). The mixture was stirred at room temperature for 1 hour before concentrated to dryness. The residue was diluted with water and washed with EtOAc twice. The aqueous layer was acidified by adding 1N aq.HCl to pH ~3 at 0° C. and extracted with DCM twice. The combined organic layers were washed with brine, dried over anhydrous $Na_2SO_4$, filtered and concentrated to dryness to give intermediate 4 (35 mg, yield 73.8%) as a yellow oil. LC/MS (ESI) m/z: 366 $(M+H)^+$.

Step 4: a mixture of intermediate 4 (35 mg, 0.1 mmol) and 5-(aminomethyl)thiophene-3-carboximidamide hydrochloride (19.2 mg, 0.1 mmol) in DMF was added to EDCI (29 mg, 0.15 mmol) and HOBt (16.2 mg, 0.12 mmol) followed by DIPEA (51.6 mg, 0.4 mmol) at 0° C. The resulting mixture was stirred at room temperature for 16 hours before diluted with EtOAc and washed with saturated aq.$NH_4Cl$ solution and brine, dried over anhydrous $Na_2SO_4$, filtered and concentrated to dryness. The residue was purified by prep-HPLC to afford COMPOUND 40 (5 mg, yield 10.0%) as white solid. $^1$H-NMR (400 MHz, $CD_3OD$) δ 8.54 (s, 1H), 8.23 (d, J=1.6 Hz, 1H), 7.53-7.30 (m, 5H), 7.12 (t, J=7.4 Hz, 1H), 7.03-6.97 (m, 2H), 6.96-6.91 (m, 2H), 5.26 (d, J=19.8 Hz, 1H), 5.08 (d, J=1.0 Hz, 1H), 4.63-4.49 (m, 4H), 4.42-4.30 (m, 1H), 3.66-3.54 (m, 1H), 3.50-3.44 (m, 1H), 2.84-2.74 (m, 2H), 2.62-2.39 (m, 2H), 2.27-2.12 (m, 1H), 2.07-1.87 (m, 3H); LC/MS (ESI) m/z: 503 $(M+H)^+$.

Scheme 13: Synthesis of (S)-N-((4-carbamimidoylthiophen-2-yl)methyl)-1-(2-(4-phenoxy-3-propylbenzamido)acetyl)pyrrolidine-2-carboxamide (COMPOUND 41)

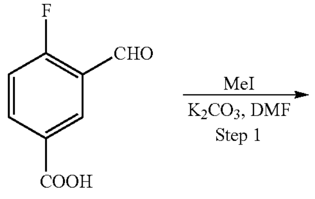

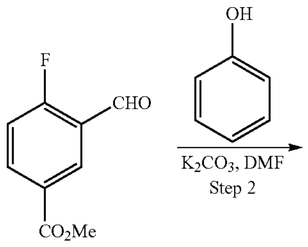

2

-continued

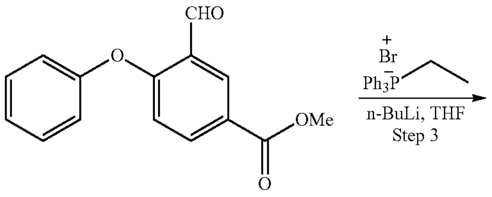

3

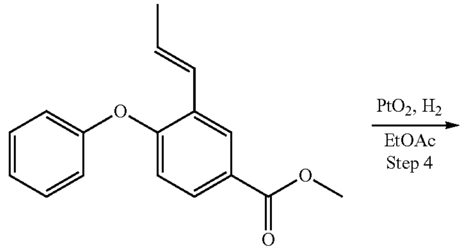

4

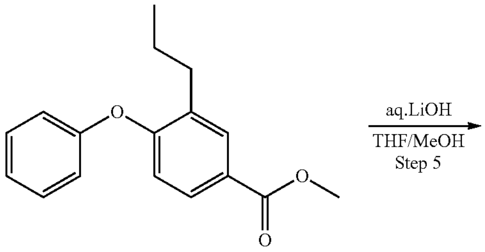

5

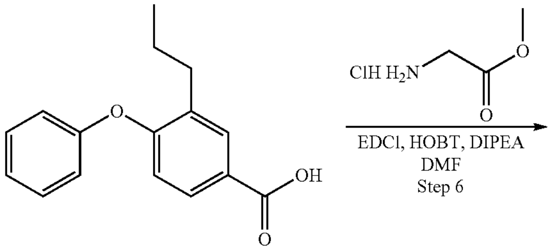

6

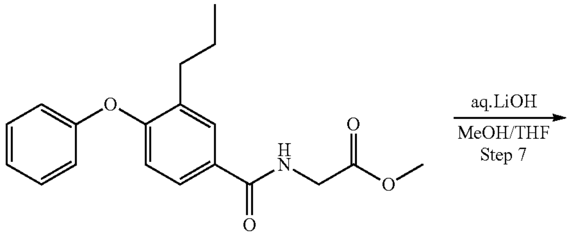

7

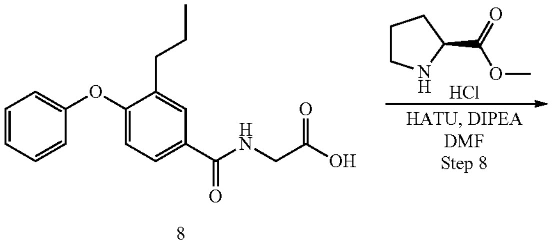

8

-continued

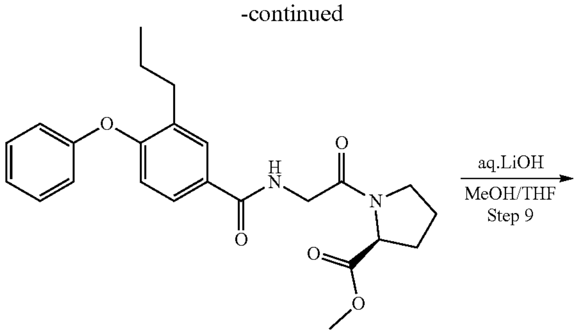

9

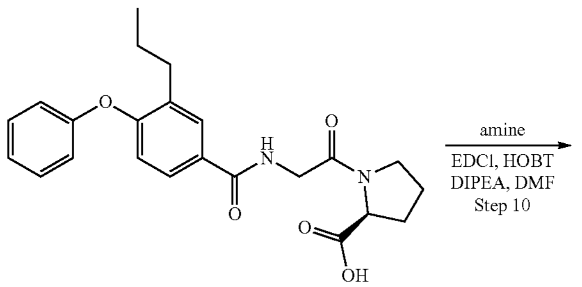

10

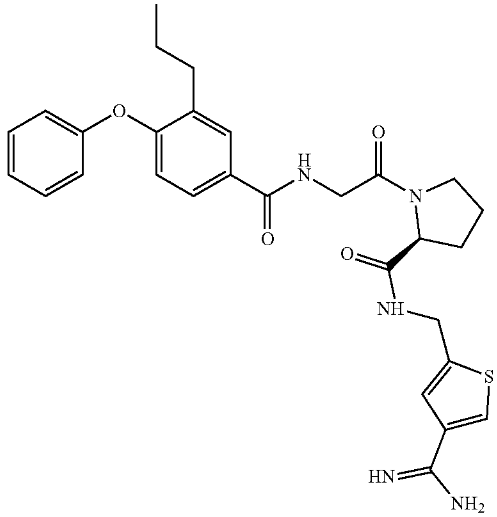

COMPOUND 41

Step 1: a solution of starting material 1 (2.0 g, 11.9 mmol) in DMF (20 mL) was added $K_2CO_3$ (4.93 g, 35.7 mmol) and MeI (2.03 g, 14.28 mmol) at 0° C. The mixture was stirred at room temperature overnight. The mixture was diluted with water and extracted with EtOAc twice. The combined organic layers were washed with aq.$NH_4Cl$ solution and brine, dried over anhydrous $Na_2SO_4$, filtered and concentrated to dryness. The residue was purified by column chromatography on silica gel (PE:EtOAc=100:1 to 50:1) to give intermediate 2 (1.87 g, yield 86.3%) as white solid. LC/MS (ESI) m/z: 183 $(M+H)^+$.

Step 2: a mixture of intermediate 2 (1.87 g, 10.27 mmol) and phenol (1.06 g, 11.3 mmol) in DMF (20 mL) was added $K_2CO_3$ (2.13 g, 15.41 mmol) and the mixture was stirred at 130° C. for 4 hours. The mixture was diluted with water and extracted with EtOAc twice. The combined organic layers were washed with aq.$NH_4Cl$ solution and brine, dried over anhydrous $Na_2SO_4$, filtered and concentrated to dryness. The residue was purified by column chromatography on silica gel (PE:EtOAc=100:1) to give intermediate 3 (2.6 g, yield 98.9%) as light oil. LC/MS (ESI) m/z: 257 $(M+H)^+$.

Step 3: a solution of ethyltriphenylphosphonium bromide (521 mg, 1.40 mmol) in THF (3 mL) was added n-butyllithium (1.13 mL, 1.84 mmol, 1.6M in hexane) at 0° C. under $N_2$ atmosphere and the mixture was stirred at 0° C. for 30 minutes. Intermediate 3 (200 mg, 0.78 mmol) was added drop-wisely to the stirring reaction mixture and stirred at 0° C. for 1.5 hours under $N_2$ atmosphere. The mixture was quenched with ice water at 0° C. and extracted with EtOAc twice. The combined organic layers were washed with brine, dried over anhydrous $Na_2SO_4$, filtered and concentrated. The residue was purified by chromatography on silica gel (PE:EtOAc=100:1 to 50:1) to give intermediate 4 (67 mg, yield 32.1%) as light oil. LC/MS (ESI) m/z: 269 $(M+H)^+$.

Step 4: a solution of intermediate 4 (67 mg, 0.25 mmol) in ethyl acetate (3 mL) was added to $PtO_2$ (23 mg, 35% wt) at 0° C., and the mixture was degassed under $N_s$ atmosphere for three times and stirred under a $H_2$ balloon at room temperature for 30 minutes. The mixture was filtered and the filtrate was concentrated under reduced pressure to give intermediate 5 (64 mg, yield 94.8%). LC/MS (ESI) m/z: 271 $(M+H)^+$.

Step 5: a solution of intermediate 5 (64 mg, 0.24 mmol) in MeOH (2 mL) and THF (1 mL) was added a solution of lithium hydroxide hydrate (50 mg, 1.19 mmol) in water (1 mL) at 0° C. The mixture was stirred at room temperature for 1 hour. The mixture was then diluted with water and washed with diethyl twice. The aqueous layer was acidified with 0.5M aq.HCl solution and extracted with DCM twice. The combined organic layers were washed with brine, dried over anhydrous $Na_2SO_4$, filtered and concentrated to dryness to give intermediate 6 (30 mg, yield 48.8%) as light oil. LC/MS (ESI) m/z: 257 $(M+H)^+$.

Step 6: a mixture of intermediate 6 (30 mg, 0.12 mmol) and methyl 2-aminoacetate hydrochloride (30 mg, 0.24 mmol) in DMF (3 mL) was added to EDCI (41 mg, 0.22 mmol), and HOBt (24 mg, 0.18 mmol), followed by DIPEA (62 mg, 0.48 mmol) at 0° C., and the mixture was stirred at 25° C. for 16 hours. The mixture was diluted with DCM and washed with water and brine, dried over anhydrous $Na_2SO_4$, filtered and concentrated to dryness under reduced pressure. The residue was purified by chromatography on silica gel (PE:EtOAc=100:1 to 10:1) to give intermediate 7 (38 mg, yield 97.4%) as yellow solid. LC/MS (ESI) (m/z): 328 $(M+H)^+$.

Step 7: a solution of intermediate 7 (38 mg, 0.12 mmol) in MeOH (2 mL) and THF (1 mL) was added a solution of lithium hydroxide hydrate (24 mg, 0.58 mmol) in water (1 mL) at 0° C., and the mixture was stirred at room temperature for 1 hour. The mixture was washed with $Et_2O$ and water. The aqueous layer was acidified with 0.5M aq.HCl solution and extracted with DCM twice. The combined organic layers were washed with brine, dried over anhydrous $Na_2SO_4$, filtered and concentrated to dryness to give intermediate 8 (36 mg, yield 97.3%) as light oil. LC/MS (ESI) m/z: 314 $(M+H)^+$.

Step 8: a mixture of intermediate 8 (36 mg, 0.12 mmol) and (S)-methyl pyrrolidine-2-carboxylate hydrochloride (20 mg, 0.12 mmol) in DMF (3 mL) was added to DIPEA (77 mg, 0.6 mmol) HATU (68 mg, 0.18 mmol) at 0° C. and the mixture was stirred at room temperature under $N_2$ atmosphere for 1 hour. The mixture was diluted with EtOAc and washed with saturated aq.$NH_4Cl$ solution and brine, dried over anhydrous $Na_2SO_4$, filtered and concentrated to reduce pressure to give intermediate 9 (48 mg, yield 98.4%) as yellow oil. LC/MS (ESI) (m/z): 425 $(M+H)^+$.

Step 9: a solution of intermediate 9 (48 mg, 0.11 mmol) in MeOH (2 mL) and THF (1 mL) was added a solution of lithium hydroxide hydrate (24 mg, 0.56 mmol) in water (1 mL) at 0° C. The mixture was stirred at room temperature for 1 hour before diluted with diethyl ether and washed with water. The aqueous layer was acidified with 0.5 M aq.HCl solution and extracted with DCM twice. The combined organic layers were washed with brine, dried over anhydrous $Na_2SO_4$, filtered and concentrated to dryness to give intermediate 10 (36 mg, yield 78.3%) as light oil. LC/MS (ESI) m/z: 411 $(M+H)^+$.

Step 10: a mixture of intermediate 10 (36 mg, 0.088 mmol) and 5-(aminomethyl)thiophene-3-carboximidamide hydrochloride (20 mg, 0.11 mmol) in DMF (3 mL) was added to EDCI (30 mg, 0.16 mmol) and HOBt (18 mg, 0.13 mmol), followed by DIPEA (45 mg, 0.35 mmol) at 0° C. The mixture was stirred at 25° C. for 16 hours before diluted with DCM and washed with water and brine, dried over anhydrous $Na_2SO_4$, filtered and concentrated to dryness under reduced pressure. The residue was purified by prep-HPLC to afford COMPOUND 41 (2.0 mg, yield 4.2%) as yellow solid. $^1$H-NMR (400 MHz, DMSO-$d_6$) δ 8.65-8.54 (m, 2H), 8.47 (s, 1H), 8.30 (dd, J=10.0, 10.0 Hz, 1H), 7.85 (t, J=1.8 Hz, 1H), 7.73-7.69 (m, 1H), 7.47-7.38 (m, 3H), 7.18-7.14 (m, 1H), 7.01-6.97 (m, 2H), 6.87 (d, J=8.4 Hz, 1H), 4.59-4.45 (m, 1H), 4.42 (dd, J=6.0, 6.0 Hz, 1H), 4.33 (dd, J=8.8, 8.8 Hz, 1H), 4.21-3.99 (m, 2H), 3.70-3.54 (m, 2H), 2.62 (t, J=7.6 Hz, 2H), 2.05-1.82 (m, 4H), 1.65-1.59 (m, 2H), 0.91 (t, J=7.2 Hz, 3H). LC/MS (ESI) (m/z): 328 $(M+H)^+$.

Scheme 14: Synthesis of (S)-N-((4-carbamimidoylthiophen-2-yl)methyl)-1-((3-pentyl-4-phenoxybenzoyl)glycyl)pyrrolidine-2-carboxamide (COMPOUND 42)

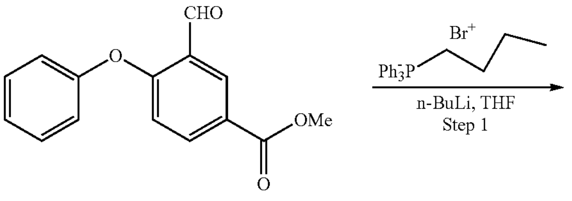

1

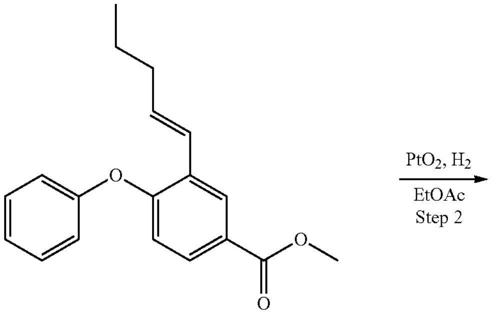

2

-continued

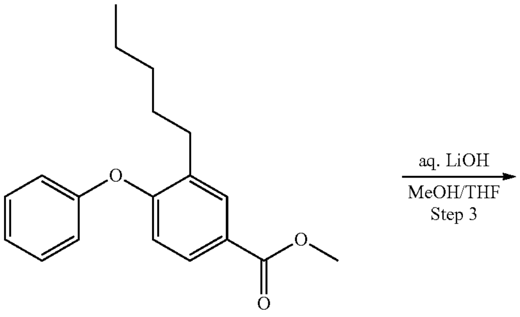

3

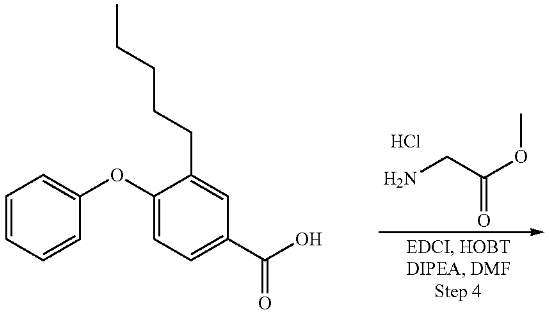

4

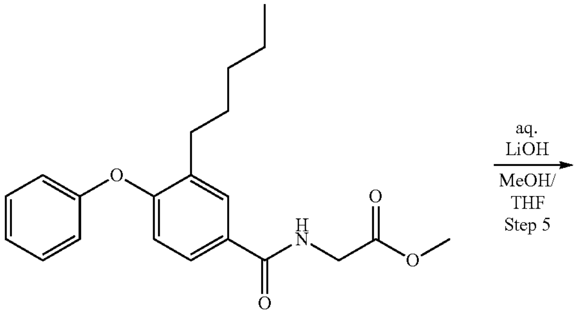

5

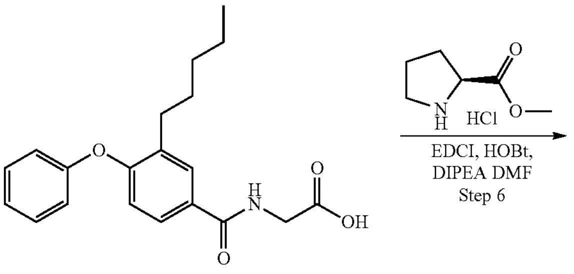

6

-continued

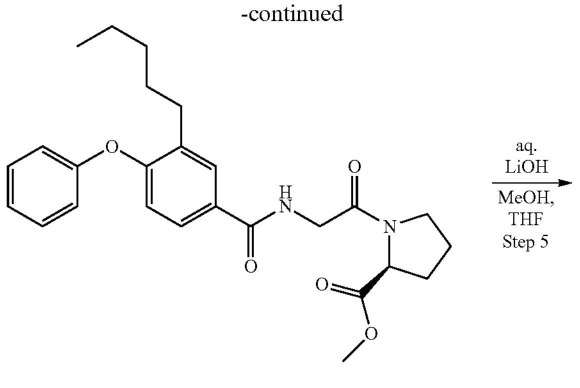

7

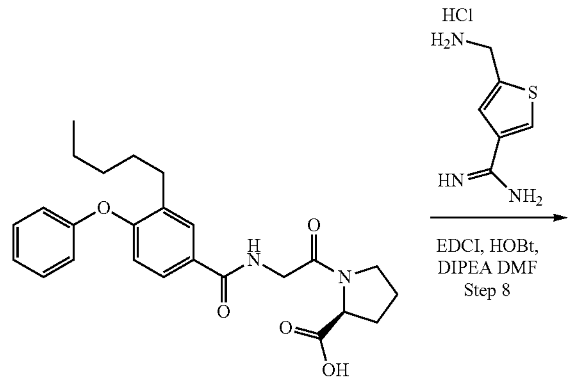

8

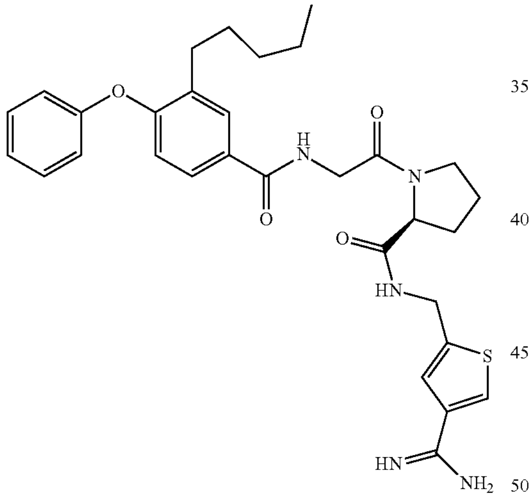

COMPOUND 42

Step 1: a solution of n-butyltriphenylphosphonium bromide (1.4 g, 3.52 mmol) in THF (5 mL) was added n-butyllithium (2.83 mL, 4.53 mmol, 1.6 M in hexane) at 0° C. under $N_2$ atmosphere. The mixture was stirred at 0° C. for 30 minutes before intermediate 1 (500 mg, 1.95 mmol) was added drop-wisely to the stirring reaction mixture. The mixture was stirred at 0° C. for 1.5 hours under $N_2$ atmosphere before quenched with ice water at 0° C. and extracted with EtOAc twice. The combined organic layers were washed with brine, dried over anhydrous $Na_2SO_4$, filtered and concentrated and the residue was purified by chromatography on silica gel (PE:EtOAc=100:1 to 50:1) to give intermediate 2 (286 mg, yield 49.5%) as light oil. LC/MS (ESI) m/z: 297 $(M+H)^+$.

Step 2: a solution of intermediate 2 (100 mg, 0.34 mmol) in ethyl acetate (8 mL) was added $PtO_2$ (35 mg, 35% wt) at 0° C., and the mixture was degassed under $N_2$ atmosphere for three times. The mixture was stirred under a $H_2$ balloon at room temperature for 30 minutes before filtered and the filtrate was concentrated under reduced pressure to give intermediate 3 (100 mg, yield 99.3%) as light oil. LC/MS (ESI) m/z: 299 $(M+H)^+$.

Step 3: a solution of intermediate 3 (72 mg, 0.20 mmol) in THF (2 mL), MeOH (2 mL) and water (2 mL) was added LiOH (25 mg, 0.61 mmol). The mixture was stirred at room temperature for 1 hour before concentrated to dryness. The residue was diluted with water and washed with EtOAc twice. The aqueous layer was acidified by adding 1N aq.HCl to pH ~3 at 0° C. and extracted with DCM twice. The combined organic layers were washed with brine, dried over anhydrous $Na_2SO_4$, filtered and concentrated to dryness to give intermediate 4 (60 mg, yield 88.0%) as a yellow oil. LC/MS (ESI) m/z: 284 $(M+H)^+$.

Step 4: a mixture of intermediate 4 (60 mg, 0.21 mmol), methyl glycinate hydrochloride (41 mg, 0.33 mmol) in DMF was added to DIPEA (108 mg, 0.84 mmol), EDCI (63 mg, 0.33 mmol) and HOBt (34 mg, 0.25 mmol) at 0° C. The resulting mixture was stirred at room temperature for 16 hours before diluted with EtOAc and washed with saturated aq.$NH_4Cl$ solution and brine, dried over anhydrous $Na_2SO_4$, filtered and concentrated to dryness. The residue was purified by column chromatography on silica gel (eluted with PE:EtOAc=15:1) to give intermediate 5 (72 mg, yield 96.6%) as yellow oil. LC/MS (ESI) m/z: 356 $(M+H)^+$.

Step 5: a solution of intermediate 5 (72 mg, 0.20 mmol) in THF (2 mL), and MeOH (2 mL) and water (2 mL) was added LiOH (25 mg, 0.61 mmol). The mixture was stirred at room temperature for 1 hour before concentrated to dryness. The residue was diluted with water and washed with EtOAc twice. The aqueous layer was acidified by adding 1N aq.HCl to pH ~3 at 0° C. and extracted with DCM twice. The combined organic layers were washed with brine, dried over anhydrous $Na_2SO_4$, filtered and concentrated to dryness to give intermediate 6 (60 mg, yield 88.0%) as a yellow oil. LC/MS (ESI) m/z: 342 $(M+H)^+$.

Step 6: a mixture of intermediate 6 (60 mg, 0.18 mmol), methyl L-prolinate hydrochloride (43.5 mg, 0.26 mmol) in DMF and was added to DIPEA (93 mg, 0.72 mmol), EDCI (50 mg, 0.26 mmol) and HOBt (29 mg, 0.22 mmol) at 0° C. The resulting mixture was stirred at room temperature for 16 hours before diluted with EtOAc and washed with saturated aq.$NH_4Cl$ solution and brine, dried over anhydrous $Na_2SO_4$, filtered and concentrated to dryness. The residue was purified by column chromatography on silica gel (eluted with PE:EtOAc=5:1) to give intermediate 7 (60 mg, yield 73.7%) as yellow oil. LC/MS (ESI) m/z: 453 $(M+H)^+$.

Step 7: a solution of intermediate 7 (60 mg, 0.13 mmol) in THF (1 mL), MeOH (1 mL) and water (1 mL) was added LiOH (16.7 mg, 0.40 mmol). The mixture was stirred at room temperature for 1 hour before concentrated to dryness. The residue was diluted with water and washed with EtOAc twice. The aqueous layer was acidified by adding 1N aq.HCl to pH ~3 at 0° C. and extracted with DCM twice. The combined organic layers were washed with brine, dried over anhydrous $Na_2SO_4$, filtered and concentrated to dryness to give intermediate 8 (48 mg, yield 84.3%) as a yellow oil. LC/MS (ESI) m/z: 439 $(M+H)^+$.

Step 8: a mixture of intermediate 8 (48 mg, 0.11 mmol) and 5-(aminomethyl)thiophene-3-carboximidamide hydrochloride (31 mg, 0.16 mmol) in DMF was added to EDCI (31 mg, 0.16 mmol) and HOBt (18 mg, 0.13 mmol), followed by DIPEA (57 mg, 0.44 mmol) at 0° C. The resulting mixture was stirred at room temperature for 16 hours before diluted with EtOAc and washed with saturated aq.$NH_4Cl$ solution and brine, dried over anhydrous $Na_2SO_4$, filtered and concentrated to dryness. The residue was purified by prep-HPLC to afford COMPOUND 42 (18 mg, yield 24.9%) as white solid. $^1$H-NMR (400 MHz, $CD_3OD$) δ 8.55 (s, 1H), 8.20 (d, J=1.6 Hz, 1H), 7.80 (d, J=2.2 Hz, 1H), 7.65 (dd, J=8.5, 2.3 Hz, 1H), 7.45-7.32 (m, 3H), 7.14 (t, J=7.4 Hz, 1H), 6.9-6.95 (m, 2H), 6.82 (d, J=8.5 Hz, 1H), 4.67-4.54 (m, 2H), 4.49 (dd, J=8.7, 3.4 Hz, 1H), 4.29-4.03 (m, 2H), 3.78 (dd, J=10.8, 5.1 Hz, 1H), 3.72-3.60 (m, 1H), 2.78-2.65 (m, 2H), 2.2-2.24 (m, 1H), 2.10-1.99 (m, 3H), 1.69-1.61 (m, 2H), 1.38-1.31 (m, 4H), 0.91-0.84 (m, 3H); LC/MS (ESI) m/z: 576 (M+H)$^+$.

Scheme 15: Synthesis of (S)-1-((3-butyl-4-phenoxybenzoyl)glycyl)-N-((4-carbamimidoylthiophen-2-yl)methyl)pyrrolidine-2-carboxamide (COMPOUND 43)

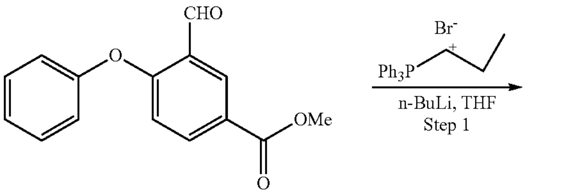

1

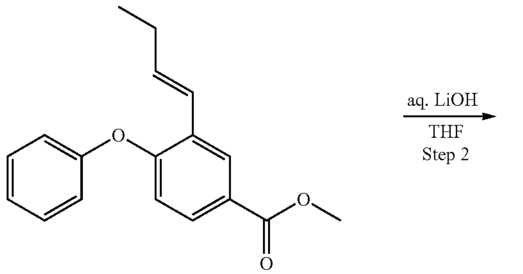

2

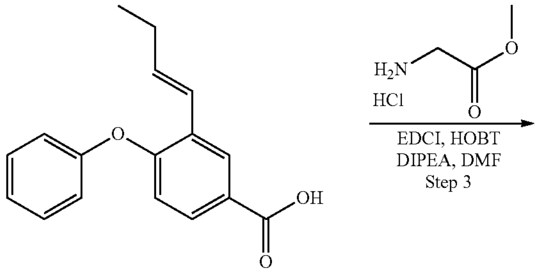

3

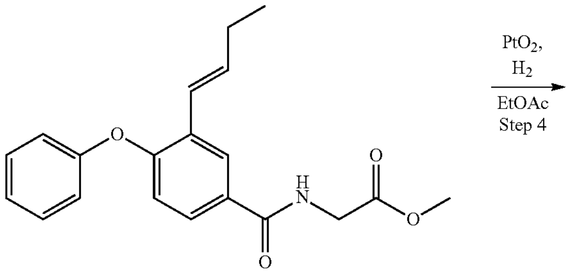

4

-continued

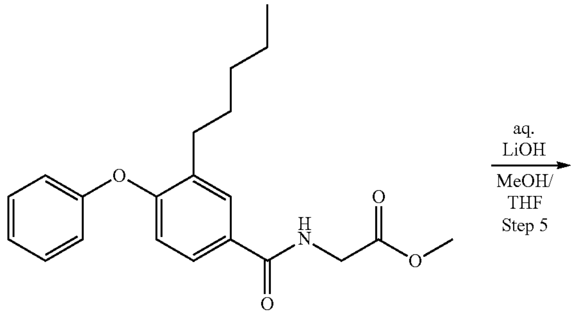

5

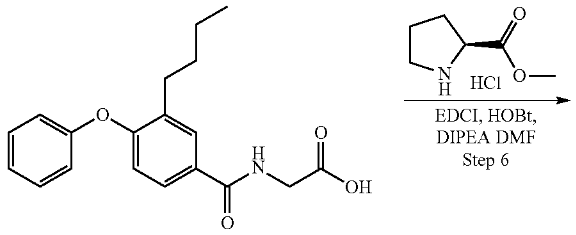

6

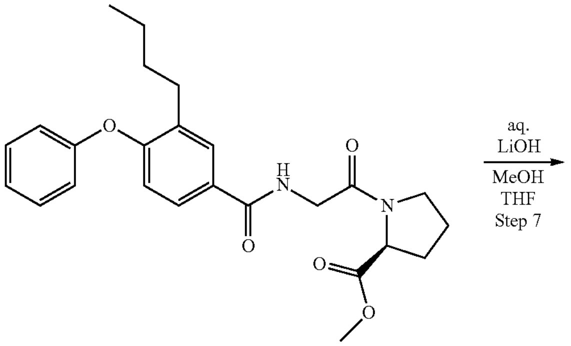

7

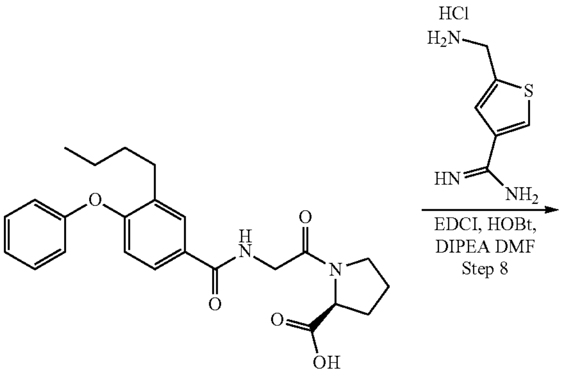

8

-continued

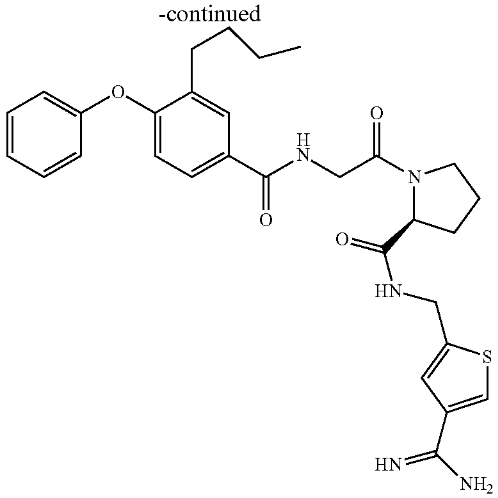

COMPOUND 43

Step 1: a mixture of triphenylpropylphosphonium bromide (963 mg, 2.5 mmol) in THF (10 mL) was added n-butyllithium (1.46 mL, 2.34 mmol, 1.6M in hexane) drop-wisely at 0° C. The reaction mixture was stirred at 0° C. for 1 hour before cooled to −78° C. and a solution of compound 1 (400 mg, 1.56 mmol) in THF (1 mL) was added. After addition, the mixture was stirred at 25° C. for 2 hours before poured into saturated aq.$NH_4Cl$ solution and extracted with EtOAc twice. The combined organic layers were washed with brine, dried over anhydrous $Na_2SO_4$, filtered and concentrated to dryness. The residue was purified by column chromatography on silica gel (eluted with PE:EtOAc=6:1) to give intermediate 2 (220 mg, yield 50.1%) as yellow oil. LC/MS (ESI) m/z: 283 $(M+H)^+$.

Step 2: a solution of intermediate 2 (130 mg, 0.46 mmol) in THF (2 mL), MeOH (2 mL) and water (2 mL) was added LiOH (57 mg, 1.38 mmol). The mixture was stirred at room temperature for 1 hour before concentrated to dryness. The residue was diluted with water and washed with EtOAc twice. The aqueous layer was acidified by adding 1N aq.HCl to pH ~3 at 0° C. and extracted with DCM twice. The combined organic layers were washed with brine, dried over anhydrous $Na_2SO_4$, filtered and concentrated to dryness to give intermediate 3 (120 mg, yield 97.3%) as a yellow oil. LC/MS (ESI) m/z: 269 $(M+H)^+$.

Step 3: a mixture of intermediate 3 (120 mg, 0.45 mmol), methyl glycinate hydrochloride (84 mg, 0.67 mmol) in DMF was added to DIPEA (0.31 mL, 1.8 mmol), EDCI (129 mg, 0.67 mmol) and HOBt (73 mg, 0.54 mmol) at 0° C. After addition, the resulting mixture was stirred at room temperature for 16 hours before diluted with EtOAc and washed with saturated aq.$NH_4Cl$ solution and brine, dried over anhydrous $Na_2SO_4$, filtered and concentrated to dryness. The residue was purified by column chromatography on silica gel (eluted with PE:EtOAc=15:1) to give intermediate 4 (140 mg, yield 92.1%) as yellow oil. LC/MS (ESI) m/z: 340 $(M+H)^+$.

Step 4: a solution of intermediate 4 (140 mg, 0.41 mmol) in EtOAc (15 mL) was added $PtO_2$ (40 mg) at 0° C. The mixture was degassed three times and stirred under a $H_2$ balloon at room temperature for 30 minutes before filtered and the filtrate was concentrated to dryness to give intermediate 5 (135 mg, yield 96.6%) as yellow oil, which was used directly in the next step without further purification. LC/MS (ESI) m/z: 342 $(M+H)^+$.

Step 5: a solution of intermediate 5 (60 mg, 0.18 mmol) in THF (2 mL), MeOH (2 mL) and water (2 mL) was added LiOH (22 mg, 0.53 mmol). The mixture was stirred at room temperature for 1 hour before concentrated to dryness. The residue was diluted with water and washed with EtOAc twice. The aqueous layer was acidified by adding 1N aq.HCl to pH ~3 at 0° C., and extracted with DCM twice. The combined organic layers were washed with brine, dried over anhydrous $Na_2SO_4$, filtered and concentrated to dryness to give intermediate 6 (55 mg, yield 93.2%) as a yellow oil. LC/MS (ESI) m/z: 328 $(M+H)^+$.

Step 6: a mixture of intermediate 6 (55 mg, 0.17 mmol), methyl L-prolinate hydrochloride (41.6 mg, 0.25 mmol) in DMF was added to DIPEA (0.12 mL, 0.68 mmol), EDCI (48 mg, 0.25 mmol) and HOBt (28 mg, 0.20 mmol) at 0° C. After addition, the resulting mixture was stirred at room temperature for 16 hours before diluted with EtAOc and washed with saturated aq.$NH_4Cl$ solution and brine, dried over anhydrous $Na_2SO_4$, filtered and concentrated to dryness. The residue was purified by column chromatography on silica gel (eluted with PE:EtOAc=5:1) to give intermediate 7 (60 mg, yield 80.6%) as yellow oil. LC/MS (ESI) m/z: 439 $(M+H)^+$.

Step 7: a solution of intermediate 7 (60 mg, 0.14 mmol) in THF (1 mL), MeOH (1 mL) and water (1 mL) was added LiOH (16.6 mg, 0.40 mmol). The mixture was stirred at room temperature for 1 hour before concentrated to dryness. The residue was diluted with water and washed with EtOAc twice. The aqueous layer was acidified by adding 1N aq. HCl to pH ~3 at 0° C. and extracted with DCM twice. The combined organic layers were washed with brine, dried over anhydrous $Na_2SO_4$, filtered and concentrated to dryness to give intermediate 8 (55 mg, yield 92.4%) as a yellow oil. LC/MS (ESI) m/z: 425 $(M+H)^+$.

Step 8: a mixture of intermediate 4 (55 mg, 0.13 mmol) and 5-(aminomethyl)thiophene-3-carboximidamide hydrochloride (37 mg, 0.19 mmol) in DMF was added to EDCI (37 mg, 0.19 mmol) and HOBt (21 mg, 0.16 mmol), followed by DIPEA (67 mg, 0.52 mmol) at 0° C. The resulting mixture was stirred at room temperature for 16 hours before diluted with EtAOc, and washed with saturated aq.$NH_4Cl$ solution and brine, dried over anhydrous $Na_2SO_4$, filtered and concentrated to dryness. The residue was purified by prep-HPLC to afford COMPOUND 43 (18 mg, yield 24.9%) as white solid. $^1$H-NMR (400 MHz, $CD_3OD$) δ 8.54 (s, 1H), 8.22 (d, J=17.8, 1H), 7.80 (d, J=2.3 Hz, 1H), 7.65 (dd, J=8.5, 2.3 Hz, 1H), 7.51-7.27 (m, 3H), 7.14 (t, J=7.4 Hz, 1H), 6.97 (dd, J=8.6, 1.0 Hz, 2H), 6.90-6.75 (m, 1H), 4.57 (s, 2H), 4.49 (dd, J=8.8, 3.3 Hz, 1H), 4.21 (q, J=16.7 Hz, 2H), 3.79-3.75 (m, 1H), 3.72-3.66 (m, 1H), 2.75-2.67 (m, 2H), 2.24 (d, J=4.1 Hz, 1H), 2.26-2.19 (m, 2H), 1.69-1.58 (m, 2H), 1.40=1.34 (m, 2H), 0.92 (t, J=7.4 Hz, 3H); LC/MS (ESI) m/z: 562 $(M+H)^+$.

Scheme 16: Synthesis of (S)-N-((4-carbamimidoylthiophen-2-yl)methyl)-1-(3-(1-(4-phenoxyphenyl)cyclopropyl)propanoyl)pyrrolidine-2-carboxamide(COMPOUND 44)

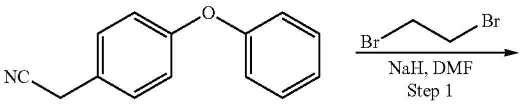

1

-continued

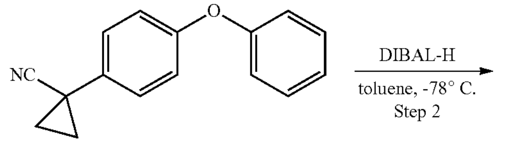

2

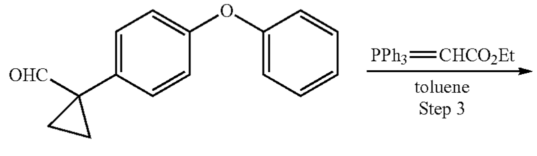

3

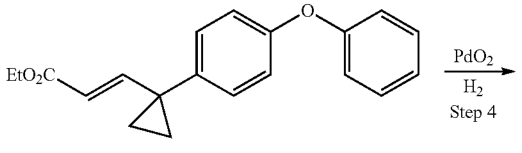

4

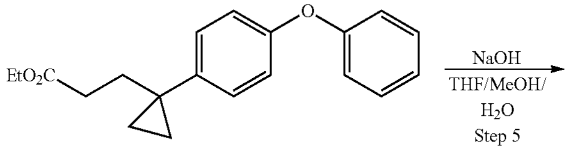

5

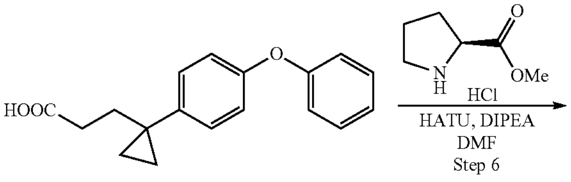

6

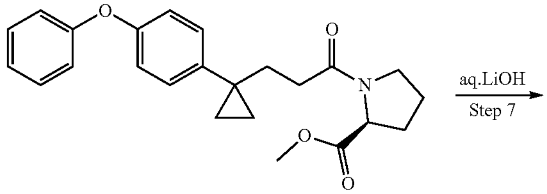

7

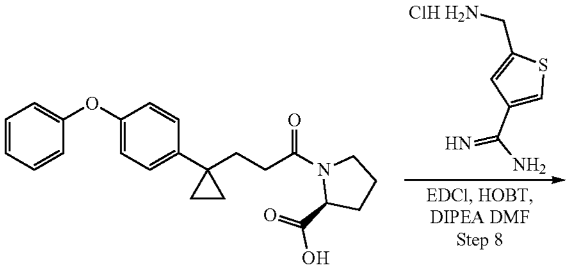

8

-continued

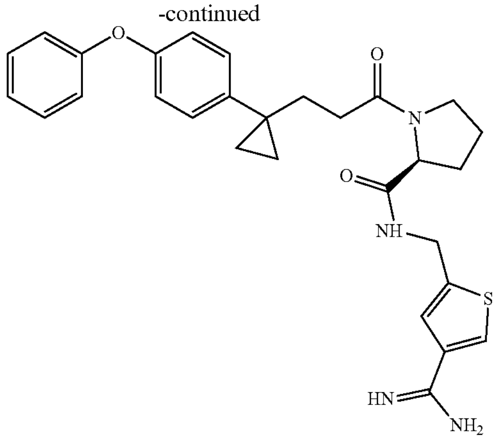

COMPOUND 44

Step 1: a solution of starting material 1 (740 g, 3.54 mmol) in anhydrous DMF (8 mL) was added NaH (389 mg, 9.74 mmol, 60% dispersion in mineral oil) in portions at 0° C. under $N_2$ atmosphere. The mixture was stirred at 0° C. for 15 minutes before 1,2-dibromoethane (998 mg, 5.31 mmol) in DMF (3 mL) was added to the above mixture. The resulting mixture was stirred at 25° C. for 2 hours under $N_2$ atmosphere before quenched with saturated aq.$NH_4Cl$ solution and extracted with EtOAc. The organic layer was washed with brine, dried over $Na_2SO_4$, filtered and concentrated to dryness. The residue was purified by column chromatography on silica gel (eluted with PE:EtOAc=100:1 to 10:1) to give intermediate 2 (618 g, yield 74.3%) as white solid. LC/MS (ESI) m/z: 236 $(M+H)^+$.

Step 2: a solution of intermediate 2 (618 mg, 2.63 mmol) in toluene (10 mL) was added DIBAL-H (3.5 mL, 1.5 M, 5.25 mmol) drop-wisely at −65° C. The mixture was stirred at room temperature for 30 minutes before quenched with saturated potassium sodium tartrate solution and extracted with EtOAc twice. The combined organic layers were washed with water and brine, dried over $Na_2SO_4$, filtered and concentrated to dryness to give crude product, which was purified by silica gel chromatography (eluted with PE:EtOAc=100:1 to 10:1) to give intermediate 3 (600 mg, yield 95.8%) as light oil. LC/MS (ESI) m/z: 239 $(M+H)^+$.

Step 3: a mixture of intermediate 3 (300 mg, 1.26 mmol) and ethyl (triphenylphosphoranylidene)acetate (526 mg, 1.51 mmol) in toluene was stirred at 80° C. for 4 hours under $N_2$ atmosphere. The mixture was concentrated and the residue was purified by silica gel chromatography (eluted with PE:EtOAc=100:1 to 10:1) to give intermediate 4 (268 mg, yield 72.4%) as light yellow oil. LC/MS (ESI) m/z: 309 $(M+H)^+$.

Step 4: a solution of intermediate 4 (268 mg, 0.87 mmol) in ethyl acetate (5 mL) was added $PtO_2$ (80 mg, 10% wt) at 0° C. The mixture was degassed under $N_2$ atmosphere for three times and stirred under a $H_2$ balloon at room temperature for 4 hours before filtered and the filtrate was concentrated under reduced pressure to give intermediate 5 (150 mg, yield 55.6%) as light oil. LC/MS (ESI) m/z: 299 $(M+H)^+$.

Step 5: a solution of intermediate 5 (150 mg, 0.48 mmol) in MeOH (4 mL) and THF (2 mL) was added a solution of sodium hydroxide (77 mg, 1.92 mmol) in water (2 mL) at 0° C. The mixture was stirred at 30° C. for 30 minutes before diluted with water and washed with diethyl ether. The aqueous layer was acidified with 0.5 M aq.HCl solution and extracted with DCM twice. The combined organic layers were washed with brine, dried over anhydrous $Na_2SO_4$, filtered and concentrated to dryness to give intermediate 6 (130 mg, yield 96.0%) as light oil. LC/MS (ESI) m/z: 283 $(M+H)^+$.

Step 6: a mixture of intermediate 6 (130 mg, 0.46 mmol) and (S)-methyl pyrrolidine-2-carboxylate hydrochloride (76 mg, 0.46 mmol) in DMF (5 mL) was added to DIPEA (297 mg, 2.3 mmol), and HATU (262 mg, 0.69 mmol) at 0° C. The mixture was stirred at room temperature under $N_2$ atmosphere for 1 hour before diluted with EtOAc and washed with saturated aq. $NH_4Cl$ solution and brine, dried over anhydrous $Na_2SO_4$, filtered and concentrated to dryness. The residue was purified by column chromatography on silica gel (PE:EtOAc=30:1 to 1:1) to give intermediate 7 (150 mg, yield 68.8%) as light oil. LC/MS (ESI) (m/z): 394 $(M+H)^+$.

Step 7: a solution of intermediate 7 (150 mg, 0.38 mmol) in MeOH (4 mL) and THF (2 mL) was added a solution of sodium hydroxide (61 mg, 1.53 mmol) in water (2 mL) at 0° C. The mixture was stirred at 30° C. for 30 minutes before diluted with water and washed with diethyl ether. The aqueous layer was acidified with 0.5 M aq.HCl solution and extracted with DCM twice. The combined organic layers were washed with brine, dried over anhydrous $Na_2SO_4$, filtered and concentrated to dryness to give intermediate 8 (130 mg, yield 90.3%) as white solid. LC/MS (ESI) m/z: 380 $(M+H)^+$.

Step 8: a mixture of intermediate 8 (130 mg, 0.34 mmol) and 5-(aminomethyl)thiophene-3-carboximidamide hydrochloride (65 mg, 0.34 mmol) in DMF (6 mL) was added to DIPEA (175 mg, 1.36 mmol) and HOBt (69 mg, 0.51 mmol), followed by EDCI (117 mg, 0.61 mmol) at 0° C. The mixture was stirred at room temperature overnight before diluted with DCM and washed with saturated aq.$NH_4Cl$ solution and brine. The combined organic layers were dried over $Na_2SO_4$ and concentrated to dryness under reduced pressure. The residue was purified by prep-HPLC to afford COMPOUND 44 (2.3 mg, yield 1.31%) as white solid. $^1H$-NMR (400 MHz, $CD_3OD$) δ 8.25 (dd, J=14.8, 14.8 Hz, 1H), 7.46-7.41 (m, 1H), 7.36-7.27 (m, 4H), 7.11=7.05 (m, 1H), 6.96-6.89 (m, 4H), 4.59-4.51 (m, 3H), 3.58-3.51 (m, 1H), 3.48-3.42 (m, 1H), 2.37-2.34 (m, 1H), 2.20-2.14 (m, 1H), 2.04-1.84 (m, 6H), 0.84-0.76 (m, 2H), 0.76-0.72 (m, 2H); LC/MS (ESI) m/z: 517 $(M+H)^+$.

Scheme 17: Synthesis of (R)-N-((4-carbamimidoylthiophen-2-yl)methyl)3,3-dimethyl-1-((3-methyl-4-phenoxybenzoyl)glycyl)-1,3-azasilolidine-5-carboxamide (COMPOUND 45)

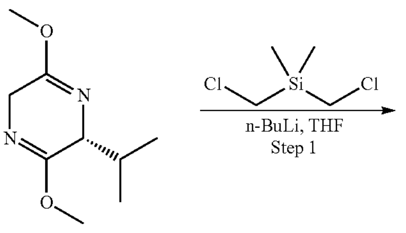

1

-continued

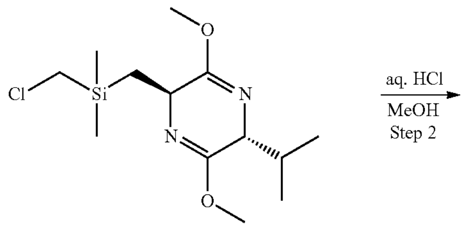

2

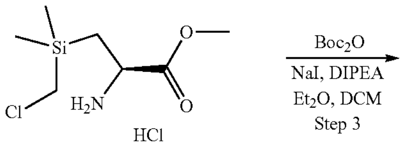

3

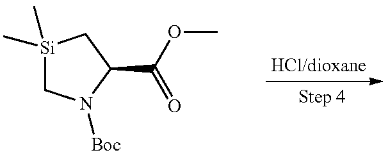

4

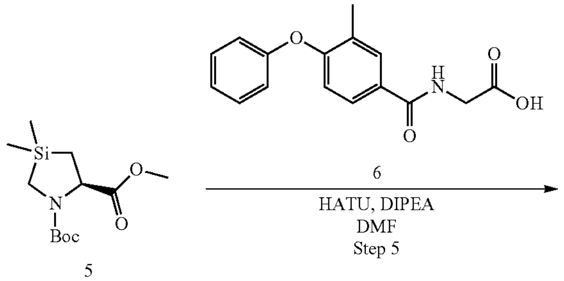

6

5

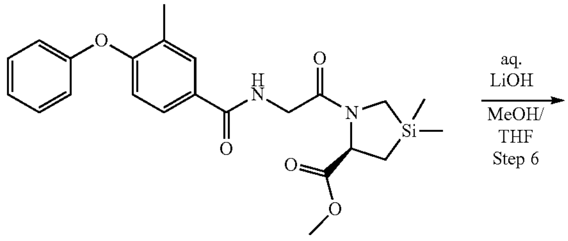

7

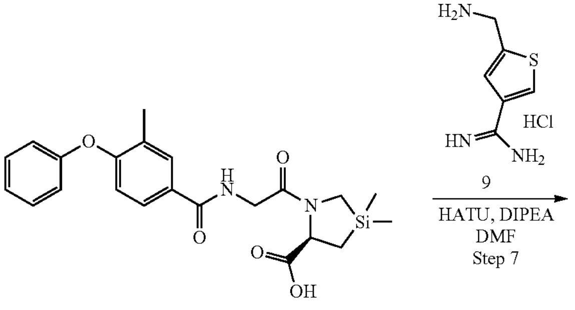

9

8

-continued

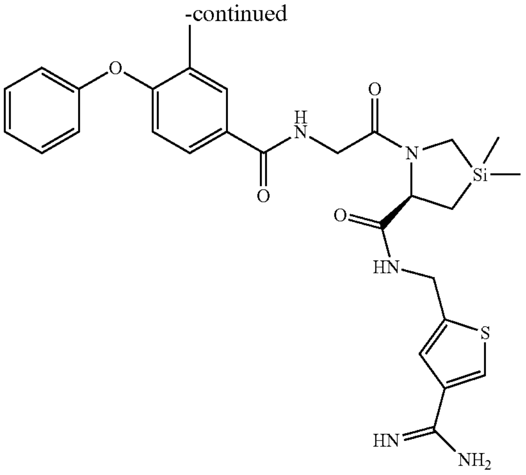

COMPOUND 45

Step 1: a mixture of starting material 1 (500 mg, 2.72 mmol) and bis(chloromethyl)dimethylsilane (636 mg, 4.08 mmol) in anhydrous THF (10 mL) at −78° C. under $N_2$ atmosphere was added n-BuLi (2.21 mL, 3.54 mmol, 1.6 M in hexane) drop-wisely at −78° C. After addition, the reaction mixture was stirred at 25° C. for 16 hours before cooled to 0° C. and quenched with saturated aq.$NH_4Cl$ solution, extracted with EtOAc twice, and washed with brine, dried over $Na_2SO_4$ and concentrated to dryness. The residue was purified by column chromatography on silica gel (PE:EtOAc=60:1) to give intermediate 2 (500 mg, yield 60.4%) as yellow oil.

Step 2: a solution of intermediate 2 (500 mg, 1.64 mmol) in MeOH (3.7 mL) at 0° C. was added aq. 10% HCl (1.3 mL) at 0° C. After addition, the reaction mixture was stirred at 25° C. for 3 hours before concentrated to dryness to give intermediate 3 (400 mg, yield 99.6%) as yellow oil, which was used directly in the next step without further purification LC/MS (ESI) m/z: 210 $(M+H)^+$.

Step 3: a solution of intermediate 3 (100 mg, 0.41 mmol) in DCM (5 mL) at 0° C. was added DIPEA (210 mg, 1.63 mmol) and NaI (61.5 mg, 0.41 mmol) at 0° C. After addition, the reaction mixture was stirred at 25° C. overnight before di-tert-butyl dicarbonate (179 mg, 0.82 mmol) was added. The reaction was stirred at 25° C. for 3 hours. After completion of the reaction, the reaction mixture was poured into ice water and extracted with DCM twice. The organic layers were washed with brine, dried over $Na_2SO_4$ and concentrated to dryness and the residue was purified by column chromatography on silica gel (PE:EtOAc=60:1) to give intermediate 4 (85 mg, yield 75.6%) as yellow solid. LC/MS (ESI) m/z: 274 $(M+H)^+$.

Step 4: a solution of intermediate 4 (75 mg, 0.27 mmol) in HCl/1,4-dioxane (3 mL, 4M) was stirred at room temperature for 1 hour before concentrated to dryness to give intermediate 5 (56 mg, yield 99.2%) as light yellow oil, which was used directly in the next step without further purification. LC/MS (ESI) m/z: 174 $(M+H)^+$.

Step 5: a mixture of intermediate 5 (56 mg, 0.27 mmol) and compound 6 (77 mg, 0.27 mmol) in DMF (2 mL) was added to DIPEA (139 mg, 1.08 mmol), followed by HATU (185 mg, 0.49 mmol) at 0° C. The mixture was stirred at room temperature for 1 hour before diluted with EtOAc and washed with saturated aq.$NH_4Cl$ solution and brine, dried over anhydrous $Na_2SO_4$, filtered and concentrated to dryness. The residue was purified by column chromatography on silica gel (eluted with PE:EtOAc=6:1 to 3:1) to give intermediate 7 (86 mg, yield 72.4%) as yellow solid. LC/MS (ESI) m/z: 441 $(M+H)^+$.

Step 6: a solution of intermediate 7 (86 mg, 0.20 mmol) in THF (1 mL), MeOH (1 mL) and water (1 mL) was added LiOH (24.6 mg, 0.59 mmol). The mixture was stirred at room temperature for 2 hours before concentrated to dryness, diluted with water and washed with EtOAc twice. The aqueous layer was acidified with 1 N aq.HCl to pH ~3 at 0° C. and extracted with DCM twice. The combined organic layers were washed with brine, dried over anhydrous $Na_2SO_4$, filtered and concentrated to dryness to give intermediate 8 (75 mg, yield 90.1%) as yellow oil. LCMS: LC/MS (ESI) m/z: 427 $(M+H)^+$.

Step 7: a mixture of intermediate 8 (75 mg, 0.18 mmol) and compound 9 (50 mg, 0.26 mmol) in DMF (2 mL) was added DIPEA (93 mg, 0.72 mmol), followed by HATU (68 mg, 0.49 mmol) at 0° C. The mixture was stirred at room temperature for 1 hour before diluted with EtOAc and washed with saturated aq.$NH_4Cl$ solution and brine, dried over anhydrous $Na_2SO_4$, filtered and concentrated to dryness. The residue was purified by prep-HPLC to afford COMPOUND 45 (12 mg, yield 12.1%) as yellow solid. $^1$H-NMR (400 MHz, $CD_3OD$) δ 8.55 (s, 1H), 8.20 (d, J=1.6 Hz, 1H), 7.80 (t, J=5.2 Hz, 1H), 7.65 (dd, J=8.5, 2.2 Hz, 1H), 7.41-7.31 (m, 3H), 7.14 (t, J=7.4 Hz, 1H), 6.96 (dd, J=8.7, 1.0 Hz, 2H), 6.82 (d, J=8.5 Hz, 1H), 4.96 (dd, J=10.4, 3.1 Hz, 1H), 4.55 (d, J=7.1 Hz, 2H), 4.35-4.27 (m, 2H), 3.02 (dd, J=16.7, 8.1 Hz, 2H), 2.31 (s, 3H), 1.34-1.26 (m, 1H), 1.23-1.16 (m, 1H), 0.29 (d, J=14.3 Hz, 6H); LC/MS (ESI) m/z: 564 $(M+H)^+$.

Scheme 18: Synthesis of (S)-N-((4-carbamimidoylthiophen-2yl) methyl)-2-(2-(3-methyl-4-phenoxybenzamido)acetyl)-2-azaspiro[4.4] nonane-3-carboxamide (COMPOUND 46)

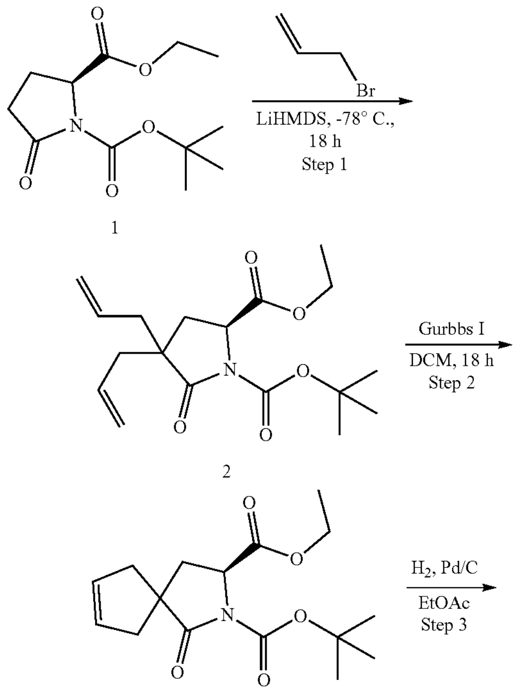

1

2

3

-continued

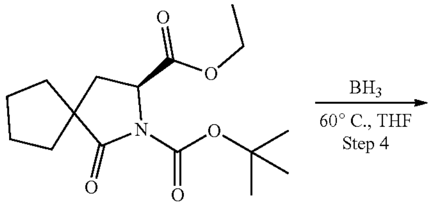

4

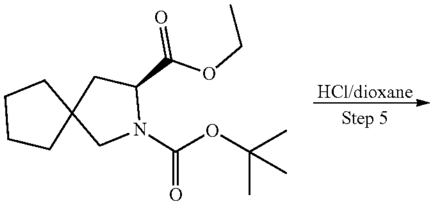

5

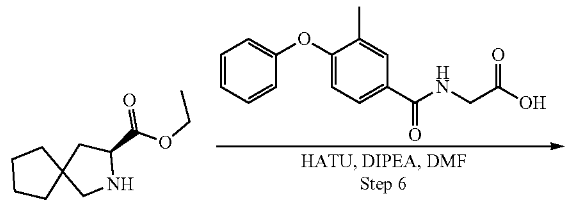

6

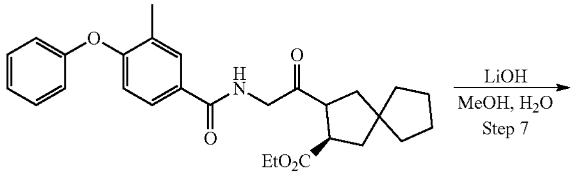

7

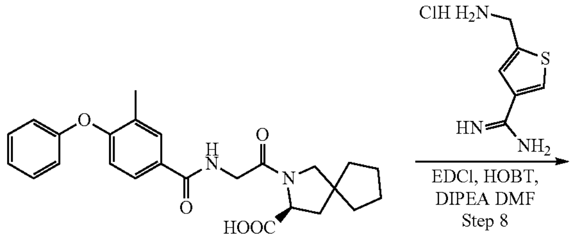

8

-continued

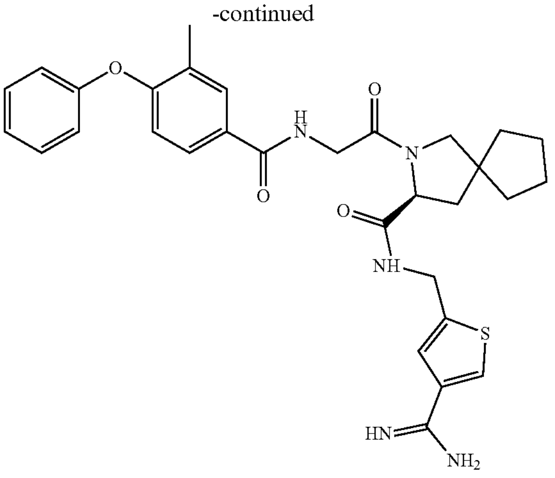

COMPOUND 46

Step 1: a solution of starting material 1 (1.5 g, 6.17 mmol) in THF (100 mL) was added LHMDS (6.17 ml, 6.17 mmol, 1 M in THF) drop-wisely at −70° C. The reaction mixture was stirred at this temperature for 1 hour before addition of 3-bromoprop-1-ene (0.52 mL, 6.17 mmol). The mixture was stirred at room temperature for 18 hours before quenched with diluted acetic acid (1.2 mL in 5 mL water) and concentrated under reduced pressure. The residue was diluted with EtOAc and washed with water, brine and dried over $Na_2SO_4$, filtered and concentrated to dryness. The residue was purified by chromatography on silica gel (PE:EtOAc=5:1) to give intermediate 2 (1 g, yield 81.0%) as colorless oil. LC/MS (ESI) (m/z): 338 $(M+H)^+$.

Step 2: Grubbs I catalyst (57 mg, 0.214 mmol) was added to a solution of intermediate 2 (1 g, 4.12 mmol) in DCM (30 ml) under $N_2$ atmosphere. The mixture was degassed under $N_2$ for three times and at room temperature stirred for 18 hours. The mixture was concentrated to dryness and the residue was purified by chromatography on silica gel (PE:EtOAc=4:1) to give intermediate 3 (700 mg, yield 76%) as brown oil, which was used directly in the next step without further purification. LC/MS (ESI) (m/z): 341 $(M+H)^+$.

Step 3: a solution of intermediate 3 (300 mg, 1.80 mmol) in EtOAc (3 mL) was added 10% Pd/C (50 mg) at 0° C. The mixture was degassed under $N_2$ atmosphere for three times and stirred under a $H_2$ balloon at room temperature for 1 hour. The mixture was filtered and the filtrate was concentrated to dryness to give intermediate 4 (265 mg, yield 82.60) as brown semi-solid. LC/MS (ESI) (m/z): 312 $(M+H)^+$.

Step 4: a mixture of intermediate 4 (150 mg, 0.47 mmol) was added $BH_3$-THF (0.5 mL, 1M in THF) drop-wisely at 0° C. The mixture was stirred at 60° C. under $N_2$ atmosphere for 12 hours. The mixture was quenched with MeOH and the mixture was concentrated to dryness. The residue was purified by chromatography on silica gel (DCM:MeOH=25:1) to give intermediate 5 (130 mg, 75.2% yield) as brown oil. LC/MS (ESI) (m/z): 298 $(M+H)^+$.

Step 5: a solution of intermediate 5 (130 mg, 0.37 mmol) HCl/1,4-dioxane (2 mL) was stirred at room temperature for 2 hours. The mixture was concentrated to dryness and the residue was washed with diethyl ether and dried under vacuum to give intermediate 6 (80 mg, yield 91%) as brown oil, which was used directly in the next step without further purification. LC/MS (ESI) (m/z): 198 $(M+H)^+$.

Step 6: a mixture of intermediate 6 (80 mg, 0.40 mmol) and 2-(3-methyl-4-phenoxybenzamido)acetic acid (115 mg, 0.56 mmol) in DMF (5 mL) was added to DIPEA (300 mg, 2.0 mmol) and HATU (360 mg, 0.8 mmol) at 0° C. The mixture was stirred at room temperature under $N_2$ atmosphere for 12 hours before diluted with EtOAc and washed with saturated aq.$NH_4Cl$ solution and brine, dried over anhydrous $Na_2SO_4$, filtered and concentrated to dryness. The residue was purified by chromatography on silica gel (DCM:MeOH=19:1) to give intermediate 7 (100 mg, yield 72.3%) as brown oil. LC/MS (ESI) (m/z): 465 $(M+H)^+$.

Step 7: a solution of intermediate 7 (100 mg, 0.151 mmol) in MeOH (5 mL) and water (1 mL) was added lithium hydroxide monohydrate (32 mg, 0.753 mmol) and the mixture was stirred at room temperature for 2 hours. The mixture was concentrated to ⅕ volume, diluted with water and washed with MTBE twice. The aqueous layer was acidified with 1N aq.HCl to pH~3 and extracted with DCM twice. The combined organic layers were washed with brine, dried over anhydrous $Na_2SO_4$, and concentrated to dryness under reduced pressure to give intermediate 8 (100 mg, yield 95%) as brown solid. LC/MS (ESI) (m/z): 437 $(M+H)^+$.

Step 8: a mixture of intermediate 8 (20 mg, 0.234 mmol) and 5-(aminomethyl)thiophene-3-carboximidamide (14 mg, 0.274 mmol) in DMF (5 mL) was added to EDCI (40 mg, 0.468 mmol) and HOBt (37 mg, 0.43 mmol), followed by DIPEA (51 mg, 0.1 mL, 0.81 mmol) at 0° C. The mixture was stirred at 25° C. for 12 hours before diluted with EtOAc and washed with water and brine, dried over anhydrous $Na_2SO_4$, filtered and concentrated to dryness under reduced pressure. The residue was purified by prep-HPLC to afford COMPOUND 46 (10 mg, yield 15.2%) as white solid. $^1$H-NMR (400 MHz, $CD_3OD$) δ 8.20 (d, J=1.6 Hz, 1H), 7.79 (s, 1H), 7.65 (d, J=8.6 Hz, 1H), 7.37 (d, J=7.6 Hz, 3H), 7.14 (t, J=7.4 Hz, 1H), 6.96 (d, J=7.7 Hz, 2H), 6.82 (d, J=8.5 Hz, 1H), 4.18 (d, J=4.3 Hz, 4H), 3.55 (s, 3H), 3.13 (s, 2H), 2.23-2.12 (m, 1H), 1.93 (dd, J=12.8, 7.6 Hz, 2H); LC/MS (ESI) m/z: 574 $(M+H)^+$.

Scheme 19: Synthesis of (S)-N-((4-carbamimidoylthiophen-2-yl)methyl)-7-(2-(3-methyl-4-phenoxybenzamido)acetyl)-1,4-dioxa-7-azaspiro[4.4]nonane-8-carboxamide (COMPOUND 47)

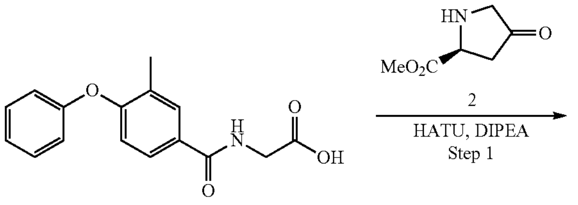

1

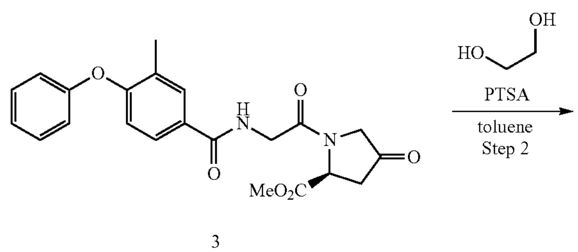

3

-continued

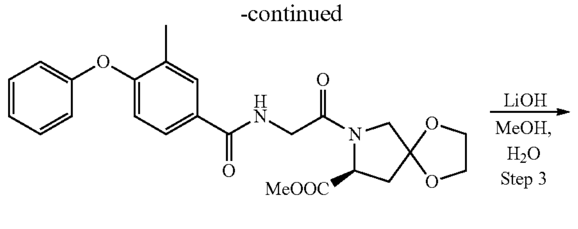

4

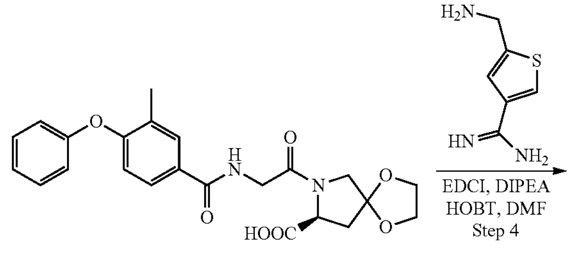

5

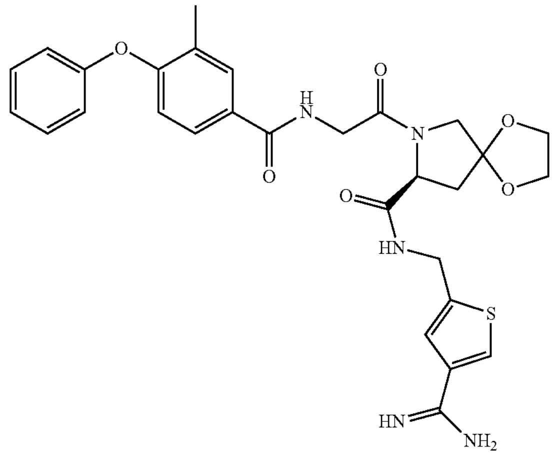

COMPOUND 47

Step 1: a solution of starting material 1 (0.276 g, 0.97 mmol) in DMF (5.0 mL) was added compound 2 (265 mg, 1.46 mmol), followed by DIPEA (0.624 g, 0.8 mL, 4.85 mmol) and HATU (0.736 g, 1.94 mmol) at 0° C. The mixture was stirred at 25° C. for 12 hours before diluted with EtOAc and washed with water and brine, dried over anhydrous $Na_2SO_4$, filtered and concentrated to dryness under reduced pressure. The residue was purified by chromatography on silica gel (PE:EtOAc=53:47) to give intermediate 3 (0.266 g, yield 66.83%) as yellow solid. LC/MS (ESI) (m/z): 411 $(M+H)^+$.

Step 2: a solution of intermediate 3 (0.216 g, 0.53 mmol) in toluene (5 mL) was added TO ethane-1,2-diol (0.4 mL, 2.10 mmol), followed by PTSA (44.0 mg, 0.265 mmol). The mixture was stirred at 120° C. for 1 hour before cooled to room temperature, diluted with water and extracted with EtOAc twice. The combined organic layers were washed with aq.$NaHCO_3$ and brine, dried over anhydrous $Na_2SO_4$, filtered and concentrated to dryness. The residue was purified by chromatography on silica gel (PE:EtOAc=1:2) to give intermediate 4 (75 mg, yield 30.25%) as yellow solid. LC/MS (ESI) (m/z): 455 $(M+H)^+$.

Step 3: a solution of intermediate 4 (75 mg, 0.16 mmol) in methanol (1 mL), THF (1 mL) and water (1 mL) was added lithium hydroxide monohydrate (35 mg, 0.82 mmol). The mixture was stirred at 25° C. for 1 hour before diluted with water and washed with MTBE twice. The aqueous layer was acidified with 0.5M aq.HCl solution to pH~3 and extracted with DCM twice. The combined organic layers were dried over anhydrous $Na_2SO_4$, filtered and concentrated to dryness to give intermediate 5 (85 mg, yield 100%) as yellow solid. LC/MS (ESI) (m/z): 441 $(M+H)^+$.

Step 5: a mixture of intermediate 5 (85 mg, 0.19 mmol) and 5-(aminomethyl)thiophene-3-carboximidamide (0.064 g, 0.29 mmol) in DMF (5 mL), then was added to DIPEA (0.13 mL, 0.76 mmol), followed by EDCI (0.067 g, 0.55 mmol) and HOBt (0.039 g, 0.29 mmol) at 0° C. The mixture was stirred at room temperature for 12 hour before diluted with EtOAc and washed with saturated aq.$NH_4Cl$ solution and brine, dried over anhydrous $Na_2SO_4$, filtered and concentrated to dryness. The residue was purified by chromatography on silica gel (DCM:MeOH=10:1) and further purified by prep-HPLC to afford COMPOUND 47 (20.3 mg, yield 18.29%) as white solid. $^1$H-NMR (400 MHz, DMSO-$d_6$) δ 8.61 (dt, J=18.9, 5.7 Hz, 2H), 8.45 (s, 1H), 8.33 (dd, J=12.0, 1.6 Hz, 1H), 7.85 (d, J=2.4 Hz, 1H), 7.70 (dt, J=8.5, 2.5 Hz, 1H), 7.49-7.35 (m, 3H), 7.20-7.11 (m, 1H), 7.03-6.94 (m, 2H), 6.88 (d, J=8.5 Hz, 1H), 4.79-4.24 (m, 3H), 4.12 (ddd, J=31.1, 16.5, 5.5 Hz, 1H), 4.02-3.84 (m, 4H), 3.80 (d, J=10.7 Hz, 1H), 3.75-3.58 (m, 1H), 2.37-2.16 (m, 2H), 2.26 (s, 3H), 2.15-1.97 (m, 1H); LC/MS (ESI) (m/z): 578 $(M+H)^+$.

Scheme 20: Synthesis of (1S,3S,5S)-N-((4-carbamimidoylthiophen-2-yl)methyl)-5-methyl-2-(2-(3-methyl-4-phenoxybenzamido)acetyl)-2-azabicyclo[3.1.0]hexane-3-carboxamide (COMPOUND 48)

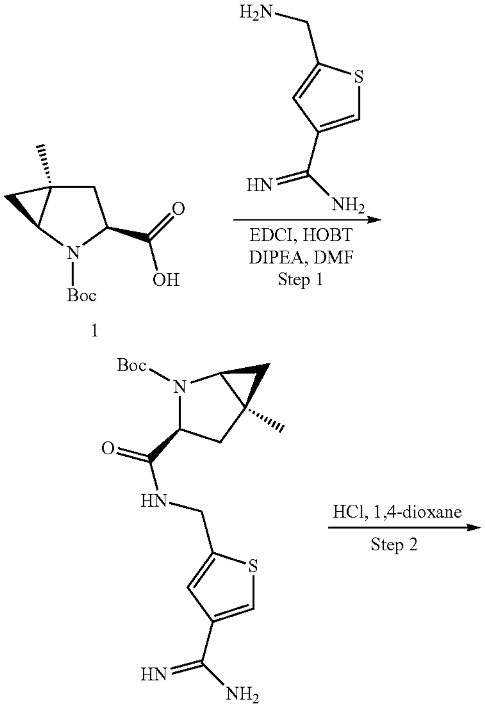

1

2

-continued

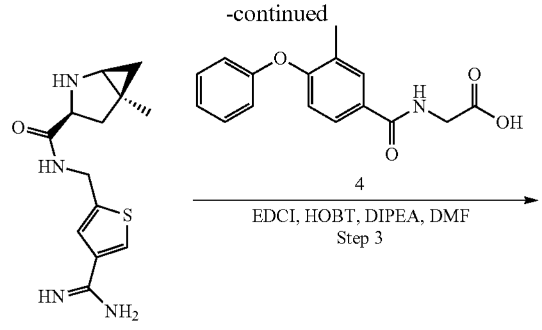

3

4

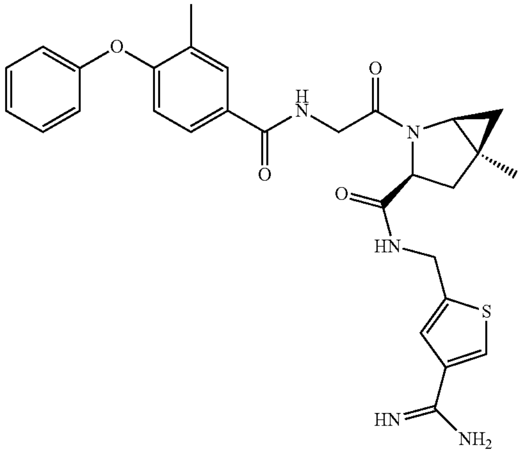

COMPOUND 48

Step 1: a mixture of starting material 1 (0.12 g, 0.50 mmol) and methyl 2-aminoacetate (0.21 g, 0.75 mmol) in DMF (5 mL) was added EDCI (0.21 g, 0.90 mmol) and HOBt (0.13 g, 0.75 mmol) followed by DIPEA (0.4 mL, 2.0 mmol) at 0° C. The mixture was stirred at 25° C. for 12 hours before diluted with EtOAc and washed with water and brine, dried over anhydrous $Na_2SO_4$, filtered and concentrated to dryness under reduced pressure. The residue was purified by chromatography on silica gel (DCM:MeOH=10:1) to give intermediate 2 (0.186 g, yield 98.94%) as yellow oil, LC/MS (ESI) (m/z): 379 $(M+H)^+$.

Step 2: intermediate 2 (0.186 g, 0.47 mmol) was dissolved in HCl/1,4-dioxane (4M, 3 mL) at 0° C. The resulting mixture was stirred at 25° C. for 1 hour before concentrated to dryness under reduced pressure to give intermediate 2 (213 mg, yield 100%) as yellow solid, which was used directly in the next step without further purification. LC/MS (ESI) (m/z): 279 $(M+H)^+$.

Step 3: a mixture of compound 4 (60 mg, 0.21 mmol) and intermediate 3 (0.111 g, 0.32 mmol) in DMF (5 mL) was added to DIPEA (0.17 mL, 1.05 mmol), followed by EDCI (0.073 g, 0.38 mmol) and HOBT (0.043 g, 0.32 mmol) at 0° C. The mixture was stirred at room temperature for 12 hour before diluted with EtOAc and washed with saturated aq.$NH_4Cl$ solution and brine, dried over anhydrous $Na_2SO_4$, filtered and concentrated to dryness. The residue was purified by chromatography on silica gel (DCM:MeOH=10:1) and further purified by prep-HPLC to afford COMPOUND 48 (12.8 mg, yield 11.1%) as white solid. $^1$H-NMR (400 MHz, DMSO-$d_6$) δ 8.61 (dd, J=19.7, 6.5 Hz, 2H), 8.45 (s, 1H), 8.37-8.29 (m, 1H), 7.85 (d, J=2.1 Hz, 1H), 7.70 (dd, J=8.4, 2.2 Hz, 1H), 7.53-7.35 (m, 3H), 7.15 (t, J=7.3 Hz, 1H), 7.02-6.84 (m, 3H), 4.67 (dd, J=11.4, 3.1 Hz, 1H), 4.41 (ddd, J=35.0, 18.0, 5.2 Hz, 3H), 4.09-3.97 (m, 1H), 3.44 (dd, J=6.0, 2.4 Hz, 1H), 2.34-2.23 (m, 1H), 2.25 (s, 3H), 2.04-1.95 (m, 1H), 1.26-1.13 (m, 4H), 0.65 (dt, J=25.8, 5.7 Hz, 1H); LC/MS (ESI) (m/z): 546 $(M+H)^+$.

Scheme 21: Synthesis of (S)-N-((4-carbamimidoylthiazol-2-yl)methyl)-7-((3-methyl-4-phenoxybenzoyl)glycyl)-1,4-dioxa-7-azaspiro[4.4]nonane-8-carboxamide (COMPOUND 49)

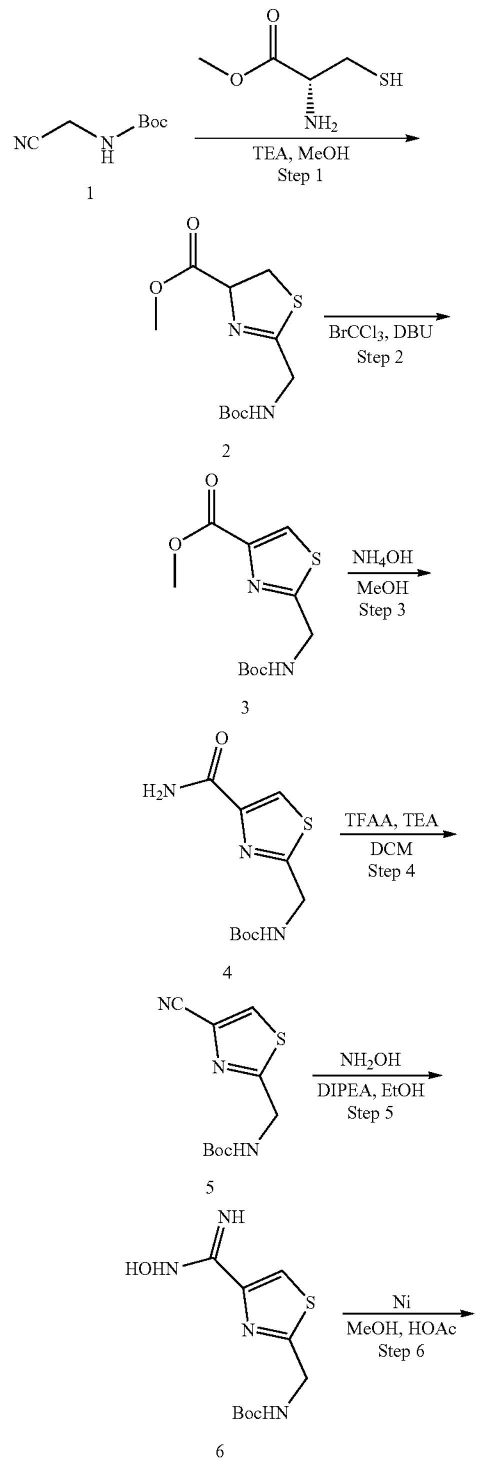

-continued

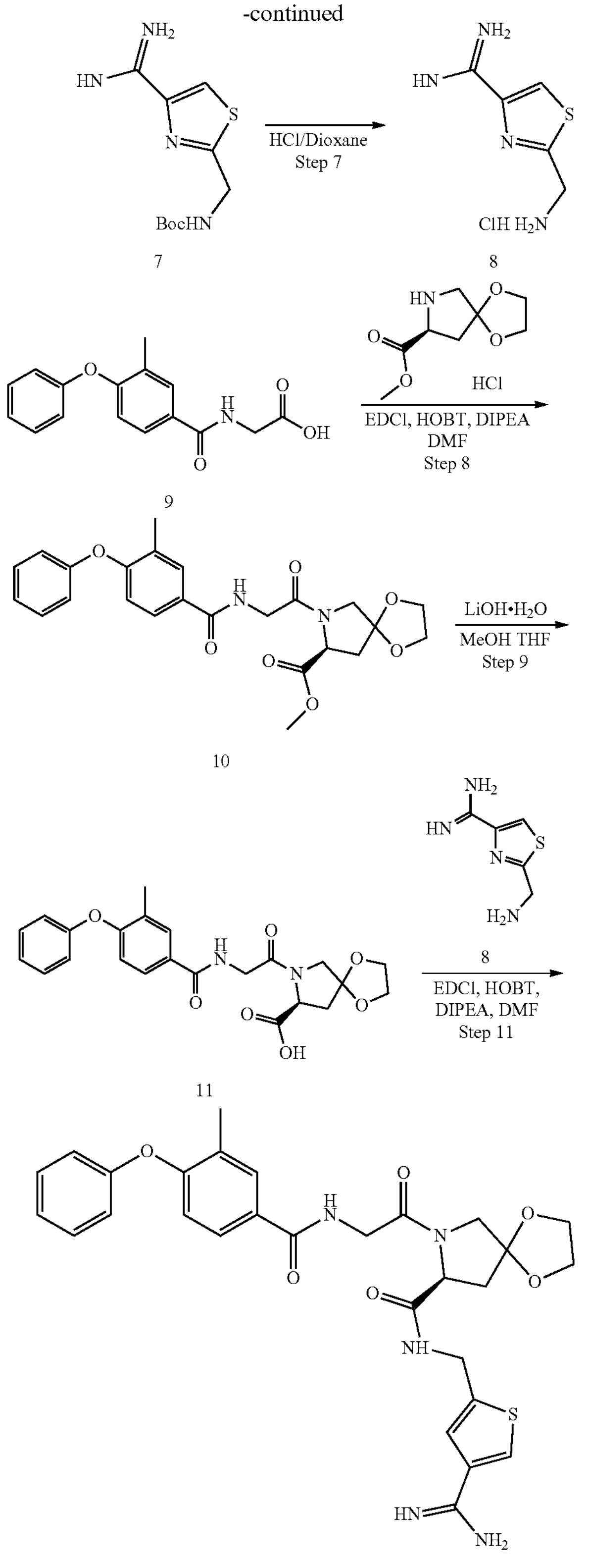

COMPOUND 49

Step 1: a mixture of starting material 1 (2.0 g, 12.8 mmol) and (R)-methyl 2-amino-3-mercaptopropanoate (2.75 g, 16.0 mmol) in MeOH (22 mL) was added to triethylamine (258 mg, 2.56 mmol) at 0° C. The reaction was stirred at 65° C. overnight before poured into ice water and extracted with DCM twice. The organic layers were washed with brine, dried over $Na_2SO_4$ and concentrated to dryness, purified by column chromatography on silica gel (PE:EtOAc=20:1 to 4:1) to give intermediate 2 (2.87 g, yield 82.0%) as light yellow oil. LC/MS (ESI) m/z: 275/175 $(M+H)^+$.

Step 2: a solution of intermediate 2 (2.83 mg, 10.3 mmol) in anhydrous DCM (30 mL) was added to DBU (1.77 g, 11.64 mmol) followed by drop-wise addition of bromotrichloromethane (2.32 g, 11.74 mmol) at 0° C. The reaction was stirred at room temperature overnight before poured into ice water and extracted with DCM twice. The organic layers were washed with brine, dried over $Na_2SO_4$ and concentrated to dryness, purified by column chromatography on silica gel (PE:EtOAc=20:1 to 3:1) to give intermediate 3 (2.2 g, yield 78.6%) as white solid. LC/MS (ESI) m/z: 273 $(M+H)^+$.

Step 3: a solution of intermediate 3 (1.0 g, 3.68 mmol) in MeOH (8 mL) was added to $NH_4OH$ (8 mL) and stirred at room temperature in a sealed tube. The reaction mixture was poured into ice water and extracted with DCM twice. The organic layers were washed with brine, dried over $Na_2SO_4$ and concentrated to dryness to give intermediate 4 (830 mg, yield 87.7%) as white solid. LC/MS (ESI) m/z: 258 $(M+H)^+$.

Step 4: a solution of intermediate 4 (830 mg, 3.23 mmol) in anhydrous DCM (10 mL) was added triethylamine (704 mg, 6.98 mmol), followed by drop-wise addition of TFAA (732 mg, 3.49 mmol) at 0° C. The reaction was stirred at room temperature 5 hours before poured into ice water and extracted with DCM twice. The organic layers were washed with brine, dried over $Na_2SO_4$ and concentrated to dryness, purified by column chromatography on silica gel (PE:EtOAc=20:1 to 5:1) to give intermediate 5 (750 mg, yield 97.2%) as light yellow oil. LC/MS (ESI) m/z: 240 $(M+H)^+$.

Step 5: a mixture of intermediate 5 (670 mg, 2.80 mmol) in EtOH (10 mL) was added to DIPEA (1.08 g, 8.4 mmol) and hydroxylamine hydrochloride (486 g, 7.0 mmol) at 0° C. The mixture was stirred at room temperature for 3 hours. After completion of the reaction, the mixture was diluted with DCM and washed with water and brine, dried over $Na_2SO_4$ and concentrated to dryness. The residue was purified by column chromatography on silica gel (DCM: MeOH=50:1 to 10:1) to give intermediate 6 (650 mg, yield 85.3%) as white solid. LC/MS (ESI) m/z: 273 $(M+H)^+$.

Step 6: a solution of intermediate 6 (550 mg, 2.02 mmol) in MeOH (10 mL) was added Raney-nickel (300 mg) and AcOH (0.8 mL). The mixture was stirred at 30° C. for 16 hours under a $H_2$ balloon. After completion of the reaction, the mixture was filtered and the filtrate was concentrated to dryness to give intermediate 7 (517 mg, yield 99.9%) as white solid. LC/MS (ESI) m/z: 257 $(M+H)^+$.

Step 7: a solution of intermediate 7 (517 g, 2.02 mmol) in HCl/1,4-dioxane (8 mL) was stirred at 25° C. for 1 hour. The mixture was concentrated to dryness to give compound 8 (317 mg, yield 100%) as white solid, which was used directly in the next step without further purification. LC/MS (ESI) m/z: 157 $(M+H)^+$.

Step 8: a mixture of intermediate 9 (150 mg, 0.53 mmol) and (S)-methyl 1,4-dioxa-7-azaspiro[4.4]nonane-8-carboxylate hydrochloride (154 mg, 0.69 mmol) in DMF (5 mL) was added to EDCI (182 mg, 0.95 mmol) and HOBt (107 mg, 0.80 mmol), followed by DIPEA (273 mg, 2.12 mmol) at 0° C. The mixture was stirred at 25° C. for 16 hours before diluted with DCM and washed with water and brine, dried over anhydrous $Na_2SO_4$, filtered and concentrated to dryness under reduced pressure. The residue was purified by chromatography on silica gel (PE:EtOAc=50:1 to 1:1) to give intermediate 10 (130 mg, yield 54.4%) as light yellow oil. LC/MS (ESI) (m/z): 455 $(M+H)^+$.

Step 9: a solution of intermediate 10 (130 mg, 0.29 mmol) in MeOH (4 mL) and THF (2 mL) was added to a solution of lithium hydroxide hydrate (60 mg, 1.43 mmol) in water (2 mL) at 0° C. The mixture was stirred at room temperature for 1 hour before washed with $Et_2O$ and water. The aqueous layer was acidified with 0.5M aq.HCl solution and extracted with DCM twice. The combined organic layers were washed with brine, dried over anhydrous $Na_2SO_4$, filtered and concentrated to dryness to give intermediate 11 (120 mg, yield 95.2%) as light yellow oil. LC/MS (ESI) m/z: 441 $(M+H)^+$.

Step 10: a mixture of intermediate 11 (60 mg, 0.14 mmol) and compound 8 (34 mg, 0.18 mmol) in DMF (3 mL) was added to EDCI (48 mg, 0.25 mmol) and HOBt (28 mg, 0.21 mmol), followed by DIPEA (72 mg, 0.56 mmol) at 0° C. The mixture was stirred at 25° C. for 16 hours before diluted with EtOAc and washed with water and brine, dried over anhydrous $Na_2SO_4$, filtered and concentrated to dryness under reduced pressure. The residue was purified by prep-HPLC to afford COMPOUND 49 (13.5 mg, yield 17.2%) as light yellow solid. $^1H$-NMR (400 MHz, DMSO-$d_6$) δ 8.95-8.87 (m, 1H), 8.7-8.63 (m, 1H), 8.59 (t, J=5.6 Hz, 1H), 8.42 (s, 1H), 7.84 (d, J=2.4 Hz, 1H), 7.70 (dd, J=8.4, 8.4 Hz, 1H), 7.45-7.35 (m, 2H), 7.20-7.11 (m, 1H), 7.02-6.93 (m, 2H), 6.87 (dd, J=8.4, 8.4 Hz, 1H), 4.62-4.56 (m, 2H), 4.45 (dd, J=8.8, 8.8 Hz, 1H), 4.21-4.11 (m, 1H), 4.04-3.86 (m, 5H), 3.82 (d, J=10.8 Hz, 1H), 3.78-3.57 (m, 1H), 2.42-2.29 (m, 1H), 2.25 (s, 3H), 2.14-2.02 (m, 1H). LC/MS (ESI) (m/z): 579 $(M+H)^+$.

Scheme 22: Synthesis of (S)-N-((4-cyanthiophen-2-yl)methyl)-7-(2-(4-phenoxybenzamido)acetyl)-1,4-dioxa-7-azaspiro[4.4]nonane-8-carboxamide (COMPOUND 50)

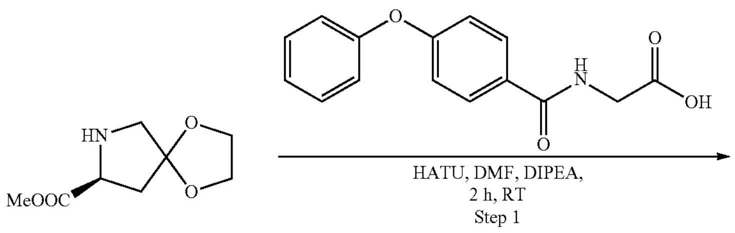

1

-continued

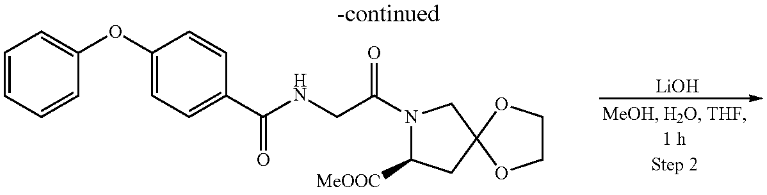

2

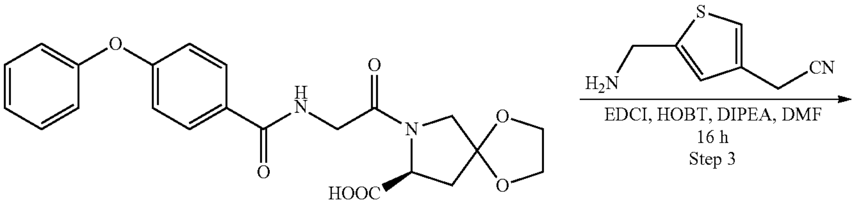

3

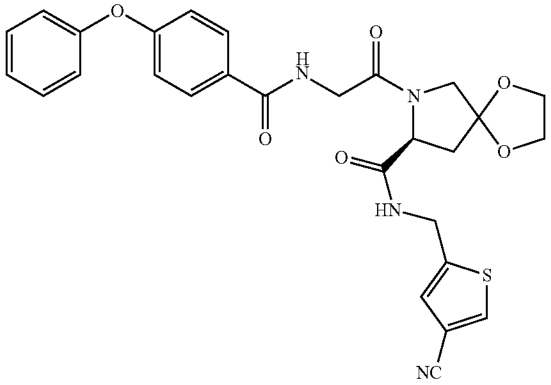

COMPOUND 50

Step 1: a mixture of starting material 1 (200 mg, 0.47 mmol) and 2-(4-phenoxybenzamido)acetic acid (140 mg, 0.56 mmol) in DMF (5 mL), then the mixture was added to DIPEA (130 mg, 0.63 mmol) and HATU (180 mg, 0.28 mmol) at 0° C. The mixture was stirred at room temperature under $N_2$ atmosphere for 12 hours before diluted with EtOAc and washed with saturated aq.$NH_4Cl$ solution and brine, dried over anhydrous $Na_2SO_4$, filtered and concentrated to dryness. The residue was purified by chromatography on silica gel (DCM:MeOH=97:3) to give intermediate 2 (130 mg, yield 75.2%) as brown oil. LC/MS (ESI) (m/z): 441 $(M+H)^+$.

Step 2: a solution of intermediate 2 (100 mg, 0.151 mmol) in MeOH (2 mL), THF (2 mL) and water (2 mL) was added lithium hydroxide monohydrate (32 mg, 0.753 mmol). The mixture was stirred at room temperature for 2 hours before concentrated to ⅕ volume, diluted with water and washed with MTBE twice. The aqueous layer was acidified with 1N aq.HCl to pH~3 and extracted with DCM twice. The combined organic layers were washed with brine, dried over anhydrous $Na_2SO_4$, and concentrated under reduced pressure to give intermediate 3 (100 mg, yield 95%) as white solid. LC/MS (ESI) (m/z): 427 $(M+H)^+$.

Step 3: a mixture of intermediate 3 (30 mg, 0.45 mmol) and 2-(5-(aminomethyl)thiophen-3-yl)acetonitrile (18 mg, 0.52 mmol) in DMF (3 mL) was added to EDCI (49 mg, 1.04 mmol) and HOBt (58 mg, 1.04 mmol), followed by DIPEA (130 mg, 0.2 mL, 1.8 mmol) at 0° C. The mixture was stirred at 25° C. for 12 hours before diluted with EtOAc and washed with water and brine, dried over anhydrous $Na_2SO_4$, filtered and concentrated to dryness. The residue was purified by prep-HPLC to afford COMPOUND 50 (4 mg, yield 21.9%) as white solid. $^1H$-NMR (400 MHz, $CDCl_3$) δ 7.76 (dd, J=4.9, 3.7 Hz, 3H), 7.46-7.32 (m, 2H), 7.24-7.11 (m, 3H), 7.05-6.89 (m, 4H), 4.65 (ddd, J=24.8, 14.2, 7.0 Hz, 3H), 3.98 (dd, J=12.6, 9.8 Hz, 6H), 3.68 (d, J=18.6 Hz, 2H), 3.63 (s, 1H), 2.59 (dt, J=36.6, 18.1 Hz, 1H), 2.27 (dd, J=34.5, 25.1 Hz, 1H), 1.25 (s, 1H); LC/MS (ESI) m/z: 547 $(M+H)^+$.

Scheme 23: Synthesis of (S)-N-((4-carbamimidoyloxazol-2-yl)methyl)-7-(2-(3-methyl-4-phenoxybenzamido)acetyl)-1,4-dioxa-7-azaspiro [4.4]nonane-8-carboxamide (COMPOUND 51)

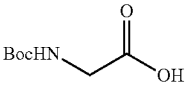

1

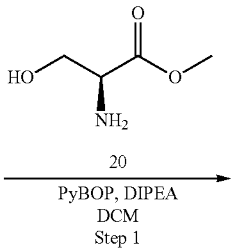

-continued

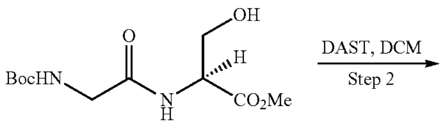

2

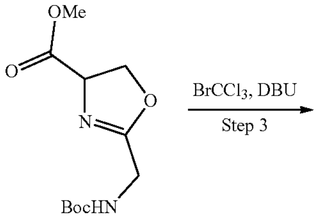

3

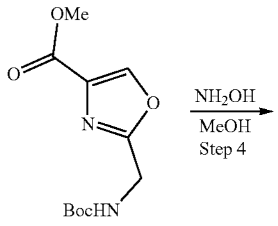

4

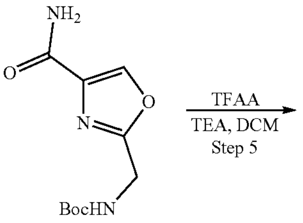

5

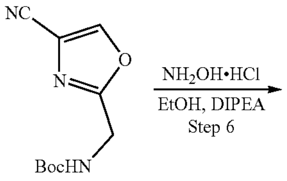

6

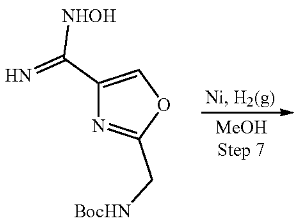

7

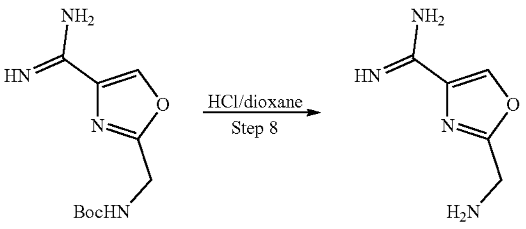

8

9

-continued

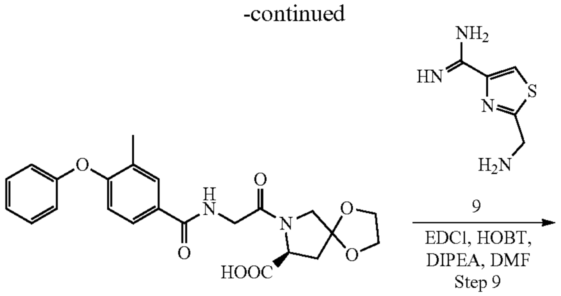

9

11

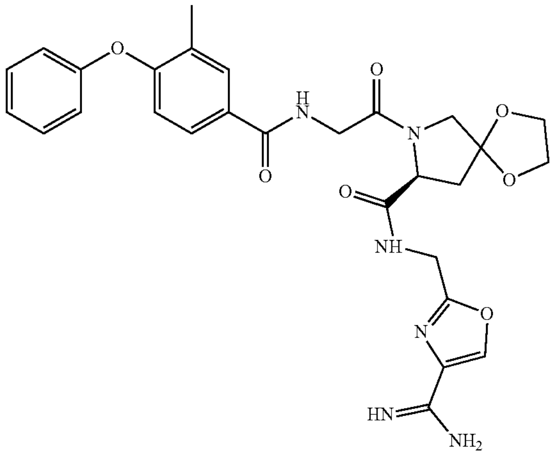

COMPOUND 51

Step 1: a solution of starting material 1 (1.126 g, 6.43 mmol) in DCM (60 mL) was added PyBOP (4.01 g, 7.7 mmol), followed by DIPEA (3.36 mL, 19.3 mmol) drop-wisely at 0° C. The mixture was allowed to stir for 10 minutes at 0° C. before compound 20 (1.0 g, 6.43 mmol) was added to the mixture, and the resulting mixture was stirred at 25° C. for 12 hours. The mixture was poured into ice water and extracted with DCM twice. The combined organic layers were washed with brine, dried over anhydrous $Na_2SO_4$, filtered and concentrated to dryness. The residue was purified by chromatography on silica gel (100% of EtOAc) to give intermediate 2 (550 mg, yield 56.52%) as colorless oil. LC/MS (ESI) (m/z): 277 $(M+H)^+$.

Step 2: a solution of intermediate 2 (550 mg, 1.98 mmol) in DCM (24 mL) was added to DAST (0.4 mL, 2.38 mmol) drop-wise at −78° C. under a nitrogen atmosphere. The mixture was stirred at −78° C. for 1 hour before warmed to room temperature and quenched with saturated bicarbonate solution (20 mL). The separated organic layer was then dried with anhydrous $Na_2SO_4$ and concentrated in vacuum to give intermediate 3 (254 mg, yield 49.42%) as light yellow oil, which was used immediately without further purification. LC/MS (ESI) (m/z): 259 $(M+H)^+$.

Step 3: a solution of intermediate 3 (254 mg, 0.98 mmol) in DCM (24 mL) was added to $BrCCl_3$ (0.7 mL, 2.94 mmol) at 0° C. The mixture was stirred at 0° C. for 5 minutes before DBU (1.13 mL, 2.94 mmol) was added drop-wisely over 2 minutes. The mixture was stirred at 25° C. for 12 hours before quenched with ice-cooled aq.$NaHCO_3$ solution and extracted with DCM twice. The combined organic layers were washed with brine, dried over anhydrous $Na_2SO_4$, filtered and concentrated to dryness. The residue was purified by chromatography on silica gel (PE:EtOAc=3:1) to give intermediate 4 (130 mg, yield 60.7%) as yellow oil. LC/MS (ESI) (m/z): 257 $(M+H)^+$.

Step 4: a solution of intermediate 4 (150 mg, 0.41 mmol) in methanol (2 mL) was added to hydroxylamine (1 mL, 50% in water) and the mixture was stirred at 25° C. for 12 hours. The mixture was diluted with DCM and washed with water and brine. The combined organic layers were dried over anhydrous $Na_2SO_4$, filtered and concentrated to dryness to give intermediate 5 (132 mg, yield 94.28%) as yellow oil. LC/MS (ESI) (m/z): 242 $(M+H)^+$.

Step 5: a solution of intermediate 5 (132 mg, 0.55 mmol) in DCM (10 mL) was added TEA (0.16 mL, 1.18 mmol) and TFAA (0.083 mL, 0.594 mmol) at 0° C. The mixture was stirred at 25° C. for 12 hours before extracted with DCM twice The combined organic layers were dried over anhydrous $Na_2SO_4$, filtered and concentrated to dryness to give intermediate 6 (146 mg, yield 100%) as light yellow oil. LC/MS (ESI) (m/z): 224 $(M+H)^+$.

Step 6: a mixture of intermediate 6 (0.146 g, 0.63 mmol) in EtOH (5 mL) was added to DIPEA (0.3 mL, 1.89 mmol) and hydroxylamine hydrochloride (0.113 g, 1.57 mmol) at 0° C. and the mixture was stirred at 25° C. for 3 hours. The mixture was diluted with DCM and washed with water and brine, dried over $Na_2SO_4$, filtered and concentrated and the residue was purified by chromatography on silica gel (PE: EtOAc=1:1) to give intermediate 7 (0.098 g, yield 58.3%) as white solid. LC/MS (ESI) (m/z): 257 $(M+H)^+$.

Step 7: a solution of intermediate 7 (0.098 g, 0.38 mmol) in MeOH (5 mL) was added Raney-Ni (0.1 g), and the mixture was degassed under $N_2$ atmosphere for three times and stirred under a $H_2$ balloon at room temperature for 1 hour before filtered and the filtrate was concentrated to dryness to give intermediate 8 (124 mg, yield 100%) as white solid, which was used directly in the next step. LC/MS (ESI) (m/z): 241 $(M+H)^+$.

Step 8: intermediate 8 (124 mg, 0.51 mmol) was dissolved in HCl/1,4-dioxane (5 mL) at 0° C. The mixture was stirred at 25° C. for 1 hour before concentrated to dryness under reduced pressure to give compound 9 (75 mg, yield 100%) as brown solid, which was used directly in the next step. LC/MS (ESI) (m/z): 141 $(M+H)^+$.

Step 9: a mixture of intermediate 10 (0.055 g, 0.125 mmol) and compound 9 (0.040 g, 0.19 mmol) in DMF (3 mL) was added to DIPEA (0.080 g, 0.1 mL, 0.63 mmol), followed by HOBt (0.025 g, 0.18 mmol) and EDCI (0.043 g, 0.23 mmol) at 0° C. The mixture was stirred at room temperature for 12 hours before extracted with ($CHCl_3$: MeOH=3:1) twice. The combined organic layers were dried over anhydrous $Na_2SO_4$, filtered and concentrated to dryness. The residue was purified by chromatography on silica gel (DCM:MeOH=3:1) and further purified by prep-HPLC to afford COMPOUND 51 (3.9 mg, yield 5.6%) as white solid. $^1$H-NMR (400 1 Hz, $CD_3OD$) δ 8.65 (s, 1H), 8.55 (s, 1H), 7.79 (d, J=2.2 Hz, 1H), 7.65 (dd, J=8.5, 2.4 Hz, 1H), 7.42-7.32 (m, 2H), 7.14 (t, J=7.4 Hz, 1H), 7.00-6.92 (m, 2H), 6.82 (dd, J=8.5, 5.1 Hz, 1H), 4.65-4.49 (m, 3H), 4.24-4.08 (m, 2H), 4.06-3.89 (m, 4H), 3.84-3.72 (m, 2H), 3.21-3.08 (m, 1H), 2.52 (s, 1H), 2.42 (td, J=12.3, 11.4, 6.6 Hz, 1H), 2.31 (d, J=3.6 Hz, 3H), 2.23 (dd, J=13.2, 5.7 Hz, 1H). LC/MS (ESI) m/z: 563 $(M+H)^+$.

Scheme 24: (S)-N-((4-carbamimidoylthiophen-2-yl)methyl)-1-(4-oxo-4-(4-phenoxyphenyl)butanoyl)pyrrolidine-2-carboxamide (COMPOUND 52)

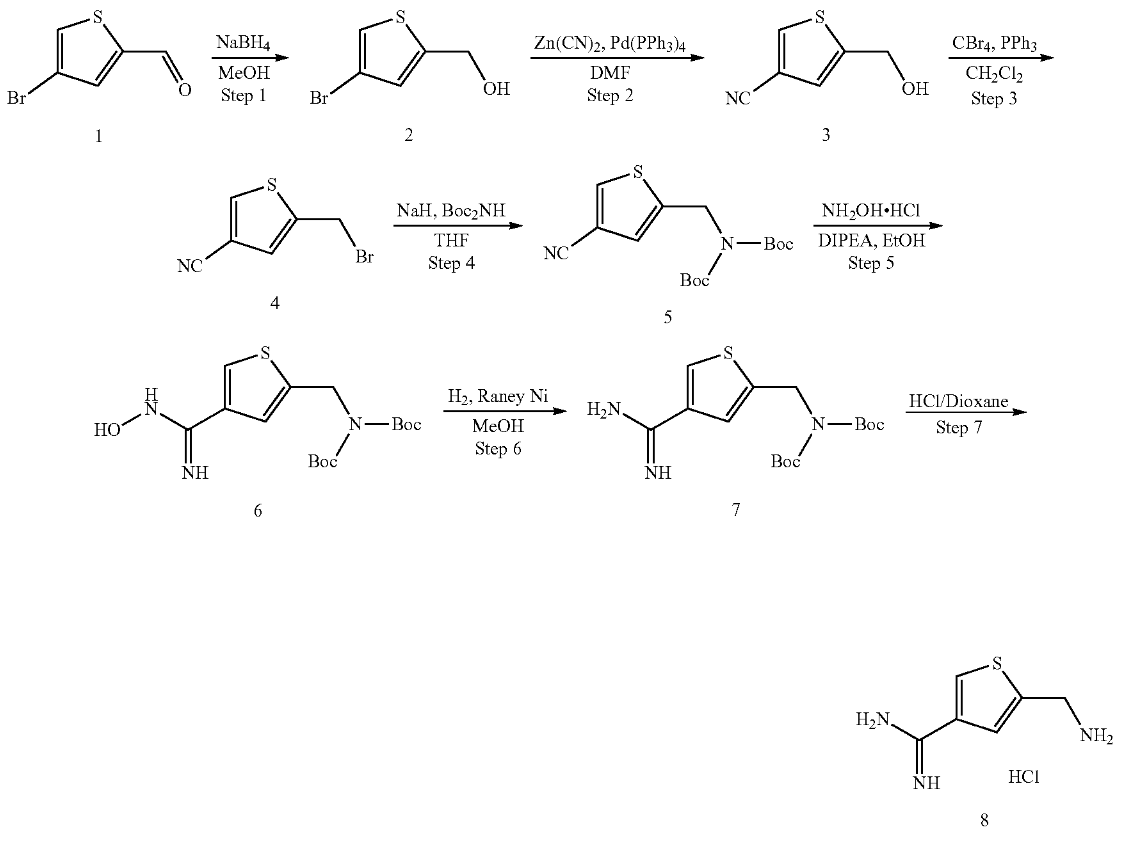

1 2 3 4 5 6 7 8

-continued

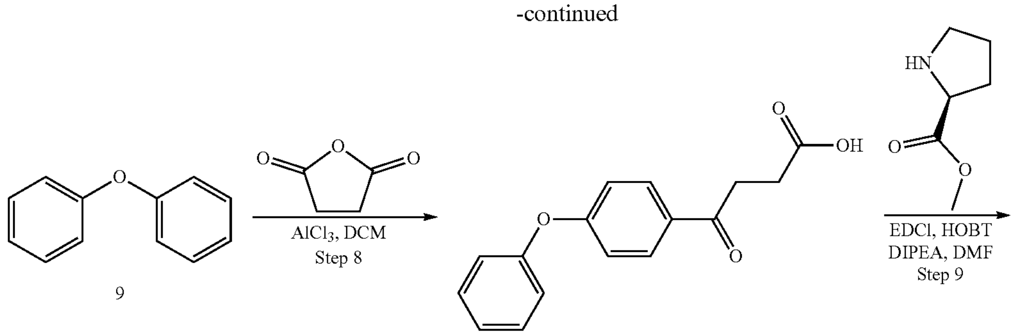

9

10

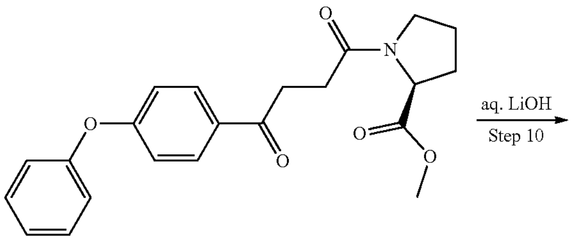

11

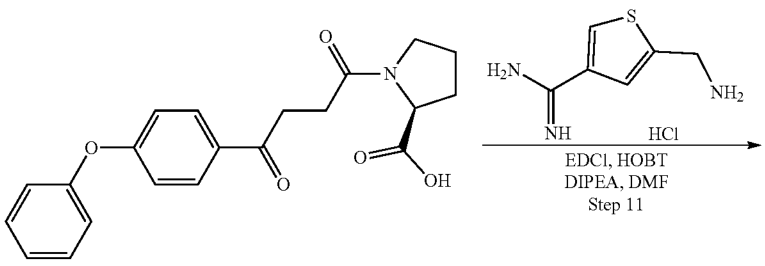

12

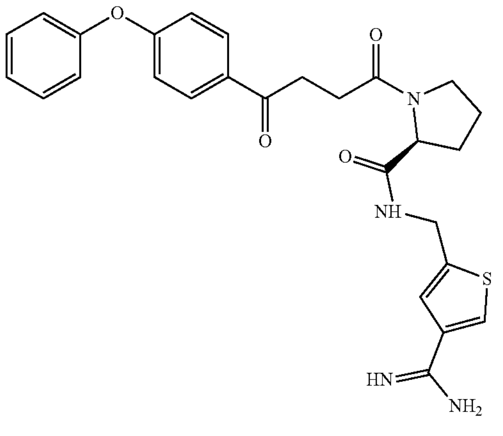

COMPOUND 52

Step 1: a mixture of starting material 1 (10 g, 52.6 mmol) in MeOH (150 mL) was added $NaBH_4$ (2.99 g, 78.9 mmol) in portions at 0° C. The reaction was stirred at 0° C. for 1 hour. After completion of the reaction, the reaction mixture was quenched by ice water and extracted with DCM. The combined organic layers was washed with brine, dried over $Na_2SO_4$ and concentrated to dryness, purified by column chromatography on silica gel (DCM:MeOH=80:1) to give intermediate 2 (9.5 g, yield 94.1%) as colorless oil.

Step 2: a mixture of intermediate 2 (4 g, 20.8 mmol) in DMF (60 mL) was added to zinc cyanide (3.2 g, 27.04 mmol) at 0° C. The mixture was degassed three times and stirred at 80° C. under $N_2$ atmosphere for 6 hours. The mixture was diluted with EtOAc and washed with saturated aq. $NH_4Cl$ solution and brine, dried over $Na_2SO_4$ and concentrated to dryness. The residue was purified by column chromatography on silica gel (eluted with PE:EtOAc=4:1) to give intermediate 3 (2.8 g, yield 96.9%) as colorless oil.

Step 3: a mixture of intermediate 3 (2.8 g, 20.1 mmol) in DCM (50 mL) was added carbon tetrabromide (7.33 g, 22.11 mmol) and triphenylphosphine (5.79 g, 22.11 mmol) at 0° C. The mixture was stirred at 25° C. for 16 hours. The mixture was diluted with DCM and washed with water and brine, dried over $Na_2SO_4$ and concentrated to dryness. The residue was purified by column chromatography on silica gel (eluted with PE:EtOAc=10:1) to give the title intermediate 4 (2.6 g, yield 64.4%) as white solid.

Step 4: a solution of di-tert-butyl iminodicarboxylate (3.65 g, 16.8 mmol) in anhydrous THF (25 mL) was added NaH (60%, 776 mg, 19.4 mmol) at 0° C. under $N_2$ atmosphere and the mixture was stirred at 0° C. for 20 minutes. Intermediate 4 (2.6 g, 12.9 mmol) in THF (10 mL) was added to the above mixture and the resulting mixture was stirred at 25° C. for another 16 hours under $N_2$ atmosphere. The mixture was quenched with saturated aq.$NH_4Cl$ solution and extracted with EtOAc. The organic layer was washed with brine, dried over $Na_2SO_4$, filtered and concentrated to dryness. The residue was purified by column chromatography via silica gel (eluted with PE:EtOAc=10:1) to give intermediate 5 (5.6 g, yield 98.3%) as white solid. LC/MS (ESI) m/z: 339 $(M+H)^+$.

Step 5: a mixture of intermediate 5 (5.6 g, 16.5 mmol) in EtOH (80 mL) was added to N,N-diisopropylethylamine (6.4 g, 49.7 mmol) and hydroxylamine hydrochloride (2.87 g, 41.25 mmol) at 0° C. The mixture was stirred at 25° C. for 16 hours. After completion of the reaction, the mixture was diluted with DCM and washed with water and brine, dried over $Na_2SO_4$ and concentrated to dryness. The residue was purified by column chromatography on silica gel (eluted with PE:EtOAc=6:1) to give intermediate 6 (5.7 g, yield 93.1%) as white solid. LC/MS (ESI) m/z: 372 $(M+H)^+$.

Step 6: a solution of intermediate 6 (3 g, 8.1 mmol) in MeOH (45 mL) was added Raney-nickel (600 mg) and AcOH (1 mL) and the mixture was stirred at 30° C. for 16 hours under a $H_2$ balloon. The mixture was filtered and the filtrate was concentrated to dryness to give intermediate 7 (2.8 g, yield 97.6%) as white solid. LC/MS (ESI) m/z: 356 $(M+H)^+$.

Step 7: a solution of intermediate 7 (2.8 g, 7.9 mmol) in HCl/dioxane (45 mL) was stirred at 25° C. for 3 hours. The mixture was concentrated to dryness to give compound 8 (1.8 g, yield 100%) as white solid, which was used directly without purification. LC/MS (ESI) m/z: 156 $(M+H)^+$.

Step 8: a solution of compound 9 (10 g, 58.8 mmol) in DCM (200 mL) was added aluminum chloride (15.64 g, 117.6 mmol) and dihydrofuran-2,5-dione (11.78 g, 117.6 mmol) drop-wisely at 0° C. and the reaction was stirred at 25° C. for 16 hours. The mixture was poured into cold 18% aq.HCl (100 mL) and the mixture was stirred for a further 30 minutes. The mixture was filtered to give compound 10 (20 g, yield 76.3%) as yellow solid. LC/MS (ESI) m/z: 271 $(M+H)^+$.

Step 9: a mixture of intermediate 10 (400 mg, 1.48 mmol) and methyl L-prolinate hydrochloride (366 mg, 2.22 mmol) in DMF was added to EDCI (506 mg, 2.66 mmol) and HOBt (300 mg, 2.55 mmol), followed by DIPEA (764 mg, 5.92 mmol) at 0° C. and the resulting mixture was stirred at room temperature for 16 hours. The mixture was diluted with EtOAc and washed with saturated aq.$NH_4Cl$ solution and brine, dried over anhydrous $Na_2SO_4$, filtered and concentrated to dryness. The residue was purified by column chromatography on silica gel (eluted with PE:EtOAc=5:1) to give intermediate 11 (450 mg, yield 79.8%) as light yellow oil. LC/MS (ESI) m/z: 382 $(M+H)^+$.

Step 10: a solution of intermediate 11 (100 mg, 0.26 mmol) in THF (1 mL) and MeOH (1 mL) and water (1 mL) was added LiOH (33 mg, 0.79 mmol). The mixture was stirred at room temperature for 2 hours. The mixture was concentrated to dryness, diluted with water and washed with EtOAc twice. The aqueous layer was acidified with 1N aq.HCl to pH~3 at 0° C. and extracted with DCM twice. The combined organic layers were washed with brine, dried over anhydrous $Na_2SO_4$, filtered and concentrated to dryness to give intermediate 12 (90 mg, yield 94.3%) as yellow solid. LCMS: LC/MS (ESI) m/z: 368 $(M+H)^+$.

Step 11: a mixture of intermediate 12 (90 mg, 0.25 mmol) and 5-(aminomethyl)thiophene-3-carboximidamide hydrochloride (71 mg, 0.37 mmol) in DMF was added to EDCI (84 mg, 0.44 mmol) and HOBt (50 mg, 0.37 mmol), followed by DIPEA (127 mg, 0.98 mmol) at 0° C. and the resulting mixture was stirred at room temperature for 16 hours. The mixture was diluted with DCM and washed with saturated aq.$NH_4Cl$ solution and brine, dried over anhydrous $Na_2SO_4$, filtered and concentrated to dryness. The residue was purified by prep-HPLC to afford COMPOUND 52 (30 mg, yield 24.4%) as white solid. $^1H$-NMR (400 MHz, $CD_3OD$) δ 8.54 (s, 1H), 8.19 (d, J=1.5 Hz, 1H), 7.98 (dd, J=8.7, 5.7 Hz, 2H), 7.48-7.34 (m, 3H), 7.23 (t, J=7.4 Hz, 1H), 7.13-7.05 (m, 2H), 7.03-6.95 (m, 2H), 4.63-4.52 (m, 2H), 4.45 (dd, J=8.4, 2.9 Hz, 1H), 3.85-3.82 (m, 1H), 3.76-3.70 (m, 1H), 3.40-3.32 (m, 2H), 2.87-2.62 (m, 2H), 2.45-2.20 (m, 1H), 2.17-1.83 (m, 3H); LC/MS (ESI) m/z: 505 $(M+H)^+$.

Scheme 25: (S)-N-((4-carbamimidoylthiophen-2-yl)methyl)-1-(4-(4-phenoxyphenyl)butanoyl)pyrrolidine-2-carboxamide (COMPOUND 53)

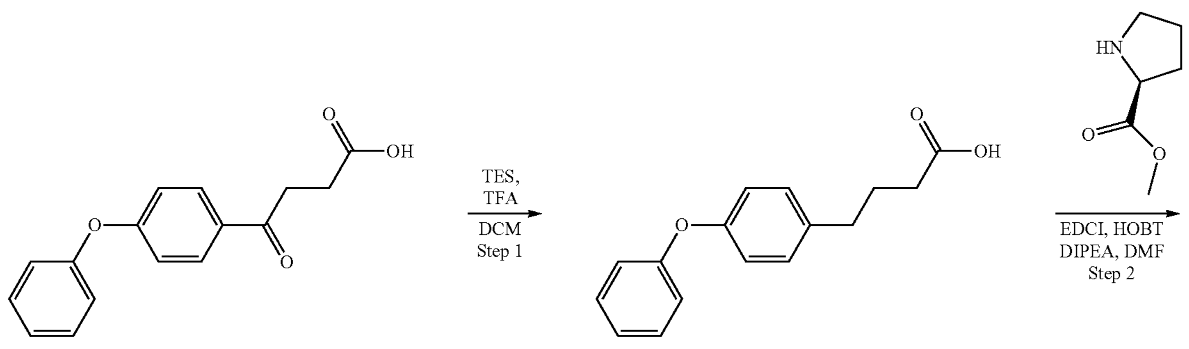

1 2

-continued

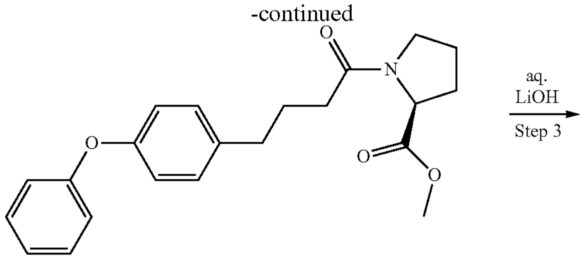

3

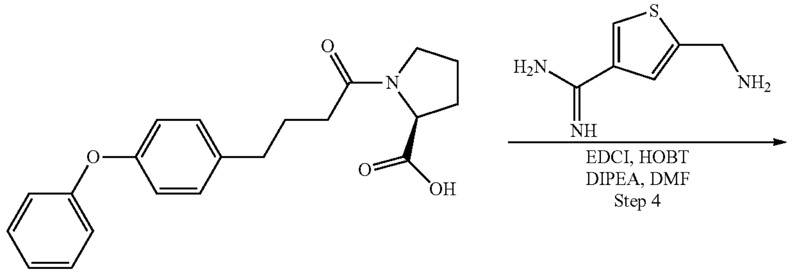

4

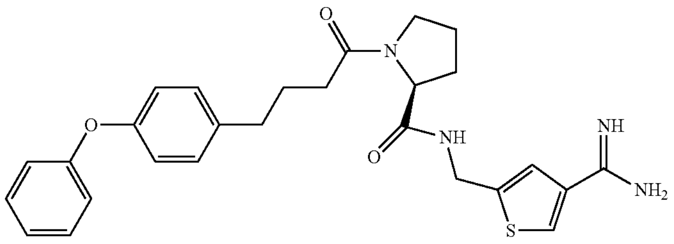

COMPOUND 53

Step 1: a mixture of starting material 1 (1 g, 3.7 mmol) in DCM (200 mL) was added trifluoroacetic acid (4.2 g, 37 mmol) and triethoxysilane (6.1 g, 37 mmol) drop-wisely at 0° C. After addition, the reaction was stirred at 25° C. for 16 hours. The mixture was poured into saturated aq.$NaHCO_3$ solution and extracted with DCM twice. The combined organic layers were washed with brine, dried over anhydrous $Na_2SO_4$, filtered and concentrated to dryness. The residue was purified by column chromatography on silica gel (eluted with PE:EtOAc=4:1) to give intermediate 2 (850 mg, yield 89.8%) as brown solid. LC/MS (ESI) m/z: 257 $(M+H)^+$.

Step 2: a mixture of intermediate 2 (850 mg, 3.3 mmol) and methyl L-prolinate hydrochloride (821 mg, 5.0 mmol) in DMF was added to EDCI (1.1 g, 5.9 mmol) and HOBt (675 mg, 5.0 mmol), followed by DIPEA (1.7 g, 13.2 mmol) at 0° C. and the resulting mixture was stirred at room temperature for 16 hours. The mixture was diluted with EtOAc and washed with saturated aq. $NH_4Cl$ solution and brine, dried over anhydrous $Na_2SO_4$, filtered and concentrated to dryness. The residue was purified by column chromatography on silica gel (eluted with PE:EtOAc=3:1) to give intermediate 3 (950 mg, yield 78.4%) as light yellow oil. LC/MS (ESI) m/z: 368 $(M+H)^+$.

Step 3: a solution of intermediate 3 (80 mg, 0.22 mmol) in THF (1 mL) and MeOH (1 mL) and water (1 mL) was added LiOH (27 mg, 0.65 mmol). The mixture was stirred at room temperature for 2 hours. The mixture was concentrated to dryness, diluted with water and washed with EtOAc twice. The aqueous layer was acidified by adding 1N aq.HCl to pH~3 at 0° C. and extracted with DCM twice. The combined organic layers were washed with brine, dried over anhydrous $Na_2SO_4$, filtered and concentrated to dryness to give intermediate 4 (70 mg, yield 90.1%) as a yellow solid. LCMS: LC/MS (ESI) m/z: 354 $(M+H)^+$.

Step 4: a mixture of intermediate 4 (70 mg, 0.20 mmol) and 5-(aminomethyl)thiophene-3-carboximidamide hydrochloride (57 mg, 0.30 mmol) in DMF, was added to EDCI (68 mg, 0.36 mmol) and HOBt (41 mg, 0.30 mmol), followed by DIPEA (102 mg, 0.79 mmol) at 0° C. and the resulting mixture was stirred at room temperature for 16 hours. The mixture was diluted with EtAOc and washed with saturated aq.$NH_4Cl$ solution and brine, dried over anhydrous $Na_2SO_4$, filtered and concentrated to dryness. The residue was purified by prep-HPLC to afford COMPOUND 53 (33 mg, yield 34.0%) as white solid. $^1$H-NMR (400 MHz, $CD_3OD$) δ 8.53 (s, 1H), 8.24 (dd, J=13.0, 1.6 Hz, 1H), 7.45 (t, J=5.6 Hz, 1H), 7.32 (dd, J=8.4, 7.6 Hz, 2H), 7.19 (d, J=8.5 Hz, 2H), 7.14-7.03 (m, 1H), 6.99-6.85 (m, 4H), 4.56 (q, J=15.9 Hz, 2H), 4.44-4.31 (m, 1H), 3.65-3.59 (m, 1H), 3.56-3.50 (m, 1H), 2.72-2.49 (m, 2H), 2.44-2.25 (m, 2H), 2.26-2.15 (m, 1H), 2.09-1.85 (m, 5H); LC/MS (ESI) m/z: 491 $(M+H)^+$.

Scheme 26: (S)-N-((4-carbamimidoylthiophen-2-yl)methyl)-1-(4-oxo-4-(4-phenoxyphenyl)butyl)pyrrolidine-2-carboxamide (COMPOUND 54)
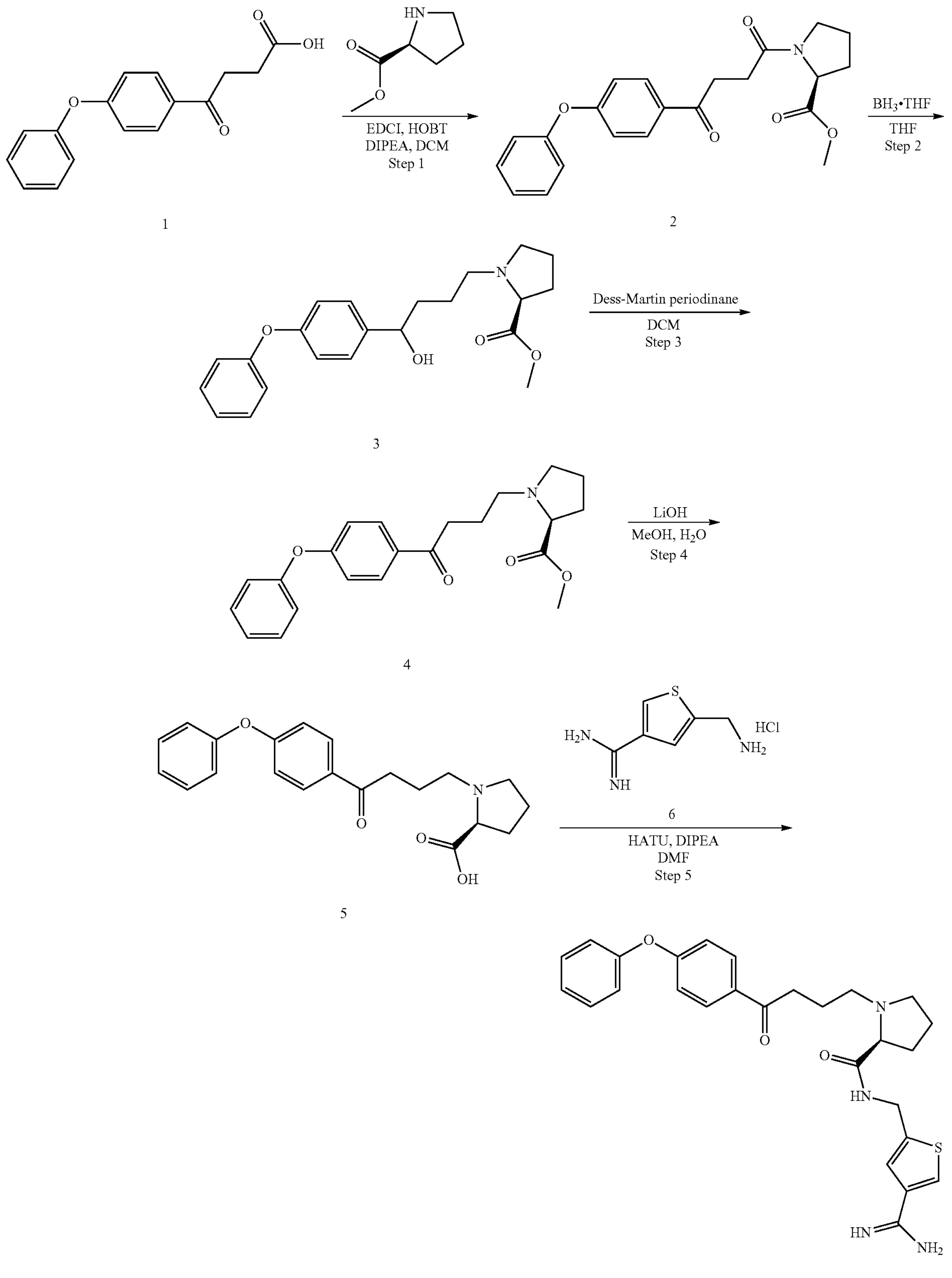
1
2
3
4
5
6
COMPOUND 54

Step 1: a solution of starting material 1 (1.0 g, 3.7 mmol) in DCM (10 mL) was added to EDCI (1.41 g, 7.4 mmol), and HOBt (0.75 g, 5.55 mmol), followed by DIPEA (2.39 g, 3.23 mL, 18.49 mmol) at 0° C. Then methyl (2S)-pyrrolidine-2-carboxylate (0.71 g, 5.55 mmol) was added to the mixture and the resulting mixture was stirred at 25° C. for 12 hours. The mixture was poured into iced-water and extracted with DCM twice. The combined organic layers were washed with brine, dried with anhydrous $Na_2SO_4$, filtered and concentrated to dryness. The residue was purified by chromatography on silica gel (PE:EtOAc=7:3) to give intermediate 2 (0.8 g, yield 56.68%) as yellow semi-solid. LC/MS (ESI) (m/z): 382 $(M+H)^+$.

Step 2: a solution of intermediate 2 (0.2 g, 0.52 mmol) in THF (2.0 mL) was added to $BH_3$-THF solution (1.6 mL, 1.6 mmol, 1M in THF) drop-wise at 0° C., and the mixture was stirred at 25° C. for 12 hours. The mixture was poured into iced-water and extracted with DCM twice. The combined organic layers were washed with brine, dried with anhydrous $Na_2SO_4$, filtered and concentrated to dryness. The residue was purified by chromatography on silica gel (DCM: MeOH=96:4) to give intermediate 3 (0.14 g, yield 72.3%) as light yellow oil. LC/MS (ESI) (m/z): 370 $(M+H)^+$.

Step 3: a solution of intermediate 3 (0.14 g, 0.37 mmol) in DCM (5 mL) was added to Dess-Martin periodinane (0.24 g, 0.56 mmol) in portions at 0° C. and the mixture was stirred at 0° C. for 2 hours. The mixture was quenched with ice-cooled aq.$NaHCO_3$ solution and extracted with DCM. The combined organic layers were washed with brine, dried with anhydrous $Na_2SO_4$, filtered and concentrated to dryness. The residue was purified by chromatography on silica gel (PE:EtOAc=7:3) to give intermediate 4 (88 mg, yield 60.7%) as yellow oil. LC/MS (ESI) (m/z): 368 $(M+H)^+$.

Step 4: a solution of intermediate 4 (88 mg, 0.239 mmol) in methanol (1 mL), THF (1 mL), and water (1 mL) was added Lithium hydroxide monohydrate (30 mg, 0.718 mmol) and the mixture was stirred at 25° C. for 1 hour. The mixture was diluted with water and washed with MTBE twice. The aqueous layer was acidified with 0.5 M aq.HCl solution to pH~2 and extracted with DCM twice. The combined organic layers were dried with anhydrous $Na_2SO_4$, filtered and concentrated to dryness to give intermediate 5 (85 mg, yield 100%) as yellow solid. LC/MS (ESI) (m/z): 354 $(M+H)^+$.

Step 5: a mixture of intermediate 5 (55 mg, 0.15 mmol) and 5-(aminomethyl)thiophene-3-carboximidamide (36 mg, 0.23 mmol) in DMF (5 mL) was added to DIPEA (0.10 g, 0.13 mL, 0.77 mmol) and HATU (0.107 g, 0.28 mmol) at 0° C., and the mixture was stirred at 25° C. for 1 hour. The mixture was diluted with EtOAc and washed with water and brine, dried and concentrated to dryness. The residue was purified by prep-HPLC to afford COMPOUND 54 (15 mg, yield 19.6%) as light yellow solid. $^1$H-NMR (400 MHz, $CD_3OD$) δ 8.39 (s, 2H), 8.21 (d, J=1.6 Hz, 1H), 8.00-7.92 (m, 2H), 7.47-7.39 (m, 3H), 7.27-7.18 (m, 1H), 7.11-7.04 (m, 2H), 7.04-6.96 (m, 2H), 4.67-4.52 (m, 2H), 3.35 (dd, J=9.6, 4.8 Hz, 2H), 3.04 (td, J=7.0, 4.3 Hz, 2H), 2.88-2.66 (m, 2H), 2.57 (td, J=9.2, 6.7 Hz, 1H), 2.33-2.19 (m, 1H), 1.97-1.77 (m, 5H). LC/MS (ESI) (m/z): 491 $(M+H)^+$.

Scheme 27: (S)-N-((4-(aminomethyl)thiophen-2-yl)methyl)-1-((4-phenoxybenzoyl)glycyl)pyrrolidine-2-carboxamide (COMPOUND 55)

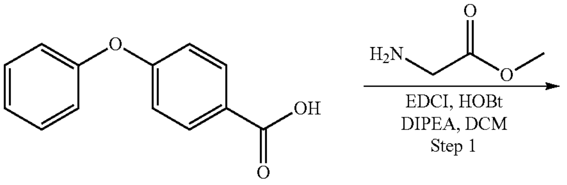

1

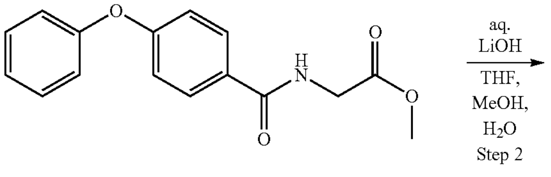

2

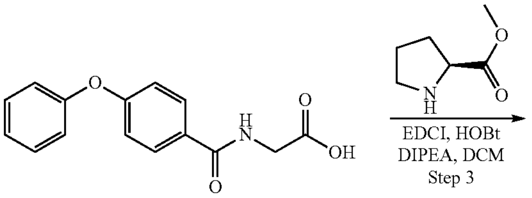

3

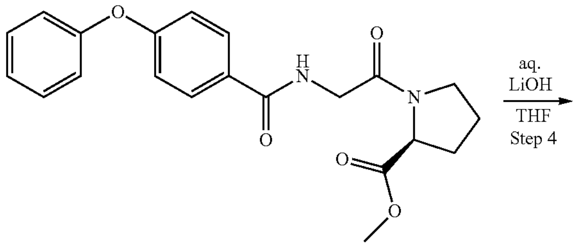

5

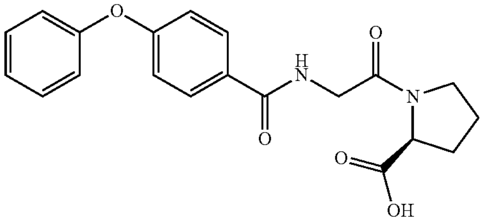

6

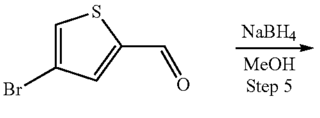

7

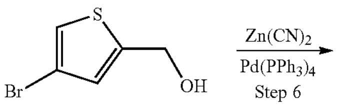

8

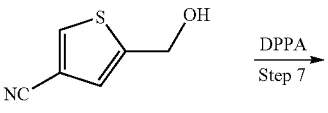

9

-continued

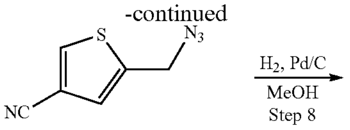

10

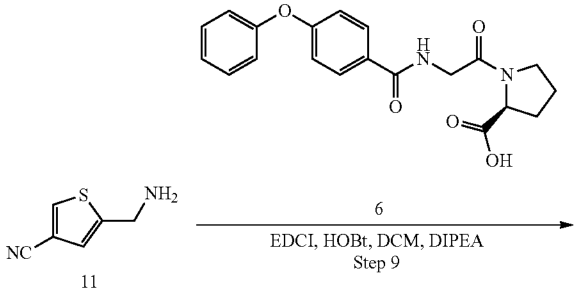

11

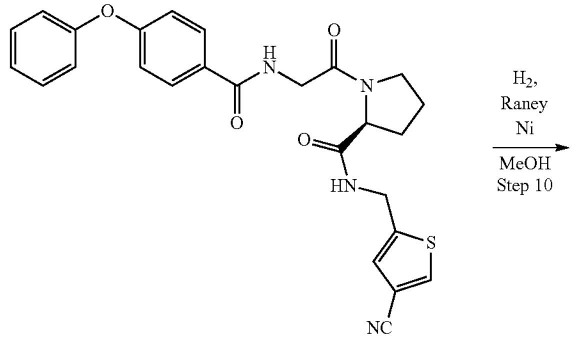

12

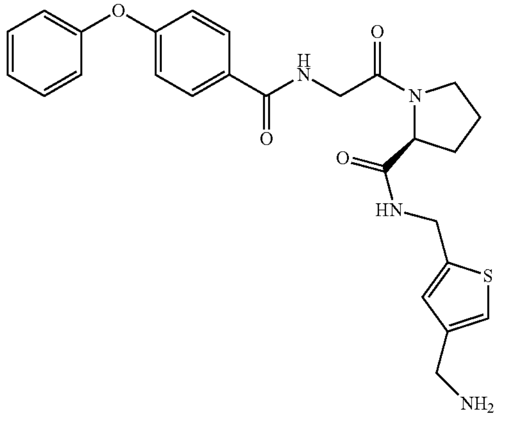

COMPOUND 55

Step 1: a mixture of starting material 1 (5 g, 23.34 mmol) and methyl 2-aminoacetate (3.119 g, 35.01 mmol) in DCM (100 mL) was added to EDCI (8.95 g, 46.7 mmol), HOBt (4.73 g, 35.0 mmol), followed by DIPEA (15.08 g, 20.38 mL, 116.70 mmol) at 0° C. and the mixture was stirred at 25° C. for 12 hours. The mixture was diluted with DCM and washed with water and brine, dried over anhydrous $Na_2SO_4$, filtered and concentrated to dryness under reduced pressure. The residue was purified by chromatography on silica gel (PE:EtOAc=1:1) to give intermediate 2 (5.3 g, yield 79.6%) as white solid, LC/MS (ESI) (m/z): 286 $(M+H)^+$.

Step 2: a solution of intermediate 2 (5.3 g, 18.577 mmol) in MeOH (30 mL), THF (30 mL) and water (6 mL) was added a solution of lithium hydroxide monohydrate (3.9 g, 92.9 mmol) at 0° C. and the mixture was stirred at room temperature for 1 hour. The mixture was concentrated to ⅕ volume, diluted with water and washed with MTBE twice. The aqueous layer was acidified with 1N aq.HCl to pH~3, extracted with DCM twice. The combined organic layers were washed with brine, dried over anhydrous $Na_2SO_4$, and concentrated under reduced pressure to dryness to give intermediate 3 (5.1 g, yield 99.2%) as white solid. LC/MS (ESI) (m/z): 272 $(M+H)^+$.

Step 3: a mixture of intermediate 3 (1 g, 3.68 mmol) and methyl (2S)-pyrrolidine-2-carboxylate (0.714 g, 5.53 mmol) in DCM (20 mL) was added EDCI (1.41 g, 7.37 mmol), HOBt (0.75 g, 5.53 mmol) followed by DIPEA (2.38 g, 3.21 mL, 18.43 mmol) at 0° C. and the mixture was stirred at room temperature for 12 hours. The mixture was diluted with DCM and washed with water and brine, dried over anhydrous $Na_2SO_4$, filtered and concentrated under reduced pressure to dryness. The residue was purified by chromatography on silica gel (PE:EtOAc=1:1) to give intermediate 5 (0.8 g, yield 57.1%) as light yellow solid. LC/MS (ESI) (m/z): 383 $(M+H)^+$.

Step 4: a solution of intermediate 5 (0.8 g, 2.09 mmol) in MeOH (10 mL) was added a solution of lithium hydroxide hydrate (0.44 g, 10.5 mmol) in water (2 mL) at 0° C. and the mixture was stirred at room temperature for 2 hours. The mixture was concentrated to ⅕ volume, diluted with water and washed with MTBE twice. The aqueous layer was acidified with 1N aq.HCl to pH~3 and extracted with DCM/MeOH (20/1) twice. The combined organic layers were washed with brine, dried over anhydrous $Na_2SO_4$, and concentrated under reduced pressure to dryness to give compound 6 (0.78, yield 98.9%) as light yellow solid. LC/MS (ESI) (m/z): 369 $(M+H)^+$.

Step 5: a solution of intermediate 7 (0.78 g, 2.15 mmol) in MeOH (10 mL) was added $NaBH_4$ (0.31 g, 4.30 mmol) in portions at 0° C. and the mixture was stirred at room temperature for 1 hour. The reaction was quenched with saturated aq.$NH_4Cl$ solution at 0° C. and the mixture was extracted with DCM twice. The combined organic layers were washed with brine, dried over anhydrous $Na_2SO_4$, filtered and concentrated to dryness to give intermediate 8 (0.8 g, yield 99.99%) as light yellow solid. LC/MS (ESI) (m/z): 192/194 $(M+H)^+$.

Step 6: a mixture of intermediate 8 (0.8 g, 4.14 mmol) in DMF (5 mL) was added zinc cyanide (0.487 g, 4.144 mmol) and tetrakis(triphenylphosphine)palladium (0.479 g, 0.414 mmol) and the mixture was stirred at 80° C. for 5 hours under $N_2$ atmosphere. The mixture was poured into ice water and extracted with EtOAc twice. The combined organic layers were washed with brine, dried over anhydrous $Na_2SO_4$, filtered and concentrated to dryness. The residue was purified on flash chromatography (PE:EtOAc=53:47) to give intermediate 9 (0.58 g, yield 98.9%) as colorless solid. LC/MS (ESI) (m/z): 140 $(M+H)^+$.

Step 7: a solution of intermediate 9 (0.2 g, 1.43 mmol) in DCM (2 mL) was added DBU (0.26 g, 1.73 mmol) followed by drop-wise addition of DPPA (0.47 g, 1.72 mmol) at 0° C. and the reaction mixture was stirred at 25° C. for 5 hours. The mixture was diluted with EtOAc, washed with water and brine, dried over anhydrous $Na_2SO_4$ and concentrated to dryness. The residue was purified by chromatography on silica gel (PE:EtOAc=9:1) to give intermediate 10 (0.28 g, yield 99.9%) as colorless oil. LC/MS (ESI) (m/z): 165 $(M+H)^+$.

Step 8: a solution of intermediate 10 (0.296 g, 1.80 mmol) in MeOH (3 mL) was added Pd/C (50 mg, 10% wt) at 0° C. and the mixture was degassed under $N_2$ atmosphere for three times and stirred under a $H_2$ balloon at room temperature for 1 hour. The mixture was filtered and the filtrate was concentrated to dryness to give intermediate 11 (0.18 g, yield 71.8%) as white semi-solid. LC/MS (ESI) (m/z): 139 $(M+H)^+$.

Step 9: a mixture of compound 6 (0.238 g, 0.64 mmol) and intermediate 11 (0.134 g, 0.96 mmol) in DCM (10 mL) was added EDCI (0.248 g, 1.29 mmol) and HOBt (0.131 g, 0.97 mmol) followed by DIPEA (0.42 g, 3.23 mmol) at 0° C. and the mixture was stirred at room temperature for 12 hours. The mixture was diluted with DCM and washed with water and brine, dried over anhydrous $Na_2SO_4$, filtered and concentrated to dryness under reduced pressure. The residue was purified by chromatography on silica gel (PE:EtOAc=5:1) to give compound 12 (0.18 g, yield 57%) as white solid. LC/MS (ESI) (m/z): 489 $(M+H)^+$.

Step 10: a solution of intermediate 12 (0.18 g, 0.37 mmol) in MeOH (5 mL) was added Raney-Ni (0.1 g), and the mixture was degassed under $N_2$ atmosphere for three times and stirred under a $H_2$ balloon at room temperature for 1 hour before filtered and the filtrate was concentrated to dryness. The residue was purified by prep-HPLC to afford COMPOUND 55 (11 mg, yield 6.06%) as white solid. $^1$H-NMR (400 MHz, $CD_3OD$) δ 8.51 (s, 1H), 7.91-7.81 (m, 2H), 7.45-7.32 (m, 4H), 7.26-6.97 (m, 2H), 7.07-6.97 (m, 6H), 4.70-4.35 (m, 3H), 4.32-3.88 (m, 4H), 3.84-3.53 (m, 2H), 2.22 (ddd, J=8.6, 5.5, 3.2 Hz, 1H), 2.11-1.67 (m, 3H). LC/MS (ESI) (m/z): 493 $(M+H)^+$.

Scheme 28: (S)-1-((4-benzylbenzoyl)glycyl)-N-((4-carbamimidoylthiophen-2-yl)methyl) pyrrolidine-2-carboxamide (COMPOUND 56)

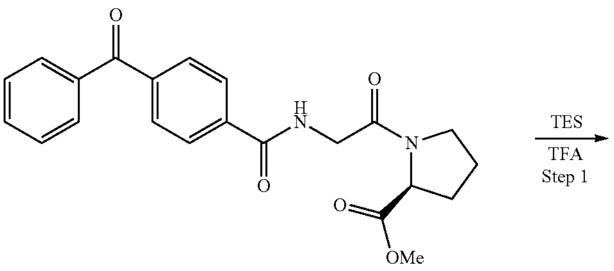

1

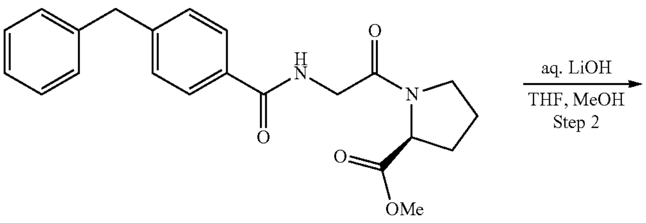

2

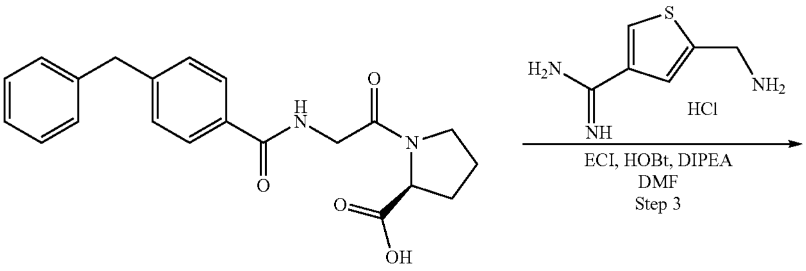

3

-continued

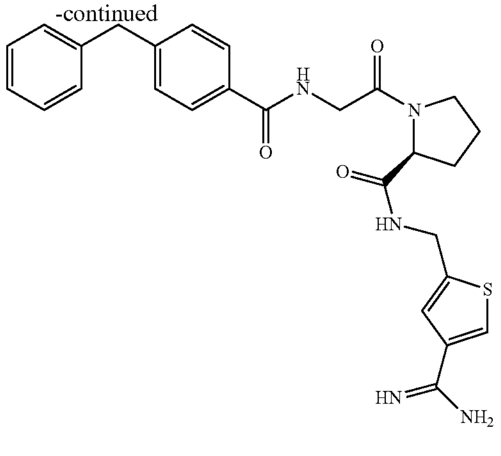

COMPOUND 56

Step 1: a mixture of starting material 1 (0.2 g, 0.51 mmol) in TFA (5 mL) was added triethoxysilane (0.183 g, 1.12 mmol) at 0° C. and the mixture was stirred at room temperature for 2 hours before poured into ice water and extracted with DCM twice. The combined organic layers were washed with brine, dried over anhydrous $Na_2SO_4$, filtered and concentrated to dryness. The residue was purified by chromatography on silica gel (PE:EtOAc=3:2) to give intermediate 2 (0.21 g, yield 99%) as white solid. LC/MS (ESI) (m/z): 381 $(M+H)^+$.

Step 2: a solution of intermediate 2 (0.267 g, 0.70 mmol) in MeOH (5 mL) was added a solution of lithium hydroxide hydrate (0.147 g, 3.509 mmol) in water (1 mL) at 0° C. and the mixture was stirred at room temperature for 1 hour. The mixture was concentrated to ⅕ volume, diluted with water and washed with MTBE twice. The aqueous layer was acidified with 1N aq.HCl to pH~3 and extracted with DCM twice. The combined organic layers were washed with brine, dried over anhydrous $Na_2SO_4$, and concentrated to dryness to give intermediate 3 (0.15 g, yield 58.3%) as brown solid. LC/MS (ESI) (m/z): 367 $(M+H)^+$.

Step 3: a mixture of intermediate 3 (0.15 g, 0.41 mmol) and 5-(aminomethyl)thiophene-3-carboximidamide (0.135 g, 0.61 mmol) in DMF (5 mL) was added EDCI (0.157 g, 0.82 mmol) and HOBt (0.083 g, 0.61 mmol) followed by DIPEA (0.264 g, 2.05 mmol) at 0° C. and the mixture was stirred at room temperature for 12 hours. The mixture was diluted with DCM and washed with water and brine, dried over anhydrous $Na_2SO_4$, filtered and concentrated to dryness under reduced pressure. The residue was purified by prep-HPLC to afford COMPOUND 56 (11 mg, yield 5.34%) as white solid. LC/MS (ESI) (m/z): 504 $(M+H)^+$.

Scheme 29: (S)-N-((4-carbamimidoylthiophen-2-yl)methyl)-1-((4-2-phenylpropan-2-yl)benzoyl)glycyl)pyrrolidine-2-carboxamide (COMPOUND 57)

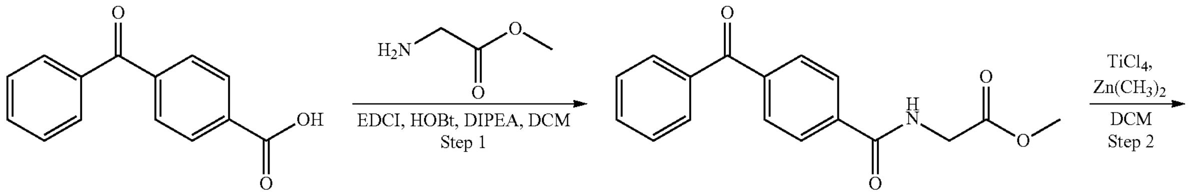

1

2

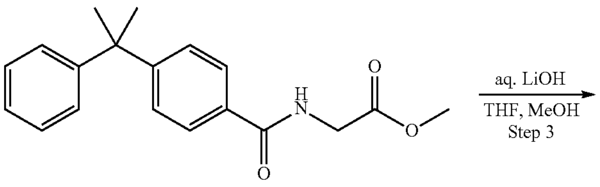

3

-continued

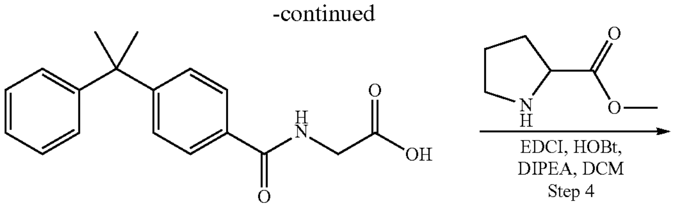

4

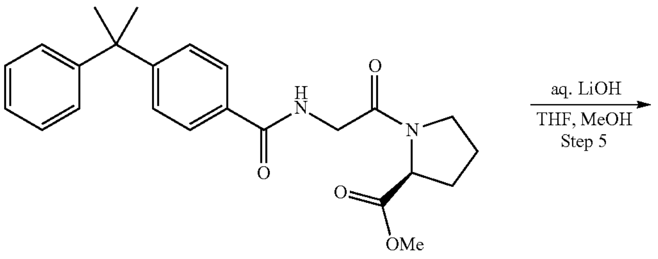

5

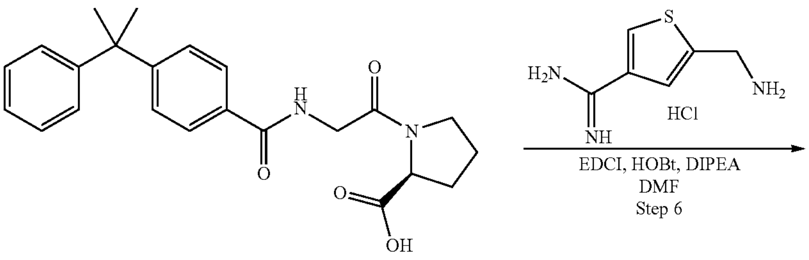

6

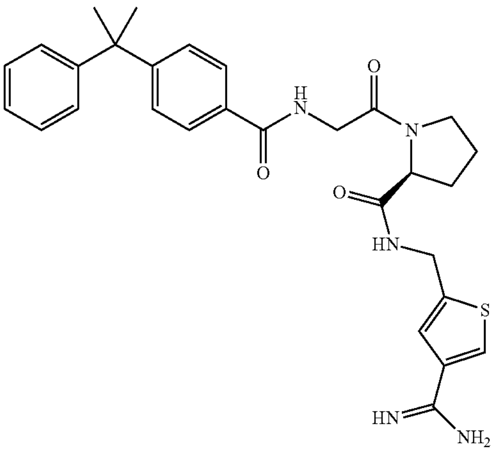

COMPOUND 57

Step 1: a mixture of starting material 1 (1.3 g, 5.75 mmol) and methyl 2-aminoacetate (0.768 g, 8.62 mmol) in dichloromethane (20 mL) was added to EDCI (2.20 g, 11.49 mmol) and HOBt (1.165 g, 8.62 mmol), followed by DIPEA (3.71 g, 5.01 mL, 28.73 mmol) at 0° C. and the mixture was stirred at room temperature for 12 hours. The mixture was diluted with DCM and washed with water and brine, dried over anhydrous $Na_2SO_4$, filtered and concentrated to dryness under reduced pressure. The residue was purified by chromatography on silica gel (PE:EtOAc=53:47) to give intermediate 2 (1.43 g, yield 83.5%) as white solid. LC/MS (ESI) (m/z): 298 $(M+H)^+$.

Step 2: a solution of titanium tetrachloride (2 mL, 2.018 mmol, 1M in DCM) was cooled to −30° C. and treated with a 2 M solution dimethylzinc in toluene (1 mL, 2.01 mmol) drop-wisely. The mixture was stirred at −30° C. for 30 minutes under $N_2$ atmosphere before a solution of intermediate 2 (0.2 g, 0.67 mmol) in DCM (2 mL) was added drop-wisely. The mixture was stirred at −30° C. for 30 minute and at room temperature for 1.5 hours under $N_2$ atmosphere. The mixture was poured into dry ice methanol solution and the mixture was stirred at room temperature for 1 hour. Water was added and the mixture was extracted with DCM twice. The combined organic layers were washed with brine, dried over $Na_2SO_4$, filtered and concentrated to dryness. The residue was purified by chromatography on silica gel (PE:EtOAc=4:1) to give intermediate 3 (0.13 g, yield 62%) as yellow solid. LC/MS (ESI) m/z: 312 $(M+H)^+$.

Step 3: a solution of intermediate 3 (90 mg, 0.29 mmol) in methanol (2 mL) and THF (2 mL) was added a solution of lithium hydroxide monohydrate (61 mg, 1.44 mmol) in water (0.5 mL) at 0° C. and the mixture was stirred at room temperature for 1 hour. The mixture was concentrated to ⅕ volume, diluted with water and washed with MTBE twice. The aqueous layer was acidified with 1N aq.HCl to pH~3 and extracted with DCM twice. The combined organic layers were washed with brine, dried over anhydrous $Na_2SO_4$, and concentrated under reduced pressure to dryness to give intermediate 4 (75 mg, yield 87.3%) as light white solid. LC/MS (ESI) m/z: 298 $(M+H)^+$.

Step 4: a mixture of intermediate 4 (0.118 g, 0.39 mmol) and methyl pyrrolidine-2-carboxylate (0.077 g, 0.595 mmol) in DCM (5 mL) was added to EDCI (0.15 g, 0.79 mmol), HOBt (80 mg, 0.59 mmol) followed by DIPEA (0.256 g, 0.34 mL, 1.98 mmol) at 0° C. and the mixture was stirred at room temperature for 12 hours. The mixture was diluted with DCM and washed with water and brine, dried over anhydrous $Na_2SO_4$, filtered and concentrated to dryness under reduced pressure. The residue was purified by chromatography on silica gel (PE:EtOAc=4:1) to give intermediate 5 (100 mg, yield 61.7%) as light yellow semi-solid. LC/MS (ESI) m/z: 409 $(M+H)^+$.

Step 5: a solution of intermediate 5 (0.1 g, 0.245 mmol) in MeOH (5 mL) was added a solution of lithium hydroxide monohydrate (51 mg, 1.22 mmol) in water (1 mL) at 0° C. and the mixture was stirred at room temperature for 1 hour. The mixture was concentrated to ⅕ volume, diluted with water and washed with MTBE twice. The aqueous layer was acidified with 1N aq.HCl to pH~3 and extracted with DCM twice. The combined organic layers were washed with brine, dried over anhydrous $Na_2SO_4$, and concentrated under reduced pressure to dryness to give intermediate 6 (84 mg, yield 86.9%) as light yellow solid. LC/MS (ESI) m/z: 395 $(M+H)^+$.

Step 6: a mixture of intermediate 6 (0.096 g, 0.243 mmol) and 5-(aminomethyl)thiophene-3-carboximidamide (0.112 g, 0.487 mmol) in DMF (5 mL) was added EDCI (93 mg, 0.487 mmol) and HOBt (49 mg, 0.365 mmol) followed by DIPEA (0.157 g, 1.21 mmol) at 0° C. and the mixture was stirred at room temperature for 12 hours. The mixture was diluted with DCM and washed with water and brine, dried over anhydrous $Na_2SO_4$, filtered and concentrated to dryness under reduced pressure. The residue was purified by chromatography on silica gel (PE:EtOAc=4:1) to afford COMPOUND 57 (2 mg, yield 1.62%) as white solid. $^1$H-NMR (400 MHz, $CD_3OD$) δ 8.54 (s, 1H), 8.26-8.16 (m, 1H), 7.93-7.79 (m, 0H), 7.78-7.71 (m, 2H), 7.45-7.32 (m, 2H), 7.37-7.27 (m, 2H), 7.31-7.15 (m, 5H), 7.20-7.11 (m, 1H), 4.65-4.54 (m, 3H), 4.48 (dd, J=8.8, 3.3 Hz, 1H), 4.28-4.03 (m, 2H), 3.81-3.72 (m, 1H), 3.74-3.55 (m, 1H), 2.29-2.17 (m, 1H), 2.04 (ddt, J=12.6, 9.1, 4.2 Hz, 2H), 1.69 (s, 6H). LC/MS (ESI) m/z: 532 $(M+H)^+$.

Scheme 30: (2S)-N-((4-carbamimidoylthiophen-2-yl)methyl)-1-((4-(1-phenylethyl)benzoyl)glycyl)pyrrolidine-2-carboxamide (COMPOUND 58)

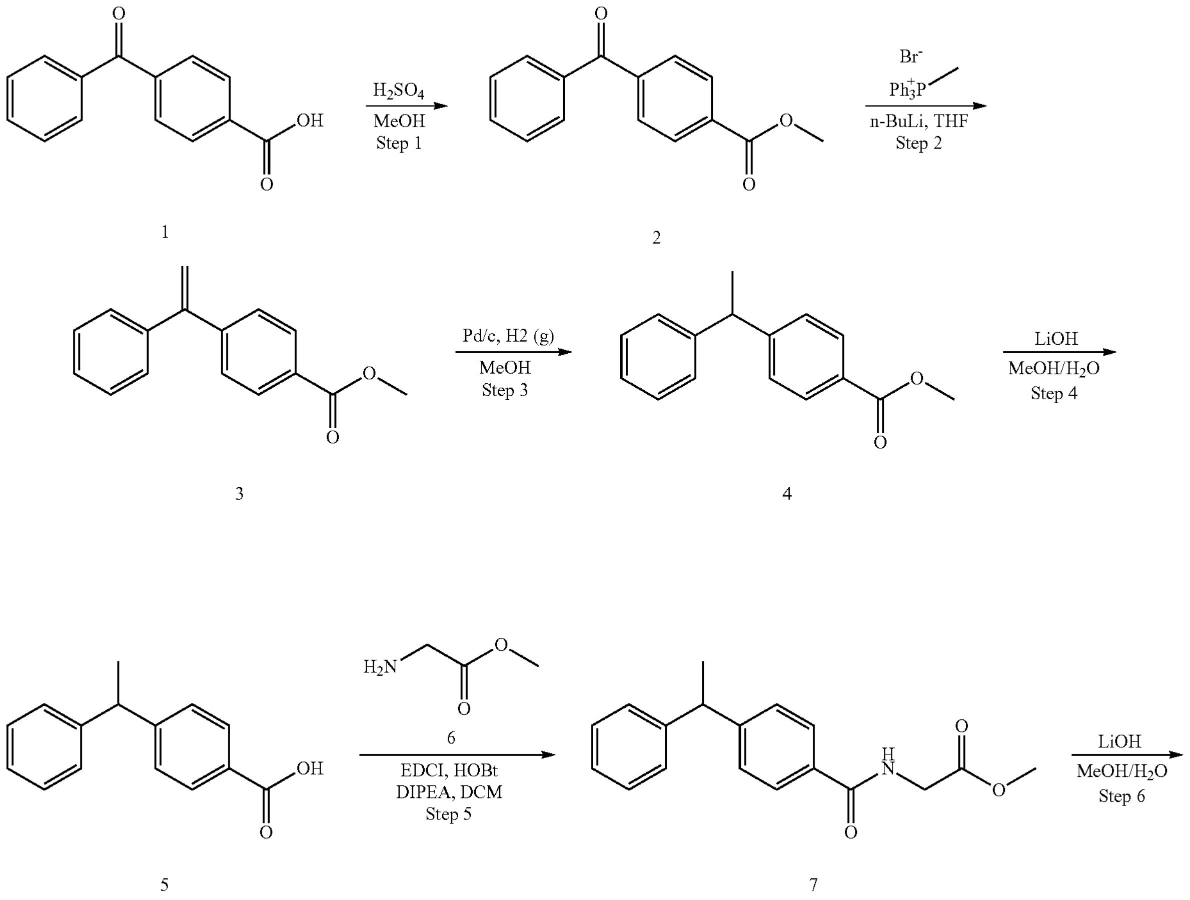

-continued

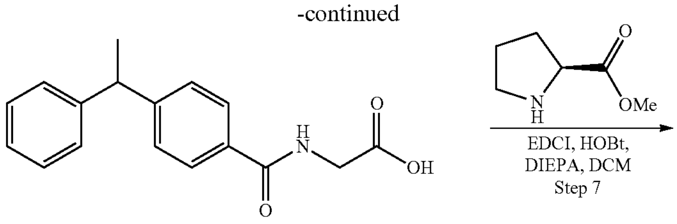

8

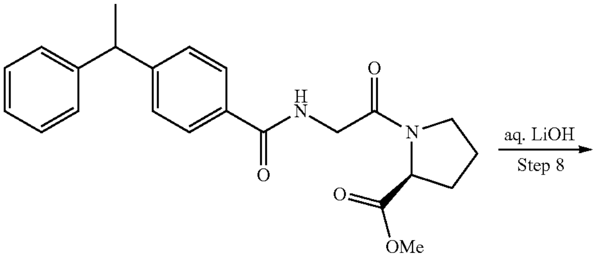

9

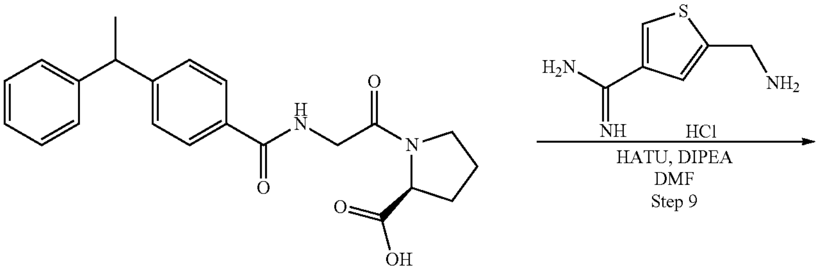

10

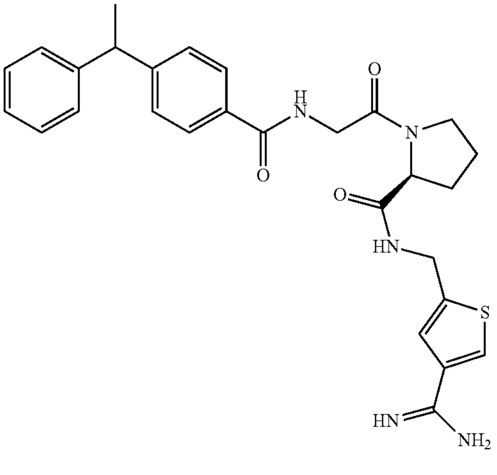

COMPOUND 58

Step 1: a solution of starting material 1 (0.5 g, 2.21 mmol) in MeOH (5 mL) was added conc.$H_2SO_4$ (0.5 mL, 11.05 mmol) and the mixture was stirred at 80° C. for 1 hour. The mixture was poured into ice-water and extracted with DCM twice. The combined organic layers were washed with saturated aq.$NaHCO_3$ solution and brine, dried over anhydrous $Na_2SO_4$, filtered and concentrated to dryness. The residue was purified by chromatography on silica gel (PE: EtOAc=4:1) to give intermediate 2 (0.45 g, yield 84.7%) as white solid. LC/MS (ESI) (m/z): 241 $(M+H)^+$.

Step 2: a solution of methyltriphenylphosphonium bromide (0.535 g, 1.49 mmol) in tetrahydrofuran (10 mL) was added n-butyllithium (1.2 mL, 1.931 mmol) at −78° C. under $N_2$ atmosphere and the mixture was stirred at −78° C. for half an hour under $N_2$ atmosphere. A solution of intermediate 2 (0.2 g, 0.83 mmol) in THF (5 mL) was added drop-wisely to the above solution. The mixture was stirred at −78° C. for 1.5 hours under $N_2$ atmosphere before quenched with ice water and extracted with EtAOc twice. The combined organic layers were washed with brine, dried over anhydrous $Na_2SO_4$, filtered and concentrated and the residue was purified by chromatography on silica gel (PE:EtOAc=8:1) to give intermediate 3 (90 mg, yield 45.4%) as white solid. LC/MS (ESI) m/z: 239 $(M+H)^+$.

Step 3: a solution of intermediate 3 (90 mg, 0.378 mmol) in MeOH (5 mL) was added Pd/C (20 mg, 10% wt) and the mixture was degassed under $N_2$ atmosphere for three times and stirred under a $H_2$ balloon at room temperature for 1 hour. The mixture was filtered and the filtrate was concentrated to dryness to give intermediate 4 (0.1 g, yield 100%) as white solid. LC/MS (ESI) m/z: 241 $(M+H)^+$.

Step 4: a solution of intermediate 4 (0.1 g, 0.41 mmol) in MeOH (5 mL) was added a solution of lithium hydroxide monohydrate (87 mg, 2.08 mmol) in water (1 mL) at 0° C. and the mixture was stirred at room temperature for 1 hour. The mixture was concentrated to ⅕ volume, diluted with water and washed with MTBE twice. The aqueous layer was acidified with 1N aq.HCl to pH~3 and extracted with DCM twice. The combined organic layers were washed with brine, dried over anhydrous $Na_2SO_4$, and concentrated under reduced pressure to dryness to give intermediate 5 (85 mg, yield 90.3%) as light yellow solid. LC/MS (ESI) m/z: 227 $(M+H)^+$.

Step 5: a mixture of intermediate 5 (0.102 g, 0.451 mmol) and methyl 2-aminoacetate (0.06 g, 0.676 mmol) in DCM (5 mL) was added EDCI (0.173 g, 0.902 mmol) and 1-hydroxybenzotriazole (0.091 g, 0.67 mmol) followed by DIPEA (0.29 g, 2.25 mmol) at 0° C. and the mixture was stirred at room temperature for 12 hours. The mixture was diluted with DCM and washed with water and brine, dried over anhydrous $Na_2SO_4$, filtered and concentrated to dryness under reduced pressure. The residue was purified by chromatography on silica gel (PE:EtOAc=4:1) to give intermediate 7 (86 mg, yield 64.2%) as colorless oil. LC/MS (ESI) m/z: 298 $(M+H)^+$.

Step 6: a solution of intermediate 7 (0.1 g, 0.34 mmol) in MeOH (5 mL) was added a solution of v (0.071 g, 1.68 mmol) in water (1 mL) at 0° C. and the mixture was stirred at room temperature for 1 hour. The mixture was concentrated to ⅕ volume, diluted with water and washed with MTBE twice. The aqueous layer was acidified with 1N aq.HCl to pH~3 and extracted with DCM twice. The combined organic layers were washed with brine, dried over anhydrous $Na_2SO_4$, and concentrated under reduced pressure to dryness to give intermediate 8 (90 mg, yield 94.5%) as light yellow solid. LC/MS (ESI) m/z: 284 $(M+H)^+$.

Step 7: a mixture of intermediate 8 (98 mg, 0.34 mmol) and methyl (2S)-pyrrolidine-2-carboxylate (67 mg, 0.519 mmol) in DCM (3 mL) was added EDCI (0.133 g, 0.692 mmol) and HOBt (70 mg, 0.519 mmol) followed by DIPEA (224 mg, 1.73 mmol) at 0° C. and the mixture was stirred at room temperature for 12 hours. The mixture was diluted with DCM and washed with water and brine, dried over anhydrous $Na_2SO_4$, filtered and concentrated to dryness under reduced pressure. The residue was purified by chromatography on silica gel (PE:EtOAc=4:1) to give intermediate 9 (0.1 g, yield 73.3%) as light yellow semi-solid. LC/MS (ESI) m/z: 395 $(M+H)^+$.

Step 8: a solution of intermediate 9 (0.1 g, 0.254 mmol) in MeOH (5 mL) was added a solution of lithium hydroxide monohydrate (53 mg, 1.27 mmol) in water (1 mL) at 0° C. and the mixture was stirred at room temperature for 1 hour. The mixture was concentrated to ⅕ volume, diluted with water and washed with MTBE twice. The aqueous layer was acidified with 1N aq.HCl to pH~3 and extracted with DCM twice. The combined organic layers were washed with brine, dried over anhydrous $Na_2SO_4$, and concentrated under reduced pressure to dryness to give intermediate 10 (98 mg, yield 100%) as white solid. LC/MS (ESI) m/z: 381 $(M+H)^+$.

Step 9: a mixture of intermediate 10 (98 mg, 0.25 mmol) and 5-(aminomethyl)thiophene-3-carboximidamide (0.089 g, 0.386 mmol) in DCM (5 mL) was added HOBt (0.052 g, 0.386 mmol) and EDCI (0.099 g, 0.515 mmol) followed by DIPEA (0.166 g, 1.29 mmol) at 0° C. and the mixture was stirred at room temperature for 12 hours. The mixture was diluted with DCM and washed with water and brine, dried over anhydrous $Na_2SO_4$, filtered and concentrated to dryness under reduced pressure. The residue was purified by chromatography on silica gel (PE:EtOAc=4:1) and further purified by prep-HPLC to afford COMPOUND 58 (32 mg, yield 24.1%) as white solid. $^1H$-NMR (400 MHz, $CD_3OD$) δ 8.53 (s, 1H), 8.21 (dd, J=18.7, 1.6 Hz, 1H), 7.83-7.71 (m, 2H), 7.43-7.33 (m, 1H), 7.37-7.26 (m, 2H), 7.31-7.19 (m, 4H), 7.16 (ddt, J=7.1, 6.2, 1.6 Hz, 1H), 4.56 (s, 1H), 4.47 (dd, J=8.8, 3.3 Hz, 1H), 4.32-4.13 (m, 3H), 3.81-3.52 (m, 2H), 2.28-2.12 (m, 1H), 2.11-1.95 (m, 2H), 1.64 (d, J=7.2 Hz, 3H), LC/MS (ESI) m/z: 518 $(M+H)^+$.

Scheme 31: (S)-N-((4-carbamimidoylthiophen-2-yl)methyl)-1-(2-(4-phenoxybenzoyl)hydrazine-1-carbonyl)pyrrolidine-2-carboxamide (COMPOUND 59)

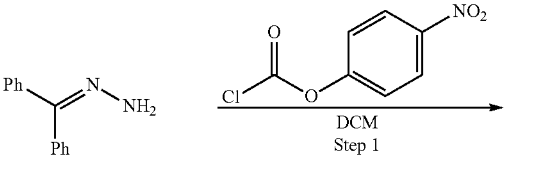

1

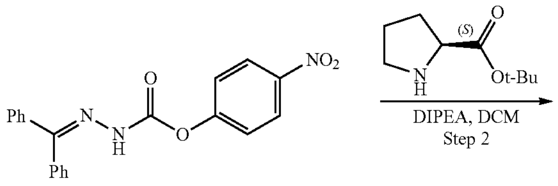

2

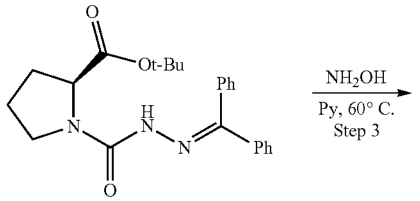

3

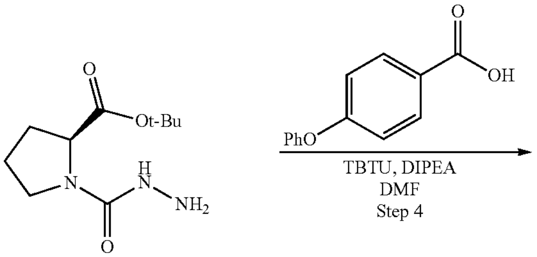

4

-continued

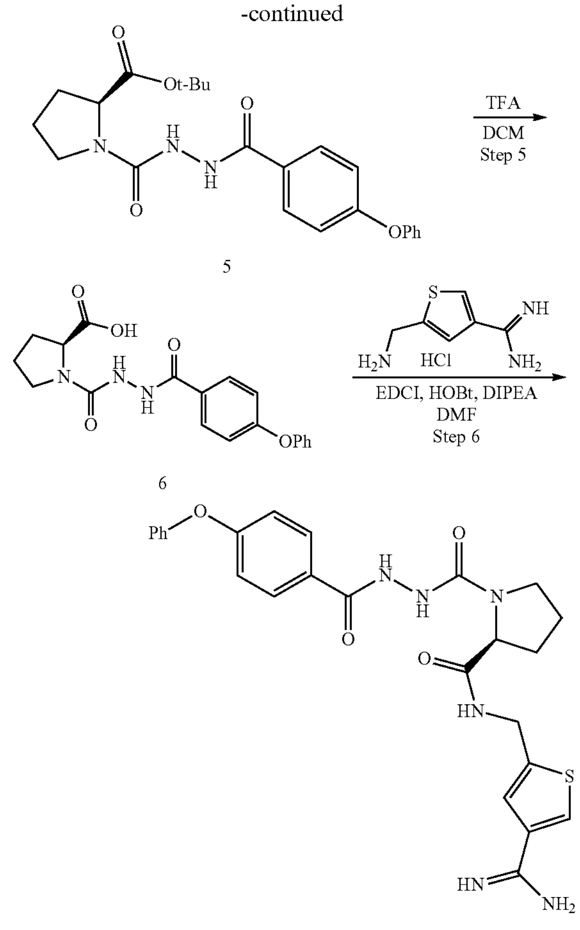

5

6

COMPOUND 59

Step 1: a solution of starting material 1 (3 g, 15.3 mmol) in DCM (45 mL) was added 4-nitrophenyl carbonochloridate (3.69 g, 18.4 mmol) at 0° C. The mixture was stirred at 25° C. for 2 hours. The mixture was diluted with DCM and washed with aq.$NaHCO_3$ solution and brine, dried over $Na_2SO_4$ and concentrated to dryness to give intermediate 2 (3.5 g, yield 63.4%) as yellow oil. LC/MS (ESI) m/z: 362 $(M+H)^+$.

Step 2: a mixture of intermediate 2 (3.5 g, 9.7 mmol) in DCM (50 mL) was added DIPEA (2.5 g, 19.4 mmol) and tert-butyl L-prolinate (2.50 g, 14.6 mmol) at 0° C. The mixture was stirred at 25° C. for 16 hours. The mixture was diluted with DCM and washed with water and brine, dried over $Na_2SO_4$ and concentrated to dryness. The residue was purified by column chromatography on silica gel (eluted with DCM:MeOH=100:1) to give intermediate 3 (3.0 g, yield 78.7%) as yellow oil. LC/MS (ESI) m/z: 394 $(M+H)^+$.

Step 3: a mixture of intermediate 3 (300 mg, 0.76 mmol) in pyridine (30 mL) was added hydroxylamine hydrochloride (238 mg, 3.42 mmol) at 0° C. The mixture was stirred at 60° C. for 16 hours. The mixture was concentrated to dryness and diluted with DCM, washed with water and brine, dried over $Na_2SO_4$ and concentrated to dryness. The residue was purified by column chromatography on silica gel (eluted with PE:EtOAc=40:1) to give intermediate 4 (140 mg, yield 80.5%) as yellow oil. LC/MS (ESI) m/z: 230 $(M+H)^+$.

Step 4: a mixture of intermediate 4 (140 mg, 0.61 mmol) and 4-phenoxybenzoic acid (130 mg, 0.61 mmol) in DMF (2 mL) was added DIPEA (315 mg, 2.44 mmol) followed by TBTU (235 mg, 0.73 mmol) at 0° C. and the mixture was stirred at room temperature for 1 hour. The mixture was diluted EtOAc and washed with saturated aq.$NH_4Cl$ solution and brine, dried over anhydrous $Na_2SO_4$, filtered and concentrated to dryness. The residue was purified by column chromatography on silica gel (DCM:MeOH=60:1) to give intermediate 5 (150 mg, yield 57.9%) as white solid. LC/MS (ESI) m/z: 426 $(M+H)^+$.

Step 5: a solution of intermediate 5 (150 mg, 0.35 mmol) in DCM (2 mL) was added TFA (2 mL) and the mixture was stirred at room temperature for 6 hours. The mixture was concentrated to dryness to give intermediate 6 (120 mg, yield 92.9%) as yellow oil, which was used directly without purification. LC/MS (ESI) m/z: 370 $(M+H)^+$.

Step 6: a mixture of intermediate 6 (40 mg, 0.168 mmol), 5-(aminomethyl)thiophene-3-carboximidamide hydrochloride (44 mg, 0.168 mmol) in DMF was added N,N-diisopropylethylamine (87 mg, 0.672 mmol) and EDCI (58 mg, 0.30 mmol) and HOBt (33 mg, 0.25 mmol) at 0° C. and the resulting mixture was stirred at room temperature for 16 hours. The mixture was diluted with DCM and washed with saturated aq. $NH_4Cl$ solution and brine, dried over anhydrous $Na_2SO_4$, filtered and concentrated to dryness. The residue was purified by prep-HPLC to afford COMPOUND 59 (5.5 mg, yield 6.5%) as white solid. $^1$H-NMR (400 MHz, $CD_3OD$) δ 8.49 (s, 1H), 8.21 (d, J=1.6 Hz, 1H), 7.92-7.81 (m, 2H), 7.42 (dd, J=10.6, 5.3 Hz, 3H), 7.21 (t, J=7.4 Hz, 1H), 7.04 (dd, J=19.3, 8.2 Hz, 4H), 4.58 (dd, J=15.9 Hz, 16.2 Hz, 2H), 4.43 (dd, J=4.5, 4.2 Hz, 1H), 3.70-3.64 (m, 1H), 3.55-3.39 (m, 1H), 2.25-2.19 (m, 1H), 2.08-1.92 (m, 3H); LC/MS (ESI) m/z: 507 $(M+H)^+$.

Scheme 32: (2S)-N-((4-(1-aminoethyl)thiophen-2-yl)methyl)-1-((4-phenoxybenzoyl)glycyl)pyrrolidine-2-carboxamide (COMPOUND 60)

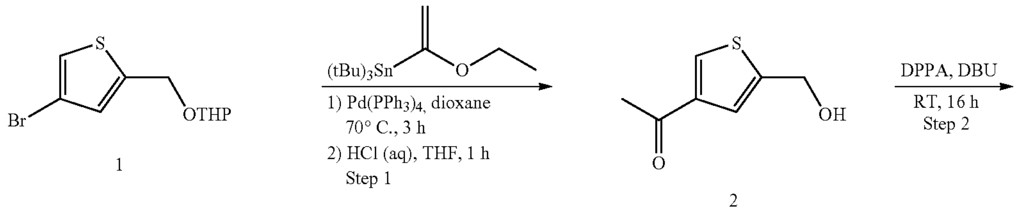

1

2

-continued

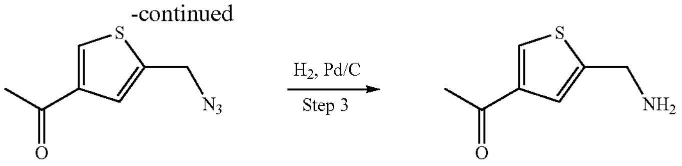

3

4

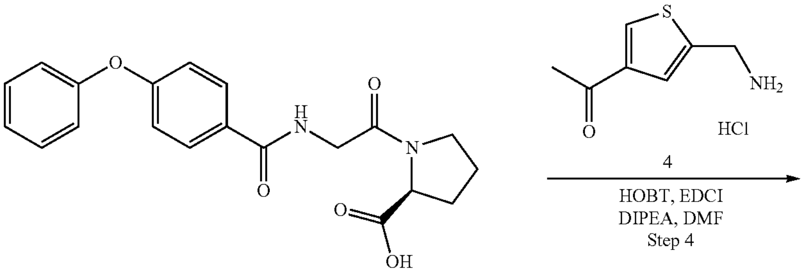

5

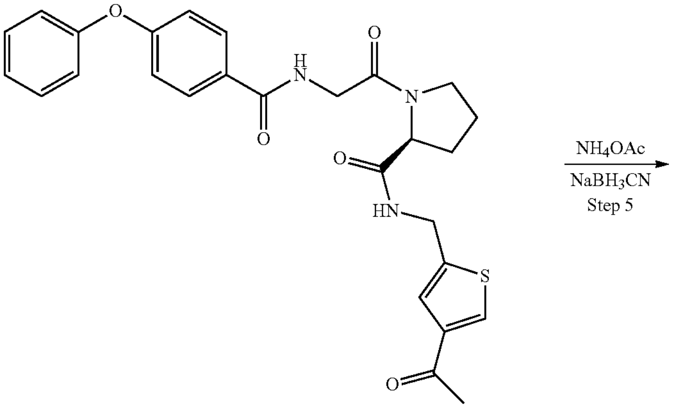

6

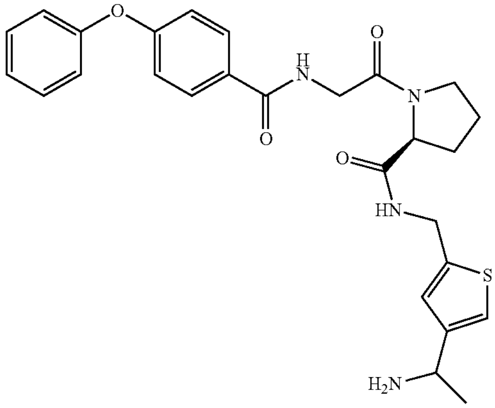

COMPOUND 60

Step 1: a mixture of starting material 1 (500 mg, 1.81 mmol) and 2-ethoxyprop-1-ene (850 mg, 2.35 mmol) in 1,4-dioxane (5 mL) was added $Pd(PPh_3)_4$ (209.1 mg, 0.181 mmol). The mixture was degassed three times and stirred at 70° C. under nitrogen atmosphere for 3 hours. The mixture was diluted with THF (5 mL) and 1N aq.HCl (2 mL) was added and the mixture was stirred at room temperature for 2 hours. The mixture was diluted with EtOAc and washed with water and brine, dried over $Na_2SO_4$ and concentrated to dryness under reduced pressure. The residue was purified by chromatography on silica gel (eluted with PE:EtOAc=10:1 to 5:1) to give intermediate 2 (108 mg, yield 50.7%) as yellow oil. LC/MS (ESI) m/z: 157 $(M+H)^+$.

Step 2: a solution of intermediate 2 (160 mg, 1.02 mmol) in DCM (3 mL) was added DPPA (338.69 mg, 1.23 mmol), DBU (187.37 mg, 1.23 mmol) at 0° C. and the mixture was stirred at RT for 5 hours before diluted with DCM. The mixture was washed with saturated $aq.NH_4Cl$ solution and brine and the organic layer was dried over $Na_2SO_4$ and concentrated to dryness under reduced pressure to give intermediate 3 (150 mg, yield 61.2%) as yellow oil. LC/MS (ESI) m/z: 182 $(M+H)^+$.

Step 3: a solution of intermediate 3 (150 mg, 0.827 mmol) in THF (3 mL) was added Pd/C (30 mg, 10% wt) and the mixture was stirred at room temperature for half an hour under $H_2$ atmosphere. After completion of the reaction, the mixture was filtered and the filtrate was concentrated to dryness under reduced pressure to give compound 4 (154 mg, crude) as yellow solid. LC/MS (ESI) m/z: 156 $(M+H)^+$.

Step 4: a mixture of compound 4 (154.2 mg, 1.02 mmol) and (S)-1-(2-(4-phenoxybenzamido)acetyl)pyrrolidine-2-carboxylic acid (194.82 mg, 0.51 mmol) in DMF (5 mL) was added DIPEA (263.24 mg, 1.0 mmol) and HOBt (103.374 mg, 0.81 mmol) followed by EDCI (175.9 mg, 0.93 mmol) at 0° C. The mixture was stirred at 25° C. for 16 hours before diluted with DCM and washed with saturated aq.$NH_4Cl$ solution and brine. The combined organic layers were dried over $Na_2SO_4$ and concentrated to dryness under reduced pressure. The residue was purified by chromatography on silica gel (eluted with PE:EtOAc=10:1 to 5:1) to give intermediate 6 (100 mg, yield 48%) as white solid. LC/MS (ESI) m/z: 506 $(M+H)^+$.

Step 5: a solution of intermediate 6 (100 mg, 0.16 mmol) in MeOH (5 mL) was added $NH_4OAc$ (200 mg, 1.65 mmol) and $NaBH_3CN$ (12 mg, 0.19 mmol) at 0° C. The mixture was stirred under the $N_2$ atmosphere at room temperature for 16 hours before filtered and the filtrate was concentrated to dryness under reduced pressure. The residue was purified by prep-HPLC to afford COMPOUND 60 (5 mg, yield 10.0%) as white solid. $^1H$-NMR (400 MHz, $CD_3OD$) δ 8.61 (s, 1H), 7.86 (s, 2H), 7.41 (m, 2H), 7.32 (m, 1H) 7.28 (m, 1H), 7.20 (m, 3H), 7.07 (m, 2H) 4.52-4.46 (m, 2H), 4.32 (m, 2H), 4.28-4.19 (m, 2H), 4.15 (m, 2H), 2.22-2.08 (m, 1H), 2.06-1.92 (m, 3H), 1.56-1.49 (m, 3H). LC/MS (ESI) m/z: 507 $(M+H)^+$.

Scheme 33: N-(2-((1R,2S,4S)-2-(((4-carbamimidoylthiophen-2-yl)methyl)carbamoyl)-4-methoxycyclopentyl)-2-oxoethyl)-4-phenoxybenzamide (COMPOUND 61) & N-(2-((1S,2R,4S)-2-(((4-carbamimidoylthiophen-2-yl)methyl)carbamoyl)-4-methoxycyclopentyl)-2-oxoethyl)-4-phenoxybenzamide (COMPOUND 34)

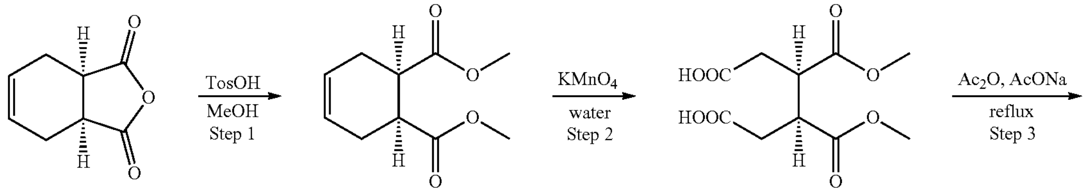

1 2 3

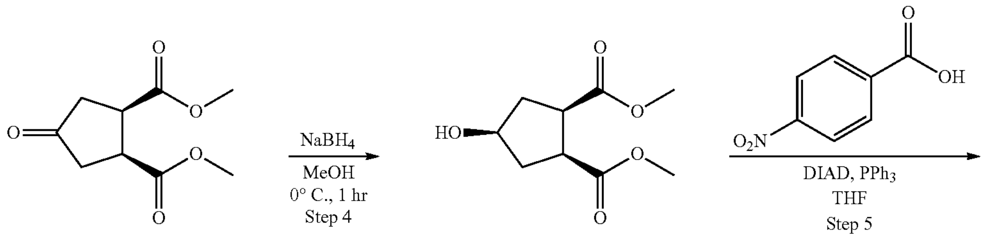

4 5

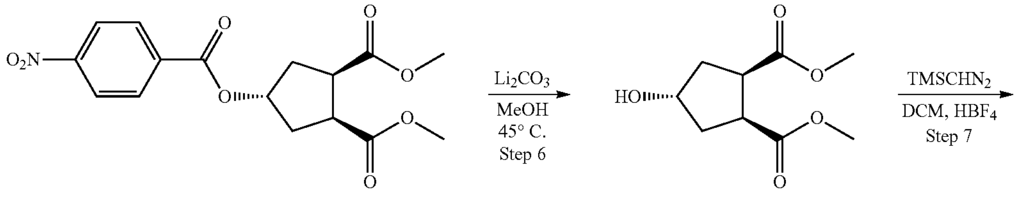

6 7

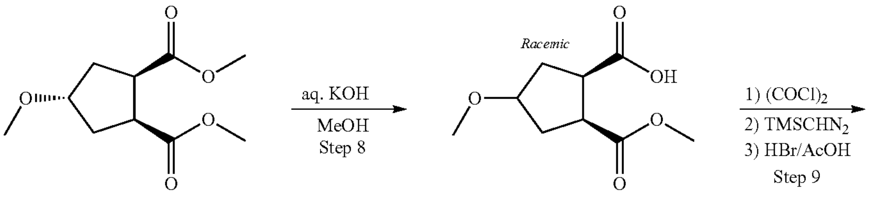

8 9

-continued

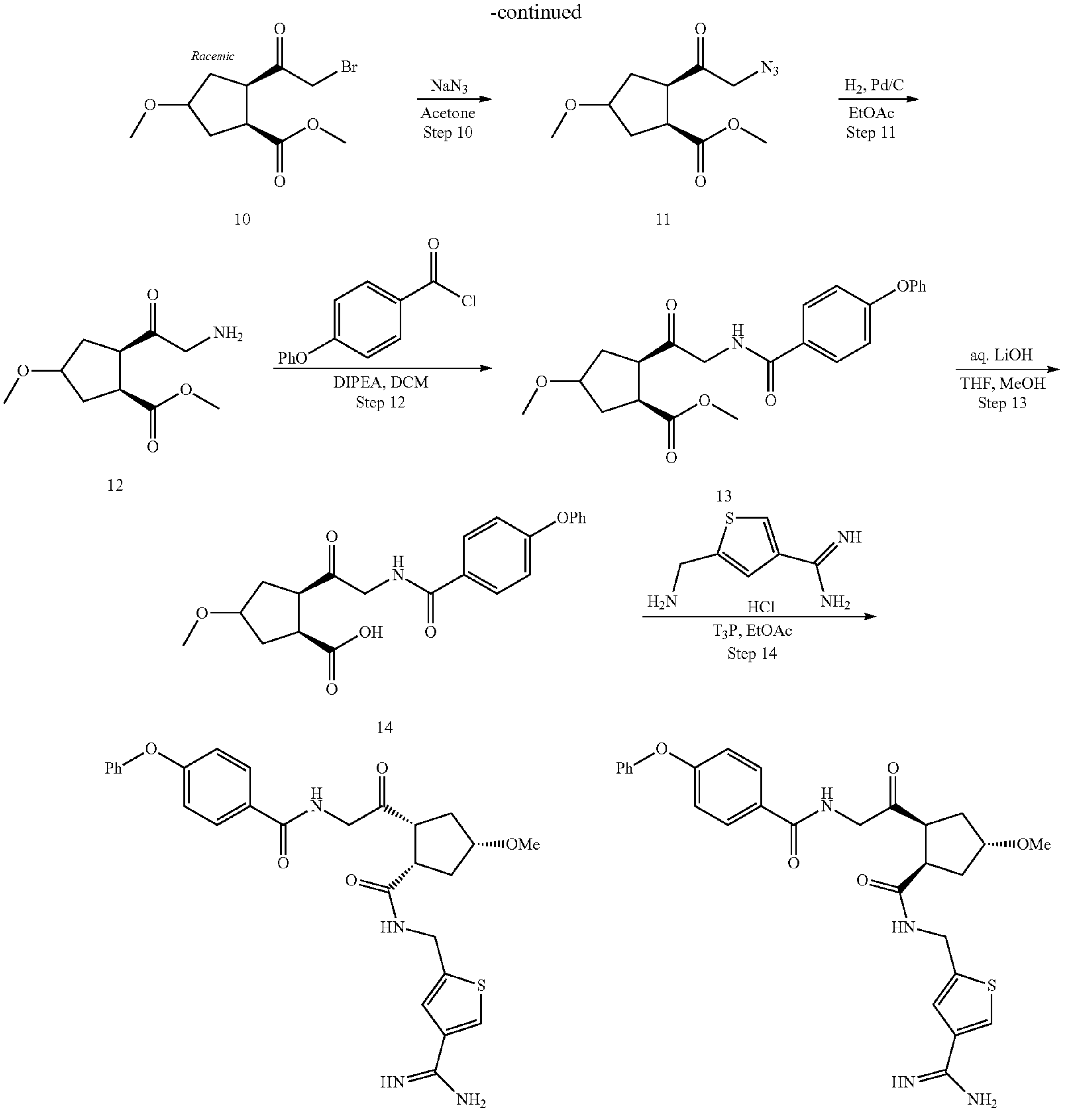

10

11

12

13

14

COMPOUND 61

COMPOUND 34

Step 1: a solution of starting material 1 (25.0 g, 164.5 mmol) in methanol (250 mL) was added p-toluenesulfonic acid (1.41 g, 8.2 mmol), and the mixture was stirred at 65° C. for 2.5 hours. The mixture was concentrated and the residue was dissolved in DCM and washed with aq.$NaHCO_3$ solution twice. The organic layer was dried over anhydrous $Na_2SO_4$, filtered and concentrated to dryness. The residue was purified by chromatography on silica gel (PE: EtOAc=50:1 to 25:1) to give intermediate 2 (13.2 g, yield 40.5%) as white solid. LC/MS (ESI) m/z: 199 $(M+H)^+$.

Step 2: a stirred solution of potassium permanganate (19.57 g, 123.8 mmol) in water (180 mL) was added a solution of intermediate 2 (8.18 g, 41.3 mmol) in acetone (108 mL) drop-wise and the mixture was stirred at 30° C. for 3.5 hours. After completion of reaction, the mixture was quenched with saturated aq.$Na_2SO_3$ solution (30 mL). Concentrated aq.HCl solution was added until the reaction mixture turned to colorless. The mixture was extracted with EtOAc twice and the combined organic layers were washed with water and brine, dried over anhydrous $Na_2SO_4$, filtered and concentrated under reduced pressure to give intermediate 3 (10.0 g, yield 92.4%) as white solid. LC/MS (ESI) m/z: 263 $(M+H)^+$.

Step 3: a solution of intermediate 3 (10.0 g, 38.1 mmol) in acetic anhydride (50 mL) was stirred at 130° C. for 1 hour. The mixture was cooled to room temperature and sodium acetate (7.78 g, 57.2 mmol) was added and the resulting mixture was stirred at 130° C. for another 3 hours. After completion of the reaction, the mixture was cooled and stored at 5° C. overnight. The mixture was filtered and the filtrate was concentrated to dryness. The residue was dissolved in water, and the mixture was basified with 1N aq. NaOH to pH~9. The mixture was extracted with EtOAC twice and dried over anhydrous $Na_2SO_4$, filtered and concentrated under reduced pressure. The residue was purified by chromatography on silica gel (PE:EtOAc=10:1) to give intermediate 4 (6.4 g, yield 83.8%) as yellow solid. LC/MS (ESI) m/z: 201 $(M+H)^+$.

Step 4: a solution of intermediate 4 (5.0 g, 25.0 mmol) in MeOH (50 mL) was added $NaBH_4$ (945 mg, 25.0 mmol) at 0° C., and the mixture was stirred at room temperature for 1 hour under $N_2$ atmosphere. The mixture was quenched with ice-water and extracted with DCM twice. The combined organic layers were washed with brine, dried over $Na_2SO_4$, filtered and concentrated to dryness. The residue was purified by chromatography on silica gel (PE: EtOAc=20:1 to 8:1) to give intermediate 5 (4.3 g, yield 85.1%) as light oil. LC/MS (ESI) m/z: 203 $(M+H)^+$.

Step 5: a mixture of intermediate 5 (4.3 g, 21.3 mmol) and p-nitrobenzoic acid (4.27 g, 25.5 mmol) in THF (40 mL) was added $PPh_3$ (6.69 g, 25.5 mmol) at 0° C., followed by diisopropylazodicarboxylate (5.16 g, 25.5 mmol), and the mixture was stirred at room temperature overnight. The mixture was diluted with EtOAc, washed with water, brine and dried over anhydrous $Na_2SO_4$, filtered and concentrated to dryness under reduced pressure. The residue was purified by chromatography on silica gel (PE:EtOAc=50:1 to 10:1) to give intermediate 6 (5.8 g, yield 77.6%) as white solid. LC/MS (ESI) m/z: 352 $(M+H)^+$.

Step 6: a solution of intermediate 6 (5.8 g, 16.5 mmol) in methanol (60 mL) was added lithium carbonate (4.88 g, 66.0 mmol) and the mixture was stirred at 45° C. for 2.5 hours. The mixture was filtered and the filtrate was concentrated. The residue was poured into ice-water and extracted with DCM twice. The combined organic layers were dried over anhydrous $Na_2SO_4$, filtered and concentrated to dryness under reduced pressure. The residue was purified by chromatography on silica gel (PE:EtOAc=10:1 to 2:1) to give intermediate 7 (3.12 g, yield 93.5%) as light yellow oil. LC/MS (ESI) m/z: 203 $(M+H)^+$.

Step 7: a mixture of intermediate 7 (3.12 g, 15.3 mmol) and fluoroboric acid (3.37 g, 15.3 mmol) in DCM (30 mL) was added (trimethylsilyl)diazomethane solution (3.50 g, 30.7 mmol) drop-wise at 0° C. and the mixture was stirred at 0° C. for 30 minutes under $N_2$ atmosphere. The mixture was poured into ice-water and extracted with DCM twice. The combined organic layers were dried over anhydrous $Na_2SO_4$, filtered and concentrated to dryness under reduced pressure. The residue was purified by chromatography on silica gel (PE:EtOAc=10:1 to 6:1) to give intermediate 8 (1.52 g, yield 45.9%) as yellow oil. LC/MS (ESI) m/z: 217 $(M+H)^+$.

Step 8: a stirred solution of intermediate 8 (1.52 g, 7.0 mmol) in methanol (10 mL) was added a solution of potassium hydroxide (235 mg, 4.2 mmol) in water (5 mL) at 0° C., and the mixture was stirred at 0° C. for 3 hours. The mixture was diluted with water and washed with diethyl ether twice. The aqueous layer was acidified with 0.5 M aq. HCl solution to pH~3 and extracted with EtOAc twice. The combined organic layers were washed with brine, dried over anhydrous $Na_2SO_4$, filtered and concentrated to dryness under reduced pressure to give intermediate 9 (600 mg, yield 42.4%) as light oil. LC/MS (ESI) m/z: 203 $(M+H)^+$.

Step 9: a stirred solution of intermediate 9 (600 mg, 2.97 mmol) in DCM (4 mL) was added oxalylchloride (942 mg, 7.43 mmol) followed by dimethylformamide (13 mg, 0.18 mmol) at 0° C., the mixture was stirred at 0° C. for 3 hours under $N_2$ atmosphere. The mixture was concentrated to dryness under reduced pressure. The residue was dissolved in THF (6 mL) and (trimethylsilyl)diazomethane solution (7.13 mL, 14.26 mmol, 2M) was added drop-wise at 0° C. and the mixture was stirred at 0° C. overnight. HBr—AcOH solution (1.16 mL, 33%) was added to the mixture and the resulting mixture was stirred at 0° C. for 0.5 hour under $N_2$ atmosphere. The mixture was quenched with ice-water and extracted with EtOAc. The organic layer was washed with brine, dried and concentrated to dryness under reduced pressure to give intermediate 10 (580 mg, yield 70.2%) as yellow oil, which was used directly in the next step. LC/MS (ESI) m/z: 279/281 $(M+H)^+$.

Step 10: a stirred solution of intermediate 10 (580 mg, 2.09 mmol) in acetone (6 mL) was added sodium azide (407 mg, 6.27 mmol) and the mixture was stirred at room temperature overnight. The mixture was diluted with EtOAc and washed with water and brine, dried over anhydrous $Na_2SO_4$, filtered and concentrated to dryness under reduced pressure. The residue was purified by chromatography on silica gel (PE:EtOAc=20:1 to 10:1) to give intermediate 11 (330 mg, yield 65.6%) as yellow oil. LC/MS (ESI) m/z: 242 $(M+H)^+$.

Step 11: a solution of intermediate 11 (230 mg, 0.95 mmol) in EtOAc (15 mL) was added Pd/C (90 mg, 10% wt) at 0° C., and the mixture was degassed under $N_2$ atmosphere for three times and stirred under a $H_2$ balloon at room temperature for 30 minutes. The mixture was filtered and the filtrate was directly used in the next step. LC/MS (ESI) m/z: 216 $(M+H)^+$.

Step 12: a stirred solution of intermediate 12 (205 mg, 0.95 mmol) in DCM (20 mL), was added 4-phenoxybenzoyl chloride (664 mg, 2.85 mmol) followed by DIPEA (492 mg, 3.80 mmol) at 0° C. and the mixture was stirred at room temperature for 1 hour. After completion of the reaction, the mixture was diluted with water and extracted with EtOAc twice. The combined organic layers were washed with brine, dried over anhydrous $Na_2SO_4$, filtered and concentrated to dryness under reduced pressure. The residue was purified by Pre-TLC (PE:acetone=2:1) to give intermediate 13 (160 mg, yield 40.8%) as light yellow solid. LC/MS (ESI) m/z: 216 $(M+H)^+$.

Step 13: a solution of intermediate 13 (160 mg, 0.39 mmol) in THF (3 mL) and MeOH (6 mL) was added a solution of lithium hydroxide (82 mg, 1.94 mmol) in water (3 mL) at 0° C., and the mixture was stirred at room temperature for 2 hours. After completion of the reaction, the mixture was diluted with water and washed with $Et_2O$ twice. The aqueous layer was acidified with 0.5 M aq. HCl solution to pH~3 and extracted with DCM twice. The combined organic layers were washed with brine, dried over anhydrous $Na_2SO_4$, filtered and concentrated to dryness under reduced pressure to give intermediate 14 (150 mg, yield 97.5%) as light yellow oil. LC/MS (ESI) m/z: 398 $(M+H)^+$.

Step 14: a mixture of intermediate 14 (150 mg, 0.38 mmol) and 5-(aminomethyl)thiophene-3-carboximidamide (88 mg, 0.57 mmol) in EtOAc (8 mL) was added propylphosphonic anhydride (242 mg, 0.76 mmol) followed by triethylamine (192 mg, 1.9 mmol) at 0° C. and the mixture was stirred at room temperature for 1 hour. The mixture was poured into ice-water and extracted with DCM twice. The combined organic layers were washed with brine, dried over anhydrous $Na_2SO_4$, filtered and concentrated to dryness under reduced pressure. The residue was purified by prep-HPLC and SFC to afford COMPOUND 61 (12.0 mg, yield 5.9%) and COMPOUND 34 (13.2 mg, yield 6.5%) as white solid. COMPOUND 61 $^1$H-NMR (400 MHz, $CD_3OD$) δ 8.08 (t, J=1.6 Hz, 1H), 7.84-7.81 (m, 2H), 7.43-7.38 (m, 3H), 7.20 (t, J=7.4 Hz, 1H), 7.07-7.05 (m, 2H), 7.02-6.99 (m, 2H), 4.57-4.52 (m, 2H), 3.97-3.92 (m, 1H), 3.39-3.32 (m, 1H), 3.28-3.20 (m, 5H), 2.41-2.32 (m, 1H), 2.16-2.08 (m, 1H), 2.04-1.83 (m, 3H); LC/MS (ESI) m/z: 535 $(M+H)^+$.

COMPOUND 34 $^1$H-NMR (400 MHz, $CD_3OD$) δ 7.97 (t, J=1.6 Hz, 1H), 7.75-7.72 (m, 2H), 7.33-7.28 (m, 3H), 7.10 (t, J=7.4 Hz, 1H), 6.98-6.95 (m, 2H), 6.92-6.90 (m, 2H), 4.46-4.39 (m, 2H), 3.88-3.82 (m, 1H), 3.29-3.22 (m, 1H), 3.18-3.11 (m, 5H), 2.31-2.23 (m, 1H), 2.04-1.97 (m, 1H), 1.95-1.76 (m, 3H); LC/MS (ESI) m/z: 535 $(M+H)^+$.

Scheme 34: Synthesis of N-(2-((1R,2R,4S)-2-(((4-carbamimidoylthiophen-2-yl)methyl)carbamoyl)-4-methoxycyclopentyl)-2-oxoethyl)-4-phenoxybenzamide (35) and N-(2-((1R,2S,4R)-2-(((4-carbamimidoylthiophen-2-yl)methyl)carbamoyl)-4-methoxycyclopentyl)-2-oxoethyl)-4-phenoxybenzamide (COMPOUND 62)

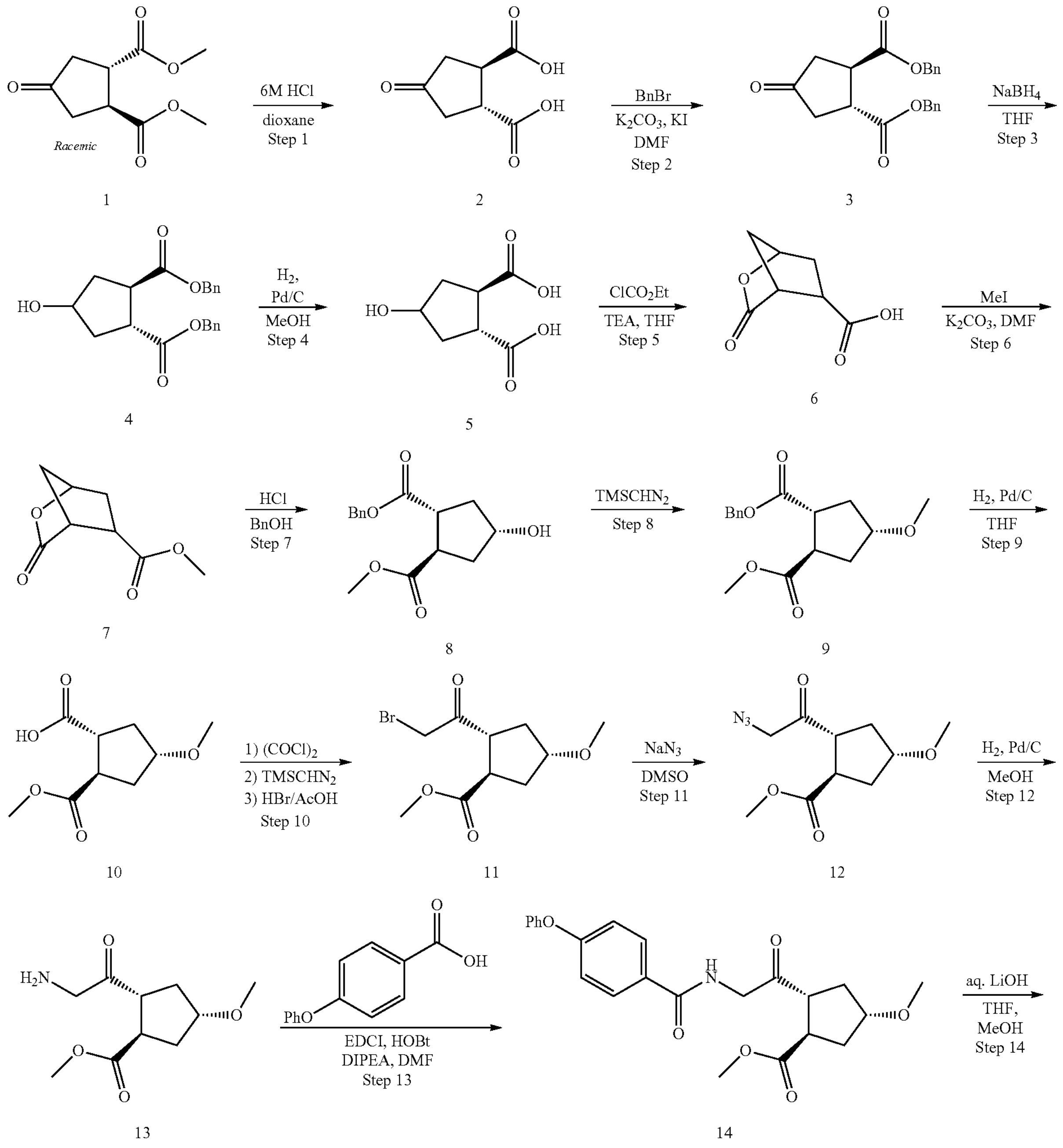

-continued

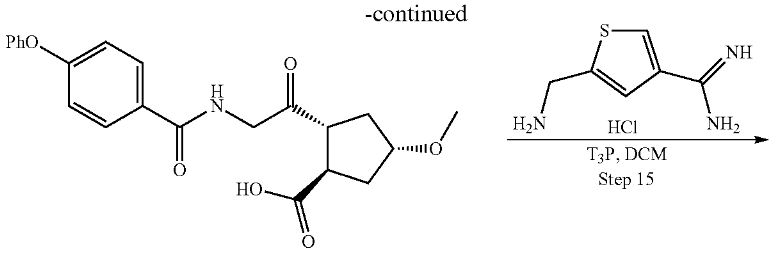

15

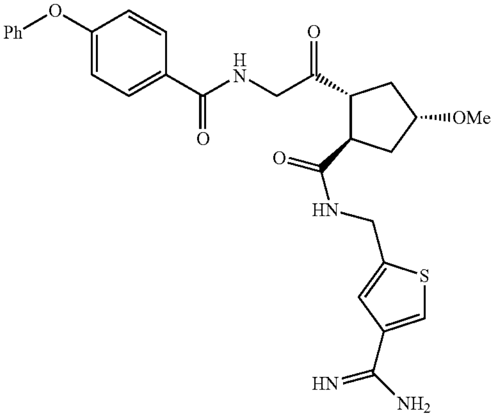

COMPOUND 35

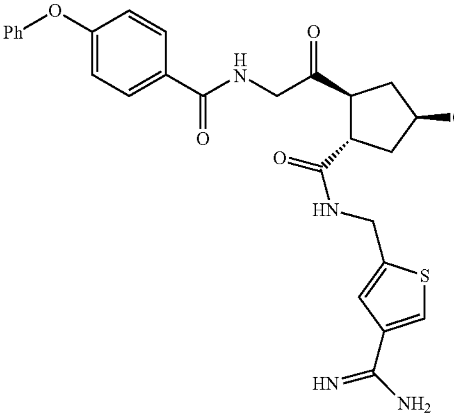

COMPOUND 62

Step 1: a solution of dimethyl (1S,2S)-4-oxocyclopentane-1,2-dicarboxylate (5 g, 25 mmol) in 1,4-dioxane (30 mL) was added 6M aq.HCl (20 mL) and the mixture was stirred at 100° C. for 16 hrs. The mixture was concentrated to dryness and the residue was washed with diethyl ether, dried under vacuum to give intermediate 2 (2.6 g, 60.4% yield) as light yellow solid. LC/MS (ESI) m/z: 171 $(M-H)^-$.

Step 2: a solution of intermediate 2 (2.6 g, 15.1 mmol) in DMF (20 mL) was added $K_2CO_3$ (5.4 g, 39.3 mmol) and KI (50 mg, catalytic amount) followed by drop-wise addition of benzyl bromide (5.7 g, 33.2 mmol) and the mixture was stirred at room temperature for 16 hours. The mixture was diluted with EtOAc and washed with saturated aq.$NH_4Cl$ solution and brine, dried and concentrated to dryness to give crude product, which was purified by silica gel chromatography (eluted with PE:EtOAc=20:1) to give intermediate 3 (2.5 g, 46.9% yield) as white solid.

Step 3: a solution of intermediate 3 (2.5 g, 7.09 mmol) in THF (30 mL) was added $NaBH_4$ (295 mg, 7.8 mmol) in portions at 0° C. and the mixture was stirred at this temperature for 3 hours. The mixture was quenched with ice-cooled saturated aq.$NH_4Cl$ solution and extracted with EtOAc twice. The combined organic layers were washed with water and brine, dried over $Na_2SO_4$, filtered and concentrated to dryness to give crude product, which was purified by silica gel chromatography (eluted with PE:EtOAc=10:1 to 5:1) to give intermediate 4 (2.5 g, 100% yield) as yellow syrup.

Step 4: a solution of intermediate 4 (2.5 g, 7.09 mmol) in MeOH (30 mL) was added Pd/C (200 mg, 10% wt) and the mixture was degassed under $N_2$ for three times and stirred under a $H_2$ balloon at room temperature for 3 hours. The mixture was filtered and the filtrate was concentrated to dryness to give intermediate 5 (1.1 g, yield 89%) as yellow solid, which was directly used in the next reaction. LC/MS (ESI) m/z: 173 $(M-H)^-$.

Step 5: a solution of intermediate 5 (1.1 g, 6.3 mmol) in THF (20 mL) was added TEA (1.9 g, 18.9 mmol) followed by drop-wise addition of ethyl chloroformate (820 mg, 7.56 mmol) at 0° C. and the mixture was stirred at room temperature for 16 hours. The mixture was diluted with EtOAc and washed with water and brine, dried and concentrated to dryness to give crude product, which was purified by silica gel chromatography (eluted with PE:EtOAc=10:1 to 5:1) to give intermediate 6 (0.92 g, yield 93.5%) as light yellow oil. LC/MS (ESI) m/z: 155 $(M-H)^-$.

Step 6: a mixture of intermediate 6 (1.5 g, 9.6 mmol) in DMF (20 mL) was added to $K_2CO_3$ (3.3 g, 24 mmol) and iodomethane (2.0 g, 14.3 mmol) drop-wise at 0° C. The reaction was stirred at 25° C. for 16 hours before the mixture was diluted with EtOAc, washed with saturated aq. $NH_4C_1$ solution, brine, dried over anhydrous $Na_2SO_4$, filtered and concentrated to dryness. The residue was purified by column chromatography on silica gel (eluted with PE:EtOAc=6:1) to give intermediate 7 (910 mg, yield 55.8%) as colorless oil. LC/MS (ESI) m/z: 171 $(M+H)^+$.

Step 7: a mixture of intermediate 7 (910 mg, 5.35 mmol) in benzyl alcohol (15 mL) was added HCl/1,4-dioxane (2.7 mL, 10.7 mmol, 4 M) at 0° C. The reaction was stirred at 45° C. for 16 hours. The mixture was diluted with EtOAc, washed with saturated aq.$NaHCO_3$ solution, brine, dried over anhydrous $Na_2SO_4$, filtered and concentrated to dryness. The residue was purified by column chromatography on silica gel (eluted with PE:EtOAc=3:1) to give intermediate 8 (835 mg, yield 56.2%) as colorless oil. LC/MS (ESI) m/z: 279 $(M+H)^+$.

Step 8: a mixture of intermediate 8 (835 mg, 3.0 mmol) and fluoroboric acid (660 mg, 3.0 mmol) in DCM (10 mL) was added to (trimethylsilyl)diazomethane solution (3 mL, 6.0 mmol, 2M in toluene) drop-wisely at 0° C. and the mixture was stirred at 0° C. for 30 minutes under $N_2$ atmosphere. The mixture was poured into ice water and extracted with DCM twice. The combined organic layers were dried over anhydrous $Na_2SO_4$, filtered and concentrated to dryness. The residue was purified by chromatography on silica gel (PE:EtOAc=6:1) to give intermediate 9 (620 mg, yield 70.5%) as yellow oil. LC/MS (ESI) m/z: 293 $(M+H)^+$.

Step 9: a solution of intermediate 9 (620 mg, 2.1 mmol) in EtOAc (5 mL) and THF (5 mL) was added Pd/C (100 mg, 10% wt). The mixture was stirred at 0° C. for 1 hour under a $H_2$ balloon before the mixture was filtered and the filtrate was concentrated to dryness to give intermediate 10 (400 mg, yield 94.3%) as colorless oil. LC/MS (ESI) m/z: 203 $(M+H)^+$.

Step 10: a solution of intermediate 10 (400 mg, 1.97 mmol) in DCM (4 mL) was added oxalyl chloride (625 mg, 4.93 mmol) and DMF (14 mg, 0.20 mmol) at 0° C. The mixture was stirred at 0° C. for 3 hours under $N_2$ atmosphere before the mixture was concentrated to dryness under reduced pressure. The residue was dissolved in THF (6 mL) and a solution of (trimethylsilyl)diazomethane (4.73 mL, 9.46 mmol, 2M in toluene) was added at 0° C. and the mixture was stirred overnight at the same temperature. Hydrogen bromide (0.77 mL, 33%) was added to the mixture and the resulting mixture was stirred at 0° C. under $N_2$ atmosphere for 0.5 hour before the mixture was diluted with water and extracted with EtOAc, the organic layers were dried and concentrated to give intermediate 11 (340 mg, yield 62.1%) as yellow oil, which was used directly in the next step. LC/MS (ESI) m/z: 279/281 $(M+H)^+$.

Step 11: a solution of intermediate 11 (340 mg, 1.22 mmol) in DMSO (5 mL) was added to sodium azide (238 mg, 3.66 mmol) and the mixture was stirred at room temperature overnight. The mixture was extracted with water and EtOAc twice. The combined organic layers were washed with brine, dried over anhydrous $Na_2SO_4$, filtered and concentrated and the residue was purified by chromatography on silica gel (PE:EtOAc=10:1) to give intermediate 12 (240 mg, yield 81.6%) as yellow oil. LC/MS (ESI) m/z: 242 $(M+H)^+$.

Step 12: a solution of intermediate 12 (240 mg, 0.10 mmol) in MeOH (15 mL) was added Pd/C (100 mg, 10% wt) at 0° C., and the mixture was degassed three times and stirred under a $H_2$ balloon at room temperature for 30 minutes. The mixture was filtered and the filtrate was used directly without further purification. LC/MS (ESI) m/z: 216 $(M+H)^+$.

Step 13: methyl (1R,2R,4S)-4-methoxy-2-((4-phenoxybenzoyl)glycyl)cyclopentane-1-carboxylate (14) 4-phenoxybenzoyl chloride (693 mg, 2.99 mmol) was added to a solution of intermediate 13 (240 mg, 1.00 mmol) in DMF (15 mL), followed by DIPEA (514 mg, 3.98 mmol) at 0° C. and the mixture was stirred at room temperature for 1 hour. The mixture was diluted with EtOAc and washed with brine, dried over anhydrous $Na_2SO_4$, filtered and concentrated to dryness. The residue was purified by chromatography on silica gel (PE:EtOAc=4:1) to give intermediate 14 (160 mg, yield 39.1%) as light yellow solid. LC/MS (ESI) m/z: 412 $(M+H)^+$.

Step 14: a solution of intermediate 14 (160 mg, 0.39 mmol) in THF (3 mL) and MeOH (6 mL) was added a solution of lithium hydroxide (82 mg, 1.94 mmol) in water (3 mL) at 0° C., and the mixture was stirred at room temperature for 2 hours. The mixture was diluted with water and washed with diethyl ether. The aqueous layers were acidified by adding 1N aq.HCl to pH~3 at 0° C. and extracted with DCM twice. The combined organic layers were washed with brine, dried over anhydrous $Na_2SO_4$, filtered and concentrated to dryness to give intermediate 15 (130 mg, yield 84.0%) as light yellow oil. LC/MS (ESI) m/z: 398 $(M+H)^+$.

Step 15: a mixture of intermediate 15 (130 mg, 0.33 mmol) and 5-(aminomethyl)thiophene-3-carboximidamide (77 mg, 0.49 mmol) in DCM (8 mL) was added propylphosphonic anhydride (210 mg, 0.66 mmol) followed by TEA (100 mg, 0.99 mmol) at 0° C. and the mixture was stirred at room temperature for 1 hour. The mixture was poured into ice water and extracted with DCM twice. The combined organic layers were washed with brine, dried over anhydrous $Na_2SO_4$, filtered and concentrated to dryness. The residue was purified by prep-HPLC and chiral-SFC to afford COMPOUND 35 (9.5 mg, yield 5.4%) and COMPOUND 62 (11.4 mg, 6.5% yield) as white solid. COMPOUND 35: $^1$H-NMR (400 MHz, $CD_3OD$) δ 8.16 (s, 1H), 7.81 (dd, J=17.0, 8.8 Hz, 2H), 7.53-7.36 (m, 3H), 7.20 (t, J=7.4 Hz, 1H), 7.06 (d, J=7.7 Hz, 2H), 7.01 (d, J=8.7 Hz, 2H), 4.55 (q, J=15.4 Hz, 2H), 3.95 (s, 1H), 3.40-3.33 (m, 1H), 3.27 (s, 3H), 3.22 (d, J=9.6 Hz, 2H), 2.43-2.39 (m, 1H), 2.18-2.07 (m, 1H), 2.08-2.13 (m Hz, 1H), 1.93-1.85 (m, 1H), 0.99 (t, J=6.1 Hz, 1H). COMPOUND 62: $^1$H-NMR (400 MHz, $CD_3OD$) δ 8.22 (s, 1H), 7.83 (d, J=8.6 Hz, 2H), 7.41 (t, J=7.9 Hz, 3H), 7.20 (t, J=7.4 Hz, 1H), 7.06 (d, J=7.8 Hz, 2H), 7.01 (d, J=8.6 Hz, 2H), 4.55 (q, J=15.5 Hz, 2H), 4.21 (d, J=9.3 Hz, 1H), 3.95 (s, 1H), 3.36 (t, J=7.2 Hz, 1H), 3.27 (s, 3H), 3.22 (d, J=9.6 Hz, 2H), 2.43-2.31 (m, 1H), 2.13-2.07 (m, 1H), 2.05-1.97 (m, 1H), 1.94-1.86 (m, 1H), 0.99 (t, J=6.1 Hz, 1H); LC/MS (ESI) m/z: 535 $(M+H)^+$.

Scheme 35: Synthesis of (S,Z)-N-((4-(N'-cyanocarbamimidoyl)thiophen-2-yl)methyl)-7-(2-(4-phenoxybenzamido)acetyl)-1,4-dioxa-7-azaspiro[4.4]nonane-8-carboxamide (COMPOUND 63)

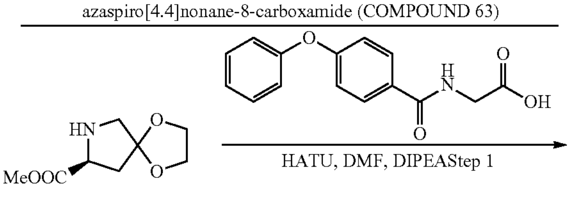

1

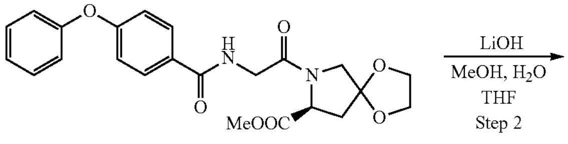

2

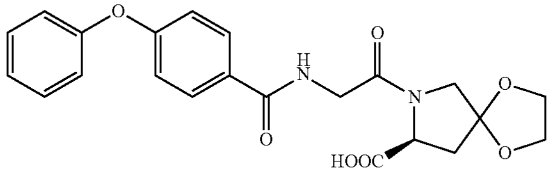

3

-continued

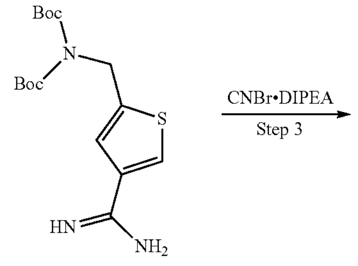

4

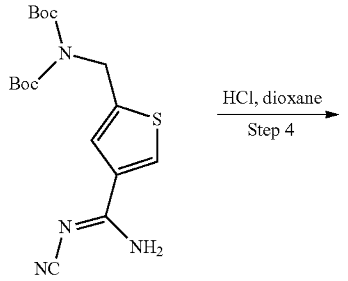

5

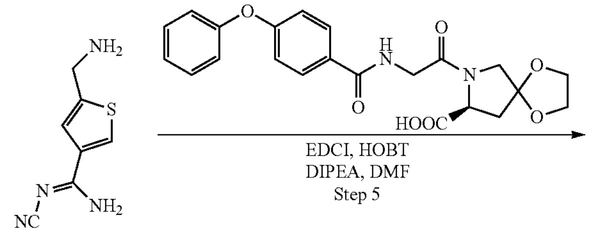

6

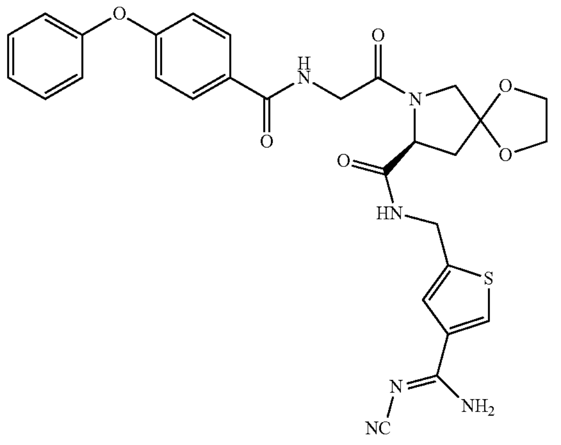

COMPOUND 63

Step 1: a mixture of starting material 1 (200 mg, 0.47 mmol) and 2-(4-phenoxybenzamido)acetic acid (140 mg, 0.56 mmol) in DMF (5 mL) was added DIPEA (130 mg, 0.63 mmol) and HATU (180 mg, 0.28 mmol) at 0° C. The mixture was stirred at room temperature under $N_2$ atmosphere for 12 hours before diluted with EtOAc and washed with saturated aq.$NH_4Cl$ solution and brine, dried over anhydrous $Na_2SO_4$, filtered and concentrated to dryness. The residue was purified by chromatography on silica gel (DCM:MeOH=97:3) to give intermediate 2 (130 mg, yield 75.2%) as brown oil. LC/MS (ESI) (m/z): 441 $(M+H)^+$.

Step 2: a solution of intermediate 2 (100 mg, 0.151 mmol) in MeOH (5 mL) and water (1 mL) was added lithium hydroxide monohydrate (32 mg, 0.753 mmol). The mixture was stirred at room temperature for 2 hours before concentrated to one-fifth volume, diluted with water and washed with MTBE twice. The aqueous layer was acidified with 1N aq.HCl to pH~3 and extracted with DCM twice. The combined organic layers were washed with brine, dried over anhydrous $Na_2SO_4$, and concentrated to dryness under reduced pressure to give compound 3 (100 mg, yield 95%) as white solid. LC/MS (ESI) (m/z): 427 $(M+H)^+$.

Step 3: a mixture of compound 4 (50 mg, 0.14 mmol) and BrCN (29.6 mg, 0.28 mmol) in DCM (2 mL) was added DIPEA (90.37 mg, 0.70 mmol) at 0° C. The mixture was stirred at room temperature under $N_2$ atmosphere for 1 hour before diluted with EtOAc and washed with saturated aq.$NH_4Cl$ solution and brine, dried over anhydrous $Na_2SO_4$, filtered and concentrated to dryness under reduced pressure. The residue was purified by chromatography on silica gel (DCM:MeOH=97:3) to give intermediate 5 (40 mg, yield 74.1%) as brown oil. LC/MS (ESI) (m/z): 381 $(M+H)^+$.

Step 4: a solution of intermediate 5 (40 mg, 0.10 mmol) in 1,4-dioxane/HCl (5 mL, 26.13 mmol) was stirred at room temperature for 2 hours. The mixture was concentrated to dryness under reduced pressure and the residue was washed with diethyl ether and dried under vacuum to give intermediate 6 (40 mg, yield 93%) as brown solid, which was directly used in the next step without further purification. LC/MS (ESI) (m/z): 181 $(M+H)^+$.

Step 5: a mixture of intermediate 6 (40 mg, 0.22 mmol) and compound 3 (93.94 mg, 0.22 mmol) in DMF (3 mL) was added EDCI (84.4 mg, 0.44 mmol), HOBt (60.72 mg, 0.44 mmol) followed by DIPEA (130 mg, 0.2 mL, 1.8 mmol) at 0° C. The mixture was stirred at 25° C. for 12 hours before diluted with EtOAc and washed with water and brine, dried over anhydrous $Na_2SO_4$, filtered and concentrated to dryness under reduced pressure. The residue was purified by prep-HPLC to afford COMPOUND 63 (4 mg, yield 21.9%) as white solid. $^1$H-NMR (400 MHz, DMSO-$d_6$) δ 8.58 (dd, J=18.1, 12.4 Hz, 2H), 7.92 (t, J=12.4 Hz, 2H), 7.44 (t, J=7.9 Hz, 2H), 7.31-7.18 (m, 2H), 7.18-7.05 (m, 3H), 7.04 (d, J=8.7 Hz, 2H), 4.38 (t, J=6.9 Hz, 2H), 4.30-4.08 (m, 1H), 3.93 (dt, J=20.8, 10.6 Hz, 5H), 3.78 (d, J=10.7 Hz, 1H), 3.72-3.54 (m, 2H), 2.26 (ddd, J=25.1, 13.1, 8.2 Hz, 2H), 2.14-1.86 (m, 2H). LC/MS (ESI) m/z: 589 $(M+H)^+$.

Scheme 36: Synthesis of S)-N-((4-aminothieno[3,2-c]pyridin-2-yl)methyl)-7-((3-methyl-4-phenoxybenzoyl)glycyl)-1,4-dioxa-7-azaspiro[4.4]nonane-8-carboxamide (COMPOUND 64)
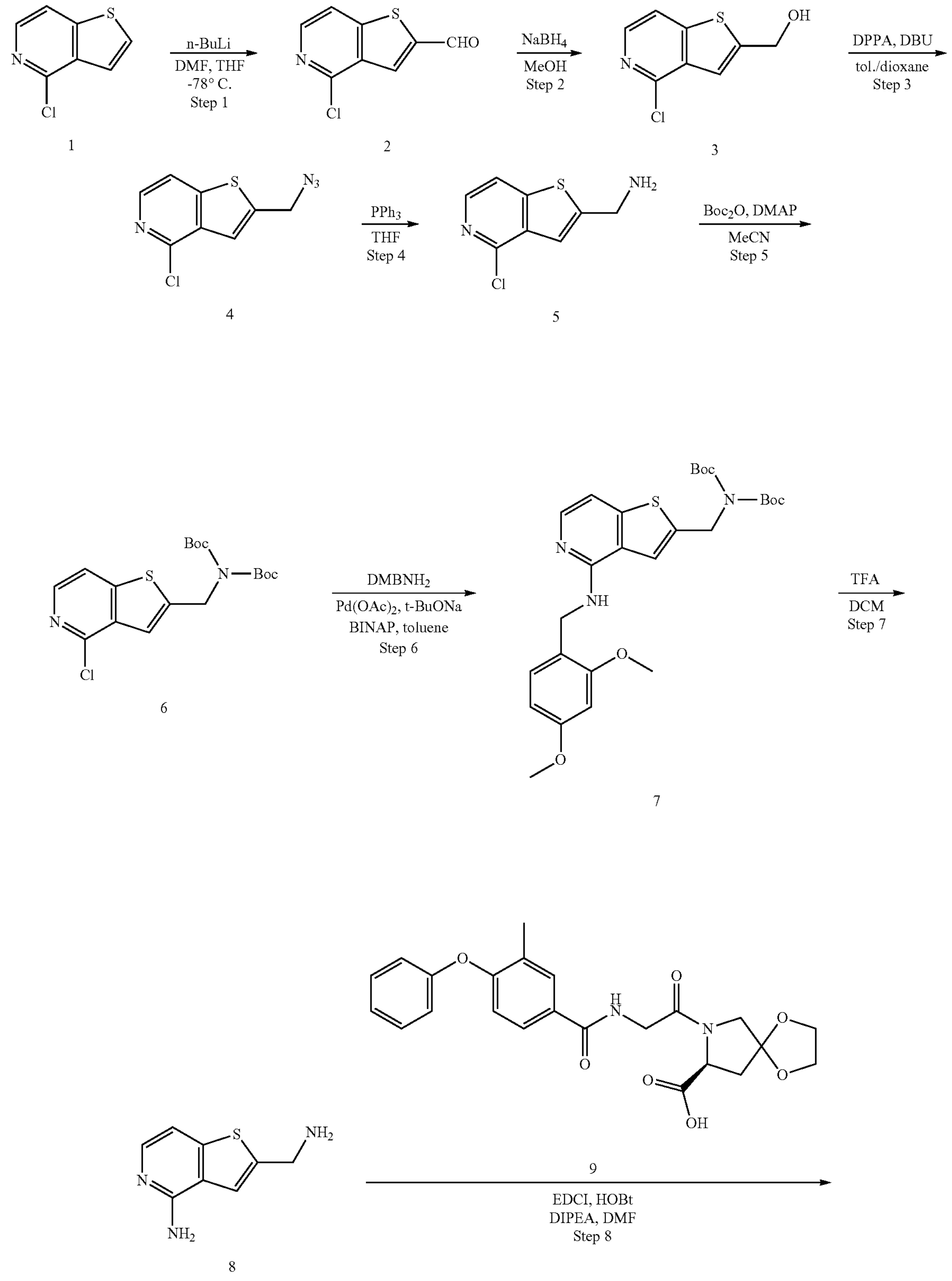

-continued

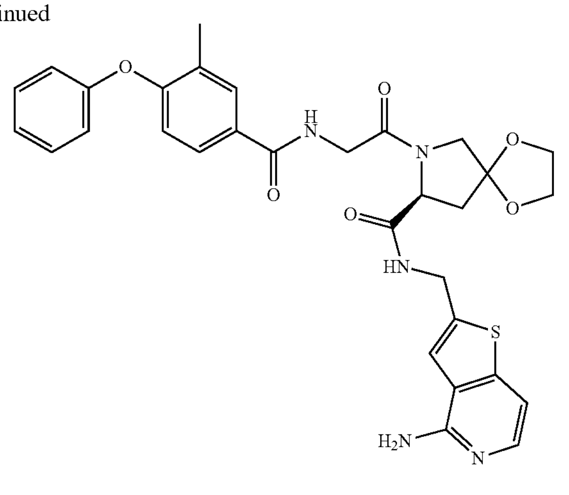

COMPOUND 64

Step 1: a solution of starting material 1 (250 mg, 1.48 mmol) in THF (8 mL) was added n-BuLi (2.78 mL, 4.44 mmol, 1.6 M in hexane) drop-wise at −78° C. and the mixture was stirred at the same temperature for 20 minutes under $N_2$ atmosphere. DMF (531 mg, 7.28 mmol) was added and the mixture was stirred at room temperature for 2 hours. The reaction was quenched with ice water and extracted with EtOAc twice. The combined organic layers were washed with brine, dried over $Na_2SO_4$ and concentrated to dryness. The residue was purified by column chromatography on silica gel (PE:EtOAc=50:1 to 10:1) to give intermediate 2 (260 mg, yield 89.3%) as yellow solid. LC/MS (ESI) m/z: 198 $(M+H)^+$.

Step 2: a solution of intermediate 2 (220 mg, 1.12 mmol) in MeOH (4 mL) was added $NaBH_4$ (63 mg, 1.68 mmol) at 0° C. The reaction was stirred at room temperature for 30 minutes before quenched with ice water and extracted with EtOAc twice. The combined organic layers were washed with brine, dried over $Na_2SO_4$ and concentrated to dryness. The residue was purified by column chromatography on silica gel (PE:EtOAc=50:1 to 5:1) to give intermediate 3 (220 mg, yield 98.7%) as white solid. LC/MS (ESI) m/z: 200 $(M+H)^+$.

Step 3: a solution of intermediate 3 (220 mg, 1.11 mmol) in toluene/dioxane (8 mL, v/v=1/1) was added DPPA (338.69 mg, 1.23 mmol), DBU (187.37 mg, 1.23 mmol) at 0° C. The reaction mixture was stirred at room temperature for 16 hours before washed with saturated aq.$NH_4Cl$ solution and extracted with EtOAc twice. The organic layer was washed with brine, dried over $Na_2SO_4$ and concentrated to dryness to give intermediate 4 (190 mg, yield 76.9%) as yellow solid. LC/MS (ESI) m/z: 225 $(M+H)^+$.

Step 4: a solution of intermediate 4 (190 mg, 0.85 mmol) in THF (5 mL) and water (1 mL) was added $PPh_3$ (445 mg, 1.70 mmol). The mixture was stirred at room temperature for 1 hour under $N_2$ atmosphere before extracted with EtOAc twice. The organic layers were washed with brine, dried over $Na_2SO_4$ and concentrated to dryness. The residue was purified by column chromatography on silica gel (PE: EtOAc=20:1 to 1:1) to give intermediate 5 (150 mg, yield 59.5%) as yellow solid. LC/MS (ESI) m/z: 199 $(M+H)^+$.

Step 5: a solution of intermediate 5 (100 mg, 0.51 mmol) in MeCN (3 mL) was added DMAP (3.0 mg, 0.03 mmol) and $Boc_2O$ (275 mg, 1.26 mmol) at 0° C. The mixture was stirred at room temperature overnight under $N_2$ atmosphere before diluted with water and extracted with EtOAc twice. The organic layer was washed with brine, dried over $Na_2SO_4$ and concentrated to dryness under reduced pressure. The residue was purified by column chromatography on silica gel (PE:EtOAc=100:1 to 10:1) to give intermediate 6 (50 mg, yield 24.9%) as yellow solid. LC/MS (ESI) m/z: 399 $(M+H)^+$.

Step 6: a mixture of intermediate 6 (50 mg, 0.13 mmol), t-BuONa (25 mg, 0.26 mmol) in toluene (3 mL) was added BINAP (16 mg, 0.026 mmol), $Pd(OAc)_2$ (6.0 mg, 0.026 mmol) and (2,4-dimethoxyphenyl)methanamine (33 mg, 0.20 mmol) at 0° C. The mixture was stirred at 80° C. overnight under $N_2$ atmosphere before poured into ice water and extracted with EtOAc twice. The combined organic layers were washed with brine, dried over anhydrous $Na_2SO_4$, filtered and concentrated to dryness. The residue was purified by prep-TLC (PE:EtOAc=8:1) to give intermediate 7 (45 mg, yield 68.2%) as yellow solid. LC/MS (ESI) m/z: 530 $(M+H)^+$.

Step 7: a solution of intermediate 7 (45 mg, 0.09 mmol) in DCM (1.6 mL) was added TFA (0.8 mL) and stirred at room temperature for 1 hour. The mixture was concentrated to dryness to give intermediate 8 (15 mg, yield 98.7%) as pink solid, which was used directly in the next step without further purification. LC/MS (ESI) m/z: 180 $(M+H)^+$.

Step 8: a mixture of intermediate 8 (15 mg, 0.08 mmol) and compound 9 (46 mg, 0.10 mmol) in DMF (3 mL) was added EDCI (28 mg, 0.14 mmol), HOBt (16 mg, 0.017 mmol) followed by DIPEA (41 mg, 0.32 mmol) at 0° C. The mixture was stirred at room temperature overnight before diluted with EtOAc and washed with saturated aq.$NH_4Cl$ solution and brine, dried over anhydrous $Na_2SO_4$, filtered and concentrated to dryness under reduced pressure. The residue was purified by prep-TLC to afford COMPOUND 64 (5.8 mg, yield 12.1%) as white solid. $^1H$-NMR (400 MHz, DMSO-$d_6$) δ 8.60 (dt, J=5.8, 5.8 Hz, 2H), 7.84 (d, J=2.4 Hz, 1H), 7.72-7.66 (m, 2H), 7.58 (d, J=19.2 Hz, 1H), 7.43-7.37 (m, 2H), 7.22-7.01 (m, 4H), 7.00-6.96 (m, 2H), 6.87 (dd, J=8.4, 8.4 Hz, 1H), 4.73-4.35 (m, 3H), 4.19-4.06 (m, 1H), 4.00-3.83 (m, 5H), 3.81-3.59 (m, 2H), 2.36-2.28 (m, 1H), 2.25 (s, 3H), 2.08-1.98 (m, 1H). LC/MS (ESI) m/z: 602 $(M+H)^+$.

Scheme 37: Synthesis of (S)-N-(2-guanidinooxy)ethyl)-7-(2-(4-phenoxybenzamido)acetyl)-1,4-dioxa-7-azaspiro[4.4]nonane-8-carboxamide
(COMPOUND 65)

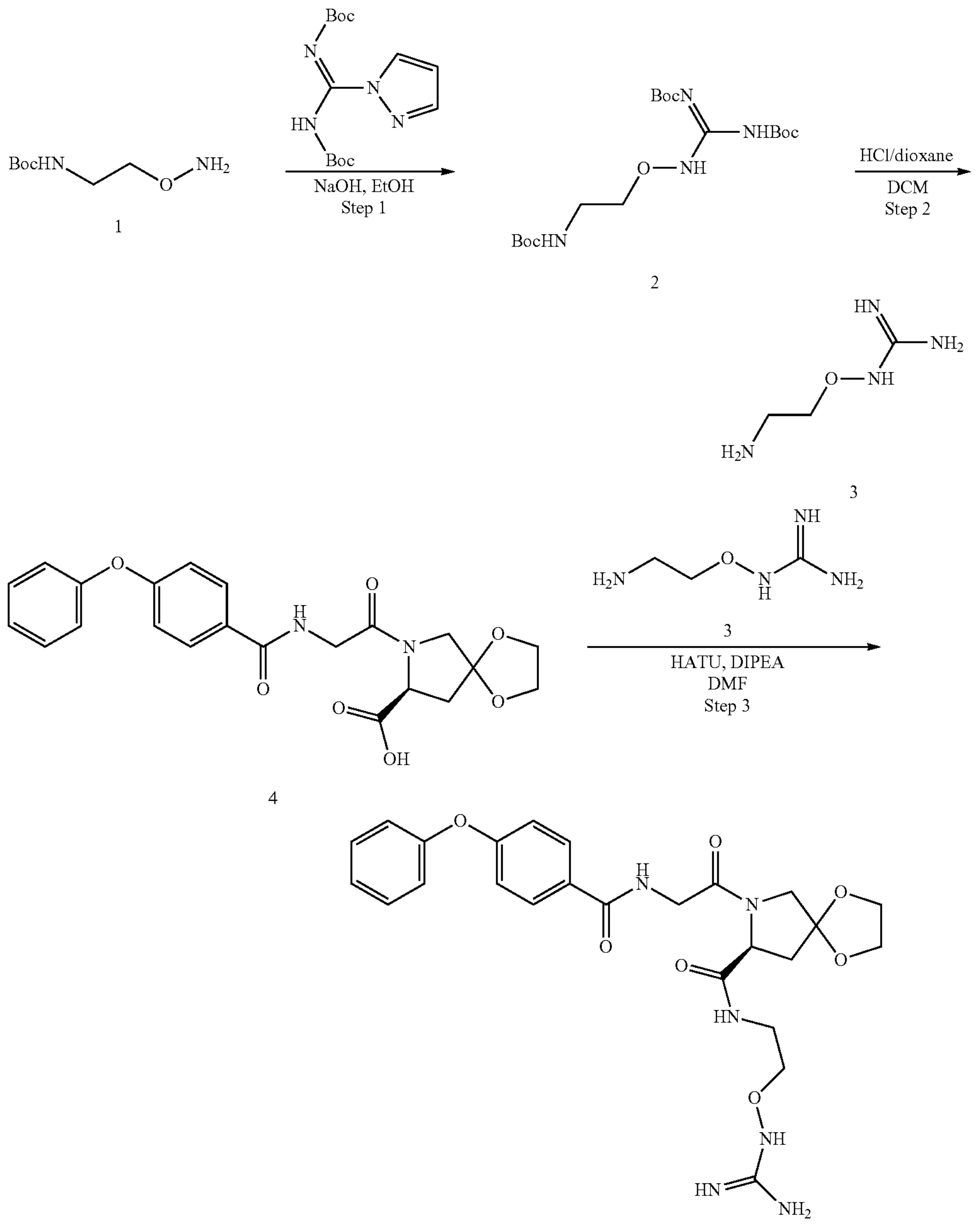

1 2 3 3 4

COMPOUND 65

Step 1: a solution of starting material 1 (200 mg, 1.13 mmol) in EtOH (5 mL) was added (Z)-tert-butyl (((tert-butoxycarbonyl)amino)(1H-pyrazol-1-yl)methylene)carbamate (423 mg, 1.36 mmol) and NaOH (97 mg, 1.13 mmol) at 0° C. The mixture was stirred at 50° C. for 2 hours before diluted with DCM, dried over anhydrous $Na_2SO_4$, filtered and concentrated to dryness under reduced pressure. The residue was purified by chromatography on silica gel (PE:EtOAc=10:1) to give intermediate 2 (200 mg, yield 81.0%) as colorless oil. LC/MS (ESI) (m/z): 419 $(M+H)^+$.

Step 2: a solution of intermediate 2 (200 mg, 0.16 mmol) in HCl/1,4-dioxane (5 mL, 26.13 mmol) was stirred at 0° C. and then warmed to 25° C. within 2 hours. The mixture was concentrated to dryness under reduced pressure and the residue was washed with diethyl ether and dried under vacuum to give compound 3 (110 mg, yield 71%) as white solid, which was directly used in the next step without further purification. LC/MS (ESI) (m/z): 118 $(M+H)^+$.

Step 3: a mixture of compound 3 (14 mg, 0.084 mmol) and 1-(3-acetyl-7-methyl-5-(2-methylpyrimidin-5-yl)-1H-indol-1-yl)propan-2-one (30 mg, 0.07 mmol) in DMF (3 mL) was added DIPEA (0.05 mL, 0.28 mmol), and HATU (44 mg, 0.14 mmol) at 0° C. The mixture was stirred at room temperature under $N_2$ atmosphere for 12 hours before diluted with EtOAc and washed with saturated aq.$NH_4Cl$ solution and brine, dried over anhydrous $Na_2SO_4$, filtered and concentrated to dryness under reduced pressure. The residue was purified by prep-HPLC to afford COMPOUND 65 (3 mg, yield 21.3%) as white solid. $^1$H-NMR (400 MHz, $CDCl_3$) δ 9.62 (s, 1H), 9.19 (s, 1H), 8.73-8.66 (m, 2H), 8.62 (s, 1H), 8.49 (d, J=1.5 Hz, 1H), 7.63 (s, 1H), 7.11 (s, 1H), 6.44 (s, 1H), 5.33 (d, J=7.4 Hz, 2H), 5.23 (s, 4H), 4.69 (dd, J=8.8, 3.6 Hz, 1H), 3.05 (d, J=3.1 Hz, 1H), 2.26 (dd, J=13.5, 8.9 Hz, 1H), 1.38 (s, 4H), 1.14 (d, J=5.2 Hz, 2H), 0.82 (d, J=10.0 Hz, 2H), 0.82 (d, J=10.0 Hz, 2H). LC/MS (ESI) m/z: 527 $(M+H)^+$.

Scheme 38: Synthesis of (S,Z)-N-((4-(N'-hydroxycarbamimidoyl) thiophen-2-yl)methyl)-7-(2-(4-phenoxybenzamido)acetyl)1,4-dioxa-7-azaspiro[4.4]nonane-8-carboxamide (COMOUND 66)

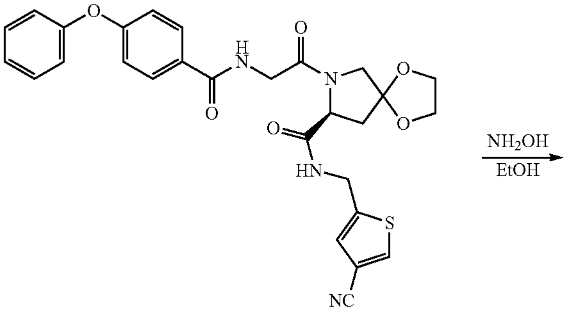

1

-continued

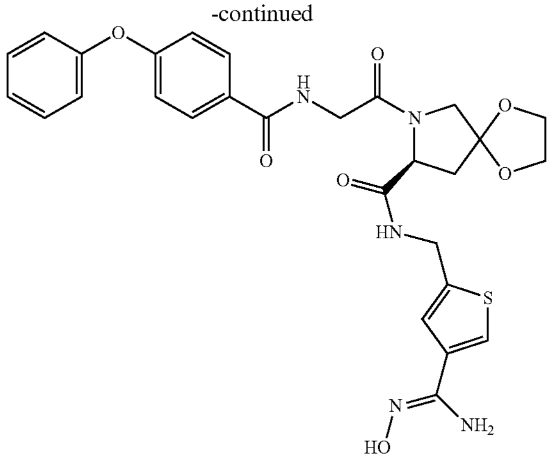

COMPOUND 66

A solution of starting material 1 (15 mg, 0.151 mmol) in EtOH (5 mL) and $NH_2OH$ (1 mL) was stirred at room temperature for 1 hour before filtered and concentrated to dryness under reduced pressure. The residue was purified by prep-HPLC to afford COMPOUND 66 (2 mg, yield 21.9%) as white solid. $^1$H NMR (400 MHz, DMSO) δ 8.58 (dd, J=18.1, 12.4 Hz, 2H), 7.87 (t, J=20.2 Hz, 3H), 7.44 (t, J=7.9 Hz, 2H), 7.22 (dd, J=13.1, 5.6 Hz, 2H), 7.09 (d, J=7.8 Hz, 2H), 7.04 (d, J=8.7 Hz, 2H), 4.42 (dt, J=13.9, 6.8 Hz, 3H), 4.14 (d, J=5.4 Hz, 1H), 3.93 (dt, J=20.8, 10.6 Hz, 5H), 3.78 (d, J=10.7 Hz, 1H), 3.63 (t, J=13.6 Hz, 1H), 2.30 (dd, J=12.8, 8.9 Hz, 1H), 2.02 (dd, J=13.0, 6.8 Hz, 1H), 1.24 (s, 2H). LC/MS (ESI) m/z: 580 $(M+H)^+$.

Scheme 39: Synthesis of Compound 67 - Compound 86.

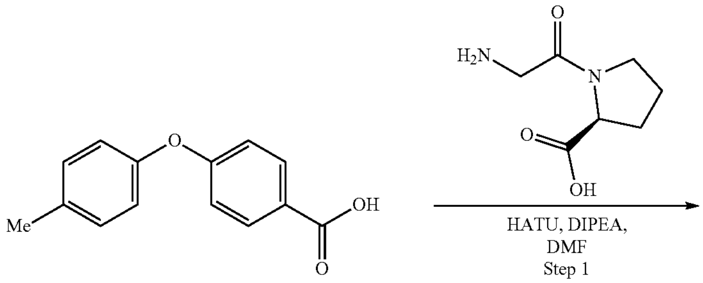

1

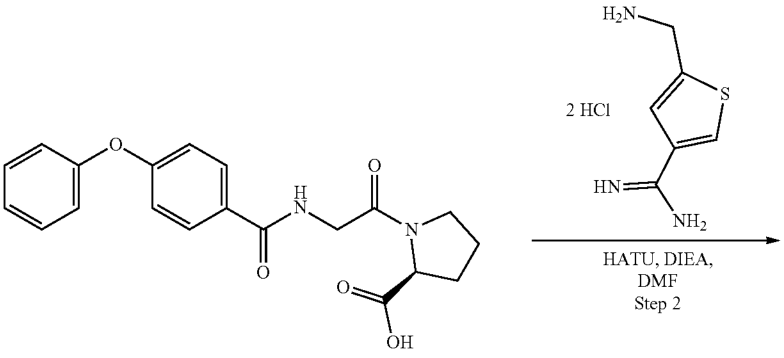

2

-continued

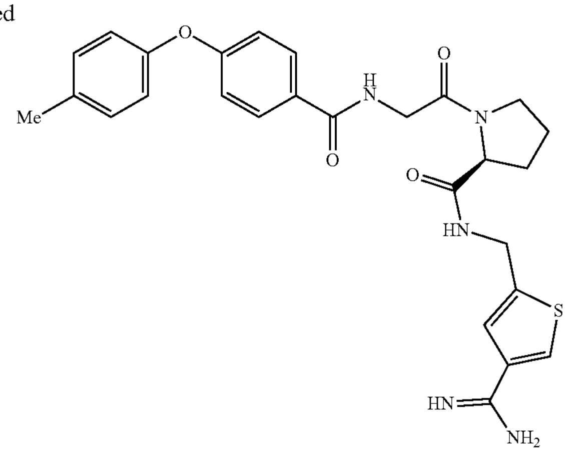

Step 1: 1-[Bis(dimethylamino)methylene]-1H-1,2,3-triazolo[4,5-b]pyridinium 3-oxid hexafluorophosphate (1 equiv.) was added to a stirring solution of compound 1 (1 equiv.) in dimethyl-formamide (0.1M) at RT. Next, diisopropylethylamine (3 equiv.) was added. The mixture was stirred at RT for 60 min. Then glycylproline (1 equiv.) was added in a single portion. This mixture was stirred at RT for an additional 1 h.

Step 2: the mixture of the coupled Gly-Pro peptide in DMF was added to 1-[Bis(dimethylamino)methylene]-1H-1,2,3-triazolo[4,5-b]pyridinium 3-oxid hexafluorophosphate (1 equiv.) and 5-(aminomethyl)thiophene-3-carboximidamide hydrochloride (1 equiv.) in a single combined portion followed by the addition of 1 mL DMF. The mixture was allowed to stir at RT for 0.5 h. LCMS shows conversion to the desired final product. The mixture was directly purified via reverse phase-HPLC to give the desired final compound usually as a white or colorless solid.

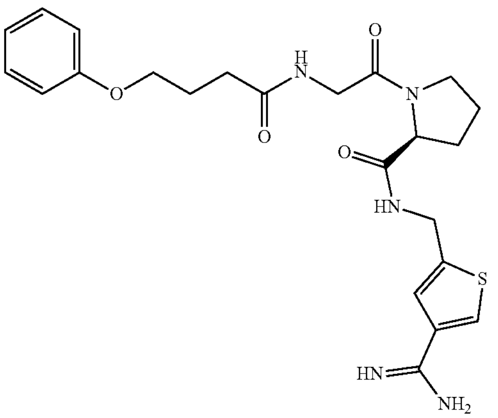 [SMILES: N=C(N)c1csc(CNC(=O)[C@@H]2CCCN2C(=O)CNC(=O)CCCOc2ccccc2)c1]

(2S)—N-[(4-carbamimidoylthiophen-2-yl)methyl]-1-[2-(4-phenoxybutanamido)acetyl]pyrrolidine-2-carboxamide (COMPOUND 67): (2S)—N-[(4-carbamimidoylthiophen-2-yl)methyl]-1-[2-(4-phenoxybutanamido)acetyl]pyrrolidine-2-carboxamide was prepared according to Scheme 39 with the use of 4-phenoxy-butyric acid. $^{1}H$ NMR (400 MHz, Methanol-$d_4$) δ 8.54 (s, 1H), 8.24 (br s, 1H), 7.49 (s, 0H), 7.46-7.40 (m, 1H), 7.26 (t, J=7.9 Hz, 2H), 6.96-6.85 (m, 3H), 4.63-4.42 (m, 1H) 4.57 (s, 2H), 4.13-3.88 (m, 3H), 3.82-3.64 (m, 1H), 3.61 (dt, J=15.2, 6.0 Hz, 1H), 2.47 (dt, J=10.5, 7.4 Hz, 2H), 2.22 (tt, J=9.0, 4.1 Hz, 1H), 2.07 (dq, J=22.1, 6.1, 5.5 Hz, 4H).

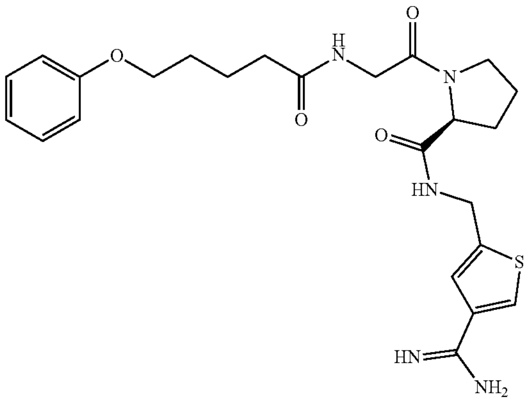

(2S)—N-[(4-carbamimidoylthiophen-2-yl)methyl]-1-[2-(5-phenoxypentanamido)acetyl]pyrrolidine-2-carboxamide (COMPOUND 68): (2S)—N-[(4-carbamimidoylthiophen-2-yl)methyl]-1-[2-(5-phenoxypentanamido)acetyl]pyrrolidine-2-carboxamide was prepared according to Scheme 39 with the use of 5-phenoxypentanoic acid. $^{1}H$ NMR (400 MHz, Methanol-$d_4$) δ 8.53 (s, 1H), 8.25 (dd, J=5.1, 1.7 Hz, 1H), 7.51-7.41 (m, 1H), 7.26 (dd, J=8.7, 7.2 Hz, 2H), 6.94-6.87 (m, 3H), 4.62-4.55 (m, 4H), 4.14-3.89 (m, 4H), 3.81-3.64 (m, 1H), 3.67-3.55 (m, 1H), 2.36 (qd, J=9.1, 8.0, 4.8 Hz, 2H), 2.22 (tt, J=9.2, 4.3 Hz, 1H), 2.11-1.96 (m, 2H), 1.82 (h, J=2.7 Hz, 4H).

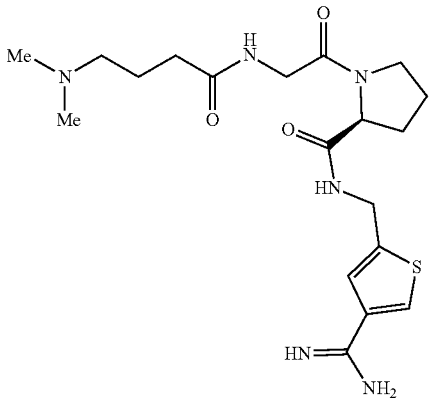 [SMILES: CN(C)CCCC(=O)NCC(=O)N1CCC[C@H]1C(=O)NCc1cc(C(=N)N)cs1]

(2S)—N-[(4-carbamimidoylthiophen-2-yl)methyl]-1-{2-[4-(dimethylamino)butanamido]acetyl}pyrrolidine-2-carboxamide (COMPOUND 69): (2S)—N-[(4-carbamimidoylthiophen-2-yl)methyl]-1-{2-[4-(dimethylamino)butanamido]acetyl}pyrrolidine-2-carboxamide was prepared according to Scheme 39 with the use of 4-(dimethylamino)butanoic acid. $^1$H NMR (400 MHz, Methanol-$d_4$) δ 8.27 (d, J=1.5 Hz, 1H), 7.45 (s, 1H), 4.70-4.43 (m, 3H), 4.16-4.01 (m, 2H), 3.71-3.55 (m, 3H), 3.14 (d, J=8.0 Hz, 2H), 2.88-2.82 (m, 7H), 2.46 (t, J=6.9 Hz, 2H), 2.24 (t, J=9.9 Hz, 2H), 2.04 (dd, J=14.7, 7.7 Hz, 2H).

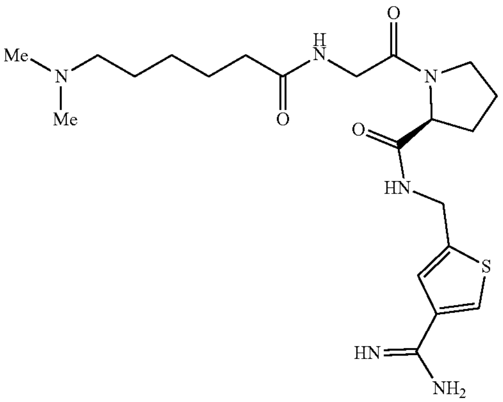

(2S)—N-[(4-carbamimidoylthiophen-2-yl)methyl]-1-{2-[6-(dimethylamino)hexanamido]acetyl}pyrrolidine-2-carboxamide (COMPOUND 71): (2S)—N-[(4-carbamimidoylthiophen-2-yl)methyl]-1-{2-[6-(dimethylamino)hexanamido]acetyl}pyrrolidine-2-carboxamide was prepared according to Scheme 39 with the use of 4-(dimethylamino)hexaanoic acid. $^1$H NMR (400 MHz, Methanol-$d_4$) δ 8.27 (t, J=2.3 Hz, 1H), 7.47 (d, J=15.7 Hz, 1H), 4.58 (s, 2H), 4.55-4.42 (m, 1H), 4.06 (s, 1H), 3.82-3.55 (m, 4H), 3.25 (q, J=7.4 Hz, 2H), 3.06-2.97 (m, 2H), 2.80 (d, J=5.5 Hz, 6H), 2.37-2.17 (m, 2H), 2.03 (td, J=13.2, 6.0 Hz, 2H), 1.69 (dd, J=15.5, 7.8 Hz, 5H).

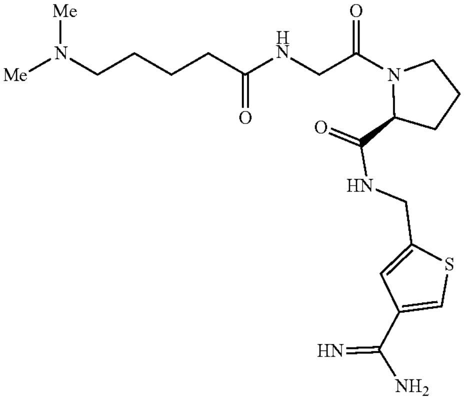 [SMILES: CN(C)CCCCC(=O)NCC(=O)N1CCC[C@H]1C(=O)NCc1cc(C(=N)N)cs1]

(2S)—N-[(4-carbamimidoylthiophen-2-yl)methyl]-1-{2-[5-(dimethylamino)pentanamido]acetyl}pyrrolidine-2-carboxamide (COMPOUND 70): (2S)—N-[(4-carbamimidoylthiophen-2-yl)methyl]-1-{2-[5-(dimethylamino)pentanamido]acetyl}pyrrolidine-2-carboxamide was prepared according to Scheme 39 with the use of 4-(dimethylamino)pentanoic acid. $^1$H NMR (400 MHz, Methanol-$d_4$) δ 8.27 (t, J=2.3 Hz, 1H), 7.44 (d, J=15.7 Hz, 1H), 4.58 (s, 2H), 4.56-4.41 (m, 1H), 4.08 (s, 1H), 3.82-3.55 (m, 4H), 3.25 (q, J=7.4 Hz, 2H), 3.06-2.99 (m, 2H), 2.95-2.73 (m, 6H), 2.37-2.17 (m, 2H), 2.05-2.00 (m, 2H), 1.74-1.68 (m, 3H).

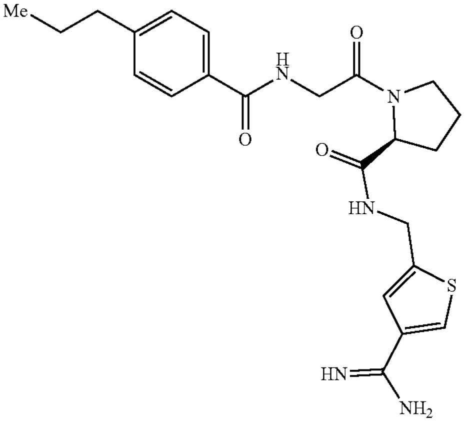 [SMILES: CCCc1ccc(C(=O)NCC(=O)N2CCC[C@H]2C(=O)NCc2cc(C(=N)N)cs2)cc1]

(2S)—N-[(4-carbamimidoylthiophen-2-yl)methyl]-1-{2-[(4-propylphenyl)formamido]acetyl}pyrrolidine-2-carboxamide (COMPOUND 72): (2S)—N-[(4-carbamimidoylthiophen-2-yl)methyl]-1-{2-[(4-propylphenyl)formamido]acetyl}pyrrolidine-2-carboxamide was prepared according to Scheme 39 with the use of 4-propylbenzoic acid. $^1$H NMR (400 MHz, Methanol-$d_4$) δ 8.54 (s, 1H), 8.29-8.17 (m, 1H), 7.83-7.74 (m, 2H), 7.54-7.38 (m, 1H), 7.31 (dd, J=7.7, 5.3 Hz, 2H), 4.69-4.43 (m, 3H), 4.31-3.88 (m, 2H), 3.85-3.54 (m, 2H), 2.67 (t, J=7.6 Hz, 2H), 2.32-2.17 (m, 1H), 2.06 (td, J=14.1, 13.5, 6.4 Hz, 2H), 1.99-1.89 (m, 0.05H), 1.68 (dt, J=14.7, 7.5 Hz, 2H), 1.25-1.15 (m, 0.5H), 0.97 (td, J=7.4, 2.4 Hz, 3H).

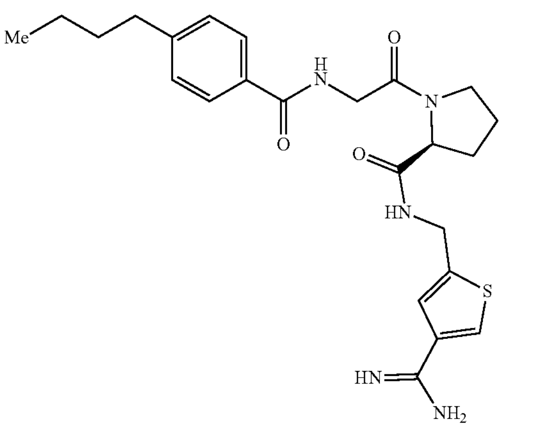 [SMILES: CCCCc1ccc(C(=O)NCC(=O)N2CCC[C@H]2C(=O)NCc2cc(C(=N)N)cs2)cc1]

(2S)-1-{2-[(4-butylphenyl)formamido]acetyl}-N-[(4-carbamimidoylthiophen-2-yl)methyl]pyrrolidine-2-carboxamide (COMPOUND 73): (2S)-1-{2-[(4-butylphenyl)formamido]acetyl}-N-[(4-carbamimidoylthiophen-2-yl)methyl] pyrrolidine-2-carboxamide was prepared according to Scheme 39 with the use of 4-butylbenzoic acid. $^1$H NMR (400 MHz, Methanol-$d_4$) δ 8.55 (s, 1H), 8.29-8.17 (m, 1H), 7.78 (dd, J=8.7, 2.4 Hz, 2H), 7.54-7.38 (m, 1H), 7.31 (dd, J=7.7, 5.1 Hz, 2H), 4.70-4.40 (m, 3H), 4.26 (d, J=16.7 Hz, 1H), 4.24-3.95 (m, 1H), 3.85-3.69 (m, 1H), 3.73-3.56 (m, 1H), 2.70 (t, J=7.7 Hz, 2H), 2.31-2.17 (m, 1H), 2.06 (td, J=13.3, 6.3 Hz, 2H), 2.00-1.87 (m, 0.5H), 1.64 (tt, J=7.9, 6.4 Hz, 2H), 1.41 (d, J=7.6 Hz, 1H), 1.41-1.29 (m, 1H), 1.25-1.15 (m, 0.5H), 0.96 (td, J=7.4, 1.7 Hz, 3H).

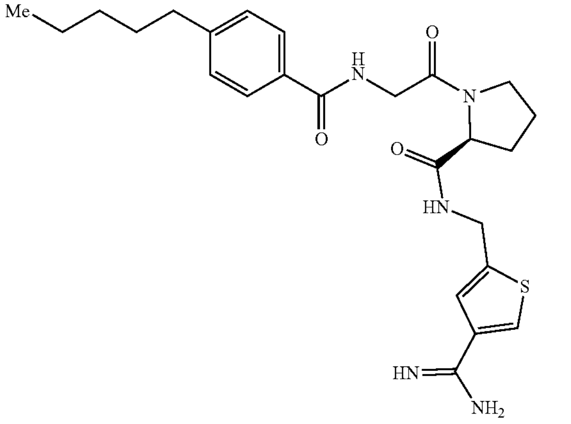

(2S)—N-[(4-carbamimidoylthiophen-2-yl)methyl]-1-{2-[(4-pentylphenyl)formamido]acetyl}pyrrolidine-2-carboxamide (COMPOUND 74): (2S)—N-[(4-carbamimidoylthiophen-2-yl)methyl]-1-{2-[(4-pentylphenyl)formamido] acetyl}pyrrolidine-2-carboxamide was prepared according to Scheme 39 with the use of 4-pentylbenzoic acid. $^1$H NMR (400 MHz, Methanol-$d_4$) δ 8.54 (s, 1H), 8.29-8.17 (m, 1H), 7.78 (dd, J=8.4, 2.2 Hz, 2H), 7.54-7.38 (m, 1H), 7.31 (dd, J=7.6, 5.2 Hz, 2H), 4.67-4.43 (m, 3H), 4.31-3.88 (m, 2H), 3.85-3.54 (m, 2H), 2.69 (t, J=7.7 Hz, 2H), 2.31-2.15 (m, 1H), 2.15-2.00 (m, 2H), 1.94 (dt, J=10.4, 7.6 Hz, 0.5H), 1.67 (p, J=7.5 Hz, 2H), 1.46-1.29 (m, 4H), 1.20 (dd, J=13.6, 7.0 Hz, 0.5H), 1.05-0.88 (m, 3H).

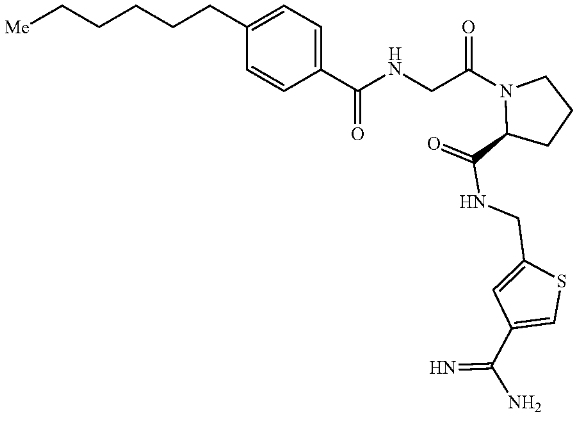 [SMILES: CCCCCCc1ccc(C(=O)NCC(=O)N2CCC[C@H]2C(=O)NCc2cc(C(=N)N)cs2)cc1]

(2S)—N-[(4-carbamimidoylthiophen-2-yl)methyl]-1-{2-[(4-hexylphenyl)formamido]acetyl}pyrrolidine-2-carboxamide (COMPOUND 75): (2S)—N-[(4-carbamimidoylthiophen-2-yl)methyl]-1-{2-[(4-hexylphenyl)formamido] acetyl}pyrrolidine-2-carboxamide was prepared according to Scheme 39 with the use of 4-hexylbenzoic acid. $^1$H NMR (400 MHz, Methanol-$d_4$) δ 8.50 (s, 1H), 8.24 (dd, J=18.3, 1.5 Hz, 1H), 7.78 (dd, J=8.3, 2.0 Hz, 2H), 7.54-7.40 (m, 1H), 7.30 (dd, J=7.7, 4.9 Hz, 2H), 4.65-4.47 (m, 3H), 4.29-3.90. (m, 2H), 3.85-3.56 (m, 2H), 2.69 (t, J=7.7 Hz, 2H), 2.31-2.17 (m, 1H), 2.15-2.00 (m, 2H), 1.98-1.91 (m, 0.5H), 1.66 (p, J=7.3 Hz, 2H), 1.43-1.29 (m, 6H), 1.20 (dd, J=13.5, 7.0 Hz, 0.5H), 1.01-0.87 (m, 3H).

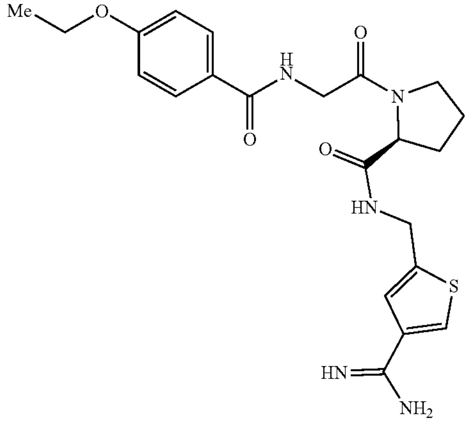 [SMILES: CCOc1ccc(C(=O)NCC(=O)N2CCC[C@H]2C(=O)NCc2cc(C(=N)N)cs2)cc1]

(2S)—N-[(4-carbamimidoylthiophen-2-yl)methyl]-1-{2-[(4-ethoxyphenyl)formamido]acetyl}pyrrolidine-2-carboxamide (COMPOUND 76): (2S)—N-[(4-carbamimidoylthiophen-2-yl)methyl]-1-{2-[(4-ethoxyphenyl)formamido] acetyl}pyrrolidine-2-carboxamide was prepared according to Scheme 39 with the use of p-ethoxybenzoic acid. $^1$H NMR (400 MHz, Methanol-$d_4$) δ 8.57 (s, 1H), 8.29-8.19 (m, 1H), 7.82 (dd, J=9.0, 2.8 Hz, 2H), 7.51-7.42 (m, 1H), 7.03-6.93 (m, 2H), 4.62 (dd, J=18.8, 4.1 Hz, 2H), 4.57-4.47 (m, 1H), 4.25 (d, J=16.7 Hz, 1H), 4.21-4.05 (m, 3H), 3.86-3.54 (m, 2H), 2.26 (tt, J=10.3, 5.1 Hz, 0.65H), 2.14-1.99 (m, 2H), 1.97-1.91 (m, 0.35H), 1.47-1.34 (m, 4H).

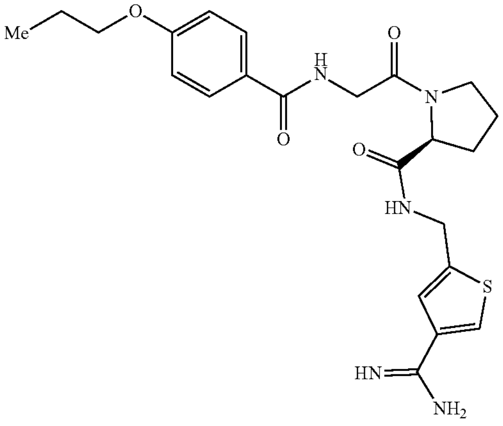 [SMILES: CCCOc1ccc(C(=O)NCC(=O)N2CCC[C@H]2C(=O)NCc2cc(C(=N)N)cs2)cc1]

(2S)—N-[(4-carbamimidoylthiophen-2-yl)methyl]-1-{2-[(4-propoxyphenyl)formamido]acetyl}pyrrolidine-2-carboxamide (COMPOUND 77): (2S)—N-[(4-carbamimidoylthiophen-2-yl)methyl]-1-{2-[(4-propoxyphenyl)formamido]acetyl}pyrrolidine-2-carboxamide was prepared according to Scheme 39 with the use of p-propoxybenzoic acid. $^1$H NMR (400 MHz, Methanol-$d_4$) δ 8.55 (s, 1H), 8.30-8.16 (m, 1H), 7.82 (dd, J=9.1, 2.6 Hz, 2H), 7.54-7.39 (m, 1H), 7.43 (s, 1H), 7.03-6.94 (m, 2H), 4.62 (dd, J=18.9, 3.7 Hz, 2H), 4.59-4.47 (m, 1H), 4.32-4.06 (m, 1H), 4.02 (t, J=6.4 Hz, 2H), 3.80 (dt, J=9.6, 5.9 Hz, 1H), 3.76-3.55 (m, 1H), 2.26 (tt, J=10.3, 5.1 Hz, 0.7H), 2.14-1.99 (m, 2H), 1.94 (d, J=7.9 Hz, 0.3H), 1.84 (h, J=7.1 Hz, 2H), 1.07 (t, J=7.4 Hz, 3H).

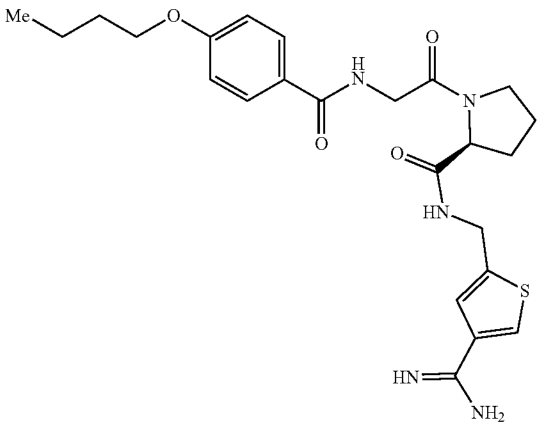 [SMILES: CCCCOc1ccc(C(=O)NCC(=O)N2CCC[C@H]2C(=O)NCc2cc(C(=N)N)cs2)cc1]

(2S)-1-{2-[(4-butoxyphenyl)formamido]acetyl}-N-[(4-carbamimidoylthiophen-2-yl)methyl]pyrrolidine-2-carboxamide (COMPOUND 78): (2S)-1-{2-[(4-butoxyphenyl)formamido]acetyl}-N-[(4-carbamimidoylthiophen-2-yl)methyl]pyrrolidine-2-carboxamide was prepared according to Scheme 39 with the use of p-butoxybenzoic acid. $^1$H NMR (400 MHz, Methanol-$d_4$) δ 8.53 (s, 1H), 8.30-8.18 (m, 1H), 7.82 (dd, J=9.0, 2.7 Hz, 2H), 7.54-7.40 (m, 1H), 7.03-6.93 (m, 2H), 4.61 (dd, J=19.0, 3.8 Hz, 2H), 4.52 (td, J=9.6, 8.3, 4.7 Hz, 1H), 4.25 (d, J=16.7 Hz, 1H), 4.28-4.11 (m, 1H), 4.06 (t, J=6.4 Hz, 2H), 3.80 (dt, J=9.7, 5.9 Hz, 1H), 3.76-3.58 (m, 1H), 2.26 (tt, J=10.2, 5.1 Hz, 0.6H), 2.06 (dq, J=13.0, 6.5 Hz, 2H), 1.93 (s, 0.4H), 1.80 (dq, J=8.3, 6.5 Hz, 2H), 1.54 (h, J=7.4 Hz, 2H), 1.01 (t, J=7.4 Hz, 3H).

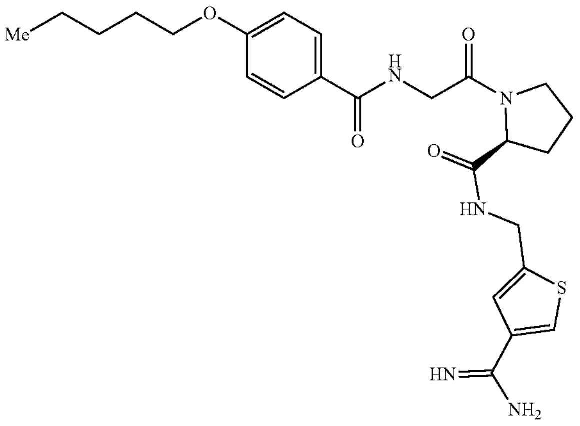 [SMILES: CCCCCOc1ccc(C(=O)NCC(=O)N2CCC[C@H]2C(=O)NCc2cc(C(=N)N)cs2)cc1]

(2S)—N-[(4-carbamimidoylthiophen-2-yl)methyl]-1-(2-{4-(pentyloxy)phenyl]formamido}acetyl)pyrrolidine-2-carboxamide (COMPOUND 79): (2S)—N-[(4-carbamimidoylthiophen-2-yl)methyl]-1-(2-{[4-(pentyloxy)phenyl]formamido}acetyl)pyrrolidine-2-carboxamide was prepared according to Scheme 39 with the use of 4-(pentoxy)benzoic acid. $^1$H NMR (400 MHz, Methanol-$d_4$) δ 8.54 (s, 1H), 8.29-8.17 (m, 1H), 7.82 (dd, J=9.1, 2.7 Hz, 2H), 7.43 (s, 1H), 7.03-6.93 (m, 2H), 4.66-4.48 (m, 2H), 4.29-4.14 (m, 1H), 4.06 (q, J=6.8 Hz, 2H), 3.80 (dt, J=9.4, 5.8 Hz, 1H), 3.76-3.58 (m, 1H), 2.31-2.17 (m, 0.7H), 2.06 (dq, J=11.5, 5.7, 4.6 Hz, 3H), 1.95 (s, 0.3H), 1.88-1.76 (m, 2H), 1.55-1.36 (m, 4H), 0.97 (t, J=7.0 Hz, 3H).

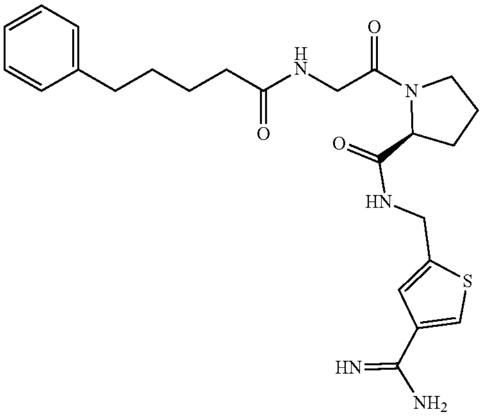 [SMILES: N=C(N)c1csc(CNC(=O)[C@@H]2CCCN2C(=O)CNC(=O)CCCCc2ccccc2)c1]

(2S)—N-[(4-carbamimidoylthiophen-2-yl)methyl]-1-[2-(5-phenylpentanamido)acetyl]pyrrolidine-2-carboxamide (COMPOUND 80): (2S)—N-[(4-carbamimidoylthiophen-2-yl)methyl]-1-[2-(5-phenylpentanamido)acetyl]pyrrolidine-2-carboxamide was prepared according to Scheme 39 with the use of 5-phenylvaleric acid. $^1$H NMR (400 MHz, Methanol-$d_4$) δ 8.40 (s, 1H), 8.24 (d, J=1.5 Hz, 1H), 7.51-7.40 (m, 1H), 7.25 (t, J=7.5 Hz, 2H), 7.16 (dd, J=17.0, 7.7 Hz, 3H), 4.2-4.42 (m, 3H), 4.12-3.87 (m, 2H), 3.80-3.57 (m, 2H), 2.64 (t, J=4.4 Hz, 2H), 2.35-2.14 (m, 3H), 2.04 (h, J=6.4, 5.8 Hz, 3H), 1.67 (p, J=3.6 Hz, 4H).

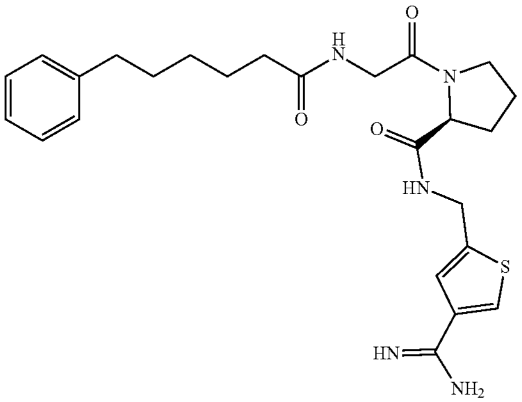 [SMILES: N=C(N)c1csc(CNC(=O)[C@@H]2CCCN2C(=O)CNC(=O)CCCCCc2ccccc2)c1]

(2S)—N-[(4-carbamimidoylthiophen-2-yl)methyl]-1-[2-(6-phenylhexanamido)acetyl]pyrrolidine-2-carboxamide (COMPOUND 81): (2S)—N-[(4-carbamimidoylthiophen-2-yl)methyl]-1-[2-(6-phenylhexanamido)acetyl]pyrrolidine-2-carboxamide was prepared according to Scheme 39 with the use of 6-phenylcaproic acid. $^{1}$H NMR (400 MHz, Methanol-$d_4$) δ 8.55 (s, 1H), 8.25 (d, J=1.5 Hz, 1H), 7.52-7.40 (m, 1H), 7.25 (t, J=7.5 Hz, 2H), 7.21-7.11 (m, 3H), 4.66-4.53 (m, 2H), 4.49 (ddd, J=20.0, 8.3, 2.8 Hz, 1H), 4.12-3.85 (m, 2H), 3.79-3.64 (m, 1H), 3.62 (dt, J=9.2, 6.4 Hz, 1H), 2.62 (t, J=7.7 Hz, 2H), 2.32-2.14 (m, 3H), 2.11-1.96 (m, 2H), 1.96-1.85 (m, 1H), 1.74-1.59 (m, 4H), 1.45-1.29 (m, 2H).

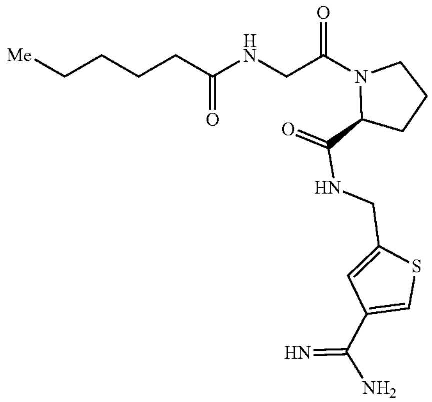 [SMILES: CCCCCC(=O)NCC(=O)N1CCC[C@H]1C(=O)NCc1cc(C(=N)N)cs1]

(2S)—N-[(4-carbamimidoylthiophen-2-yl)methyl]-1-(2-hexanamidoacetyl)pyrrolidine-2-carboxamide (COMPOUND 82): (2S)—N-[(4-carbamimidoylthiophen-2-yl)methyl]-1-(2-hexanamidoacetyl)pyrrolidine-2-carboxamide was prepared according to Scheme 39 with the use of hexanoic acid. $^{1}$H NMR (400 MHz, Methanol-$d_4$) δ 8.55 (s, 1H), 8.26 (dd, J=3.8, 1.6 Hz, 1H), 7.52-7.41 (m, 1H), 4.66-4.54 (m, 2H), 4.56-4.43 (m, 1H), 4.12-3.85 (m, 2H), 3.80-3.54 (m, 2H), 2.34-2.17 (m, 2.7H), 2.11-1.96 (m, 2H), 1.97-1.86 (m, 0.3H), 1.63 (p, J=7.4 Hz, 2H), 1.40-1.28 (m, 5H), 1.05-0.88 (m, 4H).

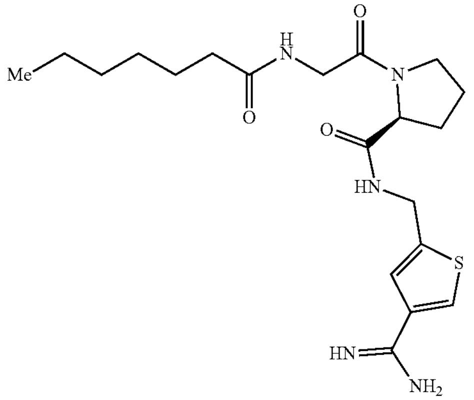 [SMILES: CCCCCCC(=O)NCC(=O)N1CCC[C@H]1C(=O)NCc1cc(C(=N)N)cs1]

(2S)—N-[(4-carbamimidoylthiophen-2-yl)methyl]-1-(2-heptanamidoacetyl)pyrrolidine-2-carboxamide (COMPOUND 83): (2S)—N-[(4-carbamimidoylthiophen-2-yl)methyl]-1-(2-heptanamidoacetyl)pyrrolidine-2-carboxamide was prepared according to Scheme 39 with the use of heptanoic acid. $^{1}$H NMR (400 MHz, Methanol-$d_4$) δ 8.58 (s, 1H), 8.29-8.24 (m, 1H), 7.52-7.41 (m, 1H), 4.68-4.52 (m, 2H), 4.50 (ddd, J=20.6, 8.2, 2.6 Hz, 1H), 4.12-4.03 (m, 1H), 4.03-3.85 (m, 1H), 3.80-3.52 (m, 2H), 2.36-2.15 (m, 2.7H), 2.11-1.96 (m, 2H), 1.98-1.87 (m, 0.3H), 1.62 (p, J=7.4 Hz, 2H), 1.44-1.29 (m, 6H), 1.05-0.88 (m, 4H).

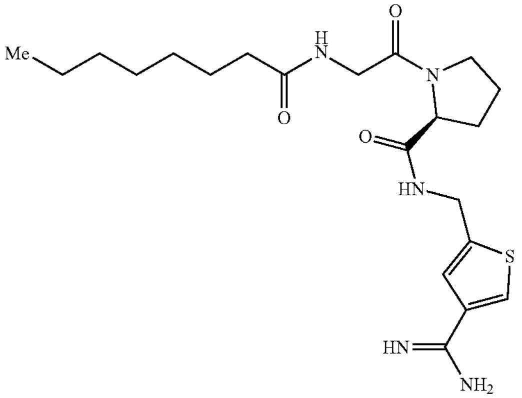 [SMILES: CCCCCCCC(=O)NCC(=O)N1CCC[C@H]1C(=O)NCc1cc(C(=N)N)cs1]

(2S)—N-[(4-carbamimidoylthiophen-2-yl)methyl]-1-(2-octanamidoacetyl)pyrrolidine-2-carboxamide (COMPOUND 84): (2S)—N-[(4-carbamimidoylthiophen-2-yl)methyl]-1-(2-octanamidoacetyl)pyrrolidine-2-carboxamide was prepared according to Scheme 39 with the use of caprylic acid. $^{1}$H NMR (400 MHz, Methanol-$d_4$) δ 8.57 (s, 1H), 8.26 (d, J=1.7 Hz, 1H), 7.52-7.42 (m, 1H), 4.64-4.44 (m, 2H), 4.50 (ddd, J=21.1, 8.2, 2.7 Hz, 1H), 4.11-3.90 (m, 2H), 3.80-3.54 (m, 3H), 2.34-2.12 (m, 2.7H), 2.11-1.96 (m, 3H), 1.93 (dd, J=12.2, 6.7 Hz, 0.3H), 1.63 (p, J=7.3 Hz, 2H), 1.39-1.28 (m, 8H), 1.01-0.88 (m, 4H).

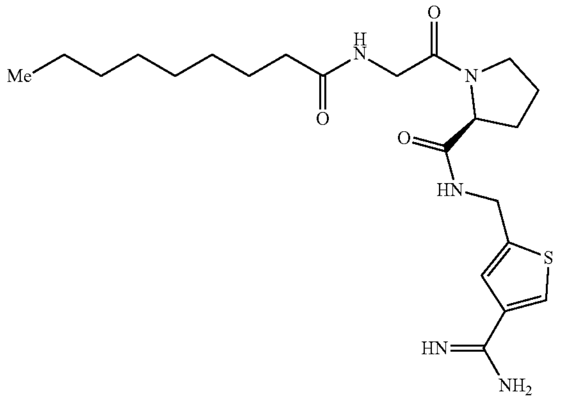 [SMILES: CCCCCCCCC(=O)NCC(=O)N1CCC[C@H]1C(=O)NCc1cc(C(=N)N)cs1]

(2S)—N-[(4-carbamimidoylthiophen-2-yl)methyl]-1-(2-nonanamidoacetyl)pyrrolidine-2-carboxamide (COMPOUND 85): (2S)—N-[(4-carbamimidoylthiophen-2-yl)methyl]-1-(2-nonanamidoacetyl)pyrrolidine-2-carboxamide was prepared according to Scheme 39 with the use of nonanoic acid. $^{1}$H NMR (400 MHz, Methanol-$d_4$) δ 8.55 (s, 1H), 8.26 (d, J=1.6 Hz, 1H), 7.52-7.42 (m, 1H), 4.64-4.44 (m, 2H), 4.50 (d, J=2.8 Hz, 1H), 4.12-3.88 (m, 2H), 3.80-3.55 (m, 2H), 2.34-2.17 (m, 2.65H), 2.11-1.96 (m, 2H), 1.93 (dd, J=12.1, 6.6 Hz, 0.35H), 1.63 (t, J=7.4 Hz, 2H), 1.33 (t, J=6.4 Hz, 10H), 1.01-0.88 (m, 4H).

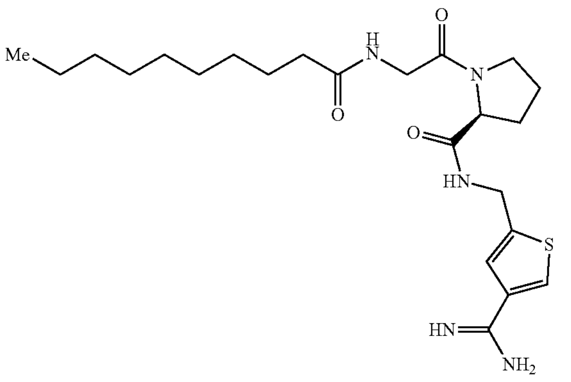 [SMILES: CCCCCCCCCC(=O)NCC(=O)N1CCC[C@H]1C(=O)NCc1cc(C(=N)N)cs1]

(2S)—N-[(4-carbamimidoylthiophen-2-yl)methyl]-1-(2-decanamidoacetyl)pyrrolidine-2-carboxamide (COMPOUND 86: (2S)—N-[(4-carbamimidoylthiophen-2-yl)methyl]-1-(2-decanamidoacetyl)pyrrolidine-2-carboxamide was prepared according to Scheme 39 with the use of capric acid. $^{1}$H NMR (400 MHz, Methanol-$d_4$) δ 8.58 (s, 1H), 8.25 (d, J=1.6 Hz, 1H), 7.52-7.42 (m, 1H), 4.64-4.44 (m, 2H), 4.50 (dd, J=8.4, 2.8 Hz, 1H), 4.12-3.95 (m, 2H), 3.80-3.55 (m, 2H), 2.32-2.17 (m, 2.7H), 2.11-1.96 (m, 2H), 1.91 (s, 0.03H), 1.67-1.57 (m, 2H), 1.32 (d, J=6.7 Hz, 12H), 1.05-0.88 (m, 4H).

SCHEME 40. Synthesis of (benzyl (2-((S)-8-(((4-carbamimidoylthiophen-2-yl)methyl)carbamoyl)-1,4-dioxa-7-azaspiro[4.4]nonan-7-yl)-2-oxoethyl)((2S,3S,4S,5S)-2,3,4,5-tetrakis(benzyloxy)hexyl)carbamate (COMPOUND 87)

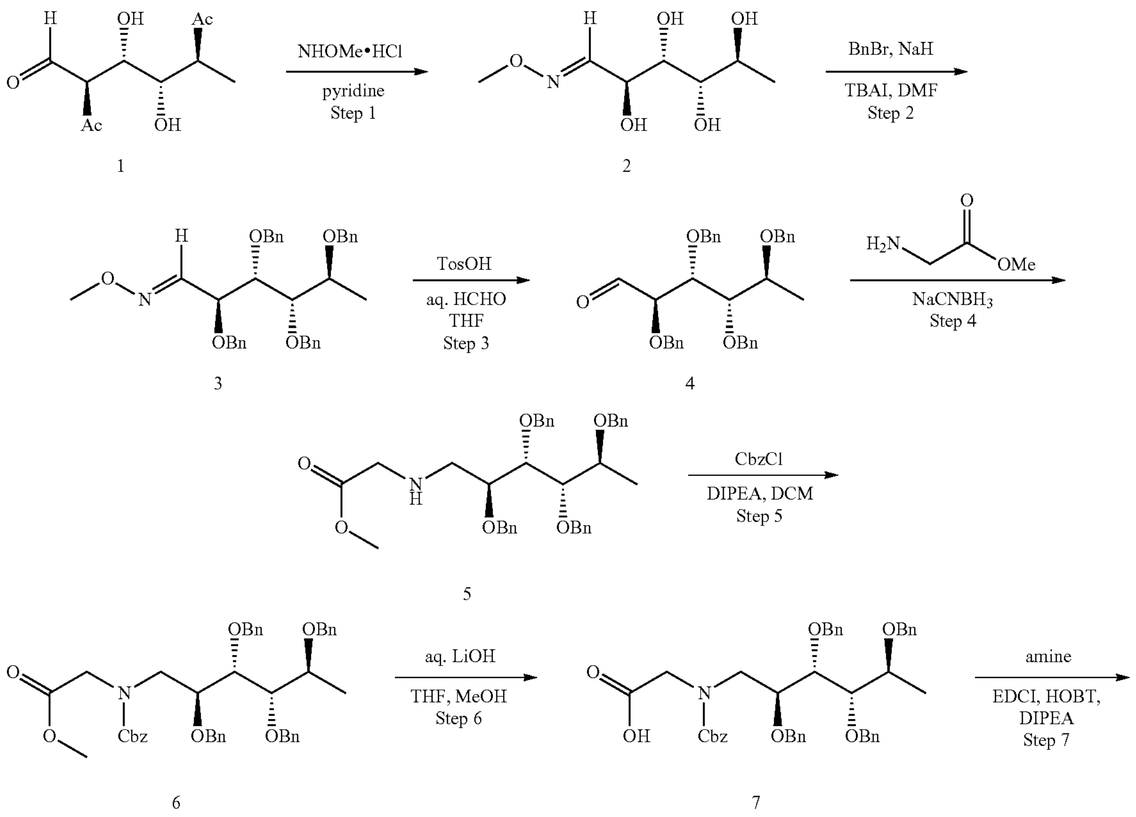

-continued

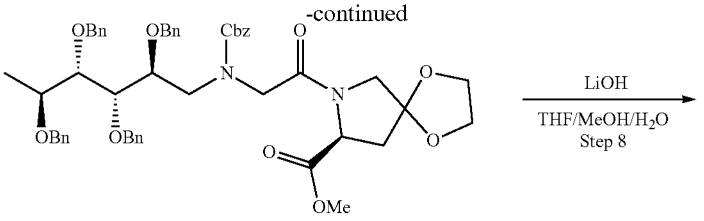

8

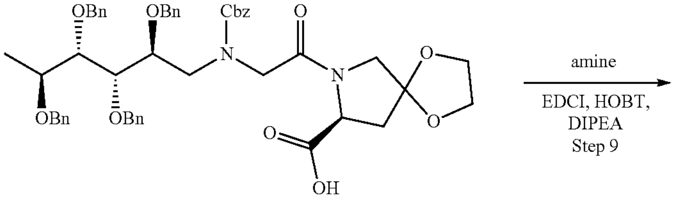

9

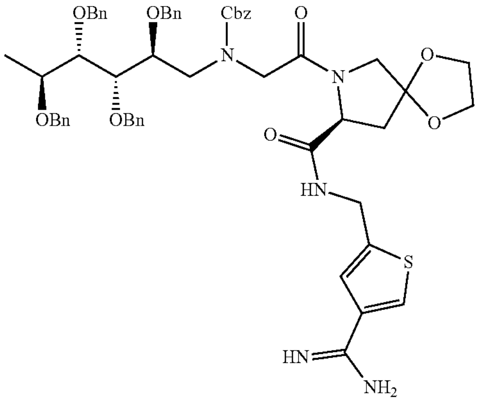

COMPOUND 87

Step 1: A solution of intermediate 1 (5.00 g, 33.3 mmol) and O-methylhydroxylamine hydrochloride (3.3 g, 24 mmol) in pyridine (50 mL) was stirred for 12 h at 70° C. under $N_2$ atmosphere. The reaction mixture was concentrated under reduced pressure to give 8 gram of crude intermediate 2 as colorless oil and used directly in the next step.

Step 2: To a stirred solution of the above crude intermediate 2 in DMF (250 mL) at 0° C. was added portion wise NaH (55% dispersion in oil, 10.2 g, 233 mmol) and the mixture was stirred for 1 h under $N_2$ atmosphere. After the resulting mixture was cooled to 0° C., BnBr (23.75 mL, 200 mmol) and Bu4NI (TBAI) (1.23 g, 3.33 mmol) was added. After stirred for 18 h at room temperature, the reaction mixture was concentrated under reduced pressure. The obtained residue was dissolved with AcOEt (500 mL), and the mixture was washed with water (2×500 mL) and brine (2×500 mL), dried over $Na_2SO_4$, filtered and concentrated under reduced pressure. The crude product was purified by silica gel column chromatography (Hexane:AcOEt=15:1) to give intermediate 3 (8.3 g, 55% yield in 2 steps) as pale yellow oil. LC/MS (ESI) m/z: 554 $(M+H)^+$.

Step 3: To a stirred solution of intermediate 3 (3.5 g, 6.5 mmol) in THF and 36-38% aqueous HCHO (2.5:1, 65 mL) at room temperature was added TsOH·$H_2O$ (1.23 g, 6.56 mmol). After the mixture was stirred for 12 h at room temperature, the reaction was quenched with saturated aqueous $NaHCO_3$. The resulting mixture was extracted with AcOEt (3×100 mL). The combined organic phases were washed with $H_2O$ (2×100 mL) and brine (2×100 mL), dried over $Na_2SO_4$, filtered and concentrated under reduced pressure. The obtained crude product was purified by silica gel column chromatography (Hexane:AcOEt=20:1) to give intermediate 4 (2.9 g, 88% yield) as pale yellow oil. LC/MS (ESI) m/z: 525 $(M+H)^+$.

Step 4: To intermediate 4 (1 g, 2 mmol) and methyl glycinate (170 mg, 2 mmol) were dissolved in THF (50 mL) and stirred at room temperature for 1 hour before $NaCNBH_3$ (140 mg, 2.22 mmol) was added and the mixture was stirred overnight. The reaction was quenched with saturated aqueous $NH_4Cl$. The resulting mixture was extracted with AcOEt (3×100 mL). The combined organic phases were washed with $H_2O$ (2×100 mL) and brine (2×100 mL), dried over $Na_2SO_4$, filtered and concentrated under reduced pressure. The obtained crude product was purified by silica gel column chromatography (Hexane:AcOEt=20:1) to give intermediate 5 (620 mg, 55% yield) as pale yellow oil. LC/MS (ESI) m/z: 598 $(M+H)^+$.

Step 5: To a solution of intermediate 5 (620 mg, 1.03 mmol) in DCM (20 mL), benzyl carbonochloridate (176 mg, 1.03 mmol) was added slowly followed by 0.5 mL DIPEA at 0° C. The reaction was allowed to warm to room temperature in 1 hour and stirred for another 6 hours before quenched with saturated aqueous $NH_4Cl$. The resulting mixture was extracted with AcOEt (3×100 mL). The combined organic phases were washed with $H_2O$ (2×100 mL)

and brine (2×100 mL), dried over $Na_2SO_4$, filtered and concentrated under reduced pressure. The obtained crude product was purified by silica gel column chromatography (Hexane:AcOEt=10:1) to give intermediate 6 (700 mg, 93% yield) as pale yellow oil. LC/MS (ESI) m/z: 732 $(M+H)^+$.

Step 6: To a solution of intermediate 6 (250 mg, 0.34 mmol) in MeOH (5 mL) and water (1 mL) was added lithium hydroxide monohydrate (40 mg, 1.695 mmol). The mixture was stirred at room temperature for 2 hours before concentrated to ⅕ volume, diluted with water and washed with MTBE twice. The aqueous layer was acidified with 1N aq.HCl to pH~3 and extracted with DCM twice. The combined organic layers were washed with brine, dried over anhydrous $Na_2SO_4$, filtered and concentrated under reduced pressure to dryness. The residue was purified by chromatography on silica gel (DCM:MeOH=30:1) to give intermediate 7 (230 mg, yield 94%) as white solid. LC/MS (ESI) (m/z): 718 $(M+H)^+$.

Step 7: To a mixture of intermediate 7 (220 mg, 0.30 mmol) and (S)-methyl 1,4-dioxa-7-azaspiro[4.4]nonane-8-carboxylate hydrochloride (67 mg, 0.30 mmol) in DMF (5 mL) was added EDCI (58 mg, 0.3 mmol) and HOBt (41 mg, 0.3 mmol) followed by DIPEA (273 mg, 2.12 mmol) at 0° C. The mixture was stirred at 25° C. for 16 hours before diluted with DCM and washed with water and brine, dried over anhydrous $Na_2SO_4$, filtered and concentrated to dryness under reduced pressure. The residue was purified by chromatography on silica gel (PE:EtOAc=50:1 to 1:1) to give compound 8 (300 mg, yield 100%) as light-yellow oil. LC/MS (ESI) (m/z): 887 $(M+H)^+$.

Step 8: To a solution of intermediate 8 (110 mg, 0.12 mmol) in MeOH (5 mL), water (1 mL), and THF, was added lithium hydroxide monohydrate (40 mg, 1.695 mmol). The mixture was stirred at room temperature for 2 hours before concentrated to ⅕ volume, diluted with water and washed with MTBE twice. The aqueous layer was acidified with 1N aq.HCl to pH~3 and extracted with DCM twice. The combined organic layers were washed with brine, dried over anhydrous $Na_2SO_4$, filtered and concentrated under reduced pressure to dryness. The residue was purified by chromatography on silica gel (DCM:MeOH=30:1) to give intermediate 9 (100 mg, yield 95%) as white solid. LC/MS (ESI) (m/z): 873 $(M+H)^+$.

Step 9: To a mixture of intermediate 9 (50 mg, 0.06 mmol) and 5-(aminomethyl)thiophene-3-carboximidamide (9.3 mg, 0.06 mmol) in DMF (5 mL) was added EDCI (12 mg, 0.06 mmol) and HOBt (8 mg, 0.06 mmol) followed by DIPEA (136 mg, 1 mmol) at 0° C. The mixture was stirred at 25° C. for 16 hours before diluted with DCM and washed with water and brine, dried over anhydrous $Na_2SO_4$, filtered and concentrated to dryness under reduced pressure. The residue was purified by prep-HPLC to give COMPOUND 87 (40 mg, yield 66%) as white solid. $^1H$ NMR (400 MHz, DMSO-$d_6$) δ 8.61 (s, 1H), 8.46 (s, 1H), 8.30 (s, 1H), 7.44 (s, 1H), 7.36-7.18 (m, 25H), 5.07-4.91 (m, 2H), 4.75-4.21 (m, 12H), 3.97-3.51 (m, 14H), 2.68 (s, 1H), 2.33 (s, 1H), 1.20-1.14 (m, 2H), 1.07 (d, J=6.3 Hz, 2H). LC/MS (ESI) (m/z): 1010 $(M+H)^+$.

SCHEME 41. Synthesis of benzyl (2-((S)-8-(((4-carbamimidoylthiazol-2-yl)methyl)carbamoyl)-1,4-dioxa-7-azaspiro[4.4]nonan-7-yl)-2-oxoethyl)((2S,3S,4S,5S)-2,3,4,5-tetrakis(benzyloxy)hexyl)carbamate (COMPOUND 89)

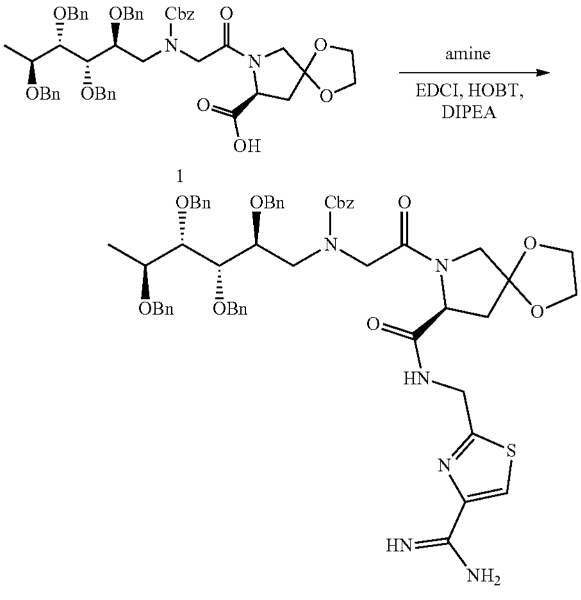

1

COMPOUND 89

Step 1: To a mixture of intermediate 1 (50 mg, 0.06 mmol) and 2-(aminomethyl)thiazole-4-carboximidamide (9.3 mg, 0.06 mmol) in DMF (5 mL) was added EDCI (12 mg, 0.06 mmol) and HOBt (8 mg, 0.06 mmol) followed by DIPEA (136 mg, 1 mmol) at 0° C. The mixture was stirred at 25° C. for 16 hours before diluted with DCM and washed with water and brine, dried over anhydrous $Na_2SO_4$, filtered and concentrated to dryness under reduced pressure. The residue was purified by prep-HPLC to give COMPOUND 89 (25 mg, yield 41%) as white solid. $^1H$ NMR (400 MHz, DMSO-$d_6$) δ 8.90 (s, 1H), 8.62 (s, 1H), 8.45 (s, 1H), 7.39-7.22 (m, 25H), 5.07-4.96 (m, 2H), 4.74-4.23 (m, 14H), 4.04-3.49 (m, 18H), 2.38-2.14 (m, 1H), 2.02 (s, 1H), 1.13 (dd, J=47.1, 5.7 Hz, 3H). LC/MS (ESI) (m/z): 1011 $(M+H)^+$.

SCHEME 42. Synthesis of (8S)-N-(4-carbamimidoylthiophen-2-yl)-7-{2-[(4-phenoxyphenyl)formamido]acetyl}-1,4-dioxa-7-azaspiro[4.4]nonane-8-carboxamide (COMPOUND 91).

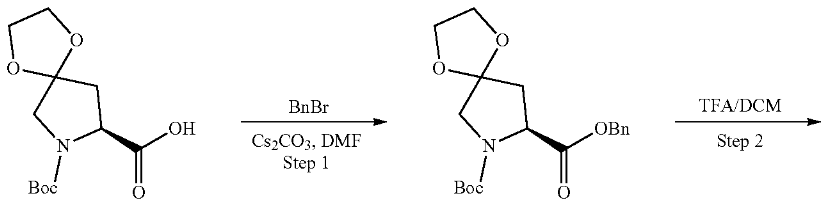

1 2

-continued
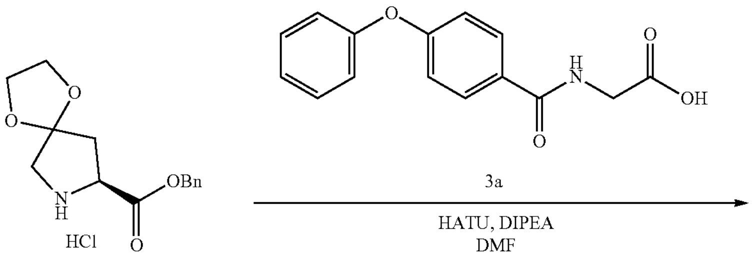
3
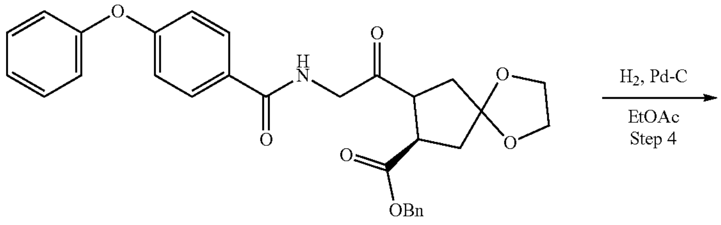
4
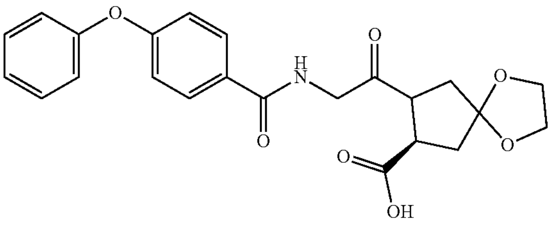
5
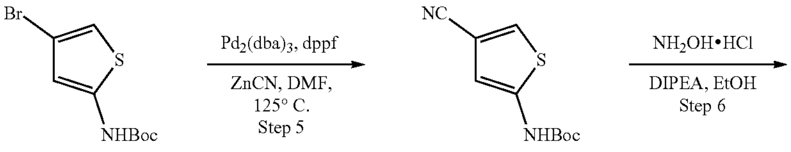
7 8
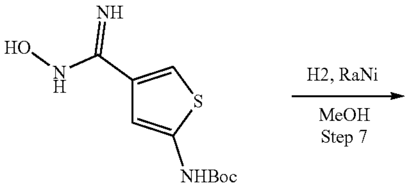
9
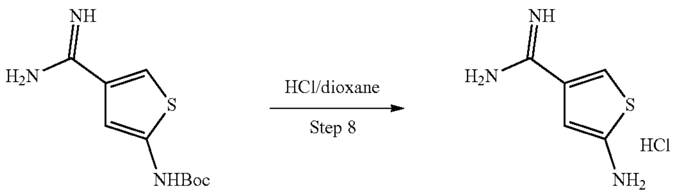
10 6

-continued

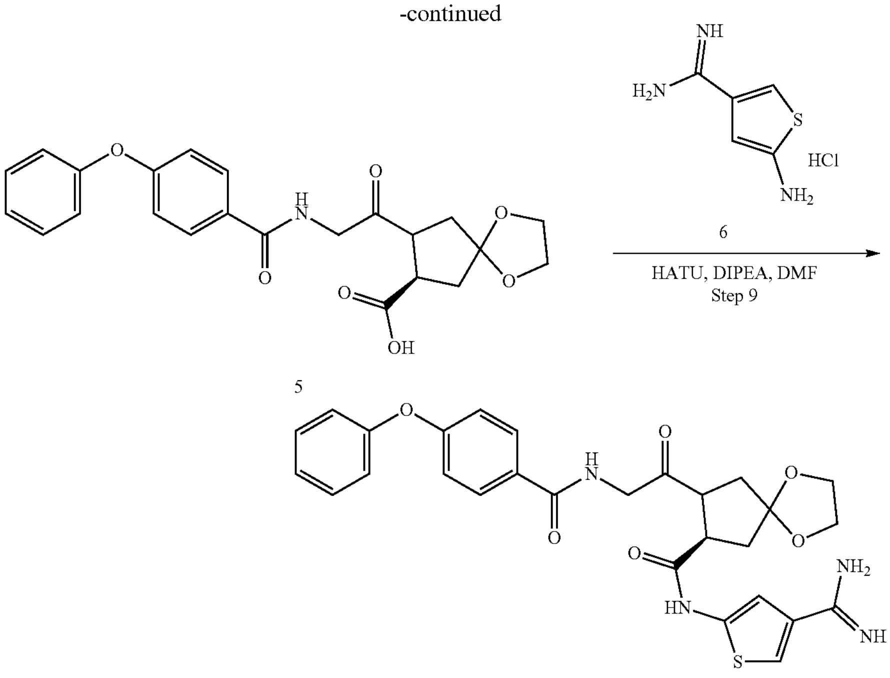

5

6

COMPOUND 91

Step 1: A solution of intermediate 1 (5 g, 18.30 mmol) in DMF (50 mL) was added cesium carbonate (8.94 g, 27.44 mmol, 1.5 equiv.) at 0° C. under argon atmosphere. BnBr (2.61 mL, 21.96 mmol, 1.2 equiv.) was added drop wise and the reaction was stirred at room temperature for 1 hour. The reaction mixture was then diluted with water and ethyl acetate. The two layers were separated, and the aqueous layer was extracted with EtOAc. The combined organic extracts were washed with brine, dried over $MgSO_4$, and concentrated to give a pale-yellow solid. The solid was triturated with hexanes to give intermediate 2 (6.5 g, 17.89 mmol, Yield 97.76%) as a white solid. LC/MS (ESI) m/z: 365 $(M+H)^+$.

Step 2: To a solution of intermediate 2 (6.5 g, 17.89 mmol, 1 equiv.) in dichloromethane (100 mL) was added trifluoroacetic acid (13.69 mL, 178.86 mmol, 10 equiv.) at room temperature. The reaction was stirred for 3 h and then concentrated to dryness. Purification by CombiFlash; 80 g column; solvent A=hexanes, solvent B=EtOAc; 100% A to 30% B gave intermediate 3 (4.56 g, 17.32 mmol, Yield 96.83%) as a white solid. LC/MS (ESI) m/z: 265 $(M+H)^+$.

Step 3: To a solution of 4-phenoxyphenyl)formamido] acetic acid, 3a (0.31 g, 1.13 mmol, 1 equiv.), intermediate 3 0.33 g, 1.24 mmol, 1.1 equiv.), and N-ethyldiisopropylamine (0.79 mL, 4.50 mmol, 4 equiv.) in dimethyl-formamide (5 mL) was added 2-(7-Aza-1H-benzotriazole-1-yl)-1,1,3,3-tetramethyluronium hexafluorophosphate) (0.64 g, 1.69 mmol, 1.5 equiv.). The reaction was stirred at room temperature for 30 minutes. Water (2 mL) was added and the precipitate filtered to obtain (0.5 g, 0.97 mmol, Yield 86.0%) of intermediate 4 as a brown solid. The solid was used in the next step without further purification. LC/MS (ESI) m/z: 517 $(M+H)^+$.

Step 4: A solution of intermediate 4 (0.5 g, 0.97 mmol, 1 equiv.) in ethyl acetate (10 mL) was added Pd/C (0.21 g, 0.1 mmol, 0.1 equiv.). The flask was evacuated and then back filled with hydrogen gas in a balloon. The reaction was stirred under hydrogen at room temperature for 1 hour. The reaction mixture was filtered through Celite pad and then concentrated to dryness to give intermediate 5 (0.4 g, 0.938 mmol, yield 96.91%) as a pale-yellow solid. LC/MS (ESI) m/z: 428 $(M+H)^+$.

Step 5: A solution of intermediate 7 (1.2 g, 4.31 mmol, 1 equiv.), ZnCN ((1.01 g, 8.63 mmol, 2 equiv.), Tris(dibenzylideneacetone) dipalladium (0) (0.40 g, 0.43 mmol, 0.1 equiv.), 1,1'-bis(diphenylphosphino) ferrocene (0.48 g, 0.86 mmol, 0.2 equiv.) in DMF (5 mL) was heated to 125° C. and stirred for 1.5 hours. The reaction was cooled to room temperature and then diluted with water and EtOAc. The two layers separated, and aq. layer was extracted with EtOAc. The combined organic extracts were washed with brine, dried over $Na_2SO_4$ and concentrated to give a brown oil. Purification by combiFlash; 40 g column, solvent A=$CH_2Cl_2$, solvent B=MeOH. 100% A to 3% B gave the intermediate 8 (0.8 g, 3.57 mmol, Yield 82.68%) as a brown sticky oil.

Step 6: To a mixture of intermediate 8 (0.15 g, 0.67 mmol, 1 equiv.) and hydroxylamine hydrochloride (0.12 g, 1.67 mmol, 2.5 equiv.) in ethanol (5 mL) was added N-Ethyldiisopropylamine (0.35 mL, 2.01 mmol, 3 equiv.). The reaction was stirred at room temperature overnight. The reaction was concentrated to dryness and the residue diluted with water and $CH_2Cl_2$. The two layers were separated, and the aq. Layer was extracted with $CH_2Cl_2$. The combined organic extracts were washed with brine, dried over $Na_2SO_4$ and concentrated. Purification by CombiFlash; 12 g column; solvent A=$CH_2Cl_2$, solvent B=MeOH. 100% A to 5% B gave intermediate 9 (0.15 g, 0.58 mmol, Yield 87.16%) as a brown solid. LC/MS (ESI) m/z: 258 $(M+H)^+$.

Step 7: To a solution of intermediate 9 (0.2 g, 0.78 mmol, 1 equiv.) in MeOH (3 mL) was added acetic acid (0.1 mL) and 50% wt Nickel on alumina catalyst (0.046 g, 0.78 mmol, 1 equiv.) The flask was evacuated and then back filled with hydrogen gas in a balloon. The reaction was stirred at 30° C.

for 2 hours, filtered through Celite pad, and concentrated to obtain intermediate 10 (0.09 g, 0.37 mmol, Yield 47.98%) as a yellow solid. Used in the next step without further purification. LC/MS (ESI) m/z: 242 $(M+H)^+$.

Step 8: A solution of intermediate 10 (0.09 g, 0.37 mmol, 1 equiv.) in HCl/1,4-dioxane (4 mL, 4M) was stirred at room temperature for 3 hours. The reaction mixture was concentrated to dryness to give compound 6 (50 mg, yield 95%) as yellow solid, which was used directly in the next step without further purification. LC/MS (ESI) m/z: 142 $(M+H)^+$.

Step 9: To a mixture of intermediate 5 (0.04 g, 0.094 mmol, 1 equiv.) and compound (6) (0.018 g, 0.103 mmol, 1.1 equiv.) in DMF (2 mL) was added HATU (0.054 g, 0.141 mmol, 1.5 equiv.), followed by N-Ethyldiisopropylamine (0.066 mL, 0.375 mmol, 4 equiv.). The reaction was stirred at room temperature for 0.5 hours and then purified directly using prep-HPLC to give COMPOUND 91 (10 mg, yield 10.0%) as a brown solid. $^1H$ NMR (400 MHz, DMSO-$d_6$) δ 9.99 (bs, 1H), 8.55 (d, J=4.0 Hz, 1H), 8.52 (t, J=6.0 Hz, 1H), 8.15 (1, s, 1H), 7.91-7.89 (m, 2H), 7.45-7.43 (m, 2H), 7.39-7.36 (m, 1H), 7.29 (d, J=0.9 Hz, 1H), 7.22 (t, J=7.4 Hz, 1H), 7.10 (d, J=7.6 Hz, 2H), 7.04-7.03 (m, 2H), 5.68 (4.66 (dd, J=11.2, 11.2 Hz, 1H), 4.43-4.38 (m, 1H), 4.74 (d, J=0.9 Hz, 1H), 4.72 (d, J=1.0 Hz, 1H), 4.44 (m, 2H) 4.37-4.30 (m, 2H), 4.03 (dd, J=16.8, 16.8 Hz, 1H), 3.95-3.80 (m, 2H), 3.77-3.61 (m, 2H), 3.59-3.48 (m, 1H), 2.30 (t, J=12.4 Hz, 1H), 2.53-2.35 (m, 2H) 2.10-2.06 (m, 1H). LC/MS (ESI) m/z: 550 $(M+H)^+$.

SCHEME 43. Synthesis of (8S)-N-[(5-carbamimidoylthiophen-2-yl)methyl]-7-{2-[(4-phenoxyphenyl) formamido]acetyl}-1,4-dioxa-7-azaspiro[4.4]nonane-8-carboxamide (COMPOUND 92)

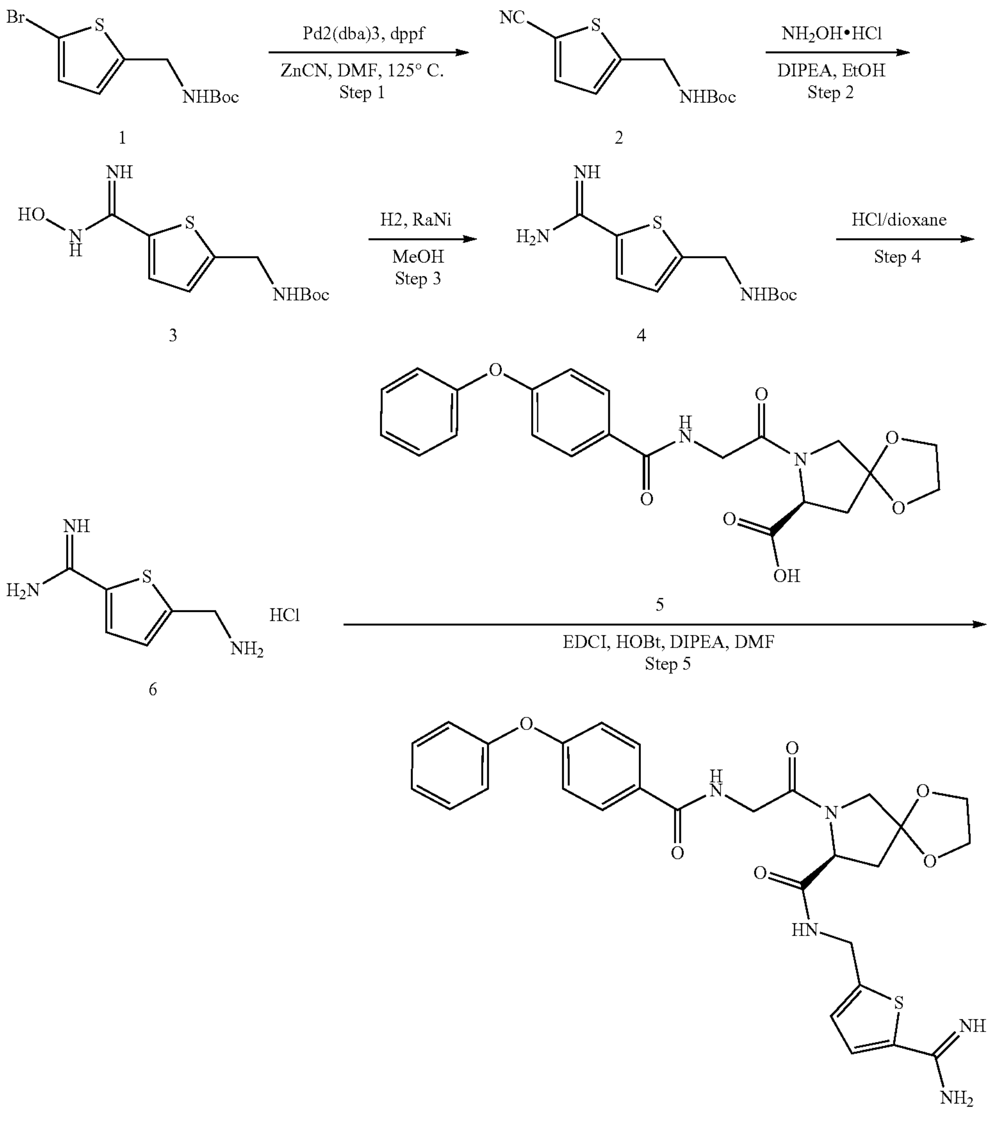

1
2
3
4
5
6

COMPOUND 92

Step 1: A mixture of intermediate 1 (2.8 g, 9.58 mmol, 1 equiv.), ZnCN (1.69 g, 14.37 mmol, 1.5 equiv.), tris(dibenzylideneacetone)dipalladium (0) (0.88 g, 0.96 mmol, 0.1 equiv.), and 1,1'-Bis(diphenylphosphino)ferrocene (1.06 g, 1.92 mmol, 0.2 equiv.) in dimethyl-formamide (15 mL) was heated and stirred for 3 hours at 125° C. under argon. The reaction was cooled to room temperature and then diluted with water and EtOAc. The two layers were separated, and aqueous layer extracted with EtOAc. The combined organic layers were washed with brine, dried over $MgSO_4$ and concentrated to give a brown oil. Purification by CombiFlash; 80 g column, solvent A=$CH_2Cl_2$, solvent B=MeOH. 100% solvent A to 5% B gave intermediate 2 (1.8 g, 7.55 mmol, Yield 78.82%) as a brown solid.

Step 2: To a mixture of intermediate 2 (2.2 g, 9.23 mmol, 1 equiv.) and hydroxylamine hydrochloride (1.64 g, 23.08 mmol, 2.5 equiv.) in ethanol (25 mL) was added N-Ethyldiisopropylamine (4.84 mL, 27.70 mmol, 3 equiv.). The reaction was stirred at room temperature overnight. The reaction was concentrated to dryness and the residue diluted with water and $CH_2Cl_2$. The two layers were separated, and the aq. Layer was extracted with $CH_2Cl_2$. The combined organic extracts were washed with brine, dried over $Na_2SO_4$ and concentrated. Purification by CombiFlash; 80 g column; solvent A=$CH_2Cl_2$, solvent B=MeOH. 100% A to 5% B gave intermediate 3 (1.58 g, 5.82 mmol, Yield 63.08%) as a brown solid. LC/MS (ESI) m/z: 272 $(M+H)^+$.

Step 3: To a solution of intermediate 3 (1.2 g, 4.42 mmol, 1 equiv.) in MeOH (15 mL) was added acetic acid (0.25 mL) and 50% wt Nickel on alumina catalyst (0.52 g, 4.42 mmol, 1 equiv.) The flask was evacuated and then back filled with hydrogen gas in a balloon. The reaction was stirred at 30° C. for 16 hours, filtered through Celite pad, and concentrated to obtain intermediate 4 (1.09 g, 4.31 mmol, yield 97.41%) as a yellow solid. Used in the next step without further purification. LC/MS (ESI) m/z: 256 $(M+H)^+$.

Step 4: A solution of intermediate 4 (0.1 g, 0.37 mmol, 1 equiv.) in HCl/1,4-dioxane (3 mL, 4M) was stirred at room temperature for 3 hours. The reaction mixture was concentrated to dryness to give intermediate 6 (60 mg, yield 98.7%) as a yellow solid, which was used directly in the next step without further purification. LC/MS (ESI) m/z: 156 $(M+H)^+$.

Step 5: To a mixture compound 5 (0.02 g, 0.047 mmol, 1 equiv.), 5, and intermediate 6 (0.013 g, 0.069 mmol, 1.48 equiv.) in DMF (3 mL) was added 1-(3-Dimethylaminopropyl)-3-ethylcarbodiimide hydrochloride (0.016 g, 0.083 mmol, 1.76 equiv.), HOBt (0.012 g, 0.069 mmol, 1.48 equiv.) and then cooled ice-bath temperature. N-Ethyldiisopropylamine (0.024 g, 0.033 mL, 0.188 mmol, 4 equiv.) was added and the reaction stirred at room temperature overnight. The reaction was concentrated and purified directly using prep-HPLC to give 1 mg of COMPOUND 92. LC/MS (ESI) m/z: 564 $(M+H)^+$.

SCHEME 44. Synthesis of (1S,3S,5S)-N-((4-cyanothiophen-2-yl)methyl)-5-methyl-2-((4-phenoxybenzoyl)glycyl)-2-azabicyclo[3.1.0]hexane-3-carboxamie (COMPOUND 93)

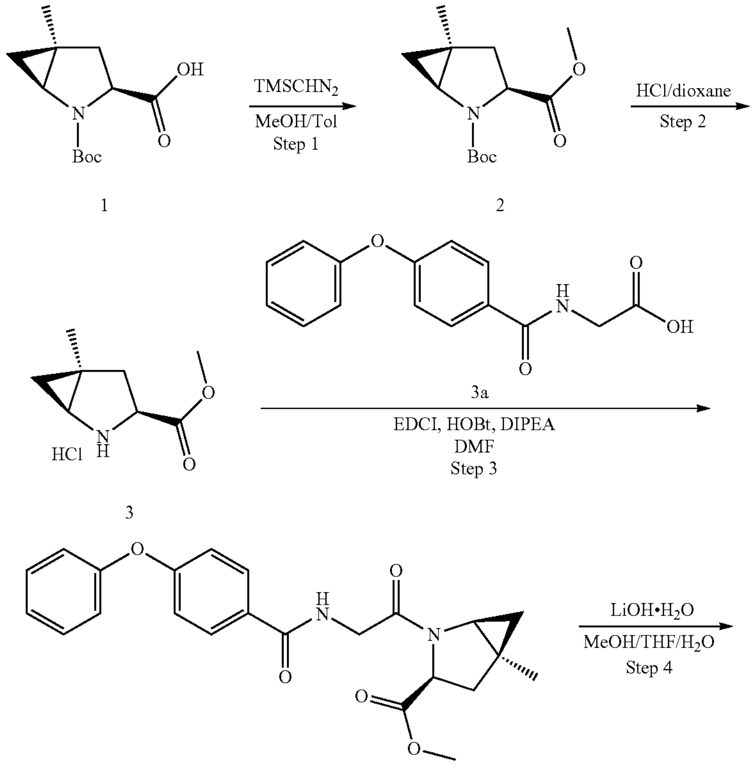

1

2

3a

3

4

-continued

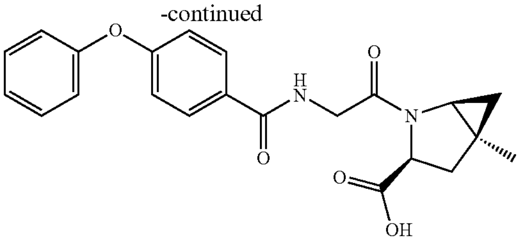

5

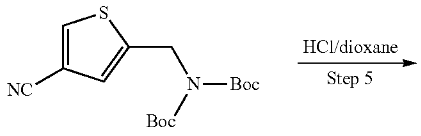

6

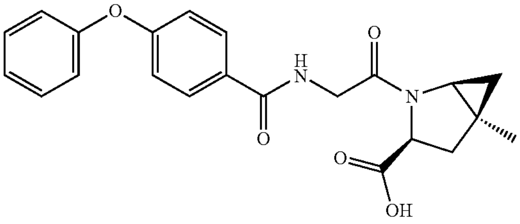

5

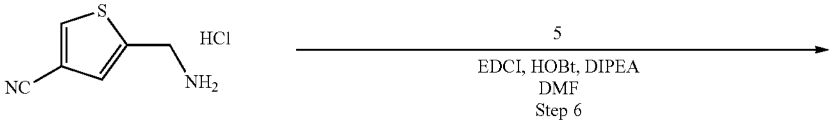

7

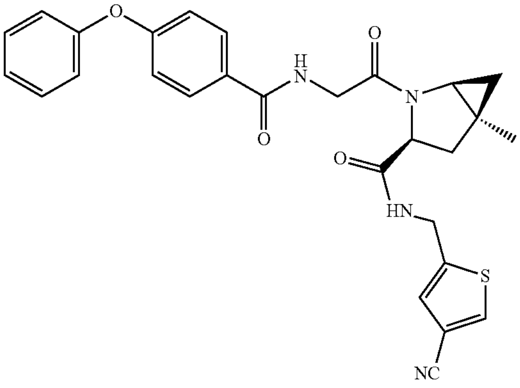

COMPOUND 93

Step 1: A solution of intermediate 1 (100 mg, 0.41 mmol) in MeOH (1 mL) and toluene (2.5 mL) was added $TMSCHN_2$ (0.41 mL, 0.84 mmol, 2 M) dropwise at 0° C. under $N_2$ atmosphere. The reaction was stirred at room temperature for 2 hours. The reaction mixture was quenched with AcOH and concentrated to dryness under vacuum. The residue was purified by column chromatography on silica gel (PE:EtOAc=50:1 to 3:1) to give intermediate 2 (100 mg, yield 94.5%) as light oil. LC/MS (ESI) m/z: 256 $(M+H)^+$.

Step 2: A mixture of intermediate 2 (100 mg, 0.41 mmol) in HCl/1,4-dioxane (2 mL, 4M) was stirred at room temperature for 2 hours. The reaction mixture was washed with ether and dried over anhydrous $Na_2SO_4$, filtered, and concentrated to dryness under vacuum to give intermediate 3 (75 mg, yield 99.9%) as colorless oil, which was used directly in the next step without further purification. LC/MS (ESI) m/z: 156 $(M+H)^+$.

Step 3: To a mixture of intermediate 3 (75 mg, 0.39 mmol) and compound 3a (106 mg, 0.39 mmol) in DMF (3 mL) was added DIPEA (252 mg, 1.95 mmol) at 0° C., followed by addition of EDCI (134 mg, 0.70 mmol), HOBt (79 mg, 0.59 mmol). The resulting mixture was stirred at room temperature overnight. The mixture was diluted with EtOAc and washed with saturated aq.$NH_4Cl$ solution and brine, dried over anhydrous $Na_2SO_4$, filtered and concentrated to dryness under reduced pressure. The residue was purified by column chromatography on silica gel (PE:EtOAc=10:1 to 2:1) to give intermediate 4 (120 mg, yield 75.1%) as yellow oil. LC/MS (ESI) m/z: 409 $(M+H)^+$.

Step 4: To a solution of intermediate 4 (120 mg, 0.29 mmol) in THF (1 mL) and MeOH (2 mL) was added a solution of lithium hydroxide (59 mg, 1.47 mmol) in water (1 mL) at 0° C. The mixture was stirred at room temperature for 1.5 hours. The mixture was diluted with water and washed with EtOAc twice. The aqueous layer was acidified with 0.5 M aq. HCl solution to pH~5 and extracted with EtOAc twice. The combined organic layers were washed with brine, dried over anhydrous $Na_2SO_4$, filtered and concentrated to dryness under reduced pressure to give intermediate 5 (115 mg, yield 99.3%) as white solid. LC/MS (ESI) m/z: 395 $(M+H)^+$.

Step 5: A mixture of intermediate 6 (500 mg, 1.48 mmol) in HCl/1,4-dioxane (5 mL, 4M) was stirred at room temperature for 1.5 hours. The reaction mixture was concentrated to dryness, washed with DCM and dried under vacuum to give intermediate 7 (200 mg, yield 98.0%) as yellow solid, which was used directly in the next step without further purification. LC/MS (ESI) m/z: 139 $(M+H)^+$.

temperature overnight. The mixture was diluted with EtOAc and washed with saturated aq.$NH_4Cl$ solution and brine, dried over anhydrous $Na_2SO_4$, filtered and concentrated to dryness under reduced pressure. The residue was purified by prep-HPLC to give COMPOUND 93 (2.3 mg, yield 1.5%) as white solid. $^1H$ NMR (400 MHz, DMSO-$d_6$) δ 8.70 (t, J=5.6 Hz, 1H), 8.57 (t, J=6.0 Hz, 1H), 8.39 (d, J=1.2 Hz, 1H), 7.91-7.88 (m, 2H), 7.47-7.43 (m, 2H), 7.30 (d, J=0.8 Hz, 1H), 7.22 (t, J=7.4 Hz, 1H), 7.10 (d, J=7.6 Hz, 2H), 7.05-7.02 (m, 2H), 4.66 (dd, J=11.2, 11.2 Hz, 1H), 4.43-4.38 (m, 2H), 4.37-4.30 (m, 1H), 4.03 (dd, J=16.8, 16.8 Hz, 1H), 3.59-3.48 (m, 1H), 2.30 (t, J=12.4 Hz, 1H), 1.97 (dd, J=13.6, 13.6 Hz, 1H), 1.23 (s, 3H), 1.17 (dd, J=4.8, 4.8 Hz, 1H), 0.68 (t, J=5.4 Hz, 1H). LC/MS (ESI) m/z: 515 $(M+H)^+$.

SCHEME 53. Synthesis of ((1S,3S,5S)-N-[(5-carbamimidoylthiophen-2-yl)methyl]-5-methyl-2-{2-[(4-phenoxyphenyl)formamido]acetyl}-2-azabicyclo[3.1.0]hexane-3-carboxamide (Compound 107).

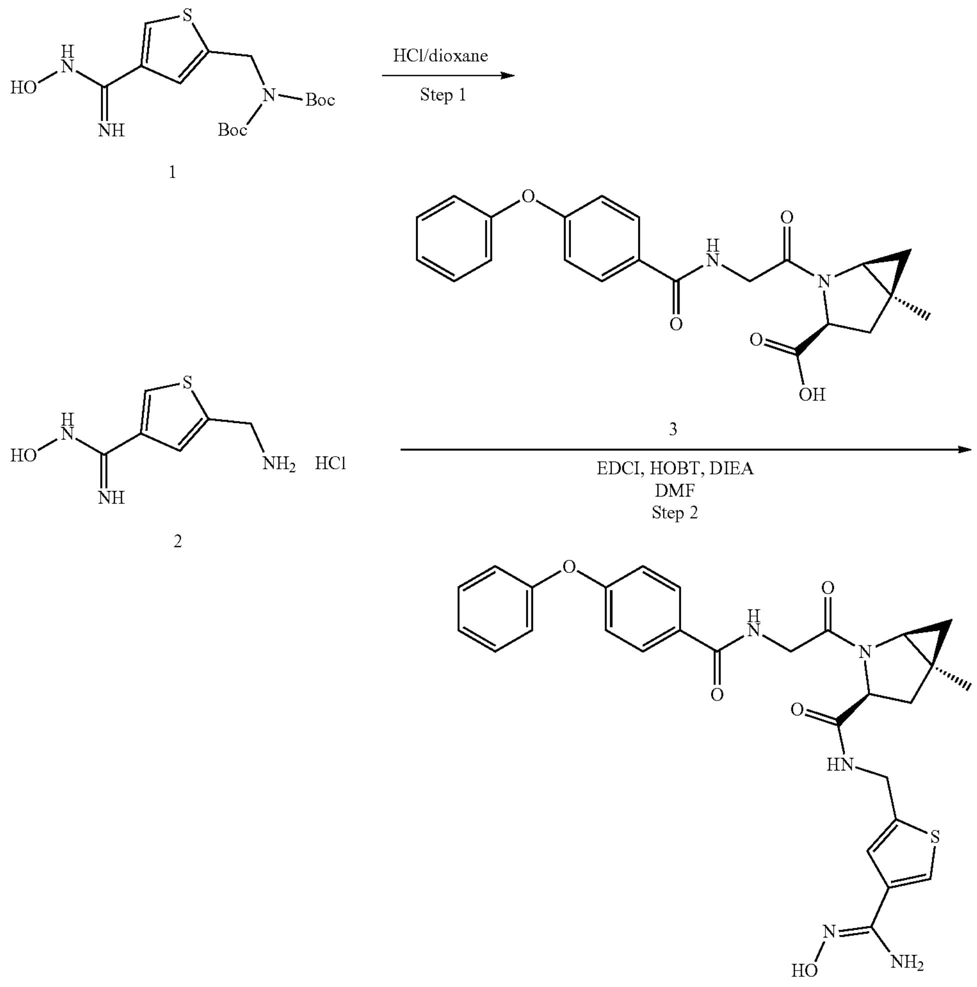

1

2

3

COMPOUND 94

Step 6: To a mixture of compound 5 (115 mg, 0.29 mmol) and intermediate 7 (75 mg, 0.44 mmol) in DMF (3 mL) was added DIPEA (187 mg, 1.45 mmol) at 0° C., followed by addition of EDCI (100 mg, 0.52 mmol) and HOBt (59 mg, 0.44 mmol). The resulting mixture was stirred at room Step 1: A mixture of intermediate 1 (300 mg, 0.81 mmol) in HCl/1,4-dioxane (3 mL, 4M) was stirred at room temperature for 2 hours. The reaction mixture was concentrated to dryness, dissolved in DCM and concentrated to dryness again under vacuum to give intermediate 2 (167 mg, yield 99.8%) as yellow solid, which was used directly in the next step without further purification. LC/MS (ESI) m/z: 172 $(M+H)^+$.

Step 2: To a mixture of intermediate 2 (115 mg, 0.20 mmol) and compound 3 (50 mg, 0.13 mmol) in DMF (3 mL) was added DIPEA (82 mg, 0.63 mmol) at 0° C., followed by addition of EDCI (44 mg, 0.23 mmol) and HOBt (26 mg, 0.19 mmol). The resulting mixture was stirred at room temperature overnight. The mixture was diluted with EtOAc and washed with saturated aq. $NH_4Cl$ solution and brine, dried over anhydrous $Na_2SO_4$, filtered and concentrated to dryness under reduced pressure. The residue was purified by prep-HPLC to give COMPOUND 94 (5.3 mg, yield 7.6%) as white solid. $^1H$ NMR (400 MHz, DMSO-$d_6$) δ 9.47 (s, 1H), 8.67 (t, J=5.8 Hz, 1H), 8.46 (t, J=5.8 Hz, 1H), 7.90 (d, J=8.8 Hz, 2H), 7.64 (d, J=1.6 Hz, 1H), 7.47-7.43 (m, 2H), 7.24-7.20 (m, 1H), 7.16 (s, 1H), 7.11-7.09 (m, 2H), 7.06-7.03 (m, 2H), 5.71 (s, 2H), 4.65 (dd, J=11.2, 11.2 Hz, 1H), 4.43-4.32 (m, 3H), 4.04-3.98 (m, 1H), 3.52-3.51 (m, 1H), 2.28 (t, J=12.4 Hz, 1H), 1.96 (dd, J=13.2, 13.2 Hz, 1H), 1.23 (s, 3H), 1.21-1.20 (m, 1H), 0.66 (t, J=5.2 Hz, 1H). LC/MS (ESI) m/z: 548 $(M+H)^+$.

SCHEME 46. Synthesis of (1S,3S,5S)-N-((4-carbamimidoylthiophen-2-yl)methyl)-5-methyl-2-((4-(4-(pentafluoro-λ⁶-sulfaneyl)phenoxy)benzoyl)glycyl)-2-azabicyclo[3.1.0]hexane-3-carboxamide (COMPOUND 95)

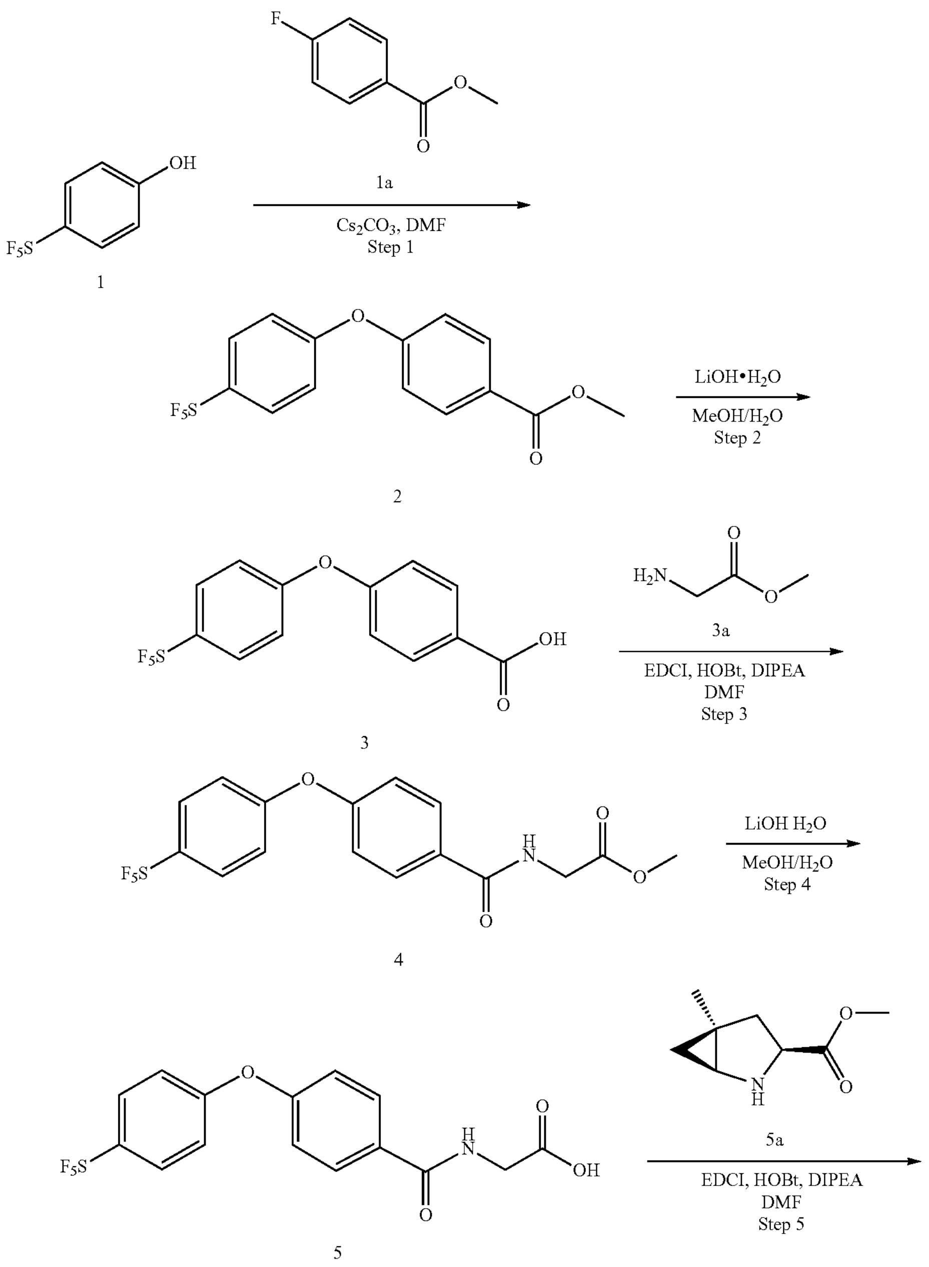

-continued

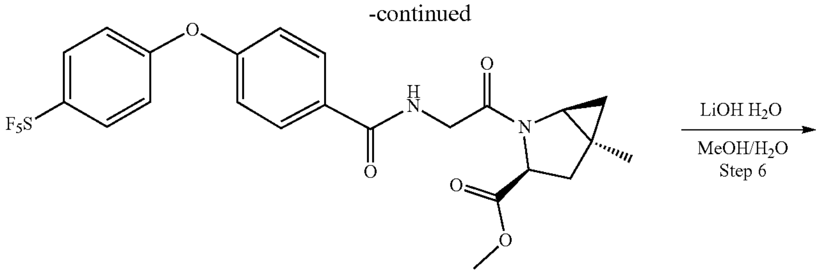

6

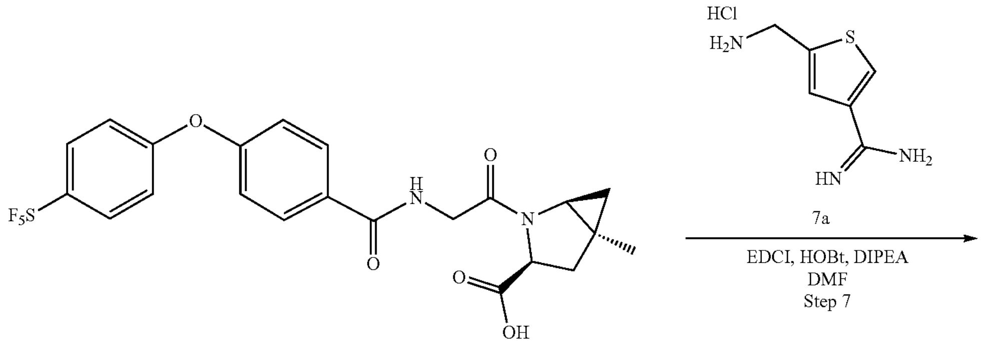

7

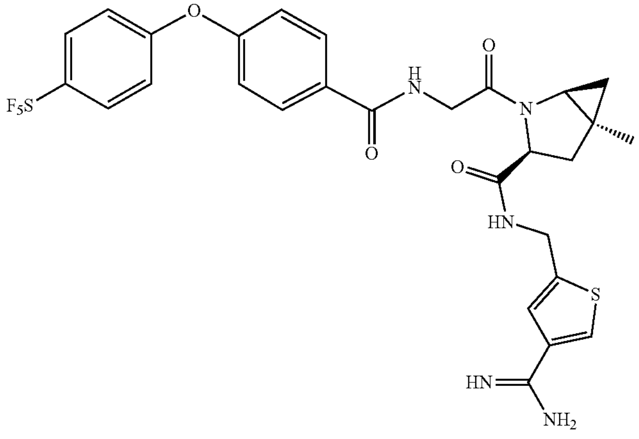

COMPOUND 95

Step 1: To a solution of intermediate 1 (260 mg, 1.18 mmol) in DMF (5 mL) were added compound 1a (273 mg, 1.77 mmol) and $Cs_2CO_3$ at room temperature. The mixture was stirred at 120° C. for 16 hours. The mixture was diluted with EtOAc and washed with saturated aq.$NH_4C_1$ solution and brine, dried over anhydrous $Na_2SO_4$, filtered and concentrated to dryness. The residue was purified by column chromatography on silica gel (PE:EtOAc=9:1) to give intermediate 2 (122 mg, yield 29.2%) as colorless oil. LC/MS (ESI) (m/z): 355 $(M+H)^+$.

Step 2: To a solution of intermediate 2 (122 mg, 0.34 mmol) in MeOH (5 mL) and water (1 mL) was added a solution of $LiOH{\cdot}H_2O$ (145 mg, 3.4 mmol) at 0° C. and the mixture was stirred at room temperature for 2 hour. The mixture was concentrated to ⅕ volume, diluted with water and washed with MTBE twice. The aqueous layer was acidified with 1N aq.HCl to pH~3, extracted with DCM twice. The combined organic layers were washed with brine, dried over anhydrous $Na_2SO_4$, and concentrated to dryness under reduced pressure to give intermediate 3 (100 mg, yield 85.1%) as yellow solid. The crude product was used directly in next step without further purification. LC/MS (ESI) (m/z): 341 $(M+H)^+$.

Step 3: To a mixture of intermediate 3 (100 mg, 0.29 mmol) and compound 3a (55 mg, 0.44 mmol) in DMF (5 mL) were added DIPEA (0.24 mL, 1.45 mmol), EDCI (113 mg, 0.58 mmol) and HOBT (60 mg, 0.44 mmol) at 0° C. under $N_2$ atmosphere. The mixture was stirred at room temperature for 16 hours. The mixture was diluted with EtOAc and washed with saturated aq.$NH_4Cl$ solution and brine, dried over anhydrous $Na_2SO_4$, filtered and concentrated to dryness under vacuum. The residue was purified by column chromatography on silica gel (PE:EtOAc=3:2) to give intermediate 4 (80 mg, yield 66.7%) as colourless oil. LC/MS (ESI) m/z: 412 $(M+H)^+$.

Step 4: To a solution of intermediate 4 (81 mg, 0.2 mmol) in MeOH (5 mL) and water (1 mL) was added a solution of $LiOH \cdot H_2O$ (83 mg, 2.0 mmol) at 0° C. and the mixture was stirred at room temperature for 2 hour. The mixture was concentrated to ⅕ volume, diluted with water and washed with MTBE twice. The aqueous layer was acidified with 1N aq.HCl to pH~3, extracted with DCM twice. The combined organic layers were washed with brine, dried over anhydrous $Na_2SO_4$, and concentrated to dryness under reduced pressure to give intermediate 5 (75 mg, yield 96.2%) as yellow solid. The crude product was used directly in next step without further purification. LC/MS (ESI) (m/z): 398 $(M+H)^+$.

Step 5: To a mixture of intermediate 5 (75 mg, 0.19 mmol) and compound 5a (36 mg, 0.23 mmol) in DMF (5 mL) were added DIPEA (0.16 mL, 0.95 mmol), EDCI (72 mg, 0.38 mmol) and HOBT (38 mg, 0.29 mmol) at 0° C. under $N_2$ atmosphere. The mixture was stirred at room temperature for 16 hours. The mixture was diluted with EtOAc and washed with saturated aq.$NH_4Cl$ solution and brine, dried over anhydrous $Na_2SO_4$, filtered and concentrated to dryness under vacuum. The residue was purified by chromatography on silica gel (PE:EtOAc=3:2) to give intermediate 6 (80 mg, yield 80.0%) as white semi-solid. LC/MS (ESI) m/z: 535 $(M+H)^+$.

Step 6: To a solution of intermediate 6 (80 mg, 0.15 mmol) in MeOH (5 mL) and water (1 mL) was added a solution of $LiOH \cdot H_2O$ (63 mg, 1.5 mmol) at 0° C. and the mixture was stirred at room temperature for 2 hours. The mixture was concentrated to ⅕ volume, diluted with water and washed with MTBE twice. The aqueous layer was acidified with 1N aq.HCl to pH~3, extracted with DCM twice. The combined organic layers were washed with brine, dried over anhydrous $Na_2SO_4$, and concentrated to dryness under reduced pressure to give intermediate 7 (52 mg, yield 66.7%) as white semi-solid. The crude product was used directly in next step without further purification. LC/MS (ESI) (m/z): 521 $(M+H)^+$.

Step 7: To a mixture of intermediate 7 (52 mg, 0.1 mmol) and compound 7a (38 mg, 0.2 mmol) in DMF (5 mL) were added DIPEA (0.08 mL, 0.5 mmol), EDCI (38 mg, 0.2 mmol) and HOBT (20 mg, 0.15 mmol) at 0° C. under $N_2$ atmosphere. The mixture was stirred at room temperature for 16 hours. The mixture was diluted with EtOAc and washed with saturated aq.$NH_4Cl$ solution and brine, dried over anhydrous $Na_2SO_4$, filtered and concentrated to dryness under vacuum. The residue was purified by column chromatography on silica gel (DCM:MeOH=94:6) to give COMPOUND 95 (12 mg, crude) as brown solid. The product was further purified by prep-HPLC to give COMPOUND 95 (1.4 mg, yield 2.1%) as white solid. $^1H$ NMR (400 MHz, $CD_3OD$) δ 8.49 (s, 1H), 8.20 (d, J=1.6 Hz, 1H), 7.92 (d, J=8.8 Hz, 2H), 7.85 (d, J=9.2 Hz, 2H), 7.40 (s, 1H), 7.15 (dd, J=8.9, 2.1 Hz, 5H), 4.60-4.52 (m, 3H), 4.37 (t, J=13.5 Hz, 2H), 3.41 (dd, J=6.0, 2.4 Hz, 1H), 2.41 (t, J=12.4 Hz, 1H), 2.17 (dt, J=6.8, 4.2 Hz, 2H), 1.29 (s, 3H), 1.15 (dd, J=5.8, 2.5 Hz, 1H), 0.80 (t, J=5.4 Hz, 1H); LC/MS (ESI) m/z: 658 $(M+H)^+$.

SCHEME 47. Synthesis of (1R,3R,5S)-N-((4-carbamimidoylthiophen-2-yl)methyl)-2-((4-phenoxybenzoyl)glycyl)-2-azabicyclo[2.2.1]heptane-3-carboxamie (96)

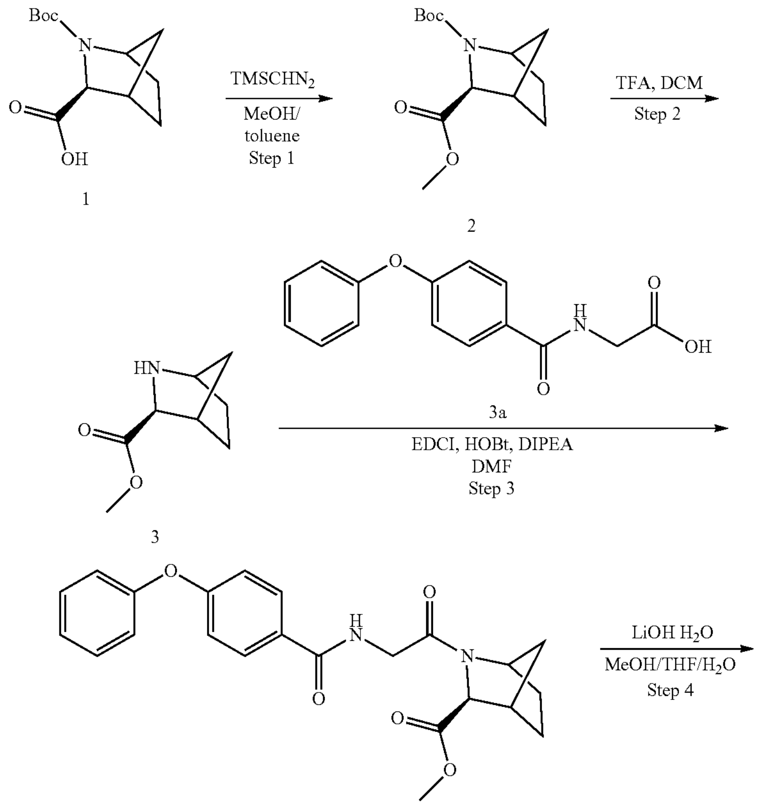

1
2
3a
3
4

-continued

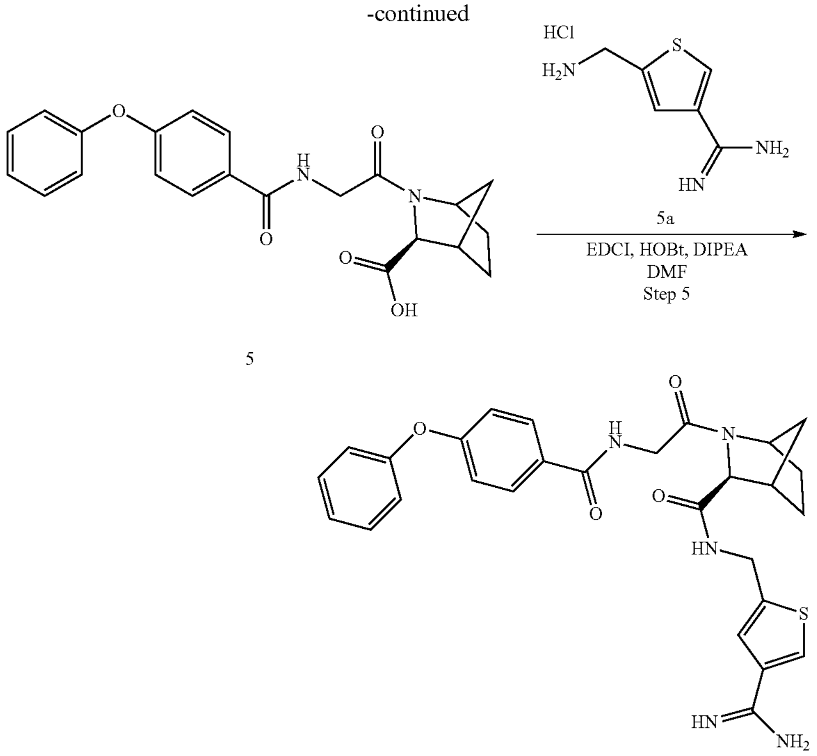

5

COMPOUND 96

Step 1: To a solution of intermediate 1 (500 mg, 2.07 mmol) in MeOH (2 mL) and toluene (5 mL) was added $TMSCHN_2$ dropwise at 0° C. under $N_2$ atmosphere. The mixture was stirred at room temperature for 1.5 hours. The mixture was quenched with glacial acetic acid, filtered and concentrated to dryness under vacuum. The residue was purified by column chromatography on silica gel (PE:EtOAc=20:1 to 5:1) to give intermediate 2 (517 mg, yield 97.7%) as yellow oil. LC/MS (ESI) m/z: 200 $(M-56+H)^+$.

Step 2: To a solution of intermediate 2 (517 mg, 2.02 mmol) in DCM (6 mL) was added TFA (3 mL) at 0° C. and the mixture was stirred at room temperature for 1 hour. The reaction mixture was concentrated to dryness under vacuum, washed with DCM and dried under vacuum to give intermediate 3 (314 mg, yield 99.9%) as yellow oil, which was used directly in the next step without further purification. LC/MS (ESI) m/z: 156 $(M+H)^+$.

Step 3: To a mixture of intermediate 3 (139 mg, 0.89 mmol) and compound 3a (243 mg, 0.89 mmol) in DMF (5 mL) were added DIPEA (0.8 mL), followed by addition of HOBt (182 mg, 1.34 mmol) and EDCI (310 mg, 1.61 mmol) at 0° C. under $N_2$ atmosphere. The mixture was stirred at 35° C. for 2.5 hours. The mixture was diluted with EtOAc and washed with saturated aq. $NH_4C_1$ solution and brine, dried over anhydrous $Na_2SO_4$, filtered and concentrated to dryness under vacuum. The residue was purified by column chromatography on silica gel (DCM:MeOH=100:1 to 20:1) to give intermediate 4 (200 mg, yield 54.6%) as yellow oil. LC/MS (ESI) m/z: 409 $(M+H)^+$.

Step 4: To a solution of intermediate 4 (195 mg, 0.48 mmol) in MeOH (2 mL) and THF (1 mL) was added a solution of $LiOH·H_2O$ (57 mg, 2.39 mmol) in $H_2O$ (1 mL) at 0° C. The mixture was stirred at 25° C. for 16 hours. The mixture was diluted with water and extracted with EtOAc twice. The water layer was acidified with 2M aq. HCl solution and washed with EtOAc twice, and the organic layer was washed with brine, dried over anhydrous $Na_2SO_4$, filtered and concentrated to dryness to give intermediate 5 (171 mg, yield 90.8%) as white solid, which was used directly in the next step without further purification. LC/MS (ESI) m/z: 395 $(M+H)^+$.

Step 5: To a mixture of intermediate 5 (60 mg, 0.15 mmol) and compound 5a (118 mg, 0.76 mmol) in DMF (3 mL) was added DIPEA (0.3 mL, 1.52 mmol), followed by addition of HOBt (62 mg, 0.46 mmol) and EDCI (105 mg, 0.55 mmol) at 0° C. under $N_2$ atmosphere. The mixture was stirred at 35° C. for 16 hours. The mixture was diluted with EtOAc and washed with saturated aq. $NH_4Cl$ solution and brine, dried over anhydrous $Na_2SO_4$, filtered and concentrated to dryness under vacuum. The residue was purified by column chromatography on silica gel (DCM:MeOH=100:1 to 20:1) and further purified by prep-HPLC to give COMPOUND 96 (1.2 mg, yield 1.4%) as white solid. $^1H$ NMR (400 MHz, DMSO-$d_6$) δ 8.58 (dt, J=11.4, 4.4 Hz, 2H), 8.44 (s, 1H), 8.33 (s, 1H), 7.89 (dd, J=8.8, 8.8 Hz, 2H), 7.53-7.41 (m, 3H), 7.22 (t, J=7.4 Hz, 1H), 7.10 (d, J=7.6 Hz, 2H), 7.04 (d, J=8.8 Hz, 2H), 4.55-4.35 (m, 3H), 4.11 (d, J=4.8 Hz, 1H), 3.92-3.74 (m, 1H), 3.65-3.48 (m, 1H), 2.60-2.53 (m, 1H), 1.97-1.87 (m, 1H), 1.74-1.70 (m, 2H), 1.61-1.51 (m, 1H), 1.49-1.32 (m, 2H). LC/MS (ESI) m/z: 532 $(M+H)^+$.

General Methods

All reagents were obtained from commercial sources and were used without purification. Chromatography was performed using a Teledyne Combiflash $Rf^+$ instrument using Redisep Gold Columns. Thin-layer chromatography (TLC) was performed on Macherey Nagel SIL G-25 $UV_{254}$ plates. Visualization of the developed chromatogram was accomplished under ultraviolet light or by staining with CAM or $KMnO_4$. $^1H$ NMR spectra were recorded on a VARIAN 400 MHz spectrometer. Chemical shifts are reported as δ values and are referenced internally according to the residual solvent signals. Data are recorded as follows: s=singlet, d=doublet, t=triplet, q=quartet, m=multiplet, br=broad. The relative purity and the mass of the products were confirmed by LC/MS on a Agilent 1200 HPLC system equipped with an Agilent multiple wavelength detector and an Agilent 6130 Quadrupole MS detector using the following conditions: Column, Kinetex EVO C18 100 Å, 50×3.0 mm. 2.6 μm. Mobile Phase, A: 0.1% formic acid in $H_2O$, B: 0.1% formic acid in ACN. Flow rate: 1.0 ml/min. Temperature, 40° C. Run time, 5 min. Unless otherwise stated; Gradient, 0 to 4.5 min, 10% B to 95% B. Purity of final compounds were determined on an Agilent 1200 HPLC system at 220 and 254 nm and reported at 254 nm using the following conditions: Column, Kinetex EVO C18 100 Å, 150×4.6 mm, 5 μm. Mobile Phase, A: 0.1% formic acid in $H_2O$, B: 0.1% formic acid in ACN. Flow rate: 1.0 ml/min. Temperature, 40° C. Run time, 30 min. Gradient, 0 to 21 min, 10% to 90% B. Final purities were reported at 254 nm. Reverse phase purifications were performed on a Waters preparative HPLC-MS system using the following conditions. Column, Gemini NX C18, 150×30 mm. Mobile Phase, A: 10 nM ammonium formate in $H_2O$, B: ACN. Flow rate: 40.0 ml/min. Temperature, RT. Run time, 9 min. Gradient, 35% to 55% B or on a Biotage Isolera One instrument using the following conditions unless specified otherwise: Column, Snap Ultra C18, 12 g; Mobile Phase, A: 0.1% FA in $H_2O$, B: CAN. Flow Rate: 12 ml/min. Gradient 10 to 50% B over 18 min.

The synthesis of 5-(aminomethyl)thiophene-3-carboximidamide dihydrochloride is described elsewhere.

Method A

SCHEME 48. Synthesis of (2S,4S)-N-((4-carbamimidoylthiophen-2-yl)methyl)-1-((4-phenoxybenzoyl)glycyl)-4-phenylpyrrolidine-2-carboxamide hydroformate (COMPOUND 97)

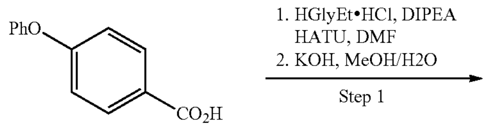

1

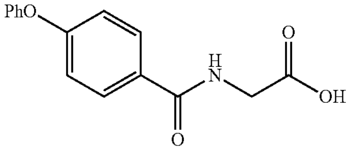

2

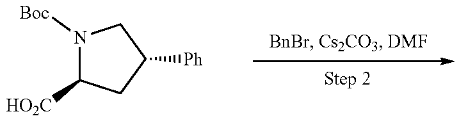

3

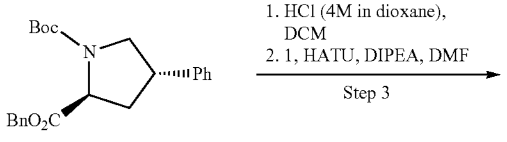

4

-continued

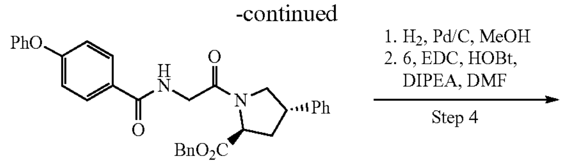

5

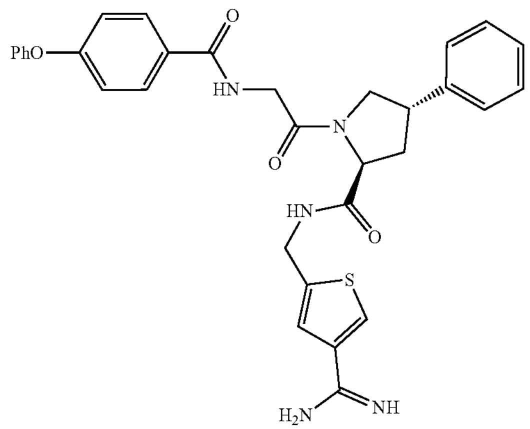

COMPOUND 97

Step 1: In a 100 mL round bottom flask equipped with a magnetic stirring bar was introduced intermediate 1 (2 g, 9.336 mmol, 1 equiv.), HATU (5.33 g, 14.0 mmol, 1.5 equiv.), and glycine ethyl ester (1.15 g, 11.2 mmol, 1.2 equiv.) which were dissolved in DMF (50 mL) at room temperature. DIPEA (6.03 g, 8.13 mL, 46.7 mmol, 5 equiv.) was added dropwise at the same temperature and left to stir. After disappearance of starting material followed by LC-MS, reaction was diluted with MeOH (25 mL) and water (25 mL) at 0° C. and sodium hydroxide (4.47 g, 187 mmol, 20 equiv.) in pellets was added to the stirring mixture. After disappearance of starting material followed by LC-MS, the reaction was extracted with ethyl acetate three times. The organic layers were gathered and washed with water and brine. Organic phase was dried with sodium sulfate and solvent was evaporated in vacuo. Crude product was suspended in a mixture of chloroform and ethanol (95:5) and recrystallized to afford compound 2 (2.21 g, 8.15 mmol, Yield 87.3%) as a white solid. HPLC-MS (ESI) (m/z) $[M+H]^+$, 271.1.

Step 2: In a 28 mL vial was introduced intermediate 3 (100 mg, 0.343 mmol, 1 equiv.) and cesium carbonate (145 mg, 0.446 mmol, 1.3 equiv.) which were dissolved in DMF (1.7 mL, 0.2 M). Benzyl bromide (76 mg, 0.446 mmol, 1.3 equiv.) was then added and the reaction was left to stir at room temperature until LC-MS analysis showed complete conversion of the starting material. Reaction was quenched with saturated ammonium chloride and extracted with ethyl acetate three times. The organic layers were gathered and washed with water and brine. Organic phase was dried with sodium sulfate and solvent was evaporated in vacuo. The crude product was purified by flash chromatography using hexanes/ethyl acetate (90:10 to 60:40) to afford intermediate 4 (127 mg, 0.334 mmol, Yield 97.2%) as a white solid). HPLC-MS (ESI) (m/z) [M+H]+: 381.2.

Step 3, part 1: In 20 mL vial equipped with a magnetic stirring bar, was introduced 2-intermediate 4 (157 mg, 0.412 mmol, 1 equiv.) which was dissolved in DCM (3 mL, 0.2 M) and the mixture was cooled to 0° C. HCl (117 mg, 0.079 mL, 1.029 mmol, 4M in dioxane, 2.5 equiv.) was added dropwise and the mixture was stirred at 0° C. overnight, upon which LC-MS analysis showed complete conversion of the starting material. The mixture was concentrated in vacuo and used without further purification in the next step.

Step 3, part 2: In a 20 mL vial equipped with a stirring bar were introduced, intermediate 4 (113 mg, 0.402 mmol, 1 equiv.) and compound 2 (0.131 g, 0.482 mmol, 1.2 equiv.) which were dissolved in DMF (2 mL, 0.201 M, 17.7 Vols). HATU (0.229 g, 0.602 mmol, 1.5 equiv.) was then added and finally DIPEA (0.26 g, 0.35 mL, 2.01 mmol, 5 equiv.) was added dropwise to the solution. The solution became instantaneously bright yellow. The reaction was left to stir at room temperature overnight. Upon completion of the reaction, monitored by LC-MS, the reaction had turned deep brown. The mixture was extracted with ethyl acetate three times. The organic layers were gathered and washed with water and brine. Organic phase was dried with sodium sulfate and solvent was evaporated in vacuo. The crude product was purified by flash chromatography, using hexanes/iPrOH (100:0 to 20:80) as eluent. The product intermediate 5 (128 mg, 0.239 mmol, Yield 59.6%) was obtained as a solid. HPLC-MS (ESI) (m/z) [M+H]+: 534.2.

Step 4, part 1: In a 8 mL vial equipped with a magnetic stirring bar was introduced intermediate 5 (128 mg, 0.239 mmol, 1 equiv.) which was dissolved in MeOH (2 mL, 0.12 M, 15.6 Vols). The mixture was degassed by bubbling nitrogen and Pd/C (0.239 mmol, 1 equiv.) was added. Finally, the reaction mixture was placed under an atmosphere of hydrogen and stirred until LC-MS analysis showed complete conversion of the starting material. The mixture was degassed by bubbling nitrogen and the mixture was filtered over celite. Solvent was evaporated in vacuo and (2S,4S)-1-{2-[(4-phenoxyphenyl)formamido]acetyl}-4-phenylpyrrolidine-2-carboxylic acid (82 mg, 0.184 mmol, Yield 77.1%) was used in subsequent step without further purification). HPLC-MS (ESI) (m/z) [M+H]+: 445.2.

Step 4, part 2: In a 20 mL vial equipped with a stirring bar were introduced, (2S,4S)-1-{2-[(4-phenoxyphenyl)formamido]acetyl}-4-phenylpyrrolidine-2-carboxylic acid (30 mg, 0.067 mmol, 1 equiv.), 5-(aminomethyl)thiophene-3-carboximidamide HCl salt (11 mg, 0.067 mmol, 1 equiv.), N-(3-Dimethylaminopropyl)-N-ethylcarbodiimide hydrochloride (19 mg, 0.101 mmol, 1.5 equiv.) and HOBt (14 mg, 0.101 mmol, 1.5 equiv.) which were dissolved in DMF (0.5 mL, 0.135 M, 16.7 Vols) and finally DIPEA (0.044 g, 0.059 mL, 0.337 mmol, 5 equiv.) was added dropwise to the solution. The reaction was monitored by LC-MS and when all starting material was consumed, the crude mixture was purified by reverse phase chromatography, using MeCN/H2O (100:0 to 50:50). Solvent was removed under reduced pressure, the solid triturated in formic acid/dioxane solution, filtered and dried under high vacuum to yield COMPOUND 97 (10 mg, 0.018 mmol, Yield 26.0%, Purity 94.3%, Rt=7.56 min) as a white solid. 1H NMR (CD3OD, 400 MHz): δ H 8.54 (1H, s), 5.99-5.91 (1H, m), 4.71 (1H, s), 4.27 (1H, s), 4.20 (1H, s), 4.18 (2H, s), 4.16-4.14 (2H, m), 3.85 (1H, s), 3.66-3.64 (2H, m), 3.61 (1H, s), 3.60 (1H, s), 3.58 (1H, s), 2.87 (5H, t, J=2.1 Hz), 2.22 (1H, s), 2.11-2.04 (2H, m). HPLC-MS (ESI) (m/z) $[M+H]^+$: 582.3, Rt=2.65 min.

SCHEME 49. Synthesis of (2S,4R)-N-((4-carbamimidoylthiophen-2-yl)methyl)-1-((4-phenoxybenzoyl)glycyl)-4-(trifluoromethyl)pyrrolidine-2-carboxamide hydrochloride (COMPOUND 98)

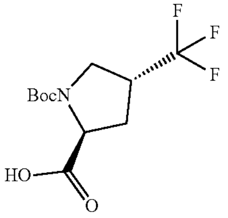

1

$Cs_2CO_3$, BnBr,
DMF
Step 1
Quantitative

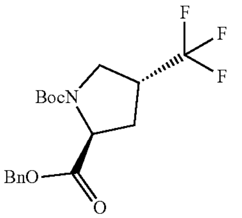

2

1. HCl, dioxane
2. 3, HATU,
DiPEA, DMF
Step 2
89%

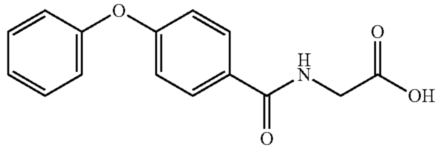

3

-continued

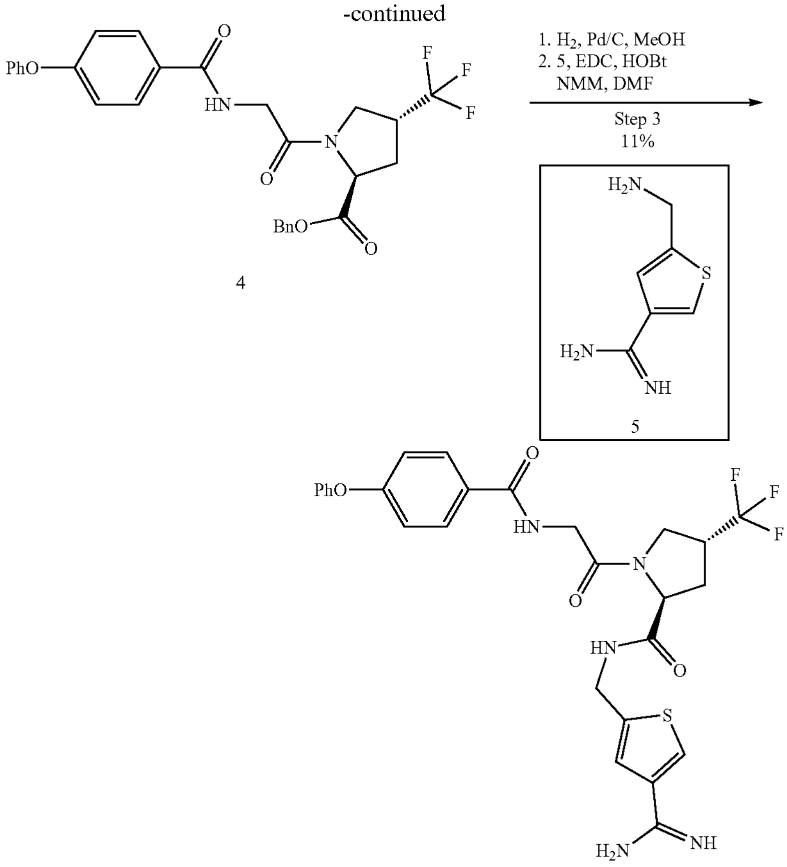

COMPOUND 98

Step 1: To a solution of intermediate 1 (0.1 g, 0.353 mmol, 1 equiv.) in DMF (0.706 mL, 0.5 M, 7.06 Vols) at 0° C. were added cesium carbonate (0.15 g, 0.459 mmol, 1.3 equiv.) followed by benzyl bromide (0.078 g, 0.055 mL, 0.459 mmol, 1.3 equiv.) and the resulting heterogeneous mixture was stirred for 16 h at 23° C. Reaction was diluted with ethyl acetate, celite was added to the suspension and the mixture was filtered on celite. Silica gel was added to prepare a drypack and the volatiles were removed in vacuo. The residue was purified on silica gel from 0-25% ethyl acetate/hexanes to give intermediate 2 (0.128 g, 0.343 mmol, Yield 97.1%) as a colorless oil. HPLC-MS (m/z) $[M+Na]^+$: 396, Rt=3.0 min.

Step 2, part 1: To a solution of intermediate 2 (0.075 g, 0.201 mmol, 1 equiv.) in dioxane (0.225 mL, 0.719 M, 3 Vols) at 0° C. was added a 4M solution of hydrochloric acid in dioxane (1.00 mL, 4.00 mmol, 20 equiv.) and the resulting mixture was stirred for 3 h at rt. The volatiles were then removed in vacuo to afford benzyl (2S,4R)-4-(trifluoromethyl)pyrrolidine-2-carboxylate hydrochloride (0.071 g, crude) as a colorless oil which was used directly in the next step without purification. HPLC-MS (m/z) $[M+H]^+$: 274, Rt=1.2 min.

Step 2, part 2: To a solution of compound 3 (0.065 g, 0.241 mmol, 1.2 equiv.) and benzyl (2S,4R)-4-(trifluoromethyl)pyrrolidine-2-carboxylate hydrochloride obtained above (0.071 g, 0.201 mmol, 1 equiv.) in DMF (0.35 mL) at 0° C. were added HATU (0.115 g, 0.302 mmol, 1.5 equiv.) followed by DIPEA (0.13 g, 0.175 mL, 1.005 mmol, 5 equiv.) and the resulting mixture was stirred at 0° C. Reaction was quenched with the addition of water. The mixture was taken in ethyl acetate, the aqueous layer separated, and the organic layer was washed twice with water. The combined aqueous layers were extracted with $Et_2O$. The combined organic layers were washed with brine, dried on $MgSO_4$, filtered and concentrated in vacuo. Silica gel was added to the mixture and the volatiles removed in vacuo. Solid residue was then chromatographed 0-100% ethyl acetate/hexanes on Isco to yield benzyl intermediate 4 (0.094 g, 0.179 mmol, Yield 88.8%) as a colorless oil. HPLC-MS (m/z) [M+H]+: 527, Rt=3.95 min.

Step 3, part 1: A solution of intermediate 4 (0.094 g, 0.178 mmol, 1 equiv.) in ethanol (1.78 mL, 0.1 M, 19.0 Vols) was degassed. Then Pd/C (0.019 g, 0.018 mmol, 0.1 equiv.) was added and the solution degassed by bubbling once more. Then a balloon of hydrogen was added, bubbling directly in the solution for 30 seconds. The resulting suspension was stirred at 23° C. for 1 h. The mixture was degassed with nitrogen, diluted with DCM, celite was added and the mixture was filtered on a pad of celite, rinsed with DCM then EtOH. The volatiles were removed in vacuo to give (2S,4R)-1-{2-[(4-phenoxyphenyl), formamido]acetyl}-4-(trifluoromethyl)pyrrolidine-2-carboxylic acid (0.085 g, crude) as a colorless solid which was used directly in the next step without purification. HPLC-MS (m/z) [M+H]+: 437, Rt=3.2 min.

Step 3, part 2: To a vial containing (2S,4R)-1-{2-[(4-phenoxyphenyl)formamido]acetyl}-4-(trifluoromethyl)pyrrolidine-2-carboxylic acid (0.042 g, 0.096 mmol, 1 equiv.), 1-hydroxybenzotriazole (0.026 g, 0.192 mmol, 2 equiv.) and N-(3-Dimethylaminopropyl)-N-ethylcarbodiimide hydrochloride (37 mg, 0.192 mmol, 2 equiv.) at 0° C. was added DMF (0.962 mL, 0.1 M, 22.9 Vols). After 45 minutes, compound 5 (26 mg, 0.115 mmol, 1.2 equiv.) followed by 4-methylmorpholine (0.049 g, 0.053 mL, 0.481 mmol, 5 equiv.) were added and the resulting mixture was stirred for 30 mins at 0° C. The reaction was quenched with the addition of water. NH4Cl(aq) and HCl 10% were added and the mixture was extracted with DCM four times. The combined organic layers were washed with brine, then Na2CO3 (aq), dried on MgSO4, filtered and concentrated in vacuo. The solid residue was then chromatographed on reverse phase 30-60% acetonitrile/water on Biotage the lyophilized. The fluffy white solid was then dissolved in methanol and HCl in methanol was added. The volatiles were removed under reduced pressure and the solid dried at high vacuum to yield COMPOUND 98 (0.006 g, 0.01 mmol, Yield 10.9%, Purity 95.8%, Rt=7.42 min) as a colorless solid. 1H NMR (400 MHz, $CD_3OD$): δ 9.13 (s, 1H); 8.83 (t, J=5.7 Hz, 1H); 8.22-8.26 (m, 1H); 7.84 (d, J=8.4 Hz, 2H); 7.38-7.50 (m, 3H); 7.20 (t, J=7.4 Hz, 1H); 6.98-7.06 (m, 4H); 4.59-4.67 (m, 3H); 3.71-4.24 (m, 4H); 3.28-3.40 (m, 1H); 2.65-2.81 (m, 1H); 2.21-2.54 (m, 2H). HPLC-MS (m/z) $[M+H]^+$: 574, Rt=2.54 min.

(1S,3S,4R)—N-((4-carbamimidoylthiophen-2-yl)methyl)-2-((4-phenoxybenzoyl)glycyl)-2-azabicyclo[2.2.1]heptane-3-carboxamide (COMPOUND 99)

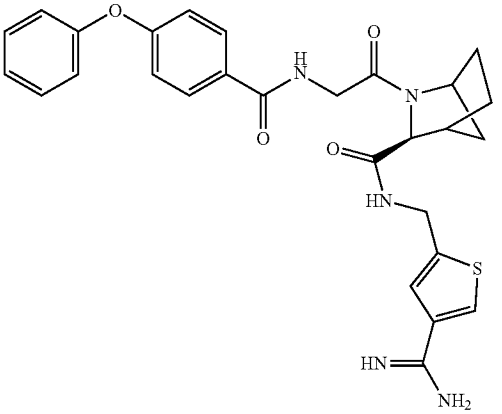 [SMILES: N=C(N)c1csc(CNC(=O)[C@@H]2C3CCC(CC3)N2C(=O)CNC(=O)c2ccc(Oc3ccccc3)cc2)c1]

Purity >99.0%, Rt=6.83 min. 1H NMR (400 MHz, CD3OD): δ 8.20-8.23 (m, 1H); 7.84 (d, J=8.3 Hz, 2H); 7.39-7.43 (m, 3H); 7.20 (t, J=7.4 Hz, 1H); 7.03 (dd, J=22.2, 8.0 Hz, 4H); 4.63 (s, 1H); 4.56 (s, 3H); 4.49 (s, 1H); 4.34 (d, J=16.7 Hz, 1H); 4.12 (d, J=17.3 Hz, 1H); 3.98 (s, 1H); 2.73 (s, 1H); 2.00 (d, J=10.3 Hz, 1H); 1.85 (s, 3H); 1.54 (t, J=13.5 Hz, 1H). HPLC-MS (m/z) $[M+H]^+$: 532.2, Rt=2.35 min.

(2S,4S)—N-((4-carbamimidoylthiophen-2-yl)methyl)-1-((4-phenoxybenzoyl)glycyl)-4-(trifluoromethyl)pyrrolidine-2-carboxamide Hydrochloride (COMPOUND 100)

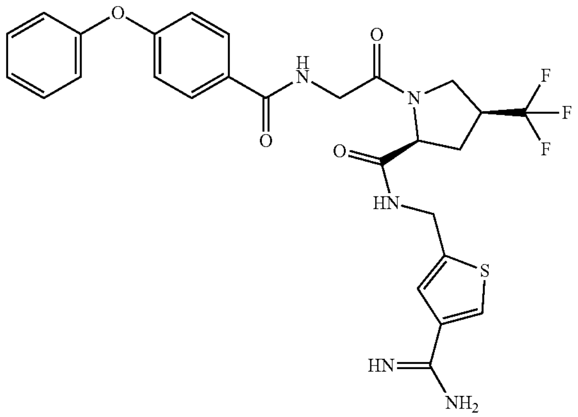 [SMILES: N=C(N)c1csc(CNC(=O)[C@@H]2C[C@H](C(F)(F)F)CN2C(=O)CNC(=O)c2ccc(Oc3ccccc3)cc2)c1]

Purity >99.0%, Rt=7.31 min. 1H NMR (400 MHz, CD3OD): δ 9.13-9.13 (m, 1H); 8.82 (t, J=8.4 Hz, 1H); 8.19-8.24 (m, 1H); 7.82-7.85 (m, 2H); 7.38-7.49 (m, 3H); 7.18-7.22 (m, 1H); 7.03 (dd, J=23.2, 8.2 Hz, 4H); 4.52-4.65 (m, 3H); 3.97-4.33 (m, 3H); 3.69-3.75 (m, 1H); 3.43-3.49 (m, 1H); 2.57-2.64 (m, 1H); 2.00-2.14 (m, 2H). HPLC-MS (m/z) [M+H]+: 574.2, Rt=2.49 min.

Method B

SCHEME 50. Synthesis of (2S,4R)-N-((4-carbamimidoylthiophen-2-yl)methyl)-4-(difluoromethoxy)-1-((4-phenoxybenzoyl)glycyl)pyrrolidine-2-carboxamide (COMPOUND 101)

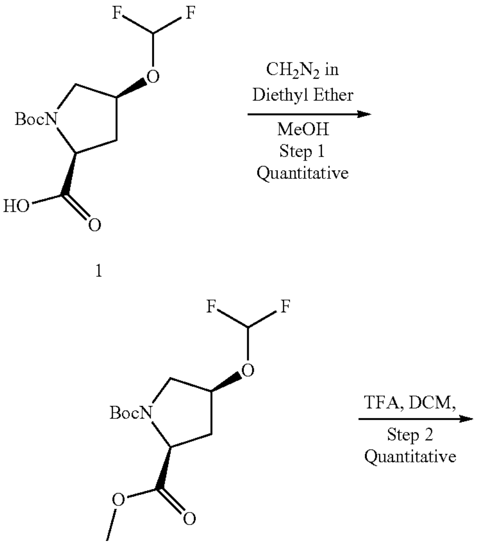

1

2

-continued

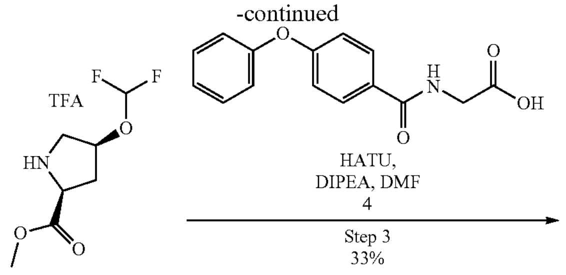

3

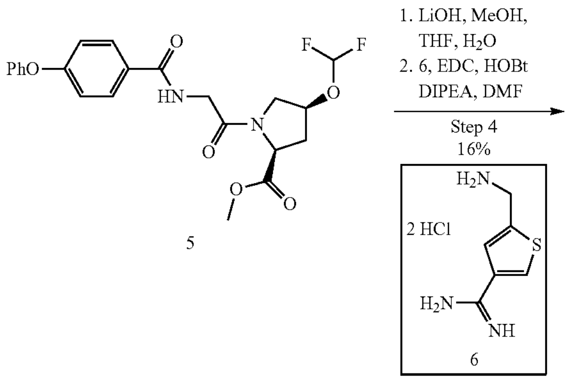

5

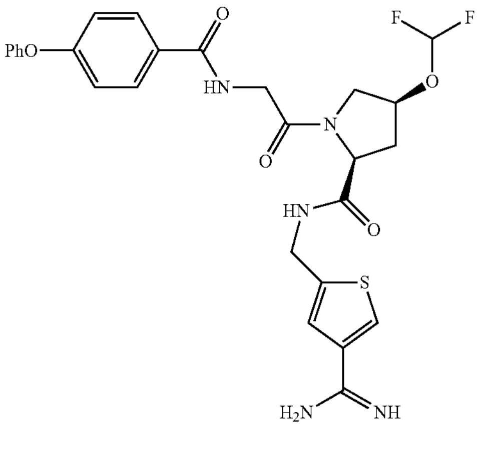

COMPOUND 102

Step 1: In a 50 mL conical bottom plastic flask equipped with a magnetic stirring bar was introduced under an atmosphere of argon, intermediate 1 (0.150 g, 0.549 mmol, 1 equiv.) diethyl ether (5 mL) and methanol (1 mL). The mixture was cooled down to 0° C. and a solution of diazomethane (0.4 M) in diethyl ether was added using a plastic pipette until a bright yellow color persisted. The reaction was left to stir for a further 30 minutes at −10° C. and then argon was bubbled into the reaction for 30 more minutes. Finally, the reaction was transferred to a glass round bottom flask and the solvent was removed in vacuo. The intermediate 2 was used without further purification. HPLC-MS (ESI) (m/z) $[M+Na]^+$: 318.2.

Step 2: To a solution of intermediate 2 (78 mg, 0.265 mmol, 1 equiv.) in DCM (0.5 mL, 0.53 M, 6.4 Vols) at 0° C. was added TFA (0.507 mL, 6.63 mmol, 25 equiv.). The reaction was stirred for 20 hours and concentrated in vacuo. Hexanes was added and the reaction concentrated, this was repeated two more times. The reaction was left under high vacuum for 16 hours and used as is in the next step. HPLC-MS (ESI) (m/z) [M+Na]+: 196.0, Rt=0.27 min. Gradient 0 to 1 min, 2% B; 1 to 4.5 min, 2 to 95% B.

Step 3: To a solution of intermediate 3 (0.083 g, 0.269 mmol, 1 equiv.) in DMF (2 mL, 0.113 M, 32.0 Vols) at 0° C. was added compound 4 (0.081 g, 0.299 mmol, 1.11 equiv.) followed by HATU (0.133 g, 0.35 mmol, 1.3 equiv.) and dropwise addition of DIPEA (0.141 mL, 0.808 mmol, 3 equiv.). The reaction was allowed to warm to RT while stirring overnight. Water was added to the reaction followed by EA and $NaHCO_3$ sat. The organic layer was separated, and the aqueous layer extracted three times with ethyl acetate. The combined organic layers were washed with brine/water (1/1), dried over Na2SO4, filtered and concentrated. The crude material was purified on a Redisep gold column (12 g) using a gradient of EA/hexanes (0 to 100%). The combined tubes were repurified on a Redisep gold column (12 g) using a gradient of DCM/DCM-MeOH 10% (0 to 40%). Provided intermediate 5 (0.040 g, 0.089 mmol, Yield 33.1%). HPLC-MS (ESI) (m/z) $[M+H]^+$: 449.0, Rt=3.77 min.

Step 4, part 1: To a solution of intermediate 5 (0.040 g, 0.089 mmol, 1 equiv.) in MeOH (0.2 mL), THF (0.2 mL) and water (0.2 mL) at 0° C. was added LiOH·H2O (4.0 mg, 0.107 mmol, 1.2 equiv.). This was stirred over night for 20 hours. 1N HCl (0.107 mL, 0.107 mmol, 1.2 equiv.) was added. Toluene was added and the reaction was concentrated in vacuo. This was repeated with toluene two more times and the material used directly in the next step without purification. HPLC-MS (ESI) (m/z) [M+H]+: 434.9, Rt=3.54 min.

Step 4, part 2: To a solution of (2S,4S)-4-(difluoromethoxy)-1-{2-[(4-phenoxyphenyl) formamido] acetyl}pyrrolidine-2-carboxylic acid (0.038 g, 0.089 mmol, 1 equiv.) in DMF (0.8 mL, 0.111 M, 20.8 Vols) at 0° C. was added EDC (0.034 g, 0.177 mmol, 2 equiv.) and HOBT (0.024 g, 0.177 mmol, 2 equiv.) followed by DIPEA (0.015 mL, 0.089 mmol, 1 equiv.). This was stirred for 10 mins. Compound 6 (0.024 g, 0.106 mmol, 1.2 equiv.) then DIPEA (0.031 mL, 0.177 mmol, 2 equiv.) were added and the reaction stirred for 16 hours. Water was added to the reaction followed by ethyl acetate. The organic layer was separated, and the aqueous layer extracted three times with ethyl acetate. The combined organic layers were washed with brine/water (1/1) and dried over Na2SO4, filtered and concentrated in vacuo. The residue was then purified on reverse phase providing COMPOUND 101 (0.007 g, 0.012 mmol, Yield 15.5%, Purity 96.9%, Rt=6.69 min) as a white solid following lyophilisation. 1H NMR (400 MHz, $CD_3OD$): Rotamers δ 8.56 (br s, 1H); 8.24 and 8.20 (s, 1H); 7.83 (d, J=8.3 Hz, 2H); 7.51 and 7.42 (s, 1H); 7.41 (t, J=7.6 Hz, 2H); 7.19 (t, J=7.4 Hz, 1H); 7.05 (d, J=8.0 Hz, 2H); 6.99 (d, J=8.3 Hz, 2H); 6.50 and 6.46 (t, J=74.4 Hz, 1H); 4.99 (s, 1H); 4.57 (m, 3H); 4.07-4.23 (m, 2H); 3.85-3.98 (m, 2H); 3.73 (dd, J=12.8, 4.7 Hz, 0.2H); 2.59-2.65 and 2.43-2.49 (m, 1H); 2.32-2.38 and 2.18-2.25 (m, 1H). (m), and 3.55-3.58 (m, 2H); 2.70 and 2.55-2.58 (m, 2H); 2.08 and 2.04 (s, 3H). HPLC-MS (ESI): m/z [M+H]+: 572.2, Rt=2.42 min.

(2S,3aS,7aS)—N-((4-carbamimidoylthiophen-2-yl)methyl)-1-((4-phenoxybenzoyl)glycyl)octahydro-1H-indole-2-carboxamide Hydroformate (COMPOUND 102)

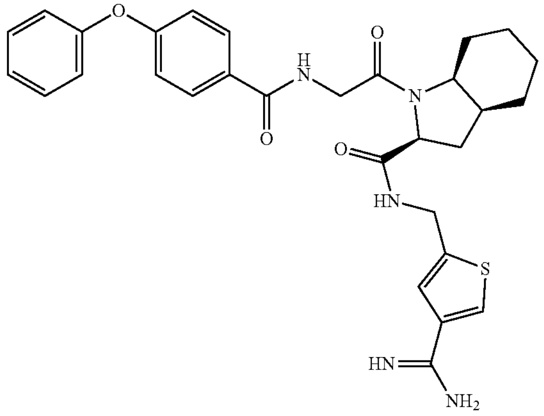 [SMILES: N=C(N)c1csc(CNC(=O)[C@@H]2C[C@@H]3CCCC[C@@H]3N2C(=O)CNC(=O)c2ccc(Oc3ccccc3)cc2)c1]

Purity 97.3%, Rt=7.62 min. 1H NMR (CD3OD, 400 MHz): δ 8.54 (1H, s), 8.19 (1H, s), 7.82 (2H, d, J=8.5 Hz), 7.43-7.39 (3H, m), 7.20 (1H, t, J=7.4 Hz), 7.02 (4H, dd, J=25.6, 8.2 Hz), 4.63-4.53 (2H, m), 4.44 (1H, t, J=9.0 Hz), 4.30 (1H, d, J=16.4 Hz), 4.14-4.04 (2H, m), 2.45 (1H, s), 2.21-2.02 (3H, m), 1.77 (3H, d, J=18.1 Hz), 1.63 (1H, d, J=13.4 Hz), 1.55-1.28 (7H, m). HPLC-MS (m/z) $[M+H]^+$: 560.2, Rt=2.34 min.

Method C.

SCHEME 51. Synthesis of (4S)-N-((4-carbamimidoylthiophen-2-yl)methyl)-4-fluorophenoxy)-1-((4-phenoxybenzoyl)glycyl)pyrrolidine-2-carboxamide hydrochloride (COMPOUND 103)

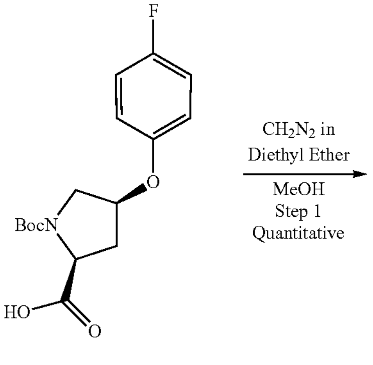

1

-continued

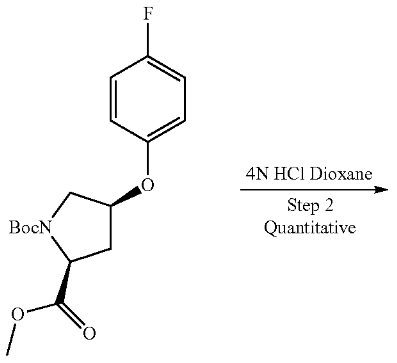

2

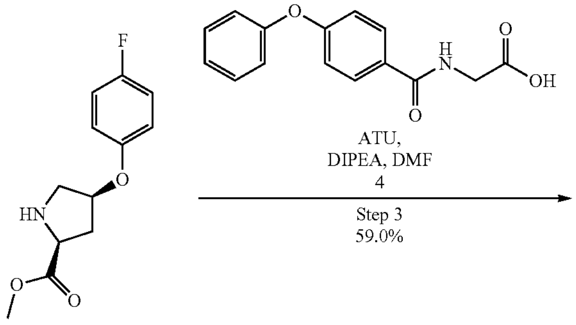

3

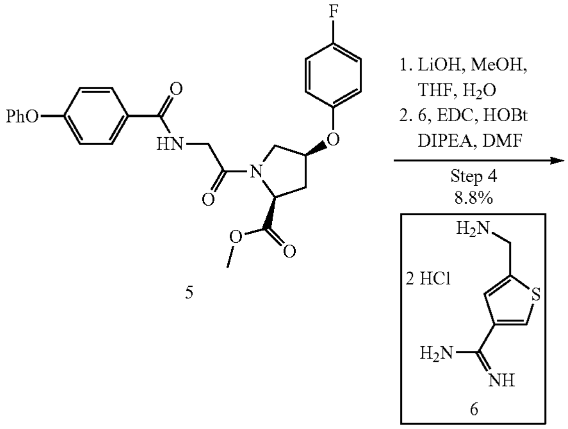

5

6

-continued

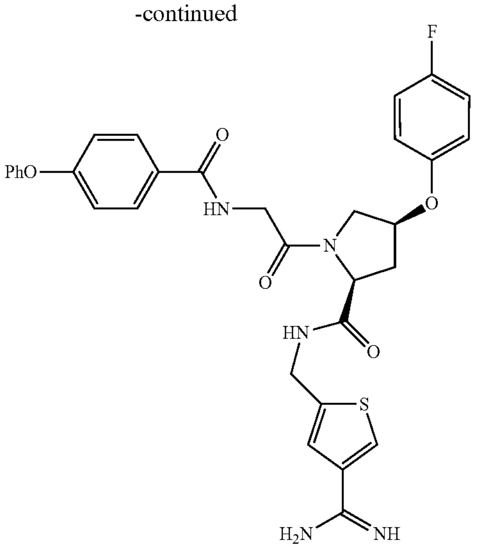

COMPOUND 103

Step 1: In a 50 mL conical bottom plastic flask equipped with a magnetic stirring bar was introduced under an atmosphere of argon, intermediate 1 (0.150 g, 0.461 mmol, 1 equiv.) diethyl ether (5 mL) and methanol (1 mL). The mixture was cooled down to 0° C. and a solution of diazomethane (0.4 M) in diethyl ether was added using a plastic pipette until a bright yellow color persisted. The reaction was left to stir for a further 30 minutes at −10° C. and then argon was bubbled into the reaction for 30 more minutes. Finally, the reaction was transferred to a glass round bottom flask and the solvent was removed in vacuo. The product was used without further purification. HPLC-MS (ESI): (m/z) $[M+Na]^+$. 362.1, Rt=3.57 min.

Step 2: To a solution of intermediate 2 (0.078 g, 0.231 mmol, 1 equiv.) in dioxane (1 mL, 0.231 M, 12.8 Vols) at 0° C. was added 4 N HCl in dioxane (0.173 mL, 0.692 mmol, 3 equiv.). This was stirred for 20 hours. The reaction was concentrated and used as is in the next step.

Step 3: To a solution of intermediate 3 (0.062 g, 0.226 mmol, 1 equiv.) in DMF (2 mL, 0.113 M, 32.0 Vols) at 0° C. was added compound 4 (0.068 g, 0.251 mmol, 1.11 equiv.) followed by HATU (0.111 g, 0.294 mmol, 1.3 equiv.) and dropwise addition of DIPEA (0.118 mL, 0.679 mmol, 3 equiv.). The reaction was allowed to warm to RT while stirring overnight. Water was added to the reaction followed by ethyl acetate and NaHCO3 sat. The organic layer was separated, and the aqueous layer extracted three times with ethyl acetate. The combined organic layers were washed with brine/water (1/1), dried over Na2SO4, filtered and concentrated in vacuo. The crude material was purified on a Redisep gold column (12 g) using a gradient of EA/hexanes (0 to 100%). The combined tunes were purified again on a Redisep gold column (12 g) using a gradient of MeOH/DCM 10% in DCM (0 to 40%). Provided intermediate 5 (0.066 g, 0.134 mmol, Yield 59.0%). HPLC-MS (ESI) (m/z) $[M+H]^+$: 493.2, Rt=3.61 min.

Step 4, part 1: To a solution of intermediate 5 (0.063 g, 0.129 mmol, 1 equiv.) in MeOH (0.3 mL), THF (0.3 mL) and H2O (0.3 mL) at 0° C. was added lithium hydroxide monohydrate (0.006 g, 0.142 mmol, 1.1 equiv.). This was stirred over night for 20 hours then 1N HCl (0.142 mL, 0.142 mmol, 1.1 equiv.) was added. The reaction was concentrated. Toluene was added to the material and the solvent removed in vacuo. This was repeated two more times. The material was placed on high vacuum for 3 hours and used without further purification in the next step.

Step 4, part 2: To a solution of intermediate 5 (0.062 g, 0.129 mmol, 1 equiv.) in DMF (1 mL, 0.129 M, 16.207 Vols) at 0° C. was added EDC (0.037 g, 0.193 mmol, 1.5 equiv.) followed by DIPEA (0.034 mL, 0.193 mmol, 1.5 equiv.). This was stirred for 10 mins then compound 6 (0.035 g, 0.155 mmol, 1.2 equiv.) then the DIPEA (0.079 mL, 0.451 mmol, 3.5 equiv.) was added and the reaction stirred for 16 hours. Water was added to the reaction followed by ethyl acetate. The organic layer was separated, and the aqueous layer extracted 3× with ethyl acetate. The combined organic layers were washed with brine/water (1/1) and dried over Na2SO4, filtered and concentrated in vacuo. The residue was then purified on reverse phase using a biotage and lyophilized. This material was dissolved in DCM. 4 N dioxane was added and the mixture concentrated. The solid was dried in vacuo providing COMPOUND 103 (0.007 g, 0.011 mmol, Yield 8.8%, Purity 92.9%, Rt=7.58 min). 1H NMR (400 MHz, CD3OD): Rotamers 8.97 and, 8.67 (t, J=6.0 Hz, 1H); 8.21 and 8.18 (d, J=1.6 Hz, 1H); 7.86 and 7.83 (d, J=8.6 Hz, 2H); 7.39-7.49 (m, 3H); 7.21 (t, J=7.4 Hz, 1H); 7.06 (d, J=8.0 Hz, 2H); 6.92-7.02 (m, 4H); 6.68-6.76 (m, 2H); 5.07 (s, 1H); 4.69 (dd, J=6.9, 4.4 Hz, 1H); 4.60-4.64 (m, 1H); 4.57 and 4.54 (d, J=5.2 Hz, 1H); 4.31 (d, J=16.6 Hz, 1H); 4.05 (m, 4H); 3.55-3.90 (m, 3H); 2.49 (m, 2H). HPLC-MS (ESI+): m/z $[M+H]^+$: 616.3, Rt=2.59 min.

(2S,4S)—N-((4-carbamimidoylthiophen-2-yl)methyl)-1-((4-phenoxybenzoyl)glycyl)-4-(m-tolyloxy)pyrrolidine-2-carboxamide (COMPOUND 104)

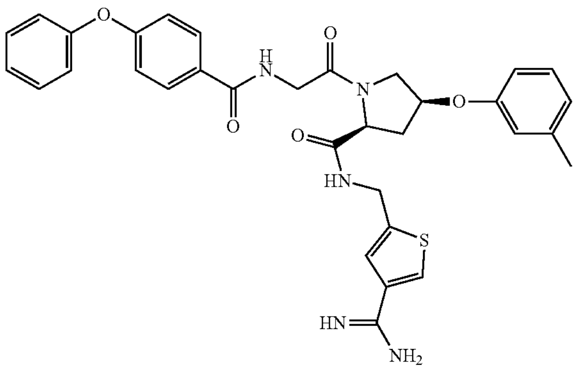 [SMILES: Cc1cccc(O[C@H]2C[C@@H](C(=O)NCc3cc(C(=N)N)cs3)N(C(=O)CNC(=O)c3ccc(Oc4ccccc4)cc3)C2)c1]

Purity 98.5%, Rt=7.39 min. 1H NMR (400 MHz, CD3OD): Rotamers δ 8.54 (br s, 1H); 8.21 and 8.17 (d, J=1.7 Hz, 1H); 7.85 and 7.82 (d, J=8.5 Hz, 2H); 7.37-7.48 (m, 3H); 7.20 (t, J=7.4 Hz, 1H); 7.10 (t, J=7.7 Hz, 1H); 7.01-7.06 (m, 2H); 6.99 (d, J=8.5 Hz, 2H); 6.76 (d, J=7.4 Hz, 1H); 6.49-6.57 (m, 2H); 5.11 (s, 1H); 4.55-4.73 (m, 3H); 4.28-4.32 (m, 1H); 3.98-4.09 (m, 3H); 2.45-2.60 (m, 2H); 2.27 (s, 3H). HPLC-MS (m/z) [M+H]+: 612.3, Rt=2.67 min.

(2S,4S)—N-((4-carbamimidoylthiophen-2-yl) methyl)-1-((4-phenoxybenzoyl)glycyl)-4-(o-tolyloxy)pyrrolidine-2-carboxamide Hydrochloride (COMPOUND 105)

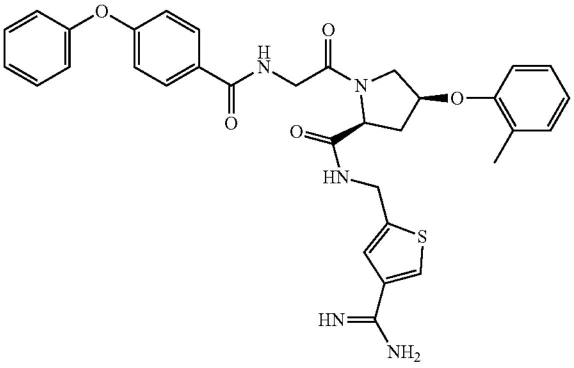 [SMILES: Cc1ccccc1O[C@H]1C[C@@H](C(=O)NCc2cc(C(=N)N)cs2)N(C(=O)CNC(=O)c2ccc(Oc3ccccc3)cc2)C1]

Purity >99%, Rt=8.14 min. 1H NMR (400 MHz, CD3OD): Rotamers δ 9.01 and 8.69 (t, J=6.1 Hz, 1H); 8.16 and 8.13 (d, J=1.6 Hz, 1H); 7.85 and 7.81 (d, J=8.5 Hz, 2H); 7.36-7.46 (m, 3H); 7.20 (t, J=7.4 Hz, 1H); 7.01-7.14 (m, 4H); 6.98 (d, J=8.7 Hz, 2H); 6.81-6.86 (m, 2H); 5.11 and 5.00 (s, 1H); 4.68-4.75 (m, 2H); 4.51 (d, J=15.5 Hz), 4.41 (d, J=15.7 Hz) and 4.30 (d, J=16.6 Hz, 2H); 3.96-4.14 (m, 3H); 3.82 (d, J=13.3 Hz), 3.73 (m), 3.65 (m), and 3.55-3.58 (m, 2H); 2.70 and 2.55-2.58 (m, 2H); 2.08 and 2.04 (s, 3H). HPLC-MS (m/z) (ESI+) [M+H]+: 612.3, Rt=2.65 min.

SCHEME 52. Synthesis of (2S,4R)-N-((4-carbamimidoylthiophen-2-yl)methyl)-4-fluoro-4-(fluoromethyl)-1-((4-phenoxybenzoyl)glycyl)pyrrolidine-2-carboxamide(COMPOUND 106)

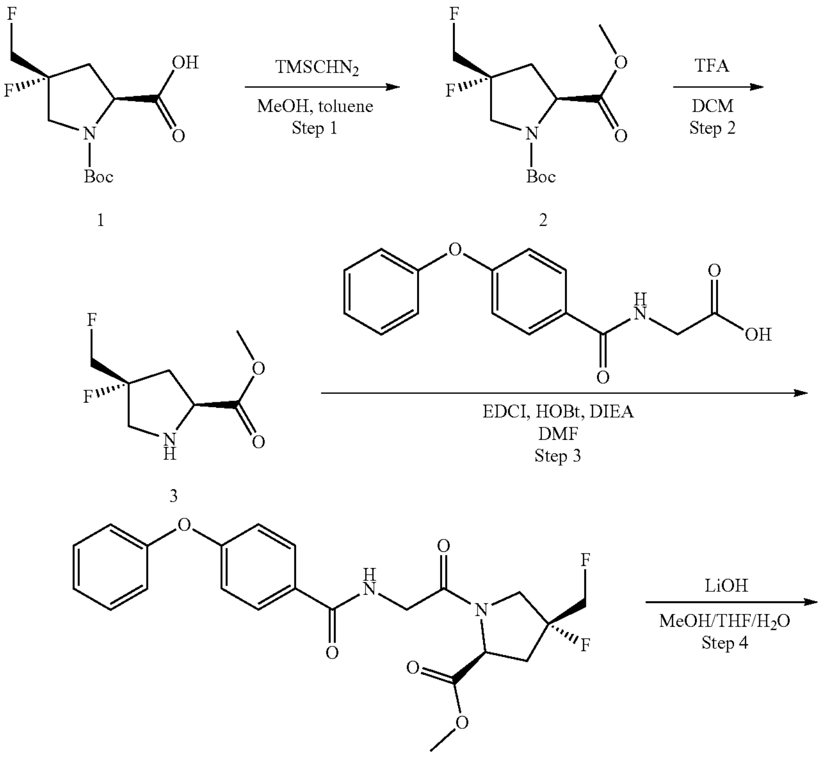

4

-continued

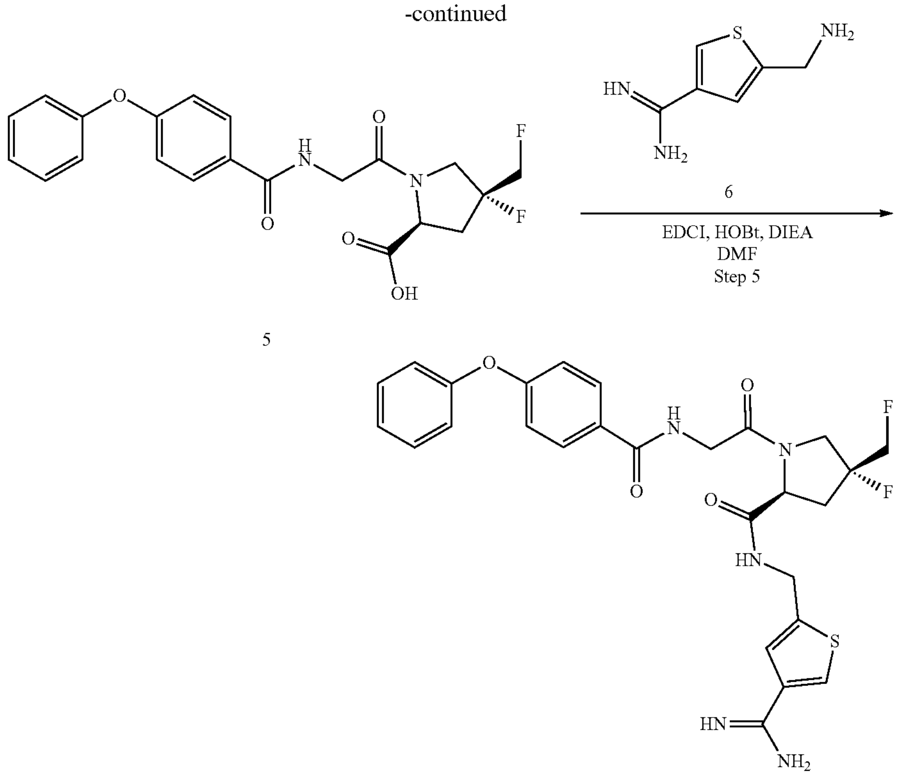

5

COMPOUND 106

Step 1: To a solution of intermediate 1 (134 mg, 0.5 mmol) in MeOH (1.2 mL) and toluene (3 mL) was added $TMSCHN_2$ (0.5 mL, 2M, 1 mmol) dropwise at 0° C. under $N_2$ atmosphere. The mixture was stirred at room temperature for 1.5 hours. The mixture was quenched with glacial acetic acid, filtered and concentrated to dryness under reduced pressure. The residue was purified by column chromatography on silica gel (PE:EtOAc=20:1 to 5:1) to give intermediate 2 (111 mg, yield 78.7%) as yellow oil. LC/MS (ESI) m/z: 280 $(M+H)^+$.

Step 2: To a solution of intermediate 2 (111 mg, 0.4 mmol) in DCM (2 mL) was added TFA (1 mL) at 0° C. The mixture was stirred at room temperature for 1 hour. The reaction mixture was concentrated to dryness under reduced pressure and the residue was re-dissolved in DCM. The mixture was again concentrated under reduced pressure to remove residual TFA and dried under vacuum to give intermediate 3 (71 mg, yield 98.6%) as yellow oil, which was used directly in the next step without further purification. LC/MS (ESI) m/z: 180 $(M+H)^+$.

Step 3: To a mixture of intermediate 3 (71 mg, 0.4 mmol) and (4-phenoxybenzoyl)glycine (108 mg, 0.4 mmol) in DMF (4 mL) was added DIPEA (0.3 mL) at 0° C. under $N_2$ atmosphere, followed by addition of HOBt (81 mg, 0.6 mmol) and EDCI (138 mg, 0.72 mmol). The mixture was stirred at 35° C. for 12 hours. The mixture was quenched with water and diluted with EtOAc. The organic layer was washed with saturated aq. $NH_4Cl$ solution and brine, dried over anhydrous $Na_2SO_4$, filtered and concentrated to dryness under reduced pressure. The residue was purified by column chromatography on silica gel (DCM:MeOH=100:1 to 20:1) to give intermediate 4 (138 mg, yield 79.8%) as yellow oil. LC/MS (ESI) m/z: 433 $(M+H)^+$.

Step 4: To a solution of intermediate 4 (100 mg, 0.23 mmol) in MeOH (2 mL) and THF (1 mL) was added a solution of $LiOH{\cdot}H_2O$ (48 mg, 1.15 mmol) in $H_2O$ (1 mL) at 0° C. The mixture was stirred at 25° C. for 2 hours. The mixture was diluted with water and extracted with EtOAc. The water layer was acidified with 2M aq. HCl solution to pH=3 and extracted with EtOAc. The organic layer was washed with brine, dried over anhydrous $Na_2SO_4$, filtered and concentrated to dryness under reduced pressure to give intermediate 5 (70 mg, yield 72.9%) as white solid, which was used directly in the next step without further purification. LC/MS (ESI) m/z: 419 $(M+H)^+$.

Step 5: To a mixture of intermediate 5 (40 mg, 0.1 mmol) and compound 6 (47 mg, 0.3 mmol) in DMF (3 mL) was added DIPEA (0.2 mL, 1 mmol) at 0° C. under $N_2$ atmosphere, followed by addition of HOBt (20 mg, 0.15 mmol) and EDCI (35 mg, 0.18 mmol). The mixture was stirred at 35° C. for 16 hours. The mixture was quenched with water and diluted with EtOAc. The organic layer was washed with saturated aq. $NH_4Cl$ solution and brine, dried over anhydrous $Na_2SO_4$, filtered and concentrated to dryness under reduced pressure. The residue was purified by column chromatography on silica gel (DCM:MeOH=100:1 to 20:1) and further purified by prep-HPLC to give COMPOUND 106 (1.8 mg, yield 3.2%) as white solid. $^1H$ NMR (400 MHz, $CD_3OD$) δ 8.53 (s, 1H), 8.21 (s, 1H), 7.85 (d, J=8.8 Hz, 2H), 7.46-7.37 (m, 3H), 7.21 (t, J=7.4 Hz, 1H), 7.06 (d, J=8.0 Hz, 2H), 7.01 (d, J=8.4 Hz, 2H), 4.79-4.58 (m, 5H), 4.28-4.08 (m, 3H), 4.00-3.89 (m, 1H), 2.83-2.50 (m, 1H), 2.30-2.13 (m, 1H); LC/MS (ESI) m/z: 556 $(M+H)^+$.

SCHEME 53. Synthesis of ((1S,3S,5S)-N-[(5-carbamididoylthiophen-2-yl)methyl]-5-methyl-2-{2-[(4-phenoxyphenyl)formamido]acetyl}-2-azabicyclo[3.1.0]hexane-3-carboxamide (Compound 107).

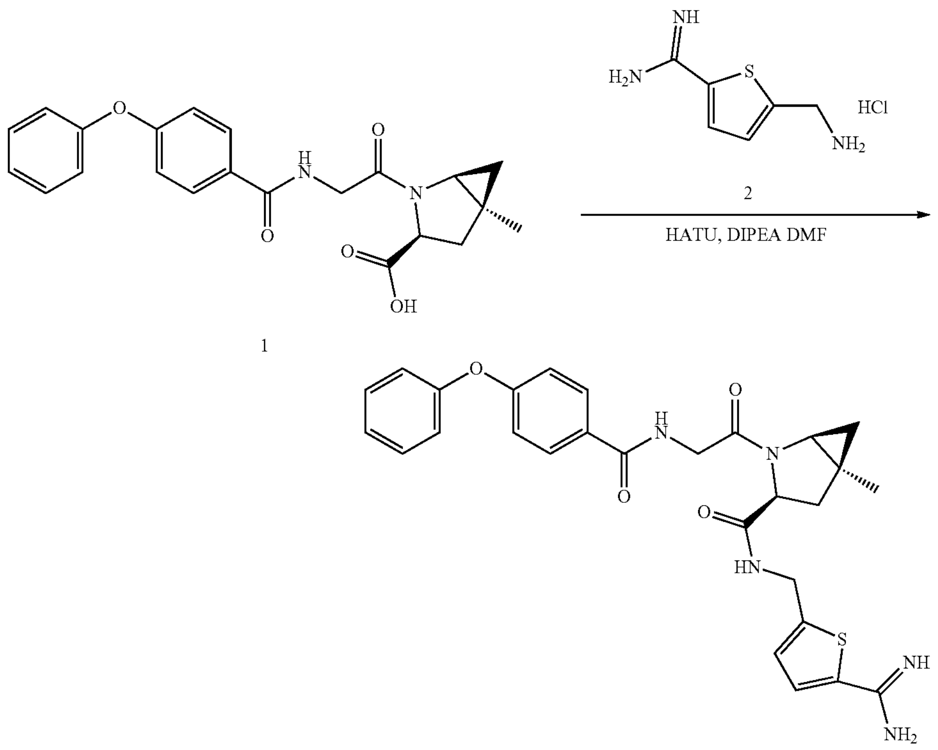

COMPOUND 107

To a mixture of intermediate 1 (20 mg, 0.046 mmol, 1 equiv.) and 5-aminothiophene-3-carboximidamide (2) (10 mg, 0.05 mmol, 1.1 equiv.) in DMF (1 mL) was added HATU (26 mg, 0.069 mmol, 1.5 equiv.), followed by N-Ethyldiisopropylamine (0.032 mL, 0.0183 mmol, 4 equiv.). The reaction was stirred at room temperature for 0.5 hours and then purified directly using prep-HPLC to give Compound 107 (16 mg, yield 62.0%) as a white sticky solid. $^1H$ NMR (400 MHz, $CDCl_3$) δ 9.84 (bs, 1H), 8.63 (bs, 1H), 8.45 (s, 1H), 8.29 (bs, 1H), 7.84 (d, J=8.4 Hz, 1H), 7.52 (s, 1H), 7.31 (t, J=6.0 Hz, 2H), 7.13 (1, m, 1H), 6.93 (d, J=8.0 Hz, 1H), 6.87 (d, J=8.41 Hz, 1H), 6.75 (s, 1H), 4.75-4.72 (m, 2H), 4.54-4.51 (m, 1H), 4.14 (d, J=12.8 Hz, 1H), 3.93 (d, J=12.8 Hz, 1H), 3.66-3.64 (m, 1H) 3.32 (s, 1H), 3.08 (m, 1H), 2.41 (t, J=8.40 Hz, 1H), 2.16 (d, J=13.2 Hz, 1H), 1.47-1.44 (m, 1H), 1.42 (d, J=3.4 Hz, 1H), 1.28-1.26 (m, 1H), 1.23 (s, 3H). LC/MS (ESI) m/z: 532 $(M+H)^+$.

Example 3. Non-Limiting Examples of Compounds of the Present Disclosure

Table 1 shows illustrative complement pathway with characterizing data. The assay of Example 4 was used to determine the $IC_{50}$'s of the compounds. Other standard complement assays are also available. Three *s are used to denote compounds with an $IC_{50}$ less than 100 nanomolar; two s indicates a compound with an $IC_{50}$ greater than 100 nanomolar and less than 1 micromolar, and one * denotes compounds with an $IC_{50}$ greater than 1 micromolar.

TABLE 1

| Non-limiting Examples of Compounds of the Present Disclosure | | | | |
|---|---|---|---|---|
| # | Structure and Name | C1s Protease Activity | RT min (Method A or B) | MS (M + 1) |
| 1 | 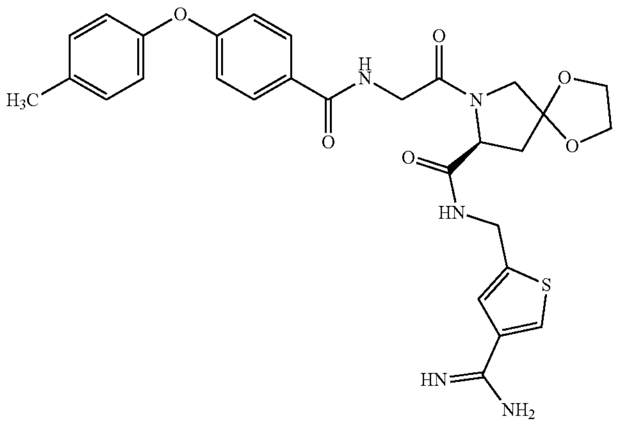 [SMILES: Cc1ccc(Oc2ccc(C(=O)NCC(=O)N3CC4(C[C@H]3C(=O)NCc3cc(C(=N)N)cs3)OCCO4)cc2)cc1] (S)-N-((4-carbamimidoylthiophen-2-yl)methyl)-7-((4-(p-tolyloxy)benzoyl)glycyl)-1,4-dioxa-7-azaspiro[4.4]nonane-8-carboxamide | *** | 1.98 (A) | 578 |
| 2 | 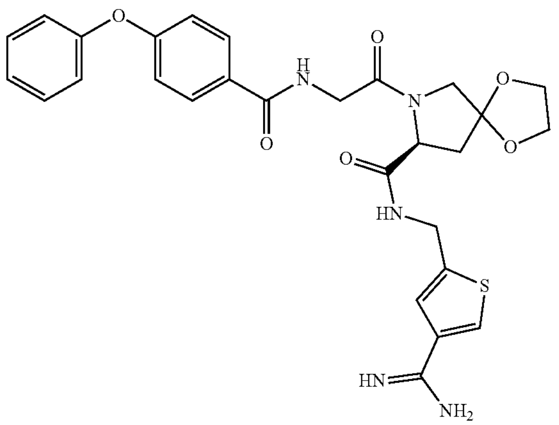 [SMILES: N=C(N)c1csc(CNC(=O)[C@@H]2CC3(CN2C(=O)CNC(=O)c2ccc(Oc4ccccc4)cc2)OCCO3)c1] (S)-N-((4-carbamimidoylthiophen-2-yl)methyl)-7-((4-phenoxybenzoyl)glycyl)-1,4-dioxa-7-azaspiro[4.4]nonane-8-carboxamide | *** | 1.82 (A) | 564 |
| 3 | 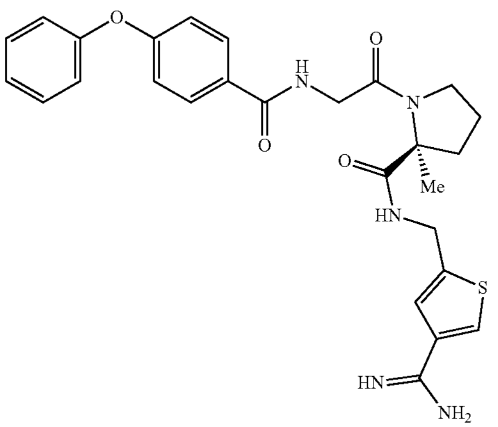 [SMILES: C[C@@]1(C(=O)NCc2cc(C(=N)N)cs2)CCCN1C(=O)CNC(=O)c1ccc(Oc2ccccc2)cc1] (S)-N-((4-carbamimidoylthiophen-2-yl)methyl)-2-methyl-1-((4-phenoxybenzoyl)glycyl)pyrrolidine-2-carboxamide | *** | 1.87 (A) | 520 |

TABLE 1-continued

| Non-limiting Examples of Compounds of the Present Disclosure | | | | |
|---|---|---|---|---|
| # | Structure and Name | C1s Protease Activity | RT min (Method A or B) | MS (M + 1) |
| 4 | 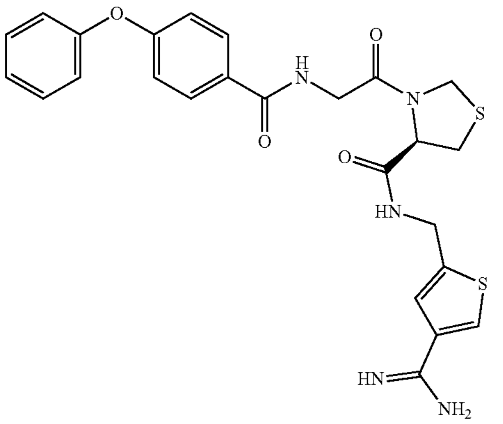 [SMILES: N=C(N)c1csc(CNC(=O)[C@@H]2CSCN2C(=O)CNC(=O)c2ccc(Oc3ccccc3)cc2)c1] (R)-N-((4-carbamimidoylthiophen-2-yl)methyl)-3-((4-phenoxybenzoyl)glycyl)thiazolidine-4-carboxamide | *** | 1.28 (A) | 524 |
| 5 | 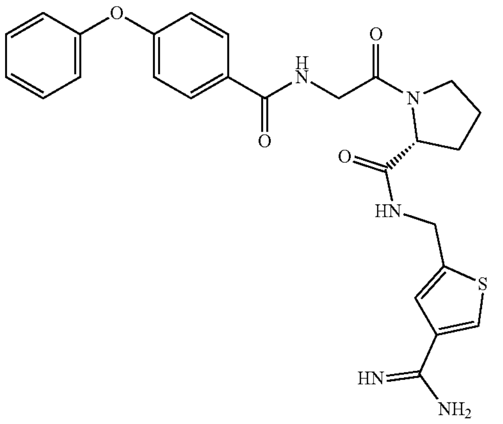 (R)-N-((4-carbamimidoylthiophen-2-yl)methyl)-1-((4-phenoxybenzoyl)glycyl)pyrrolidine-2-carboxamide | * | 1.22 (A) | 506 |
| 6 | 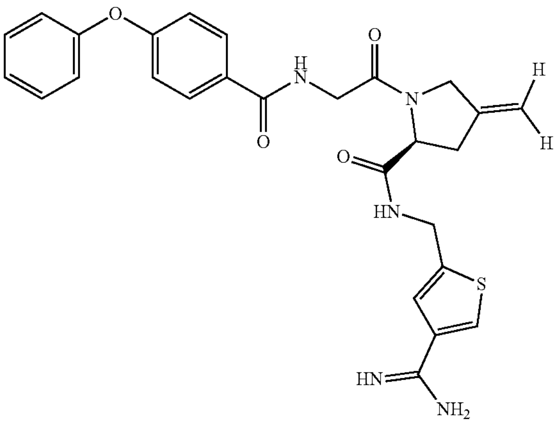 [SMILES: C=C1C[C@@H](C(=O)NCc2cc(C(=N)N)cs2)N(C(=O)CNC(=O)c2ccc(Oc3ccccc3)cc2)C1] (S)-N-((4-carbamimidoylthiophen-2-yl)methyl)-4-methylene-1-((4-phenoxybenzoyl)glycyl)pyrrolidine-2-carboxamide | *** | 1.34 (A) | 518 |

TABLE 1-continued

Non-limiting Examples of Compounds of the Present Disclosure

| # | Structure and Name | C1s Protease Activity | RT min (Method A or B) | MS (M + 1) |
|---|---|---|---|---|
| 7 | 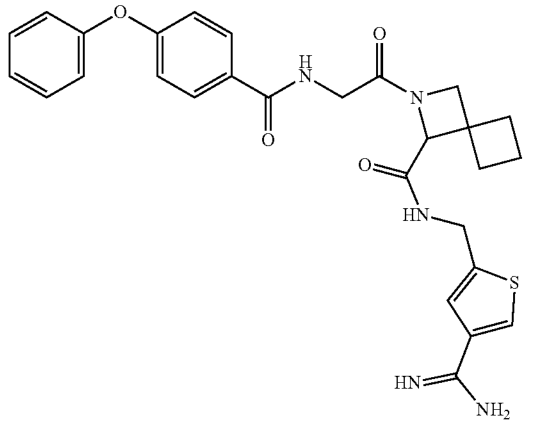 [SMILES: N=C(N)c1csc(CNC(=O)C2N(C(=O)CNC(=O)c3ccc(Oc4ccccc4)cc3)CC23CCC3)c1] N-((4-carbamimidoylthiophen-2-yl)methyl)-2-((4-phenoxybenzoyl)glycyl)-2-azaspiro[3.3]heptane-1-carboxamide | *** | 1.41 (A) | 532 |
| 8 | 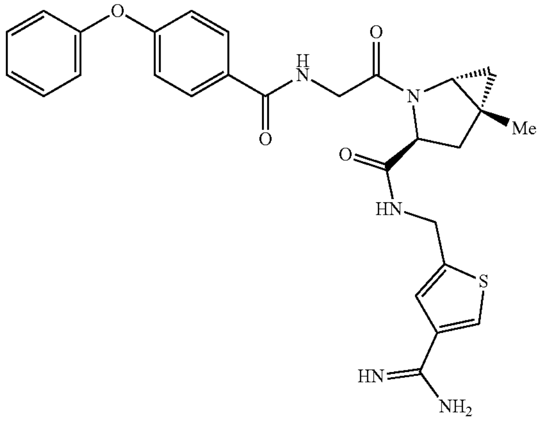 [SMILES: C[C@@]12C[C@@H](C(=O)NCc3cc(C(=N)N)cs3)N(C(=O)CNC(=O)c3ccc(Oc4ccccc4)cc3)[C@@H]1C2] (1R,3S,5R)-N-((4-carbamimidoylthiophen-2-yl)methyl)-5-methyl-2-((4-phenoxybenzoyl)glycyl)-2-azabicyclo[3.1.0]hexane-3-carboxamide | *** | 1.43 (A) | 532 |
| 9 | 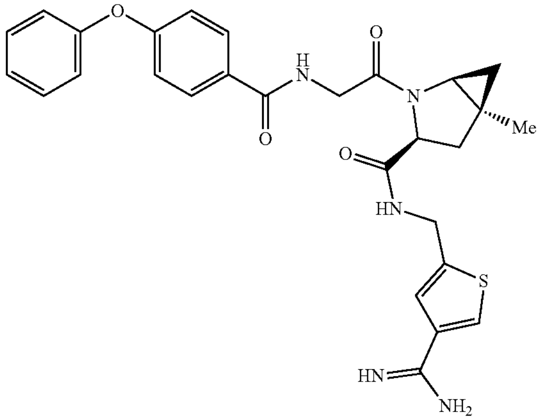 [SMILES: C[C@@]12C[C@@H]1N(C(=O)CNC(=O)c1ccc(Oc3ccccc3)cc1)[C@H](C(=O)NCc1cc(C(=N)N)cs1)C2] (1S,3S,5S)-N-((4-carbamimidoylthiophen-2-yl)methyl)-5-methyl-2-((4-phenoxybenzoyl)glycyl)-2-azabicyclo[3.1.0]hexane-3-carboxamide | *** | 1.38 (A) | 532 |

TABLE 1-continued

| Non-limiting Examples of Compounds of the Present Disclosure | | | | |
|---|---|---|---|---|
| # | Structure and Name | C1s Protease Activity | RT min (Method A or B) | MS (M + 1) |
| 10 | 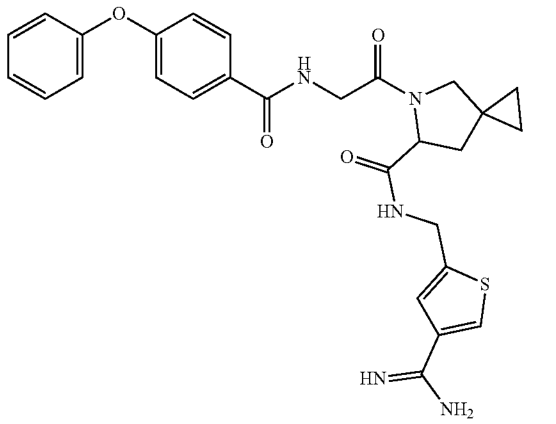 [SMILES: N=C(N)c1csc(CNC(=O)C2CC3(CC3)CN2C(=O)CNC(=O)c2ccc(Oc3ccccc3)cc2)c1] N-((4-carbamimidoylthiophen-2-yl)methyl)-5-((4-phenoxybenzoyl)glycyl)-5-azaspiro[2.4]heptane-6-carboxamide | ** | 1.33 (A) | 532 |
| 11 | 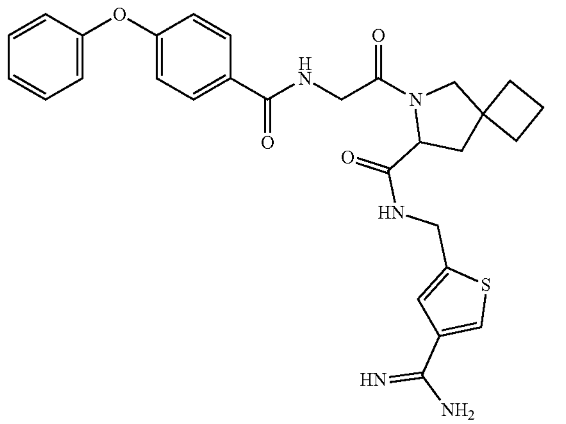 [SMILES: N=C(N)c1csc(CNC(=O)C2CC3(CCC3)CN2C(=O)CNC(=O)c2ccc(Oc3ccccc3)cc2)c1] N-((4-carbamimidoylthiophen-2-yl)methyl)-6-((4-phenoxybenzoyl)glycyl)-6-azaspiro[3.4]octane-7-carboxamide | *** | 1.47 (A) | 546 |
| 12 | 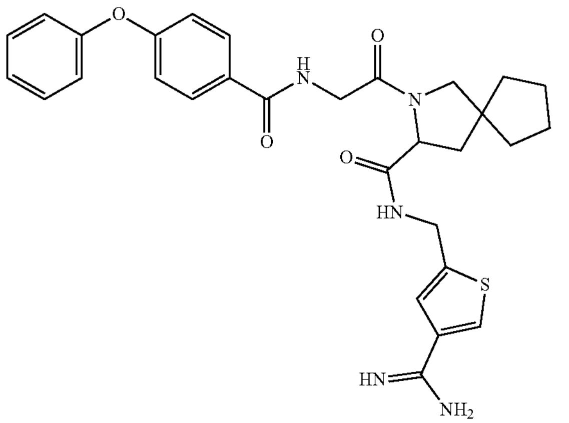 [SMILES: N=C(N)c1csc(CNC(=O)C2CC3(CCCC3)CN2C(=O)CNC(=O)c2ccc(Oc3ccccc3)cc2)c1] N-((4-carbamimidoylthiophen-2-yl)methyl)-2-((4-phenoxybenzoyl)glycyl)-2-azaspiro[4.4]nonane-3-carboxamide | *** | 1.59 (A) | 560 |

TABLE 1-continued

| # | Structure and Name | C1s Protease Activity | RT min (Method A or B) | MS (M + 1) |
|---|---|---|---|---|
| | Non-limiting Examples of Compounds of the Present Disclosure | | | |
| 13 | 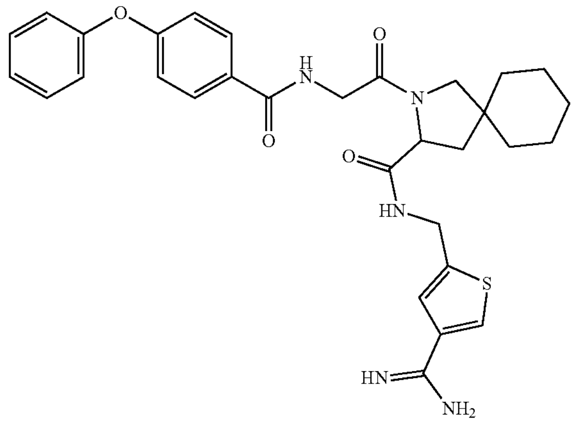 [SMILES: N=C(N)c1csc(CNC(=O)C2CC3(CCCCC3)CN2C(=O)CNC(=O)c2ccc(Oc3ccccc3)cc2)c1] N-((4-carbamimidoylthiophen-2-yl)methyl)-2-((4-phenoxybenzoyl)glycyl)-2-azaspiro[4.5]decane-3-carboxamide | * | 1.59 (A) | 574 |
| 14 | 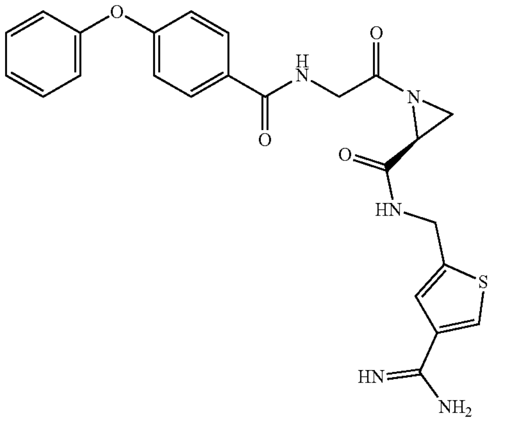 [SMILES: N=C(N)c1csc(CNC(=O)[C@@H]2CN2C(=O)CNC(=O)c2ccc(Oc3ccccc3)cc2)c1] (S)-N-((4-carbamimidoylthiophen-2-yl)methyl) 1-((4-phenoxybenzoyl)glycyl)aziridine-2-carboxamide | ** | 1.19 (A) | 478 |
| 15 | 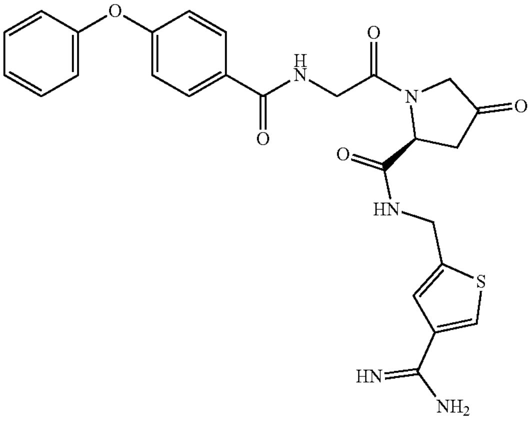 [SMILES: N=C(N)c1csc(CNC(=O)[C@@H]2CC(=O)CN2C(=O)CNC(=O)c2ccc(Oc3ccccc3)cc2)c1] (S)-N-((4-carbamimidoylthiophen-2-yl)methyl)-4-oxo-1-((4-phenoxybenzoyl)glycyl)pyrrolidine-2-carboxamide | *** | 1.18 (A) | 520 |

TABLE 1-continued

| Non-limiting Examples of Compounds of the Present Disclosure | | | | |
|---|---|---|---|---|
| # | Structure and Name | C1s Protease Activity | RT min (Method A or B) | MS (M + 1) |
| 16 | 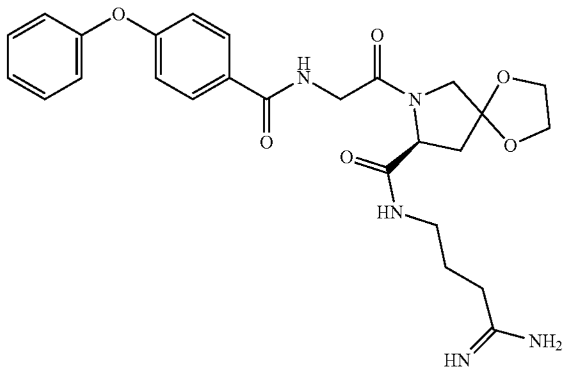 [SMILES: N=C(N)CCCNC(=O)[C@@H]1CC2(CN1C(=O)CNC(=O)c1ccc(Oc3ccccc3)cc1)OCCO2] (S)-N-(4-amino-4-iminobutyl)-7-((4-phenoxybenzoyl)glycyl)-1,4-dioxa-7-azaspiro[4.4]nonane-8-carboxamide | * | 1.17 (A) | 510 |
| 17 | 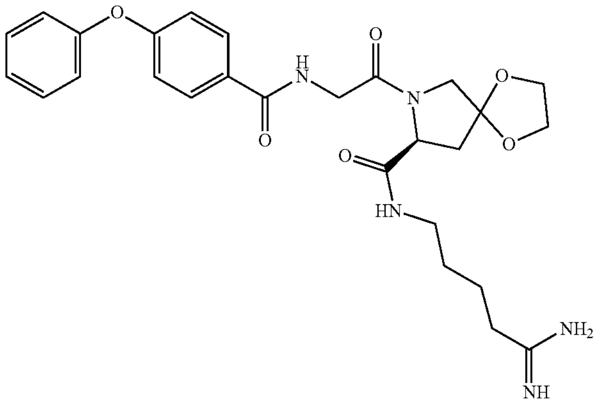 [SMILES: N=C(N)CCCCNC(=O)[C@@H]1CC2(CN1C(=O)CNC(=O)c1ccc(Oc3ccccc3)cc1)OCCO2] (S)-N-(5-amino-5-iminopentyl)-7-((4-phenoxybenzoyl)glycyl)-1,4-dioxa-7-azaspiro[4.4]nonane-8-carboxamide | * | 1.18 (A) | 525 |
| 18 | 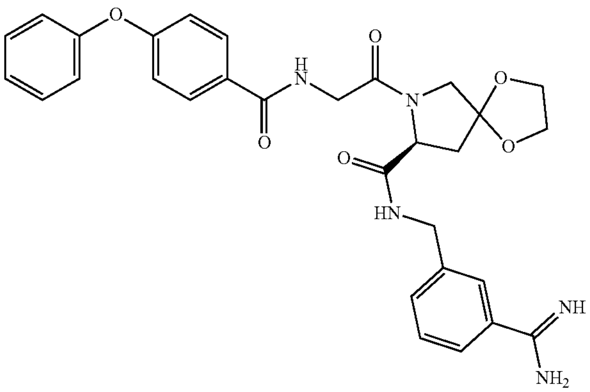 [SMILES: N=C(N)c1cccc(CNC(=O)[C@@H]2CC3(CN2C(=O)CNC(=O)c2ccc(Oc4ccccc4)cc2)OCCO3)c1] (S)-N-(3-carbamimidoylbenzyl)-7-((4-phenoxybenzoyl)glycyl)-1,4-dioxa-7-azaspiro[4.4]nonane-8-carboxamide | * | 1.26 (A) | 558 |

TABLE 1-continued

| Non-limiting Examples of Compounds of the Present Disclosure | | | | |
|---|---|---|---|---|
| # | Structure and Name | C1s Protease Activity | RT min (Method A or B) | MS (M + 1) |
| 19 | 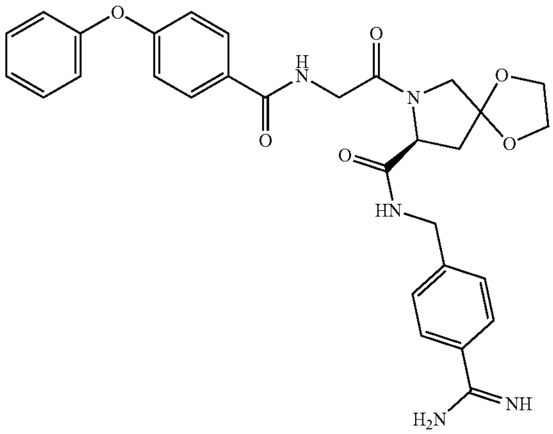 [SMILES: N=C(N)c1ccc(CNC(=O)[C@@H]2CC3(CN2C(=O)CNC(=O)c2ccc(Oc4ccccc4)cc2)OCCO3)cc1] (S)-N-(4-carbamimidoylbenzyl)-7-((4-phenoxybenzoyl)glycyl)-1,4-dioxa-7-azaspiro[4.4]nonane-8-carboxamide | *** | 1.23 (A) | 558 |
| 20 | 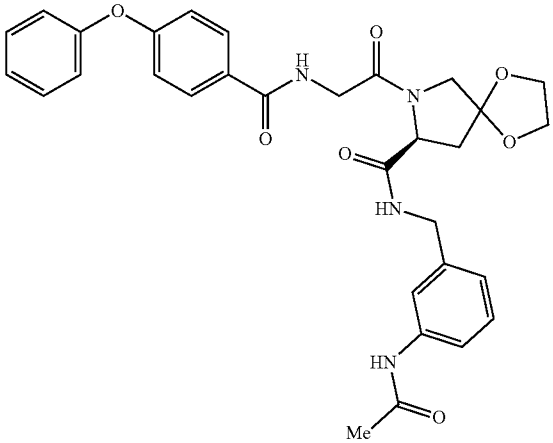 [SMILES: CC(=O)Nc1cccc(CNC(=O)[C@@H]2CC3(CN2C(=O)CNC(=O)c2ccc(Oc4ccccc4)cc2)OCCO3)c1] (S)-N-(3-acetamidobenzyl)-7-((4-phenoxybenzoyl)glycyl)-1,4-dioxa-7-azaspiro[4.4]nonane-8-carboxamide | * | 1.69 (A) | 573 |
| 21 | 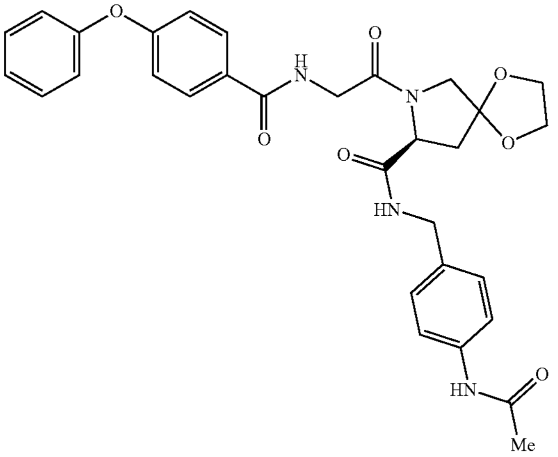 [SMILES: CC(=O)Nc1ccc(CNC(=O)[C@@H]2CC3(CN2C(=O)CNC(=O)c2ccc(Oc4ccccc4)cc2)OCCO3)cc1] (S)-N-(4-acetamidobenzyl)-7-((4-phenoxybenzoyl)glycyl)-1,4-dioxa-7-azaspiro[4.4]nonane-8-carboxamide | * | 1.63 (A) | 573 |

TABLE 1-continued

| # | Structure and Name | C1s Protease Activity | RT min (Method A or B) | MS (M + 1) |
|---|---|---|---|---|
| | Non-limiting Examples of Compounds of the Present Disclosure | | | |
| 22 | 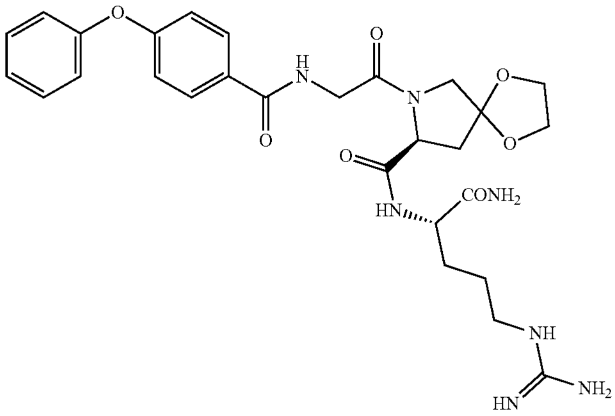 [SMILES: N=C(N)NCCC[C@H](NC(=O)[C@@H]1CC2(CN1C(=O)CNC(=O)c1ccc(Oc3ccccc3)cc1)OCCO2)C(N)=O] (S)-N-((S)-1-amino-5-guanidino-1-oxopentan-2-yl)-7-((4-phenoxybenzoyl)glycyl)-1,4-dioxa-7-azaspiro[4.4]nonane-8-carboxamide | * | 1.11 (A) | 582 |
| 23 | 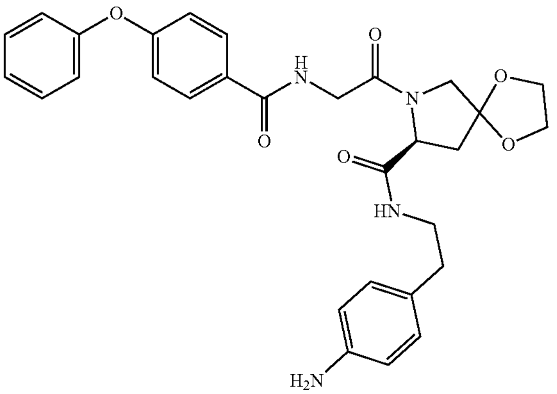 [SMILES: Nc1ccc(CCNC(=O)[C@@H]2CC3(CN2C(=O)CNC(=O)c2ccc(Oc4ccccc4)cc2)OCCO3)cc1] (S)-N-(4-aminophenethyl)-7-((4-phenoxybenzoyl)glycyl)-1,4-dioxa-7-azaspiro[4.4]nonane-8-carboxamide | * | 1.30 (A) | 545 |
| 24 | 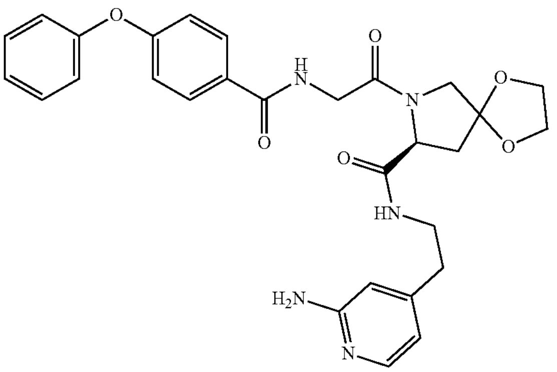 [SMILES: Nc1cc(CCNC(=O)[C@@H]2CC3(CN2C(=O)CNC(=O)c2ccc(Oc4ccccc4)cc2)OCCO3)ccn1] (S)-N-(2-(2-aminopyridin-4-yl)ethyl)-7-((4-phenoxybenzoyl)glycyl)-1,4-dioxa-7-azaspiro[4.4]nonane-8-carboxamide | * | 1.19 (A) | 546 |

TABLE 1-continued

| Non-limiting Examples of Compounds of the Present Disclosure | | | | |
|---|---|---|---|---|
| # | Structure and Name | C1s Protease Activity | RT min (Method A or B) | MS (M + 1) |
| 25 | 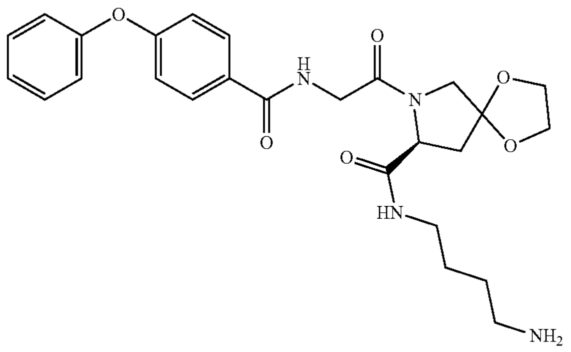 [SMILES: NCCCCNC(=O)[C@@H]1CC2(CN1C(=O)CNC(=O)c1ccc(Oc3ccccc3)cc1)OCCO2] (S)-N-(4-aminobutyl)-7-((4-phenoxybenzoyl)glycyl)-1,4-dioxa-7-azaspiro[4.4]nonane-8-carboxamide | * | 1.12 (A) | 497 |
| 26 | 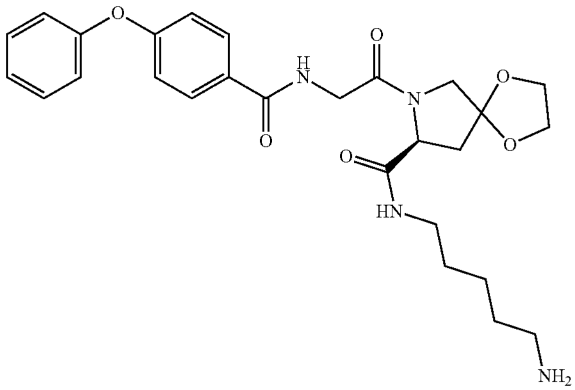 [SMILES: NCCCCCNC(=O)[C@@H]1CC2(CN1C(=O)CNC(=O)c1ccc(Oc3ccccc3)cc1)OCCO2] (S)-N-(5-aminopentyl)-7-((4-phenoxybenzoyl)glycyl)-1,4-dioxa-7-azaspiro[4.4]nonane-8-carboxamide | * | 1.16 (A) | 511 |
| 27 | 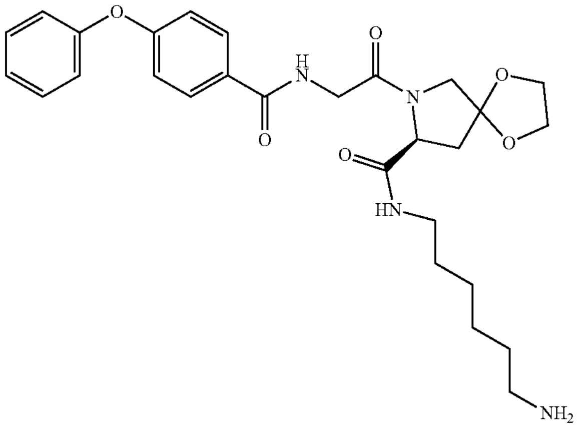 [SMILES: NCCCCCCNC(=O)[C@@H]1CC2(CN1C(=O)CNC(=O)c1ccc(Oc3ccccc3)cc1)OCCO2] (S)-N-(6-aminohexyl)-7-((4-phenoxybenzoyl)glycyl)-1,4-dioxa-7-azaspiro[4.4]nonane-8-carboxamide | * | 1.22 (A) | 526 |

TABLE 1-continued

| # | Non-limiting Examples of Compounds of the Present Disclosure<br>Structure and Name | C1s Protease Activity | RT min (Method A or B) | MS (M + 1) |
|---|---|---|---|---|
| 28 | 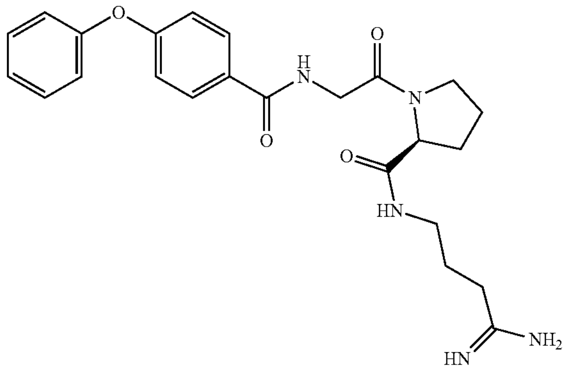 [SMILES: N=C(N)CCCNC(=O)[C@@H]1CCCN1C(=O)CNC(=O)c1ccc(Oc2ccccc2)cc1]<br>(S)-N-(4-amino-4-iminobutyl)-1-((4-phenoxybenzoyl)glycyl)pyrrolidine-2-carboxamide | * | | |
| 29 | 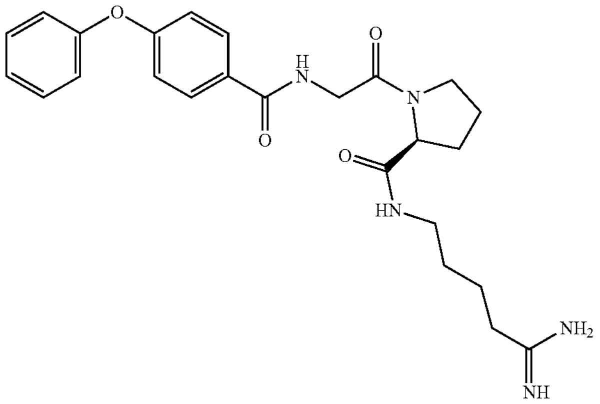 [SMILES: N=C(N)CCCCNC(=O)[C@@H]1CCCN1C(=O)CNC(=O)c1ccc(Oc2ccccc2)cc1]<br>(S)-N-(5-amino-5-iminopentyl)-1-((4-phenoxybenzoyl)glycyl)pyrrolidine-2-carboxamide | * | | |
| 30 | 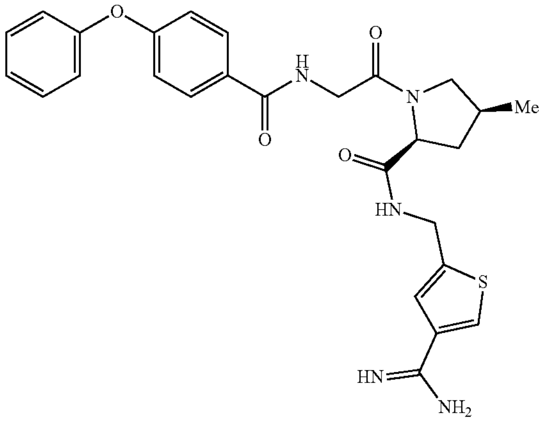 [SMILES: C[C@H]1C[C@@H](C(=O)NCc2cc(C(=N)N)cs2)N(C(=O)CNC(=O)c2ccc(Oc3ccccc3)cc2)C1]<br>(2S,4S)-N-((4-carbamimidoylthiophen-2-yl)methyl)-4-methyl-1-((4-phenoxybenzoyl)glycyl)pyrrolidine-2-carboxamide | *** | 1.31 (A) | 520 |

TABLE 1-continued

Non-limiting Examples of Compounds of the Present Disclosure

| # | Structure and Name | C1s Protease Activity | RT min (Method A or B) | MS (M + 1) |
| --- | --- | --- | --- | --- |
| 31 | 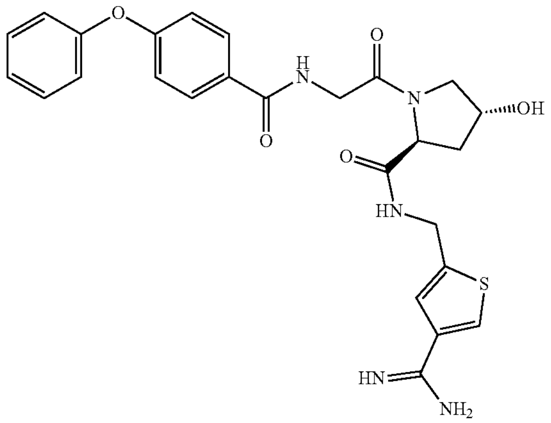 [SMILES: N=C(N)c1csc(CNC(=O)[C@@H]2C[C@@H](O)CN2C(=O)CNC(=O)c2ccc(Oc3ccccc3)cc2)c1] (2S,4R)-N-((4-carbamimidoylthiophen-2-yl)methyl)-4-hydroxy-1-((4-phenoxybenzoyl)glycyl)pyrrolidine-2-carboxamide | *** | 1.05 (A) | 522 |
| 32 | 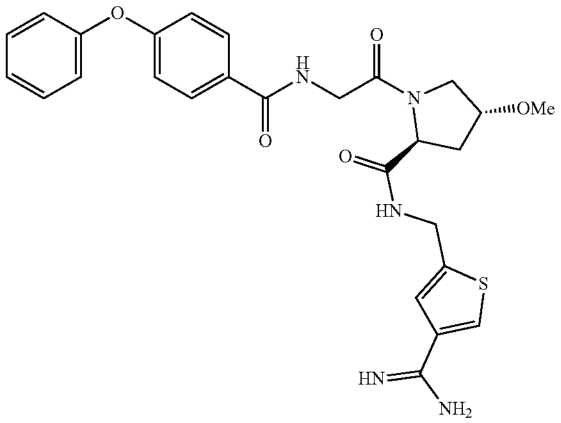 [SMILES: CO[C@@H]1C[C@@H](C(=O)NCc2cc(C(=N)N)cs2)N(C(=O)CNC(=O)c2ccc(Oc3ccccc3)cc2)C1] (2S,4R)-N-((4-carbamimidoylthiophen-2-yl)methyl)-4-methoxy-1-((4-phenoxybenzoyl)glycyl)pyrrolidine-2-carboxamide | *** | | |
| 33 | 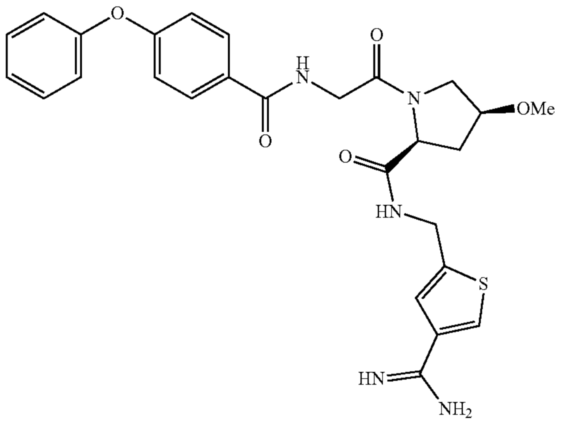 [SMILES: CO[C@H]1C[C@@H](C(=O)NCc2cc(C(=N)N)cs2)N(C(=O)CNC(=O)c2ccc(Oc3ccccc3)cc2)C1] (2S,4S)-N-((4-carbamimidoylthiophen-2-yl)methyl)-4-methoxy-1-((4-phenoxybenzoyl)glycyl)pyrrolidine-2-carboxamide | *** | | |

TABLE 1-continued

| # | Structure and Name | C1s Protease Activity | RT min (Method A or B) | MS (M + 1) |
|---|---|---|---|---|
| | Non-limiting Examples of Compounds of the Present Disclosure | | | |
| 34 | 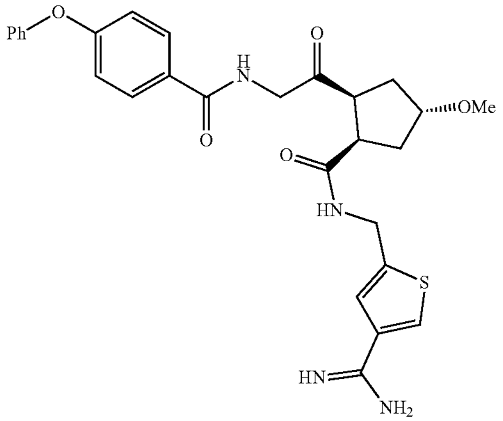 [SMILES: CO[C@H]1C[C@H](C(=O)CNC(=O)c2ccc(Oc3ccccc3)cc2)[C@H](C(=O)NCc2cc(C(=N)N)cs2)C1] N-(2-((1S,2R,4S)-2-(((4-carbamimidoylthiophen-2-yl)methyl)carbamoyl)-4-methoxycyclopentyl)-2-oxoethyl)-4-phenoxybenzamide | * | 2.29 (B) | 535 |
| 35 | 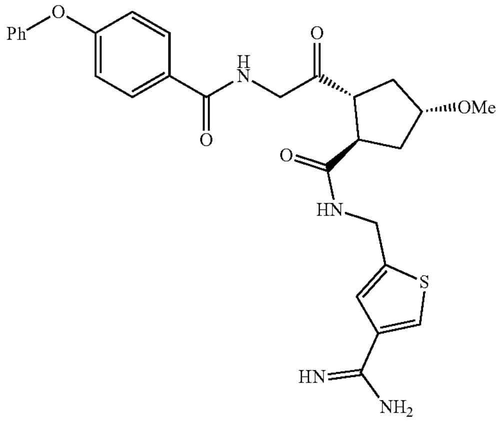 [SMILES: CO[C@H]1C[C@@H](C(=O)CNC(=O)c2ccc(Oc3ccccc3)cc2)[C@H](C(=O)NCc2cc(C(=N)N)cs2)C1] N-(2-((1R,2R,4S)-2-(((4-carbamimidoylthiophen-2-yl)methyl)carbamoyl)-4-methoxycyclopentyl)-2-oxoethyl)-4-phenoxybenzamide | ** | 2.85 (B) | 535 |
| 36 | 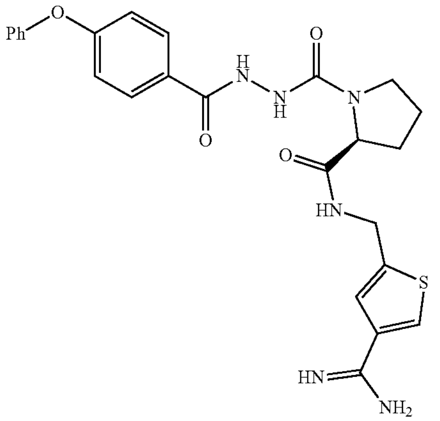 [SMILES: N=C(N)c1csc(CNC(=O)[C@@H]2CCCN2C(=O)NNC(=O)c2ccc(Oc3ccccc3)cc2)c1] (S)-N-((4-carbamimidoylthiophen-2-yl)methyl)-1-(2-(4-phenoxybenzoyl)hydrazine-1-carbonyl)pyrrolidine-2-carboxamide | ** | 3.81 (B) | 507 |

TABLE 2

| Additional Non-limiting Examples of Compounds of the Present Disclosure | | | | |
|---|---|---|---|---|
| # | Structure | C1s Protease Activity | RT min (Method A or B) | MS (M + 1) |
| 37 | 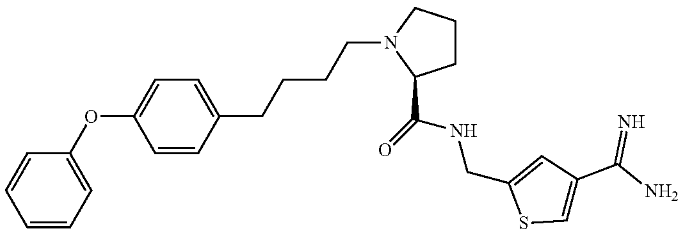 [SMILES: N=C(N)c1csc(CNC(=O)[C@@H]2CCCN2CCCCc2ccc(Oc3ccccc3)cc2)c1] (S)-N-((4-carbamimidoylthiophen-2-yl)methyl)-1-(4-(4-phenoxyphenyl)butyl)pyrrolidine-2-carboxamide | * | 2.22 (B) | 477 |
| 38 | 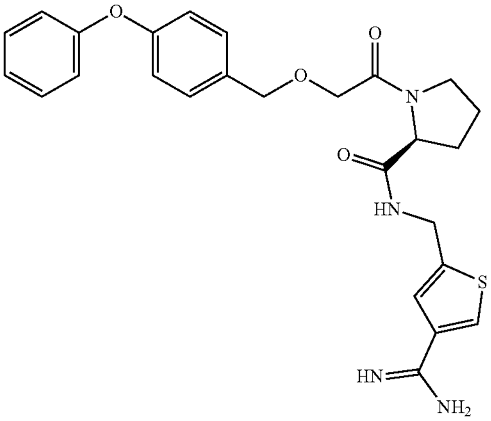 [SMILES: N=C(N)c1csc(CNC(=O)[C@@H]2CCCN2C(=O)COCc2ccc(Oc3ccccc3)cc2)c1] (S)-N-((4-carbamimidoylthiophen-2-yl)methyl)-1-(2-((4-phenoxybenzyl)oxy)acetyl)pyrrolidine-2-carboxamide | ** | 2.74 (B) | 493 |
| 39 | 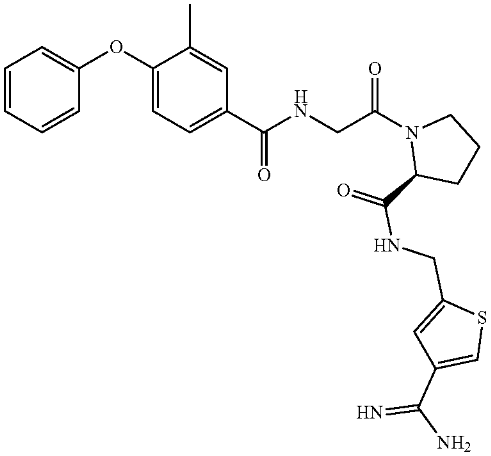 [SMILES: Cc1cc(C(=O)NCC(=O)N2CCC[C@H]2C(=O)NCc2cc(C(=N)N)cs2)ccc1Oc1ccccc1] (S)-N-((4-carbamimidoylthiophen-2-yl)methyl)-1-((3-methyl-4-phenoxybenzoyl)glycyl)pyrrolidine-2-carboxamide | *** | 2.56 (B) | 520 |

TABLE 2-continued
Additional Non-limiting Examples of Compounds of the Present Disclosure
| # | Structure | C1s Protease Activity | RT min (Method A or B) | MS (M + 1) |
|---|---|---|---|---|
| 40 | 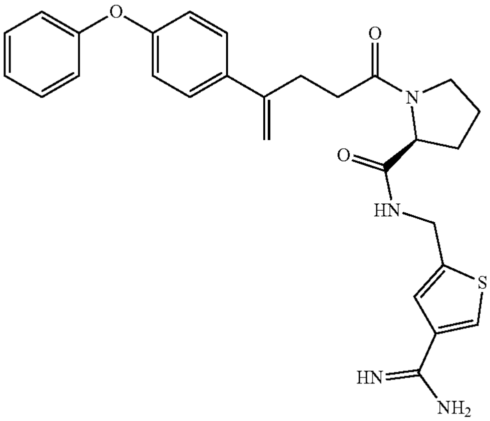 [SMILES: C=C(CCC(=O)N1CCC[C@H]1C(=O)NCc1cc(C(=N)N)cs1)c1ccc(Oc2ccccc2)cc1] (S)-N-((4-carbamimidoylthiophen-2-yl)methyl)-1-(4-(4-phenoxyphenyl)pent-4-enoyl)pyrrolidine-2-carboxamide | ** | 3.24 (B) | 503 |
| 41 | 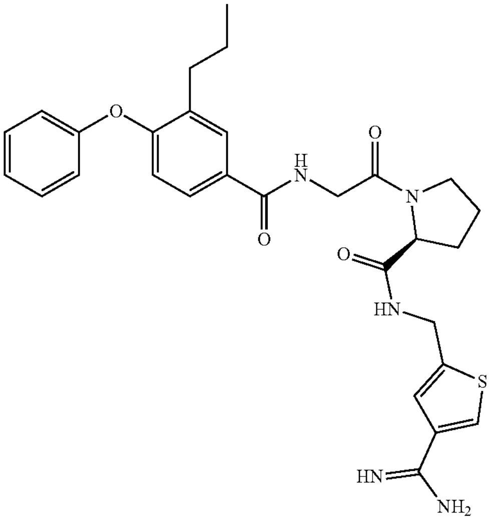 [SMILES: CCCc1cc(C(=O)NCC(=O)N2CCC[C@H]2C(=O)NCc2cc(C(=N)N)cs2)ccc1Oc1ccccc1] (S)-N-((4-carbamimidoylthiophen-2-yl)methyl)-1-((4-phenoxy-3-propylbenzoyl)glycyl)pyrrolidine-2-carboxamide | *** | 3.68 (B) | 549 |

TABLE 2-continued
| Additional Non-limiting Examples of Compounds of the Present Disclosure | | | | |
|---|---|---|---|---|
| # | Structure | C1s Protease Activity | RT min (Method A or B) | MS (M + 1) |
| 42 | 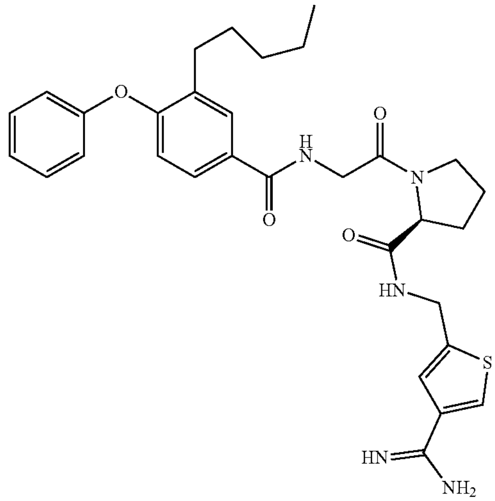 [SMILES: CCCCCc1cc(C(=O)NCC(=O)N2CCC[C@H]2C(=O)NCc2cc(C(=N)N)cs2)ccc1Oc1ccccc1] (S)-N-((4-carbamimidoylthiophen-2-yl)methyl)-1-((3-pentyl-4-phenoxybenzoyl)glycyl)pyrrolidine-2-carboxamide | *** | 3.61 (B) | 576 |
| 43 | 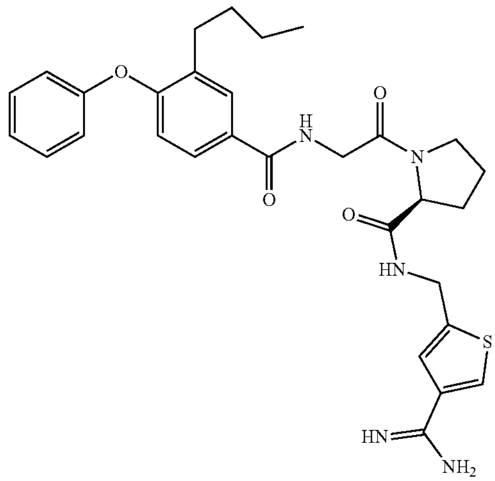 [SMILES: CCCCc1cc(C(=O)NCC(=O)N2CCC[C@H]2C(=O)NCc2cc(C(=N)N)cs2)ccc1Oc1ccccc1] (S)-1-((3-butyl-4-phenoxybenzoyl)glycyl)-N-((4-carbamimidoylthiophen-2-yl)methyl)pyrrolidine-2-carboxamide | *** | 3.59 (B) | 562 |

TABLE 2-continued

| # | Structure | C1s Protease Activity | RT min (Method A or B) | MS (M + 1) |
|---|---|---|---|---|
| Additional Non-limiting Examples of Compounds of the Present Disclosure | | | | |
| 44 | 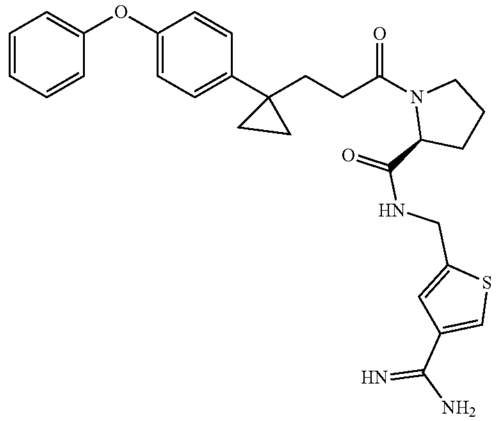 [SMILES: N=C(N)c1csc(CNC(=O)[C@@H]2CCCN2C(=O)CCC2(c3ccc(Oc4ccccc4)cc3)CC2)c1] (S)-N-((4-carbamimidoylthiophen-2-yl)methyl)-1-(3-(1-(4-phenoxyphenyl)cyclopropyl)propanoyl)pyrrolidine-2-carboxamide | * | 1.61 (A) | 517 |
| 45 | 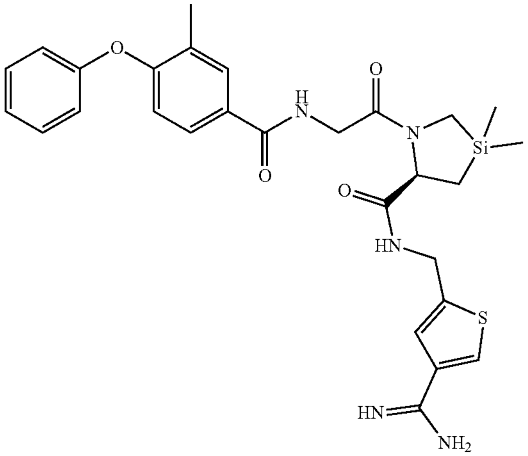 [SMILES: Cc1cc(C(=O)NCC(=O)N2C[Si](C)(C)C[C@H]2C(=O)NCc2cc(C(=N)N)cs2)ccc1Oc1ccccc1] (R)-N-((4-carbamimidoylthiophen-2-yl)methyl)-3,3-dimethyl-1-((3-methyl-4-phenoxybenzoyl)glycyl)-1,3-azasilolidine-5-carboxamide | *** | 1.46 (A) | 564 |
| 46 | 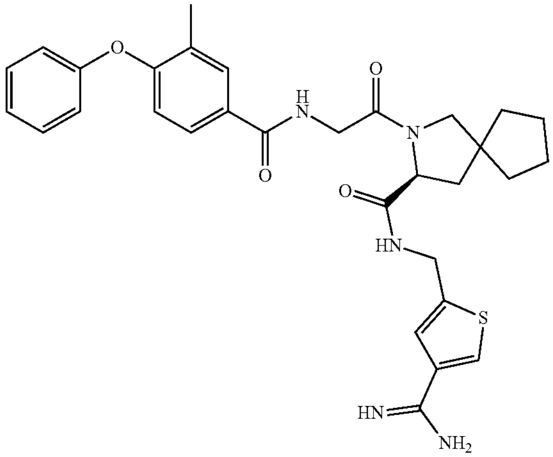 [SMILES: Cc1cc(C(=O)NCC(=O)N2CC3(CCCC3)C[C@H]2C(=O)NCc2cc(C(=N)N)cs2)ccc1Oc1ccccc1] (S)-N-((4-carbamimidoylthiophen-2-yl)methyl)-2-((3-methyl-4-phenoxybenzoyl)glycyl)-2-azaspiro[4.4]nonane-3-carboxamide | *** | 1.60 (A) | 574 |

TABLE 2-continued

| # | Structure | C1s Protease Activity | RT min (Method A or B) | MS (M + 1) |
|---|---|---|---|---|
| | Additional Non-limiting Examples of Compounds of the Present Disclosure | | | |
| 47 | 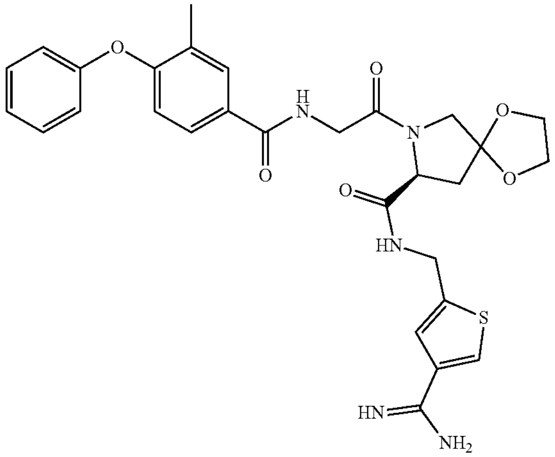 [SMILES: Cc1cc(C(=O)NCC(=O)N2CC3(C[C@H]2C(=O)NCc2cc(C(=N)N)cs2)OCCO3)ccc1Oc1ccccc1] (S)-N-((4-carbamimidoylthiophen-2-yl)methyl)-7-((3-methyl-4-phenoxybenzoyl)glycyl)-1,4-dioxa-7-azaspiro[4.4]nonane-8-carboxamide | *** | 2.99 (B) | 578 |
| 48 | 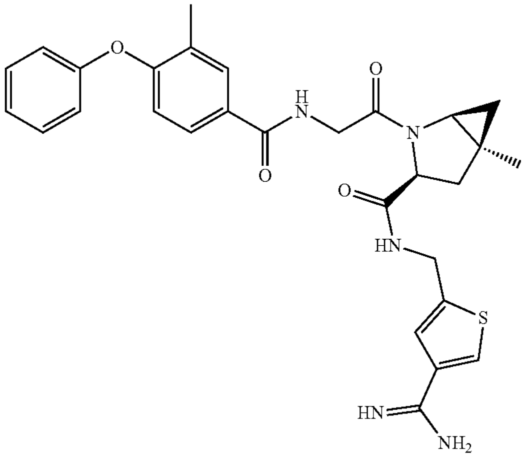 [SMILES: Cc1cc(C(=O)NCC(=O)N2[C@H]3C[C@@]3(C)C[C@H]2C(=O)NCc2cc(C(=N)N)cs2)ccc1Oc1ccccc1] (1S,3S,5S)-N-((4-carbamimidoylthiophen-2-yl)methyl)-5-methyl-2-((3-methyl-4-phenoxybenzoyl)glycyl)-2-azabicyclo[3.1.0]hexane-3-carboxamide | *** | 3.04 (B) | 546 |
| 49 | 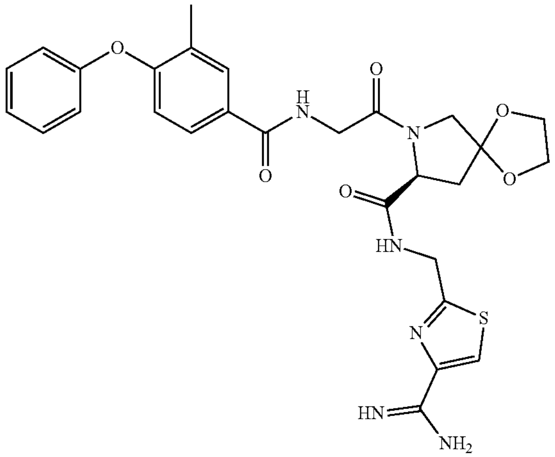 [SMILES: Cc1cc(C(=O)NCC(=O)N2CC3(C[C@H]2C(=O)NCc2nc(C(=N)N)cs2)OCCO3)ccc1Oc1ccccc1] | *** | 2.19 (B) | 579 |

TABLE 2-continued

Additional Non-limiting Examples of Compounds of the Present Disclosure

| # | Structure | C1s Protease Activity | RT min (Method A or B) | MS (M + 1) |
|---|---|---|---|---|
| | (S)-N-((4-carbamimidoylthiazol-2-yl)methyl)-7-((3-methyl-4-phenoxybenzoyl)glycyl)-1,4-dioxa-7-azaspiro[4.4]nonane-8-carboxamide | | | |
| 50 | 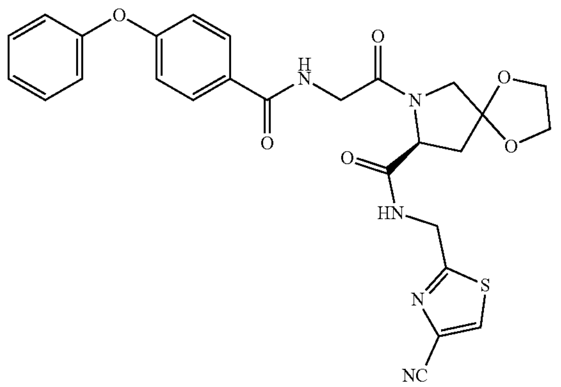 [SMILES: N#Cc1csc(CNC(=O)[C@@H]2CC3(CN2C(=O)CNC(=O)c2ccc(Oc4ccccc4)cc2)OCCO3)n1] (S)-N-((4-cyanothiophen-2-yl)methyl)-7-((4-phenoxybenzoyl)glycyl)-1,4-dioxa-7-azaspiro[4.4]nonane-8-carboxamide | * | 3.16 (B) | 547 |
| 51 | 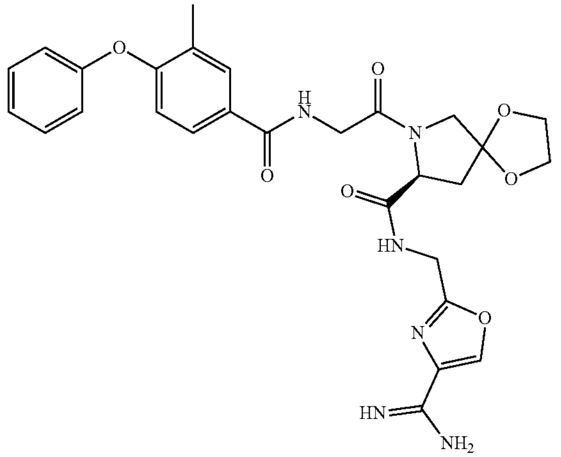 [SMILES: Cc1cc(C(=O)NCC(=O)N2CC3(C[C@H]2C(=O)NCc2nc(C(=N)N)co2)OCCO3)ccc1Oc1ccccc1] (S)-N-((4-carbamimidoyloxazol-2-yl)methyl)-7-((3-methyl-4-phenoxybenzoyl)glycyl)-1,4-dioxa-7-azaspiro[4.4]nonane-8-carboxamide | *** | 2.54 (B) | 563 |
| 52 | 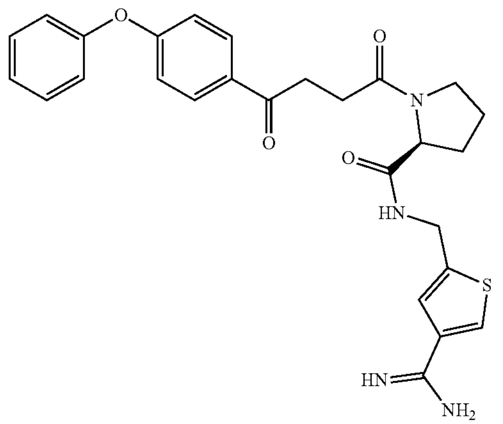 [SMILES: N=C(N)c1csc(CNC(=O)[C@@H]2CCCN2C(=O)CCC(=O)c2ccc(Oc3ccccc3)cc2)c1] (S)-N-((4-carbamimidoylthiophen-2-yl)methyl)-1-(4-oxo-4-(4-phenoxyphenyl)butanoyl)pyrrolidine-2-carboxamide | *** | 2.84 (B) | 505 |

TABLE 2-continued

| Additional Non-limiting Examples of Compounds of the Present Disclosure | | | | |
|---|---|---|---|---|
| # | Structure | C1s Protease Activity | RT min (Method A or B) | MS (M + 1) |
| 53 | 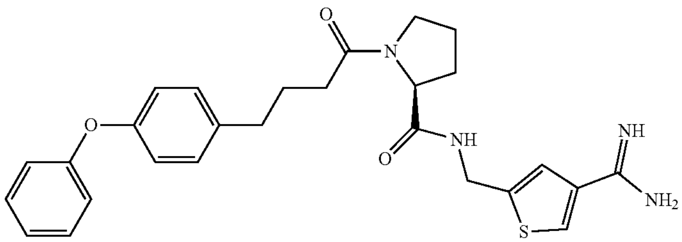 [SMILES: N=C(N)c1csc(CNC(=O)[C@@H]2CCCN2C(=O)CCCc2ccc(Oc3ccccc3)cc2)c1] (S)-N-((4-carbamimidoylthiophen-2-yl)methyl)-1-(4-(4-phenoxyphenyl)butanoyl)pyrrolidine-2-carboxamide | *** | 3.12 (B) | 491 |
| 54 | 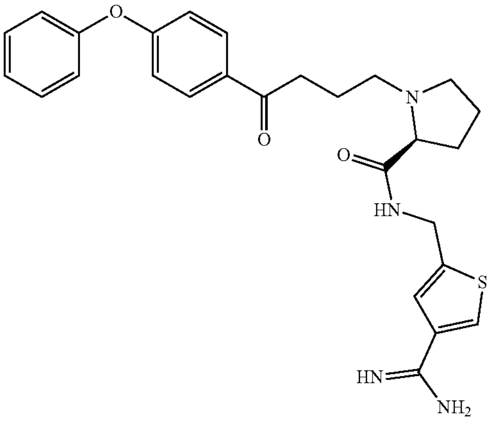 [SMILES: N=C(N)c1csc(CNC(=O)[C@@H]2CCCN2CCCC(=O)c2ccc(Oc3ccccc3)cc2)c1] (S)-N-((4-carbamimidoylthiophen-2-yl)methyl)-1-(4-oxo-4-(4-phenoxyphenyl)butyl)pyrrolidine-2-carboxamide | * | 2.67 (B) | 491 |
| 55 | 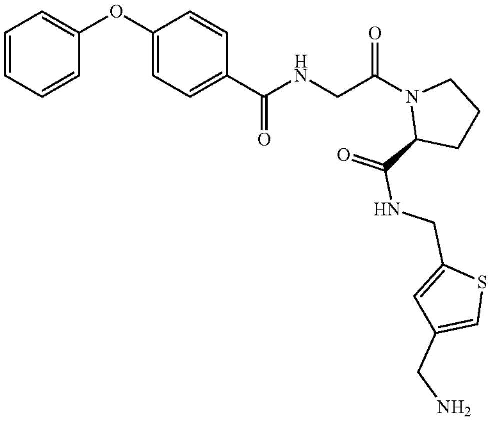 [SMILES: NCc1csc(CNC(=O)[C@@H]2CCCN2C(=O)CNC(=O)c2ccc(Oc3ccccc3)cc2)c1] (S)-N-((4-(aminomethyl)thiophen-2-yl)methyl)-1-((4-phenoxybenzoyl)glycyl)pyrrolidine-2-carboxamide | * | 4.16 (B) | 494 |

TABLE 2-continued

Additional Non-limiting Examples of Compounds of the Present Disclosure

| # | Structure | C1s Protease Activity | RT min (Method A or B) | MS (M + 1) |
|---|---|---|---|---|
| 56 | 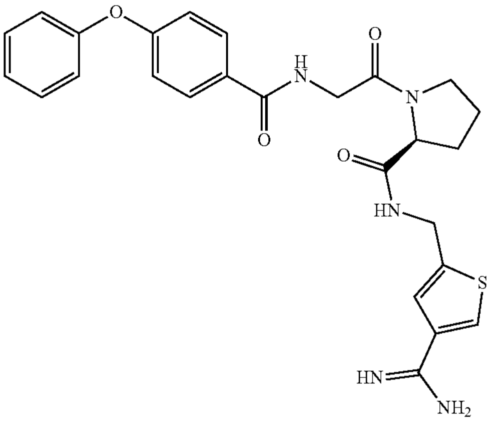 [SMILES: N=C(N)c1csc(CNC(=O)[C@@H]2CCCN2C(=O)CNC(=O)c2ccc(Oc3ccccc3)cc2)c1] (S)-1-((4-benzylbenzoyl)glycyl)-N-((4-carbamimidoylthiophen-2-yl)methyl)pyrrolidine-2-carboxamide | *** | 3.01 (B) | 504 |
| 57 | 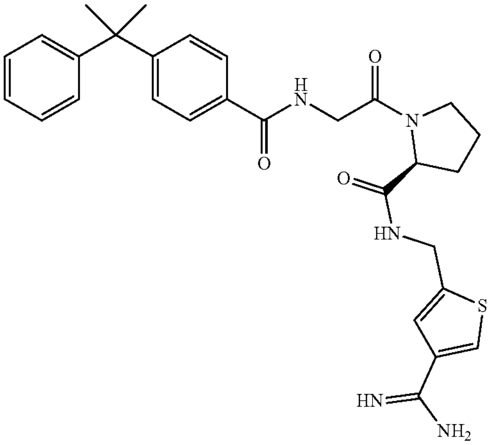 [SMILES: CC(C)(c1ccccc1)c1ccc(C(=O)NCC(=O)N2CCC[C@H]2C(=O)NCc2cc(C(=N)N)cs2)cc1] (S)-N-((4-carbamimidoylthiophen-2-yl)methyl)-1-((4-(2-phenylpropan-2-yl)benzoyl)glycyl)pyrrolidine-2-carboxamide | *** | 2.85 (B) | 532 |
| 58 | 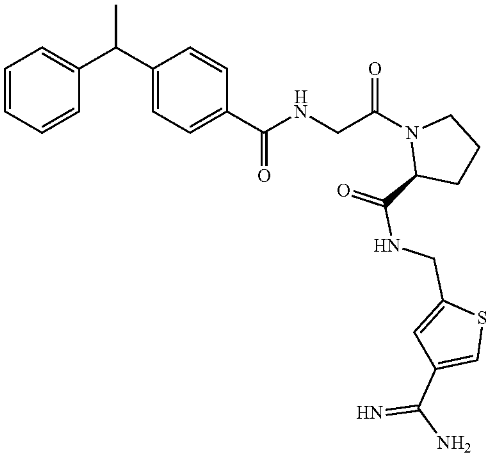 [SMILES: CC(c1ccccc1)c1ccc(C(=O)NCC(=O)N2CCC[C@H]2C(=O)NCc2cc(C(=N)N)cs2)cc1] (2S)-N-((4-carbamimidoylthiophen-2-yl)methyl)-1-((4-(1-phenylethyl)benzoyl)glycyl)pyrrolidine-2-carboxamide | *** | 3.84 (B) | 518 |

TABLE 2-continued

| # | Structure | C1s Protease Activity | RT min (Method A or B) | MS (M + 1) |
|---|---|---|---|---|
| Additional Non-limiting Examples of Compounds of the Present Disclosure | | | | |
| 59 | 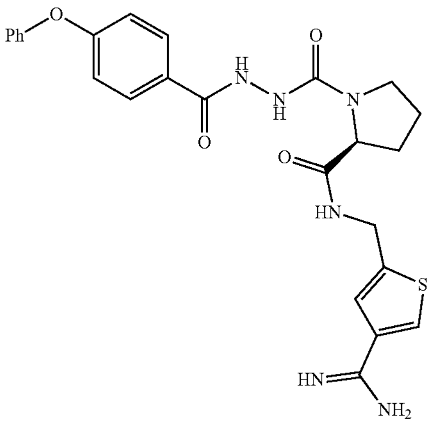 [SMILES: N=C(N)c1csc(CNC(=O)[C@@H]2CCCN2C(=O)NNC(=O)c2ccc(Oc3ccccc3)cc2)c1] (S)-N-((4-carbamimidoylthiophen-2-yl)methyl)-1-(2-(4-phenoxybenzoyl)hydrazine-1-carbonyl)pyrrolidine-2-carboxamide | ** | 3.81 (B) | 507 |
| 60 | 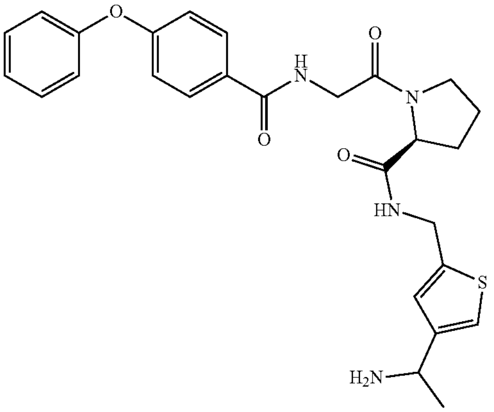 [SMILES: CC(N)c1csc(CNC(=O)[C@@H]2CCCN2C(=O)CNC(=O)c2ccc(Oc3ccccc3)cc2)c1] (2S)-N-((4-(1-aminoethyl)thiophen-2-yl)methyl)-1-((4-phenoxybenzoyl)glycyl)pyrrolidine-2-carboxamide | * | 2.34 (B) | 507 |
| 61 | 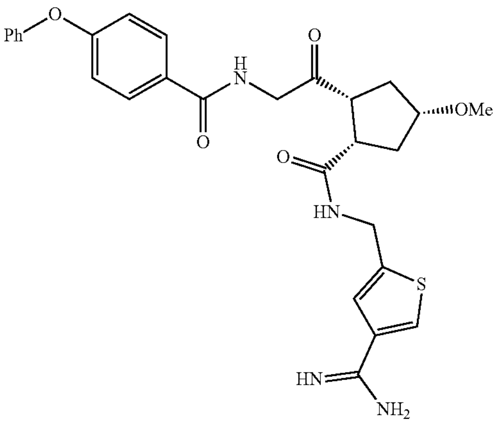 [SMILES: CO[C@@H]1C[C@H](C(=O)NCc2cc(C(=N)N)cs2)[C@H](C(=O)CNC(=O)c2ccc(Oc3ccccc3)cc2)C1] N-(2-((1R,2S,4S)-2-(((4-carbamimidoylthiophen-2-yl)methyl)carbamoyl)-4-methoxycyclopentyl)-2-oxoethyl)-4-phenoxybenzamide | * | 2.40 (B) | 535 |

TABLE 2-continued

| # | Additional Non-limiting Examples of Compounds of the Present Disclosure<br>Structure | C1s Protease Activity | RT min (Method A or B) | MS (M + 1) |
|---|---|---|---|---|
| 62 | 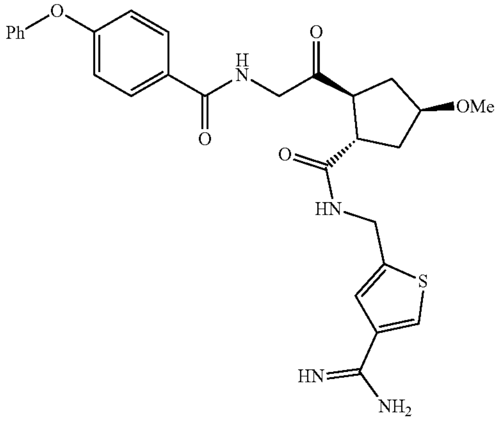 [SMILES: CO[C@@H]1C[C@H](C(=O)CNC(=O)c2ccc(Oc3ccccc3)cc2)[C@@H](C(=O)NCc2cc(C(=N)N)cs2)C1]<br>N-(2-((1S,2S,4R)-2-(((4-carbamimidoylthiophen-2-yl)methyl)carbamoyl)-4-methoxycyclopentyl)-2-oxoethyl)-4-phenoxybenzamide | * | 2.87 (B) | 535 |
| 63 | 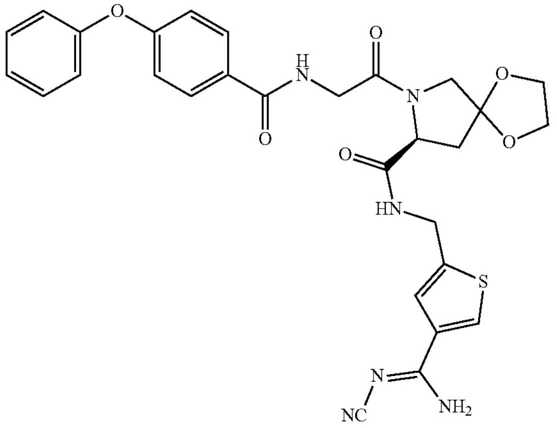 [SMILES: N#C/N=C(\N)c1csc(CNC(=O)[C@@H]2CC3(CN2C(=O)CNC(=O)c2ccc(Oc4ccccc4)cc2)OCCO3)c1]<br>(S,Z)-N-((4-(N'-cyanocarbamimidoyl)thiophen-2-yl)methyl)-7-((4-phenoxybenzoyl)glycyl)-1,4-dioxa-7-azaspiro[4.4]nonane-8-carboxamide | *** | 1.69 (A) | 589 |
| 64 | 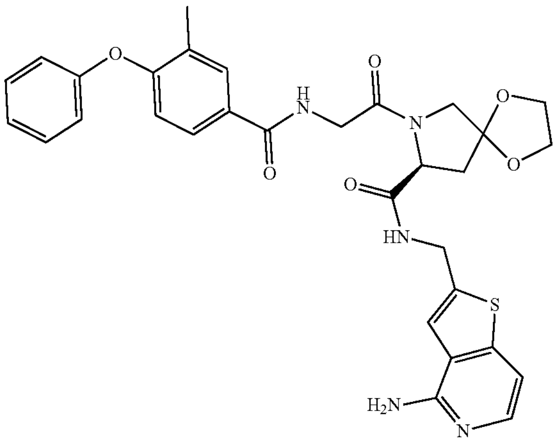 [SMILES: Cc1cc(C(=O)NCC(=O)N2CC3(C[C@H]2C(=O)NCc2cc4c(N)nccc4s2)OCCO3)ccc1Oc1ccccc1]<br>(S)-N-((4-aminothieno[3,2-c]pyridin-2-yl)methyl)-7-((3-methyl-4-phenoxybenzoyl)glycyl)-1,4-dioxa-7-azaspiro[4.4]nonane-8-carboxamide | ** | 2.66 (B) | 602 |

TABLE 2-continued

Additional Non-limiting Examples of Compounds of the Present Disclosure

| # | Structure | C1s Protease Activity | RT min (Method A or B) | MS (M + 1) |
|---|---|---|---|---|
| 65 | 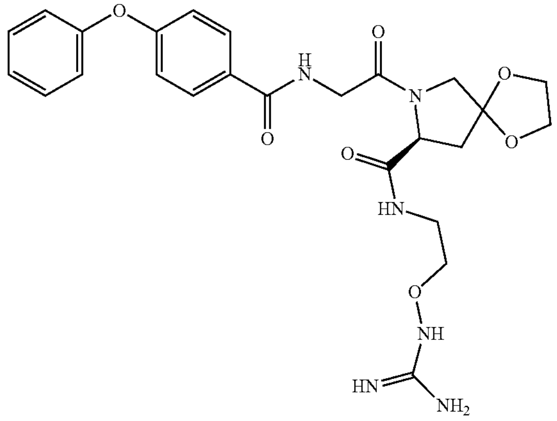 [SMILES: N=C(N)NOCCNC(=O)[C@@H]1CC2(CN1C(=O)CNC(=O)c1ccc(Oc3ccccc3)cc1)OCCO2] (S)-N-(2-(guanidinooxy)ethyl)-7-((4-phenoxybenzoyl)glycyl)-1,4-dioxa-7-azaspiro[4.4]nonane-8-carboxamide | * | 3.15 (B) | 528 |
| 66 | 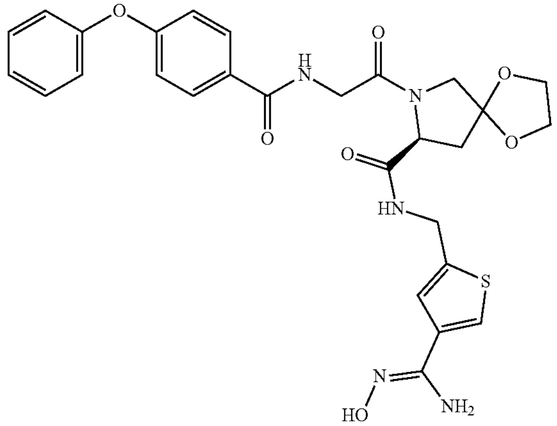 [SMILES: N/C(=N\O)c1csc(CNC(=O)[C@@H]2CC3(CN2C(=O)CNC(=O)c2ccc(Oc4ccccc4)cc2)OCCO3)c1] (S,Z)-N-((4-(N'-hydroxycarbamimidoyl)thiophen-2-yl)methyl)-7-((4-phenoxybenzoyl)glycyl)-1,4-dioxa-7-azaspiro[4.4]nonane-8-carboxamide | *** | 3.45 (B) | 580 |
| 67 | 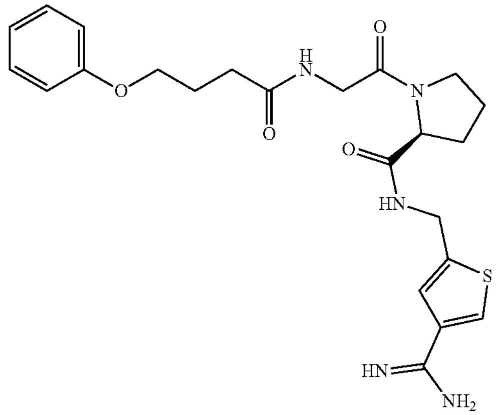 [SMILES: N=C(N)c1csc(CNC(=O)[C@@H]2CCCN2C(=O)CNC(=O)CCCOc2ccccc2)c1] (S)-N-((4-carbamimidoylthiophen-2-yl)methyl)-1-((4-phenoxybutanoyl)glycyl)pyrrolidine-2-carboxamide | *** | 0.83 (A) | 472 |

TABLE 2-continued

| # | Structure | C1s Protease Activity | RT min (Method A or B) | MS (M + 1) |
|---|---|---|---|---|
| | Additional Non-limiting Examples of Compounds of the Present Disclosure | | | |
| 68 | 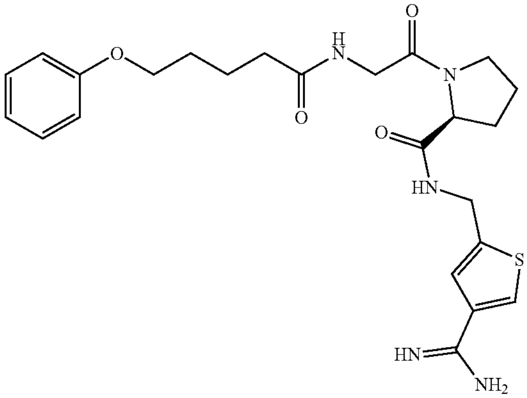 (S)-N-((4-carbamimidoylthiophen-2-yl)methyl)-1-((5-phenoxypentanoyl)glycyl)pyrrolidine-2-carboxamide | *** | 0.97 (A) | 486 |
| 69 | 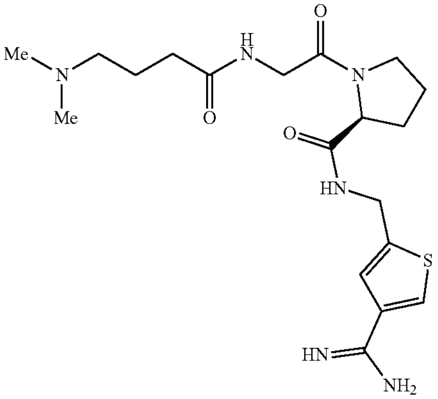 [SMILES: CN(C)CCCC(=O)NCC(=O)N1CCC[C@H]1C(=O)NCc1cc(C(=N)N)cs1] (S)-N-((4-carbamimidoylthiophen-2-yl)methyl)-1-((4-(dimethylamino)butanoyl)glycyl)pyrrolidine-2-carboxamide | * | 0.18 (A) | 423 |
| 70 | 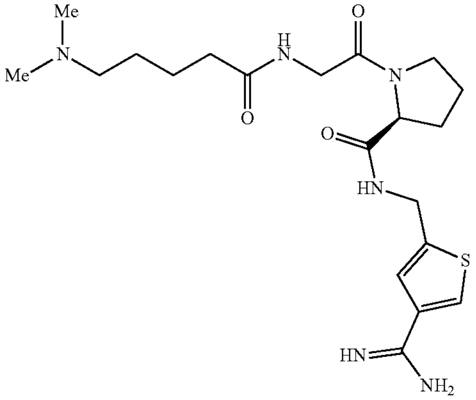 [SMILES: CN(C)CCCCC(=O)NCC(=O)N1CCC[C@H]1C(=O)NCc1cc(C(=N)N)cs1] (S)-N-((4-carbamimidoylthiophen-2-yl)methyl)-1-((5-(dimethylamino)pentanoyl)glycyl)pyrrolidine-2-carboxamide | * | 0.18 (A) | 437 |

TABLE 2-continued

Additional Non-limiting Examples of Compounds of the Present Disclosure

| # | Structure | C1s Protease Activity | RT min (Method A or B) | MS (M + 1) |
|---|---|---|---|---|
| 71 | 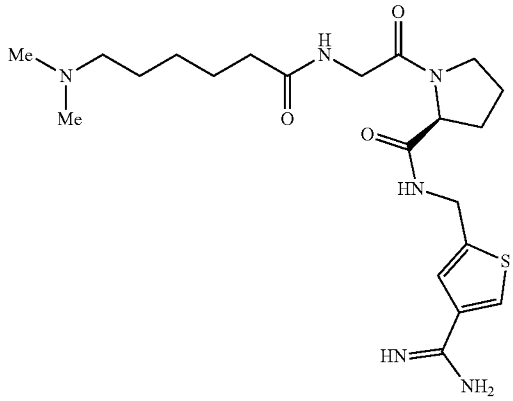 [SMILES: CN(C)CCCCCC(=O)NCC(=O)N1CCC[C@H]1C(=O)NCc1cc(C(=N)N)cs1] (S)-N-((4-carbamimidoylthiophen-2-yl)methyl)-1-((6-(dimethylamino)hexanoyl)glycyl)pyrrolidine-2-carboxamide | * | 0.18 (A) | 451 |
| 72 | 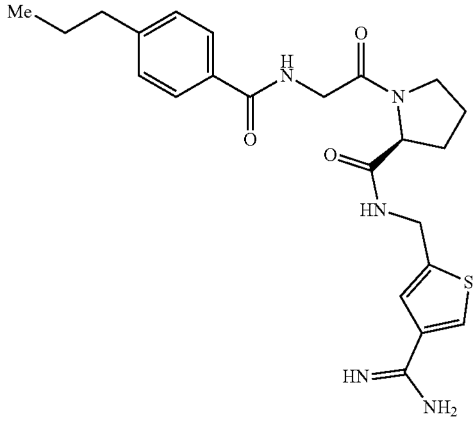 [SMILES: CCCc1ccc(C(=O)NCC(=O)N2CCC[C@H]2C(=O)NCc2cc(C(=N)N)cs2)cc1] (S)-N-((4-carbamimidoylthiophen-2-yl)methyl)-1-((4-propylbenzoyl)glycyl)pyrrolidine-2-carboxamide | *** | 1.05 (A) | 456 |
| 73 | 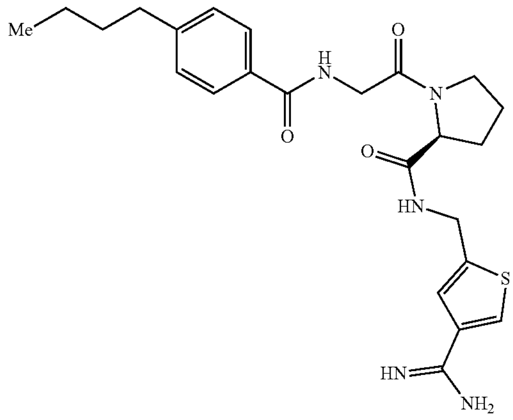 [SMILES: CCCCc1ccc(C(=O)NCC(=O)N2CCC[C@H]2C(=O)NCc2cc(C(=N)N)cs2)cc1] (S)-1-((4-butylbenzoyl)glycyl)-N-((4-carbamimidoylthiophen-2-yl)methyl)pyrrolidine-2-carboxamide | *** | 1.25 (A) | 470 |

TABLE 2-continued

| Additional Non-limiting Examples of Compounds of the Present Disclosure | | | | |
|---|---|---|---|---|
| # | Structure | C1s Protease Activity | RT min (Method A or B) | MS (M + 1) |
| 74 | 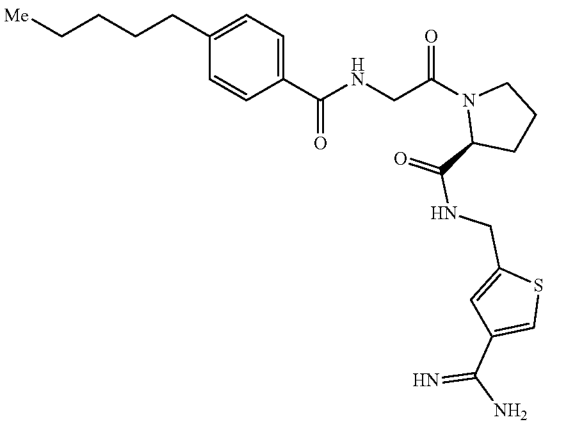 [SMILES: CCCCCc1ccc(C(=O)NCC(=O)N2CCC[C@H]2C(=O)NCc2cc(C(=N)N)cs2)cc1] (S)-N-((4-carbamimidoylthiophen-2-yl)methyl)-1-((4-pentylbenzoyl)glycyl)pyrrolidine-2-carboxamide | *** | 1.43 (A) | 484 |
| 75 | 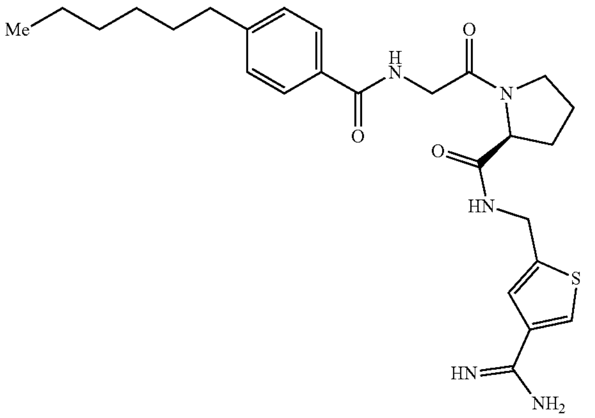 [SMILES: CCCCCCc1ccc(C(=O)NCC(=O)N2CCC[C@H]2C(=O)NCc2cc(C(=N)N)cs2)cc1] (S)-N-((4-carbamimidoylthiophen-2-yl)methyl)-1-((4-hexylbenzoyl)glycyl)pyrrolidine-2-carboxamide | *** | 1.62 (A) | 498 |
| 76 | 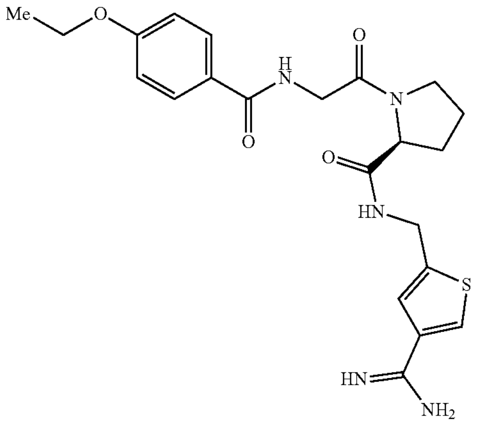 [SMILES: CCOc1ccc(C(=O)NCC(=O)N2CCC[C@H]2C(=O)NCc2cc(C(=N)N)cs2)cc1] (S)-N-((4-carbamimidoylthiophen-2-yl)methyl)-1-((4-ethoxybenzoyl)glycyl)pyrrolidine-2-carboxamide | ** | 0.71 (A) | 458 |

TABLE 2-continued

Additional Non-limiting Examples of Compounds of the Present Disclosure

| # | Structure | C1s Protease Activity | RT min (Method A or B) | MS (M + 1) |
|---|---|---|---|---|
| 77 | 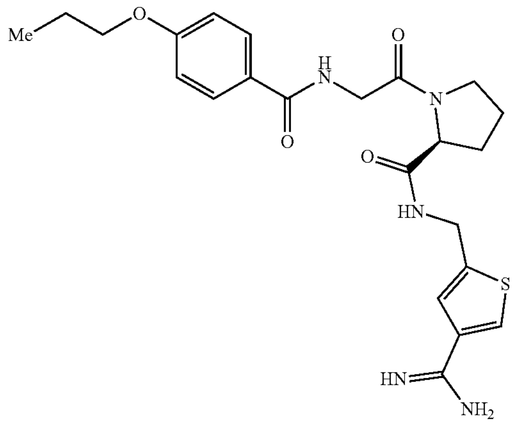 [SMILES: CCCOc1ccc(C(=O)NCC(=O)N2CCC[C@H]2C(=O)NCc2cc(C(=N)N)cs2)cc1] (S)-N-((4-carbamimidoylthiophen-2-yl)methyl)-1-((4-propoxybenzoyl)glycyl)pyrrolidine-2-carboxamide | *** | 0.94 (A) | 472 |
| 78 | 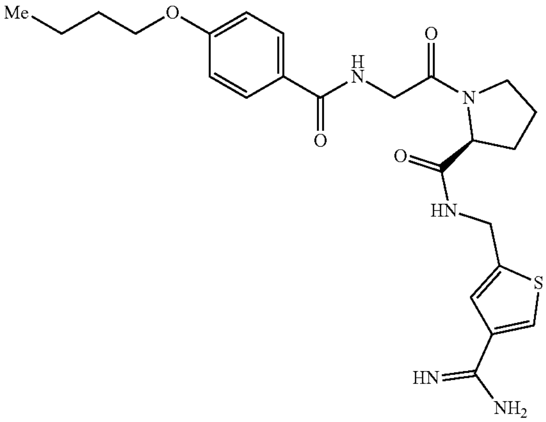 [SMILES: CCCCOc1ccc(C(=O)NCC(=O)N2CCC[C@H]2C(=O)NCc2cc(C(=N)N)cs2)cc1] (S)-1-((4-butoxybenzoyl)glycyl)-N-((4-carbamimidoylthiophen-2-yl)methyl)pyrrolidine-2-carboxamide | *** | 1.19 (A) | 486 |
| 79 | 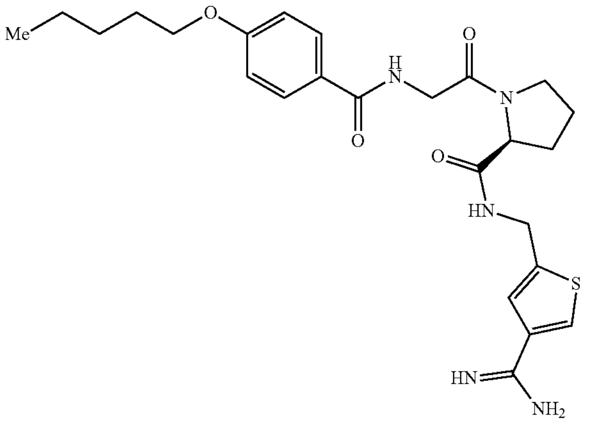 [SMILES: CCCCCOc1ccc(C(=O)NCC(=O)N2CCC[C@H]2C(=O)NCc2cc(C(=N)N)cs2)cc1] (S)-N-((4-carbamimidoylthiophen-2-yl)methyl)-1-((4-(pentyloxy)benzoyl)glycyl)pyrrolidine-2-carboxamide | *** | 1.39 (A) | 500 |

TABLE 2-continued

Additional Non-limiting Examples of Compounds of the Present Disclosure

| # | Structure | C1s Protease Activity | RT min (Method A or B) | MS (M + 1) |
|---|---|---|---|---|
| 80 | 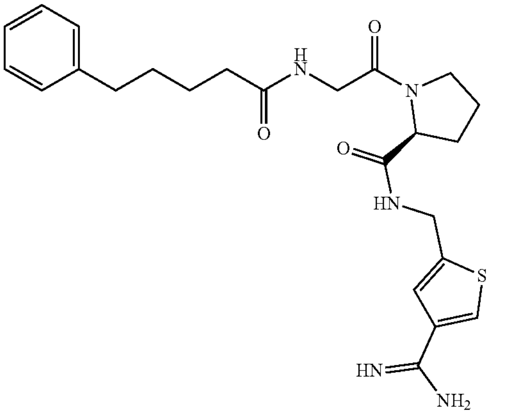 (S)-N-((4-carbamimidoylthiophen-2-yl)methyl)-1-((5-phenylpentanoyl)glycyl)pyrrolidine-2-carboxamide | *** | 1.02 (A) | 470 |
| 81 | 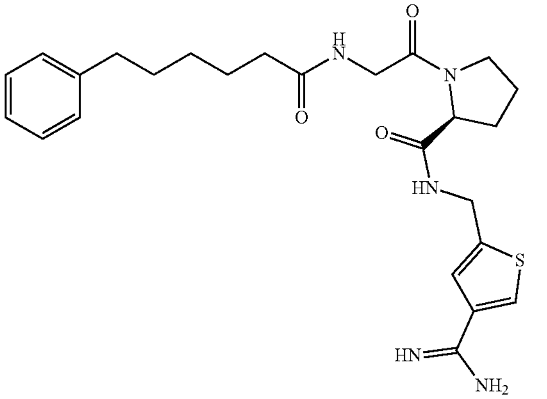 (S)-N-((4-carbamimidoylthiophen-2-yl)methyl)-1-((6-phenylhexanoyl)glycyl)pyrrolidine-2-carboxamide | *** | 1.15 (A) | 484 |
| 82 | 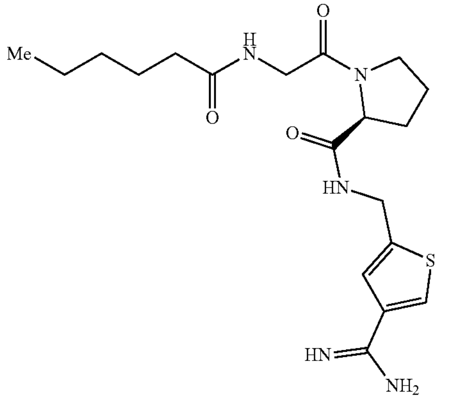 [SMILES: CCCCCC(=O)NCC(=O)N1CCC[C@H]1C(=O)NCc1cc(C(=N)N)cs1] (S)-N-((4-carbamimidoylthiophen-2-yl)methyl)-1-(hexanoylglycyl)pyrrolidine-2-carboxamide | ** | 0.57 (A) | 408 |

TABLE 2-continued

| Additional Non-limiting Examples of Compounds of the Present Disclosure | | | | |
|---|---|---|---|---|
| # | Structure | C1s Protease Activity | RT min (Method A or B) | MS (M + 1) |
| 83 | 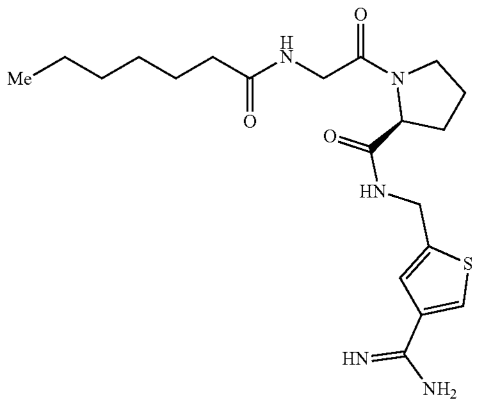 [SMILES: CCCCCCC(=O)NCC(=O)N1CCC[C@H]1C(=O)NCc1cc(C(=N)N)cs1] (S)-N-((4-carbamimidoylthiophen-2-yl)methyl)-1-(heptanoylglycyl)pyrrolidine-2-carboxamide | ** | 0.85 (A) | 422 |
| 84 | 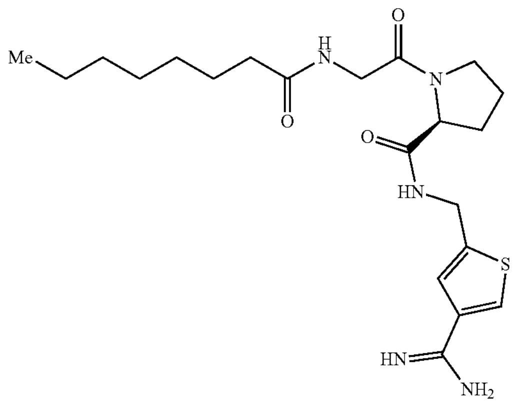 [SMILES: CCCCCCCC(=O)NCC(=O)N1CCC[C@H]1C(=O)NCc1cc(C(=N)N)cs1] (S)-N-((4-carbamimidoylthiophen-2-yl)methyl)-1-(octanoylglycyl)pyrrolidine-2-carboxamide | *** | 1.06 (A) | 436 |
| 85 | 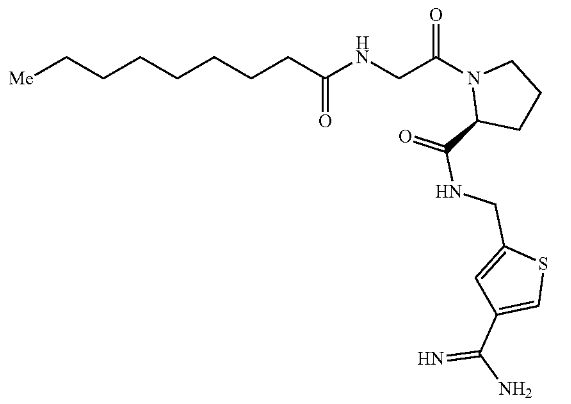 [SMILES: CCCCCCCCC(=O)NCC(=O)N1CCC[C@H]1C(=O)NCc1cc(C(=N)N)cs1] (S)-N-((4-carbamimidoylthiophen-2-yl)methyl)-1-(nonanoylglycyl)pyrrolidine-2-carboxamide | *** | 1.24 (A) | 450 |

TABLE 2-continued

| # | Structure | C1s Protease Activity | RT min (Method A or B) | MS (M + 1) |
|---|---|---|---|---|
| Additional Non-limiting Examples of Compounds of the Present Disclosure | | | | |
| 86 | 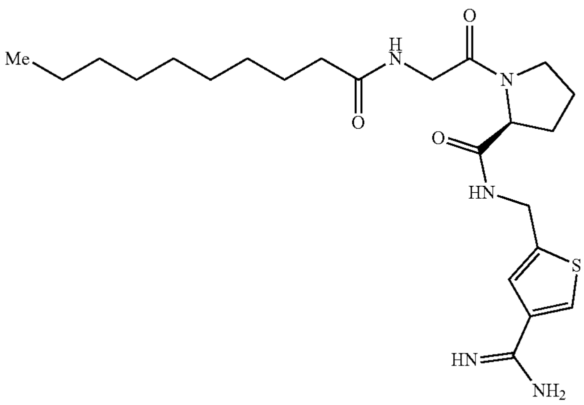 [SMILES: CCCCCCCCCC(=O)NCC(=O)N1CCC[C@H]1C(=O)NCc1cc(C(=N)N)cs1] (S)-N-((4-carbamimidoylthiophen-2-yl)methyl)-1-(decanoylglycyl)pyrrolidine-2-carboxamide | *** | 1.45 (A) | 464 |
| 87 | 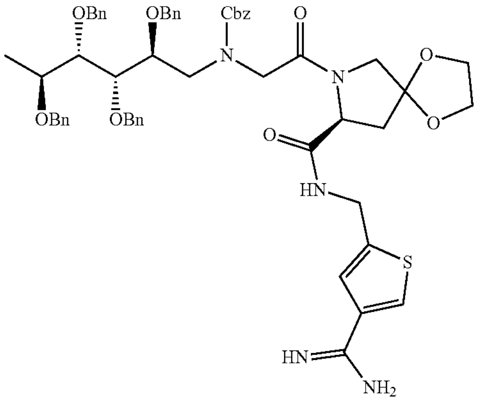 [SMILES: C[C@H](OCc1ccccc1)[C@H](OCc1ccccc1)[C@@H](OCc1ccccc1)[C@H](CN(CC(=O)N1CC2(C[C@H]1C(=O)NCc1cc(C(=N)N)cs1)OCCO2)C(=O)OCc1ccccc1)OCc1ccccc1] benzyl (2-((S)-8-(((4-carbamimidoylthiophen-2-yl)methyl)carbamoyl)-1,4-dioxa-7-azaspiro[4.4]nonan-7-yl)-2-oxoethyl)((2S,3S,4S,5S)-2,3,4,5-tetrakis(benzyloxy)hexyl)carbamate | * | 2.50 (A) | 1011 |
| 88 | 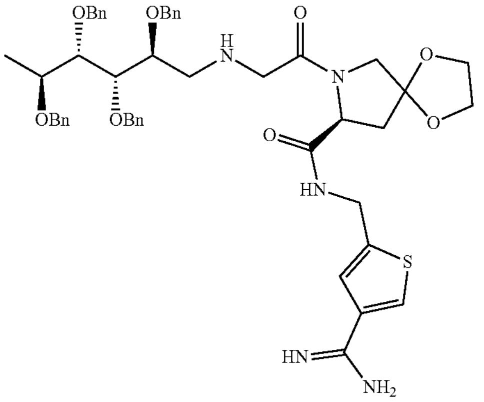 [SMILES: C[C@H](OCc1ccccc1)[C@H](OCc1ccccc1)[C@@H](OCc1ccccc1)[C@H](CNCC(=O)N1CC2(C[C@H]1C(=O)NCc1cc(C(=N)N)cs1)OCCO2)OCc1ccccc1] (S)-N-((4-carbamimidoylthiophen-2-yl)methyl)-7-(((2S,3S,4S,5S)-2,3,4,5-tetrakis(benzyloxy)hexyl)glycyl)-1,4-dioxa-7-azaspiro[4.4]nonane-8-carboxamide | | | |

TABLE 2-continued

| Additional Non-limiting Examples of Compounds of the Present Disclosure | | | | |
|---|---|---|---|---|
| # | Structure | C1s Protease Activity | RT min (Method A or B) | MS (M + 1) |
| 89 | 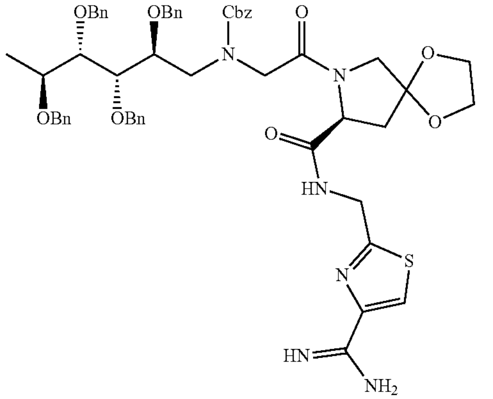 [SMILES: C[C@H](OCc1ccccc1)[C@H](OCc1ccccc1)[C@@H](OCc1ccccc1)[C@H](CN(CC(=O)N1CC2(C[C@H]1C(=O)NCc1nc(C(=N)N)cs1)OCCO2)C(=O)OCc1ccccc1)OCc1ccccc1] benzyl (2-((S)-8-(((4-carbamimidoylthiazol-2-yl)methyl)carbamoyl)-1,4-dioxa-7-azaspiro[4.4]nonan-7-yl)-2-oxoethyl)((2S,3S,4S,5S)-2,3,4,5-tetrakis(benzyloxy)hexyl)carbamate | * | 2.47 (A) | 1012 |
| 90 | 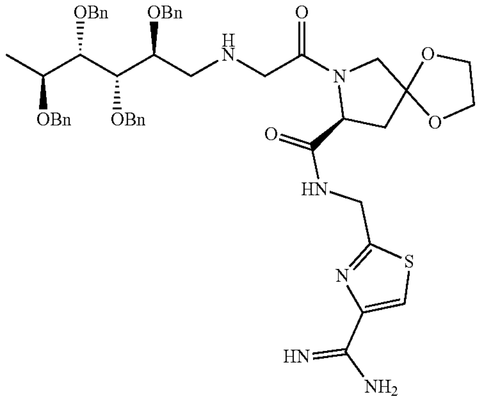 [SMILES: C[C@H](OCc1ccccc1)[C@H](OCc1ccccc1)[C@@H](OCc1ccccc1)[C@H](CNCC(=O)N1CC2(C[C@H]1C(=O)NCc1nc(C(=N)N)cs1)OCCO2)OCc1ccccc1] (S)-N-((4-carbamimidoylthiazol-2-yl)methyl)-7-(((2S,3S,4S,5S)-2,3,4,5-tetrakis(benzyloxy)hexyl)glycyl)-1,4-dioxa-7-azaspiro[4.4]nonane-8-carboxamide | | | |

TABLE 3

| Additional Non-limiting Examples of Compounds of the Present Disclosure | | | | |
|---|---|---|---|---|
| # | Structure | C1s Protease Activity | RT min (Method A or B) | MS (M + 1) |
| 91 | 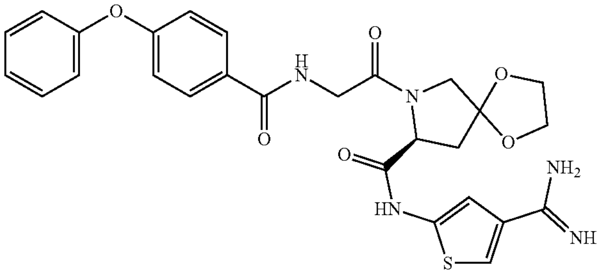 [SMILES: N=C(N)c1csc(NC(=O)[C@@H]2CC3(CN2C(=O)CNC(=O)c2ccc(Oc4ccccc4)cc2)OCCO3)c1] (S)-N-(4-carbamimidoylthiophen-2-yl)-7-((4-phenoxybenzoyl)glycyl)-1,4-dioxa-7-azaspiro[4.4]nonane-8-carboxamide | * | 1.25 (A) | 550 |

TABLE 3-continued

| # | Structure | C1s Protease Activity | RT min (Method A or B) | MS (M + 1) |
|---|---|---|---|---|
| Additional Non-limiting Examples of Compounds of the Present Disclosure | | | | |
| 92 | 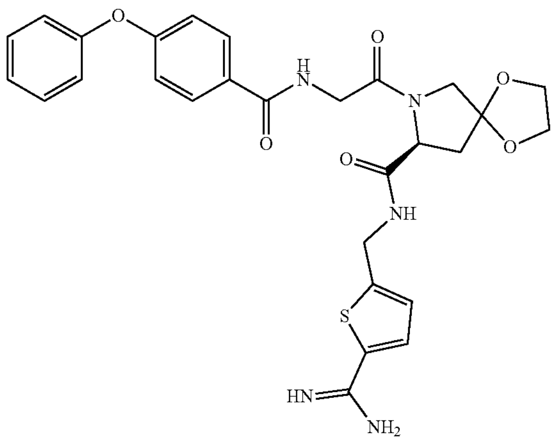 [SMILES: N=C(N)c1ccc(CNC(=O)[C@@H]2CC3(CN2C(=O)CNC(=O)c2ccc(Oc4ccccc4)cc2)OCCO3)s1] (S)-N-((5-carbamimidoylthiophen-2-yl)methyl)-7-((4-phenoxybenzoyl)glycyl)-1,4-dioxa-7-azaspiro[4.4]nonane-8-carboxamide | *** | 1.16 (A) | 564 |
| 93 | 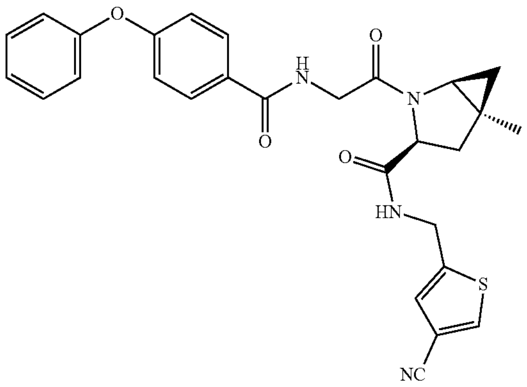 [SMILES: C[C@@]12C[C@@H]1N(C(=O)CNC(=O)c1ccc(Oc3ccccc3)cc1)[C@H](C(=O)NCc1cc(C#N)cs1)C2] (1S,3S,5S)-N-((4-cyanothiophen-2-yl)methyl)-5-methyl-2-((4-phenoxybenzoyl)glycyl)-2-azabicyclo[3.1.0]hexane-3-carboxamide | * | 2.05 (A) | 515 |
| 94 | 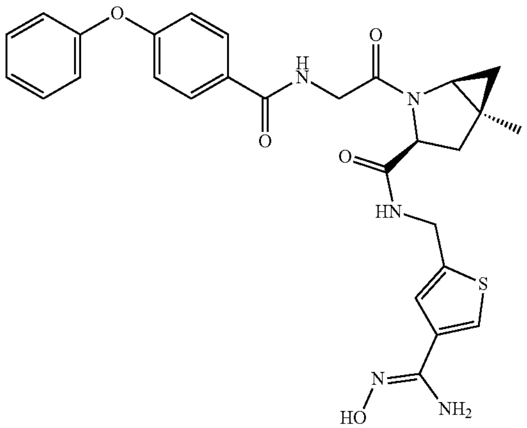 [SMILES: C[C@@]12C[C@@H]1N(C(=O)CNC(=O)c1ccc(Oc3ccccc3)cc1)[C@H](C(=O)NCc1cc(/C(N)=N/O)cs1)C2] (1S,3S,5S)-N-((4-((Z)-N'-hydroxycarbamimidoyl)thiophen-2-yl)methyl)-5-methyl-2-((4-phenoxybenzoyl)glycyl)-2-azabicyclo[3.1.0]heptane-3-carboxamide | * | 1.30 (A) | 548 |

TABLE 3-continued

| # | Structure | C1s Protease Activity | RT min (Method A or B) | MS (M + 1) |
|---|---|---|---|---|
| | Additional Non-limiting Examples of Compounds of the Present Disclosure | | | |
| 95 | 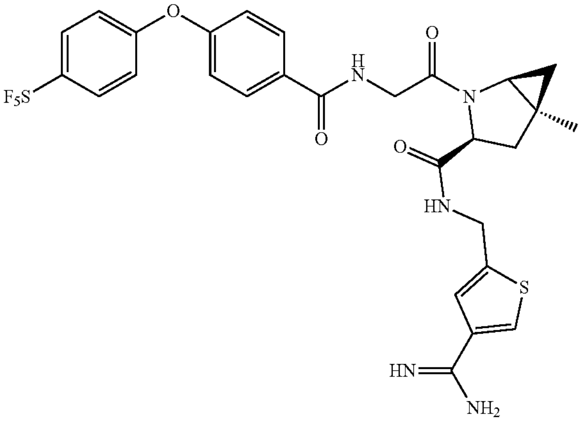 (1S,3S,5S)-N-((4-carbamimidoylthiophen-2-yl)methyl)-5-methyl-2-((4-(4-(pentafluoro-16-sulfaneyl)phenoxy)benzoyl)glycyl)-2-azabicyclo[3.1.0]hexane-3-carboxamide | *** | 1.64 (A) | 656 |
| 96 | 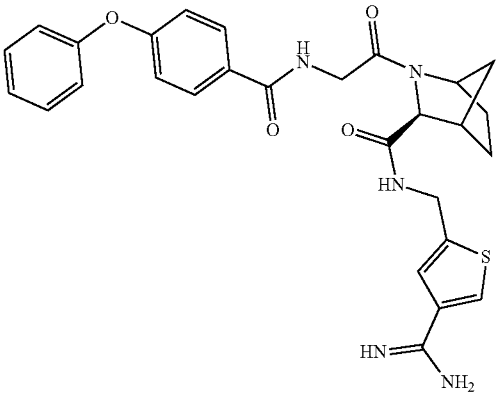 [SMILES: N=C(N)c1csc(CNC(=O)[C@@H]2C3CCC(C3)N2C(=O)CNC(=O)c2ccc(Oc3ccccc3)cc2)c1] (1R,3R,4S)-N-((4-carbamimidoylthiophen-2-yl)methyl)-2-((4-phenoxybenzoyl)glycyl)-2-azabicyclo[2.2.1]heptane-3-carboxamide | *** | 1.17 (A) | 532 |
| 97 | 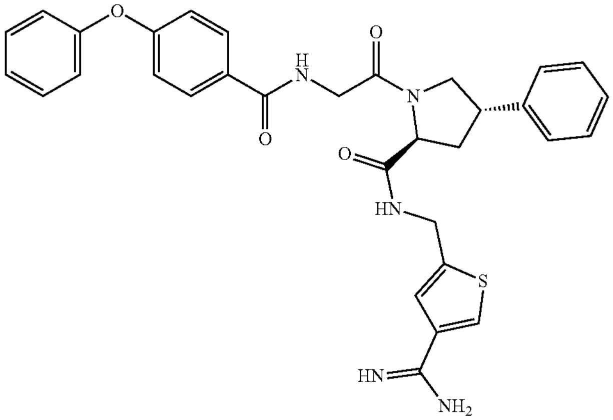 [SMILES: N=C(N)c1csc(CNC(=O)[C@@H]2C[C@@H](c3ccccc3)CN2C(=O)CNC(=O)c2ccc(Oc3ccccc3)cc2)c1] (2S,4S)-N-((4-carbamimidoylthiophen-2-yl)methyl)-1-((4-phenoxybenzoyl)glycyl)-4-phenylpyrrolidine-2-carboxamide | *** | 1.48 (A) | 582 |

TABLE 3-continued

| Additional Non-limiting Examples of Compounds of the Present Disclosure | | | | |
|---|---|---|---|---|
| # | Structure | C1s Protease Activity | RT min (Method A or B) | MS (M + 1) |
| 98 | 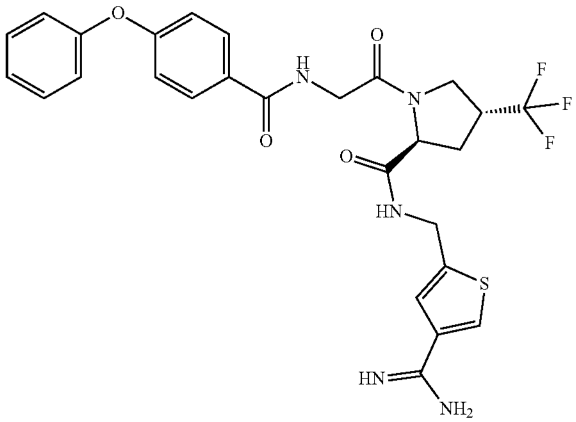 [SMILES: N=C(N)c1csc(CNC(=O)[C@@H]2C[C@@H](C(F)(F)F)CN2C(=O)CNC(=O)c2ccc(Oc3ccccc3)cc2)c1] (2S,4R)-N-((4-carbamimidoylthiophen-2-yl)methyl)-1-((4-phenoxybenzoyl)glycyl)-4-(trifluoromethyl)pyrrolidine-2-carboxamide | *** | 1.31 (A) | 574 |
| 99 | 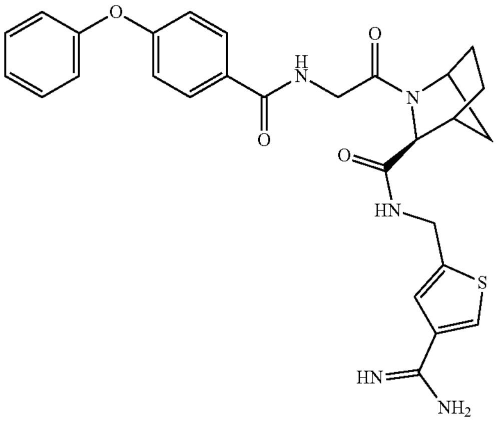 [SMILES: N=C(N)c1csc(CNC(=O)[C@@H]2C3CCC(C3)N2C(=O)CNC(=O)c2ccc(Oc3ccccc3)cc2)c1] (3S)-N-((4-carbamimidoylthiophen-2-yl)methyl)-2-((4-phenoxybenzoyl)glycyl)-2-azabicyclo[2.2.1]heptane-3-carboxamide | *** | 1.18 (A) | 532 |
| 100 | 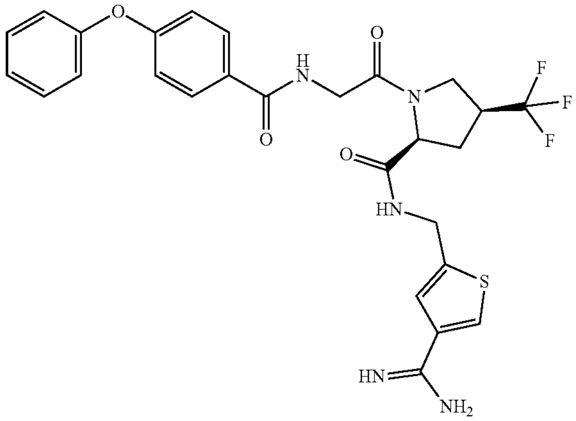 [SMILES: N=C(N)c1csc(CNC(=O)[C@@H]2C[C@H](C(F)(F)F)CN2C(=O)CNC(=O)c2ccc(Oc3ccccc3)cc2)c1] (2S,4S)-N-((4-carbamimidoylthiophen-2-yl)methyl)-1-((4-phenoxybenzoyl)glycyl)-4-(trifluoromethyl)pyrrolidine-2-carboxamide | *** | 1.27 (A) | 574 |

TABLE 3-continued

Additional Non-limiting Examples of Compounds of the Present Disclosure

| # | Structure | C1s Protease Activity | RT min (Method A or B) | MS (M + 1) |
|---|---|---|---|---|
| 101 | 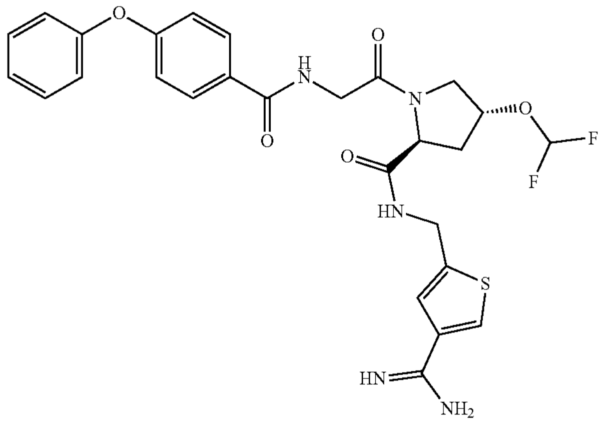 [SMILES: N=C(N)c1csc(CNC(=O)[C@@H]2C[C@@H](OC(F)F)CN2C(=O)CNC(=O)c2ccc(Oc3ccccc3)cc2)c1] (2S,4R)-N-((4-carbamimidoylthiophen-2-yl)methyl)-4-(difluoromethoxy)-1-((4-phenoxybenzoyl)glycyl)pyrrolidine-2-carboxamide | *** | 1.22 (A) | 572 |
| 102 | 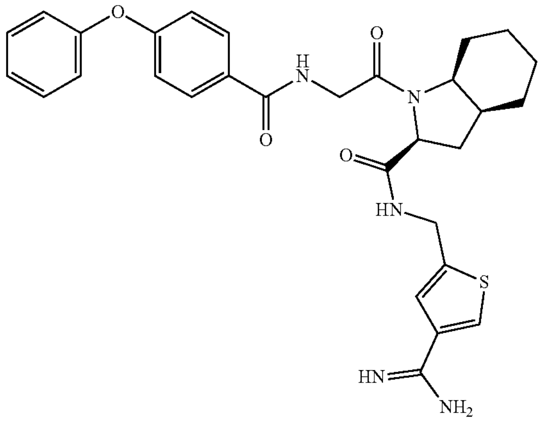 [SMILES: N=C(N)c1csc(CNC(=O)[C@@H]2C[C@@H]3CCCC[C@@H]3N2C(=O)CNC(=O)c2ccc(Oc3ccccc3)cc2)c1] (2S,3aS,7aS)-N-((4-carbamimidoylthiophen-2-yl)methyl)-1-((4-phenoxybenzoyl)glycyl)octahydro-1H-indole-2-carboxamide | *** | 1.40 (A) | 560 |
| 103 | 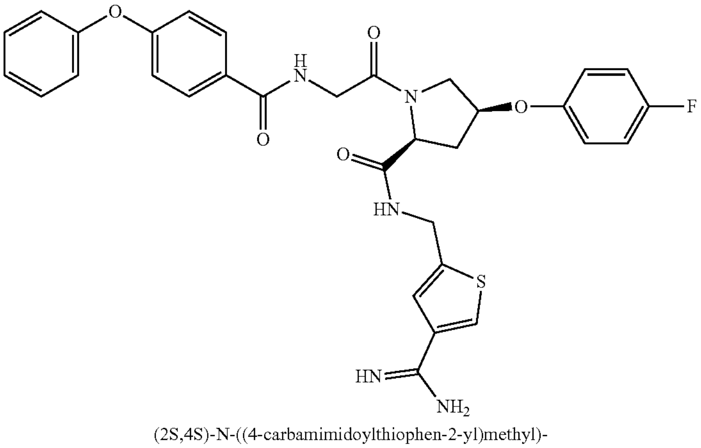 (2S,4S)-N-((4-carbamimidoylthiophen-2-yl)methyl)-4-(4-fluorophenoxy)-1-((4-phenoxybenzoyl)glycyl)pyrrolidine-2-carboxamide | *** | 1.38 (A) | 616 |

TABLE 3-continued

| Additional Non-limiting Examples of Compounds of the Present Disclosure | | | | |
|---|---|---|---|---|
| # | Structure | C1s Protease Activity | RT min (Method A or B) | MS (M + 1) |
| 104 | 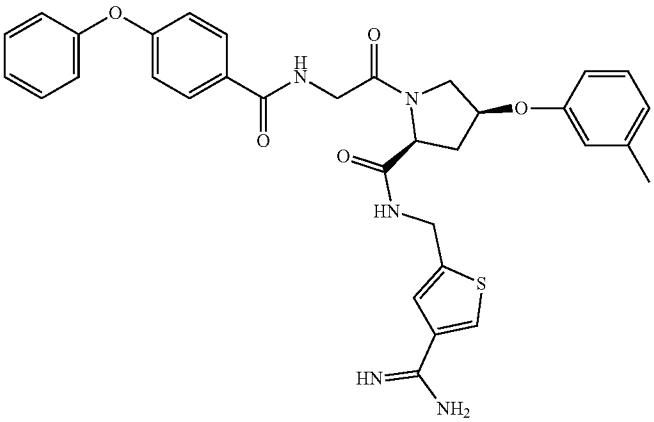 [SMILES: Cc1cccc(O[C@H]2C[C@@H](C(=O)NCc3cc(C(=N)N)cs3)N(C(=O)CNC(=O)c3ccc(Oc4ccccc4)cc3)C2)c1] (2S,4S)-N-((4-carbamimidoylthiophen-2-yl)methyl)-1-((4-phenoxybenzoyl)glycyl)-4-(m-tolyloxy)pyrrolidine-2-carboxamide | *** | 1.48 (A) | 612 |
| 105 | 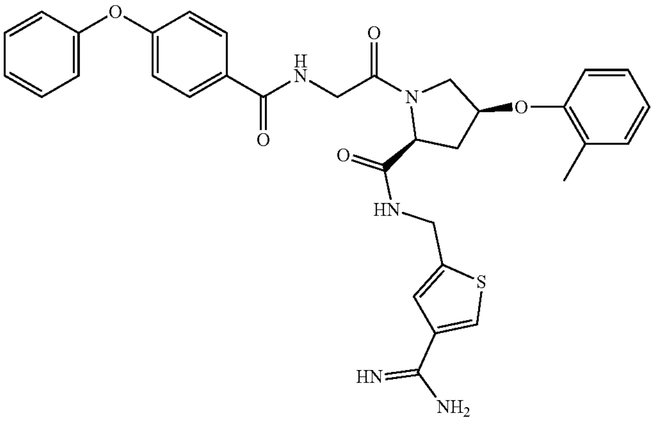 [SMILES: Cc1ccccc1O[C@H]1C[C@@H](C(=O)NCc2cc(C(=N)N)cs2)N(C(=O)CNC(=O)c2ccc(Oc3ccccc3)cc2)C1] (2S,4S)-N-((4-carbamimidoylthiophen-2-yl)methyl)-1-((4-phenoxybenzoyl)glycyl)-4-(o-tolyloxy)pyrrolidine-2-carboxamide | *** | 1.50 (A) | 612 |
| 106 | 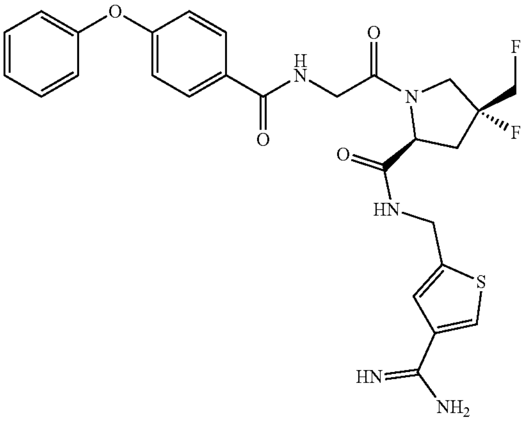 [SMILES: N=C(N)c1csc(CNC(=O)[C@@H]2C[C@](F)(CF)CN2C(=O)CNC(=O)c2ccc(Oc3ccccc3)cc2)c1] (2S,4R)-N-((4-carbamimidoylthiophen-2-yl)methyl)-4-fluoro-4-(fluoromethyl)-1-((4-phenoxybenzoyl)glycyl)pyrrolidine-2-carboxamide | *** | 1.19 (A) | 556 |

TABLE 3-continued

| Additional Non-limiting Examples of Compounds of the Present Disclosure | | | | |
|---|---|---|---|---|
| # | Structure | C1s Protease Activity | RT min (Method A or B) | MS (M + 1) |
| 107 | 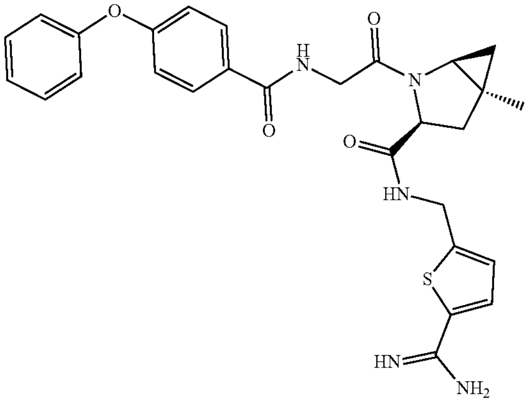 [SMILES: C[C@@]12C[C@@H]1N(C(=O)CNC(=O)c1ccc(Oc3ccccc3)cc1)[C@H](C(=O)NCc1ccc(C(=N)N)s1)C2] (1S,3S,5S)-N-((5-carbamimidoylthiophen-2-yl)methyl)-5-methyl-2-((4-phenoxybenzoyl)glycyl)-2-azabicyclo[3.1.0]hexane-3-carboxamide | *** | 1.33 (A) | 532 |
| 108 | 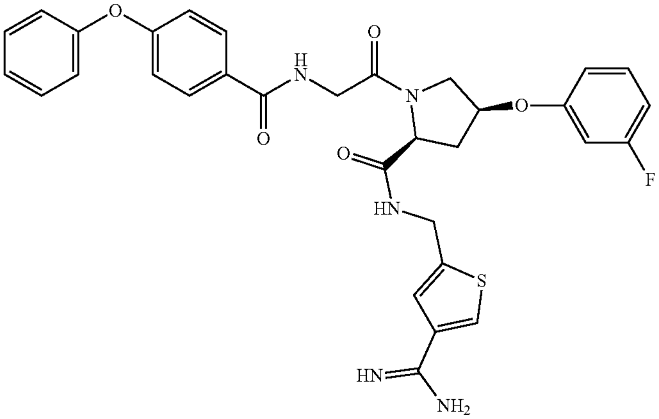 [SMILES: N=C(N)c1csc(CNC(=O)[C@@H]2C[C@H](Oc3cccc(F)c3)CN2C(=O)CNC(=O)c2ccc(Oc3ccccc3)cc2)c1] (2S,4S)-N-((4-carbamimidoylthiophen-2-yl)methyl)-4-(3-fluorophenoxy)-1-((4-phenoxybenzoyl)glycyl)pyrrolidine-2-carboxamide | *** | 1.40 (A) | 616 |

Additional compounds of the present disclosure include:

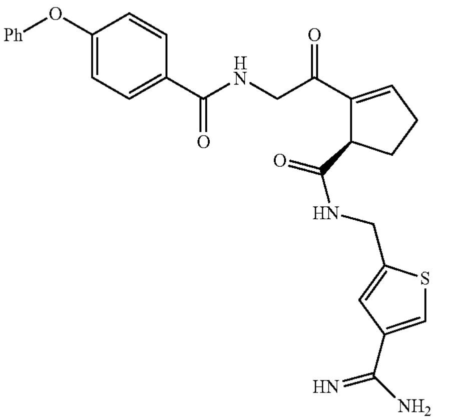

(R)-N-(2-(5-(((4-carbamimidoylthiophen-2-yl)methyl)carbamoyl)cyclopent-1-en-1-yl)-2-oxoethyl)-4-phenoxybenzamide -continued

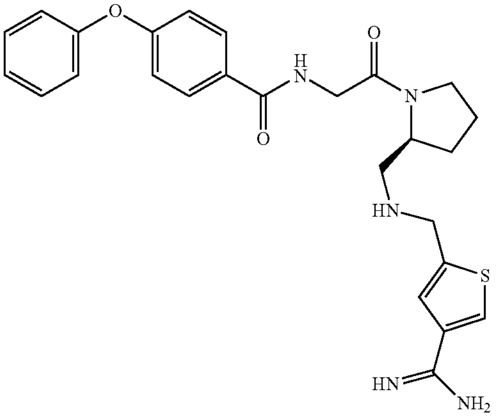

(S)-N-(2-(2-((((4-carbamimidoylthiophen-2-yl)methyl)amino)methyl)pyrrolidin-1-yl)-2-oxoethyl)-4-phenoxybenzamide -continued

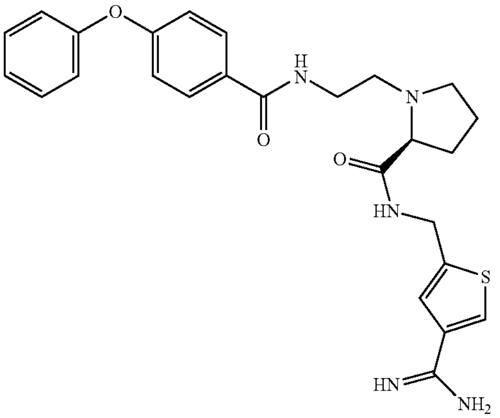

(S)-N-((4-carbamimidoylthiophen-2-yl)methyl)-1-(2-(4-phenoxybenzamido)ethyl)pyrrolidine-2-carboxamide

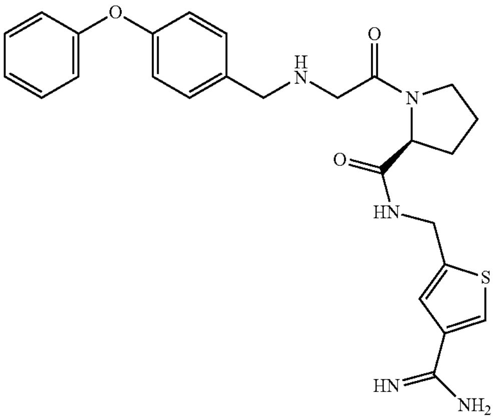

(S)-N-((4-carbamimidoylthiophen-2-yl)methyl)-1-((4-phenoxybenzyl)glycyl)pyrrolidine-2-carboxamide

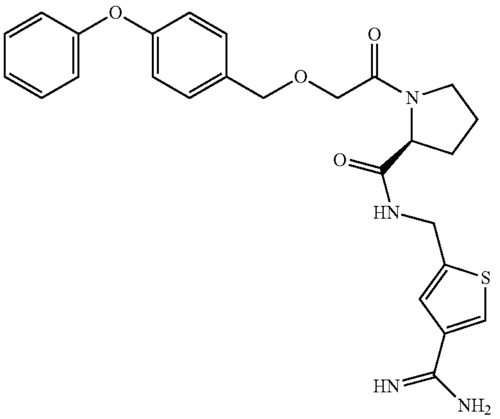

(S)-N-((4-carbamimidoylthiophen-2-yl)methyl)-1-(2-((4-phenoxybenzyl)oxy)acetyl))pyrrolidine-2-carboxamide -continued

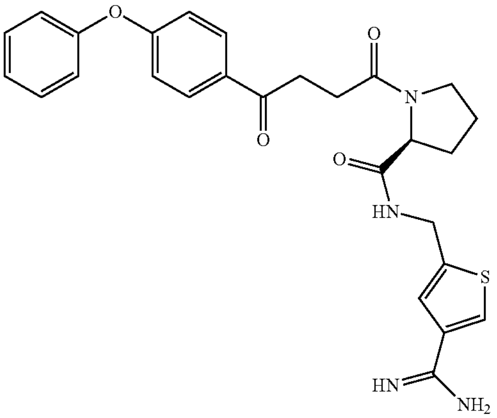

(S)-N-((4-carbamimidoylthiophen-2-yl)methyl)-1-(4-oxo-4-(4-phenoxyphenyl)butanoyl)pyrrolidine-2-carboxamide

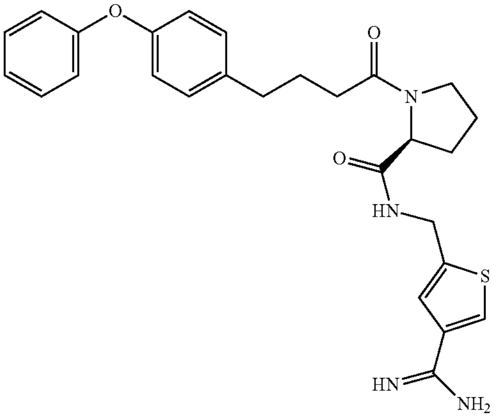

(S)-N-((4-carbamimidoylthiophen-2-yl)methyl)-1-(4-(4-phenoxyphenyl)butanoyl)pyrrolidine-2-carboxamide

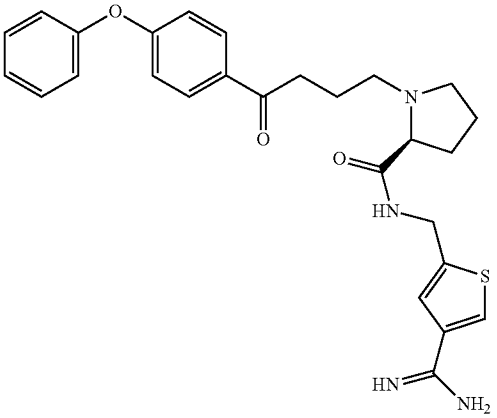

(S)-N-((4-carbamimidoylthiophen-2-yl)methyl)-1-(4-oxo-4-(4-phenoxyphenyl)butyl)pyrrolidine-2-carboxamide -continued

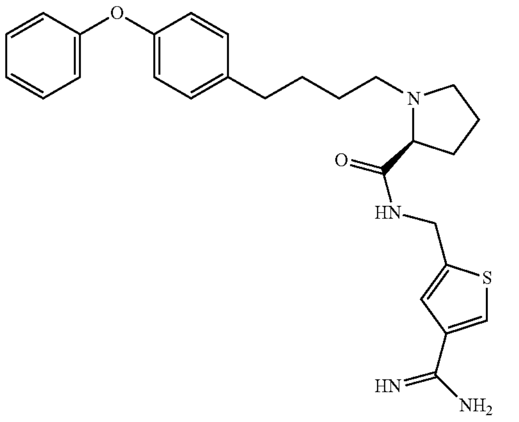

(S)-N-((4-carbamimidoylthiophen-2-yl)methyl)-1-(4-(4-phenoxyphenyl)butyl)pyrrolidine-2-carboxamide

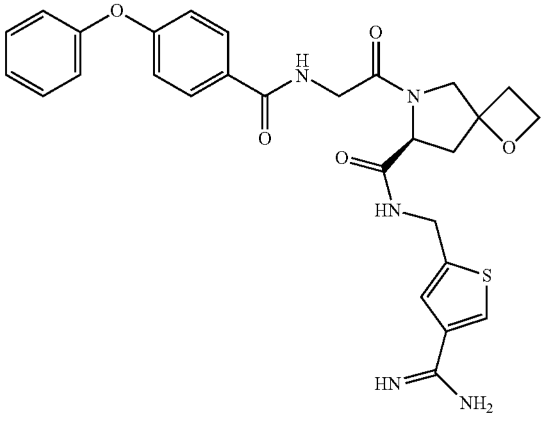

(7S)-N-((4-carbamimidoylthiophen-2-yl)methyl)-6-((4-phenoxybenzoyl)glycyl)-1-oxa-6-azaspiro[3.4]octane-7-carboxamide

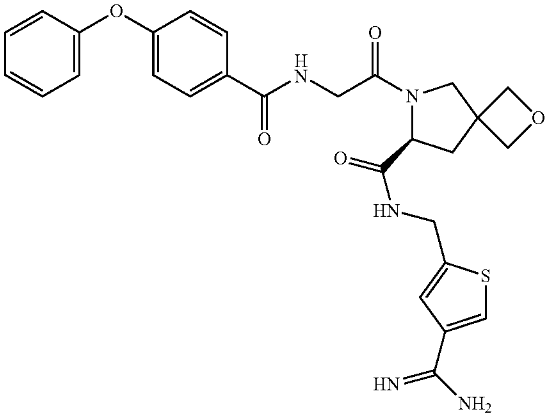

(S)-N-((4-carbamimidoylthiophen-2-yl)methyl)-6-((4-phenoxybenzoyl)glycyl)-2-oxa-6-azaspiro[3.4]octane-7-carboxamide -continued

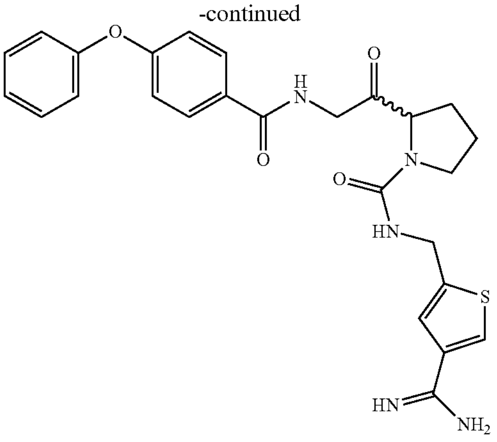

N-((4-carbamimidoylthiophen-2-yl)methyl)-2-((4-phenoxybenzoyl)glycyl)pyrrolidine-1-carboxamide

Example 4. Human C1s Enzyme Assay

Human complement C1s enzyme (purified from human serum, Complement Technology, Inc.) at 1.16 nM final concentration is incubated with test compound at various concentrations for 5 min at room temperature in 50 mM Tris, 1 M NaCl, pH 7.5. A synthetic substrate Z-L-Lys-SBzl and DTNB (Ellman's reagent) are added to final concentrations of 100 μM each. Absorbance at 405 nm (A405) is recorded at 30 second intervals for 30 min using a microplate spectrophotometer. IC50 values are calculated by nonlinear regression of complement C1s reaction rates as a function of test compound concentration.

Example 5. Hemolysis Assay

The hemolysis assay was previously described by Dodds, A. W. and Sim, R. B. (1997); Morgan, B. P. (2000). Prior to the assay, the optimum concentration of Normal Human Serum (NHS) needed to achieve 100% lysis of antibody sensitized sheep erythrocytes (EA) is determined by titration. EA are sheep erythrocytes with rabbit IgM anti-sheep erythrocyte antibodies bound to their surface. In the assay, NHS (Complement Technology) is diluted in GVB++ Buffer (0.1% gelatin, 5 mM Veronal, 145 mM NaCl, 0.025% NaN3, pH 7.3, 0.15 mM calcium chloride and 0.5 mM magnesium chloride, Complement Technology) and incubated with test compound at various concentrations for 2 min at room temperature. EA (Complement Technology) freshly suspended in GVB++ are added to a final concentration of $1\times10^8$ cells/mL and reactions are incubated for 60 min at 37° C. Positive control reactions (100% lysis) consist of GVB++ with NHS and EA but without test compound; negative control reactions (0% lysis) consist of GVB++ with EA only. Samples are centrifuged at 2000 g for 3 min and supernatants collected. Absorbance at 405 nm (A405) is recorded using a microplate spectrophotometer. IC50 values are calculated by nonlinear regression from the percentage of hemolysis as a function of test compound concentration.

This specification has been described with reference to various specific embodiments. However, one of ordinary skill in the art appreciates that various modifications and changes can be made without departing from the scope of the invention as set forth in the claims. Accordingly, the specification is to be regarded in an illustrative rather than a restrictive sense, and all such modifications are intended to be included within the scope of the claimed invention.
We claim:
1. A compound, wherein
(i) the compound is selected from:
(I)
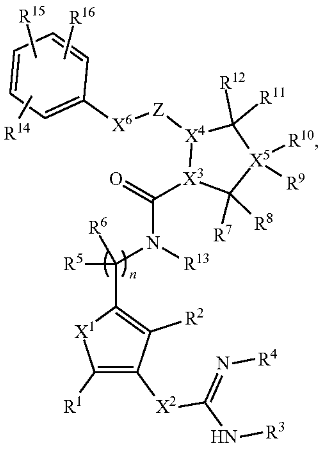
(II)
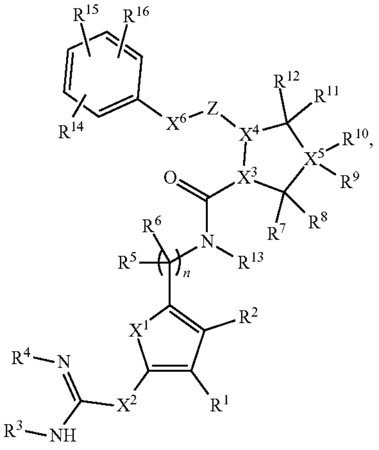
(III)
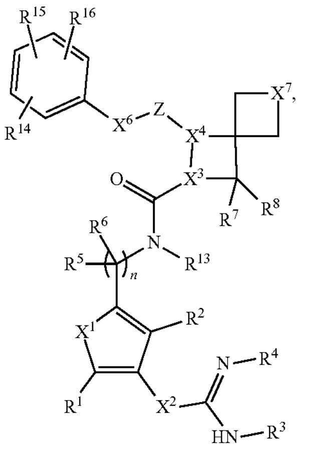
-continued
(IV)
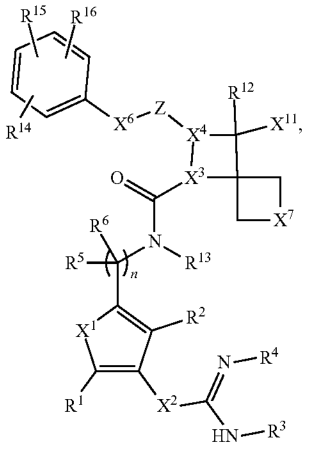
(IX)
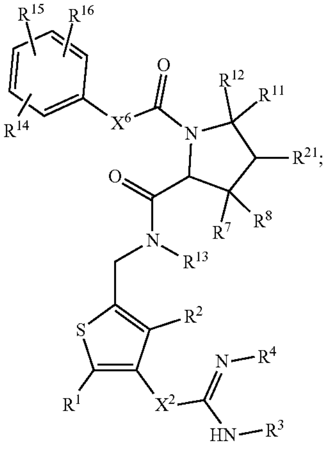
(XIII)
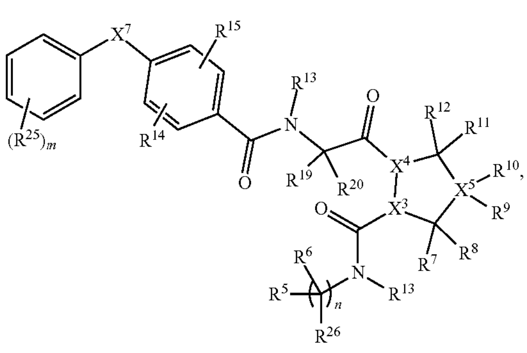

-continued (XIV)

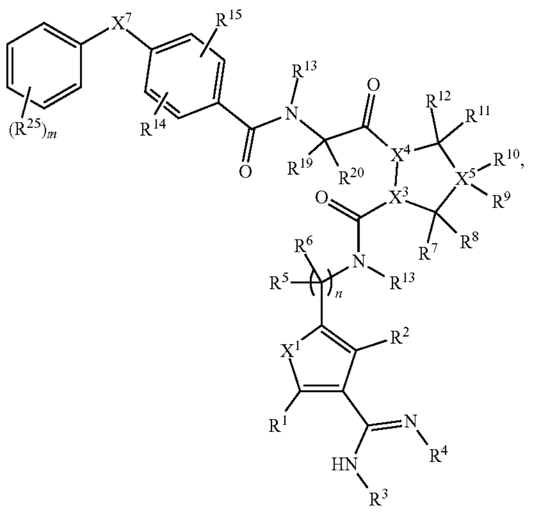

(XIX)

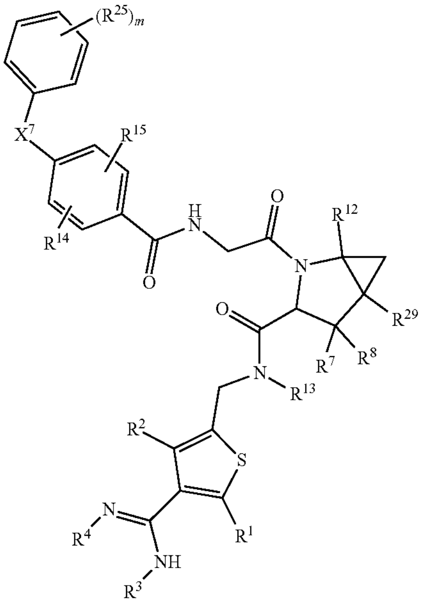

and

-continued (XX)

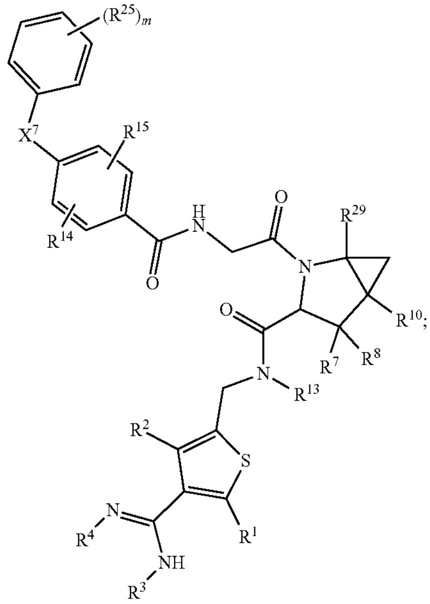

or a pharmaceutically acceptable salt thereof;

wherein:

n is 1;

each m is independently 0 or 1;

Z is C(O);

$X^1$ is S;

$X^2$ is a bond;

$X^3$ is $C(R^{17})$;

$X^4$ is N;

$X^5$ is C or Si;

$X^6$ is

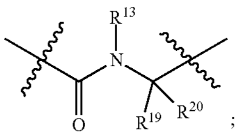

;

$X^7$ is selected from O— and $CR^5R^6$;

$R^1$ and $R^2$ are independently selected from hydrogen, halogen, and $C_1$-$C_6$alkyl;

$R^3$ and $R^4$ are both hydrogen; or $R^3$ is hydrogen and $R^4$ is hydroxyl;

$R^5$ and $R^6$ are both hydrogen;

each of $R^7$, $R^8$, $R^{11}$, and $R^{12}$ is hydrogen;

$R^9$ is selected from hydrogen, halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, and heteroaryl, wherein each $R^9$ other than hydrogen and halogen is optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

$R^{10}$ is selected from halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —$C(O)R^{31}$, —S(O)

$R^{31}$, —$S(O)_2R^{31}$, heterocycle, aryl, and heteroaryl, wherein each $R^{10}$ other than halogen is optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

or $R^9$ and $R^{10}$ may be taken together with the atom to which they are attached to form a 3- to 6-membered carbocyclic spiro ring; a 4- to 6-membered heterocyclic spiro ring containing 1 or 2 heteroatoms independently chosen from N, O, and S;

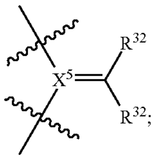

or carbonyl;

or $R^9$ and $R^{11}$ are taken together with the atoms to which they are attached to form a 3- to 8-membered carbocycle;

or $R^7$ and $R^{11}$ are taken together with the atoms to which they are attached to form a 1 or 2 carbon bridge, and $R^{10}$ is hydrogen;

each $R^{13}$ is hydrogen;

$R^{14}$, $R^{15}$, and $R^{16}$ are independently selected from hydrogen, halogen, $C_1$-$C_6$alkyl, and —O-phenyl;

$R^{17}$ is hydrogen;

$R^{19}$ and $R^{20}$ are both hydrogen;

$R^{21}$ is selected from $C_1$-$C_6$haloalkyl, —O—$C_1$-$C_6$haloalkyl, $C_1$-$C_6$alkyl, —O—$C_1$-$C_6$alkyl, aryl, —O-aryl, heteroaryl, or —O-heteroaryl, each of which $R^{21}$ group is optionally substituted with 1, 2, 3, or 4 substituents independently selected from $SF_5$, $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

each $R^{25}$ is independently selected from hydrogen, $SF_5$, halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro; each of which $R^{25}$ groups other than hydrogen, halogen, cyano, and nitro are optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

$R^{26}$ is

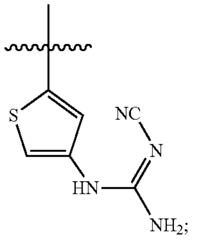 [SMILES: *c1cc(N/C(N)=N\C#N)cs1]

$R^{29}$ is selected from halogen, $C_1$-$C_6$alkyl, $C_2$-$C_6$alkenyl, $C_2$-$C_6$alkynyl, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, and heteroaryl, each of which $R^{29}$ groups other than halogen are optionally substituted with 1, 2, 3, or 4 substituents independently selected from $C_1$-$C_6$alkyl, $C_2$-$C_6$alkenyl, $C_2$-$C_6$alkynyl, halogen, $C_1$-$C_6$haloalkyl, —$OR^{30}$, —$SR^{30}$, —$N(R^{30})_2$, —$C(O)R^{31}$, —$S(O)R^{31}$, —$S(O)_2R^{31}$, heterocycle, aryl, heteroaryl, cyano, and nitro;

each $R^{30}$ is independently selected from hydrogen, $C_1$-$C_6$alkyl, $C_1$-$C_6$haloalkyl, aryl, heteroaryl, heterocycle, and $C(O)R^{31}$;

each $R^{31}$ is independently selected from hydrogen, $C_1$-$C_6$alkyl, $C_1$-$C_6$haloalkyl, —$OR^{32}$, —$SR^{32}$, —$N(R^{32})_2$, heterocycle, aryl, and heteroaryl; and each $R^{32}$ is independently selected from hydrogen, $C_1$-$C_6$alkyl, and $C_1$-$C_6$haloalkyl;

wherein for compounds of Formula I and Formula II at least one of the following is satisfied:

a. $X^5$ is Si;

b. $R^9$ and $R^{10}$ are taken together with the carbon to which they are attached to form a 3- to 6-membered carbocyclic spiro ring; a 4- to 6-membered heterocyclic spiro ring containing 1 or 2 heteroatoms independently chosen from N, O, and S;

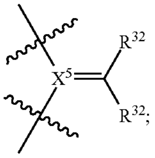

or a carbonyl;

c. $R^9$ and $R^{11}$ are taken together with the atoms to which they are attached to form a 3- to 8-membered carbocycle; or d. $R^7$ and $R^{11}$ are taken together with the atoms to which they are attached to form a 1 or 2 carbon bridge wherein for compounds of Formula XIV at least one of the following is satisfied:

a. $R^{14}$ is not hydrogen;

b. $R^1$ is not hydrogen;

c. $R^2$ is not hydrogen;

or d. $R^4$ is not hydrogen.

2. The compound of claim 1, or a pharmaceutically acceptable salt thereof, selected from:

(I)
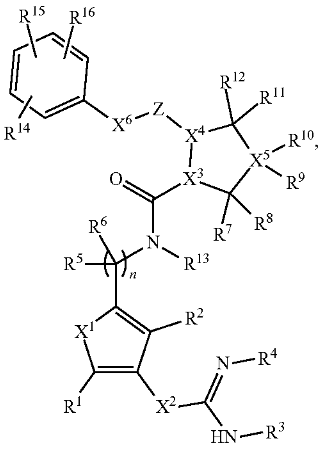
(II)
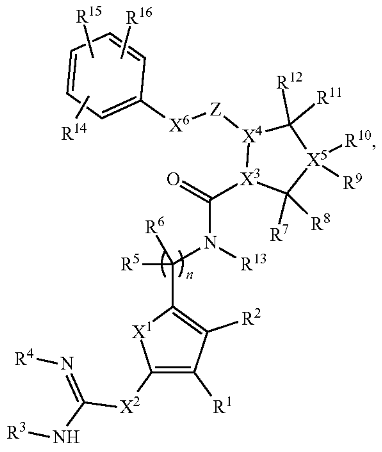
(III)
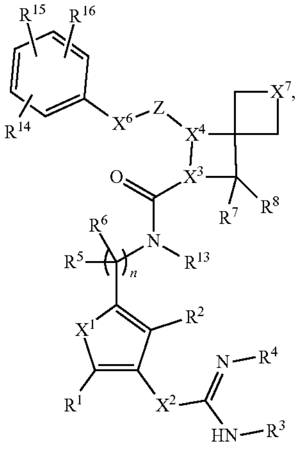
-continued
(IV)
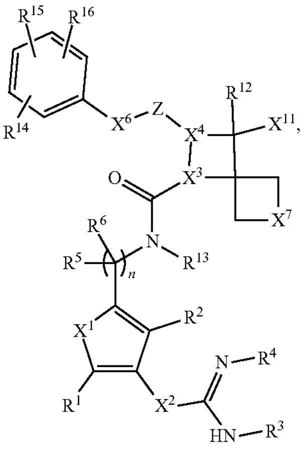
(IX)
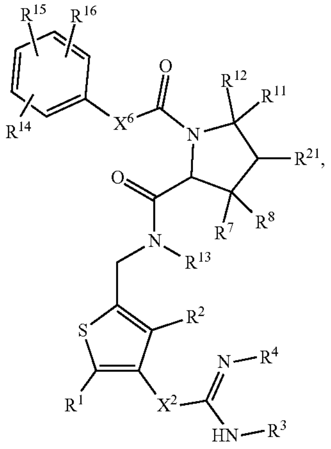
(XIII)
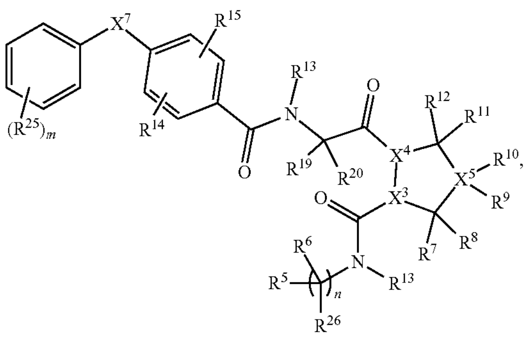
and -continued (XIV)

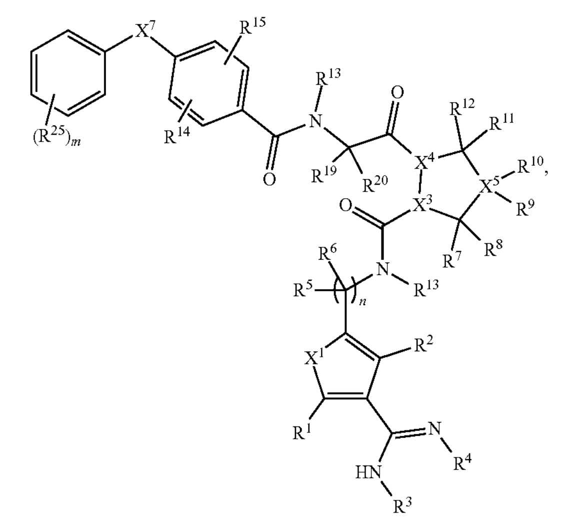

or a pharmaceutically acceptable salt thereof, wherein $R^{21}$ is selected from $C_1$-$C_6$alkyl and —O—$C_1$-$C_6$alkyl.

3. The compound of claim 1, or a pharmaceutically acceptable salt thereof, wherein:

$X^5$ is C; and/or $X^7$ is O.

4. The compound of claim 1, or a pharmaceutically acceptable salt thereof, wherein $R^1$ and $R^2$ are both hydrogen.

5. The compound of claim 1, wherein $R^3$ and $R^4$ are both hydrogen.

6. The compound of claim 1, or a pharmaceutically acceptable salt thereof, wherein:

$R^7$ is hydrogen and $R^{11}$ is hydrogen.

7. The compound of claim 1, or a pharmaceutically acceptable salt thereof, wherein:

$R^9$ and $R^{11}$ are combined to form a 4-8 membered carbocycle ring; or $R^9$ and $R^{11}$ are combined to form a cyclopropyl ring; or $R^9$ and $R^{10}$ are combined to form a spirocycle.

8. The compound of claim 1, or a pharmaceutically acceptable salt thereof, wherein $R^{10}$ is $C_1$-$C_6$alkyl.

9. A compound selected from:

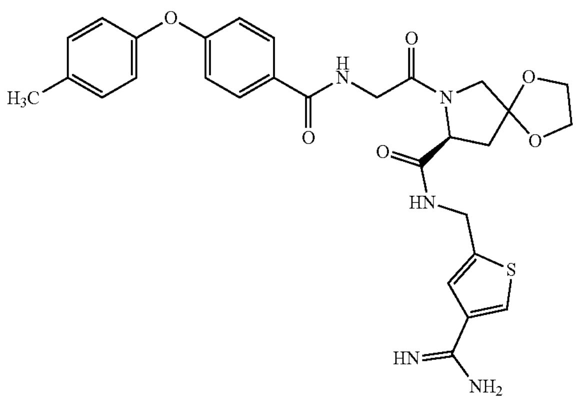

-continued

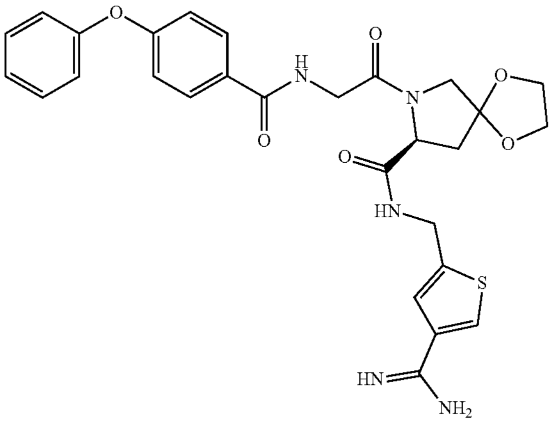

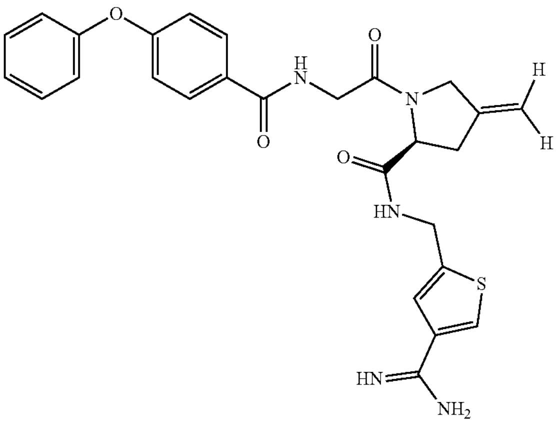

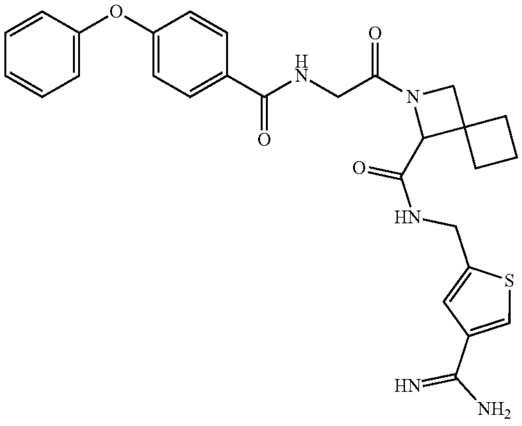

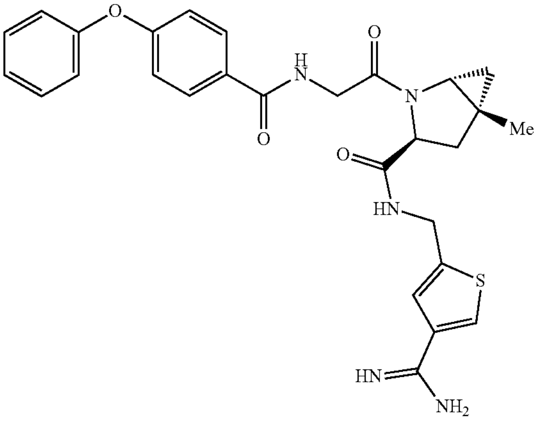

-continued
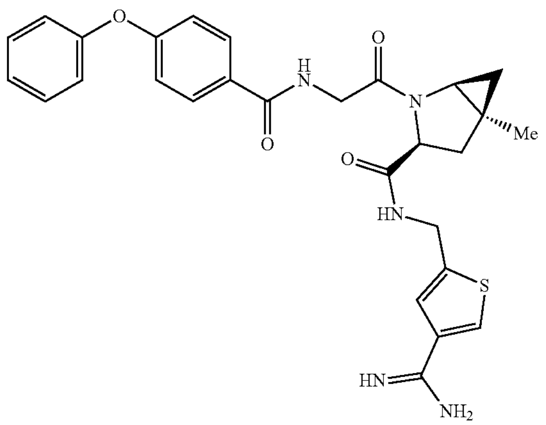
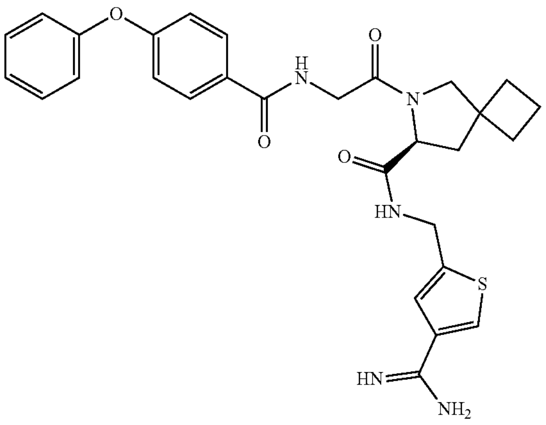
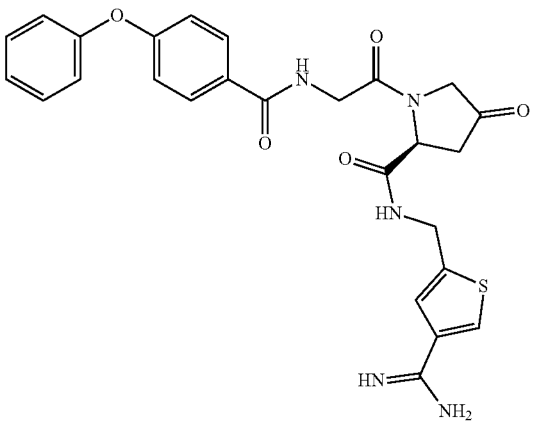
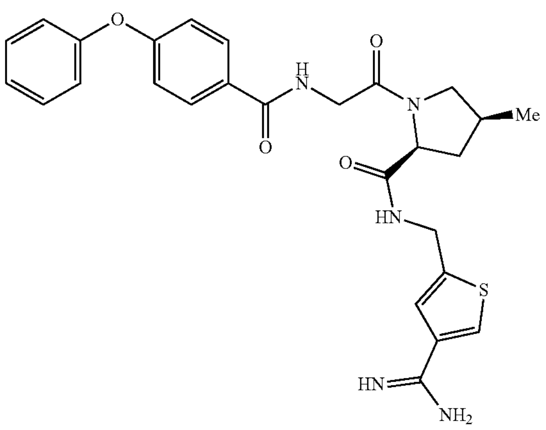
-continued
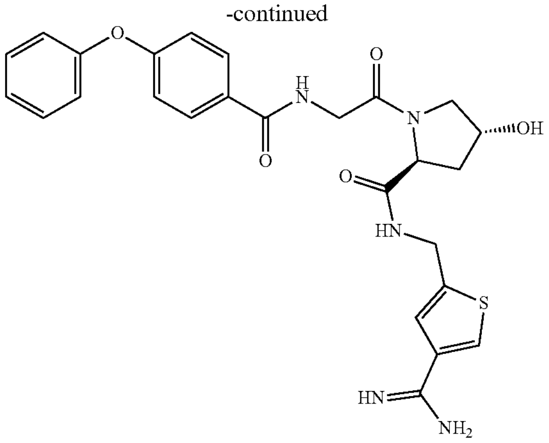
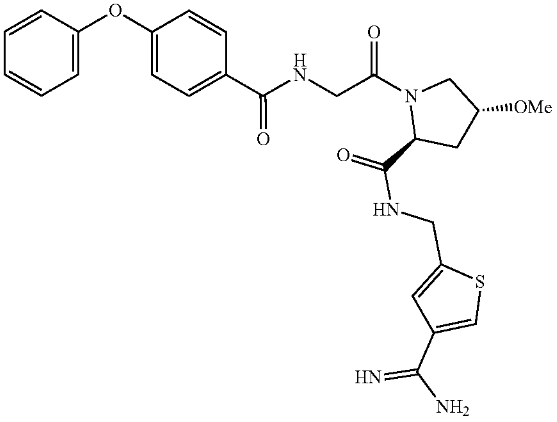
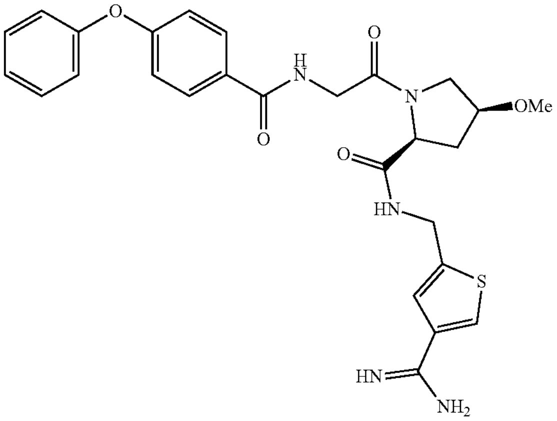
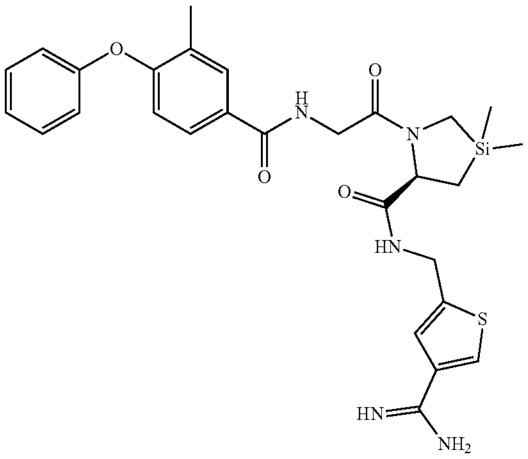

-continued
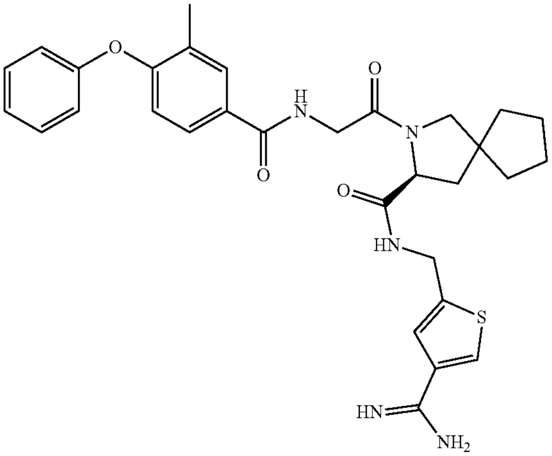
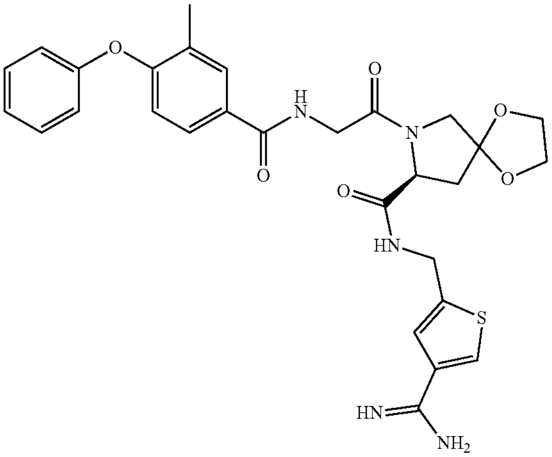
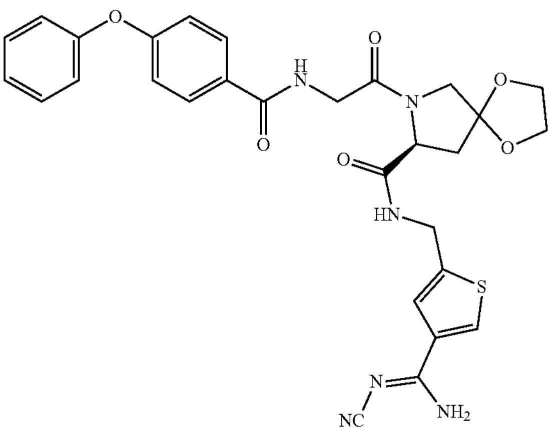
-continued
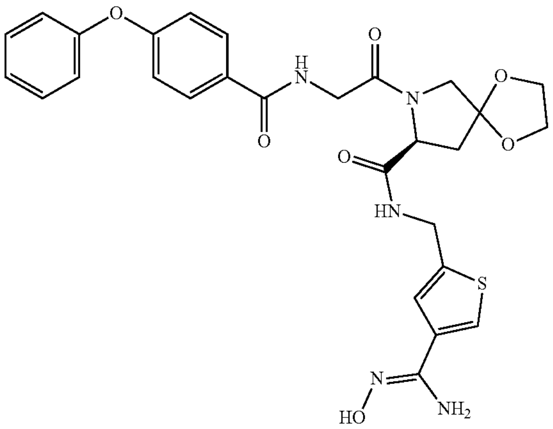
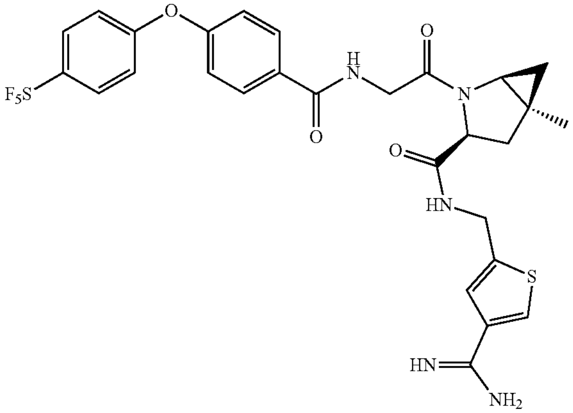
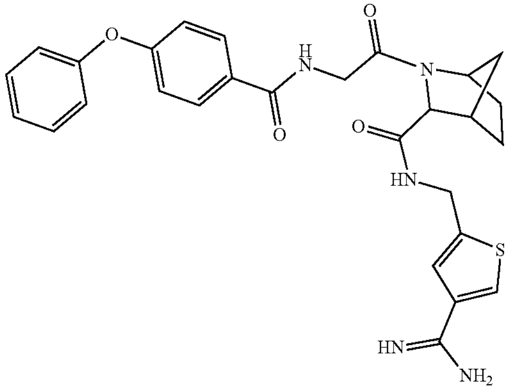
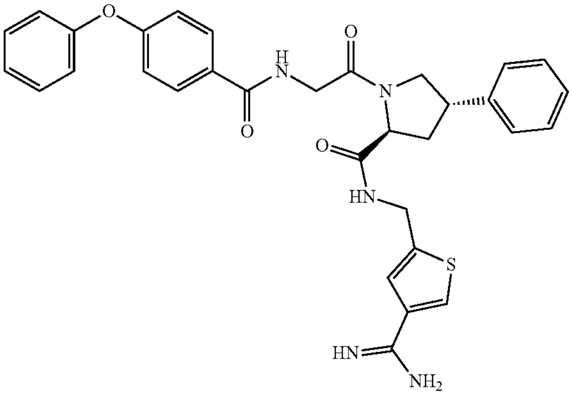

-continued
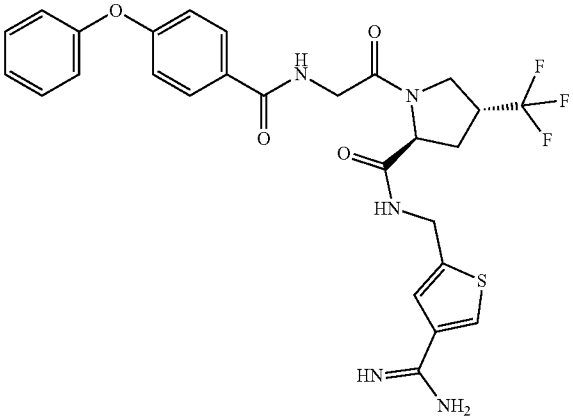
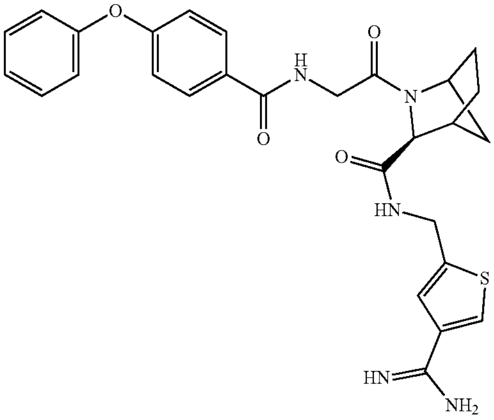
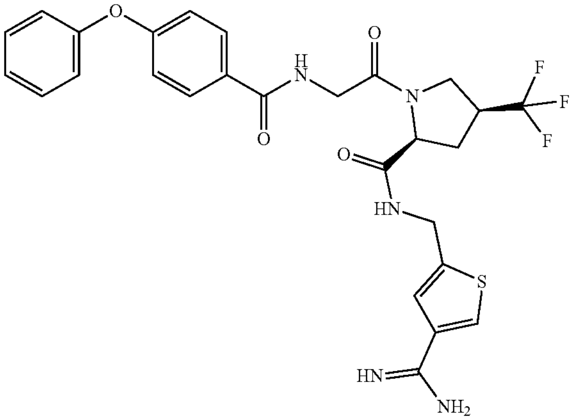
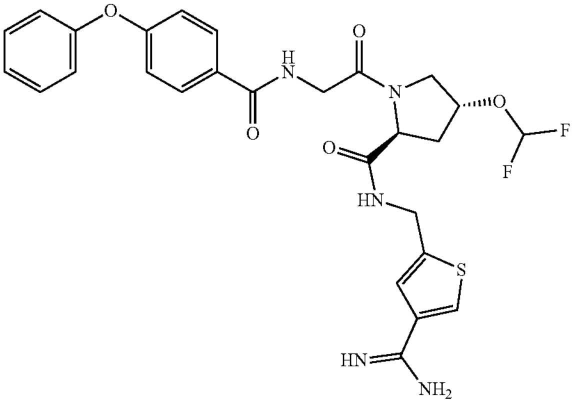
-continued
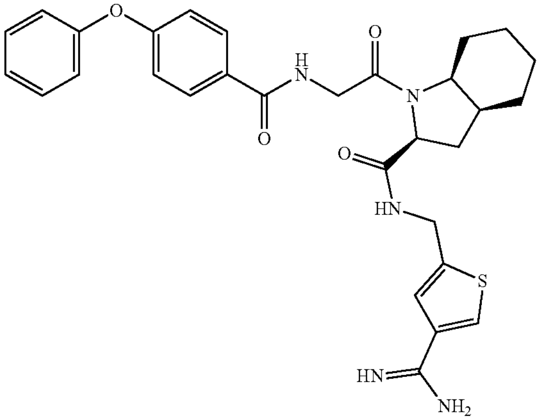
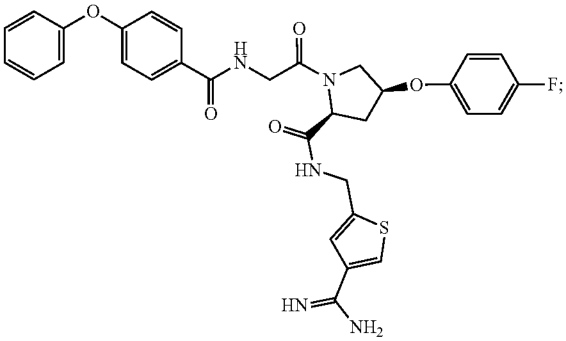
;
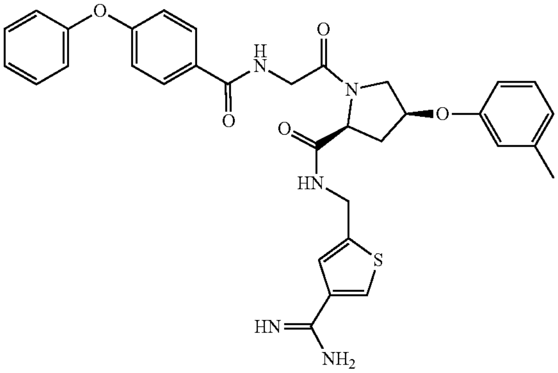
;
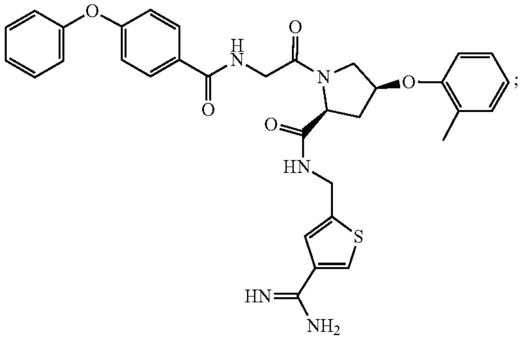
; and -continued

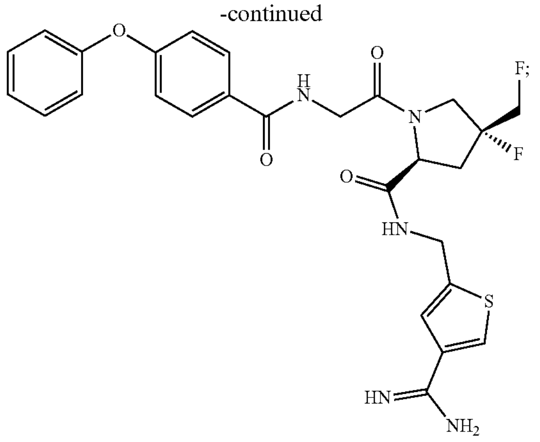

or a pharmaceutically acceptable salt thereof.

10. A pharmaceutical composition comprising a compound of claim 1 and a pharmaceutically acceptable carrier.

11. A method of treating a C1s mediated disorder comprising administering to a subject in need thereof a therapeutically effective amount of a compound or pharmaceutical composition thereof according to claim 1 or a pharmaceutically acceptable salt thereof, wherein the disorder is C3 glomerulopathy, an ophthalmic disorder, age-related macular degeneration (AMD), paroxysmal nocturnal hemoglobinuria (PNH), C3 glomerulonephritis, dense deposit disease, angioedema, hereditary angioedema, autoimmune hemolytic anemia, cold agglutinin disease, hereditary angioedema type 1, hereditary angioedema type 2, trauma, inflammation, sepsis, multiple organ dysfunction syndrome, endotoxemia, end stage renal disease, kidney failure, delayed graft function, ischemic reperfusion injury, neuromyelitis optica, common variable immunodeficiency, antibody-mediated rejection, graft rejection, asthma, allergic asthma, angioneurotic edema, acute ACE-induced angioedema, kidney transplantation, or acute kidney injury.

12. The method of claim 11, wherein the subject is a human.

* * * * *